US011603542B2

(12) United States Patent
Sah et al.

(10) Patent No.: US 11,603,542 B2
(45) Date of Patent: Mar. 14, 2023

(54) COMPOSITIONS AND METHODS OF TREATING AMYOTROPHIC LATERAL SCLEROSIS (ALS)

(71) Applicant: VOYAGER THERAPEUTICS, INC., Cambridge, MA (US)

(72) Inventors: Dinah Wen-Yee Sah, Cambridge, MA (US); Qingmin Chen, Belmont, MA (US); Jinzhao Hou, Cambridge, MA (US)

(73) Assignee: Voyager Therapeutics, Inc., Cambridge, MA (US)

( * ) Notice: Subject to any disclaimer, the term of this patent is extended or adjusted under 35 U.S.C. 154(b) by 443 days.

(21) Appl. No.: 16/611,054

(22) PCT Filed: May 4, 2018

(86) PCT No.: PCT/US2018/031089
§ 371 (c)(1),
(2) Date: Nov. 5, 2019

(87) PCT Pub. No.: WO2018/204786
PCT Pub. Date: Nov. 8, 2018

(65) Prior Publication Data
US 2020/0123574 A1 Apr. 23, 2020

Related U.S. Application Data

(60) Provisional application No. 62/566,609, filed on Oct. 2, 2017, provisional application No. 62/520,100, filed on Jun. 15, 2017, provisional application No. 62/507,927, filed on May 18, 2017, provisional application No. 62/501,788, filed on May 5, 2017.

(51) Int. Cl.
*C12N 15/861* (2006.01)
*C12N 9/00* (2006.01)
*C12N 15/113* (2010.01)
*A61K 45/06* (2006.01)
*C12N 9/02* (2006.01)

(52) U.S. Cl.
CPC ......... *C12N 15/861* (2013.01); *C12N 9/0089* (2013.01); *C12N 15/113* (2013.01); *A61K 45/06* (2013.01); *C12N 2310/14* (2013.01); *C12N 2330/51* (2013.01); *C12N 2750/14143* (2013.01); *C12Y 115/01001* (2013.01)

(58) Field of Classification Search
None
See application file for complete search history.

(56) References Cited

U.S. PATENT DOCUMENTS

| | | |
|---|---|---|
| 5,064,764 A | 11/1991 | Besnainon |
| 5,171,680 A | 12/1992 | Mullenbach et al. |
| 5,474,935 A | 12/1995 | Chatterjee |
| 5,587,308 A | 12/1996 | Carter |
| 5,652,224 A | 7/1997 | Wilson |
| 5,658,785 A | 8/1997 | Johnson |
| 5,688,676 A | 11/1997 | Zhou |
| 5,691,176 A | 11/1997 | Lebkowski |
| 5,693,531 A | 12/1997 | Chiorini |
| 5,741,683 A | 4/1998 | Zhou |
| 5,756,283 A | 5/1998 | Wilson |
| 5,856,152 A | 1/1999 | Wilson |
| 5,858,351 A | 1/1999 | Podsakoff |
| 5,858,775 A | 1/1999 | Johnson |
| 5,866,552 A | 2/1999 | Wilson |
| 5,866,696 A | 2/1999 | Carter |
| 5,871,982 A | 2/1999 | Wilson |
| 5,952,221 A | 9/1999 | Kurtzman |
| 5,962,313 A | 10/1999 | Podsakoff |
| 5,989,540 A | 11/1999 | Carter |
| 6,083,716 A | 7/2000 | Wilson |
| 6,143,548 A | 11/2000 | ORiordan |
| 6,143,567 A | 11/2000 | Van Agthoven |
| 6,146,874 A | 11/2000 | Zolotukhin |
| 6,156,303 A | 12/2000 | Russell |
| 6,174,527 B1 | 1/2001 | Wilson |
| 6,180,613 B1 | 1/2001 | Kaplitt |
| 6,194,191 B1 | 2/2001 | Zhang |
| 6,200,560 B1 | 3/2001 | Couto |
| 6,204,059 B1 | 3/2001 | Samulski |
| 6,211,163 B1 | 4/2001 | Podsakoff |
| 6,251,677 B1 | 6/2001 | Wilson |
| 6,258,595 B1 | 7/2001 | Gao |
| 6,261,551 B1 | 7/2001 | Wilson |
| 6,265,389 B1 | 7/2001 | Burke |
| 6,270,996 B1 | 8/2001 | Wilson |

(Continued)

FOREIGN PATENT DOCUMENTS

| | | |
|---|---|---|
| AU | 2007201330 A1 | 4/2007 |
| CA | 2453183 A1 | 1/2003 |

(Continued)

OTHER PUBLICATIONS

Li D, et al. Slow intrathecal injection of rAAVrh10 enhances its transduction of spinal cord and therapeutic efficacy in a mutant SOD1 model of ALS Neuroscience Oct. 9, 2017 Epub ahead of print.

Merkel SR, et al. Trafficking of adeno-associated virus vectors across a model of the blood-brain barrier; a comparative study of transcytosis and transduction using primary human brain endothelial cells. J Neurochem. Jan. 2017;140(2):216-230. doi: 10.1111/jnc.13861.

Hinderer C, et al. Delivery of an Adeno-Associated Virus Vector into Cerebrospinal Fluid Attenuates Central Nervous System Disease in Mucopolysaccharidosis Type II Mice. Hum Gene Ther. Nov. 2016;27(11):906-915. Epub Aug. 10, 2016.

(Continued)

*Primary Examiner* — Nicole Kinsey White
(74) *Attorney, Agent, or Firm* — Nelson Mullins Riley & Scarborough LLP; Jane E. Remillard, Esq.; Cynthia L. Kanik

(57) ABSTRACT

The present invention relates to adeno-associated viral (AAV) particles encoding siRNA molecules and methods for treating amyotrophic lateral sclerosis (ALS).

28 Claims, 3 Drawing Sheets
Specification includes a Sequence Listing.

(56) References Cited

U.S. PATENT DOCUMENTS

| | | |
|---|---|---|
| 6,274,354 B1 | 8/2001 | Wilson |
| 6,281,010 B1 | 8/2001 | Gao |
| 6,325,998 B1 | 12/2001 | Podsakoff |
| 6,335,011 B1 | 1/2002 | Podsakoff |
| 6,365,394 B1 | 4/2002 | Gao |
| 6,387,368 B1 | 5/2002 | Wilson |
| 6,399,385 B1 | 6/2002 | Croyle |
| 6,410,300 B1 | 6/2002 | Samulski |
| 6,416,992 B1 | 7/2002 | Mejza |
| 6,428,988 B1 | 8/2002 | Wilson |
| 6,436,392 B1 | 8/2002 | Engelhardt |
| 6,436,394 B1 | 8/2002 | Henderson |
| 6,468,524 B1 | 10/2002 | Chiorini |
| 6,468,771 B1 | 10/2002 | Einerhand |
| 6,475,769 B1 | 11/2002 | Wilson |
| 6,482,634 B1 | 11/2002 | Wilson |
| 6,485,966 B2 | 11/2002 | Gao |
| 6,503,888 B1 | 1/2003 | Kaplitt |
| 6,509,150 B1 | 1/2003 | Salvetti |
| 6,521,426 B1 | 2/2003 | Ciliberto |
| 6,555,525 B2 | 4/2003 | Burke |
| 6,566,118 B1 | 5/2003 | Atkinson |
| 6,582,692 B1 | 6/2003 | Podsakoff |
| 6,593,123 B1 | 7/2003 | Wright |
| 6,610,290 B2 | 8/2003 | Podsakoff |
| 6,642,051 B1 | 11/2003 | Lynch |
| 6,660,514 B1 | 12/2003 | Zolotukhin |
| 6,660,521 B2 | 12/2003 | Brough |
| 6,670,176 B1 | 12/2003 | Samulski |
| 6,676,935 B2 | 1/2004 | Henderson |
| 6,699,706 B1 | 3/2004 | Brooks |
| 6,710,036 B2 | 3/2004 | Kurtzman |
| 6,723,551 B2 | 4/2004 | Kotin |
| 6,726,907 B1 | 4/2004 | Zhang |
| 6,753,419 B1 | 6/2004 | Toniatti |
| 6,759,237 B1 | 7/2004 | Wilson |
| 6,846,665 B1 | 1/2005 | Horer |
| 6,855,314 B1 | 2/2005 | Chiorini |
| 6,887,463 B2 | 5/2005 | Wilson |
| 6,897,045 B2 | 5/2005 | Engelhardt |
| 6,933,310 B1 | 8/2005 | Ikeda |
| 6,943,019 B2 | 9/2005 | Wilson |
| 6,953,690 B1 | 10/2005 | Gao |
| 6,984,517 B1 | 1/2006 | Chiorini |
| 6,995,006 B2 | 2/2006 | Atkinson |
| 7,015,026 B2 | 3/2006 | ORiordan |
| 7,022,519 B2 | 4/2006 | Gao |
| 7,048,920 B2 | 5/2006 | Yu |
| 7,056,502 B2 | 6/2006 | Hildinger |
| 7,070,998 B2 | 7/2006 | Johnson |
| 7,091,030 B2 | 8/2006 | Setiawan |
| 7,094,604 B2 | 8/2006 | Snyder |
| 7,097,980 B2 | 8/2006 | Barany et al. |
| 7,105,345 B2 | 9/2006 | Wilson |
| 7,112,321 B2 | 9/2006 | Wang |
| 7,125,705 B2 | 10/2006 | Colosi |
| 7,125,706 B2 | 10/2006 | Zhang |
| 7,166,434 B2 | 1/2007 | Barany et al. |
| 7,169,612 B2 | 1/2007 | Kostenis |
| 7,186,552 B2 | 3/2007 | Wilson |
| 7,198,951 B2 | 4/2007 | Gao |
| 7,223,585 B2 | 5/2007 | Coffey |
| 7,235,393 B2 | 6/2007 | Gao |
| 7,238,526 B2 | 7/2007 | Wilson |
| 7,241,447 B1 | 7/2007 | Engelhardt |
| 7,247,472 B2 | 7/2007 | Wilson |
| 7,271,002 B2 | 9/2007 | Kotin |
| 7,282,199 B2 | 10/2007 | Gao |
| 7,291,498 B2 | 11/2007 | Roy |
| 7,300,797 B2 | 11/2007 | Van Agthoven |
| 7,306,794 B2 | 12/2007 | Wilson |
| 7,312,039 B2 | 12/2007 | Barany et al. |
| 7,319,002 B2 | 1/2008 | Wilson |
| 7,320,865 B2 | 1/2008 | Barany et al. |
| 7,326,555 B2 | 2/2008 | Konz |
| 7,332,285 B2 | 2/2008 | Barany et al. |
| 7,342,111 B2 | 3/2008 | Lewin et al. |
| 7,344,872 B2 | 3/2008 | Gao |
| 7,364,858 B2 | 4/2008 | Barany et al. |
| 7,419,817 B2 | 9/2008 | Chiorini |
| 7,419,956 B2 | 9/2008 | Ohtaki |
| 7,429,453 B2 | 9/2008 | Barany et al. |
| 7,445,930 B2 | 11/2008 | Zhang |
| 7,459,547 B2 | 12/2008 | Zamore et al. |
| 7,465,583 B2 | 12/2008 | Samulski et al. |
| 7,479,554 B2 | 1/2009 | Chiorini |
| 7,491,508 B2 | 2/2009 | Roy |
| 7,498,316 B2 | 3/2009 | Xu et al. |
| 7,510,872 B2 | 3/2009 | Clark |
| 7,510,875 B2 | 3/2009 | Zhang |
| 7,556,924 B2 | 7/2009 | Barany et al. |
| 7,579,181 B2 | 8/2009 | ORiordan |
| 7,625,570 B1 | 12/2009 | Schaffer |
| 7,632,938 B2 | 12/2009 | Khvorova et al. |
| 7,638,120 B2 | 12/2009 | Liu |
| 7,662,627 B2 | 2/2010 | Johnson |
| 7,678,895 B2 | 3/2010 | Bennett et al. |
| 7,691,995 B2 | 4/2010 | Zamore et al. |
| 7,704,492 B2 | 4/2010 | Podsakoff |
| 7,704,721 B2 | 4/2010 | Wright |
| 7,732,129 B1 | 6/2010 | Zhang |
| 7,732,593 B2 | 6/2010 | Zamore et al. |
| 7,772,203 B2 | 8/2010 | Zamore et al. |
| 7,790,154 B2 | 9/2010 | Samulski et al. |
| 7,790,449 B2 | 9/2010 | Gao |
| 7,794,443 B2 | 9/2010 | Nelson et al. |
| 7,794,692 B2 | 9/2010 | Chakrabartty et al. |
| 7,803,622 B2 | 9/2010 | Engelhardt |
| 7,838,277 B2 | 11/2010 | Gao |
| 7,867,484 B2 | 1/2011 | Samulski et al. |
| 7,887,803 B2 | 2/2011 | Cashman |
| 7,888,096 B2 | 2/2011 | Wu |
| 7,892,809 B2 | 2/2011 | Bowles et al. |
| 7,893,036 B2 | 2/2011 | Zamore et al. |
| 7,901,921 B2 | 3/2011 | Coffey |
| 7,906,111 B2 | 3/2011 | Wilson |
| 7,951,784 B2 | 5/2011 | Rana et al. |
| 7,968,333 B2 | 6/2011 | Yu |
| 7,977,314 B2 | 7/2011 | Cashman |
| 8,008,271 B2 | 8/2011 | Xu et al. |
| 8,039,610 B2 | 10/2011 | Khvorova et al. |
| 8,090,542 B2 | 1/2012 | Khvorova et al. |
| 8,105,574 B2 | 1/2012 | Wilson |
| 8,110,351 B2 | 2/2012 | Bosnes |
| 8,137,948 B2 | 3/2012 | Qu |
| 8,163,543 B2 | 4/2012 | Urabe |
| 8,173,614 B2 | 5/2012 | Burright et al. |
| 8,183,219 B2 | 5/2012 | Burright |
| 8,231,880 B2 | 7/2012 | Roy |
| 8,232,260 B2 | 7/2012 | Zamore et al. |
| 8,236,495 B2 | 8/2012 | Nochumson |
| 8,241,622 B2 | 8/2012 | Englehardt |
| 8,273,344 B2 | 9/2012 | Wang |
| 8,283,151 B2 | 10/2012 | Schmidt |
| 8,304,530 B2 | 11/2012 | Zamore et al. |
| 8,309,533 B2 | 11/2012 | Xu |
| 8,309,705 B2 | 11/2012 | Zamore et al. |
| 8,318,480 B2 | 11/2012 | Gao |
| 8,318,687 B2 | 11/2012 | Tabira |
| 8,329,892 B2 | 12/2012 | Zamore et al. |
| 8,361,457 B2 | 1/2013 | Samulski et al. |
| 8,394,386 B2 | 3/2013 | Wilson |
| 8,409,842 B2 | 4/2013 | Clark |
| 8,470,310 B2 | 6/2013 | Roy |
| 8,476,418 B2 | 7/2013 | Mueller |
| 8,512,981 B2 | 8/2013 | Mermens |
| 8,513,387 B2 | 8/2013 | Chakrabartty et al. |
| 8,524,219 B2 | 9/2013 | Roy |
| 8,524,446 B2 | 9/2013 | Gao |
| 8,530,438 B2 | 9/2013 | Zamore et al. |
| 8,557,785 B2 | 10/2013 | Zamore et al. |
| 8,586,554 B2 | 11/2013 | Bhanot et al. |
| 8,603,459 B2 | 12/2013 | Wilson |
| 8,614,101 B2 | 12/2013 | VanDine |

(56) References Cited

U.S. PATENT DOCUMENTS

| | | |
|---|---|---|
| 8,632,764 B2 | 1/2014 | Xiao et al. |
| 8,637,255 B2 | 1/2014 | Wilson |
| 8,642,314 B2 | 2/2014 | Bakker |
| 8,685,734 B2 | 4/2014 | Coffey |
| 8,697,417 B2 | 4/2014 | Bakker |
| 8,697,665 B2 | 4/2014 | Rom |
| 8,709,422 B2 | 4/2014 | Cashman et al. |
| 8,734,809 B2 | 5/2014 | Gao et al. |
| 8,778,885 B2 | 7/2014 | Cashman et al. |
| 8,784,799 B2 | 7/2014 | Samulski et al. |
| 8,834,863 B2 | 9/2014 | Roy |
| 8,846,030 B2 | 9/2014 | Engelhardt |
| 8,846,389 B2 | 9/2014 | Chiorini |
| 8,906,387 B2 | 12/2014 | Kay |
| 8,906,675 B2 | 12/2014 | Gao |
| 8,927,514 B2 | 1/2015 | Chatterjee |
| 8,962,330 B2 | 2/2015 | Gao |
| 8,962,332 B2 | 2/2015 | Gao |
| 8,999,678 B2 | 4/2015 | Vandenberghe |
| 9,012,224 B2 | 4/2015 | Bowles et al. |
| 9,051,542 B2 | 6/2015 | Wright |
| 9,056,892 B2 | 6/2015 | Pun |
| 9,080,183 B2 | 7/2015 | Klein |
| 9,089,667 B2 | 7/2015 | Bankiewicz |
| 9,101,645 B2 | 8/2015 | Watts |
| 9,102,943 B2 | 8/2015 | Shinmura |
| 9,102,949 B2 | 8/2015 | Gao et al. |
| 9,107,884 B2 | 8/2015 | Chedotal |
| 9,115,373 B2 | 8/2015 | Mermens |
| 9,163,260 B2 | 10/2015 | Wilson |
| 9,169,483 B2 | 10/2015 | Davidson |
| 9,175,287 B2 | 11/2015 | Zamore et al. |
| 9,186,419 B2 | 11/2015 | Xiao et al. |
| 9,217,155 B2 | 12/2015 | Gao |
| 9,217,159 B2 | 12/2015 | Roy |
| 9,228,174 B2 | 1/2016 | Noordman |
| 9,233,174 B2 | 1/2016 | Chen |
| 9,238,800 B2 | 1/2016 | Bossis |
| 9,260,724 B2 | 2/2016 | Bakker |
| 9,284,357 B2 | 3/2016 | Gao et al. |
| 9,402,921 B2 | 8/2016 | Xiao et al. |
| 9,434,776 B2 | 9/2016 | Ando |
| 9,434,930 B2 | 9/2016 | Doudna |
| 9,439,979 B2 | 9/2016 | Chiorini |
| 9,441,206 B2 | 9/2016 | Grieger |
| 9,441,244 B2 | 9/2016 | Schaffer |
| 9,447,433 B2 | 9/2016 | Hirsch |
| 9,457,103 B2 | 10/2016 | Schaffer |
| 9,458,517 B2 | 10/2016 | Schaffer |
| 9,464,119 B2 | 10/2016 | Sonntag |
| 9,475,845 B2 | 10/2016 | Asokan |
| 9,487,779 B2 | 11/2016 | Davidson |
| 9,493,788 B2 | 11/2016 | Gao |
| 9,506,068 B2 | 11/2016 | Inturrisi |
| 9,506,083 B2 | 11/2016 | Arbetman |
| 9,523,093 B2 | 12/2016 | Davidson |
| 9,528,126 B2 | 12/2016 | Qu |
| 9,539,307 B2 | 1/2017 | Kaspar |
| 9,540,659 B2 | 1/2017 | Davidson |
| 9,546,112 B2 | 1/2017 | Voit |
| 9,546,369 B2 | 1/2017 | Gao |
| 9,567,376 B2 | 2/2017 | Cronin |
| 9,567,607 B2 | 2/2017 | Wilson |
| 9,580,691 B2 | 2/2017 | Bakker |
| 9,585,971 B2 | 3/2017 | Deverman |
| 9,587,250 B2 | 3/2017 | Gao |
| 9,587,282 B2 | 3/2017 | Schaffer |
| 9,593,346 B2 | 3/2017 | Roy |
| 9,596,835 B2 | 3/2017 | Gao |
| 9,597,363 B2 | 3/2017 | Roy |
| 9,598,468 B2 | 3/2017 | Weigel-Van Aken |
| 9,598,703 B2 | 3/2017 | Garcia |
| 9,611,302 B2 | 4/2017 | Srivastava |
| 9,617,561 B2 | 4/2017 | Roy |
| 9,623,120 B2 | 4/2017 | Chatterjee |
| 9,624,274 B2 | 4/2017 | Lux |
| 9,636,370 B2 | 5/2017 | McCown |
| 9,650,631 B2 | 5/2017 | Davidson |
| 9,670,507 B2 | 6/2017 | Xiao |
| 9,677,088 B2 | 6/2017 | Nakai |
| 9,677,089 B2 | 6/2017 | Gao |
| 9,682,193 B2 | 6/2017 | Anand |
| 9,695,220 B2 | 7/2017 | Vandenberghe |
| 9,701,984 B2 | 7/2017 | Gao |
| 9,708,627 B2 | 7/2017 | Mermens |
| 9,719,070 B2 | 8/2017 | Vandenberghe |
| 9,719,106 B2 | 8/2017 | Wilson |
| 9,725,485 B2 | 8/2017 | Srivastava |
| 9,732,345 B2 | 8/2017 | Martin |
| 9,733,237 B2 | 8/2017 | Wichterle |
| 9,737,618 B2 | 8/2017 | Wilson |
| 9,745,590 B2 | 8/2017 | Kay |
| 9,775,918 B2 | 10/2017 | Zhong |
| 9,777,291 B2 | 10/2017 | Chatterjee |
| 9,783,824 B2 | 10/2017 | Kay |
| 9,783,825 B2 | 10/2017 | Chatterjee |
| 9,790,472 B2 | 10/2017 | Gao |
| 9,803,218 B2 | 10/2017 | Chatterjee |
| 9,850,487 B2 | 12/2017 | Zamore et al. |
| 10,035,825 B2 | 7/2018 | Gao et al. |
| 10,041,090 B2 | 8/2018 | Gao |
| 10,047,377 B2 | 8/2018 | Piedras-Renteria |
| 10,570,395 B2 | 2/2020 | Hou et al. |
| 10,584,337 B2 | 3/2020 | Sah et al. |
| 10,597,660 B2 | 3/2020 | Sah et al. |
| 10,689,420 B2 | 6/2020 | Gao et al. |
| 10,731,155 B2 | 8/2020 | Zamore et al. |
| 10,731,178 B2 | 8/2020 | Gao et al. |
| 10,920,227 B2 | 2/2021 | Sah et al. |
| 2001/0006955 A1 | 7/2001 | Wilson |
| 2001/0049144 A1 | 12/2001 | Rivera |
| 2002/0019050 A1 | 2/2002 | Gao |
| 2002/0037867 A1 | 3/2002 | Wilson |
| 2002/0081721 A1 | 6/2002 | Allen |
| 2002/0090717 A1 | 7/2002 | Gao |
| 2002/0102714 A1 | 8/2002 | Wilson |
| 2002/0131961 A1 | 9/2002 | Wilson |
| 2003/0013189 A1 | 1/2003 | Wilson |
| 2003/0032613 A1 | 2/2003 | Gao |
| 2003/0092161 A1 | 5/2003 | Gao |
| 2003/0100115 A1 | 5/2003 | Raj |
| 2003/0119191 A1 | 6/2003 | Gao |
| 2003/0138772 A1 | 7/2003 | Gao |
| 2003/0180756 A1 | 9/2003 | Shi |
| 2004/0043490 A1 | 3/2004 | Shimada |
| 2004/0057931 A1 | 3/2004 | Wilson |
| 2004/0136963 A1 | 7/2004 | Wilson |
| 2004/0171807 A1 | 9/2004 | Gao |
| 2005/0059005 A1 | 3/2005 | Tuschl |
| 2005/0064489 A1 | 3/2005 | Zhang |
| 2005/0130184 A1 | 6/2005 | Xu et al. |
| 2005/0255086 A1 | 11/2005 | Davidson et al. |
| 2005/0255487 A1 | 11/2005 | Khvorova et al. |
| 2005/0261218 A1 | 11/2005 | Esau |
| 2006/0003451 A1 | 1/2006 | Gao |
| 2006/0009402 A1 | 1/2006 | Zamore et al. |
| 2006/0041022 A1 | 2/2006 | Pasinetti |
| 2006/0204479 A1 | 9/2006 | Wilson |
| 2006/0229268 A1 | 10/2006 | Benjamin |
| 2006/0246517 A1 | 11/2006 | Cashman |
| 2007/0003977 A1 | 1/2007 | Cashman et al. |
| 2007/0004042 A1 | 1/2007 | Gao |
| 2008/0008684 A1 | 1/2008 | Wilson |
| 2008/0020992 A1 | 1/2008 | Rao |
| 2008/0050343 A1 | 2/2008 | Wilson |
| 2008/0050345 A1 | 2/2008 | Wilson |
| 2008/0075737 A1 | 3/2008 | Gao |
| 2008/0113375 A1 | 5/2008 | Khvorova |
| 2009/0098151 A1 | 4/2009 | Cashman |
| 2009/0143764 A1 | 6/2009 | Nelson |
| 2009/0215871 A1 | 8/2009 | Wilson |
| 2009/0275107 A1 | 11/2009 | Lock |
| 2009/0317417 A1 | 12/2009 | Vandenberghe |
| 2010/0004320 A1 | 1/2010 | Elmen |

(56) References Cited

U.S. PATENT DOCUMENTS

| | | |
|---|---|---|
| 2010/0036107 A1 | 2/2010 | Clawson |
| 2010/0130594 A1 | 5/2010 | Barkats |
| 2010/0132060 A1 | 5/2010 | Burright |
| 2010/0240739 A1 | 9/2010 | Barkats |
| 2010/0247490 A1 | 9/2010 | Roy |
| 2010/0278791 A1 | 11/2010 | Wilson |
| 2010/0286378 A1 | 11/2010 | Li |
| 2011/0020816 A1 | 1/2011 | Chen |
| 2011/0039914 A1 | 2/2011 | Pavco |
| 2011/0104120 A1 | 5/2011 | Xiao et al. |
| 2011/0105517 A1 | 5/2011 | Ikeda et al. |
| 2011/0111496 A1 | 5/2011 | Li |
| 2011/0124018 A1 | 5/2011 | Cashman et al. |
| 2011/0135673 A1 | 6/2011 | Cashman |
| 2011/0136227 A1 | 6/2011 | Bakker |
| 2011/0171262 A1 | 7/2011 | Bakker |
| 2011/0223135 A1 | 9/2011 | Roy |
| 2011/0229971 A1 | 9/2011 | Knop |
| 2011/0251258 A1 | 10/2011 | Samarsky et al. |
| 2011/0263680 A1 | 10/2011 | Khvorova et al. |
| 2012/0015850 A1 | 1/2012 | Khvorova et al. |
| 2012/0046349 A1 | 2/2012 | Bell |
| 2012/0058102 A1 | 3/2012 | Wilson |
| 2012/0077212 A1 | 3/2012 | Cashman |
| 2012/0093853 A1 | 4/2012 | Wilson |
| 2012/0093916 A1 | 4/2012 | Kaemmerer |
| 2012/0137379 A1 | 5/2012 | Gao |
| 2012/0258046 A1 | 10/2012 | Mutzke |
| 2012/0309050 A1 | 12/2012 | Kumon |
| 2013/0019580 A1 | 1/2013 | Anderson et al. |
| 2013/0023033 A1 | 1/2013 | Wilson |
| 2013/0045186 A1 | 2/2013 | Gao |
| 2013/0101558 A1 | 4/2013 | Gao |
| 2013/0171726 A1 | 7/2013 | Roelvink |
| 2013/0195801 A1 | 8/2013 | Gao |
| 2013/0225642 A1 | 8/2013 | Inoue et al. |
| 2013/0267582 A1 | 10/2013 | Kollipara |
| 2013/0296532 A1 | 11/2013 | Hermens |
| 2013/0323226 A1 | 12/2013 | Wilson |
| 2013/0323302 A1 | 12/2013 | Constable |
| 2014/0031418 A1 | 1/2014 | Wilson |
| 2014/0044680 A1 | 2/2014 | Roy |
| 2014/0065105 A1 | 3/2014 | Wilson |
| 2014/0087361 A1 | 3/2014 | Dobbelaer |
| 2014/0099666 A1 | 4/2014 | Rossomando |
| 2014/0107186 A1 | 4/2014 | Garcia |
| 2014/0234274 A1 | 8/2014 | Xiao et al. |
| 2014/0243783 A1 | 8/2014 | Raghavan et al. |
| 2014/0335054 A1 | 11/2014 | Gao et al. |
| 2014/0335538 A1 | 11/2014 | Cashman |
| 2014/0336245 A1 | 11/2014 | Mingozzi |
| 2014/0341852 A1 | 11/2014 | Srivastava |
| 2014/0342434 A1 | 11/2014 | Hermens |
| 2014/0348822 A1 | 11/2014 | Cashman et al. |
| 2014/0349390 A1 | 11/2014 | Pachuk |
| 2015/0005369 A1 | 1/2015 | Muzyczka |
| 2015/0023924 A1 | 1/2015 | High |
| 2015/0065562 A1 | 3/2015 | Yazicioglu |
| 2015/0111955 A1 | 4/2015 | High et al. |
| 2015/0118201 A1 | 4/2015 | Xiao et al. |
| 2015/0118287 A1 | 4/2015 | Hammond |
| 2015/0139952 A1 | 5/2015 | Webster |
| 2015/0159173 A1 | 6/2015 | Vandenberghe |
| 2015/0164906 A1 | 6/2015 | Zack |
| 2015/0197751 A1 | 7/2015 | Roelvink |
| 2015/0232840 A1 | 8/2015 | Aronin |
| 2015/0238610 A1 | 8/2015 | Sista |
| 2015/0267189 A1 | 9/2015 | Angel et al. |
| 2015/0275193 A1 | 10/2015 | Angel et al. |
| 2015/0307898 A2 | 10/2015 | Hermens |
| 2015/0315610 A1 | 11/2015 | Nishie |
| 2015/0322813 A1 | 11/2015 | Tralshawala et al. |
| 2015/0335708 A1 | 11/2015 | Froelich |
| 2015/0374803 A1 | 12/2015 | Wolfe |
| 2016/0032319 A1 | 2/2016 | Wright |
| 2016/0102309 A1 | 4/2016 | Zamore et al. |
| 2016/0108373 A1 | 4/2016 | Bennett |
| 2016/0153992 A1 | 6/2016 | Buening |
| 2016/0166709 A1 | 6/2016 | Davidson |
| 2016/0251653 A1 | 9/2016 | Davidson |
| 2016/0264994 A1 | 9/2016 | Lawrence |
| 2016/0271192 A1 | 9/2016 | Roy |
| 2016/0272976 A1 | 9/2016 | Kaspar |
| 2016/0273058 A1 | 9/2016 | Akashika |
| 2016/0281084 A1 | 9/2016 | Davidson |
| 2016/0289275 A1 | 10/2016 | Chiorini |
| 2016/0289676 A1 | 10/2016 | Kaspar |
| 2016/0296694 A1 | 10/2016 | Bankiewicz |
| 2016/0319278 A1 | 11/2016 | Khvorova |
| 2016/0331897 A1 | 11/2016 | Anand |
| 2016/0333372 A1 | 11/2016 | Srivastava |
| 2016/0333373 A1 | 11/2016 | Farley |
| 2016/0333375 A1 | 11/2016 | Chen |
| 2016/0340393 A1 | 11/2016 | Schaffer |
| 2016/0340692 A1 | 11/2016 | Wang |
| 2016/0346359 A1 | 12/2016 | Buchlis |
| 2016/0348106 A1 | 12/2016 | Harper |
| 2016/0354487 A1 | 12/2016 | Zhang |
| 2016/0355577 A1 | 12/2016 | Kelley |
| 2016/0355796 A1 | 12/2016 | Davidson |
| 2016/0355808 A1 | 12/2016 | Khvorova |
| 2016/0361439 A1 | 12/2016 | Agbandje-Mckenna |
| 2016/0369298 A1 | 12/2016 | Marsic |
| 2016/0369299 A1 | 12/2016 | Boye |
| 2016/0375151 A1 | 12/2016 | Schaffer |
| 2016/0376323 A1 | 12/2016 | Schaffer |
| 2016/0376608 A1 | 12/2016 | Chou |
| 2017/0000904 A1 | 1/2017 | Wilson |
| 2017/0007669 A1 | 1/2017 | Sarkar |
| 2017/0007720 A1 | 1/2017 | Boye |
| 2017/0009304 A1 | 1/2017 | Zhuo |
| 2017/0022498 A1 | 1/2017 | Cullen |
| 2017/0028082 A1 | 2/2017 | Wilson |
| 2017/0037410 A1 | 2/2017 | Swayze |
| 2017/0044504 A1 | 2/2017 | Schaffer |
| 2017/0044530 A1 | 2/2017 | Kay |
| 2017/0067028 A1 | 3/2017 | Ballon |
| 2017/0071972 A1 | 3/2017 | Buj Bello |
| 2017/0073703 A1 | 3/2017 | Chatterjee |
| 2017/0088819 A1 | 3/2017 | Vandendriessche |
| 2017/0088858 A1 | 3/2017 | Gao |
| 2017/0096646 A1 | 4/2017 | Roy |
| 2017/0105927 A1 | 4/2017 | Thorne |
| 2017/0107536 A1 | 4/2017 | Zhang |
| 2017/0112946 A1 | 4/2017 | Ikeda |
| 2017/0114340 A1 | 4/2017 | Mueller |
| 2017/0121734 A1 | 5/2017 | Cairns |
| 2017/0128594 A1 | 5/2017 | Wright |
| 2017/0130208 A1 | 5/2017 | Potter |
| 2017/0130245 A1 | 5/2017 | Kotin |
| 2017/0145440 A1 | 5/2017 | Hermens |
| 2017/0151348 A1 | 6/2017 | Kaspar |
| 2017/0151416 A1 | 6/2017 | Kutikov |
| 2017/0152517 A1 | 6/2017 | Barkats |
| 2017/0152525 A1 | 6/2017 | Hermens |
| 2017/0157267 A1 | 6/2017 | Kay |
| 2017/0159026 A1 | 6/2017 | Kay |
| 2017/0159027 A1 | 6/2017 | Wilson |
| 2017/0159072 A9 | 6/2017 | Arbeit |
| 2017/0165377 A1 | 6/2017 | Gao |
| 2017/0166871 A1 | 6/2017 | Nishie |
| 2017/0166925 A1 | 6/2017 | Gao |
| 2017/0166926 A1 | 6/2017 | Deverman |
| 2017/0166927 A1 | 6/2017 | Gao |
| 2017/0183636 A1 | 6/2017 | Roy |
| 2017/0191039 A1 | 7/2017 | Gao |
| 2017/0191079 A1 | 7/2017 | Vandenberghe |
| 2017/0198304 A1 | 7/2017 | Wilson |
| 2017/0204144 A1 | 7/2017 | Deverman |
| 2017/0211092 A1 | 7/2017 | Chatterjee |
| 2017/0211093 A1 | 7/2017 | Chatterjee |
| 2017/0211094 A1 | 7/2017 | Chatterjee |
| 2017/0211095 A1 | 7/2017 | Chatterjee |
| 2017/0216458 A1 | 8/2017 | Kaspar |

(56) References Cited

U.S. PATENT DOCUMENTS

| | | |
|---|---|---|
| 2017/0218395 A1 | 8/2017 | Byrne |
| 2017/0226160 A1 | 8/2017 | Sonntag |
| 2017/0232072 A1 | 8/2017 | Ikeda |
| 2017/0232117 A1 | 8/2017 | Arbetman |
| 2017/0240885 A1 | 8/2017 | Deverman |
| 2017/0240921 A1 | 8/2017 | Gao |
| 2017/0246322 A1 | 8/2017 | Mendell |
| 2017/0247664 A1 | 8/2017 | Wright |
| 2017/0258996 A1 | 9/2017 | Anand |
| 2017/0260545 A1 | 9/2017 | Qu |
| 2017/0274024 A1 | 9/2017 | McCown |
| 2017/0275337 A1 | 9/2017 | Srivastava |
| 2017/0298323 A1 | 10/2017 | Vandenberghe |
| 2017/0304464 A1 | 10/2017 | Sebastian |
| 2017/0306354 A1 | 10/2017 | Gao |
| 2017/0306355 A1 | 10/2017 | Davidson |
| 2017/0321290 A1 | 11/2017 | Lubelski |
| 2018/0230490 A1 | 8/2018 | O'Riordan |
| 2018/0237772 A1 | 8/2018 | Yu |
| 2018/0282732 A1 | 10/2018 | Sah et al. |
| 2018/0298380 A1 | 10/2018 | Gao |
| 2019/0038777 A1 | 2/2019 | Donsante |
| 2019/0194688 A1 | 6/2019 | Gao et al. |
| 2019/0194689 A1 | 6/2019 | Gao et al. |
| 2019/0276848 A1 | 9/2019 | Gao et al. |
| 2019/0276849 A1 | 9/2019 | Gao et al. |
| 2020/0149045 A1 | 5/2020 | Sah et al. |
| 2020/0157547 A1 | 5/2020 | Sah et al. |
| 2020/0199597 A1 | 6/2020 | Hou et al. |
| 2020/0237799 A1 | 7/2020 | Sah et al. |
| 2020/0239912 A1 | 7/2020 | Sah et al. |
| 2020/0270635 A1 | 8/2020 | Hou et al. |
| 2021/0139915 A1 | 5/2021 | Sah et al. |
| 2021/0163985 A1 | 6/2021 | Sah et al. |
| 2021/0230632 A1 | 7/2021 | Sah et al. |
| 2021/0254103 A1 | 8/2021 | Sah et al. |
| 2021/0361318 A1 | 11/2021 | Patzke et al. |

FOREIGN PATENT DOCUMENTS

| | | |
|---|---|---|
| CA | 3077426 A1 | 4/2019 |
| CN | 102016036 A | 4/2011 |
| EP | 1015619 A1 | 7/2000 |
| EP | 1046711 | 10/2000 |
| EP | 1078096 A1 | 2/2001 |
| EP | 1164195 | 12/2001 |
| EP | 1183380 A1 | 3/2002 |
| EP | 1218035 | 7/2002 |
| EP | 1240345 | 9/2002 |
| EP | 1279740 | 1/2003 |
| EP | 1412371 A1 | 4/2004 |
| EP | 1453547 | 9/2004 |
| EP | 1692262 A2 | 8/2006 |
| EP | 1696036 | 8/2006 |
| EP | 1847614 | 10/2007 |
| EP | 1849872 | 10/2007 |
| EP | 1857552 | 11/2007 |
| EP | 1900815 | 3/2008 |
| EP | 1944043 | 7/2008 |
| EP | 2007795 | 12/2008 |
| EP | 2164967 | 3/2010 |
| EP | 2172549 | 4/2010 |
| EP | 2198016 | 6/2010 |
| EP | 2213738 A2 | 8/2010 |
| EP | 2220241 | 8/2010 |
| EP | 2220242 | 8/2010 |
| EP | 2292779 | 3/2011 |
| EP | 2292780 | 3/2011 |
| EP | 2301582 | 3/2011 |
| EP | 2325298 | 5/2011 |
| EP | 2359866 | 8/2011 |
| EP | 2360251 | 8/2011 |
| EP | 2383346 | 11/2011 |
| EP | 2453735 | 5/2012 |
| EP | 2497500 | 9/2012 |
| EP | 2524037 | 11/2012 |
| EP | 2531604 | 12/2012 |
| EP | 2561073 A1 | 2/2013 |
| EP | 2572661 A1 | 3/2013 |
| EP | 2660325 | 11/2013 |
| EP | 2699270 | 2/2014 |
| EP | 2737071 | 6/2014 |
| EP | 2814958 | 12/2014 |
| EP | 2826860 A1 | 1/2015 |
| EP | 2871239 | 5/2015 |
| EP | 2879719 | 6/2015 |
| EP | 2906580 | 8/2015 |
| EP | 2933336 | 10/2015 |
| EP | 3058959 | 8/2016 |
| EP | 3067417 | 9/2016 |
| EP | 2176283 | 11/2016 |
| EP | 3108000 | 12/2016 |
| EP | 3117005 | 1/2017 |
| EP | 3134431 | 3/2017 |
| EP | 3168298 | 5/2017 |
| EP | 3174981 | 6/2017 |
| EP | 3209311 | 8/2017 |
| EP | 3221456 | 9/2017 |
| EP | 3235827 | 10/2017 |
| JP | 2013-143917 A | 7/2013 |
| WO | 1989012677 A1 | 12/1989 |
| WO | 1993009239 | 5/1993 |
| WO | 1995028493 A1 | 10/1995 |
| WO | 1995034670 | 12/1995 |
| WO | 1996017947 | 6/1996 |
| WO | 1996023810 | 8/1996 |
| WO | 1996030540 | 10/1996 |
| WO | 1997045559 A1 | 12/1997 |
| WO | 1998010088 | 3/1998 |
| WO | 1999027110 | 6/1999 |
| WO | 1999043360 | 9/1999 |
| WO | 1999058700 | 11/1999 |
| WO | 1999061595 | 12/1999 |
| WO | 1999060146 | 5/2000 |
| WO | 2000024916 | 5/2000 |
| WO | 2000066780 | 11/2000 |
| WO | 2000075353 | 12/2000 |
| WO | 2001014539 | 3/2001 |
| WO | 2001023001 | 4/2001 |
| WO | 2001025465 | 4/2001 |
| WO | 2001032711 | 5/2001 |
| WO | 2001036623 | 5/2001 |
| WO | 2001042444 | 6/2001 |
| WO | 2001068888 | 9/2001 |
| WO | 2001075164 A3 | 10/2001 |
| WO | 2001092551 A2 | 12/2001 |
| WO | 2001096587 | 12/2001 |
| WO | 2002012525 | 2/2002 |
| WO | 2002014487 | 2/2002 |
| WO | 2002020748 | 3/2002 |
| WO | 2002070719 | 9/2002 |
| WO | 2002071843 | 9/2002 |
| WO | 2003/006477 A1 | 1/2003 |
| WO | 2003010320 | 2/2003 |
| WO | 2003024502 | 3/2003 |
| WO | 2003042397 | 5/2003 |
| WO | 03080807 A2 | 10/2003 |
| WO | 2003087382 | 10/2003 |
| WO | 2003087383 | 10/2003 |
| WO | 2004027030 A2 | 4/2004 |
| WO | 2004044003 | 5/2004 |
| WO | 2004045543 A2 | 6/2004 |
| WO | 2004083441 | 9/2004 |
| WO | 2004108922 | 12/2004 |
| WO | 2004111191 A2 | 12/2004 |
| WO | 2004111248 | 12/2004 |
| WO | 2005001043 A2 | 1/2005 |
| WO | 2005005610 | 1/2005 |
| WO | 2005007875 A2 | 1/2005 |
| WO | 2005012537 | 2/2005 |
| WO | 2005019828 A1 | 3/2005 |
| WO | 2005027980 A1 | 3/2005 |
| WO | 2005062937 A2 | 7/2005 |
| WO | 2005096781 A2 | 10/2005 |

(56) References Cited

FOREIGN PATENT DOCUMENTS

| | | |
|---|---|---|
| WO | 2005111220 | 11/2005 |
| WO | 2006006948 A2 | 1/2006 |
| WO | 2006066066 A2 | 6/2006 |
| WO | 2006066203 A2 | 6/2006 |
| WO | 2006075434 A1 | 7/2006 |
| WO | 2006102072 | 9/2006 |
| WO | 2007044362 A2 | 4/2007 |
| WO | 2007089632 A2 | 8/2007 |
| WO | 2007/109097 A2 | 9/2007 |
| WO | 2007098607 A1 | 9/2007 |
| WO | 2007130519 | 11/2007 |
| WO | 2008086079 A2 | 7/2008 |
| WO | 2007148971 | 7/2009 |
| WO | 2009102427 A2 | 8/2009 |
| WO | 2009134681 | 11/2009 |
| WO | 2009137006 A2 | 11/2009 |
| WO | 2010011346 A1 | 1/2010 |
| WO | 2010138263 A2 | 12/2010 |
| WO | 2011038187 | 3/2011 |
| WO | 2011054976 | 5/2011 |
| WO | 2011122950 | 10/2011 |
| WO | 2011133890 A1 | 10/2011 |
| WO | 2010109053 | 11/2011 |
| WO | 2012057363 | 5/2012 |
| WO | 2012114090 | 8/2012 |
| WO | 2012123430 A1 | 9/2012 |
| WO | 2012144446 | 10/2012 |
| WO | 2012149646 A1 | 11/2012 |
| WO | 2013078199 | 5/2013 |
| WO | 2013123503 A1 | 8/2013 |
| WO | 2013164793 | 11/2013 |
| WO | 2013170078 | 11/2013 |
| WO | 2014016817 A2 | 1/2014 |
| WO | 2014071219 A1 | 5/2014 |
| WO | 2014107763 A1 | 7/2014 |
| WO | 2014144486 A2 | 9/2014 |
| WO | 2014160092 | 10/2014 |
| WO | 2014168953 | 10/2014 |
| WO | 2014170470 | 10/2014 |
| WO | 2014170480 | 10/2014 |
| WO | 2014172669 | 10/2014 |
| WO | 2014186579 | 11/2014 |
| WO | 2014194132 | 12/2014 |
| WO | 2014201252 | 12/2014 |
| WO | 2015012924 | 1/2015 |
| WO | 2015013148 | 1/2015 |
| WO | 2015013313 A2 | 1/2015 |
| WO | 2015018503 | 2/2015 |
| WO | 2015023503 A2 | 2/2015 |
| WO | 2014186746 | 3/2015 |
| WO | 2015031392 | 3/2015 |
| WO | 2015031686 | 4/2015 |
| WO | 2015044292 | 4/2015 |
| WO | 2015060722 | 4/2015 |
| WO | 2015069647 A1 | 5/2015 |
| WO | 2015084254 A1 | 6/2015 |
| WO | 2015108610 | 7/2015 |
| WO | 2015114365 | 8/2015 |
| WO | 2015121501 | 8/2015 |
| WO | 2015124546 | 8/2015 |
| WO | 2015137802 | 9/2015 |
| WO | 2015143078 A1 | 9/2015 |
| WO | 2015143078 A1 | 9/2015 |
| WO | 2015153800 A2 | 10/2015 |
| WO | 2015127128 | 11/2015 |
| WO | 2015196179 | 12/2015 |
| WO | 2016/016449 A1 | 2/2016 |
| WO | 2016019364 | 2/2016 |
| WO | 2016040347 | 3/2016 |
| WO | 2016054554 | 4/2016 |
| WO | 2016054557 | 4/2016 |
| WO | 2016065001 | 4/2016 |
| WO | 2016077607 A1 | 5/2016 |
| WO | 2016077687 A1 | 5/2016 |
| WO | 2016077687 A1 | 5/2016 |
| WO | 2016077689 A1 | 5/2016 |
| WO | 2016077689 A1 | 5/2016 |
| WO | 2016081811 | 5/2016 |
| WO | 2016081927 | 5/2016 |
| WO | 2016115382 | 7/2016 |
| WO | 2016115503 A1 | 7/2016 |
| WO | 2016122791 | 8/2016 |
| WO | 2016126857 | 8/2016 |
| WO | 2016130591 | 8/2016 |
| WO | 2016137949 | 9/2016 |
| WO | 2016154055 | 9/2016 |
| WO | 2016154344 | 9/2016 |
| WO | 2016164609 | 10/2016 |
| WO | 2016168728 | 10/2016 |
| WO | 2016172008 | 10/2016 |
| WO | 2016172155 | 10/2016 |
| WO | 2016179496 | 11/2016 |
| WO | 2016183297 | 11/2016 |
| WO | 2016191418 | 12/2016 |
| WO | 2016196328 | 12/2016 |
| WO | 2016196507 | 12/2016 |
| WO | 2017004514 | 1/2017 |
| WO | 2017005806 | 1/2017 |
| WO | 2017015102 | 1/2017 |
| WO | 2017019876 | 2/2017 |
| WO | 2017019994 | 2/2017 |
| WO | 2017024111 | 2/2017 |
| WO | 2017058892 | 4/2017 |
| WO | 2017070476 | 4/2017 |
| WO | 2017070516 | 4/2017 |
| WO | 2017070525 | 4/2017 |
| WO | 2017070678 | 4/2017 |
| WO | 2017075335 | 5/2017 |
| WO | 2017079768 | 5/2017 |
| WO | 2017083423 | 5/2017 |
| WO | 2017093330 | 6/2017 |
| WO | 2017096039 | 6/2017 |
| WO | 2017100671 | 6/2017 |
| WO | 2017100674 | 6/2017 |
| WO | 2017100676 | 6/2017 |
| WO | 2017100704 | 6/2017 |
| WO | 2017122789 | 7/2017 |
| WO | 2017136202 | 8/2017 |
| WO | 2017136536 | 8/2017 |
| WO | 2017155973 | 9/2017 |
| WO | 2017161273 | 9/2017 |
| WO | 2017172733 | 10/2017 |
| WO | 2017180854 | 10/2017 |
| WO | 2017/189963 A1 | 11/2017 |
| WO | 2017/201258 A1 | 11/2017 |
| WO | 2017189963 A1 | 11/2017 |
| WO | 2017192699 | 11/2017 |
| WO | 2017192750 | 11/2017 |
| WO | 2017201248 A1 | 11/2017 |
| WO | 2018/204786 A1 | 11/2018 |
| WO | 2018/204797 A1 | 11/2018 |
| WO | 2018220211 A1 | 12/2018 |
| WO | 2019/028306 A2 | 2/2019 |
| WO | 2019/079242 A1 | 4/2019 |
| WO | 2019079240 A1 | 4/2019 |
| WO | 2019222329 A1 | 11/2019 |
| WO | 2020/010035 A1 | 1/2020 |
| WO | 2020/010042 A1 | 1/2020 |
| WO | 2020077165 A1 | 4/2020 |
| WO | 2020223296 A1 | 11/2020 |

OTHER PUBLICATIONS

Gombash SE, et al. Systemic gene delivery transduces the enteric nervous system of guinea pigs and cynomolgus macaques. Gene Ther. Aug. 3, 2017. doi: 10.1038/gt.2017.72.

Hinderer C, et al. Evaluation of intrathecal routes of administration for adeno-associated virus vectors in large animals. Hum Gene Ther. Aug. 15, 2017. doi: 10.1089/hum.2017.026.

Iwamoto N, et al. Control of phosphorothioate stereochemistry substantially increases the efficacy of antisense oligonucleotides. Nat Biotechnol Aug. 21, 2017.

(56) References Cited

OTHER PUBLICATIONS

Jin X, et al. Direct LC/MS Analysis for Complete Characterization of Recombinant Adeno-Associated Virus Capsid Proteins. Hum Gene Ther Methods. Jun. 18, 2017. Epub ahead of print.
Kanaan NM, et al. Rationally Engineered AAV Capsids Improve Transduction and Volumetric Spread in the CNS. Molecular Therapy-Nucleic Acids 8: 184-197 Sep. 15, 2017.
Chan KY, et al. Engineered AAVs for efficient noninvasive gene delivery to the central and peripheral nervous systems. Nat Neurosci. Jun. 26, 2017. Epub ahead of print.
Herrera-Carrillo E, et al. Improving miRNA delivery by optimizing miRNA expression cassettes in viral vectors. Hum Gene Ther Methods. Jul. 16, 2017.
Timothy M. Miller et al: "Virus-delivered small RNA silencing sustains strength in amyotrophic lateral sclerosis", Annals of Neurology., vol. 57, No. 5, May 1, 2005 (May 1, 2005), pp. 773-776.
Chris Towne et al: "Systemic AAV6 Delivery Mediating RNA Interference Against SOD1: Neuromuscular Transduction Does Not Alter Disease Progression in fALS Mice", Molecular Therapy: The Journal of the American Society of Gene Therapy, vol. 16, No. 6, Jun. 1, 2008 (Jun. 1, 2008), pp. 1018-1025.
Takayuki Kubodera et al: "In Vivo Application of an RNAi Strategy for the Selective Suppression of a Mutant Allele", Human Gene Therapy, vol. 22, No. 1, Jan. 1, 2011 (Jan. 1, 2011), pp. 27-34.
Yuki Saito et al: "Transgenic Small Interfering RNA Halts Amyotrophic Lateral Sclerosis in a Mouse Model", Journal of Biological Chemistry, vol. 280, No. 52, Oct. 12, 2005 (Oct. 12, 2005), pp. 42826-42830.
Rui Wu et al: "Nerve Injection of Viral Vectors Efficiently Transfers Transgenes into Motor Neurons and Delivers RNAi Therapy Against ALS", Antioxidants and Redox Signaling, vol. 11, No. 7, Jul. 1, 2009 (Jul. 1, 2009), pp. 1523-1534.
H. Zhou: "An RNA polymerase II construct synthesizes short-hairpin RNA with a quantitative indicatorand mediates highly efficien RNAi", Nucleic Acids Research, vol. 33, No. 6, Mar. 23, 2005 (Mar. 23, 2005), pp. e62-e62.
Monica Nizzardo et al: "Research advances in gene therapy approaches for the treatment of amyotrophic lateral sclerosis", CMLS Cellular and Molecular Life Sciences, Birkhauser-Verlag, BA, vol. 69, No. 10, Nov. 18, 2011 (Nov. 18, 2011), pp. 1641-1650.
Extended European Search Report issued in corresponding EP Application No. 15859973.8 dated Apr. 30, 2018.
Ly CV and Miller TM. Emerging antisense olgionucleotide and viral therapies for amyotrophic lateral sclerosis. Curr Opin. Neurol. Jul. 19, 2018 Epub ahead of print.
Larson TC, et al. Amyotrophic Lateral Sclerosis Mortality in the United States, 2011-2014. Neuroepidemiology. Jul. 10, 2018;51(1-2):96-103.
Hudry E, et al. Efficient gene transfer to the central nervous system by single stranded Anc80L65. Mol Ther Meth Clin Dev. Jul. 15, 2018, pp. 197-209.
McCampbell A, et al. Antisense oligonucleotides extend survival and reverse decrement in muscle response in ALS models. J Clin Invest. Jul. 16, 2018 Epub ahead of print.
Conlon EG, et al. Unexpected similarities between C9ORF/2 and sporadic forms of ALS/FTD suggest a common disease mechanism. Elife Jul. 13, 2018;7.
Iannitti T, et al. Translating SOD1 Gene Silencing toward the Clinic: A Highly Efficacious, Off-Target-free, and Biomarker-Supported Strategy for fALS. Mol Ther Nucleic Acids. Sep. 7, 2018.
Chandran JS, et al. Gene therapy in the nervous system: failures and successes. Adv Exp Med Biol. 2017;1007:241-257.
Tse LV, et al. Mapping and engineering function domains of the assembly-activating protein of adeno-associated viruses. J. Virol. Jun. 29, 2018;92(14).
Albright BH, et al. Mapping the Structural Determinants Required for AAVrh. 10 Transport across the Blood-Brain Barrier. Mol Ther. Feb. 7, 2018;26(2):510-523.
Gaj T, et al. In vivo genome editing improves motor function and extends survival in a mouse model of ALS. Sci Adv. Dec. 20, 2017;3(12):eaar3952.
Auyeung VC, et al. Beyond secondary structure: primary sequence determinants license pri-miRNA hairpins for processing. Cell Feb. 2013;152(4):844-858.
Fellman C, et al. An optimized microRNA backbone for effective single-copy RNAi. Cell Rep. Dec. 2013;5(6):1704-1713.
Medinas DB, et al. Endoplasmic reticulum stress leads to accumulation of wild-type SOD1 aggregates associated with sporadic amyotrophic lateral sclerosis. Proc Natl Acad Sci USA Aug. 17, 2018;115(32):8209-8214.
Balendra R and Issacs AM. C9orf72-mediated ALS and FTD: multiple pathways to disease. Nat Rev Neurol. Aug. 17, 2018 Epub ahead of print.
Gowanlock D, et al. A designer AAV variant permits efficient retrograde access to projection neurons. Neuron. Oct. 19, 2016;92(2):372-382.
International Search Report issued in corresponding PCT Application No. PCT/US2015/060562 dated Apr. 19, 2016.
Ha et al., Regulation of microRNA biogenesis. Nat Rev Mol Cell Bio, Aug. 2014, vol. 15, No. 8, pp. 509-524.
Hardcastle N. AAV gene delivery to the spinal cord: serotypes, methods, candidate diseases and clinical trials. Expert Opinion on Biological Therapy. Mar. 2018;18(3):293-307.
Boudreau RL, et al. Artificial microRNAs as siRNA shuttles: improved safety as compared to shRNAs in vitro and in vivo. The American Society of Gene Therapy. 2009; 17(1):169-175.
Dirren JA, et al. SOD1 silencing in motor neurons or glia rescues neuromuscular function in ALS mice. Annals of Clinical and Translational Neurology 2015;2(2):167-184.
Federici T, et al. Surgical technique for spinal cord delivery of therapies: demonstration of procedure in gottingen minipigs. J Vis Exp Dec. 7, 2012;(70):e4371.
Foust KD et al. Therapeutic AAV9 mediated suppression of mutant SOD1 slows disease progression and extends survival in models of inherited ALS. Mol Ther Dec. 21, 2013(12):2148-59.
Ralph GS et al. Silencing mutant SOD1 using RNAi protects against neurodegeneration and extends survival in an ALS model. Nature Medicine. Apr. 11, 2005(4):429-33.
Raoul C et al. Lentiviral-mediated silencing of SOD1 through RNA interference retards disease onset and progression in a mouse model of ALS. Nature Medicine, vol. 11, No. 4, Apr. 2005, pp. 423-428.
Wang H, et al. Widespread spinal cord transduction by intrathecal injection of rAAV delivers efficacious RNAi therapy for amyotrophic lateral sclerosis. Hum Mol Genet Feb. 1, 2014; 23(3):668-81.
Borel, F et al. Safe and effective superoxide dismutase 1 silencing using artificial microRNA in macaques. Sci Transl Med. Oct. 31, 2018;10(465).
ParéB, et al. Misfolded SOD1 pathology in sporadic Amyotrophic Lateral Sclerosis. Sci Rep. Sep. 21, 2018;8(1):14223.
Mondo E, et al. Selective Neuronal Uptake and Distribution of AAVrh8, AAV9, and AAVrh10 in Sheep After Intra-Striatal Administration. Selective Neuronal Uptake and Distribution of AAVrh8, AAV9, and AAVrh10 in Sheep After Intra-Striatal Administration. J Huntingtons Dis. 2018;7(4):309-319.
Wang D, et al. Adeno-associated virus vector as a platform for gene therapy delivery. Nat Rev Drug Discov. Feb. 1, 2019. doi: 10.1038/S41573-019-0012-9. [Epub ahead of print] Review.
Martier R, et al. Artificial microRNAs targeting C9ORF72 have the potential to reduce accumulation of the intra-nuclear transcripts in ALS and FTD patients. Molecular Therapy Nucleic Acids. Jan. 22, 2019. DOI: https://doi.org/10.1016 [Epub ahead of print] Review.
Büning and Srivastava. Capsid Modifications for Targeting and Improving the Efficacy of AAV Vectors. vol. 12, P248-265, Mar. 15, 2019.
Bensimon G et al., "A study of riluzole in the treatment of advanced stage or elderly patients with amyotrophic lateral sclerosis," J Neurol., vol. 249: 609-615 (2002).

(56) References Cited

OTHER PUBLICATIONS

Brown, J. et al., Intraparenchymal Spinal Cord Delivery of AAV VY-SOD102 Reduces Disease Burden in the G93A Mouse Model of ALS-SOD1, ASGCT—2020 Annual Meeting, May 12-15, 2020, 1 page.
BY999593, GenBank EST No. BY999593, BY999593 human cDNA library, immortalized cell line of corneal epithelial cells Homo sapiens cDNA clone cp1739 3, mRNA sequence, Apr. 14, 2008 [online]. [Retrieved on Apr. 5, 2016], Retrieved from the internet <URL: http://www.ncbi.nlm.nih.gov/nucest/BY999593>.
Ding H et al., "Design of functional small interfering RNAs targeting amyotrophic lateral sclerosis-associated mutant alleles," Chinese Medical J., vol. 124(1): 106-110 (2011).
Foust, K. et al., "Therapeutic AAV9-mediated Suppression of Mutant SOD1 Slows Disease Progression and Extends Survival in Models of Inherited ALS," Molecular Therapy, The Journal of the American Society of Gene Therapy, vol. 21(12):2148-2159 (2013).
Fujita, Y. et al., "The Golgi apparatus is fragmented in spinal cord motor neurons of amyotrophic lateral sclerosis with basophilic inclusions," Acta Neuropathol, vol. 103:243-247 (2002).
Ghatak et al., "Anterior horn changes of motor neuron disease associated with demyelinating radiculopathy" J Neuropathol Exp Neurol., vol. 45: 385-395 (1986).
Holger Patzke, "Robust SOD1 Knockdown in Large Mammal Spinal Cord Using a Novel Delivery Paradigm With AAV Gene Therapy Targeting SOD1 for the Treatment of SOD1-ALS," ALSMND Dec. 7-9, 2018.
International Search Report and Written Opinion, PCT/US2018/055999, dated Jan. 28, 2019, 22 pages.
International Search Report and Written Opinion, PCT/US2018/056001, dated Jan. 24, 2019, 19 pages.
International Search Report and Written Opinion, PCT/US2019/040222, dated Sep. 10, 2020, 14 pages.
International Search Report and Written Opinion, PCT/US2019/040230, dated Dec. 12, 2019, 24 pages.
International Search Report and Written Opinion, PCT/US2020/030393, dated Sep. 10, 2020, 12 pages.
Kawamata, T. et al., "Immunologic reactions in amyotrophic lateral sclerosis brain and spinal cord tissue," Am J Pathol., vol. 140:691-707 (1992).
Kim C., et al., "Amyotrophic lateral sclerosis—cell based therapy and novel therapeutic development," Exp. Neurobiol., vol. 23(3): 207-214 (2014).
Lepore. et al., "Intraparenchymal spinal cord delivery of adeno-associated virus IGF-1 is protective in the SOD1 G93A model of ALS," Brain Research, vol. 1185: 256-265 (2007).
Maekawa, S. et al., Cortical selective vulnerability in motor neuron disease: a morphometric study Brain, vol. 27:1237-1251 (2004).
Matsumoto et al., "Ubiquitin-positive inclusion in anterior horn cells in subgroups of motor neuron diseases: a comparative study of adult-onset amyotrophic lateral sclerosis, juvenile amyotrophic lateral sclerosis and Werdnig-Hoffmann disease," J Neurol Sci., vol. 115: 208-213 (1993).
Maxwell MM et al., "RNA interference-mediated silencing of mutant superoxide dismutase rescues cyclosporin A-induced death in cultured neuroblastoma cells," PNAS, vol. 101(9):3178-3183 (2004).
McBride, J. et al., "Preclinical Safety of RNAi-Mediated HTT Suppression in the Rhesus Macaque as a Potential Therapy for Huntington's Disease," Molecular Therapy, vol. 19(12):2152-2162 (2011).
Mitroshina, EV et al., "Ration of Recombinant Adenoassociated Viruses for Transduction of Cell Cultures," The State University of Nizhny Novgorod (2013) No English Translation available.
Partial European Search Report, European Application No. 18794385, dated Feb. 1, 2021, 13 pages.
Philips, T, and J D Rothstein. "Glial cells in amyotrophic lateral sclerosis." Experimental Neurology, vol. 262 Pt B (2014): 111-20 doi:10.1016/j.expneurol.2014.05.015.

Renton, A. et al., "State of play in amyotrophic lateral sclerosis genetics," Nat. Neurosci., vol. 17:17-23 (2014).
Rizvanov AA et al., "Retrogradely transported siRNA silences human mutant SOD1 in spinal cord motor neurons," Exp. Brain Res., vol. 195(1): 1-4 (2009).
Robberecht and Philip, "The changing scene of amyotrophic lateral sclerosis," Nat. Rev. Neurosci., vol. 14: 248-264 (2013).
Rosen DR et al., "Mutations in Cu/Zn superoxide dismutase gene are associated with familial amyotrophic lateral sclerosis," Nature, vol. 362: 59-62 (1993).
Rotunno MS and Bosco DA, "An emerging role for misfolded wild-type SOD1 in sporadic ALS pathogenesis," Front Cell Neurosci., vol. 16 (7): 253 (2013).
Rowland LP and Shneibder, "Amyotrophic lateral sclerosis," NA, N Engl. J. Med., vol. 344: 1688-1700 (2001).
Sasaki and Maruyama, "Immunocytochemical and ultrastructural studies of the motor cortex in amyotrophic lateral sclerosis" Acta Neuropathol., vol. 87: 578-585 (1994).
Schiffer D. et al., "Reactive astrogliosis of the spinal cord in amyotrophic lateral sclerosis," J Neurol Sci., vol. 139: 27-33 (1996).
Schwarz DS et al., "Designing siRNA that distinguish between genes that differ by a single nucleotide," Plos Genet., vol. 2(9): e140 (2006).
Thomsen, G.M., et al.,"Delayed Disease Onset and Extended Survival in the SOD1G93A Rat Model of Amyotrophic Lateral Sclerosis after Suppression of Mutant SOD1 in the Motor Cortex," The Journal of Neuroscience, vol. 34 (47):15587-15600 (2014).
Towne C et al., "Neuroprotection by gene therapy targeting mutant SOD1 in individual pools of motor neurons does nol translate into therapeutic benefit in fALS mice," Mol Ther., vol. 19(2): 274-283 (2011).
Udaka et al., "Degeneration of Betz cells in motor neuron disease. A Golgi study," Acta Neuropathol., vol. 70:289-295 (1986).
Vehvilainen P et al., "Mechanisms of mutant SOD1 induced mitochondrial toxicity in amyotrophic lateral sclerosis," Front Cell Neurosci., vol. 8: 126 (2014).
Voyager Therapeutics: "Intravenous Delivery of Novel AAV Capsids," Oct. 20, 2017 (Oct. 20, 2017), XP055630466, Retrieved from the Internet: URL:https://www.voyagertherapeutics.com/wp-content/uploads/2017/10/ESGCT_slides.pdf [retrieved on Oct. 9, 2019].
Wang, H. et al., "Widespread spinal cord transduction by intrathecal injection of rAAV delivers efficacious RNAi therapy for amyotrophic lateral sclerosis," Human Molecular Genetics, vol. 23(3):668-681 (2014).
Wroe R et al., "ALSOD: the Amyotrophic Lateral Sclerosis Online Database," Amyotroph Lateral Scler., vol. 9:249-250 (2008).
Xue, J. et al., "Epigenetics: Principles, Protocols and practices," 121-122 (2006) No English Translation available.
Yacila and Sari, "Potential therapeutic drugs and methods for the treatment of amyotrophic lateral sclerosis," Curr Med Chem., vol. 21(31): 3583-3593 (2014).
Maniatis T. et al.,Molecular Cloning. CSH Laboratory, NY, N.Y. (1982).
Merten OW, et al. Viral vectors for gene therapy and gene modification approaches. Biochem Eng J. Apr. 2016;108:98-115.
Muzyczka N, et al. AAV's Golden Jubilee. Mol Ther. May 2015;23(5):807-8.
Philiport, et al. Liposomes as tools in Basic Research and Industry. CRC Press, Ann Arbor, Mich. (1995).
Kailasan S, et al. Parvovirus Family Conundrum: What makes a killer? Annu Rev Virol. Nov. 2015;2(1):425-50.
Rutledge EA, et al. Infectious clones and vectors derived from adeno-associated virus (AAV) serotypes other than AAV type 2. J Virol. Jan. 1998;72(1):309-19.
Pillay S, et al. An essential receptor for adeno-associated virus infection. Nature. Nov. 17, 2016;539(7629):456.
Platt MP, et al. Embryonic disruption of the candidate dyslexia susceptibility gene homolog Kiaa0319-like results in neuronal migration disorders. Neuroscience. Sep. 17, 2013;248:585-93.
Poon MW, et al. Distribution of Kiaa0319-like immunoreactivity in the adult mouse brain-a novel protein encoded by the putative dyslexia susceptibility gene KIAA0319-like. Histol Histopathol Aug. 2011;26(8):953-63.

(56) References Cited

OTHER PUBLICATIONS

Poon MW, et al. Dyslexia-associated kiaa0319-like protein interacts with axon guidance receptor nogo receptor 1. Cell Mol Neurobiol. Jan. 2011;31(1):27-35.
Myers EW, et al. Optimal alignments in linear space. Comput Appl Biosci. Mar. 1988;4(1):11-7.
Smith DW, et al. Biocomputing: Informatics and Genome Projects. Academic Press, New York, 1993.
Kozak M. Interpreting cDNA sequences: some insights from studies on translation. Mamm Genome. Aug. 1996;7(8):563-74.
Kozak M. Point mutations define a sequence flanking the AUG initiator codon that modulates translation by eukaryotic ribosomes Cell. Jan. 31, 1986,44(2):283-92.
Kozak M. The scanning model for translation: an update. J Cell Biol. Feb. 1989;108(2):229-41.
Heim R, et al. Engineering green fluorescent protein for improved brightness, longer wavelengths and fluorescence resonance energy transfer. Curr Biol. Feb. 1, 1996;6(2):178-82.
HEIM R,et al. Improved green fluorescence Nature 373, 663-664 (Feb. 23, 1995); doi:10.1038/373663b0.
Nygaard S, et al. A universal system to select gene-modified hepatocytes in vivo. Sci Transl Med. Jun. 2016;8(342):342ra79.
Smith RH, et al. Germline viral "fossils" guide in silico reconstruction of a mid-Cenozoic era marsupial adeno-associated virus. Sci Rep. Jul. 2016;6:28965.
Li L, et al. Production and characterization of novel recombinant adeno-associated virus replicative-form genomes: a eukaryotic source of DNA for gene transfer. PLoS One. Aug. 1, 2013;8(8):e69879. doi: 10.1371/journal.pone.0069879. Print 2013.
O'reilly DR, et al. Baculovirus expression vectors: a laboratory manual. Oxford University Press, 1994.
Oliva B, et al. An automated classification of the structure of protein loops. J Mol Biol. Mar. 7, 1997;266(4):814-30.
Samaranch L, et al. MR-guided parenchymal delivery of adeno-associated viral vector serotype 5 in non-human primate brain. Gene Ther. Apr. 2017;24(4):253-261.
Petit L, et al. Rod Outer Segment Development Influences AAV-Mediated Photoreceptor Transduction After Subretinal Injection. Hum Gene Ther. May 16, 2017. Epub ahead of print.
Hinderer C et al. Delivery of an Adeno-Associated Virus Vector into CSF Attenuates Central Nervous System Disease in Mucopolysaccharidosis Type II Mice Hum Gene Ther. Aug. 10, 2016.
Hordeaux J., et al. Efficient central nervous system AAVrh10-mediated intrathecal gene transfers in adult and neonate rats. Gene Ther.Apr. 2015, 22(4):316-24.
Merkel SF et al. Trafficking of AAV Vectors Across a Model of the Blood-Brain Barrier; a Comaparative Study of Transcytosis and Transduction Using Primary Human Brain Endothelial Cells. J Neurochem. Oct. 8, 2016.
Miyanohara A et al. Potent Spinal Parenchymal AAV9-mediated Gene Delivery by Subpial Injection in Adult Rats and Pigs. Mol Ther Methods Clin Dev. Jul. 13, 2016;3:16046.
Muralidharan G , et al. Unique glycan signatures regulate adeno-associated virus tropism in the developing brain. J Virol. Apr. 2015;89(7):3976-87.
Ponder K, et al. Intrathecal injection of lentiviral vector results in high expression in the brain of mucopolysaccharidosis VII dogs but the pattern of expression is different than for AAV9 or AAV-rh10. J Control Release. Dec. 2014, 196:71-8.
Salegio EA, et al. MRI-Guided Delivery of Viral Vectors. Methods Mol Viol. 2016;1382:217-30.
Samaranch L et al. Cerebellomedullary Cistern Delivery for AAV-Based Gene Therapy: A Technical Note for Monhuman Primates. Hum Gene Ther Methods. Feb. 2016;27(1):13-6.
Saraiva J et al. Gene Therapy for the CNS Using AAVs: The Impact of Systemic Delivery by AAV9. J Control Release Nov. 10, 2016;241:94-109.
Shen F, et al. Inhibition of pathological brain angiogenesis through systemic delivery of AAV vector expressing soluble FLT1. Gene Therapy. Nov. 22, 2015(11):893-900.

Hinderer C, et al. Neonatal Systemic AAV Induces Tolerance to CNS Gene Therapy in MPS I Dogs and Nonhuman Primates. Mol Ther. Aug. 2015, 23(8):1298-307.
Ojala DS, et al. Adeno-associated virus vectors and neurological gene therapy. Neuroscientist. Feb. 2015;21(1):84-98.
Katz ML, et al. AAV gene transfer delays disease onset in a TPP1-deficient canine model of the late infantile form of Batten Disease. Sci Transl Med. Nov. 2015;7(313):313ra180.
Kothari P, et al. Iodine-124 Labeled Adeno-Associated Virus: A Promising Tool for Tracking Gene Therapy. Journal of Nuclear Medicine. May 2015, 56 (supplement 3), 494-494.
Landegger LD, et al. A synthetic AAV vector enables safe and efficient gene transfer to the mammalian inner ear. Nat Biotechnol. Mar. 2017;35(3):280-284.
Mason JB, et al. Delivery and evaluation of recombinant adeno-associated viral vectors in the equine distal extremity for the treatment of laminitis. Equine Vet J. Jan. 2017;49(1):79-86.
Jeong D, et al. Matricellular Protein CCN5 Reverses Established Cardiac Fibrosis. J Am Coll Cardiol. Apr. 5, 2016;67(13):1556-68.
Knezevic T, et al. Adeno-associated Virus Serotype 9—Driven Expression of BAG3 Improves Left Ventricular Function in Murine Hearts with Left Ventricular Dysfunction Secondary to a Myocardial Infarction. JACC Basic Transl Sci. Dec. 2016;1(7):647-656.
Ibrahim S, et al. Stable liver specific expression of human IDOL in humanized mice raises plasma cholesterol. Cardiovasc Res. May 2016;110(1):23-9.
Li Sy, et al. Efficient and targeted transduction of nonhuman primate liver with systemically delivered optimized AAV3E vectors. Mol Ther. Dec. 2015;23(12):1867-76.
Heller KN, et al. Human alpha 7 integrin gene (ITGA7) delivered by adeno-associated virus extends survival of severely affected dystrophin/utrophin deficient mice. Oct. 2015;26(10):647-56.
Mendell JR, et al. Follistatin Gene Therapy for Sporadic Inclusion Body Myositis Improves Functional Outcomes. Mol Ther. Apr. 2017;25(4):870-879.
Schnepp BC, et al. Recombinant adeno-associated virus vector genomes take the form of long-lived transcriptionally competent episomes in human muscle. Hum Gene Ther Jan. 2016;27(1):32-42.
Murlidharan G et al. Glymphatic Fluid Transport Controls Paravascular Clearance of AAV Vectors from the Brain. JCI Insight. Sep. 8, 2016;1(14).
Neuberger Ewi, et al. Establishment of two quantitative nested qPCR assays targeting the human EPO transgene. Gene Ther. Apr. 2016;23(4):330-9.
Lentz TB, et al. Insight into the Mechanism of Inhibition of Adeno-Associated Virus by the Mre11/Rad50/Nbs1 Complex. J Virol. Jan. 2015, 89(1):181-94.
De Leeuw CN et al. rAAV-compatible MiniPromoters for Restricted Expression in the Brain and Eye. Mol Brain. May 10, 2016;9(1):52.
Hirsch ML, et al. Delivering Transgenic DNA Exceeding the Carrying Capacity of AAV Vectors. Methods Mol Biol. 2016;1382:21-39.
Lu J, et al. A 5'non-coding exon containing engineered intron enhances transgene expression from recombinant AAV vectors in vivo Hum Gene Ther. Jan. 2017;28(1):125-134.
Powell SK, et al. Viral expression cassette elements to enhance transgene target specificity and expression in gene therapy. Discov Med Jan. 2015;19(102):49-57.
Rosario AM et al. Microglia-specific Targeting by Novel Capsid-modified AAV6 Vectors. Mol Ther Methods Clin Dev. Apr. 13, 2016;3:16026.
Wang L, et al. Productive life cycle of adeno-associated virus serotype 2 in the complete absence of a conventional polyadenylation signal. J Gen Virol. Sep. 2015;96(9):2780-7.
Yan ZY, et al. Optimization of recombinant adeno-associated virus mediated expression for large transgenes, using a synthetic promoter and tandem array enhancers. Hum Gene Ther. Jun. 2015;26(6):334-46.
Jackson KL, et al. Better Targeting, Better Efficiency for Wide-Scale Neuronal Transduction with the Synapsin Promoter and AAV-PHP. B. Front Mol Neurosci. Nov. 2016;6:116.

(56) References Cited

OTHER PUBLICATIONS

McClements ME, et al. A fragmented adeno-associated viral dual vector strategy for treatment of diseases caused by mutations in large genes leads to expression of hybrid transcripts. J Genet Syndr Gene Ther. Nov. 2016;7(5):311.
Parr MJ, et al. Tumor-selective transgene expression in vivo mediated by an E2F-responsive adenoviral vector. Nat Wed. Oct. 1997;3(10):1145-9.
Reid CA, et al. miRNA mediated post-transcriptional silencing of transgenes leads to increased adeno-associated viral vector yield and targeting specificity. Gene Ther. Jun. 15, 2017. Epub ahead of print.
Sawada Y et al. Inflammation-induced Reversible Switch of the Neuron-specific Enolase Promoter from Purkinje Neurons to Bergmann Glia. Sci Rep. Jun. 13, 2016;6:27758.
Lukashcuk V et al. AAV9-mediated central nervous system-targeted gene delivery via cisterna magna route in mice. Mol Ther Methods Clin Dev. Feb. 17, 2016;3:15055.
Tarantal AF, et al. Systemic and Persistent Muscle Gene Expression in Rhesus Monkeys with a Liver De-targeted Adeno-Associated Virus (AAV) Vector. Hum Gene Ther. May 2017;28(5):385-391.
Huang LY, et al. Characterization of the Adeno-Associated Virus 1 and 6 Sialic Acid Binding Site. J Virol. May 12, 2016;90(11):5219-30.
Siu JJ, et al. Improved gene delivery to adult mouse spinal cord through the use of engineered hybrid adeno-associated viral serotypes. Gene Ther. Apr. 25, 2017. Epub ahead of print.
Deng XF, et al. Replication of an autonomous human parvovirus in non-dividing human airway epithelium is facilitated through the DNA damage and repair pathways. PLoS Pathog. Jan. 2016;12(1):e1005399.
Kailasan S, et al. Structure of an Enteric Pathogen, Bovine Parvovirus.J Virol. Mar. 2015, 89(5):2603-14.
Alton EW, et al. Repeated nebulisation of non-viral CFTR gene therapy in patients with cystic fibrosis: a randomised, double-blind, placebo-controlled, phase 2b trial. Lancet Respir Med Sep. 2015;3(9):684-91.
Baum BJ, et al. Early responses to adenoviral-mediated transfer of the aquaporin-1 cDNA for radiation-induced salivary hypofunction. Proc Natl Acad Sci U S A. Nov. 20, 2012;109(47):19403-7.
Shen W, et al. Analysis of the Cis and Trans Requirements for DNA Replication at the Right End Hairpin of the Human Bocavirus 1 Genome. J Virol. Aug. 2016;90(17):7761-77.
Valdmanis P, et al. Future of rAAV gene therapy: Platform for RNAi, Gene Editing and Beyond. Hum Gene Ther. Apr. 2017;28(4):361-372.
Cirulli ET, et al. Exome sequencing in amyotrophic lateral sclerosis identifies risk genes and pathways. Science. Mar. 27, 2015;347(6229):1436-41.
Haggmark A, et al. Plasma profiling reveals three proteins associated to amyotrophic lateral sclerosis. Ann Clin Transl Neurol. Aug. 2014;1(8):544-53.
Jackson KL, et al. Preservation of forelimb function by UPF1 gene therapy in a rat model of TDP-43-induced motor paralysis Gene Ther.Jan. 2015, 22(1):20-8.
Herranz-Martin S, et al. Viral delivery of C9ORF72 hexanucleotide repeat expansions in mice lead to repeat length dependent neuropathology and behavioral deficits. Dis Model Mech. May 26, 2017. Epub ahead of print.
Jara JH, et al. Healthy and diseased corticospinal motor neurons are selectively transduced upon direct AAV2-2 injection into the motor cortex. Gene Ther. Mar. 2016;23(3):272-82.
Borel F et al.Therapeutic rAAVrh10 Mediated SOD1 Silencing in Adult SOD1(G93A) Mice and Nonhuman Primates. Hum Gene Ther. Jan. 2016;27(1):19-31.
Frakes AE, et al. Additive amelioration of ALS by co-targeting independent pathogenic mechanisms. Ann Clin Transl Neurol. Jan. 2017;4(2):76-86.
'Stoica L et al. Adeno Associated Viral Vector Delivered RNAi for Gene Therapy of SOD1 Amyotrophic Lateral Sclerosis Front Mol Neurosci Aug. 2, 2016;9:56.
Van Zundert B et al. Silencing Strategies for Therapy of SOD1-Mediated ALS. Neurosci Lett. Aug. 6, 2016.
Stoica et al. Adeno-associated virus-delivered artificial microRNA extends survival and delays paralysis in an amyotrophic lateral sclerosis mouse model. Ann Neurol. Apr. 2016;79(4):687-700.
Picher-Martel V et al. From Animal Models to Human Disease: A Genetic Approach for Personalized Medicine in ALS. Acta Neuropathol Commun. Jul. 11, 2016;4(1):70.
Hocquemiller M et al. Adeno-Associated Virus-Based Gene Therapy for CNS Diseases. Hum Gene Ther. Jul. 2016;27(7):478-96.
Bisset DR, et al. Therapeutic impact of systemic AAV-mediated RNA interference in a mouse model of myotonic dystrophy. Hum Mol Genet. Sep. 2015;24(17):4971-83.
He X, et al. Recombinant adeno-associated virus-mediated inhibition of microRNA-21 protects mice against the lethal schistosome infection by repressing both IL-13 and transforming growth factor beta 1 pathways. Hepatology. Jun. 2015, 61(6):2008-17. d.
Xie J et al. Adeno-Associated Virus-Mediated MicroRNA Delivery and Therapeutics. Semin Liver Dis. Feb. 2015, 35(1):81-8.
Keiser MS et al. Broad distribution of ataxin 1 silencing in rhesus cerebella for spinocerebellar ataxia type 1 therapy. Brain. Dec. 2015;138(Pt 12):3555-66.
Enomoto M, et al. Efficient Gene Suppression in Dorsal Root Ganglia and Spinal Cord Using Adeno-Associated Virus Vectors Encoding Short-Hairpin RNA. Methods Mol Biol. 2016;1364:77-90.
Tse LV, et al. Structure-guided evolution of antigenically distinct adeno-associated virus variants for immune evasion. Proc Natl Acad Sci U S A. May 30, 2017. Epub ahead of print.
Vandamme C, et al. Unraveling the complex story of immune responses to AAV vectors trial after trial. Hum Gene Ther. Aug. 23, 2017.
Mingozzi F, et al. Overcoming the Host Immune Response to Adeno-Associated Virus Gene Delivery Vectors: The Race Between Clearance, Tolerance, Neutralization, and Escape. Annu Rev Virol Sep. 29, 2017;4(1):511-534.
Kim Y, et al. Mutagenic Analysis of an Adeno-Associated Virus Variant Capable of Simultaneously Promoting Immune Resistance and Robust Gene Delivery. Hum Gene Ther. Jun. 24, 2017. Epub ahead of print.
Pillay S, et al. AAV serotypes have distinctive interactions with domains of the cellular receptor AAVR. J Virol. Jul. 5, 2017. Epub ahead of print.
Wang M, Sun J, Crosby A, Woodard K, Hirsch ML, Samulski RJ, Li C. Direct interaction of human serum proteins with AAV virions to enhance AAV transduction: immediate impact on clinical applications. Gene Ther. Jan. 2017;24(1):49-59. doi: 10.1038/gt.2016.75. Epub Nov. 11, 2016.
Bennett A, et al. Thermal Stability as a Determinant of AAV Serotype Identity. Mol Ther Methods Clin Dev. Jul. 24, 2017;6:171-182. doi: 10.1016/j.omtm.2017.07.003.
Bennett A, et al. Understanding capsid assembly and genome packaging for adeno-associated viruses. Future Virology Jun. 2017; 12(6): 283-297.
Grimm et al. Small but increasingly mightly—latest advances in AAV vector research, design and evolution. Hum Gene Ther. Nov. 2017 (Epub Aug. 23, 2017); 28(11):1075-1086.
Pillay S, et al. Host determinants of adeno-associated viral vector entry. Curr Opin Virol. Jun. 30, 2017;24:124-131. Epub ahead of print.
Mietzsch M, et al. OneBac 2.0: Sf9 Cell Lines for Production of AAV1, AAV2 and AAV8 Vectors with Minimal Encapsidation of Foreign DNA. Hum Gene Ther Methods. Feb. 2017;28(1):15-22.
Mietzsch M, et al. OneBac 2.0: Sf9 cell lines for production of AAV5 vectors with enhanced infectivity and minimal encapsidation of foreign DNA. Hum Gene Ther. Oct. 26, 2015(10):688-97.
Nambiar B, et al. Characteristics of minimally oversized adeno-associated virus vectors encoding human Factor VIII generated using producer cell lines and triple transfection. Hum Gene Ther Methods. Feb. 2017;28(1):23-38.

(56) References Cited

OTHER PUBLICATIONS

Pacouret S, et al. AAV-ID: A Rapid and Robust Assay for Batch-to-Batch Consistency Evaluation of AAV Preparations Mol Ther. Apr. 17, 2017. Epub ahead of print.
Penaud-Budloo M, et al. Accurate identification and quantification of DNA species by next-generation sequencing in adeno-associated viral vectors produced in insect cells. Hum Gene Ther Methods. May 2, 2017. Epub ahead of print.
Ruffing M, et al. Assembly of viruslike particles by recombinant structural proteins of adeno-associated virus type 2 in insect cells. J Virol. Dec. 1992,66(12):6922-30.
Samulski RJ, et al. Helper-free stocks of recombinant adeno-associated viruses: normal integration does not require viral gene expression. J Virol. Sep. 1989;63(9):3822-8.
Smith RH, et al. A simplified baculovirus-AAV expression vector system coupled with one-step affinity purification yields high-titer rAAV stocks from insect cells. Mol Ther. Nov. 2009;17(11):1888-96. doi: 10.1038/mt.2009.128. Epub Jun. 16, 2009.
Urabe M, et al. Scalable generation of high-titer recombinant adeno-associated virus type 5 in insect cells. J Virol. Feb. 2006;80(4):1874-85.
Van Der Loo JCM, et al. Progress and challenges in viral vector manufacturing. Hum Mol Genet. Apr. 2016;25(R1):R42-52.
Wasilko DJ, et al. The titerless infected-cells preservation and scale-up (TIPS) method for large-scale production of NO-sensitive human soluble guanylate cyclase (sGC) from insect cells infected with recombinant baculovirus. Protein Expr Purif. Jun. 2009;65(2):122-32. doi: 10.1016/j.pep.2009.01.002. Epub Jan. 11, 2009.
Zhao KN, et al. BPV1 E2 protein enhances packaging of full-length plasmid DNA in BPV1 pseudovirions. Virology. Jul. 5, 2000;272(2):382-93.
Pierson EE, et al. Resolving adeno-associated viral particle diversity with charge detection mass spectrometry. Anal Chem. Jul. 2016;88(13):6718-25.
Rashnonejad A, et al. Large-Scale Production of Adeno-Associated Viral Vector Serotype-9 Carrying the Human Survival Motor Neuron Gene. Mol Biotechnol Jan. 2016;58(1):30-6.
Ling C, et al. Strategies to generate high-titer, high-potency recombinant AAV3 serotype vectors. Mol Ther Methods Clin Dev. May 2016;3:16029.
Afione S, et al. Identification and Mutagenesis of the Adeno-Associated Virus 5 Sialic Acid Binding Region.J Virol. Feb. 2015, 89(3):1660-72.
Drouin LM, et al. Cryo-electron microscopy reconstruction and stability studies of Wild-Type and R432A Variant of AAV2 Reveals Capsid Structural Stability is a Major Factor in Genome Packaging. J Virol. Sep. 2016;90(19):8542-51.
Halder S, et al. Structure of neurotropic adeno-associated virus AAVrh.8. J Struct Biol. Oct. 2015;192(1):21-36.
Huang LY, et al. Characterization of the adeno-associated virus 1 and 6 sialic acid binding site. J Virol. May 2016;90(11):5219-30.
Mao Y, et al. Single point mutation in adeno-associated viral vectors—DJ capsid leads to improvement for gene delivery in vivo. BMC Biotechnol. Jan. 2016;16:1.
Marsic D et al. Altering Tropism of rAAV by Directed Evolution. Methods of Mol Biol. 2016;1382:151-73.
Tu My, et al. Role of capsid proteins in parvoviruses infection. Virol J. Aug. 2015, 4;12:114.
Zeng C, et al. Probing the Link between Genomic Cargo, Contact Mechanics and Nanoindentation in Recombinant Adeno-Associated Virus 2. J Phys Chem B. Mar. 2017;121(8):1843-1853.
Zinn E, et al. In Silico Reconstruction of the Viral Evolutionary Lineage Yields a Potent Gene Therapy Vector. Cell Rep. Aug. 2015, 12(6):1056-68.
Grimm D, et al. E Pluribus Unum: 50 years of research, millions of viruses and one goal—tailored acceleration of AAV evolution. Mol Ther. Dec. 2015;23(12):1819-1831.
Karamuthil-Melethil S, et al. Novel Vector Design and Hexosaminidase Variant Enabling Self-Complementary Adeno-Associated Virus for the Treatment of Tay-Sachs Disease. Hum Gene Ther. Jul. 2016;27(7):509-21.
Ling C, et al. Development of Optimized AAV Serotype Vectors for High-Efficiency Transduction at Further Reduced Doses. Hum Gene Ther Methods. Aug. 2016;27(4):143-9.
Pillay S, et al. An essential receptor for adeno-associated virus infection. Nature. Feb. 2016;530(7588):108-12.
Li Bz, et al. Site directed mutagenesis of surface-exposed lysine residues leads to improved transduction by AAV2 but not AAV8 vectors in murine hepatocytes in vivo. Hum Gene Ther Methods. Dec. 2015;26(6):211-20.
Shen S, et al. Functional Analysis of the Putative Integrin Recognition Motif on Adeno-associated virus 9. J Biol Chem. Jan. 2015, 290(3):1496-504.
Steines B, et al. CFTR gene transfer with AAV improves early cystic fibrosis pig phenotypes. JCI Insight. Sep. 2016;1(14):e88728.
Bensky MJ, et al. Targeted gene delivery to the enteric nervous system using AAV: a comparison across serotypes and capsid mutants.Mol Ther Mar. 2015;23(3):488-500.
Castle MJ, et al. Controlling AAV Tropism in the Nervous System with Natural and Engineered Capsids. Methods Mol Biol. 2016;1382:133-49.
Choudhury SR, et al. Widespread CNS gene transfer and silencing after systemic delivery of novel AAV-AS vectors. Mol Ther. Apr. 2016;24(4):726-35.
Davis AS, et al. Rational design and engineering of a modified adeno-associated virus (AAV1)-based vector system for enhanced retrograde gene delivery. Neurosurgery Feb. 2015;76(2):216-25.
Deverman BE et al. Cre-dependent selection yields AAV variants for widespread gene transfer to the adult brain. Nat Biotechnol. Feb. 2016;34(2):204-9.
Powell SK et al. Characterization of a novel adeno-associated viral vector with preferential oligodendrocyte tropism. Gene Ther. Sep. 15, 2016.
Tervo et al. A Designer AAV Variant Permits Efficient Retrograde Access to Projection Neurons. Neuron. Oct. 19, 2016;92(2):372-382.
Choudhury et al. In Vivo Selection Yields AAV-B1 Capsid for Central Nervous System and Muscle Gene Therapy. Mol Ther. Aug. 2016;24(7):1247-57.
Keravala A, et al. Evaluating AAV Hybrid Variants for Improved Tropism after Intravitreal Gene Delivery to the Retina. Molecular Therapy, vol. 23, Supplement 1, May 2015, pp. S127-S128.
Vercauteren K, et al. Superior in vivo Transduction of Human Hepatocytes Using Engineered AAV3 Capsid. Mol Ther. Jun. 2016;24(6):1042-9.
Chen M, et al. Efficient Gene Delivery and Expression in Pancreas and Pancreatic Tumors by Capsid-optimized AAV8 Vectors. Hum Gene Ther Methods. Feb. 2017;28(1):49-59.
Ling C, et al. High-Efficiency Transduction of Primary Human Hematopoietic Stem/Progenitor Cells by AAV6 Vectors: Strategies for Overcoming Donor-Variation and Implications in Genome Editing. Sci Rep. Oct. 2016;6:35495.
Earley LF, et al. Identification and Characterization of Nuclear and Nucleolar Localization Signals in the Adeno-Associated Virus Serotype 2 Assembly-Activating Protein. J Virol. Mar. 2015, 89(6):3038-48.
Zou W, et al. Nonstructural protein NP1 of human bocavirus 1 plays a critical role in the expression of viral capsid proteins. J Virol. Apr. 2016;90(9):4658-69.
Mingozzi F, et al. Adeno-associated viral vectors at the frontier between tolerance and immunity. Front Immunol.Mar. 2015, 6:120.
Ling C, et al. Enhanced Transgene Expression from Recombinant Single-Stranded D-Sequence-Substituted Adeno-Associated Virus Vectors in Human Cell Lines In Vitro and in Murine Hepatocytes In Vivo. J Virol. Jan. 2015, 89(2):952-61.
Xie J, et al. Short DNA Hairpins Compromise Recombinant Adeno-Associated Virus Genome Homogeneity. Mol Ther. Jun. 7, 2017;25(6):1363-1374.
Davidsson M, et al. A novel process of viral vector barcoding and library preparation enables high-diversity library generation and recombination-free paired-end sequencing. Sci Rep. Nov. 2016;6:3563.

(56) References Cited

OTHER PUBLICATIONS

Chamberlain K, et al. Expressing transgenes that exceed the packaging capacity of AAV capsids. Hum Gene Ther Methods. Feb. 2016;27(1):1-12.

Hudry E, Vandenberghe LH. Therapeutic AAV Gene Transfer to the Nervous System: A Clinical Reality. Neuron. Mar. 6, 2019;101(5):839-862.

Betancur JG et al., miRNA-like duplexes as RNAi triggers with improved specificity. Front Genet. Jul. 12, 2012;3:127.

Chung et al., Polycystronic RNA polymerase II expression vectors for RNA interference based on BIC/miR-155. Nucleic Acids Res. Apr. 13, 2006;34(7):e53.

Cullen BR. Induction of stable RNA interference in mammalian cells. Gene Ther. Mar. 2006;13(6):503-8.

Dow LE et al., A pipeline for the generation of shRNA transgenic mice. Nat Protoc. Feb. 2, 2012;7(2):374-93.

Fellmann C. et al., Functional identification of optimized RNAi triggers using a massivelyparallel sensor assay. Mol Cell. Mar. 18, 2011;41(6):733-46.

Gu S et al., The loop position of shRNAs and pre-miRNAs is critical for the accuracy of dicer processing in vivo. Cell. Nov. 9, 2012;151(4):900-911.

Han J. et al., Molecular basis for the recognition of primary microRNAs by the Drosha-DGCR8 complex. Cell. Jun. 2, 2006;125(5):887-901.

Ketley A. et al., The miR-20 microRNA family targets smoothened to regulate hedgehog signallling in zebrafish early muscle development. PLoS One. Jun. 5, 2013;8(6):e65170.

Liu YP et al., Inhibition of HIV-1 by multiple siRNAs expressed from a single microRNApolycistron. Nucleic Acids Res. May 2008;36(9):2811-24.

Park JE et al., Dicer recognizes the 5' end of RNA for efficient and accurate processing. Nature. Jul. 13, 2011;475(7355):201-5.

Schwarz DS et al., Asymmetry in the assembly of the RNAi enzyme complex. Cell. Oct. 17, 2003;115(2):199-208.

Seitz H et al., A 5"-uridine amplifies miRNA/miRNA* asymmetry in Drosophila by promoting RNA-induced silencing complex formation. Silence. Jun. 7, 2011;2:4.

Maniatis S et al., Spatiotemporal dynamics of molecular pathology in amyotrophic lateral sclerosis.Science Apr. 5, 2019: vol. 364, Issue 6435, pp. 89-93.

Borel F et al., Recombinant AAV as a platform for translating the therapeutic potential of RNA interference .Mol Ther. Apr. 2014;22(4):692-701.

Pfeifer A et al., Pharmacological potential of RNAi-focus on miRNA. Pharmacol Ther. Jun. 2010;126(3):217-27.

Poesen et al., Neurofilament markers for ALS correlate with extent of upper and lower motor neuron disease. Neurology Jun. 13, 2017; 88(24):2302-2309. Epub May 12, 2017.

Toedebusch et al., Cerebrospinal Fluid Levels of Phosphorylated Neurofilament Heavy as a Diagnostic Marker of Canine Degenerative Myelopathy. J Vet Intern Med. Mar.-Apr. 2017; 31(2): 513-520. Published online Feb. 10, 2017.

Nardone et al., Canine degenerative myelopathy: a model of human amyotrophic lateral sclerosis. Zoology (Jena). Feb. 2016;119(1):64-73 Epub Sep. 21, 2015.

Crisp et al., Canine degenerative myelopathy: Biochemical characterization of superoxide dismutase 1 in the first naturally occurring. Exp Neurol Oct. 2013; 248:1-9 Epub May 23, 2013.

Awano et al., Genome-wide association analysis reveals a SOD1 mutation in canine degenerative myelopathy that resembles amyotrophic lateral sclerosis. Proc Natl Acad Sci U S A. Feb. 24, 2009; 106(8): 2794-2799. Published online Feb. 2, 2009.

Al-Chalabi et al., Deletions of the heavy neurofilament subunit tail in amyotrophic lateral sclerosis. Hum Mol Genet. Feb. 1999;8(2):157-64.

Al-Chalabi et al., The epidemiology of ALS: a conspiracy of genes, environment and time. Nat Rev Neurol. Nov. 2013;9(11):617-28.

Alonso et al., Incidence and lifetime risk of motor neuron disease in the United Kingdom: a population-based study. Eur J Neurol. Jun. 2009;16(6):745-51.

Armon et al., Sports and trauma in amyotrophic lateral sclerosis revisited. J Neurol Sci. Nov. 15, 2007;262(1-2):45-53.

Arnold et al., ALS-linked TDP-43 mutations produce aberrant RNA splicing and adult-onset motor neuron disease without aggregation or loss of nuclear TDP-43. Proc Natl Acad Sci U S A. Feb. 19, 2013;110(8):E736-45.

Ayala et al., TDP-43 regulates retinoblastoma protein phosphorylation through the repression of cyclin-dependent kinase 6 expression. Proc Natl Acad Sci U S A. Mar. 11, 2008;105(10):3785-9.

Bali et al., Defining SOD1 ALS natural history to guide therapeutic clinical trial design. J Neurol Neurosurg Psychiatry. Feb. 2017;88(2):99-105.

Battistini et al., SOD1 mutations in amyotrophic lateral sclerosis. Results from a multicenter Italian study. J Neurol. Jul. 2005;252(7):782-8.

Berry JD et al., New considerations in the design of clinical trials for amyotrophic lateral sclerosis. Clin Investig (Lond). Oct. 2011;1(10):1375-1389.

Bevan AK et al., Systemic gene delivery in large species for targeting spinal cord, brain, and peripheral tissues for pediatric disorders. Mol Ther. Nov. 2011;19(11):1971-80.

Van Blitterswijk et al., Anti-superoxide dismutase antibodies are associated with survival in patients with sporadic amyotrophic lateral sclerosis. Amyotroph Lateral Scler. Nov. 2011;12(6):430-8.

Boillée S et al., Onset and progression in inherited ALS determined by motor neurons and microglia. Science. Jun. 2, 2006;312(5778):1389-92.

Borchelt DR et al., Superoxide dismutase 1 with mutations linked to familial amyotrophic lateral sclerosis possesses significant activity. Proc Natl Acad Sci U S A. Aug. 16, 1994;91(17):8292-6.

Bosco DA et al., Wild-type and mutant SOD1 share an aberrant conformation and a common pathogenic pathway in ALS. Nat Neurosci. Nov. 2010;13(11):1396-403.

Brown et al. Analysis of mutant SOD1 electrophoretic mobility by Blue Native gel electrophoresis; evidence for soluble multimeric assemblies. PLoS One. Aug. 14, 2014;9(8):e104583.

Cedarbaum JM et al., The ALSFRS-R: a revised ALS functional rating scale that incorporates assessments of respiratory function. BDNF ALS Study Group (Phase III). J Neurol Sci. Oct. 31, 1999;169(1-2):13-21.

Chung et al., Cu/Zn superoxide dismutase can form pore-like structures. Biochem Biophys Res Commun. Dec. 26, 2003;312(4):873-6.

Clement et al., Wild-type nonneuronal cells extend survival of SOD1 mutant motor neurons in ALS mice. Science. Oct. 3, 2003;302(5642):113-7.

Cudkowicz et al., Epidemiology of mutations in superoxide dismutase in amyotrophic lateral sclerosis. Ann Neurol. Feb. 1997;41(2):210-21.

De Boer et al., Genetic validation of a therapeutic target in a mouse model of ALS. Sci Transl Med. Aug. 6, 2014;6(248):248ra104.

De la Maza. Molecular sturcture of adeno-associated virus variant DNA. JBC. Apr. 1980;255(7):3194-3203.

Deng et al., FUS-immunoreactive inclusions are a common feature in sporadic and non-SOD1 familial amyotrophic lateral sclerosis. Ann Neurol. Jun. 2010;67(6):739-48.

Deng HX et al., Mutations in UBQLN2 cause dominant X-linked juvenile and adult-onset ALS and ALS/dementia. Nature. Aug. 21, 2011;477(7363):211-5.

Di Giorgio et al., Non-cell autonomous effect of glia on motor neurons in an embryonic stem cell-based ALS model. Nat Neurosci. May 2007;10(5):608-14.

Dirren et al., SOD1 silencing in motoneurons or glia rescues neuromuscular function in ALS mice. Ann Clin Transl Neurol. Feb. 2015; 2(2):167-184.

Dupuis L et al., Differential screening of mutated SOD1 transgenic mice reveals early up-regulation of a fast axonal transport component in spinal cord motor neurons. Neurobiol Dis. Aug. 2000;7(4):274-85.

(56) References Cited

OTHER PUBLICATIONS

Elchuri et al., CuZnSOD deficiency leads to persistent and widespread oxidative damage and hepatocarcinogenesis later in life Oncogene. Jan. 13, 2005;24(3):367-80.
Nicolson SC, et al. Identification and validation of small molecules that enhance recombinant Adeno-associated virus transduction following high throughput screen. J Virol. Jul. 2016;90(16):7019-31.
Wang M, et al. Direct interaction of human serum proteins with AAV virions to enhance AAV transduction: Immediate impact on clinical applications. Gene Ther. Jan. 2017;24(1):49-59.
Watakabe A, et al. Comparative analyses of adeno-associated viral vector serotypes 1 2 5 8 and 9 in marmoset mouse and macaque cerebral cortex. Neurosci Res.Apr. 2015, 93:144-57.
Xiao P, et al. Disruption of microtubules post virus entry enhances adeno-associated virus vector transduction Hum Gene Ther. Apr. 2016;27(4):309-24.
Hudry EM, et al. Exosome-associated AAV vector as a robust and convenient neurosocience tool. Gene Ther. Apr. 2016;23(4):380-92.
Nery FC, et al. New methods for investigation of neuronal migration in embryonic brain explants J Neurosci Methods.Jan. 2015, 239:80-4.
Su W et al. Recombinant adeno-associated viral (rAAV) vectors mediate efficient gene transduction in cultured neonatal and adult microglia. J Neurochem. Jan. 2016;136 Suppl 1:49-62.
Ren XF, et al. Adeno-associated virus-mediated BMP-7 and SOX9 in vitro co-transfection of human degenerative intervertebral disc cells. Genet Mol Res. Apr. 22, 2015;14(2):3736-44.
Alves S et al. Ultramicroscopy as a Novel Tool to Unravel the Tropism of AAV Gene Therapy Vectors in the Brain. Sci Rep Jun. 20, 2016;6:28272.
Kothari P, et al. Radioiodinated Capsids Facilitate In Vivo Non-lnvasive Tracking of Adeno-Associated Gene Transfer Vectors. Sci Rep. Jan. 2017;7:39594.
Xie Q, et al. The 2.8 Å Electron Microscopy Structure of Adeno-Associated Virus-DJ Bound by a Heparinoid Pentasaccharide. Mol Ther Methods Clin Dev. Mar. 8, 2017;5:1-12.
Srivastava A. Adeno-Associated Virus: The Naturally Occurring Virus Versus the Recombinant Vector. Hum Gene Ther. Jan. 2016;27(1):1-6.
Thorne B, et al. Gene Therapy. Adv Biochem Eng Biotechnol. Mar. 14, 2017 Epub ahead of print.
Tratschin JD, et al. Adeno-associated virus vector for high-frequency integration, expression, and rescue of genes in mammalian cells. Mol Cell Biol. Nov. 1985;5(11):3251-60.
Srivastava A, et al. Nucleotide sequence and organization of the adeno-associated virus 2 genome. J Virol. Feb. 1983;45(2):555-64.
Summerford C, et al. AAVR: A multi-serotype receptor for AAV. Mol Ther. Apr. 2016;24(4):663-6.
Xie Q, et al. The atomic structure of adeno-associated virus (AAV-2), a vector for human gene therapy. Proc Natl Acad Sci U S A. Aug. 6, 2002;99(16):10405-10. Epub Jul. 22, 2002.
Wu P, et al. Mutational analysis of the adeno-associated virus type 2 (AAV2) capsid gene and construction of AAV2 vectors with altered tropism. J Virol. Sep. 2000;74(18):8635-47.
Von Heinje G. Sequence Analysis in Molecular Biology. Academic Press, 1987.
Stahl PH, et al. Pharmaceutical Salts: Properties, Selection, and Use. Wiley-VCH, 2008.
Yang C, et al. Sequential adeno-associated viral vector serotype 9-green fluorescent protein gene transfer causes massive inflammation and intense immune response in rat striatum. Hum Gene Ther. Jul. 2016;27(7):528-43.
Chandler RJ, et al. rAAV integration and genotoxicity: insights from animal models. Hum Gene Ther. Apr. 2017;28(4):314-322.
Ye L., et al. Adeno-Associated Virus Vector Mediated Delivery of the HBV Genome Induces Chronic Hepatitis B Virus Infection and Liver Fibrosis in Mice. PLoS One. Jun. 2015, 10(6):e0130052.
Wang S, et al. Direct brain infusion can be enhanced with focused ultrasound and microbubbles. J Cereb Blood Flow Metab. Feb. 2017;37(2):706-714.

Wang et al., Noninvasive, neuron-specific gene therapy can be facilitated by focused ultrasound and recombinant adeno-associated virus. Gene Therapy. Nov. 22, 2014. 104-110.
Weber-Adrian D, et al. Gene delivery to the spinal cord using MRI-guided focused ultrasound. Gene Ther. Jul. 2015, 22(7):568-77.
Wu D et al. Expressing Constitutively Active Rheb in Adult Dorsal Root Ganglion Neurons Enhances the Integration of Sensory Axons that Regenerate Across a Chondroitinase-Treated Dorsal Root Entry Zone Following Dorsal Root Crush. Front Mol Neurosci. Jul. 5, 2016;9:49.
Zhu W, et al. Soluble FLT1 Gene Therapy Alleviates Brain Arteriovenous Malformation Severity. Stroke. May 2017;48(5):1420-1423.
Watson ZL, et al. Adeno-associated Virus Vectors Efficiently Transduce Mouse and Rabbit Sensory Neurons Coinfected with Herpes Simplex Virus 1 following Peripheral Inoculation. J Virol. Aug. 12, 2016;90(17):7894-901.
Suzuki J, et al. Cochlear gene therapy with ancestral AAV in adult mice: complete transduction of inner hair cells without cochlear dysfunction. Apr. 3, 2017,7:45524.
Woodard KT et al. Heparan Sulfate Binding Promotes Accumulation of Intravitreally Delivered Adeno-associated Viral Vectors at the Retina for Enhanced Transduction but Weakly Influences Tropism. J Virol. Oct. 14, 2016,90(21):9878-9888.
Wang LL, et al. Comparative study of liver gene transfer with AAV vectors based on endogenous and engineered AAV capsids Mol Ther. Dec. 2015;23(12):1877-87.
Sondhi D, et al. Genetic Modification of the Lung Directed Toward Treatment of Human Disease. Hum Gene Ther. Jan. 2017;28(1):3-84.
Yalvac ME, et al. AAV1.NT-3 gene therapy attenuates spontaneous autoimmune peripheral polyneuropathy. Gene Ther. Jan. 2016;23(1):95-102.
Srivastava A. In Vivo Tissue-tropism of Adeno-associated Viral Vectors. Curr Opin Virol. Sep. 2, 2016;21:75-80.
Adamson-Small L, et al. Sodium chloride enhances rAAV production in a serum-free suspension manufacturing platform using the Herpes Simplex Virus System. Hum Gene Ther Methods. Feb. 2017;28(1):1-14.
Al J, et al. A Scalable and Accurate Method for Quantifying Vector Genomes of Recombinant Adeno-Associated Viruses in Crude Lysate. Hum Gene Ther Methods Apr. 13, 2017. Epub ahead of print.
Buclez PO, et al. Rapid, scalable, and low-cost purification of recombinant adeno-associated virus produced by baculovirus expression vector system. Mol Ther Methods Clin Dev. May 2016;3:16035.
Burnham B, et al. Analytical ultracentrifugation as an approach to characterize recombinant adeno-associated viral vectors. Hum Gene Ther Methods. Dec. 2015;26(6):228-42.
Clement N, et al. Manufacturing of recombinant adeno-associated viral vectors for clinical trials. Mol Ther Methods Clin Dev. Mar. 2016;3:16002.
D'costa S, et al. Practical utilization of recombinant AAV vector reference standards: focus on vector genome titration by free ITR qPCR. Mol Ther Methods Clin Dev. Mar. 2016;5:16019.
Grieger JC, et al. Production of Recombinant Adeno-associated Virus Vectors Using Suspension HEK293 Cells and Continuous Harvest of Vector From the Culture Media for GMP FIX and FLT1 Clinical Vector. Mol Ther. Feb. 2016;24(2):287-97.
Gruntman AM, et al. Stability and Compatibility of Recombinant Adeno-Associated Virus Under Conditions Commonly Encountered in Human Gene Therapy Trials. Hum Gene Ther Methods. Apr. 2015, 26(2):71-6.
Kajigaya S, et al. Self-assembled B19 parvovirus capsids, produced in a baculovirus system, are antigenically and immunogenically similar to native virions. Proc Natl Acad Sci U S A. Jun. 1, 1991;88(11):4646-50.
Kirnbauer R, et al. Virus-like particles of bovine papillomavirus type 4 in prophylactic and therapeutic immunization. Virology May 1, 1996;219(1):37-44.
Kohlbrenner E, et al. Production and Characterization of Vectors Based on the Cardiotropic AAV Serotype 9. Methods Mol Biol. 2017;1521:91-107.

(56) References Cited

OTHER PUBLICATIONS

Kotin RM, et al. Large-scale recombinant adeno-associated virus production. Hum Mol Genet. Apr. 15, 2011;20(R1): R2-6. doi: 10.1093/hmg/ddr141. Epub Apr. 29, 2011.
Kotin RM, et al. Manufacturing clinical grade recombinant adeno-associated virus using invertebrate cell lines. Hum Gene Ther. Mar. 28, 2017. Epub ahead of print.
Kotterman MA, et al. Enhanced cellular secretion of AAV2 by expression of foreign viral envelope proteins. Biochemical Engineering Journal, vol. 93, Jan. 15, 2015, pp. 108-114.
Methods in Molecular Biology, ed. Richard, Humana Press, NJ (1995).
Carter BJ. Adeno-associated virus and the development of adeno-associated virus vectors: a historical perspective. Mol Ther. Dec. 2004;10(6):981-9.
G. S. Banker, Modern Pharmaceutics, Drugs and the Pharmaceutical Sciences, v. 72, Marcel Dekker, New York, Inc., 1996.
Grimm D, et al. Progress in adeno-associated virus type 2 vector production: promises and prospects for clinical use. Hum Gene Ther. Oct. 10, 1999;10(15):2445-50.
Grimson A, et al. MicroRNA targeting specificity in mammals: determinants beyond seed pairing. Mol Cell. Jul. 6, 2007;27(1):91-105.
Hastie E, et al. Adeno-Associated Virus at 50: A Golden Anniversary of Discovery, Research, and Gene Therapy Success-A Personal Perspective. Hum Gene Ther. May 2015, 26(5):257-65.
Aydemir F, et al. Mutants at the 2-fold interface of AAV2 structural proteins suggest a role in viral transcription for AAV capsids. J Virol. Jul. 2016;90(16):7196-204.
Bantel-Schaal U, et al. Human adeno-associated virus type 5 is only distantly related to other known primate helper-dependent parvoviruses. J Virol. Feb. 1999;73(2):939-47.
Berry GE, et al. Cellular transduction mechanisms of adeno-associated viral vectors. Curr Opin Virol. Dec. 2016;21:54-60.
Chiorini JA, et al. Adeno-associated virus (AAV) type 5 Rep protein cleaves a unique terminal resolution site compared with other AAV serotypes. J Virol. May 1999;73(5):4293-8.
Chiorini JA, et al. Cloning and characterization of adeno-associated virus type 5. J Virol. Feb. 1999;73(2):1309-19.
Chiorini JA, et al. Cloning of adeno-associated virus type 4 (AAV4) and generation of recombinant AAV4 particles. J Virol. Sep. 1997;71(9):6823-33.
Earley LF, et al. Adeno-Associated Virus Assembly-Activating Protein Is Not an Essential Requirement for Capsid Assembly of AAV Serotypes 4, 5 and 11. J Virol. Jan. 2017;91(3):pii:e0198-16.
Ding C, et al., Biochemical Characterization of Junonia Coenia Densovirus Nonstructural Protein NS-1. J. Virol., 76(1):338-345 2002.
Adachi K, et al. Drawing a high-resolution functional map of adeno-associated virus capsid by massively parallel sequencing. Nat Commun. 2014;5:3075. doi: 10 1038/ncomms4075.
Altschul SF, et al. Basic local alignment search tool. J Mol Biol. Oct. 5, 1990;215(3):403-10.
Carillo H, et al. The Multiple Sequence Alignment Problem in Biology. SIAM J. Appl. Math. 48-5 (1988), pp. 1073-1082.
Devereux J A comprehensive set of sequence analysis programs for the VAX. Nucleic Acids Res. Jan. 11, 1984;12(1 Pt 1):387-95.
Gribskov M, et al. Sequence Analysis Primer. M Stockton Press, New York, 1991.
Griffin AM, et al. Computer Analysis of Sequence Data, Part I. Humana Press, New Jersey, 1994.
Berge Sm Pharmaceutical salts. J Pharm Sci. Jan. 1977;66(1):1-19.
Bell P, et al. Effects of self-complementarity, codon optimization, transgene, and dose on liver transduction with AAV8. Hum Gene Ther Methods. Dec. 2016;27(6):228-237.
Heim et al., Wavelength mutations and posttranslational autoxidation of green fluorescent protein. Proc. Natl. Acad. Sci. USA (1994).
Hastie E, et al. Recombinant adeno-associated virus vectors in the treatment of rare diseases. Expert Opin Orphan Drugs. 2015;3(6):675-689.

Fargnoli AS, et al. Liquid jet delivery method featuring S100A1 gene therapy in the rodent model following acute myocardial infarction. Gene Ther. Feb. 2016;23(2):151-7.
Aubourg P. Gene therapy for rare central nervous system diseases comes to age. Endocr Dev. 2016;30:141-6.
Bankiewicz KS et al. AAV Viral Vector Delivery to the Brain by Shape-conforming MR-guided Infusions. J Control Release. Oct. 28, 2016;240:434-442.
Bey K, et al. Efficient CNS targeting in adult mice by intrathecal infusion of single-stranded AAV9-GFP for gene therapy of neurological disorders. Gene Ther. Apr. 20, 2017. Epub ahead of print.
Brulet R, et al. NEUROD1 Instructs Neuronal Conversion in Non-Reactive Astrocytes. Stem Cell Reports. May 11, 2017. Epub ahead of print.
Cabral-Miranda F, et al. rAAV8-733-Mediated Gene Transfer of CHIP/Stub-1 Prevents Hippocampal Neuronal Death in Experimental Brain Ischemia. Mol Ther. Feb. 2017;25(2):392-400.
Chandler RJ, et al. Systemic AAV9 gene therapy improves the lifespan of mice with Niemann-Pick disease, type C1. Hum Mol Genet. Jan. 2017;26(1):52-64.
Dang CH, et al. In vivo dynamics of AAV-mediated gene delivery to sensory neurons of the trigeminal ganglia. Sci Rep. Apr. 19, 2017;7(1):927.
Dimidschstein J, et al. A viral strategy for targeting and manipulating interneurons across vertebrate species. Nat Neurosci. Dec. 2016;19(12):1743-1749.
Donsante A et al. Intracerebroventricular delivery of self-complementary adeno-associated virus serotype 9 to the adult rat brain. Gene Ther. May 2016;23(5):401-7.
El-Shamayleh Y, et al. Strategies for targeting primate neural circuits with viral vectors. J Neurophysiol. Jul. 2016;116(1):122-34.
Foust KD, et al. Intravascular AAV9 preferentially targets neonatal neurons and adult astrocytes. Nat Biotechnol. Jan. 2009;27(1):59-65. doi: 10.1038/nbt.1515. Epub Dec. 21, 2008.
Gessler Dj et al. Gene Therapy for the Treatment of Neurological Disorders: Metabolic Disorders. Methods Mol Biol. 2016;1382:429-65.
Gilkes JA et al. Preferred Transduction with AAV8 and AAV9 Via Thalamic Administration in the MPS IIIB Model: A Comparison of Four rAAV Serotypes. Mol Genet Metab Rep. Dec. 7, 2015;6:48-54.
Gombash SE, et al. Systemic Gene Therapy for Targeting the CNS. Methods Mol Biol. 2016;1382:231-7.
Gurda BL, et al. Evaluation of AAV-mediated gene therapy for central nervous system disease in canine mucopolysaccharidosis VII. Mol Ther. Feb. 2016;24(2):206-16.
Ahmed SS, et al. rAAV gene therapy in a Canavan's disease mouse model reveals immune impairments and an extended pathology beyond the central nervous system. Mol Ther. Jun. 2016;24(6):1030-41.
Dashkoff J, et al. Tailored transgene expression to specific cell types in the central nervous system after peripheral injection with AAV9. Mol Ther Methods Clin Dev. Dec. 2016;3:16081.
Gruntman AM, et al. Retro-Orbital Venous Sinus Delivery of rAAV9 Mediates High-Level Transduction of Brain and Retina Compared with Temporal Vein Delivery in Neonatal Mouse Pups. Hum Gene Ther. Mar. 2017;28(3):228-230.
Aoyama Y, et al. Wnt11 gene therapy with adeno-associated virus 9 improves the survival of mice with myocarditis induced by coxsackievirus B3 through the suppression of the inflammatory reaction. J Mol Cell Cardiol. Jul. 2015;84:45-51.
Greig JA, et al. Impact of intravenous infusion time on AAV8 vector pharmacokinetics, safety, and liver transduction in cynomolgus macaques. Mol Ther Methods Clin Dev. Dec. 2016;3:16079.
Gruntman AM, et al. Delivery of Adeno-associated virus gene therapy by intravascular limb infusion methods. Hum Gene Ther Clin Dev Sep. 2015;26(3):159-64.
Hagg A, et al. Using AAV vectors expressing the beta 2-adrenoceptor or associated G alpha proteins to modulate skeletal muscle mass and muscle fiber size. Sci Rep. Mar. 2016;6:23042.
Greig JA, et al. Intramuscular administration of AAV overcomes pre-existing neutralizing antibodies in rhesus macaques. Vaccine. Dec. 2016;34(50):6323-6329.

(56) References Cited

OTHER PUBLICATIONS

Al J, et al. Adeno-associated virus serotype rh.10 displays strong muscle tropism following intraperitoneal delivery. Sci Rep. Jan. 2017;7:40336.

Baum BJ, et al. Advances in salivary gland gene therapy—oral and systemic implications. Expert Opinion on Biological Therapy. 2015;15(10):1443-54.

Hai B, et al. Long-term transduction of miniature pig parotid glands using serotype 2 adeno-associated viral vectors. J Gene Med. Jun. 2009;11(6):506-14.

Epstein et al., Transgenic mice with increased Cu/Zn-superoxide dismutase activity: animal model of dosage effects in Down syndrome. Proc Natl Acad Sci U S A. Nov. 1987,84(22):8044-8.

Estévez et al., Induction of nitric oxide-dependent apoptosis in motor neurons by zinc-deficient superoxide dismutase. Science. Dec. 24, 1999;286(5449):2498-500.

Gurney et al., Motor neuron degeneration in mice that express a human Cu,Zn superoxide dismutase mutation. Science. Jun. 17, 1994;264(5166):1772-5.

Haidet-Phillips et al., Astrocytes from familial and sporadic ALS patients are toxic to motor neurons. Nat Biotechnol. Aug. 10, 2011;29(9):824-8.

Johnston et al., Amyotrophic lateral sclerosis in an urban setting: a population based study of inner city London. J Neurol. Dec. 2006;253(12):1642-3.

Jonsson el al., Minute quantities of misfolded mutant superoxide dismutase-1 cause amyotrophic lateral sclerosis. Brain. Jan. 2004;127(Pt 1):73-88.

Kanning et al., Motor neuron diversity in development and disease. Annu Rev Neurosci. 2010;33:409-40.

Ly CV et al., Emerging antisense oligonucleotide and viral therapies for amyotrophic lateral sclerosis. Curr Opin Neurol. Oct. 2018;31(5):648-654.

Challis et al., Systemic AAV vectors for widespread and targeted gene delivery in rodents. Nat Protoc. Feb. 2019;14(2):379-414.

Elbashir et al., Functional anatomy of siRNAs for mediating efficient RNAi in Drosophila melanogaster embryo lysate. Embo J. Dec. 3, 2001; 20(23):6877-88.

Powell et al., Viral Expression Cassette Elements to Enhance Transgene Target Specificity and Expression in Gene Therapy. Discov Med. Jan. 2015;19(102):49-57.

Mitroshina EV, et al. Production of Recombinant Adeno-Associated viruses for Transduction of Cell Cultures, Study Guide, Nizhny Novgorod: Nizhny Novgorod State University, 2013, 1-30.

Lee SH et al., Intrathecal delivery of recombinant AAV1 encoding hepatocyte growth factor improves motor functions and protects neuromuscular system in the nerve crush and SOD1-G93A transgenic mouse models. Acta Neuropathol Commun. Jun. 12, 2019;7(1):14.

Leyton-Jaimes et al., AAV2/9-mediated overexpression of MIF inhibits SOD1 misfolding, delays disease onset, and extends survival in mouse models of ALS. Proc Natl Acad Sci U S A. Jul. 1, 2019.

Bofill-De Ros et al. Guidelines for the optimal design of miRNA-based shRNAs. Methods. Jul. 1, 2016;103:157-66.

Miyagishi et al. Optimization of an siRNA-expression system with an improved hairpin and its significant suppressive affects in mammalian cells. The Journal of Gene Medicine: A cross-disciplinary journal for research on the science of gene transfer and its clinical applications. Jul. 2004;6(7):715-23.

Du et al. Design of expression vectors for RNA interference based on miRNAs and RNA splicing. The FEBS journal. Dec. 2006;273(23):5421-7.

Calloni et al. Scaffolds for artificial miRNA expression in animal cells. Human gene therapy methods. Aug. 27, 2015;26(5):162-74.

Schopman et al. Optimization of shRNA inhibitors by variation of the terminal loop sequence. Antiviral research. May 1, 2010;86(2):204-11.

Bravo-Hernandez et al., Spinal subpial delivery of AAV9 enables widespread gene silencing and blocks motoneuron degeneration in ALS. Nat Med. Dec. 23, 2019.

International Search Report & Written Opinion dated Sep. 13, 2018 in co-pending application No. PCT/US2018/031089, entitled Compositions and Methods of Treating Amyotrophic Lateral Sclerosis (ALS).

COMPOSITIONS AND METHODS OF TREATING AMYOTROPHIC LATERAL SCLEROSIS (ALS)

CROSS REFERENCE TO RELATED APPLICATIONS

This application is a 35 U.S.C. § 371 U.S. National Stage Entry of International Application No. PCT/US2018/031089 filed May 4, 2018, which claims priority to U.S. Provisional Patent Application No. 62/501,788, entitled COMPOSITIONS AND METHODS OF TREATING AMYOTROPHIC LATERAL SCLEROSIS (ALS), filed May 5, 2017, U.S. Provisional Patent Application No. 62/507,927, entitled COMPOSITIONS AND METHODS OF TREATING AMYOTROPHIC LATERAL SCLEROSIS (ALS), filed May 18, 2017, U.S. Provisional Patent Application No. 62/520,100, entitled COMPOSITIONS AND METHODS OF TREATING AMYOTROPHIC LATERAL SCLEROSIS (ALS), filed Jun. 15, 2017 and U.S. Provisional Patent Application No. 62/566,609, entitled COMPOSITIONS AND METHODS OF TREATING AMYOTROPHIC LATERAL SCLEROSIS (ALS), filed Oct. 2, 2017; the contents of each of which are herein incorporated by reference in their entirety.

REFERENCE TO SEQUENCE LISTING

The instant application contains a replacement Sequence Listing which has been submitted electronically in ASCII format and is hereby incorporated by reference in its entirety. Said ASCII copy, created on Mar. 11, 2020 is named 2057_1048US371_SL and is 6,596,998 bytes in size.

FIELD OF THE INVENTION

The present invention relates to compositions, methods and processes for the design, preparation, manufacture, use and/or formulation of AAV particles comprising modulatory polynucleotides, e.g., polynucleotides encoding at least one small interfering RNA (siRNA) molecules which target the superoxide dismutase 1 (SOD1) gene. Targeting of the SOD1 gene may interfere with SOD1 gene expression and the resultant SOD1 protein production. The AAV particles comprising modulatory polynucleotides encoding at least one siRNA molecules may be inserted into recombinant adeno-associated virus (AAV) vectors. Methods for using the AAV particles to inhibit the expression of the SOD1 gene in a subject with a neurodegenerative disease (e.g., amyotrophic lateral sclerosis (ALS)) are also disclosed.

BACKGROUND OF THE INVENTION

Amyotrophic lateral sclerosis (ALS), also known as Lou Gehrig's disease, is the most fatal progressive neurodegenerative disease, characterized by the predominant loss of motor neurons (MNs) in primary motor cortex, the brainstem, and the spinal cord. The loss of motor neurons devastates basic, fundamental movements, such as breathing, and typically causes death to patients within 2-5 years after diagnosis. Progressive deterioration of motor function in patients severely disrupts their breathing ability, requiring some form of breathing aid for survival of the patients. Other symptoms also include muscle weakness in hands, arms, legs or the muscles of swallowing. Some patients (e.g., FTD-ALS) may also develop frontotemporal dementia.

According to the ALS Association, approximately 5,600 people in the United States of America are diagnosed with ALS each year. The incidence of ALS is two per 100,000 people, and it is estimated that as many as 30.000 Americans may have the disease at any given time.

Two forms of ALS have been described: one is sporadic ALS (sALS), which is the most common form of ALS in the United States of America and accounts for 90 to 95% of all cases diagnosed; the other is familial ALS (fALS), which occurs in a family lineage mainly with a dominant inheritance and only accounts for about 5 to 10% of all cases in the United States of America. sALS and fALS are clinically indistinguishable.

Pathological studies found that disturbance of some cellular processes occur after disease onset, including increased ER stress, generation of free radicals (i.e., reactive oxygen species (ROS)), mitochondrial dysfunction, protein aggregation, apoptosis, inflammation and glutamate excitotoxicity, specifically in the motor neurons (MNs).

The causes of ALS are complicated and heterogeneous. In general, ALS is considered to be a complex genetic disorder in which multiple genes in combination with environmental exposures combine to render a person susceptible. More than a dozen genes associated with ALS have been discovered, including, SOD-1 ($Cu^{2+}/Zn^{2+}$ superoxide dismutase), TDP-43 (TARDBP, TAR DNA binding protein-43), FUS (Fused in Sarcoma/Translocated in Sarcoma), ANG (Angiogenin), ATXN2 (Ataxin-2), valosin containing protein (VCP), OPTN (Optineurin) and an expansion of the non-coding GGGGCC hexanucleotide repeat in the chromosome 9, open reading frame 72 (C9ORF72). However, the exact mechanisms of motor neuron degeneration are still elusive.

Currently, there is no curative treatment for ALS. The only FDA approved drug is Riluzole, which antagonizes the glutamate response to reduce the pathological development of ALS. However, only about a three-month life span expansion for ALS patients in the early stages has been reported, and no therapeutic benefit for ALS patients in the late stages has been observed, indicating a lack of therapeutic options for the patients (Bensimon G et al., *J Neurol.* 2002, 249, 609-615). Therefore, a new treatment strategy that can effectively prevent the disease progression is still in demand.

Many different strategies are under investigation for potential treatment of both sporadic and familial ALS. One strategy is based on the neuroprotective and/or regenerative effect of neurotrophic factors, such as Insulin-like growth factor I (IGF-I), Glial cell line-derived neurotrophic factor (GDNF). Vascular endothelial growth factor (VEGF), Colivelin and Activity dependent neurotrophic factor (ADNF) derived peptide, which can promote neuronal survival. Several studies demonstrated that neurotrophic factors can preserve motor neuron functionality, therefore improving motor performance in the SOD1 transgenic mice. However, such treatment often fails to prolong the survival of SOD1 mice, suggesting that neurotrophic factors are not sufficient to prolong neuronal survival (See a review by Yacila and Sari, *Curr Med Chem.,* 2014, 21(31), 3583-3593).

Another strategy for ALS treatment has focused on stem cell based therapy. Stem cells have the potential to generate motor neurons, thereby replacing degenerating motor neurons in the ALS-affected CNS such as primary motor cortex, brainstem and spinal cord. Stem cells derived from multiple sources have been investigated, including induced pluripotent stem cells (iPSCs), mesenchymal stromal cells (MSCs) (e.g. bone marrow mesenchymal stromal cells (BMSCs) and adipocyte stem cells (ASCs)) and neural tissue origin neural stem cells (e.g., fetal spinal neural stem cells (NSCs), multipotent neural progenitor cells (NPCs)) (e.g., reviewed by Kim C et al., *Exp. Neurobiol.*, 2014, 23(3), 207-214).

Mutations in the gene of superoxide dismutase type I (SOD1, $Cu^{2+}/Zn^{2+}$ superoxide dismutase type I) are the most common cause of fALS, accounting for about 20 to 30% of all fALS cases. Recent reports indicate that SOD1 mutations may also be linked to about 4% of all sALS cases (Robberecht and Philip, *Nat. Rev. Neurosci.*, 2013, 14, 248-264). SOD1-linked fALS is most likely not caused by loss of the normal SOD1 activity, but rather by a gain of a toxic function. One of the hypotheses for mutant SOD1-linked fALS toxicity proposes that an aberrant SOD1 enzyme causes small molecules such as peroxynitrite or hydrogen peroxide to produce damaging free radicals. Other hypotheses for mutant SOD1 neurotoxicity include inhibition of the proteasome activity, mitochondrial damage, disruption of RNA processing and formation of intracellular aggregates. Abnormal accumulation of mutant SOD1 variants and/or wild-type SOD1 in ALS forms insoluble fibrillar aggregates which are identified as pathological inclusions. Aggregated SOD1 protein can induce mitochondria stress (Vehvilainen P et al., *Front Cell Neurosci.*, 2014, 8, 126) and other toxicity to cells, particularly to motor neurons.

These findings indicate that SOD1 can be a potential therapeutic target for both familial and sporadic ALS. A therapy that can reduce the SOD1 protein produced in the central nervous system of ALS patients may ameliorate the symptoms of ALS in patients such as motor neuron degeneration and muscle weakness and atrophy. Agents and methods that aim to prevent the formation of wild type and/or mutant SOD1 protein aggregation may prevent disease progression and allow for amelioration of ALS symptoms. RNA interfering (RNAi) mediated gene silencing has drawn researchers' interest in recent years. Small double stranded RNA (small interfering RNA) molecules that target the SOD1 gene haven been taught in the art for their potential in treating ALS (See, e.g., U.S. Pat. No. 7,632,938 and U.S. Patent Publication No. 20060229268, the contents of which is herein incorporated by reference in its entirety).

The present invention develops an RNA interference based approach to inhibit or prevent the expression of SOD1 in ALS patients for treatment of the disease.

The present invention provides novel double stranded RNA (dsRNA) constructs and siRNA constructs and methods of their design. In addition, these novel siRNA constructs may be synthetic molecules or be encoded in an expression vector (one or both strands) for delivery into cells. Such vectors include, but are not limited to adeno-associated viral vectors such as vector genomes of any of the AAV serotypes or other viral delivery vehicles such as lentivirus, etc.

SUMMARY OF THE INVENTION

Described herein are methods, processes, compositions kits and devices for the administration of AAV particles comprising modulatory polynucleotides encoding at least one siRNA molecules for the treatment, prophylaxis, palliation and/or amelioration of a disease and/or disorder (e.g., amyotrophic lateral sclerosis (ALS)).

The present invention relates to RNA molecule mediated gene specific interference with gene expression and protein production. Methods for treating motor neuron degeneration diseases such as amyotrophic lateral sclerosis are also included in the present invention. The siRNA included in the compositions featured herein encompass a dsRNA having an antisense strand (the antisense strand) having a region that is 30 nucleotides or less, generally 19-24 nucleotides in length, that is substantially complementary to at least part of an mRNA transcript of the SOD1 gene.

The present invention provides short double stranded RNA molecules such as small interfering RNA (siRNA) duplexes that target SOD1 mRNA to interfere with SOD1 gene expression and/or SOD1 protein production. The siRNA duplexes of the present invention may interfere with both alleles of the SOD1 gene irrespective of any particular mutation in the SOD1 gene, and may particularly interact with those found in ALS disease.

In some embodiments, such siRNA molecules, or a single strand of the siRNA molecules, are inserted into adeno-associated viral (AAV) vectors to be introduced into cells, specifically motor neurons and/or other surrounding cells in the central nervous system. The AAV vector may comprise sequences encoding 1, 2, 3, 4, or more than 4 siRNA duplexes.

The siRNA duplex of the present invention comprises an antisense strand and a sense strand hybridized together forming a duplex structure, wherein the antisense strand is complementary to the nucleic acid sequence of the targeted SOD1 gene, and wherein the sense strand is homologous to the nucleic acid sequence of the targeted SOD1 gene. In some aspects, the 5'end of the antisense strand has a 5' phosphate group and the 3'end of the sense strand contains a 3'hydroxyl group. In other aspects, there are none, one or 2 nucleotides overhangs at the 3'end of each strand.

According to the present invention, each strand of the siRNA duplex targeting the SOD1 gene is about 19-25 nucleotides in length, preferably about 19 nucleotides, 20 nucleotides, 21 nucleotides, 22 nucleotides, 23 nucleotides, 24 nucleotides, or 25 nucleotides in length. In some aspects, the siRNAs may be unmodified RNA molecules.

In other aspects, the siRNAs may contain at least one modified nucleotide, such as base, sugar or backbone modification.

In one embodiment, an siRNA or dsRNA includes at least two sequences that are complementary to each other. The dsRNA includes a sense strand having a first sequence and an antisense strand having a second sequence. The antisense strand includes a nucleotide sequence that is substantially complementary to at least part of an mRNA encoding SOD1, and the region of complementarity is 30 nucleotides or less, and at least 15 nucleotides in length. Generally, the dsRNA is 19 to 24, e.g., 19 to 21 nucleotides in length. In some embodiments the dsRNA is from about 15 to about 25 nucleotides in length, and in other embodiments the dsRNA is from about 25 to about 30 nucleotides in length.

The dsRNA, either upon contacting with a cell expressing SOD1 or upon transcription within a cell expressing SOD1, inhibits or suppresses the expression of a SOD1 gene by at least 10%, at least 20%, at least 25%, at least 30%, at least 35% or at least 40% or more, such as when assayed by a method as described herein.

According to the present invention, AAV vectors comprising the nucleic acids encoding the siRNA duplexes, one strand of the siRNA duplex or the dsRNA targeting SOD1 gene are produced, the AAV vector serotype may be AAV1, AAV2, AAV3, AAV4, AAV5, AAV6, AAV7, AAV8, AAV9, AAV9.47, AAV9(hu14), AAV10, AAV11, AAV12, AAVrh8, AAVrh10, AAV-DJ8 and/or AAV-DJ, and variants thereof.

The present invention also provides pharmaceutical compositions comprising at least one siRNA duplex targeting the SOD1 gene and a pharmaceutically acceptable carrier. In some aspects, a nucleic acid sequence encoding the siRNA duplex is inserted into an AAV vector.

In some embodiments, the present invention provides methods for inhibiting/silencing SOD1 gene expression in a cell. Accordingly, the siRNA duplexes or dsRNA can be used to substantially inhibit SOD1 gene expression in a cell, in particular in a motor neuron. In some aspects, the inhibition of SOD1 gene expression refers to an inhibition by at least about 20%, preferably by at least about 30%, 40%, 50%, 60%, 70%, 80%, 85%, 90%, 95% and 100%. Accordingly, the protein product of the targeted gene may be inhibited by at least about 20%, preferably by at least about 30%, 40%, 50%, 60%, 70%, 80%, 85%, 90%, 95% and 100%. The SOD1 gene can be either a wild type gene or a mutated SOD1 gene with at least one mutation. Accordingly, the SOD1 protein is either wild type protein or a mutated polypeptide with at least one mutation.

In some embodiments, the present invention provides methods for treating, or ameliorating amyotrophic lateral sclerosis associated with abnormal SOD1 gene and/or SOD1 protein in a subject in need of treatment, the method comprising administering to the subject a pharmaceutically effective amount of at least one siRNA duplex targeting the SOD1 gene, delivering said siRNA duplex into targeted cells, inhibiting SOD1 gene expression and protein production, and ameliorating symptoms of ALS in the subject.

In some embodiments, an AAV vector comprising the nucleic acid sequence encoding at least one siRNA duplex targeting the SOD1 gene is administered to the subject in need for treating and/or ameliorating ALS. The AAV vector serotype may be selected from the group consisting of AAV1, AAV2, AAV3, AAV4, AAV5, AAV6, AAV7, AAV8, AAV9, AAV9.47, AAV9(hu14), AAV10, AAV11, AAV12, AAVrh8, AAVrh10 and AAV-DJ, and variants thereof.

In some aspects, ALS is familial ALS linked to SOD1 mutations. In other aspects, ALS is sporadic ALS which is characterized by abnormal aggregation of SOD1 protein or disruption of SOD1 protein function or localization, though not necessarily as a result of genetic mutation. The symptoms of ALS ameliorated by the present method may include motor neuron degeneration, muscle weakness, stiffness of muscles, slurred speech and/or difficulty in breathing.

In some embodiments, the siRNA duplexes or dsRNA targeting SOD1 gene or the AAV vectors comprising such siRNA-encoding molecules may be introduced directly into the central nervous system of the subject, for example, by intracranial injection.

In some embodiments, the pharmaceutical composition of the present invention is used as a solo therapy. In other embodiments, the pharmaceutical composition of the present invention is used in combination therapy. The combination therapy may be in combination with one or more neuroprotective agents such as small molecule compounds, growth factors and hormones which have been tested for their neuroprotective effect on motor neuron degeneration.

In some embodiments, the present invention provides methods for treating, or ameliorating amyotrophic lateral sclerosis by administering to a subject in need thereof a therapeutically effective amount of a plasmid or AAV vector described herein. The ALS may be familial ALS or sporadic ALS.

The details of various embodiments of the invention are set forth in the description below. Other features, objects, and advantages of the invention will be apparent from the description and the drawings, and from the claims.

BRIEF DESCRIPTION OF THE DRAWINGS

The foregoing and other objects, features and advantages will be apparent from the following description of particular embodiments of the invention, as illustrated in the accompanying drawings. The drawings are not necessarily to scale, emphasis instead being placed upon illustrating the principles of various embodiments of the invention.

Figure 1:
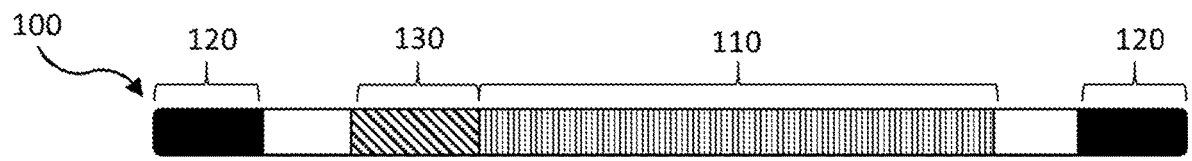
FIG. 1 is a schematic of a viral genome of the invention.

The details of one or more embodiments of the invention are set forth in the accompanying description below. Although any materials and methods similar or equivalent to those described herein can be used in the practice or testing of the present invention, the preferred materials and methods are now described. Other features, objects and advantages of the invention will be apparent from the description. In the description, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present description will control.

DETAILED DESCRIPTION OF THE INVENTION

I. Compositions of the Invention

According to the present invention, compositions for delivering modulatory polynucleotides and/or modulatory polynucleotide-based compositions by adeno-associated viruses (AAVs) are provided. AAV particles of the invention may be provided via any of several routes of administration, to a cell, tissue, organ, or organism, in vivo, ex vivo or in vitro.

As used herein, an "AAV particle" is a virus which comprises a viral genome with at least one payload region and at least one inverted terminal repeat (ITR) region.

As used herein, "viral genome" or "vector genome" or "viral vector" refers to the nucleic acid sequence(s) encapsulated in an AAV particle. Viral genomes comprise at least one payload region encoding polypeptides or fragments thereof.

As used herein, a "payload" or "payload region" is any nucleic acid molecule which encodes one or more polypeptides of the invention. At a minimum, a payload region comprises nucleic acid sequences that encode a sense and antisense sequence, an siRNA-based composition, or a fragment thereof, but may also optionally comprise one or more functional or regulatory elements to facilitate transcriptional expression and/or polypeptide translation.

The nucleic acid sequences and polypeptides disclosed herein may be engineered to contain modular elements and/or sequence motifs assembled to enable expression of the modulatory polynucleotides and/or modulatory polynucleotide-based compositions of the invention. In some embodiments, the nucleic acid sequence comprising the payload region may comprise one or more of a promoter region, an intron, a Kozak sequence, an enhancer or a polyadenylation sequence. Payload regions of the invention typically encode at least one sense and antisense sequence, an siRNA-based compositions, or fragments of the foregoing in combination with each other or in combination with other polypeptide moieties.

The payload regions of the invention may be delivered to one or more target cells, tissues, organs or organisms within the viral genome of an AAV particle.

Adeno-Associated Viruses (AAVs) and AAV Particles

Viruses of the Parvoviridae family are small non-enveloped icosahedral capsid viruses characterized by a single stranded DNA genome. Parvoviridae family viruses consist of two subfamilies: Parvovirinae, which infect vertebrates, and Densovirinae, which infect invertebrates. Due to its relatively simple structure, and due to the fact that it is easily manipulated using standard molecular biology techniques, this virus family is useful as a biological tool. The genome of the virus may be modified to contain a minimum of components for the assembly of a functional recombinant virus, or viral particle, which is loaded with or engineered to express or deliver a desired payload, which may be delivered to a target cell, tissue, organ, or organism.

The parvoviruses and other members of the Parvoviridae family are generally described in Kenneth I. Berns, "Parvoviridae: The Viruses and Their Replication," Chapter 69 in FIELDS VIROLOGY (3d Ed. 1996), the contents of which are incorporated by reference in their entirety.

The Parvoviridae family comprises the Dependovirus genus which includes adeno-associated viruses (AAV) capable of replication in vertebrate hosts including, but not limited to, human, primate, bovine, canine, equine, and ovine species.

The AAV viral genome is a linear, single-stranded DNA (ssDNA) molecule approximately 5,000 nucleotides (nt) in length. The AAV viral genome can comprise a payload region and at least one inverted terminal repeat (ITR) or ITR region. ITRs traditionally flank the coding nucleotide sequences for the non-structural proteins (encoded by Rep genes) and the structural proteins (encoded by capsid genes or Cap genes). While not wishing to be bound by theory, an AAV viral genome typically comprises two ITR sequences. The AAV viral genome comprises a characteristic T-shaped hairpin structure defined by the self-complementary terminal 145 nt of the 5' and 3' ends of the ssDNA which form an energetically stable double stranded region. The double stranded hairpin structures comprise multiple functions including, but not limited to, acting as an origin for DNA replication by functioning as primers for the endogenous DNA polymerase complex of the host viral replication cell.

In addition to the encoded heterologous payload. AAV vectors may comprise the viral genome, in whole or in part, of any naturally occurring and/or recombinant AAV serotype nucleotide sequence or variant. AAV variants may have sequences of significant homology at the nucleic acid (genome or capsid) and amino acid levels (capsids), to produce constructs which are generally physical and functional equivalents, replicate by similar mechanisms, and assemble by similar mechanisms. Chiorini et al., J. Vir. 71: 6823-33 (1997), Srivastava et al., J. Vir. 45:555-64 (1983); Chiorini et al., J. Vir. 73:1309-1319 (1999); Rutledge et al., J. Vir. 72:309-319 (1998); and Wu et al., J. Vir. 74: 8635-47 (2000), the contents of each of which are incorporated herein by reference in their entirety.

In one embodiment, AAV particles of the present invention are recombinant AAV vectors which are replication defective, lacking sequences encoding functional Rep and Cap proteins within their viral genome. These defective AAV vectors may lack most or all parental coding sequences and essentially carry only one or two AAV ITR sequences and the nucleic acid of interest for delivery to a cell, a tissue, an organ or an organism.

In one embodiment, the viral genome of the AAV particles of the present invention comprise at least one control element which provides for the replication, transcription and translation of a coding sequence encoded therein. Not all of the control elements need always be present as long as the coding sequence is capable of being replicated, transcribed and/or translated in an appropriate host cell. Non-limiting examples of expression control elements include sequences for transcription initiation and/or termination, promoter and/or enhancer sequences, efficient RNA processing signals such as splicing and polyadenylation signals, sequences that stabilize cytoplasmic mRNA, sequences that enhance translation efficacy (e.g., Kozak consensus sequence), sequences that enhance protein stability, and/or sequences that enhance protein processing and/or secretion.

According to the present invention, AAV particles for use in therapeutics and/or diagnostics comprise a virus that has been distilled or reduced to the minimum components necessary for transduction of a nucleic acid payload or cargo of interest. In this manner, AAV particles are engineered as vehicles for specific delivery while lacking the deleterious replication and/or integration features found in wild-type viruses.

AAV vectors of the present invention may be produced recombinantly and may be based on adeno-associated virus (AAV) parent or reference sequences. As used herein, a "vector" is any molecule or moiety which transports, transduces or otherwise acts as a carrier of a heterologous molecule such as the nucleic acids described herein.

In addition to single stranded AAV viral genomes (e.g., ssAAVs), the present invention also provides for self-complementary AAV (scAAVs) viral genomes. scAAV viral genomes contain DNA strands which anneal together to form double stranded DNA. By skipping second strand synthesis, scAAVs allow for rapid expression in the cell.

In one embodiment, the AAV particle of the present invention is an scAAV.

In one embodiment, the AAV particle of the present invention is an ssAAV.

Methods for producing and/or modifying AAV particles are disclosed in the art such as pseudotyped AAV vectors (PCT Patent Publication Nos. WO200028004; WO200123001; WO2004112727; WO 2005005610 and WO 2005072364, the content of each of which is incorporated herein by reference in its entirety).

AAV particles may be modified to enhance the efficiency of delivery. Such modified AAV particles can be packaged efficiently and be used to successfully infect the target cells at high frequency and with minimal toxicity. In some embodiments the capsids of the AAV particles are engineered according to the methods described in US Publication Number US 20130195801, the contents of which are incorporated herein by reference in their entirety.

In one embodiment, the AAV particles comprising a payload region encoding the polypeptides of the invention may be introduced into mammalian cells.

AAV Serotypes

AAV particles of the present invention may comprise or be derived from any natural or recombinant AAV serotype. According to the present invention, the AAV particles may utilize or be based on a serotype selected from any of the following AAV1, AAV2, AAV2G9, AAV3, AAV3a, AAV3b, AAV3-3, AAV4, AAV4-4, AAV5, AAV6, AAV6.1, AAV6.2, AAV6.1.2, AAV7, AAV7.2, AAV8, AAV9, AAV9.11, AAV9.13, AAV9.16, AAV9.24, AAV9.45, AAV9.47, AAV9.61, AAV9.68, AAV9.84, AAV9.9, AAV100, AAV11, AAV12, AAV16.3, AAV24.1, AAV27.3, AAV42.12, AAV42-1b, AAV42-2, AAV42-3a, AAV42-3b, AAV42-4, AAV42-5a, AAV42-5b, AAV42-6b, AAV42-8, AAV42-10, AAV42-11, AAV42-12, AAV42-13, AAV42-15, AAV42-aa, AAV43-1, AAV43-12, AAV43-20, AAV43-21, AAV43-23, AAV43-25, AAV43-5, AAV44.1, AAV44.2, AAV44.5, AAV223.1, AAV223.2, AAV223.4, AAV223.5, AAV223.6, AAV223.7, AAV1-7/rh.48, AAV1-8/rh.49, AAV2-15/rh.62, AAV2-3/rh.61, AAV2-4/rh.50, AAV2-5/rh.51, AAV3.1/hu.6, AAV3.1/hu.9, AAV3-9/rh.52, AAV3-11/rh.53, AAV4-8/r11.64, AAV4-9/rh.54, AAV4-19/rh.55, AAV5-3/rh.57, AAV5-22/rh.58, AAV7.3/hu.7, AAV16.8/hu.10, AAV16.12/hu.11, AAV29.3/bb.1, AAV29.5/bb.2, AAV106, 1/hu.37, AAV114.3/hu.40, AAV127.2/hu.41, AAV127.5/hu.42, AAV128.3/hu.44, AAV130.4/hu.48, AAV45.1/hu.53, AAV145.5/hu.54, AAV145.6/hu.55, AAV161.10/hu.60, AAV161.6/hu.61, AAV33.12/hu.17, AAV33.4/hu.15, AAV33.8/hu.16, AAV52/hu.19, AAV52.1/hu.20, AAV58.2/hu.25, AAVA3.3, AAVA3.4, AAVA3.5, AAVA3.7, AAVC1, AAVC2, AAVC5, AAV-DJ, AAV-DJ8, AAVF3, AAVF5, AAVH2, AAVrh.72, AAVhu.8, AAVrh.68, AAVrh.70, AAVpi.1, AAVpi.3, AAVpi.2, AAVrh.60, AAVrh.44, AAVrh.65, AAVrh.55, AAVrh.47, AAVrh.69, AAVrh.45, AAVrh.59, AAVhu.12, AAVH6, AAVLK03, AAVH-1/hu.1, AAVH-5/hu.3, AAVLG-10/rh.40, AAVLG-4/rh.38, AAVLG-9/hu.39, AAVN721-8/rh.43, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAVhu.1, AAVhu.2, AAVhu.3, AAVhu.4, AAVhu.5, AAVhu.6, AAVhu.7, AAVhu.9, AAVhu.10, AAVhu.11, AAVhu.13, AAVhu.15, AAVhu.16, AAVhu.17, AAVhu.18, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.31, AAVhu.32, AAVhu.34, AAVhu.35, AAVhu.37, AAVhu.39, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.51, AAVhu.52, AAVhu.54, AAVhu.55, AAVhu.56, AAVhu.57, AAVhu.58, AAVhu.60, AAVhu.61, AAVhu.63, AAVhu.64, AAVhu.66, AAVhu.67, AAVhu.14/9, AAVhu.t 19, AAVrh.2, AAVrh.2R, AAVrh.8, AAVrh.8R, AAVrh.10, AAVrh.12, AAVrh.13, AAVrh.13R, AAVrh.14, AAVrh.17, AAVrh.18, AAVrh.19, AAVrh.20, AAVrh.21, AAVrh.22, AAVrh.23, AAVrh.24, AAVrh.25, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.46, AAVrh.48, AAVrh.48.1, AAVrh.48.1.2, AAVrh.48.2, AAVrh.49, AAVrh.51, AAVrh.52, AAVrh.53, AAVrh.54, AAVrh.56, AAVrh.57, AAVrh.58, AAVrh.61, AAVrh.64, AAVrh.64R1, AAVrh.64R2, AAVrh.67, AAVrh.73, AAVrh.74, AAVrh8R, AAVrh8R A586R mutant, AAVrh8R R533A mutant, AAAV, BAAV, caprine AAV, bovine AAV, AAVhE1.1, AAVhEr1.5, AAVhER1.14, AAVhEr1.8, AAVhEr1.16, AAVhEr1.18, AAVhEr1.35, AAVhEr1.7, AAVhEr1.36, AAVhEr2.29, AAVhEr2.4, AAVhEr2.16, AAVhEr2.30, AAVhEr2.31, AAVhEr2.36, AAVhER1.23, AAVhEr3.1, AAV2.5T, AAV-PAEC, AAV-LK01, AAV-LK02, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK16, AAV-LK17, AAV-LK18, AAV-LK19, AAV-PAEC2, AAV-PAEC4, AAV-PAEC6, AAV-PAEC7, AAV-PAEC8, AAV-PAEC11, AAV-PAEC12, AAV-2-pre-miRNA-101, AAV-8h, AAV-8b, AAV-h, AAV-b, AAV SM 10-2, AAV Shuffle 100-1, AAV Shuffle 100-3, AAV Shuffle 100-7, AAV Shuffle 10-2, AAV Shuffle 10-6, AAV Shuffle 10-8, AAV Shuffle 100-2, AAV SM 10-1, AAV SM 10-8, AAV SM 100-3, AAV SM 10-10, BNP61 AAV, BNP62 AAV, BNP63 AAV, AAVrh.50, AAVrh.43, AAVrh.62, AAVrh.48, AAVhu.19, AAVhu.11, AAVhu.53, AAV4-8/rh.64, AAVLG-9/hu.39, AAV54.5/hu.23, AAV54.2/hu.22, AAV54, 7/hu.24, AAV54, 1/hu.21, AAV54.4R/hu.27, AAV46.2/hu.28, AAV46.6/hu.29, AAV128, 1/hu.43, true type AAV (ttAAV), UPENN AAV10, Japanese AAV10 serotypes, AAV CBr-7.1, AAV CBr-7.10, AAV CBr-7.2, AAV CBr-7.3, AAV CBr-7.4, AAV CBr-7.5, AAV CBr-7.7, AAV CBr-7.8, AAV CBr-B7.3, AAV CBr-B7.4, AAV CBr-E1, AAV CBr-E2, AAV CBr-E3, AAV CBr-E4, AAV CBr-E5, AAV CBr-e5, AAV CBr-E6, AAV CBr-E7, AAV CBr-E8, AAV CHt-1, AAV CHt-2, AAV CHt-3, AAV CHt-6.1, AAV CHt-6.10, AAV CHt-6.5, AAV CHt-6.6, AAV CHt-6.7, AAV CHt-6.8, AAV CHt-P1, AAV CHt-P2, AAV CHt-P5, AAV CHt-P6, AAV CHt-P8, AAV CHt-P9, AAV CKd-1, AAV CKd-10, AAV CKd-2, AAV CKd-3, AAV CKd-4, AAV CKd-6, AAV CKd-7, AAV CKd-8, AAV CKd-B1, AAV CKd-B2, AAV CKd-B3, AAV CKd-B4, AAV CKd-B5, AAV CKd-B6, AAV CKd-B7, AAV CKd-B8, AAV CKd-H1, AAV CKd-H2, AAV CKd-H3, AAV CKd-H4, AAV CKd-H5, AAV CKd-H6, AAV CKd-N3, AAV CKd-N4, AAV CKd-N9, AAV CLg-F1, AAV CLg-F2, AAV CLg-F3, AAV CLg-F4, AAV CLg-F5, AAV CLg-F6, AAV CLg-F7, AAV CLg-F8, AAV CLv-1, AAV CLv1-1, AAV Clv1-10, AAV CLv1-2, AAV CLv-12, AAV CLv1-3, AAV CLv-13, AAV CLv1-4, AAV Clv1-7, AAV Clv1-8, AAV Clv1-9, AAV CLv-2, AAV CLv-3, AAV CLv-4, AAV CLv-6, AAV CLv-8, AAV CLv-D1, AAV CLv-D2, AAV CLv-D3, AAV CLv-D4, AAV CLv-D5, AAV CLv-D6, AAV CLv-D7, AAV CLv-D8, AAV CLv-E1, AAV CLv-K1, AAV CLv-K3, AAV CLv-K6, AAV CLv-L4, AAV CLv-L5, AAV CLv-L6, AAV CLv-M1, AAV CLv-M11, AAV CLv-M2, AAV CLv-M5, AAV CLv-M6, AAV CLv-M7, AAV CLv-M8, AAV CLv-M9, AAV CLv-R1, AAV CLv-R2, AAV CLv-R3, AAV CLv-R4, AAV CLv-R5, AAV CLv-R6, AAV CLv-R7, AAV CLv-R8, AAV CLv-R9, AAV CSp-1, AAV CSp-10, AAV CSp-11, AAV CSp-2, AAV CSp-3, AAV CSp-4, AAV CSp-6, AAV CSp-7, AAV CSp-8, AAV CSp-8.10, AAV CSp-8.2, AAV CSp-8.4, AAV CSp-8.5, AAV CSp-8.6, AAV CSp-8.7, AAV CSp-8.8, AAV CSp-8.9, AAV CSp-9, AAV.hu.48R3, AAV.VR-355, AAV3B, AAV4, AAV5, AAVF1/HSC1, AAVF11/HSC11, AAVF12/HSC12, AAVF13/HSC13, AAVF14/HSC14, AAVF15/HSC15, AAVF16/HSC16, AAVF17/HSC17, AAVF2/HSC2, AAVF3/HSC3, AAVF4/HSC4, AAVF5/HSC5, AAVF6/HSC6, AAVF7/HSC7, AAVF8/HSC8, AAVF9/HSC9, AAV-PHP.B (PHP.B), AAV-PHP.A (PHP.A), G2B-26, G2B-13, TH1.1-32, TH1.1-35, AAVPHP.B2, AAVPHP.B3, AAVPHP.N/PHP.B-DGT, AAVPHP.B-EST, AAVPHP.B-GGT, AAVPHP.B-ATP, AAVPHP.B-ATT-T, AAVPHP.B-DGT-T, AAVPHP.B-GGT-T, AAVPHP.B-SGS, AAVPHP.B-AQP, AAVPHP.B-QQP, AAVPHP.B-SNP(3), AAVPHP.B-SNP, AAVPHP.B-QGT, AAVPHP.B-NQT, AAVPHP.B-EGS, AAVPHP.B-SGN, AAVPHP.B-EGT, AAVPHP.B-DST, AAVPHP.B-DST, AAVPHP.B-STP, AAVPHP.B-PQP, AAVPHP.B-SQP, AAVPHP.B-QLP, AAVPHP.B-TMP, AAVPHP.B-TTP, AAVPHP.S/G2A12, AAVG2A15/G2A3, AAVG2B4, AAVG2B5 and variants thereof.

In some embodiments, the AAV serotype may be, or have, a sequence as described in United States Publication No. US20030138772, the contents of which are herein incorporated by reference in their entirety, such as, but not limited to, AAV1 (SEQ ID NO: 6 and 64 of US20030138772), AAV2 (SEQ ID NO: 7 and 70 of US20030138772), AAV3 (SEQ ID NO: 8 and 71 of US20030138772), AAV4 (SEQ ID NO: 63 of US20030138772), AAV5 (SEQ ID NO: 114 of US20030138772), AAV6 (SEQ ID NO: 65 of US20030138772), AAV7 (SEQ ID NO: 1-3 of US20030138772), AAV8 (SEQ ID NO: 4 and 95 of US20030138772), AAV9 (SEQ ID NO: 5 and 100 of US20030138772), AAV10 (SEQ ID NO: 117 of US20030138772), AAV11 (SEQ ID NO: 118 of US20030138772), AAV12 (SEQ ID NO: 119 of US20030138772), AAVrh10 (amino acids 1 to 738 of SEQ ID NO: 81 of US20030138772), AAV16.3 (US20030138772 SEQ ID NO: 10), AAV29.3/bb.1 (US20030138772 SEQ ID NO: 11), AAV29.4 (US20030138772 SEQ ID NO: 12), AAV29.5/bb.2 (US20030138772 SEQ ID NO: 13), AAV1.3 (US20030138772 SEQ ID NO: 14), AAV13.3 (US20030138772 SEQ ID NO: 15), AAV24.1 (US20030138772 SEQ ID NO: 16), AAV27.3 (US20030138772 SEQ ID NO: 17), AAV7.2 (US20030138772 SEQ ID NO: 18), AAVC1 (US20030138772 SEQ ID NO: 19), AAVC3 (US20030138772 SEQ ID NO: 20), AAVC5 (US20030138772 SEQ ID NO: 21), AAVF1 (US20030138772 SEQ ID NO: 22), AAVF3 (US20030138772 SEQ ID NO: 23), AAVF5 (US20030138772 SEQ ID NO: 24), AAVH6 (US20030138772 SEQ ID NO: 25), AAVH2 (US20030138772 SEQ ID NO: 26), AAV42-8 (US20030138772 SEQ ID NO: 27), AAV42-15 (US20030138772 SEQ ID NO: 28), AAV42-5b (US20030138772 SEQ ID NO: 29), AAV42-1b (US20030138772 SEQ ID NO: 30), AAV42-13 (US20030138772 SEQ ID NO: 31), AAV42-3a (US20030138772 SEQ ID NO: 32), AAV42-4 (US20030138772 SEQ ID NO: 33), AAV42-5a (US20030138772 SEQ ID NO: 34), AAV42-10 (US20030138772 SEQ ID NO: 35), AAV42-3b (US20030138772 SEQ ID NO: 36), AAV42-11 (US20030138772 SEQ ID NO: 37), AAV42-6b (US20030138772 SEQ ID NO: 38), AAV43-1 (US20030138772 SEQ ID NO: 39), AAV43-5 (US20030138772 SEQ ID NO: 40), AAV43-12 (US20030138772 SEQ ID NO: 41), AAV43-20 (US20030138772 SEQ ID NO: 42), AAV43-21 (US20030138772 SEQ ID NO: 43), AAV43-23 (US20030138772 SEQ ID NO: 44), AAV43-25 (US20030138772 SEQ ID NO: 45), AAV44.1 (US20030138772 SEQ ID NO: 46), AAV44.5 (US20030138772 SEQ ID NO: 47), AAV223.1 (US20030138772 SEQ ID NO: 48), AAV223.2 (US20030138772 SEQ ID NO: 49), AAV223.4 (US20030138772 SEQ ID NO: 50), AAV223.5 (US20030138772 SEQ ID NO: 51), AAV223.6 (US20030138772 SEQ ID NO: 52), AAV223.7 (US20030138772 SEQ ID NO: 53), AAVA3.4 (US20030138772 SEQ ID NO: 54), AAVA3.5 (US20030138772 SEQ ID NO: 55), AAVA3.7 (US20030138772 SEQ ID NO: 56), AAVA3.3 (US20030138772 SEQ ID NO: 57), AAV42.12 (US20030138772 SEQ ID NO: 58), AAV44.2 (US20030138772 SEQ ID NO: 59), AAV42-2 (US20030138772 SEQ ID NO: 9), or variants thereof.

In some embodiments, the AAV serotype may be, or have, a sequence as described in United States Publication No. US20150159173, the contents of which are herein incorporated by reference in their entirety, such as, but not limited to, AAV2 (SEQ ID NO: 7 and 23 of US20150159173), rh20 (SEQ ID NO: 1 of US20150159173), rh32/33 (SEQ ID NO: 2 of US20150159173), rh39 (SEQ ID NO: 3, 20 and 36 of US20150159173), rh46 (SEQ ID NO: 4 and 22 of US20150159173), rh73 (SEQ ID NO: 5 of US20150159173), rh74 (SEQ ID NO: 6 of US20150159173), AAV6.1 (SEQ ID NO: 29 of US20150159173), rh.8 (SEQ ID NO: 41 of US20150159173), rh.48.1 (SEQ ID NO: 44 of US20150159173), hu.44 (SEQ ID NO: 45 of US20150159173), hu.29 (SEQ ID NO: 42 of US20150159173), hu.48 (SEQ ID NO: 38 of US20150159173), rh54 (SEQ ID NO: 49 of US20150159173), AAV2 (SEQ ID NO: 7 of US20150159173), cy.5 (SEQ ID NO: 8 and 24 of US20150159173), rh.10 (SEQ ID NO: 9 and 25 of US20150159173), rh.13 (SEQ ID NO: 10 and 26 of US20150159173), AAV1 (SEQ ID NO: 11 and 27 of US20150159173), AAV3 (SEQ ID NO: 12 and 28 of US20150159173), AAV6 (SEQ ID NO: 13 and 29 of US20150159173), AAV7 (SEQ ID NO: 14 and 30 of US20150159173), AAV8 (SEQ ID NO: 15 and 31 of US20150159173), hu.13 (SEQ ID NO: 16 and 32 of US20150159173), hu.26 (SEQ ID NO: 17 and 33 of US20150159173), hu.37 (SEQ ID NO: 18 and 34 of US20150159173), hu.53 (SEQ ID NO: 19 and 35 of US20150159173), rh.43 (SEQ ID NO: 21 and 37 of US20150159173), rh2 (SEQ ID NO: 39 of US20150159173), rh.37 (SEQ ID NO: 40 of US20150159173), rh.64 (SEQ ID NO: 43 of US20150159173), rh.48 (SEQ ID NO: 44 of US20150159173), ch.5 (SEQ ID NO 46 of US20150159173), rh.67 (SEQ ID NO: 47 of US20150159173), rh.58 (SEQ ID NO: 48 of US20150159173), or variants thereof including, but not limited to Cy5R1, Cy5R2, Cy5R3, Cy5R4, rh.13R, rh.37R2, rh.2R, rh.8R, rh.48.1, rh.48.2, rh.48.1.2, hu.44R1, hu.44R2, hu.44R3, hu.29R, ch.5R1, rh64R1, rh64R2, AAV6.2, AAV6.1, AAV6.12, hu.48R1, hu.48R2, and hu.48R3.

In some embodiments, the AAV serotype may be, or have, a sequence as described in U.S. Pat. No. 7,198,951, the contents of which are herein incorporated by reference in their entirety, such as, but not limited to, AAV9 (SEQ ID NO: 1-3 of U.S. Pat. No. 7,198,951), AAV2 (SEQ ID NO: 4 of U.S. Pat. No. 7,198,951), AAV1 (SEQ ID NO: 5 of U.S. Pat. No. 7,198,951), AAV3 (SEQ ID NO: 6 of U.S. Pat. No. 7,198,951), and AAV8 (SEQ ID NO: 7 of U.S. Pat. No. 7,198,951).

In some embodiments, the AAV serotype may be, or have, a mutation in the AAV9 sequence as described by N Pulicherla et al. (Molecular Therapy 19(6): 1070-1078 (2011), herein incorporated by reference in its entirety), such as but not limited to, AAV9.9, AAV9.11, AAV9.13, AAV9.16, AAV9.24, AAV9.45, AAV9.47, AAV9.61, AAV9.68, AAV9.84.

In some embodiments, the AAV serotype may be, or have, a sequence as described in U.S. Pat. No. 6,156,303, the contents of which are herein incorporated by reference in their entirety, such as, but not limited to, AAV3B (SEQ ID NO: 1 and 10 of U.S. Pat. No. 6,156,303), AAV6 (SEQ ID NO: 2, 7 and 11 of U.S. Pat. No. 6,156,303), AAV2 (SEQ ID NO: 3 and 8 of U.S. Pat. No. 6,156,303), AAV3A (SEQ ID NO: 4 and 9, of U.S. Pat. No. 6,156,303), or derivatives thereof.

In some embodiments, the AAV serotype may be, or have, a sequence as described in United States Publication No. US20140359799, the contents of which are herein incorporated by reference in their entirety, such as, but not limited to, AAV8 (SEQ ID NO: 1 of US20140359799), AAVDJ (SEQ ID NO: 2 and 3 of US20140359799), or variants thereof.

In some embodiments, the serotype may be AAVDJ (or AAV-DJ) or a variant thereof, such as AAVDJ8 (or AAV-DJ8), as described by Grimm et al. (Journal of Virology 82(12): 5887-5911 (2008), herein incorporated by reference in its entirety). The amino acid sequence of AAVDJ8 may comprise two or more mutations in order to remove the heparin binding domain (HBD). As a non-limiting example, the AAV-DJ sequence described as SEQ ID NO: 1 in U.S. Pat. No. 7,588,772, the contents of which are herein incorporated by reference in their entirety, may comprise two mutations: (1) R587Q where arginine (R; Arg) at amino acid 587 is changed to glutamine (Q; Gln) and (2) R590T where arginine (R; Arg) at amino acid 590 is changed to threonine (T; Thr). As another non-limiting example, may comprise three mutations: (1) K406R where lysine (K; Lys) at amino acid 406 is changed to arginine (R; Arg), (2) R587Q where arginine (R; Arg) at amino acid 587 is changed to glutamine (Q; Gln) and (3) R590T where arginine (R; Arg) at amino acid 590 is changed to threonine (T; Thr).

In some embodiments, the AAV serotype may be, or have, a sequence of AAV4 as described in International Publication No. WO 1998011244, the contents of which are herein incorporated by reference in their entirety, such as, but not limited to AAV4 (SEQ ID NO: 1-20 of WO1998011244).

In some embodiments, the AAV serotype may be, or have, a mutation in the AAV2 sequence to generate AAV2G9 as described in International Publication No. WO2014144229 and herein incorporated by reference in its entirety.

In some embodiments, the AAV serotype may be, or have, a sequence as described in International Publication No. WO2005033321, the contents of which are herein incorporated by reference in their entirety, such as, but not limited to AAV3-3 (SEQ ID NO: 217 of WO2005033321), AAV1 (SEQ ID NO: 219 and 202 of WO2005033321), AAV106.1/hu.37 (SEQ ID No: 10 of WO2005033321), AAV114.3/hu.40 (SEQ ID No: 11 of WO2005033321), AAV127.2/hu.41 (SEQ ID NO:6 and 8 of WO2005033321), AAV128.3/hu.44 (SEQ ID No: 81 of WO2005033321), AAV130.4/hu.48 (SEQ ID NO: 78 of WO2005033321), AAV145.1/hu.53 (SEQ ID No: 176 and 177 of WO2005033321), AAV145.6/hu.56 (SEQ ID NO: 168 and 192 of WO2005033321), AAV16.12/hu.11 (SEQ ID NO: 153 and 57 of WO2005033321), AAV16.8/hu.10 (SEQ ID NO: 156 and 56 of WO02005033321), AAV161.10/hu.60 (SEQ ID No: 170 of WO2005033321), AAV161.6/hu.61 (SEQ ID No: 174 of WO2005033321), AAV1-7/rh.48 (SEQ ID NO: 32 of WO2005033321), AAV1-8/rh.49 (SEQ ID NOs: 103 and 25 of WO2005033321), AAV2 (SEQ ID NO: 211 and 221 of WO2005033321), AAV2-15/rh.62 (SEQ ID No: 33 and 114 of WO2005033321), AAV2-3/rh.61 (SEQ ID NO: 21 of WO2005033321), AAV2-4/rh.50 (SEQ ID No: 23 and 108 of WO2005033321), AAV2-5/rh.51 (SEQ ID NO: 104 and 22 of WO2005033321), AAV3.1/hu.6 (SEQ ID NO: 5 and 84 of WO2005033321), AAV3.1/hu.9 (SEQ ID NO: 155 and 58 of WO2005033321), AAV3-11/rh.53 (SEQ ID NO: 186 and 176 of WO2005033321), AAV3-3 (SEQ ID NO: 200 of WO2005033321), AAV33.12/hu.17 (SEQ ID NO:4 of WO2005033321), AAV33.4/hu.15 (SEQ ID No: 50 of WO2005033321), AAV33.8/hu.16 (SEQ ID No: 51 of WO2005033321), AAV3-9/rh.52 (SEQ ID NO: 96 and 18 of WO2005033321), AAV4-19/rh.55 (SEQ ID NO: 117 of WO2005033321), AAV4-4 (SEQ ID NO: 201 and 218 of WO2005033321), AAV4-9/rh.54 (SEQ ID NO: 116 of WO2005033321), AAV5 (SEQ ID NO: 199 and 216 of WO2005033321), AAV52.1/hu.20 (SEQ ID NO: 63 of WO2005033321), AAV52/hu.19 (SEQ ID NO: 133 of WO2005033321), AAV5-22/rh.58 (SEQ ID No: 27 of WO2005033321), AAV5-3/rh.57 (SEQ ID NO: 105 of WO2005033321), AAV5-3/rh.57 (SEQ ID No: 26 of WO2005033321), AAV58.2/hu.25 (SEQ ID No: 49 of WO2005033321), AAV6 (SEQ ID NO: 203 and 220 of WO2005033321), AAV7 (SEQ ID NO: 222 and 213 of WO2005033321), AAV7.3/hu.7 (SEQ ID No: 55 of WO2005033321), AAV8 (SEQ ID NO: 223 and 214 of WO2005033321), AAVH-1/hu.1 (SEQ ID No: 46 of WO2005033321), AAVH-5/hu.3 (SEQ ID No: 44 of WO2005033321), AAVhu.1 (SEQ ID NO: 144 of WO2005033321), AAVhu.10 (SEQ ID NO: 156 of WO2005033321), AAVhu.11 (SEQ ID NO: 153 of WO2005033321), AAVhu.12 (WO2005033321 SEQ ID NO: 59), AAVhu.13 (SEQ ID NO: 129 of WO2005033321), AAVhu.14/AAV9 (SEQ ID NO: 123 and 3 of WO2005033321), AAVhu.15 (SEQ ID NO: 147 of WO2005033321), AAVhu.16 (SEQ ID NO: 148 of WO2005033321), AAVhu.17 (SEQ ID NO: 83 of WO2005033321), AAVhu.18 (SEQ ID NO: 149 of WO2005033321), AAVhu.19 (SEQ ID NO: 133 of WO2005033321), AAVhu.2 (SEQ ID NO: 143 of WO2005033321), AAVhu.20 (SEQ ID NO: 134 of WO2005033321), AAVhu.21 (SEQ ID NO: 135 of WO2005033321), AAVhu.22 (SEQ ID NO: 138 of WO2005033321), AAVhu.23.2 (SEQ ID NO: 137 of WO02005033321), AAVhu.24 (SEQ ID NO: 136 of WO2005033321), AAVhu.25 (SEQ ID NO: 146 of WO2005033321), AAVhu.27 (SEQ ID NO: 140 of WO2005033321), AAVhu.29 (SEQ ID NO: 132 of WO2005033321), AAVhu.3 (SEQ ID NO: 145 of WO2005033321), AAVhu.31 (SEQ ID NO: 121 of WO2005033321), AAVhu.32 (SEQ ID NO: 122 of WO2005033321), AAVhu.34 (SEQ ID NO: 125 of WO2005033321), AAVhu.35 (SEQ ID NO: 164 of WO2005033321), AAVhu.37 (SEQ ID NO: 88 of WO2005033321), AAVhu.39 (SEQ ID NO: 102 of WO2005033321), AAVhu.4 (SEQ ID NO: 141 of WO2005033321), AAVhu.40 (SEQ ID NO: 87 of WO2005033321), AAVhu.41 (SEQ ID NO: 91 of WO2005033321), AAVhu.42 (SEQ ID NO: 85 of WO2005033321), AAVhu.43 (SEQ ID NO: 160 of WO2005033321), AAVhu.44 (SEQ ID NO: 144 of WO2005033321), AAVhu.45 (SEQ ID NO: 127 of WO2005033321), AAVhu.46 (SEQ ID NO: 159 of WO2005033321), AAVhu.47 (SEQ ID NO: 128 of WO2005033321), AAVhu.48 (SEQ ID NO: 157 of WO2005033321), AAVhu.49 (SEQ ID NO: 189 of WO2005033321), AAVhu.51 (SEQ ID NO: 190 of WO2005033321), AAVhu.52 (SEQ ID NO: 191 of WO2005033321), AAVhu.53 (SEQ ID NO: 186 of WO2005033321), AAVhu.54 (SEQ ID NO: 188 of WO02005033321), AAVhu.55 (SEQ ID NO: 187 of WO02005033321), AAVhu.56 (SEQ ID NO: 192 of WO2005033321), AAVhu.57 (SEQ ID NO: 193 of WO2005033321), AAVhu.58 (SEQ ID NO: 194 of WO2005033321), AAVhu.6 (SEQ ID NO: 84 of WO2005033321), AAVhu.60 (SEQ ID NO: 184 of WO2005033321), AAVhu.61 (SEQ ID NO: 185 of WO2005033321), AAVhu.63 (SEQ ID NO: 195 of WO2005033321), AAVhu.64 (SEQ ID NO: 196 of WO2005033321), AAVhu.66 (SEQ ID NO: 197 of WO2005033321), AAVhu.67 (SEQ ID NO: 198 of WO2005033321), AAVhu.7 (SEQ ID NO: 150 of WO2005033321), AAVhu.8 (WO2005033321 SEQ ID NO: 12), AAVhu.9 (SEQ ID NO: 155 of WO2005033321), AAVLG-10/rh.40 (SEQ ID No: 14 of WO2005033321), AAVLG-4/rh.38 (SEQ ID NO: 86 of WO2005033321), AAVLG-4/rh.38 (SEQ ID No: 7 of WO2005033321), AAVN721-8/rh.43 (SEQ ID NO: 163 of WO2005033321), AAVN721-8/rh.43 (SEQ ID No: 43 of WO2005033321), AAVpi.1 (WO2005033321 SEQ ID NO: 28), AAVpi.2 (WO2005033321 SEQ ID NO: 30), AAVpi.3 (WO2005033321 SEQ ID NO: 29), AAVrh.38 (SEQ ID NO: 86 of WO2005033321), AAVrh.40 (SEQ ID NO: 92 of WO2005033321), AAVrh.43 (SEQ ID NO: 163 of WO2005033321), AAVrh.44 (WO2005033321 SEQ ID NO: 34), AAVrh.45 (WO2005033321 SEQ ID NO: 41), AAVrh.47 (WO02005033321 SEQ ID NO: 38), AAVrh.48 (SEQ ID NO: 115 of WO2005033321), AAVrh.49 (SEQ ID NO: 103 of WO2005033321), AAVrh.50 (SEQ ID NO: 108 of WO2005033321), AAVrh.51 (SEQ ID NO: 104 of WO2005033321), AAVrh.52 (SEQ ID NO: 96 of WO2005033321), AAVrh.53 (SEQ ID NO: 97 of WO2005033321), AAVrh.55 (WO2005033321 SEQ ID NO: 37), AAVrh.56 (SEQ ID NO: 152 of WO2005033321), AAVrh.57 (SEQ ID NO: 105 of WO2005033321), AAVrh.58 (SEQ ID NO: 106 of WO2005033321), AAVrh.59 (WO2005033321 SEQ ID NO: 42), AAVrh.60 (WO2005033321 SEQ ID NO: 31), AAVrh.61 (SEQ ID NO: 107 of WO02005033321), AAVrh.62 (SEQ ID NO: 114 of WO2005033321), AAVrh.64 (SEQ ID NO: 99 of WO2005033321), AAVrh.65 (WO2005033321 SEQ ID NO: 35), AAVrh.68 (WO2005033321 SEQ ID NO: 16), AAVrh.69 (WO2005033321 SEQ ID NO: 39), AAVrh.70 (WO2005033321 SEQ ID NO: 20), AAVrh.72 (WO2005033321 SEQ ID NO: 9), or variants thereof including, but not limited to, AAVcy.2, AAVcy.3, AAVcy.4, AAVcy.5, AAVcy.6, AAVrh.12, AAVrh.17, AAVrh.18, AAVrh.19, AAVrh.21, AAVrh.22, AAVrh.23, AAVrh.24, AAVrh.25, AAVrh.25/42 15, AAVrh.31, AAVrh.32, AAVrh.33, AAVrh.34, AAVrh.35, AAVrh.36, AAVrh.37, AAVrh14. Non limiting examples of variants include SEQ ID NO: 13, 15, 17, 19, 24, 36, 40, 45, 47, 48, 51-54, 60-62, 64-77, 79, 80, 82, 89, 90, 93-95, 98, 100, 101, 109-113, 118-120, 124, 126, 131, 139, 142, 151, 154, 158, 161, 162, 165-183, 202, 204-212, 215, 219, 224-236, of WO2005033321, the contents of which are herein incorporated by reference in their entirety.

In some embodiments, the AAV serotype may be, or have, a sequence as described in International Publication No. WO2015168666, the contents of which are herein incorporated by reference in their entirety, such as, but not limited to, AAVrh8R (SEQ ID NO: 9 of WO2015168666), AAVrh8R A586R mutant (SEQ ID NO: 10 of WO2015168666), AAVrh8R R533A mutant (SEQ ID NO: 11 of WO2015168666), or variants thereof.

In some embodiments, the AAV serotype may be, or have, a sequence as described in U.S. Pat. No. 9,233,131, the contents of which are herein incorporated by reference in their entirety, such as, but not limited to, AAVhE1.1 (SEQ ID NO:44 of U.S. Pat. No. 9,233,131), AAVhEr1.5 (SEQ ID NO:45 of U.S. Pat. No. 9,233,131), AAVhER1.14 (SEQ ID NO:46 of U.S. Pat. No. 9,233,131), AAVhEr1.8 (SEQ ID NO:47 of U.S. Pat. No. 9,233,131), AAVhEr1.16 (SEQ ID NO:48 of U.S. Pat. No. 9,233,131), AAVhEr1.18 (SEQ ID NO:49 of U.S. Pat. No. 9,233,131), AAVhEr1.35 (SEQ ID NO:50 of U.S. Pat. No. 9,233,131), AAVhEr1.7 (SEQ ID NO:51 of U.S. Pat. No. 9,233,131), AAVhEr1.36 (SEQ ID NO:52 of U.S. Pat. No. 9,233,131), AAVhEr2.29 (SEQ ID NO:53 of U.S. Pat. No. 9,233,131), AAVhEr2.4 (SEQ ID NO:54 of U.S. Pat. No. 9,233,131), AAVhEr2.16 (SEQ ID NO:55 of U.S. Pat. No. 9,233,131), AAVhEr2.30 (SEQ ID NO:56 of U.S. Pat. No. 9,233,131), AAVhEr2.31 (SEQ ID NO:58 of U.S. Pat. No. 9,233,131), AAVhEr2.36 (SEQ ID NO:57 of U.S. Pat. No. 9,233,131), AAVhER1.23 (SEQ ID NO:53 of U.S. Pat. No. 9,233,131), AAVhEr3.1 (SEQ ID NO:59 of U.S. Pat. No. 9,233,131), AAV2.5T (SEQ ID NO:42 of U.S. Pat. No. 9,233,131), or variants thereof.

In some embodiments, the AAV serotype may be, or have, a sequence as described in United States Patent Publication No. US20150376607, the contents of which are herein incorporated by reference in their entirety, such as, but not limited to, AAV-PAEC (SEQ ID NO:1 of US20150376607), AAV-LK01 (SEQ ID NO:2 of US20150376607), AAV-LK02 (SEQ ID NO:3 of US20150376607), AAV-LK03 (SEQ ID NO:4 of US20150376607), AAV-LK04 (SEQ ID NO:5 of US20150376607), AAV-LK05 (SEQ ID NO:6 of US20150376607), AAV-LK06 (SEQ ID NO:7 of US20150376607), AAV-LK07 (SEQ ID NO:8 of US20150376607), AAV-LK08 (SEQ ID NO:9 of US20150376607), AAV-LK09 (SEQ ID NO: 10 of US20150376607), AAV-LK10 (SEQ ID NO: 11 of US20150376607), AAV-LK11 (SEQ ID NO:12 of US20150376607), AAV-LK12 (SEQ ID NO: 13 of US20150376607), AAV-LK13 (SEQ ID NO: 14 of US20150376607), AAV-LK14 (SEQ ID NO: 15 of US20150376607), AAV-LK15 (SEQ ID NO: 16 of US20150376607), AAV-LK16 (SEQ ID NO: 17 of US20150376607), AAV-LK17 (SEQ ID NO:18 of US20150376607), AAV-LK18 (SEQ ID NO: 19 of US20150376607), AAV-LK19 (SEQ ID NO:20 of US20150376607), AAV-PAEC2 (SEQ ID NO:21 of US20150376607), AAV-PAEC4 (SEQ ID NO:22 of US20150376607), AAV-PAEC6 (SEQ ID NO:23 of US20150376607), AAV-PAEC7 (SEQ ID NO:24 of US20150376607), AAV-PAEC8 (SEQ ID NO:25 of US20150376607), AAV-PAEC11 (SEQ ID NO:26 of US20150376607), AAV-PAEC12 (SEQ ID NO:27 of US20150376607), or variants thereof.

In some embodiments, the AAV serotype may be, or have, a sequence as described in U.S. Pat. No. 9,163,261, the contents of which are herein incorporated by reference in their entirety, such as, but not limited to, AAV-2-pre-miRNA-101 (SEQ ID NO: 1 U.S. Pat. No. 9,163,261), or variants thereof.

In some embodiments, the AAV serotype may be, or have, a sequence as described in United States Patent Publication No. US20150376240, the contents of which are herein incorporated by reference in their entirety, such as, but not limited to, AAV-8h (SEQ ID NO: 6 of US20150376240), AAV-8b (SEQ ID NO: 5 of US20150376240), AAV-h (SEQ ID NO: 2 of US20150376240), AAV-b (SEQ ID NO: 1 of US20150376240), or variants thereof.

In some embodiments, the AAV serotype may be, or have, a sequence as described in United States Patent Publication No. US20160017295, the contents of which are herein incorporated by reference in their entirety, such as, but not limited to, AAV SM 10-2 (SEQ ID NO: 22 of US20160017295), AAV Shuffle 100-1 (SEQ ID NO: 23 of US20160017295), AAV Shuffle 100-3 (SEQ ID NO: 24 of US20160017295), AAV Shuffle 100-7 (SEQ ID NO: 25 of US20160017295), AAV Shuffle 10-2 (SEQ ID NO: 34 of US20160017295), AAV Shuffle 10-6 (SEQ ID NO: 35 of US20160017295), AAV Shuffle 10-8 (SEQ ID NO: 36 of US20160017295), AAV Shuffle 100-2 (SEQ ID NO: 37 of US20160017295), AAV SM 10-1 (SEQ ID NO: 38 of US20160017295), AAV SM 10-8 (SEQ ID NO: 39 of US20160017295), AAV SM 100-3 (SEQ ID NO: 40 of US20160017295), AAV SM 100-10 (SEQ ID NO: 41 of US20160017295), or variants thereof.

In some embodiments, the AAV serotype may be, or have, a sequence as described in United States Patent Publication No. US20150238550, the contents of which are herein incorporated by reference in their entirety, such as, but not limited to, BNP61 AAV (SEQ ID NO: 1 of US20150238550), BNP62 AAV (SEQ ID NO: 3 of US20150238550), BNP63 AAV (SEQ ID NO: 4 of US20150238550), or variants thereof.

In some embodiments, the AAV serotype may be or may have a sequence as described in United States Patent Publication No. US20150315612, the contents of which are herein incorporated by reference in their entirety, such as, but not limited to, AAVrh.50 (SEQ ID NO: 108 of US20150315612), AAVrh.43 (SEQ ID NO: 163 of US20150315612), AAVrh.62 (SEQ ID NO: 114 of US20150315612), AAVrh.48 (SEQ ID NO: 115 of US20150315612), AAVhu.19 (SEQ ID NO: 133 of US20150315612), AAVhu.11 (SEQ ID NO: 153 of US20150315612), AAVhu.53 (SEQ ID NO: 186 of US20150315612), AAV4-8/rh.64 (SEQ ID No: 15 of US20150315612), AAVLG-9/hu.39 (SEQ ID No: 24 of US20150315612), AAV54.5/hu.23 (SEQ ID No: 60 of US20150315612), AAV54.2/hu.22 (SEQ ID No: 67 of US20150315612), AAV54.7/hu.24 (SEQ ID No: 66 of US20150315612), AAV54.1/hu.21 (SEQ ID No: 65 of US20150315612), AAV54.4R/hu.27 (SEQ ID No: 64 of US20150315612), AAV46.2/hu.28 (SEQ ID No: 68 of US20150315612), AAV46.6/hu.29 (SEQ ID No: 69 of US20150315612), AAV128.1/hu.43 (SEQ ID No: 80 of US20150315612), or variants thereof.

In some embodiments, the AAV serotype may be, or have, a sequence as described in International Publication No. WO2015121501, the contents of which are herein incorporated by reference in their entirety, such as, but not limited to, true type AAV (ttAAV) (SEQ ID NO: 2 of WO2015121501), "UPenn AAV10" (SEQ ID NO: 8 of WO2015121501), "Japanese AAV10" (SEQ ID NO: 9 of WO2015121501), or variants thereof.

According to the present invention, AAV capsid serotype selection or use may be from a variety of species. In one embodiment, the AAV may be an avian AAV (AAAV). The AAAV serotype may be, or have, a sequence as described in U.S. Pat. No. 9,238,800, the contents of which are herein incorporated by reference in their entirety, such as, but not limited to, AAAV (SEQ ID NO: 1, 2, 4, 6, 8, 10, 12, and 14 of U.S. Pat. No. 9,238,800), or variants thereof.

In one embodiment, the AAV may be a bovine AAV (BAAV). The BAAV serotype may be, or have, a sequence as described in U.S. Pat. No. 9,193,769, the contents of which are herein incorporated by reference in their entirety, such as, but not limited to, BAAV (SEQ ID NO: 1 and 6 of U.S. Pat. No. 9,193,769), or variants thereof. The BAAV serotype may be or have a sequence as described in U.S. Pat. No. 7,427,396, the contents of which are herein incorporated by reference in their entirety, such as, but not limited to, BAAV (SEQ ID NO: 5 and 6 of U.S. Pat. No. 7,427,396), or variants thereof.

In one embodiment, the AAV may be a caprine AAV. The caprine AAV serotype may be, or have, a sequence as described in U.S. Pat. No. 7,427,396, the contents of which are herein incorporated by reference in their entirety, such as, but not limited to, caprine AAV (SEQ ID NO: 3 of U.S. Pat. No. 7,427,396), or variants thereof.

In other embodiments the AAV may be engineered as a hybrid AAV from two or more parental serotypes. In one embodiment, the AAV may be AAV2G9 which comprises sequences from AAV2 and AAV9. The AAV2G9 AAV serotype may be, or have, a sequence as described in United States Patent Publication No. US20160017005, the contents of which are herein incorporated by reference in its entirety.

In one embodiment, the AAV may be a serotype generated by the AAV9 capsid library with mutations in amino acids 390-627 (VP1 numbering) as described by Pulicherla et al. (Molecular Therapy 19(6): 1070-1078 (2011), the contents of which are herein incorporated by reference in their entirety. The serotype and corresponding nucleotide and amino acid substitutions may be, but is not limited to, AAV9.1 (G1594C; D532H), AAV6.2 (T1418A and T1436X; V473D and I479K), AAV9.3 (T1238A; F413Y), AAV9.4 (T1250C and A1617T; F417S), AAV9.5 (A1235G, A1314T, A1642G, C1760T; Q412R, T548A, A587V), AAV9.6 (T1231A; F411I), AAV9.9 (G1203A, G1785T; W595C), AAV9.10 (A1500G, T1676C; M559T), AAV9.11 (A1425T, A1702C, A1769T; T568P, Q590L), AAV9.13 (A1369C, A1720T; N457H, T574S), AAV9.14 (T1340A, T1362C, T1560C, G1713A; L447H), AAV9.16 (A1775T; Q592L), AAV9.24 (T1507C, T1521G; W503R), AAV9.26 (A1337G, A1769C; Y446C, Q590P), AAV9.33 (A1667C; D556A), AAV9.34 (A1534G, C1794T N512D), AAV9.35 (A1289T, T1450A, C1494T, A1515T, C1794A, G1816A; Q430L, Y484N, N98K, V606I), AAV9.40 (A1694T, E565V), AAV9.41 (A1348T, T1362C; T450S), AAV9.44 (A1684C, A1701T, A1737G; N562H, K567N), AAV9.45 (A1492T, C1804T; N498Y, L602F), AAV9.46 (G1441C, T1525C, T1549G; G481R, W509R, L517V), 9.47 (G1241A, G1358A, A1669G, C1745T; S414N, G453D, K557E, T582I), AAV9.48 (C1445T, A1736T; P482L, Q579L), AAV9.50 (A1638T, C1683T, T1805A; Q546H, L602H), AAV9.53 (G1301A, A1405C, C1664T, G1811T; R134Q, S469R, A555V, G604V), AAV9.54 (C1531A, T1609A; L511I, L537M), AAV9.55 (T1605A; F535L), AAV9.58 (C1475T, C1579A, T492I, H527N), AAV.59 (T1336C; Y446H), AAV9.61 (A1493T; N498I), AAV9.64 (C1531A, A1617T; L511I), AAV9.65 (C1335T, T1530C, C1568A; A523D), AAV9.68 (C1510A; P504T), AAV9.80 (G1441A; G481R), AAV9.83 (C1402A, A1500T; P468T, E500D), AAV9.87 (T1464C, T1468C; S490P), AAV9.90 (A1196T; Y399F), AAV9.91 (T1316G, A1583T, C1782G, T1806C; L439R, K528I), AAV9.93 (A1273G, A1421G, A1638C, C1712T, G1732A, A1744T, A1832T; S425G, Q474R, Q546H, P571L, G578R, T582S, D611V), AAV9.94 (A1675T; M559L) and AAV9.95 (T1605A; F535L).

In some embodiments, the AAV serotype may be, or have, a sequence as described in International Publication No. WO2016049230, the contents of which are herein incorporated by reference in their entirety, such as, but not limited to AAVF1/HSC1 (SEQ ID NO: 2 and 20 of WO2016049230), AAVF2/HSC2 (SEQ ID NO: 3 and 21 of WO2016049230), AAVF3/HSC3 (SEQ ID NO: 5 and 22 of WO2016049230), AAVF4/HSC4 (SEQ ID NO: 6 and 23 of WO2016049230), AAVF5/HSC5 (SEQ ID NO: 11 and 25 of WO2016049230), AAVF6/HSC6 (SEQ ID NO: 7 and 24 of WO2016049230), AAVF7/HSC7 (SEQ ID NO: 8 and 27 of WO02016049230), AAVF8/HSC8 (SEQ ID NO: 9 and 28 of WO2016049230), AAVF9/HSC9 (SEQ ID NO: 10 and 29 of WO2016049230), AAVF11/HSC11 (SEQ ID NO: 4 and 26 of WO2016049230), AAVF12/HSC12 (SEQ ID NO: 12 and 30 of WO2016049230), AAVF13/HSC13 (SEQ ID NO: 14 and 31 of WO2016049230), AAVF14/HSC14 (SEQ ID NO: 15 and 32 of WO2016049230), AAVF15/HSC15 (SEQ ID NO: 16 and 33 of WO2016049230), AAVF16/HSC16 (SEQ ID NO: 17 and 34 of WO2016049230), AAVF17/HSC17 (SEQ ID NO: 13 and 35 of WO2016049230), or variants or derivatives thereof.

In some embodiments, the AAV serotype may be, or have, a sequence as described in U.S. Pat. No. 8,734,809, the contents of which are herein incorporated by reference in their entirety, such as, but not limited to, AAV CBr-E1 (SEQ ID NO: 13 and 87 of U.S. Pat. No. 8,734,809), AAV CBr-E2 (SEQ ID NO: 14 and 88 of U.S. Pat. No. 8,734,809), AAV CBr-E3 (SEQ ID NO: 15 and 89 of U.S. Pat. No. 8,734,809), AAV CBr-E4 (SEQ ID NO: 16 and 90 of U.S. Pat. No. 8,734,809), AAV CBr-E5 (SEQ ID NO: 17 and 91 of U.S. Pat. No. 8,734,809), AAV CBr-e5 (SEQ ID NO: 18 and 92 of U.S. Pat. No. 8,734,809), AAV CBr-E6 (SEQ ID NO: 19 and 93 of U.S. Pat. No. 8,734,809), AAV CBr-E7 (SEQ ID NO: 20 and 94 of U.S. Pat. No. 8,734,809), AAV CBr-E8 (SEQ ID NO: 21 and 95 of U.S. Pat. No. 8,734,809), AAV CLv-D1 (SEQ ID NO: 22 and 96 of U.S. Pat. No. 8,734,809), AAV CLv-D2 (SEQ ID NO: 23 and 97 of U.S. Pat. No. 8,734,809), AAV CLv-D3 (SEQ ID NO: 24 and 98 of U.S. Pat. No. 8,734,809), AAV CLv-D4 (SEQ ID NO: 25 and 99 of U.S. Pat. No. 8,734,809), AAV CLv-D5 (SEQ ID NO: 26 and 100 of U.S. Pat. No. 8,734,809), AAV CLv-D6 (SEQ ID NO: 27 and 101 of U.S. Pat. No. 8,734,809), AAV CLv-D7 (SEQ ID NO: 28 and 102 of U.S. Pat. No. 8,734,809), AAV CLv-D8 (SEQ ID NO: 29 and 103 of U.S. Pat. No. 8,734, 809), AAV CLv-E1 (SEQ ID NO: 13 and 87 of U.S. Pat. No. 8,734,809), AAV CLv-R1 (SEQ ID NO: 30 and 104 of U.S. Pat. No. 8,734,809), AAV CLv-R2 (SEQ ID NO: 31 and 105 of U.S. Pat. No. 8,734,809), AAV CLv-R3 (SEQ ID NO: 32 and 106 of U.S. Pat. No. 8,734,809), AAV CLv-R4 (SEQ ID NO: 33 and 107 of U.S. Pat. No. 8,734,809), AAV CLv-R5 (SEQ ID NO: 34 and 108 of U.S. Pat. No. 8,734,809), AAV CLv-R6 (SEQ ID NO: 35 and 109 of U.S. Pat. No. 8,734, 809), AAV CLv-R7 (SEQ ID NO: 36 and 110 of U.S. Pat. No. 8,734,809), AAV CLv-R8 (SEQ ID NO: 37 and 111 of U.S. Pat. No. 8,734,809), AAV CLv-R9 (SEQ ID NO: 38 and 112 of US8734809), AAV CLg-F1 (SEQ ID NO: 39 and 113 of U.S. Pat. No. 8,734,809), AAV CLg-F2 (SEQ ID NO: 40 and 114 of U.S. Pat. No. 8,734,809), AAV CLg-F3 (SEQ ID NO: 41 and 115 of U.S. Pat. No. 8,734,809), AAV CLg-F4 (SEQ ID NO: 42 and 116 of U.S. Pat. No. 8,734, 809), AAV CLg-F5 (SEQ ID NO: 43 and 117 of U.S. Pat. No. 8,734,809), AAV CLg-F6 (SEQ ID NO: 43 and 117 of U.S. Pat. No. 8,734,809), AAV CLg-F7 (SEQ ID NO: 44 and 118 of U.S. Pat. No. 8,734,809), AAV CLg-F8 (SEQ ID NO: 43 and 17 of U.S. Pat. No. 8,734,809), AAV CSp-1 (SEQ ID NO: 45 and 119 of U.S. Pat. No. 8,734,809), AAV CSp-10 (SEQ ID NO: 46 and 120 of U.S. Pat. No. 8,734,809), AAV CSp-11 (SEQ ID NO: 47 and 121 of U.S. Pat. No. 8,734, 809), AAV CSp-2 (SEQ ID NO: 48 and 122 of U.S. Pat. No. 8,734,809), AAV CSp-3 (SEQ ID NO: 49 and 123 of U.S. Pat. No. 8,734,809), AAV CSp-4 (SEQ ID NO: 50 and 124 of U.S. Pat. No. 8,734,809), AAV CSp-6 (SEQ ID NO: 51 and 125 of U.S. Pat. No. 8,734,809), AAV CSp-7 (SEQ ID NO: 52 and 126 of U.S. Pat. No. 8,734,809), AAV CSp-8 (SEQ ID NO: 53 and 127 of U.S. Pat. No. 8,734,809), AAV CSp-9 (SEQ ID NO: 54 and 128 of U.S. Pat. No. 8,734,809), AAV CHt-2 (SEQ ID NO: 55 and 129 of U.S. Pat. No. 8,734,809), AAV CHt-3 (SEQ ID NO: 56 and 130 of U.S. Pat. No. 8,734,809), AAV CKd-1 (SEQ ID NO: 57 and 131 of U.S. Pat. No. 8,734,809), AAV CKd-10 (SEQ ID NO: 58 and 132 of U.S. Pat. No. 8,734,809), AAV CKd-2 (SEQ ID NO: 59 and 133 of U.S. Pat. No. 8,734,809), AAV CKd-3 (SEQ ID NO: 60 and 134 of U.S. Pat. No. 8,734,809), AAV CKd-4 (SEQ ID NO: 61 and 135 of U.S. Pat. No. 8,734, 809), AAV CKd-6 (SEQ ID NO: 62 and 136 of U.S. Pat. No. 8,734,809), AAV CKd-7 (SEQ ID NO: 63 and 137 of U.S. Pat. No. 8,734,809), AAV CKd-8 (SEQ ID NO: 64 and 138 of U.S. Pat. No. 8,734,809), AAV CLv-1 (SEQ ID NO: 35 and 139 of U.S. Pat. No. 8,734,809), AAV CLv-12 (SEQ ID NO: 66 and 140 of U.S. Pat. No. 8,734,809), AAV CLv-13 (SEQ ID NO: 67 and 141 of U.S. Pat. No. 8,734,809), AAV CLv-2 (SEQ ID NO: 68 and 142 of U.S. Pat. No. 8,734,809), AAV CLv-3 (SEQ ID NO: 69 and 143 of U.S. Pat. No. 8,734,809), AAV CLv-4 (SEQ ID NO: 70 and 144 of U.S. Pat. No. 8,734,809), AAV CLv-6 (SEQ ID NO: 71 and 145 of U.S. Pat. No. 8,734,809), AAV CLv-8 (SEQ ID NO: 72 and 146 of U.S. Pat. No. 8,734,809), AAV CKd-B1 (SEQ ID NO: 73 and 147 of U.S. Pat. No. 8,734,809), AAV CKd-B2 (SEQ ID NO: 74 and 148 of U.S. Pat. No. 8,734,809), AAV CKd-B3 (SEQ ID NO: 75 and 149 of U.S. Pat. No. 8,734, 809), AAV CKd-B4 (SEQ ID NO: 76 and 150 of U.S. Pat. No. 8,734,809), AAV CKd-B5 (SEQ ID NO: 77 and 151 of U.S. Pat. No. 8,734,809), AAV CKd-B6 (SEQ ID NO: 78 and 152 of U.S. Pat. No. 8,734,809), AAV CKd-B7 (SEQ ID NO: 79 and 153 of U.S. Pat. No. 8,734,809), AAV CKd-B8 (SEQ ID NO: 80 and 154 of U.S. Pat. No. 8,734,809), AAV CKd-H1 (SEQ ID NO: 81 and 155 of U.S. Pat. No. 8,734, 809), AAV CKd-H2 (SEQ ID NO: 82 and 156 of U.S. Pat. No. 8,734,809), AAV CKd-H3 (SEQ ID NO: 83 and 157 of U.S. Pat. No. 8,734,809), AAV CKd-H4 (SEQ ID NO: 84 and 158 of U.S. Pat. No. 8,734,809), AAV CKd-H5 (SEQ ID NO: 85 and 159 of U.S. Pat. No. 8,734,809), AAV CKd-H6 (SEQ ID NO: 77 and 151 of U.S. Pat. No. 8,734,809), AAV CHt-1 (SEQ ID NO: 86 and 160 of U.S. Pat. No. 8,734,809), AAV CLv1-1 (SEQ ID NO: 171 of U.S. Pat. No. 8,734,809), AAV CLv1-2 (SEQ ID NO: 172 of U.S. Pat. No. 8,734,809), AAV CLv1-3 (SEQ ID NO: 173 of U.S. Pat. No. 8,734,809), AAV CLv1-4 (SEQ ID NO: 174 of U.S. Pat. No. 8,734,809), AAV Clv1-7 (SEQ ID NO: 175 of U.S. Pat. No. 8,734,809), AAV Clv1-8 (SEQ ID NO: 176 of U.S. Pat. No. 8,734,809), AAV Clv1-9 (SEQ ID NO: 177 of U.S. Pat. No. 8,734,809), AAV Clv1-10 (SEQ ID NO: 178 of U.S. Pat. No. 8,734,809), AAV.VR-355 (SEQ ID NO: 181 of U.S. Pat. No. 8,734,809), AAV.hu.48R3 (SEQ ID NO: 183 of U.S. Pat. No. 8,734, 809), or variants or derivatives thereof.

In some embodiments, the AAV serotype may be, or have, a sequence as described in International Publication No. WO2016065001, the contents of which are herein incorporated by reference in their entirety, such as, but not limited to AAV CHt-P2 (SEQ ID NO: 1 and 51 of WO2016065001), AAV CHt-P5 (SEQ ID NO: 2 and 52 of WO2016065001), AAV CHt-P9 (SEQ ID NO: 3 and 53 of WO2016065001), AAV CBr-7.1 (SEQ ID NO: 4 and 54 of WO2016065001), AAV CBr-7.2 (SEQ ID NO: 5 and 55 of WO2016065001), AAV CBr-7.3 (SEQ ID NO: 6 and 56 of WO2016065001), AAV CBr-7.4 (SEQ ID NO: 7 and 57 of WO2016065001), AAV CBr-7.5 (SEQ ID NO: 8 and 58 of WO2016065001), AAV CBr-7.7 (SEQ ID NO: 9 and 59 of WO2016065001), AAV CBr-7.8 (SEQ ID NO: 10 and 60 of WO2016065001), AAV CBr-7.10 (SEQ ID NO: 11 and 61 of WO2016065001), AAV CKd-N3 (SEQ ID NO: 12 and 62 of WO2016065001), AAV CKd-N4 (SEQ ID NO: 13 and 63 of WO2016065001), AAV CKd-N9 (SEQ ID NO: 14 and 64 of WO2016065001), AAV CLv-L4 (SEQ ID NO: 15 and 65 of WO2016065001), AAV CLv-L5 (SEQ ID NO: 16 and 66 of WO2016065001), AAV CLv-L6 (SEQ ID NO: 17 and 67 of WO2016065001), AAV CLv-K1 (SEQ ID NO: 18 and 68 of WO2016065001), AAV CLv-K3 (SEQ ID NO: 19 and 69 of WO2016065001), AAV CLv-K6 (SEQ ID NO: 20 and 70 of WO2016065001), AAV CLv-M1 (SEQ ID NO: 21 and 71 of WO2016065001), AAV CLv-M11 (SEQ ID NO: 22 and 72 of WO2016065001), AAV CLv-M2 (SEQ ID NO: 23 and 73 of WO2016065001), AAV CLv-M5 (SEQ ID NO: 24 and 74 of WO2016065001), AAV CLv-M6 (SEQ ID NO: 25 and 75 of WO2016065001), AAV CLv-M7 (SEQ ID NO: 26 and 76 of WO2016065001), AAV CLv-M8 (SEQ ID NO: 27 and 77 of WO2016065001), AAV CLv-M9 (SEQ ID NO: 28 and 78 of WO2016065001), AAV CHt-P1 (SEQ ID NO: 29 and 79 of WO2016065001), AAV CHt-P6 (SEQ ID NO: 30 and 80 of WO2016065001), AAV CHt-P8 (SEQ ID NO: 31 and 81 of WO2016065001), AAV CHt-6.1 (SEQ ID NO: 32 and 82 of WO2016065001), AAV CHt-6.10 (SEQ ID NO: 33 and 83 of WO2016065001), AAV CHt-6.5 (SEQ ID NO: 34 and 84 of WO2016065001), AAV CHt-6.6 (SEQ ID NO: 35 and 85 of WO2016065001), AAV CHt-6.7 (SEQ ID NO: 36 and 86 of WO2016065001), AAV CHt-6.8 (SEQ ID NO: 37 and 87 of WO2016065001), AAV CSp-8.10 (SEQ ID NO: 38 and 88 of WO2016065001), AAV CSp-8.2 (SEQ ID NO: 39 and 89 of WO2016065001), AAV CSp-8.4 (SEQ ID NO: 40 and 90 of WO2016065001), AAV CSp-8.5 (SEQ ID NO: 41 and 91 of WO2016065001), AAV CSp-8.6 (SEQ ID NO: 42 and 92 of WO2016065001), AAV CSp-8.7 (SEQ ID NO: 43 and 93 of WO2016065001), AAV CSp-8.8 (SEQ ID NO: 44 and 94 of WO2016065001), AAV CSp-8.9 (SEQ ID NO: 45 and 95 of WO2016065001), AAV CBr-B7.3 (SEQ ID NO: 46 and 96 of WO2016065001), AAV CBr-B7.4 (SEQ ID NO: 47 and 97 of WO2016065001), AAV3B (SEQ ID NO: 48 and 98 of WO2016065001), AAV4 (SEQ ID NO: 49 and 99 of WO2016065001), AAV5 (SEQ ID NO: 50 and 100 of WO2016065001), or variants or derivatives thereof.

In one embodiment, the AAV may be a serotype selected from any of those found in Table 1.

In one embodiment, the AAV may comprise a sequence, fragment or variant thereof, of the sequences in Table 1.

In one embodiment, the AAV may be encoded by a sequence, fragment or variant as described in Table 1.

TABLE 1

AAV Serotypes

| Serotype | SEQ ID NO | Relerenee Inforivalion |
|---|---|---|
| AAV1 | 1 | US20150159173 SEQ ID NO: 11, US20150315612 SEQ ID NO: 202 |
| AAV1 | 2 | US20160017295 SEQ ID NO: 1US20030138772 SEQ ID NO: 64, US20150159173 SEQ ID NO: 27, US2015035612 SEQ ID NO: 219, US7198951 SEQ ID NO: 5 |
| AAV1 | 3 | US20030138772 SEQ ID NO: 6 |
| AAV1.3 | 4 | US20030138772 SEQ ID NO: 14 |
| AAV10 | 5 | US20030138772 SEQ ID NO: 117 |
| AAV10 | 6 | WO2015121501 SEQ ID NO: 9 |
| AAV10 | 7 | WO2015121501 SEQ ID NO: 8 |
| AAV11 | 8 | US20030138772 SEQ ID NO: 118 |
| AAV12 | 9 | US20030138772 SEQ ID NO: 119 |
| AAV2 | 10 | US2050159173 SEQ ID NO: 7, US20150315612 SEQ ID NO: 211 |
| AAV2 | 11 | US20030138772 SEQ ID NO: 70, US20150159173 SEQ ID NO: 23, US2015035612 SEQ ID NO: 221, US20160017295 SEQ ID NO: 2, US6156303 SEQ ID NO: 4, US7198951 SEQ ID NO: 4, WO2015121501 SEQ ID NO: 1 |
| AAV2 | 12 | US6156303 SEQ ID NO: 8 |
| AAV2 | 13 | US20030138772 SEQ ID NO: 7 |
| AAV2 | 14 | US6156303 SEQ ID NO: 3 |
| AAV2.5T | 15 | US9233131 SEQ ID NO: 42 |
| AAV223.10 | 16 | US20030138772 SEQ ID NO: 75 |
| AAV223.2 | 17 | US20030138772 SEQ ID NO: 49 |
| AAV223.2 | 18 | US20030138772 SEQ ID NO: 76 |
| AAV223.4 | 19 | US20030138772 SEQ ID NO: 50 |
| AAV223.4 | 20 | US20030138772 SEQ ID NO: 73 |
| AAV223.5 | 21 | US20030138772 SEQ ID NO: 51 |
| AAV223.5 | 22 | US20030138772 SEQ ID NO: 74 |
| AAV223.6 | 23 | US20030138772 SEQ ID NO: 52 |
| AAV22306 | 24 | US20030138772 SEQ ID NO: 78 |
| AAV723.7 | 25 | US20030138772 SEQ ID NO: 53 |
| AAV223.7 | 26 | US20030138772 SEQ ID NO: 77 |
| AAV29.3 | 27 | US20030138772 SEQ ID NO: 82 |
| AAV29,4 | 28 | US20030138772 SEQ ID NO: 12 |
| AAV29.5 | 29 | US20030138772 SEQ ID NO: 83 |
| AAV29.5 (AAVbb.2) | 30 | US20030138772 SEQ ID NO: 13 |
| AAV3 | 31 | US20150159173 SEQ ID NO: 12 |
| AAV3 | 32 | US20030138772 SEQ ID NO: 71, US20150591.73 SEQ ID NO: 28, US20160017295 SEQ ID NO: :3, US7198951 SEQ ID NO: 6 |
| AAV3 | 33 | US20030138772 SEQ ID NO: 8 |
| AAV3.3b | 34 | US21030138772 SEQ ID NO: 72 |
| AAV3-3 | 35 | US20150315612 SEQ ID NO: 200 |
| AAV3-3 | 36 | US20150315612 SEQ ID NO: 217 |
| AAV3a | 37 | US6156303 SEQ ID NO: 5 |
| AAV3a | 38 | US6156303 SEQ ID NO: 9 |
| AAV3b | 39 | US6156303 SEQ ID NO: 6 |
| AAV3b | 40 | US6156303 SEQ ID NO: 10 |
| AAV3b | 41 | US6156303 SEQ ID NO: 1 |
| AAV4 | 42 | US20140348794 SEQ ID NO: 17 |
| AAV4 | 43 | US20140348794 SEQ ID NO: 5 |
| AAV4 | 44 | US20140348794 SEQ ID NO: 3 |
| AAV4 | 45 | US20140348794 SEQ ID NO: 14 |
| AAV4 | 46 | US20140348794 SEQ ID NO: 15 |

TABLE 1-continued

AAV Serotypes

| Serotype | SEQ ID NO | Reference Information |
|---|---|---|
| AAV4 | 47 | US20140348794 SEQ ID NO: 19 |
| AAV4 | 48 | US201140348794 SEQ ID NO: 12 |
| AAV4 | 49 | US201140348794 SEQ ID NO: 13 |
| AAV4 | 50 | US20140348794 SEQ ID NO: 7 |
| AAV4 | Si | US20140348794 SEQ ID NO: 8 |
| AAV4 | 52 | US20140348794 SEQ ID NO: 9 |
| AAV4 | 53 | US20140348794 SEQ ID NO: 2 |
| AAV4 | 54 | US20140348794 SEQ ID NO: 10 |
| AAV4 | 55 | US20140348794 SEQ ID NO: 11 |
| AAV4 | 56 | US201140348794 SEQ ID NO: 18 |
| AAV4 | 57 | US20030138772 SEQ ID NO: 63, US20160017295 SEQ ID NO: 4, US20140348794 SEQ ID NO: 4 |
| AAV4 | 58 | US20140348794 SEQ ID NO: 16 |
| AAV4 | 59 | US201140348794 SEQ ID NO: 20 |
| AAV4 | 60 | US20140348794 SEQ ID NO: 6 |
| AAV4 | 61 | US20140348794 SEQ ID NO: 1 |
| AAV42.2 | 62 | US20030138772 SEQ ID NO: 9 |
| AAV42.2 | 63 | US20030138772 SEQ ID NO: 102 |
| AAV42.3b | 64 | US20030138772 SEQ ID NO: 36 |
| AAV42.3B | 65 | US20030138772 SEQ ID NO: 107 |
| AAV42.4 | 66 | US20030138772 SEQ ID NO: 33 |
| AAV42.4 | 67 | US201030138772 SEQ ID NO: 88 |
| AAV42.8 | 68 | US20030138772 SEQ ID NO: 27 |
| AAV42.8 | 69 | US20030138772 SEQ ID NO: 85 |
| AAV43.1 | 70 | US20030138772 SEQ ID NO: 39 |
| AAV43.1 | 71 | US20030138772 SEQ ID NO: 92 |
| AAV43.12 | 72 | US20030138772 SEQ ID NO: 41 |
| AAV43.12 | 73 | US20030138772 SEQ ID NO: 93 |
| AAV43.20 | 74 | US20030138772 SEQ ID NO: 42 |
| AAV43.20 | 75 | US20030138772 SEQ ID NO: 99 |
| AAV43.21 | 76 | US20030138772 SEQ ID NO: 43 |
| AAV43.21 | 77 | US20030138772 SEQ ID NO: 96 |
| AAV43.23 | 78 | US20030138772 SEQ ID NO: 44 |
| AAV43.23 | 79 | US20030138772 SEQ ID NO: 98 |
| AAV43.25 | 80 | US20030138772 SEQ ID NO: 45 |
| AAV43.25 | 81 | US20030138772 SEQ ID NO: 97 |
| AAV43.5 | 82 | US20030138772 SEQ ID NO: 40 |
| AAV43.5 | 83 | US20030138772 SEQ ID NO: 94 |
| AAV4-4 | 84 | US20150315612 SEQ ID NO: 201 |
| AAV4-4 | 85 | US20150315612 SEQ ID NO: 218 |
| AAV44.1 | 86 | US20030138772 SEQ ID NO: 46 |
| AAV44.1 | 87 | US20030138772 SEQ ID NO: 79 |
| AAV44.5 | 88 | US20030138772 SEQ ID NO: 47 |
| AAV44.5 | 89 | US20030138772 SEQ ID NO: 80 |
| AAV4407 | 90 | US20150315612 SEQ ID NO: 90 |
| AAV5 | 91 | US7427396 SEQ ID NO: 1 |
| AAV5 | 92 | US20030138772 SEQ ID NO: 114 |
| AAV5 | 93 | US20160017295 SEQ ID NO: 5, US7427396 SEQ ID NO: 2, US20150315612 SEQ ID NO: 216 |
| AAV5 | 94 | US20150315612 SEQ ID NO: 199 |
| AAV6 | 95 | US20150159173 SEQ ID NO: 13 |
| AAV6 | 96 | US0030138772 SEQ ID NO: 65, US20150159173 SEQ ID NO: 29, US520160017295 SEQ ID NO: 6, US6156303 SEQ ID NO: 7 |
| AAV6 | 97 | US6156303 SEQ ID NO: 11 |
| AAV6 | 98 | US6156303 SEQ ID NO: 2 |
| AAV6 | 99 | US20150315612 SEQ ID NO: 203 |
| AAV6 | 100 | US20150315612 SEQ ID NO: 220 |
| AAV6.1 | 101 | US20150159173 |
| AAV6.12 | 102 | US20150159173 |
| AAV6.2 | 103 | US20150159173 |
| AAV7 | 104 | US20150159173 SEQ ID NO: 14 |
| AAV7 | 105 | US20150315612 SEQ ID NO: 183 |
| AAV7 | 106 | US20030138772 SEQ ID NO: 2, US20150159173 SEQ ID NO: 30, US20150315612 SEQ. ID NO: 181, US20160017295 SEQ ID NO: 7 |
| AAV7 | 107 | US20030138772 SEQ ID NO: 3 |
| AAV7 | 108 | US20030138772 SEQ ID NO: 1, US20150315612 SEQ ID NO: 180 |
| AAV7 | 109 | US20150315612 SEQ ID NO: 213 |
| AAV7 | 110 | US20150315612 SEQ ID NO: 222 |
| AAV8 | 111 | US20150159173 SEQ ID NO: 15 |
| AAV8 | 112 | US20150376240 SEQ ID NO: 7 |
| AAV8 | 113 | US20030138772 SEQ ID NO: 4, US20150315612 SEQ ID NO: 182 |
| AAV8 | 114 | US20030138772 SEQ ID NO: 95, US20140359799 SEQ ID NO: 1, US20150159173 SEQ ID NO: 31, US0160017295 SEQ ID NO: 8, US7198951 SEQ ID NO: 7, US20150315612 SEQ ID NO: 223 |

TABLE 1-continued

| Serotype | SEQ ID NO | Reference Information |
|---|---|---|
| AAV8 | 115 | US20150376240 SEQ ID NO: 8 |
| AAV8 | 116 | US20150315612 SEQ ID NO: 214 |
| AAV-8b | 117 | US20150376240 SEQ ID NO: 5 |
| AAV-8b | 118 | US20150376240 SEQ ID NO: 3 |
| AAV-8h | 119 | US20150376240 SEQ ID NO: 6 |
| AAV-8h | 120 | US20150376240 SEQ ID NO: 4 |
| AAV9 | 121 | US20030138772 SEQ ID NO: 5 |
| AAV9 | 122 | US7198951 SEQ ID NO: 1 |
| AAV9 | 123 | US20160017295 SEQ ID NO: 9 |
| AAV9 | 124 | US20030138772 SEQ ID NO: 100, US7198951 SEQ ID NO. 2 |
| AAV9 | 125 | US7198951 SEQ ID NO: 3 |
| AAV9 (AAVhu.14) | 126 | US7906111 SEQ ID NO: 3; WO2015038958 SEQ ID NO: 11 |
| AAV9 (AAVhu.14) | 127 | US7906111 SEQ ID NO: 123; WO2015038958 SEQ ID NO: 2 |
| AAVA3.1 | 128 | US20030138772 SEQ ID NO: 120 |
| AAVA3.3 | 129 | US20030138772 SEQ ID NO: 57 |
| AAVA3.3 | 130 | US20030138772 SEQ ID NO: 66 |
| AAVA3.4 | 131 | US20030138772 SEQ ID NO: 54 |
| AAVA3.4 | 132 | US20030138772 SEQ ID NO: 68 |
| AAVA3.5 | 133 | US201030138772 SEQ ID NO: 55 |
| AAVA3.5 | 134 | US20030138772 SEQ ID NO: 69 |
| AAVA3.7 | 135 | US20030138772 SEQ ID NO: 56 |
| AAVA3.7 | 136 | US20030138772 SEQ ID NO: 67 |
| AAV29.3 (AAVbb.1) | 137 | US20030138772 SEQ ID NO: 11 |
| AAVC2 | 138 | US20030138772 SEQ ID NO: 61 |
| AAVC11.5 | 139 | US201150159173 SEQ ID NO: 46, US20150315612 SEQ ID NO: 234 |
| AAVcy.2 (AAV 13.3) | 140 | US20030138772 SEQ ID NO: 15 |
| AAV24.1 | 141 | US20030138772 SEQ ID NO: 101 |
| AAVcy.3 (AAV24,1) | 142 | US201030138772 SEQ ID NO: 16 |
| AAV27.3 | 143 | US20030138772 SEQ ID NO: 104 |
| AAVey.4 (AAV27.3) | 144 | US20030138772 SEQ ID NO: 17 |
| AAVey.5 | 145 | US20150315612 SEQ ID NO: 227 |
| AAV7.2 | 146 | US20030138772 SEQ ID NO: 103 |
| AAVey.5 (AAV7.2) | 147 | US20030138772 SEQ ID NO: 18 |
| AAV16.3 | 148 | US20030138772 SEQ ID NO: 105 |
| AAVcy.6 (AAV16.3) | 149 | US20030138772 SEQ ID NO: 10 |
| AAVcy.5 | 150 | US20150159173 SEQ ID NO: 8 |
| AAVcy.5 | 151 | US20150159173 SEQ ID NO: 24 |
| AAVCy.5R1 | 152 | US20150159173 |
| AAVCy.5R2 | 153 | US20150159173 |
| AAVCy.51-23 | 154 | US20150159173 |
| AAVCy.5R4 | 155 | US20150159173 |
| AAVDJ | 156 | US20140359799 SEQ ID NO: 3, US7588772 SEQ ID NO: 2 |
| AAVDJ | 157 | US201140359799 SEQ ID NO: 2, US7588772 SEQ ID NO: 1 |
| AAVDJ-8 | 158 | US7588772, Grimm et al 2008 |
| AAVDJ-8 | 159 | US7588772; Grimm et al 2008 |
| AAVF5 | 160 | US20030138772 SEQ ID NO: 110 |
| AAVH2 | 161 | US20030138772 SEQ ID NO: 26 |
| AAVH6 | 162 | US201030138772 SEQ ID NO: 25 |
| AAVHE1.1 | 163 | US9233131 SEQ ID NO: 44 |
| AAVEIErl.14 | 164 | US9233131 SEQ ID NO: 46 |
| AAVhEr1.16 | 165 | US9233131 SEQ ID NO: 48 |
| AAVhEr1.18 | 166 | US9233131 SEQ ID NO: 49 |
| AAVhEr1.23 (AAVhEr2.29) | 167 | US9233131 SEQ ID NO: 53 |
| AAVhEr1.35 | 168 | US9233131 SEQ ID NO: 50 |
| AAVhEr1.36 | 169 | US9233131 SEQ ID NO: 52 |
| AAVITIEr1.5 | 170 | US9233131 SEQ ID NO: 45 |
| AAVhEr1.7 | 171 | US9233131 SEQ ID NO: 51 |
| AAVhErt.8 | 172 | US9233131 SEQ ID NO: 47 |
| AAVhEr2.16 | 173 | US9233131 SEQ ID NO: 55 |
| AAVhEr2.30 | 174 | US9233131 SEQ ID NO: 56 |
| AAVIiEt2.31 | 175 | US9233131 SEQ ID NO: 58 |
| AAVhEr2.36 | 176 | US9233131 SEQ ID NO: 57 |
| AAVhEr2.4 | 177 | US9233131 SEQ ID NO: 54 |
| A AVITIEr3.1 | 178 | US9233131 SEQ ID NO: 59 |
| AAVElu.1 | 179 | US20150315612 SEQ ID NO: 46 |

TABLE 1-continued

AAV Serotypes

| Serotype | SEQ ID NO | Relerence Inforivalion |
|---|---|---|
| AAVhu.1 | 180 | US20150315612 SEQ ID NO: 144 |
| AAVhu.10 (AAV6.8) | 181 | US20150315612 SEQ ID NO: 56 |
| AAVhu.10 (AAV6.8) | 182 | US20150315612 SEQ ID NO: 156 |
| AAVhu.11 (AAV16.12) | 183 | US20150315612 SEQ ID NO: 57 |
| AAVhu.11 (AAV16.12) | 184 | US20150315612 SEQ ID NO: 153 |
| AAVhu.12 | 185 | US20150315612 SEQ ID NO: 59 |
| AAVhu.12 | 186 | US20150315612 SEQ ID NO: 154 |
| AAVhu.13 | 187 | US20150159173 SEQ ID NO: 16, US20150315612 SEQ ID NO: 71 |
| AAVhu.13 | 188 | US20150159173 SEQ ID NO: 32, US20150315612 SEQ ID NO: 129 |
| AAVhu.136.1 | 189 | US201150315612 SEQ ID NO: 165 |
| AVhu.140.1 | 190 | US20150315612 SEQ ID NO: 166 |
| AAVhu.140.2 | 191 | US20150315612 SEQ ID NO: 167 |
| AAVhu.145.6 | 192 | US20150315612 SEQ ID No: 178 |
| AAVhu.15 | 193 | US20150315612 SEQ ID NO: 147 |
| AAVhu.15 (AAV33.4) | 194 | US20150315612 SEQ ID NO: 50 |
| AAVhu.156.1 | 195 | US20150315612 SEQ ID No: 179 |
| AAVhu.16 | 196 | US20150315612 SEQ ID NO: 148 |
| AAVhu.16 (AAV33.8) | 197 | US201150315612 SEQ ID NO: 51 |
| AAVhu.17 | 198 | US20150315612 SEQ ID NO: 83 |
| AAVhu.17 (AAV33.12) | 199 | US20150315612 SEQ ID NO: 4 |
| AAVhu.172.1 | 200 | US20150315612 SEQ ID NO: 171 |
| AAVhu.172.2 | 201 | US20150315612 SEQ ID NO: 172 |
| AAVhu.173.4 | 202 | US20150315612 SEQ ID NO: 173 |
| AAVhu.173.8 | 203 | US20150315612 SEQ ID NO: 175 |
| AAVhu.18 | 204 | US20150315612 SEQ ID NO: 52 |
| AAVhu.18 | 205 | US20150315612 SEQ ID NO: 149 |
| AAVhu.19 | 206 | US20150315612 SEQ ID NO: 62 |
| AAVhu.19 | 207 | US20150315612 SEQ ID NO: 133 |
| AAVhu.2 | 208 | US20150315612 SEQ ID NO: 48 |
| AAVhu.2 | 209 | US20150315612 SEQ ID NO: 143 |
| AAVhu.20 | 210 | US20150315612 SEQ ID NO: 63 |
| AAVhu.20 | 211 | US20150315612 SEQ ID NO: 134 |
| AAVhu.21 | 212 | US20150315612 SEQ ID NO: 65 |
| AAVhu.21 | 213 | US20150315612 SEQ ID NO: 135 |
| AAVhu.22 | 214 | US20150315612 SEQ ID NO: 67 |
| AAVhu.22 | 215 | US20150315612 SEQ ID NO: 138 |
| AAVhu.23 | 216 | US20150315612 SEQ ID NO: 60 |
| AAVhu.23.2 | 217 | US20150315612 SEQ ID NO: 137 |
| AAVhu.24 | 218 | US20150315612 SEQ ID NO: 66 |
| AAVhu.24 | 219 | US20150315612 SEQ ID NO: 136 |
| AAVhu.25 | 220 | US20150315612 SEQ ID NO: 49 |
| AAVhu.25 | 221 | US20150315612 SEQ ID NO: 146 |
| AAVhu.26 | 222 | US20150159173 SEQ ID NO: 17, US20150315612 SEQ ID NO: 61 |
| AAVhu.26 | 223 | US20150159173 SEQ ID NO: 33, US0150315612 SEQ ID NO: 139 |
| AAVhu.27 | 224 | US20150315612 SEQ ID NO: 64 |
| AAVhu.27 | 225 | US20150315612 SEQ ID NO: 140 |
| AAVhu.28 | 226 | US20150315612 SEQ ID NO: 68 |
| AAVhu.28 | 227 | US20150315612 SEQ ID NO: 130 |
| AAVhu.29 | 228 | US20150315612 SEQ ID NO: 69 |
| AAVhu.29 | 229 | US20150159173 SEQ ID NO: 42, US0150315612 SEQ ID NO: 132 |
| AAVhu.29 | 230 | US20150315612 SEQ ID NO: 225 |
| AAVhu.29R | 231 | US20150159173 |
| AAVhu.3 | 232 | US20150315612 SEQ ID NO: 44 |
| AAVhu.3 | 233 | US20150315612 SEQ ID NO: 145 |
| AAVhu.30 | 234 | US20150315612 SEQ ID NO: 70 |
| AAVhu.30 | 235 | US20150315612 SEQ ID NO: 131 |
| AAVhu.31 | 236 | US20150315612 SEQ ID NO: 1 |
| AAVhu.31 | 237 | US20150315612 SEQ ID NO: 121 |
| AAVhu.32 | 238 | US20150315612 SEQ ID NO: 2 |
| AAVhu.32 | 239 | US20150315612 SEQ ID NO: 122 |
| AAVhu.33 | 240 | US20150315612 SEQ ID NO: 75 |
| AAVhu.33 | 241 | US20150315612 SEQ ID NO: 124 |
| AAVhu.34 | 242 | US20150315612 SEQ ID NO: 72 |
| AAVhu.34 | 243 | US20150315612 SEQ ID NO: 125 |
| AAVhu.35 | 244 | US20150315612 SEQ ID NO: 73 |
| AAVhu.35 | 245 | US20150315612 SEQ ID NO: 164 |
| AAVhu.36 | 246 | US20150315612 SEQ ID NO: 74 |

TABLE 1-continued

AAV Serotypes

| Serotype | SEQ ID NO | Relerenee Inforivalion |
|---|---|---|
| AAVhu.36 | 247 | US0150315612 SEQ ID NO: 126 |
| AAVIRI.37 | 248 | US20150159173 SEQ ID NO: 34, US20150315612 SEQ ID NO: 88 |
| AAVhu.37 (AAV106. I) | 249 | US20150315612 SEQ ID NO: 10, US20150159173 SEQ ID NO: 18 |
| AAVhu.38 | 250 | US0150315612 SEQ ID NO: 161 |
| AAVIRI.39 | 251 | US20150315612 SEQ ID NO: 102 |
| AAVhu.39 (AAVI,G-9) | 252 | US20150315612 SEQ ID NO: 24 |
| AAVhu.4 | 253 | US0150315612 SEQ ID NO: 47 |
| AAVhu.4 | 254 | US20150315612 SEQ ID NO: 141 |
| AAVhu.40 | 255 | US20150315612 SEQ ID NO: 87 |
| AAVhu.40 (AAVIA 4.3) | 256 | US20150315612 SEQ ID No: 11 |
| AAVhu.41 | 257 | US20150315612 SEQ ID NO: 91 |
| AAVhu.41 (AAV 1272) | 258 | US20150315612 SEQ ID NO: 6 |
| AAVhu.42 | 259 | US20150315612 SEQ ID NO: 85 |
| AAVhu.42 (AAV127.5) | 260 | US20150315612 SEQ ID NO: 8 |
| AAVhu.43 | 261 | US20150315612 SEQ ID NO: 160 |
| AAVhu.43 | 262 | US20150315612 SEQ ID NO: 236 |
| AAVhu.43 (AAV128.1) | 263 | US20150315612 SEQ ID NO: 80 |
| AAVhu.44 | 264 | US20150159173 SEQ ID NO: 45, US20150315612 SEQ ID NO: 158 |
| AAVhu.44 (AAV128.3) | 265 | US20150315612 SEQ ID NO: 81 |
| AAVhu.44R1 | 266 | US20150159173 |
| AAVhu.44R2 | 267 | US20150159173 |
| AAVhu.44R3 | 268 | 11520150159173 |
| AAVEhu.45 | 269 | US20150315612 SEQ ID NO: 76 |
| AAVhu.45 | 270 | US201503 15612 SEQ ID NO: 127 |
| AAVhu.46 | 271 | US20150315612 SEQ ID NO: 82 |
| AAVIRI.46 | 272 | US20150315612 SEQ ID NO: 159 |
| AAVIhu.46 | 273 | US20150315612 SEQ ID NO: 224 |
| AAVEhu.47 | 274 | US20150315612 SEQ ID NO: 77 |
| AAVhu.47 | 275 | US20150315612 SEQ ID NO: 128 |
| AAVhu.48 | 276 | US20150159173 SEQ ID NO: 38 |
| AAVhu.48 | 277 | US20150315612 SEQ ID NO: 157 |
| AAVIhu.48 (AAV130.4) | 278 | US20150315612 SEQ ID NO: 78 |
| AAVhu.48R1 | 279 | US20150159173 |
| AAVhu.48R2 | 280 | US20150159173 |
| AAVIlu.48R3 | 281 | US20150159173 |
| AAVhu.49 | 282 | US20150315612 SEQ ID NO: 209 |
| AAVhu.49 | 283 | US20150315612 SEQ ID NO: 189 |
| AAVhu.5 | 284 | US20150315612 SEQ ID NO: 45 |
| AAV1hu.5 | 285 | US20150315612 SEQ ID NO: 142 |
| AAVhu.51 | 286 | US20150315612 SEQ ID NO: 208 |
| AAVhu.51 | 287 | US20150315612 SEQ ID NO: 190 |
| AAVhu.52 | 288 | US20150315612 SEQ ID NO: 210 |
| AAVhu.52 | 289 | US20150315612 SEQ ID NO: 191 |
| AAVhu.53 | 290 | US20150315612 SEQ ID NO: 19 |
| AAVhu.53 | 291 | US20150159173 SEQ ID NO: 35 |
| AAVhu.53 (AAVI45.1) | 292 | US20150315612 SEQ ID NO: 176 |
| AAVhu.54 | 293 | US20150315612 SEQ ID NO: 188 |
| AAVhu.54 (AAV145.5) | 294 | US20150315612 SEQ ID No: 177 |
| AAVhu.55 | 295 | US20150315612 SEQ ID NO: 187 |
| AAVhu.56 | 296 | US20150315612 SEQ ID NO: 205 |
| AAVhu.56 (AAV145.6) | 297 | US20150315612 SEQ ID NO: 168 |
| AAVhu.56 (AAV 1456) | 298 | US20150315612 SEQ ID NO: 192 |
| AAVhu.57 | 299 | US20150315612 SEQ ID NO: 206 |
| AAV1iu.57 | 300 | US20150315612 SEQ ID NO: 169 |
| A AVhu.57 | 301 | US20150315612 SEQ ID NO: 193 |
| AAVhu.58 | 302 | US20150315612 SEQ ID NO: 207 |
| AAVhu.58 | 303 | US20150315612 SEQ ID NO: 194 |
| AAVhu.6 (AAV3.1) | 304 | US20150315612 SEQ ID NO: 5 |
| AAVhu.6 (AAV3.1) | 305 | US20150315612 SEQ ID NO: 84 |
| AAV1iu.60 | 306 | US20150315612 SEQ ID NO: 184 |

TABLE 1-continued

AAV Serotypes

| Serotype | SEQ ID NO | Reference Information |
|---|---|---|
| AAVhu.60 (AAV161.10) | 307 | US20150315612 SEQ ID NO: 170 |
| AAVhu.61 | 308 | US20150315612 SEQ ID NO: 185 |
| AAVhu.61 (AAV161.6) | 309 | US20150315612 SEQ ID NO: 174 |
| AAVhu.63 | 310 | US20150315612 SEQ ID NO: 204 |
| AAVhu.63 | 311 | US20150315612 SEQ ID NO: 195 |
| AAVhu.64 | 312 | US20150315612 SEQ ID NO: 212 |
| AAVhu.64 | 313 | US20150315612 SEQ ID NO: 196 |
| AAVhu.66 | 314 | US20150315612 SEQ ID NO: 197 |
| AAVhu.67 | 315 | US20150315612 SEQ ID NO: 215 |
| AAVhu.67 | 316 | US20150315612 SEQ ID NO: 198 |
| AAVhu.7 | 317 | US20150315612 SEQ ID NO: 226 |
| AAVhu.7 | 318 | US20150315612 SEQ ID NO: 150 |
| AAVhu.7 (AAV7.3) | 319 | US20150315612 SEQ ID NO: 55 |
| AAVhu.71 | 320 | US20150315612 SEQ ID NO: 79 |
| AAVEhu.8 | 321 | US20150315612 SEQ ID NO: 53 |
| AAVhu.8 | 322 | US20150315612 SEQ ID NO: 12 |
| AAVInt.8 | 323 | US20150315612 SEQ ID NO: 151 |
| AA:Vhu.9 (AAV3.1.) | 324 | US20150315612 SEQ ID NO: 58 |
| AAVhu.9 (AANT3.1) | 325 | US20150315612 SEQ ID NO: 155 |
| AAV-LK01 | 326 | US20150376607 SEQ ID NO: 2 |
| AAV-LK01 | 327 | US20150376607 SEQ ID NO: 29 |
| AAV-1K02 | 328 | US20150376607 SEQ ID NO: 3 |
| AAV-1K02 | 329 | US20150376607 SEQ ID NO: 30 |
| AAV-LK03 | 330 | US20150376607 SEQ ID NO: 4 |
| AAV-LKO3 | 331 | WO2015121501 SEQ ID NO: 12, US20150376607 SEQ ID NO: 31 |
| AAV-LKO4 | 332 | US20150376607 SEQ ID NO: 5 |
| AAV-LKO4 | 333 | US20150376607 SEQ ID NO: 32 |
| AAV-LK05 | 334 | US20150376607 SEQ ID NO: 6 |
| AAV-LK05 | 335 | US20150376607 SEQ ID NO: 33 |
| AAV-LK06 | 336 | US20150376607 SEQ ID NO: 7 |
| AAV-LKO6 | 337 | US20150376607 SEQ ID NO: 34 |
| AAV-LK07 | 338 | US20150376607 SEQ ID NO: 8 |
| AAV-LK07 | 339 | US20150376607 SEQ ID NO: 35 |
| AAV-LK08 | 340 | US20150376607 SEQ ID NO: 9 |
| AAV-LK08 | 341 | US20150376607 SEQ ID NO: 36 |
| AAV-LK09 | 342 | US20150376607 SEQ ID NO: 10 |
| AAV-LK09 | 343 | US20150376607 SEQ ID NO: 37 |
| AAV-LK10 | 344 | US20150376607 SEQ ID NO: 11 |
| AAV-LK10 | 345 | US20150376607 SEQ ID NO: 38 |
| AAV-LK11 | 346 | US20150376607 SEQ ID NO: 12 |
| AAV-LK11 | 347 | US20150376607 SEQ ID NO: 39 |
| AAV-LK12 | 348 | US20150376607 SEQ ID NO: 13 |
| AAV-LK12 | 349 | US20150376607 SEQ ID NO: 40 |
| AAV-LK13 | 350 | US20150376607 SEQ ID NO: 14 |
| AAV-LK13 | 351 | US20150376607 SEQ ID NO: 41 |
| AAV-LK14 | 352 | US20150376607 SEQ ID NO: 15 |
| AAV-LK14 | 353 | US20150376607 SEQ ID NO: 42 |
| AAV-LK15 | 354 | US20150376607 SEQ ID NO: 16 |
| AAV-LK15 | 355 | US20150376607 SEQ ID NO: 43 |
| AAV-LK16 | 356 | US20150376607 SEQ ID NO: 17 |
| AAV-LK16 | 357 | US20150376607 SEQ ID NO: 44 |
| AAV-LK17 | 358 | US20150376607 SEQ ID NO: 18 |
| AAV-LK17 | 359 | US20150376607 SEQ ID NO: 45 |
| AAV-LK18 | 360 | US20150376607 SEQ ID NO: 19 |
| AAV-LK18 | 361 | US20150376607 SEQ ID NO: 46 |
| AAV-LK19 | 362 | US20150376607 SEQ ID NO: 20 |
| AAV-LK19 | 363 | US20150376607 SEQ ID NO: 47 |
| AAV-PAEC | 364 | US20150376607 SEQ ID NO: 1 |
| AAV-PAEC | 365 | US20150376607 SEQ ID NO: 48 |
| AAV-PAEC11 | 366 | US20150376607 SEQ ID NO: 26 |
| AAV-PAEC11 | 367 | US20150376607 SEQ ID NO: 54 |
| AAV-PAEC12 | 368 | US20150376607 SEQ ID NO: 27 |
| AAV-PAEC12 | 369 | US20150376607 SEQ ID NO: Si |
| AAV-PAEC13 | 370 | US20150376607 SEQ ID NO: 28 |

TABLE 1-continued

AAV Serotypes

| Serotype | SEQ ID NO | Reference Information |
|---|---|---|
| AAV-PAEC13 | 371 | US20150376607 SEQ ID NO: 49 |
| AAV-PAEC2 | 372 | US20150376607 SEQ ID NO: 21 |
| AAV-PAEC2 | 373 | US20150376607 SEQ ID NO: 56 |
| AAV-PAEC4 | 374 | US20150376607 SEQ ID NO: 22 |
| AAV-PAEC4 | 375 | US20150376607 SEQ ID NO: 55 |
| AAV-PAEC6 | 376 | US20150376607 SEQ ID NO: 23 |
| AAV-PAEC6 | 377 | US20150376607 SEQ ID NO: 52 |
| AAV-PAEC7 | 378 | US20450376607 SEQ ID NO: 24 |
| AAV-PA1X7 | 379 | US20150376607 SEQ ID NO: 53 |
| AAV-PAEC8 | 380 | US20150376607 SEQ ID NO: 25 |
| AAV-PAEC8 | 381 | US20150376607 SEQ ID NO: 50 |
| AAVpi.1 | 382 | US20150315612 SEQ ID NO: 28 |
| AAVp1.1 | 383 | US20150315612 SEQ ID NO: 93 |
| AAVpi.2 | 384 | US20150315612 SEQ ID NO: 30 |
| AAVpi.2 | 385 | US20150315612 SEQ ID NO: 95 |
| AAVpi.3 | 386 | US20150315612 SEQ ID NO: 29 |
| AAVpi.3 | 387 | US20150315612 SEQ ID NO: 94 |
| AAVrh.10 | 388 | US20150159173 SEQ ID NO: 9 |
| AAVrh.10 | 389 | US20150159173 SEQ ID NO: 25 |
| AAV44.2 | 390 | US20030138772 SEQ ID NO: 59 |
| AAVrh.10 (AAV44.2) | 391 | US20030138772 SEQ ID NO: 81 |
| AAV42.IB | 392 | US20030138772 SEQ ID NO: 90 |
| AAVrh.12 (AAV42.1b) | 393 | US20030138772 SEQ ID NO: 30 |
| AAVrh.13 | 394 | US201501.591.73 SEQ ID NO: 10 |
| AAVrh.13 | 395 | US20150159173 SEQ ID NO: 26 |
| AAVrh.13 | 396 | US20150315612 SEQ ID NO: 228 |
| AAVrh.13R | 397 | US20150159173 |
| AAV42.3A | 398 | US20030138772 SEQ ID NO: 87 |
| AAVrh.14 (AAV42.3a) | 399 | US20030138772 SEQ ID NO: 32 |
| AAV42.5A | 400 | US201030138772 SEQ ID NO: 89 |
| AAVrh.17 (AAV42.5a) | 401 | US20030138772 SEQ ID NO: 34 |
| AAV42.5B | 402 | US20030138772 SEQ ID NO: 91 |
| AAVr11.18 (AAV42.5b) | 403 | US20030138772 SEQ ID NO: 29 |
| AAV42.6B | 404 | US20030138772 SEQ ID NO: 112 |
| AAVr11.19 (AAV42.6b) | 405 | US20030138772 SEQ ID NO: 38 |
| AAVrh.2 | 406 | US20150159173 SEQ ID NO: 39 |
| AAVrh.2 | 407 | US201150315612 SEQ ID NO: 231 |
| AAVrh.20 | 408 | US20150159173 SEQ ID NO: 1 |
| AAV42.10 | 409 | US20030138772 SEQ ID NO: 106 |
| AAVrh.21 (AAV42.10) | 410 | US20030138772 SEQ ID NO: 35 |
| AAV42.11 | 411 | US20030138772 SEQ ID NO: 108 |
| AAVrh.22 (AAV42.10) | 412 | US20030138772 SEQ ID NO: 37 |
| AAV42.12 | 413 | US201030138772 SEQ ID NO: 113 |
| AAVrh.23 (AAV42.12) | 414 | US20030138772 SEQ ID NO: 58 |
| AAV42.13 | 415 | US20030138772 SEQ ID NO: 86 |
| AAVrh.24 (AAV42.13) | 416 | US20030138772 SEQ ID NO: 31 |
| AAV42.15 | 417 | US20030138772 SEQ ID NO: 84 |
| AAVr11.25 (AAV42.15) | 418 | US20030138772 SEQ ID NO: 28 |
| AAVrh.2R | 419 | US20150159173 |
| AAVrh.31 (AAV223.1) | 420 | US20030138772 SEQ ID NO: 48 |
| AAVC1 | 421 | US20030138772 SEQ ID NO: 60 |
| AAVrh.32 (AAVC1) | 422 | US20030138772 SEQ ID NO: 19 |
| AAVrh.32/33 | 423 | US20150159173 SEQ ID NO: 2 |
| AAVrh.33 (AAVC3) | 424 | US20030138772 SEQ ID NO: 20 |
| AAVC5 | 425 | US20030138772 SEQ ID NO: 62 |
| AAVr11.34 (AAVC5) | 426 | US20030138772 SEQ ID NO: 21 |
| AAVF1 | 427 | US201030138772 SEQ ID NO: 109 |

TABLE 1-continued

AAV Serotypes

| Serotype | SEQ ID NO | Reference Information |
|---|---|---|
| AAVrh.35 (AAVF1) | 428 | US20030138772 SEQ ID NO: 22 |
| AANT3 | 429 | US20030138772 SEQ ID NO: 111 |
| AAVrh.36 (AAVI-73) | 430 | US201030138772 SEQ ID NO: 23 |
| AAVrh.37 | 431 | US20030138772 SEQ ID NO: 24 |
| AAVH1.37 | 432 | US20150159173 SEQ ID NO: 40 |
| AAVrh.37 | 433 | US20150315612 SEQ ID NO: 229 |
| AAVrl3.37R2 | 434 | US20150159173 |
| AAVrh.38 (AAVI-G-4) | 435 | US20150315612 SEQ ID NO: 7 |
| AAVrl1.38 (AAVLG-4) | 436 | US20150315612 SEQ ID NO: 86 |
| AAVrh.39 | 437 | US20450159173 SEQ ID NO: 20, US20150345612 SEQ ID NO: 13 |
| AAVrh.39 | 438 | US20150159173 SEQ ID NO: 3, US20150159173 SEQ ID NO: 36, US20150315612 SEQ ID NO: 89 |
| AAVrh.40 | 439 | US20150315612 SEQ ID NO: 92 |
| AAVrh.40 (AAVLG-10) | 440 | US20150315612 SEQ ID No: 14 |
| AAVrh.43 (AAVN721-8) | 441 | US20150315612 SEQ ID NO: 43, US20150159173 SEQ ID NO: 21 |
| AAVrh.43 (AAVN721-8) | 442 | US20150315612 SEQ ID NO: 163, US20150159173 SEQ ID NO: 37 |
| AAVrh.44 | 443 | US20150315612 SEQ ID NO: 34 |
| AAVrh.44 | 444 | US20150315612 SEQ ID NO: 111 |
| AAVrh.45 | 445 | US20150315612 SEQ ID NO: 41 |
| AAVrh.45 | 446 | US20150315612 SEQ ID NO: 109 |
| AAVrh.46 | 447 | US20150159173 SEQ ID NO: 22, US20150315612 SEQ ID NO: 19 |
| AAVrh.46 | 448 | US20150159173 SEQ ID NO: 4, US20150315612 SEQ ID NO: 101 |
| AAVrh.47 | 449 | US20150315612 SEQ ID NO: 38 |
| AAVrh.47 | 450 | US20150315612 SEQ ID NO: 118 |
| AAVrh.48 | 451 | US201501591.73 SEQ ID NO: 44, US20150315612 SEQ ID NO: 115 |
| AAVrh.48.1 | 452 | US20150159173 |
| AAVrh.48.1.2 | 453 | US20150159173 |
| AAVrh.48.2 | 454 | US20150159173 |
| AAVrh.48 (AAV1-7) | 455 | US20150315612 SEQ ID NO: 32 |
| AAVrh.49 (AAV1-8) | 456 | US201503 15612 SEQ ID NO: 25 |
| AAVrh.49 (AAV1-8) | 457 | US20150315612 SEQ ID NO: 103 |
| AAVrh.50 (AAV2-4) | 458 | US20150315612 SEQ ID NO: 23 |
| AAVrh.50 (AAV2-4) | 459 | US20150315612 SEQ ID NO: 108 |
| AAVrh.51 (AAV2-5) | 460 | US20150315612 SEQ ID No: 22 |
| AAVrh.51 (AAV2-5) | 461 | VS20150315612 SEQ ID NO: 104 |
| AAVrh.52 (AAV3-9) | 462 | US20150315612 SEQ ID NO: 18 |
| AAVrh.52 (AAV3-9) | 463 | US20150315612 SEQ ID NO: 96 |
| AAVrh.53 | 464 | US20150315612 SEQ ID NO: 97 |
| AAVrh.53 (AAV3-11) | 465 | US201503 15612 SEQ ID NO: 17 |
| AAVrh.53 (AAV3-11) | 466 | US20150315612 SEQ ID NO: 186 |
| AAVrh.54 | 467 | US20150315612 SEQ ID NO: 40 |
| AAVrh.54 | 468 | US20150159173 SEQ ID NO: 49, US20150315612 SEQ ID NO: 116 |
| AAVrh.55 | 469 | US20150315612 SEQ ID NO: 37 |
| AAVrh.55 (AAV4-19) | 470 | US20150315612 SEQ ID NO: 117 |
| AAVrh.56 | 471 | US20150315612 SEQ ID NO: 54 |
| AAVrh.56 | 472 | US20150315612 SEQ ID NO: 152 |
| AAVrh.57 | 473 | US20150315612 SEQ ID NO: 26 |
| AAVrh.57 | 474 | US20150315612 SEQ ID NO: 105 |
| AAVrh.58 | 475 | US20150315612 SEQ ID NO: 27 |
| AAVrh.58 | 476 | US20150159173 SEQ ID NO: 48, US20150315612 SEQ ID NO: 106 |
| AAVrh.58 | 477 | US201503 15612 SEQ ID NO: 232 |
| AAVrh.59 | 478 | US20150315612 SEQ ID NO: 42 |
| AAVrh.59 | 479 | US20150315612 SEQ ID NO: 110 |

TABLE 1-continued

AAV Serotypes

| Serotype | SEQ ID NO | Reference Information |
|---|---|---|
| AAVrh.60 | 480 | US20150315612 SEQ ID NO: 31 |
| AAVrh.60 | 481 | US20150315612 SEQ ID NO: 120 |
| AAVrh.61 | 482 | US20150315612 SEQ ID NO: 107 |
| AAVrh.61 (AAV2-3) | 483 | US520150315612 SEQ ID NO: 21 |
| AAVrh.62 (AAV2-15) | 484 | US20150315612 SEQ ID No: 33 |
| AAVrh.62 (AAV2-15) | 485 | US20150315612 SEQ ID NO: 114 |
| AAVrh.64 | 486 | US20150315612 SEQ ID No: 15 |
| AAVrh.64 | 487 | US20150159173 SEQ ID NO: 43, US20150315612 SEQ ID NO: 99 |
| AAVrh.64 | 488 | US20150315612 SEQ ID NO: 233 |
| AAVRh.64R1 | 489 | US20150159173 |
| AAVRh.64R2 | 490 | US20150159173 |
| AAVrh.65 | 491 | US20150315612 SEQ ID NO: 35 |
| AAVrh.65 | 492 | US20150315612 SEQ ID NO: 112 |
| AAVrh.67 | 493 | US20150315612 SEQ ID NO: 36 |
| AAVrh.67 | 494 | US20150315612 SEQ ID NO: 230 |
| AAArh.67 | 495 | US20150159173 SEQ ID NO: 47, US20150315612 SEQ ID NO: 113 |
| AAVrh.68 | 496 | US20150315612 SEQ ID NO: 16 |
| AAVrh.68 | 497 | US20150315612 SEQ ID NO: 100 |
| AAVrh.69 | 498 | US20150315612 SEQ ID NO: 39 |
| AAVrh.69 | 499 | US20150315612 SEQ ID NO: 119 |
| AAVrh.70 | 500 | US20150315612 SEQ ID NO: 20 |
| AAVrh.70 | 501 | US20150315612 SEQ ID NO: 98 |
| AAVrh.71 | 502 | US20150315612 SEQ ID NO: 162 |
| AAVrh.72 | 503 | US20150315612 SEQ ID NO: 9 |
| AAVrh.73 | 504 | US20150159173 SEQ ID NO: 5 |
| AAVrh.74 | 505 | US20150159173 SEQ ID NO: 6 |
| AAVrh.8 | 506 | US20150159173 SEQ ID NO: 41 |
| AAVrh.8 | 507 | US20150315612 SEQ ID NO: 235 |
| AAVrh.8R | 508 | US20150159173, WO2015168666 SEQ ID NO: 9 |
| AAVrh.8R A586R mutant | 509 | WO2015168666 SEQ ID NO: 10 |
| AAVrh.8R R533A mutant | 510 | WO2015168666 SEQ ID NO: 11 |
| BAAV (bovine AAV) | 511 | US9193769 SEQ ID NO: 8 |
| BAAV (bovine AAV) | 512 | US9193769 SEQ ID NO: 10 |
| BAAV (bovine AAV) | 513 | US9193769 SEQ ID NO: 4 |
| BAAV (bovine AAV) | 514 | US9193769 SEQ ID NO: 2 |
| BAAV (bovine AAV) | 515 | US9193769 SEQ ID NO: 6 |
| BAAV (bovine AAV) | 516 | US9193769 SEQ ID NO: 1 |
| BAAV (bovine AAV) | 517 | US9193769 SEQ ID NO: 5 |
| BAAV (bovine AAV) | 518 | US9193769 SEQ ID NO: 3 |
| BAAV (bovine AAV) | 519 | US9193769 SEQ ID NO: 11 |
| BAAV (bovine AAV) | 520 | US7427396 SEQ ID NO: 5 |
| BAAV (bovine AAV) | 521 | US7427396 SEQ ID NO: 6 |

TABLE 1-continued

AAV Serotypes

| Serotype | SEQ ID NO | Reference Information |
|---|---|---|
| BAAV (bovine AAV) | 522 | US9193769 SEQ ID NO: 7 |
| BAAV (bovine AAV) | 523 | US9193769 SEQ ID NO: 9 |
| BNP61 AAV | 524 | US20150238550 SEQ ID NO: 1 |
| BNP61 AAV | 525 | US20150238550 SEQ ID NO: 2 |
| BNP62 AAV | 526 | US20150238550 SEQ ID NO: 3 |
| BNP63 AAV | 527 | US20150238550 SEQ ID NO: 4 |
| caprine AAV | 528 | US7427396 SEQ ID NO: 3 |
| caprine AAV | 529 | US7427396 SEQ ID NO: 4 |
| true type AAV (ttAAV) | 530 | WO2015121501 SEQ ID NO: 2 |
| AAAV (Avian AAV) | 531 | US9238800 SEQ ID NO: 12 |
| AAAV (Avian AAV) | 532 | US9238800 SEQ ID NO: 2 |
| AAAV (Avian AAV) | 533 | US9238800 SEQ ID NO: 6 |
| AAAV (Avian AAV) | 534 | US9238800 SEQ ID NO: 4 |
| AAAV (Avian AAV) | 535 | US9238800 SEQ ID NO: 8 |
| AAAV (Avian AAV) | 536 | US9238800 SEQ ID NO: 14 |
| AAAV (Avian AAV) | 537 | US9238800 SEQ ID NO: 10 |
| AAAV (Avian AAV) | 538 | US9238800 SEQ ID NO: 15 |
| AAAV (Avian AAV) | 539 | US9238800 SEQ ID NO: 5 |
| AAAV (Avian AAV) | 540 | US9238800 SEQ ID NO: 9 |
| AAAV (Avian AAV) | 541 | US9238800 SEQ ID NO: 3 |
| AAAV (Avian AAV) | 542 | US9238800 SEQ ID NO: 7 |
| AAAV (Avian AAV) | 543 | US9238800 SEQ ID NO: 11 |
| AAAV (Avian AAV) | 544 | US9238800 SEQ ID NO: 13 |
| AAAV (Avian AAV) | 545 | US9238800 SEQ ID NO: 1 |
| AAV Shuffle 100-4 | 546 | US20160017295 SEQ ID NO: 23 |
| AAV Shuffle 100-4 | 547 | US20160017295 SEQ ID NO: 11 |
| AAV Shuffle 100-2 | 548 | US20160017295 SEQ ID NO: 37 |
| AAV Shuffle 100-2 | 549 | US20160017295 SEQ ID NO: 29 |
| AAV Shuffle 100-3 | 550 | US20160017295 SEQ ID NO: 24 |
| AAV Shuffle 100-3 | 551 | US20160017295 SEQ ID NO: 12 |
| AAV Shuffle 100-7 | 552 | US20160017295 SEQ ID NO: 25 |
| AAV Shuffle 100-7 | 553 | US20160017295 SEQ ID NO: 13 |
| AAV Shuffle 10-2 | 554 | US20160017295 SEQ ID NO: 34 |
| AAV Shuffle 10-2 | 555 | US20160017295 SEQ ID NO: 26 |
| AAV Shuffle 10-6 | 556 | US20160017295 SEQ ID NO: 35 |
| AAV Shuffle 10-6 | 557 | US20160017295 SEQ ID NO: 27 |
| AAV Shuffle 10-8 | 558 | US20160017295 SEQ ID NO: 36 |
| AAV Shuffle 10-8 | 559 | US20160017295 SEQ ID NO: 28 |

TABLE 1-continued

AAV Serotypes

| Serotype | SEQ ID NO | Reference Information |
|---|---|---|
| AAV SM 100-10 | 560 | US20160017295 SEQ ID NO: 41 |
| AAV SM 100-10 | 561 | US20160017295 SEQ ID NO: 33 |
| AAV SM 100-3 | 562 | US20160017295 SEQ ID NO: 40 |
| AAV SM 100-3 | 563 | US20160017295 SEQ ID NO: 32 |
| AAV SM 10-1 | 564 | US20160017295 SEQ ID NO: 38 |
| AAV SM 10-1 | 565 | US20160017295 SEQ ID NO: 30 |
| AAV SM 10-2 | 566 | US20160017295 SEQ ID NO: 10 |
| AAV SM 10-2 | 567 | US20160017295 SEQ ID NO: 22 |
| AAV SM 10-8 | 568 | US20160017295 SEQ ID NO: 39 |
| AAV SM 10-8 | 569 | US20160017295 SEQ ID NO: 31 |
| AAV SM 100-10 | 560 | US20160017295 SEQ ID NO: 41 |
| AAV SM 100-10 | 561 | US20160017295 SEQ ID NO: 33 |
| AAV SM 100-3 | 562 | US20160017295 SEQ ID NO: 40 |
| AAV SM 100-3 | 563 | US20160017295 SEQ ID NO: 32 |
| AAV SM 10-1 | 564 | US20160017295 SEQ ID NO: 38 |
| AAV SM 10-1 | 565 | US20160017295 SEQ ID NO: 30 |
| AAV SM 10-2 | 566 | US20160017295 SEQ ID NO: 10 |
| AAV SM 10-2 | 567 | US20160017295 SEQ ID NO: 22 |
| AAV SM 10-8 | 568 | US20160017295 SEQ ID NO: 39 |
| AAV SM 10-8 | 569 | US20160017295 SEQ ID NO: 31 |
| AAVF1/HSC1 | 570 | WO2016049230 SEQ ID NO: 20 |
| AAVF2/HSC2 | 571 | WO2016049230 SEQ ID NO: 21 |
| AAVF3/HSC3 | 572 | WO2016049230 SEQ ID NO: 22 |
| AAVF4/HSC4 | 573 | WO2016049230 SEQ ID NO: 23 |
| AAVF5/HSC5 | 574 | WO2016049230 SEQ ID NO: 25 |
| AAVF6/HSC6 | 575 | WO2016049230 SEQ ID NO: 24 |
| AAVF7/HSC7 | 576 | WO2016049230 SEQ ID NO: 27 |
| AAVF8/HSC8 | 577 | WO2016049230 SEQ ID NO: 28 |
| AAVF9/HSC9 | 578 | WO2016049230 SEQ ID NO: 29 |
| AAVF11/HSC11 | 579 | WO2016049230 SEQ ID NO: 26 |
| AAVF12/HSC12 | 580 | WO2016049230 SEQ ID NO: 30 |
| AAVF13/HSC13 | 581 | WO2016049230 SEQ ID NO: 31 |
| AAVF14/HSC14 | 582 | WO2016049230 SEQ ID NO: 32 |
| AAVF15/HSC15 | 583 | WO2016049230 SEQ ID NO: 33 |
| AAVF16/HSC16 | 584 | WO2016049230 SEQ ID NO: 34 |
| AAVF17/HSC17 | 585 | WO2016049230 SEQ ID NO: 35 |
| AAVF1/HSC1 | 586 | WO2016049230 SEQ ID NO: 2 |
| AAVF2/HSC2 | 587 | WO2016049230 SEQ ID NO: 3 |
| AAVF3/HSC3 | 588 | WO2016049230 SEQ ID NO: 5 |
| AAVF4/HSC4 | 589 | WO2016049230 SEQ ID NO: 6 |
| AAVF5/HSC5 | 590 | WO2016049230 SEQ ID NO: 11 |
| AAVF6/HSC6 | 591 | WO2016049230 SEQ ID NO: 7 |
| AAVF7/HSC7 | 592 | WO2016049230 SEQ ID NO: 8 |
| AAVF8/HSC8 | 593 | WO2016049230 SEQ ID NO: 9 |
| AAVF9/HSC9 | 594 | WO2016049230 SEQ ID NO: 10 |
| AAVF11/HSC11 | 595 | WO2016049230 SEQ ID NO: 4 |
| AAVF12/HSC12 | 596 | WO2016049230 SEQ ID NO: 12 |
| AAVF13/HSC13 | 597 | WO2016049230 SEQ ID NO: 14 |
| AAVF14/HSC14 | 598 | WO2016049230 SEQ ID NO: 15 |
| AAVF15/HSC15 | 599 | WO2016049230 SEQ ID NO: 16 |
| AAVF16/HSC16 | 600 | WO2016049230 SEQ ID NO: 17 |
| AAVF17/HSC17 | 601 | WO2016049230 SEQ ID NO: 13 |
| AAV CBr-E1 | 602 | US8734809 SEQ ID NO: 13 |
| AAV CBr-E2 | 603 | US8734809 SEQ ID NO: 14 |

TABLE 1-continued

AAV Serotypes

| Serotype | SEQ ID NO | Reference Information |
|---|---|---|
| AAV CBr-E3 | 604 | US8734809 SEQ ID NO: 15 |
| AAV CBr-E4 | 605 | US8734809 SEQ ID NO: 16 |
| AAV CBr-E5 | 606 | US8734809 SEQ ID NO: 17 |
| AAV CBr-e5 | 607 | US8734809 SEQ ID NO: 18 |
| AAV CBr-E6 | 608 | US8734809 SEQ ID NO: 19 |
| AAV CBr-E7 | 609 | US8734809 SEQ ID NO: 20 |
| AAV CBr-E8 | 610 | US8734809 SEQ ID NO: 21 |
| AAV CLv-D1 | 611 | US8734809 SEQ ID NO: 22 |
| AAV CLv-D2 | 612 | US8734809 SEQ ID NO: 23 |
| AAV CLv-D3 | 613 | US8734809 SEQ ID NO: 24 |
| AAV CLv-D4 | 614 | US8734809 SEQ ID NO: 25 |
| AAV CLv-D5 | 615 | US8734809 SEQ ID NO: 26 |
| AAV CLv-D6 | 616 | US8734809 SEQ ID NO: 27 |
| AAV CLv-D7 | 617 | US8734809 SEQ ID NO: 28 |
| AAV Ctv-138 | 618 | US8734809 SEQ ID NO: 29 |
| AAV Ctv-E1 | 619 | US8734809 SEQ ID NO: 13 |
| AAV CLv-R1 | 620 | US8734809 SEQ ID NO: 30 |
| AAV CLv-R2 | 621 | US8734809 SEQ ID NO: 31 |
| AAV CLv-R3 | 622 | US8734809 SEQ ID NO: 32 |
| AAV Ctv-R4 | 623 | US8734809 SEQ ID NO: 33 |
| AAV CLv-R5 | 624 | US8734809 SEQ ID NO: 34 |
| AAV CLv-R6 | 625 | US8734809 SEQ ID NO: 35 |
| AAV CLv-R7 | 626 | US8734809 SEQ ID NO: 36 |
| AAV CLv-R8 | 627 | US8734809 SEQ ID NO: 37 |
| AAV Ctv-R9 | 628 | US8734809 SEQ ID NO: 38 |
| AAV Ctg-F1 | 629 | US8734809 SEQ ID NO: 39 |
| AAV CLg-F2 | 630 | US8734809 SEQ ID NO: 40 |
| AAV Ctg-F3 | 631 | US8734809 SEQ ID NO: 41 |
| AAV CLg-F4 | 632 | US8734809 SEQ ID NO: 42 |
| AAV CLg-F5 | 633 | US8734809 SEQ ID NO: 43 |
| AAV Ctg-F6 | 634 | US8734809 SEQ ID NO: 43 |
| AAV CLg-F7 | 635 | US8734809 SEQ ID NO: 44 |
| AAV Ctg-F8 | 636 | US8734809 SEQ ID NO: 43 |
| AAV CSp-1 | 637 | US8734809 SEQ ID NO: 45 |
| AAV CSp-10 | 638 | US8734809 SEQ ID NO: 46 |
| AAV CSp-11 | 639 | US8734809 SEQ ID NO: 47 |
| AAV CSp-2 | 640 | US8734809 SEQ ID NO: 48 |
| AAV CSp-3 | 641 | US8734809 SEQ ID NO: 49 |
| AAV CSp-4 | 642 | US8734809 SEQ ID NO: 50 |
| AAV CSp-6 | 643 | US8734809 SEQ ID NO: 51 |
| AAV CSp-7 | 644 | US8734809 SEQ ID NO: 52 |
| AAV CSp-8 | 645 | US8734809 SEQ ID NO: 53 |
| AAV CSp-9 | 646 | US8734809 SEQ ID NO: 54 |
| AAV CHt-2 | 647 | US8734809 SEQ ID NO: 55 |
| AAV CHt-3 | 648 | US8734809 SEQ ID NO: 56 |
| AAV CKd-1 | 649 | US8734809 SEQ ID NO: 57 |
| AAV CKd-10 | 650 | US8734809 SEQ ID NO: 58 |
| AAV CKd-2 | 651 | US8734809 SEQ ID NO: 59 |
| AAV CKd-3 | 652 | US8734809 SEQ ID NO: 60 |
| AAV CKd-4 | 653 | US8734809 SEQ ID NO: 61 |
| AAV CKd-6 | 654 | US8734809 SEQ ID NO: 62 |
| AAV CKd-7 | 655 | US8734809 SEQ ID NO: 63 |
| AAV CKd-8 | 656 | US8734809 SEQ ID NO: 64 |
| AAV CLv-1 | 657 | US8734809 SEQ ID NO: 65 |
| AAV CLv-12 | 658 | US8734809 SEQ ID NO: 66 |
| AAV CLv-13 | 659 | US8734809 SEQ ID NO: 67 |
| AAV CLv-2 | 660 | US8734809 SEQ ID NO: 68 |

TABLE 1-continued

AAV Serotypes

| Serotype | SEQ ID NO | Reference Information |
|---|---|---|
| AAV CLv-3 | 661 | US8734809 SEQ ID NO: 69 |
| AAV CLv-4 | 662 | US8734809 SEQ ID NO: 70 |
| AAV CLv-6 | 663 | US8734809 SEQ ID NO: 71 |
| AAV CLv-8 | 664 | US8734809 SEQ ID NO: 72 |
| AAV CKd-B1 | 665 | US8734809 SEQ ID NO: 73 |
| AAV CKd-B2 | 666 | US8734809 SEQ ID NO: 74 |
| AAV CKd-B3 | 667 | US8734809 SEQ ID NO: 75 |
| AAV CKd-B4 | 668 | US8734809 SEQ ID NO: 76 |
| AAV CKd-B5 | 669 | US8734809 SEQ ID NO: 77 |
| AAV CKd-B6 | 670 | US8734809 SEQ ID NO: 78 |
| AAV CKd-B7 | 671 | US8734809 SEQ ID NO: 79 |
| AAV CKd-B8 | 672 | US8734809 SEQ ID NO: 80 |
| AAV CKd-H1 | 673 | US8734809 SEQ ID NO: 81 |
| AAV CKd-H2 | 674 | US8734809 SEQ ID NO: 82 |
| AAV CKd-H3 | 675 | US8734809 SEQ ID NO: 83 |
| AAV CKd-H4 | 676 | US8734809 SEQ ID NO: 84 |
| AAV CKd-H5 | 677 | US8734809 SEQ ID NO: 85 |
| AAV CKd-H6 | 678 | US8734809 SEQ ID NO: 77 |
| AAV CHt-1 | 679 | US8734809 SEQ ID NO: 86 |
| AAV CLv1-1 | 680 | US8734809 SEQ ID NO: 171 |
| AAV CLv1-2 | 681 | US8734809 SEQ ID NO: 172 |
| AAV CLv1-3 | 682 | US8734809 SEQ ID NO: 173 |
| AAV CLv1-4 | 683 | US8734809 SEQ ID NO: 174 |
| AAV Clv1-7 | 684 | US18734809 SEQ ID NO: 175 |
| AAV Clv1-8 | 685 | US8734809 SEQ ID NO: 176 |
| AAV Clv1-9 | 686 | US8734809 SEQ ID NO: 177 |
| AAV Clv1-10 | 687 | US8734809 SEQ ID NO: 178 |
| AAV.VR-355 | 688 | US8734809 SEQ ID NO: 181 |
| AAV.hu.48R3 | 689 | US8734809 SEQ ID NO: 183 |
| AAV CBr-E1 | 690 | US8734809 SEQ ID NO: 87 |
| AAV CBr-E2 | 691 | US8734809 SEQ ID NO: 88 |
| AAV CBr-E3 | 692 | US8734809 SEQ ID NO: 89 |
| AAV CBr-E4 | 693 | US8734809 SEQ ID NO: 90 |
| AAV CBr-E5 | 694 | US8734809 SEQ ID NO: 91 |
| AAV CBL-e5 | 695 | US8734809 SEQ ID NO: 92 |
| AAV CBr-E6 | 696 | US8734809 SEQ ID NO: 93 |
| AAV CBr-E7 | 697 | US8734809 SEQ ID NO: 94 |
| AAV CBr-E8 | 698 | US8734809 SEQ ID NO: 95 |
| AAV CLv-D1 | 699 | US8734809 SEQ ID NO: 96 |
| AAV CLv-D2 | 700 | US8734809 SEQ ID NO: 97 |
| AAV CLv-D3 | 701 | US8734809 SEQ ID NO: 98 |
| AAV CLv-D4 | 702 | US8734809 SEQ ID NO: 99 |
| AAV CLv-D5 | 703 | US8734809 SEQ ID NO: 100 |
| AAV CLv-D6 | 704 | US8734809 SEQ ID NO: 101 |
| AAV CLv-D7 | 705 | US8734809 SEQ ID NO: 102 |
| AAV CLv-D8 | 706 | US8734809 SEQ ID NO: 103 |
| AAV CLv-E1 | 707 | US8734809 SEQ ID NO: 87 |
| AAV CLv-R1 | 708 | US8734809 SEQ ID NO: 104 |

TABLE 1-continued

AAV Serotypes

| Serotype | SEQ ID NO | Reference Information |
|---|---|---|
| AAV CLv-R2 | 709 | US8734809 SEQ ID NO: 105 |
| AAV CLv-R3 | 710 | US8734809 SEQ ID NO: 106 |
| AAV CLv-R4 | 711 | US8734809 SEQ ID NO: 107 |
| AAV CLv-R5 | 712 | US8734809 SEQ ID NO: 108 |
| AAV CLv-R6 | 713 | US8734809 SEQ ID NO: 109 |
| AAV CLv-R7 | 714 | US8734809 SEQ ID NO: 110 |
| AAV CLv-R8 | 715 | US8734809 SEQ ID NO: 111 |
| AAV CLv-R9 | 716 | US8734809 SEQ ID NO: 112 |
| AAV CLg-F1 | 717 | US8734809 SEQ ID NO: 113 |
| AAV CLg-F2 | 718 | US8734809 SEQ ID NO: 114 |
| AAV CLg-F3 | 719 | US8734809 SEQ ID NO: 115 |
| AAV CLg-F4 | 720 | US8734809 SEQ ID NO: 116 |
| AAV CLg-F5 | 721 | US8734809 SEQ ID NO: 117 |
| AAV CLg-F6 | 722 | US8734809 SEQ ID NO: 117 |
| AAV CLg-F7 | 723 | US8734809 SEQ ID NO: 118 |
| AAV CLg-F8 | 724 | US8734809 SEQ ID NO: 117 |
| AAV CSp-1 | 725 | US8734809 SEQ ID NO: 119 |
| AAV CSp-10 | 726 | US8734809 SEQ ID NO: 120 |
| AAV CSp-11 | 727 | US8734809 SEQ ID NO: 121 |
| AAV CSp-2 | 728 | US8734809 SEQ ID NO: 122 |
| AAV CSp-3 | 729 | US8734809 SEQ ID NO: 123 |
| AAV CSp-4 | 730 | US8734809 SEQ ID NO: 124 |
| AAV CSp-6 | 731 | US8734809 SEQ ID NO: 125 |
| AAV CSp-7 | 732 | US8734809 SEQ ID NO: 126 |
| AAV CSp-8 | 733 | US8734809 SEQ ID NO: 127 |
| AAV CSp-9 | 734 | US8734809 SEQ ID NO: 128 |
| AAV CHt-2 | 735 | US8734809 SEQ ID NO: 129 |
| AAV CHt-3 | 736 | US8734809 SEQ ID NO: 130 |
| AAV CKd-1 | 737 | US8734809 SEQ ID NO: 131 |
| AAV CKd-10 | 738 | US8734809 SEQ ID NO: 132 |
| AAV CKd-2 | 739 | US8734809 SEQ ID NO: 133 |
| AAV CKd-3 | 740 | US8734809 SEQ ID NO: 134 |
| AAV CKd-4 | 741 | US8734809 SEQ ID NO: 135 |
| AAV CKd-6 | 742 | US8734809 SEQ ID NO: 136 |
| AAV CKd-7 | 743 | US8734809 SEQ ID NO: 137 |
| AAV CKd-8 | 744 | US8734809 SEQ ID NO: 138 |
| AAV CLv-1 | 745 | US8734809 SEQ ID NO: 139 |
| AAV CLv-2 | 746 | US8734809 SEQ ID NO: 140 |
| AAV CLv-3 | 747 | US8734809 SEQ ID NO: 141 |
| AAV CLv-2 | 748 | US8734809 SEQ ID NO: 142 |
| AAV CLv-3 | 749 | US8734809 SEQ ID NO: 143 |
| AAV CLv-4 | 750 | US8734809 SEQ ID NO: 144 |
| AAV CLv-6 | 751 | US8734809 SEQ ID NO: 145 |
| AAV CLy-8 | 752 | US8734809 SEQ ID NO: 146 |
| AAV CKd-B1 | 753 | US8734809 SEQ ID NO: 147 |
| AAV CKd-B2 | 754 | US8734809 SEQ ID NO: 148 |
| AAV CKd-B3 | 755 | US8734809 SEQ ID NO: 149 |
| AAV CKd-B4 | 756 | US8734809 SEQ ID NO: 150 |
| AAV CKd-B5 | 757 | US8734809 SEQ ID NO: 151 |
| AAV CKd-B6 | 758 | US8734809 SEQ ID NO: 152 |
| AAV CKd-B7 | 759 | US8734809 SEQ ID NO: 153 |
| AAV CKd-B8 | 760 | US8734809 SEQ ID NO: 154 |
| AAV CKd-H1 | 761 | US8734809 SEQ ID NO: 155 |
| AAV CKd-H2 | 762 | US8734809 SW ID NO: 156 |
| AAV CKd-H3 | 763 | US8734809 SEQ ID NO: 157 |

TABLE 1-continued

AAV Serotypes

| Serotype | SEQ ID NO | Reference Information |
|---|---|---|
| AAV CKd-H4 | 764 | US8734809 SEQ ID NO: 158 |
| AAV CKd-H5 | 765 | US8734809 SEQ ID NO: 159 |
| AAV CKd-H6 | 766 | US8734809 SEQ ID NO: 151 |
| AAV CHt-1 | 767 | US8734809 SEQ ID NO: 160 |
| AAV CHt-P2 | 768 | WO2016065001 SEQ ID NO: 1 |
| AAV CHt-P5 | 769 | WO2016065001 SEQ ID NO: 2 |
| AAV CHt-P9 | 770 | WO2016065001 SEQ ID NO: 3 |
| AAV CBr-7.1 | 771 | WO2016065001 SEQ ID NO: 4 |
| AAV CBr-7.2 | 772 | WO2016065001 SEQ ID NO: 5 |
| AAV CBr-7.3 | 773 | WO2016065001 SEQ ID NO: 6 |
| AAV CBr-7.4 | 774 | WO2016065001 SEQ ID NO: 7 |
| AAV CBr-7.5 | 775 | WO2016065001 SEQ ID NO: 8 |
| AAV CBr-7.7 | 776 | WO2016065001 SEQ ID NO: 9 |
| AAV CBr-7.8 | 777 | WO2016065001 SEQ ID NO: 10 |
| AAV CBr-7.10 | 778 | WO2016065001 SEQ ID NO: 11 |
| AAV CKd-N3 | 779 | WO2016065001 SEQ ID NO: 12 |
| AAV CKd-N4 | 780 | WO2016065001 SEQ ID NO: 13 |
| AAV CKd-N9 | 781 | WO2016065001 SEQ ID NO: 14 |
| AAV CLv-L4 | 782 | WO2016065001 SEQ ID NO: 15 |
| AAV CLv-L5 | 783 | WO2016065001 SEQ ID NO: 16 |
| AAV CLv-L6 | 784 | WO2016065001 SEQ ID NO: 17 |
| AAV CLv-K1 | 785 | WO2016065001 SEQ ID NO: 18 |
| AAV CLv-K3 | 786 | WO2016065001 SEQ ID NO: 19 |
| AAV CLv-K6 | 787 | WO2016065001 SEQ ID NO: 20 |
| AAV CLv-M1 | 788 | WO2016065001 SEQ ID NO: 21 |
| AAV CLv-M11 | 789 | WO2016065001 SEQ ID NO: 22 |
| AAV CLv-M2 | 790 | WO2016065001 SEQ ID NO: 23 |
| AAV CLv-M5 | 791 | WO2016065001 SEQ ID NO: 24 |
| AAV CLv-M6 | 792 | WO2016065001 SEQ ID NO: 25 |
| AAV CLv-M7 | 793 | WO2016065001 SEQ ID NO: 26 |
| AAV CLv-M8 | 794 | WO2016065001 SEQ ID NO: 27 |
| AAV CLv-M9 | 795 | WO2016065001 SEQ ID NO: 28 |
| AAV CHt-P1 | 796 | WO2016065001 SEQ ID NO: 29 |
| AAV CHt-P6 | 797 | WO2016065001 SEQ ID NO: 30 |
| AAV CHt-P8 | 798 | WO2016065001 SEQ ID NO: 31 |
| AAV CHt-6.1 | 799 | WO2016065001 SEQ ID NO: 32 |
| AAV CHt-6.10 | 800 | WO2016065001 SEQ ID NO: 33 |
| AAV CHt-6.5 | 801 | WO2016065001 SEQ ID NO: 34 |
| AAV CHt-6.6 | 802 | WO2016065001 SEQ ID NO: 35 |
| AAV CHt-6.7 | 803 | WO2016065001 SEQ ID NO: 36 |
| AAV CHt-6.8 | 804 | WO2016065001 SEQ ID NO: 37 |
| AAV CSp-8.10 | 805 | WO2016065001 SEQ ID NO: 38 |

TABLE 1-continued

AAV Serotypes

| Serotype | SEQ ID NO | Reference Information |
|---|---|---|
| AAV CSp-8.2 | 806 | WO2016065001 SEQ ID NO: 39 |
| AAV CSp-8.4 | 807 | WO2016065001 SEQ ID NO: 40 |
| AAV CSp-8.5 | 808 | WO2016065001 SEQ ID NO: 41 |
| AAV CSp-8.6 | 809 | WO2016065001 SEQ ID NO: 42 |
| AAV CSp-8.7 | 810 | WO2016065001 SEQ ID NO: 43 |
| AAV CSp-8.8 | 811 | WO2016065001 SEQ ID NO: 44 |
| AAV CSp-8.9 | 812 | WO2016065001 SEQ ID NO: 45 |
| AAV CBr-B7.3 | 813 | WO2016065001 SEQ ID NO: 46 |
| AAV CBr-B7.4 | 814 | WO2016065001 SEQ ID NO: 47 |
| AAV3B | 815 | WO2016065001 SEQ ID NO: 48 |
| AAV4 | 816 | WO2016065001 SEQ ID NO: 49 |
| AAV5 | 817 | WO2016065001 SEQ ID NO: 50 |
| AAV CHt-P2 | 818 | WO2016065001 SEQ ID NO: 51 |
| AAV CHt-P5 | 819 | WO2016065001 SEQ ID NO: 52 |
| AAV CHt-P9 | 820 | WO2016065001 SEQ ID NO: 53 |
| AAV CBr-7.1 | 821 | WO2016065001 SEQ ID NO: 54 |
| AAV CBr-7.2 | 822 | WO2016065001 SEQ ID NO: 55 |
| AAV CBr-7.3 | 823 | WO2016065001 SEQ ID NO: 56 |
| AAV CBr-7.4 | 824 | WO2016065001 SEQ ID NO: 57 |
| AAV CBr-7.5 | 825 | WO2016065001 SEQ ID NO: 58 |
| AAV CBr-7.7 | 826 | WO2016065001 SEQ ID NO: 59 |
| AAV CBr-7.8 | 827 | WO2016065001 SEQ ID NO: 60 |
| AAV CBr-7.10 | 828 | WO2016065001 SEQ ID NO: 61 |
| AAV CKd-N3 | 829 | WO2016065001 SEQ ID NO: 62 |
| AAV CKd-N4 | 830 | WO2016065001 SEQ ID NO: 63 |
| AAV CKd-N9 | 831 | WO2016C65001 SEQ ID NO: 64 |
| AAV CLv-L4 | 832 | WO2016065001 SEQ ID NO: 65 |
| AAV CLv-L5 | 833 | WO2016065001 SEQ ID NO: 66 |
| AAV CLv-L6 | 834 | WO2016065001 SEQ ID NO: 67 |
| AAV CLv-K1 | 835 | WO2016065001 SEQ ID NO: 68 |
| AAV CLv-K3 | 836 | WO2016065001 SEQ ID NO: 69 |
| AAV CLv-K6 | 837 | WO2016065001 SEQ ID NO: 70 |
| AAV CLv-M1 | 838 | WO2016065001 SEQ ID NO: 71 |
| AAV CLv-M11 | 839 | WO2016065001 SEQ ID NO: 72 |
| AAV CLv-M2 | 840 | WO2016065001 SEQ ID NO: 73 |
| AAV CLv-M5 | 841 | WO2016065001 SEQ ID NO: 74 |
| AAV CLv-M6 | 842 | WO2016065001 SEQ ID NO 75 |
| AAV CLv-M7 | 843 | WO2016065001 SEQ ID NO: 76 |
| AAV CLv-M8 | 844 | WO2016065001 SEQ ID NO: 77 |
| AAV CLv-M9 | 845 | WO2016065001 SEQ ID NO: 78 |
| AAV CHt-P1 | 846 | WO2016065001 SEQ ID NO: 79 |
| AAV CHt-P6 | 847 | WO2016065001 SEQ ID NO: 80 |
| AAV CHt-P8 | 848 | WO2016065001 SEQ ID NO: 81 |

TABLE 1-continued

AAV Serotypes

| Serotype | SEQ ID NO | Reference Information |
|---|---|---|
| AAV CHt-6.1 | 849 | WO2016065001 SEQ ID NO: 82 |
| AAV CHt-6.10 | 850 | WO2016065001 SEQ ID NO: 83 |
| AAV CHt-6.5 | 851 | WO2016065001 SEQ ID NO: 84 |
| AAV CHt-6.6 | 852 | WO2016065001 SEQ ID NO: 85 |
| AAV CHt-6.7 | 853 | WO2016065001 SEQ ID NO: 86 |
| AAV CHt-6.8 | 854 | WO2016065001 SEQ ID NO: 87 |
| AAV CSp-8.10 | 855 | WO2016065001 SEQ ID NO: 88 |
| AAV CSp-8.2 | 856 | WO2016065001 SEQ ID NO: 89 |
| AAV CSp-8.4 | 857 | WO2016065001 SEQ ID NO: 90 |
| AAV CSp-8.5 | 858 | WO2016065001 SEQ ID NO: 91 |
| AAV CSp-8.6 | 859 | WO2016065001 SEQ ID NO: 92 |
| AAV CSp-8.7 | 860 | WO2016065001 SEQ ID NO: 93 |
| AAV CSp-8.8 | 861 | WO2016065001 SEQ ID NO: 94 |
| AAV CSp-8.9 | 862 | WO2016C65001 SEQ ID NO: 95 |
| AAV CBr-B7.3 | 863 | WO2016065001 SEQ ID NO: 96 |
| AAV CBr-B7.4 | 864 | WO2016065001 SEQ ID NO: 97 |
| AAV3B | 865 | WO2016065001 SEQ ID NO: 98 |
| AAV4 | 866 | WO2016065001 SEQ ID NO: 99 |
| AAV5 | 867 | WO2016065001 SEQ ID NO: 100 |
| AAVPHP.B or G2B-26 | 868 | WO2015038958 SEQ ID NO: 8 and 13; GenBankALUS85156.1 |
| AAVPHP.B | 869 | WO2015038958 SEQ ID NO: 9 |
| AAVG2B-13 | 870 | WO2015038958 SEQ ID NO: 12 |
| AAVTH1.1-32 | 871 | WO2015038958 SEQ ID NO: 14 |
| AAVTH1.1-35 | 872 | WO2015038958 SEQ ID NO: 15 |
| PHP.N/PHP.B-DGT | 1418 | WO2017100671 SEQ ID NO: 46 |
| PHP.S/G2A12 | 1419 | WO2017100671 SEQ ID NO: 47 |
| AAV9/hu.14 K449R | 1420 | WO2017100671 SEQ ID NO: 45 |
| GPV | 1421 | US9624274B2 SEQ ID NO: 192 |
| B19 | 1422 | US9624274B2 SEQ ID NO: 193 |
| MVM | 1423 | US9624274B2 SEQ ID NO: 194 |
| FPV | 1424 | US9624274B2 SEQ ID NO: 195 |
| CPV | 1425 | US9624274B2 SEQ ID NO: 196 |
| AAV6 | 1426 | US9546112B2 SEQ ID NO: 5 |
| AAV6 | 1427 | US9457103B2 SEQ ID NO: 1 |
| AAV2 | 1428 | US9457103B2 SEQ ID NO: 2 |
| ShH10 | 1429 | US9457103B2 SEQ ID NO: 3 |
| ShH13 | 1430 | US9457103B2 SEQ ID NO: 4 |
| ShH10 | 1431 | US9457103B2 SEQ ID NO: 5 |
| ShH10 | 1432 | US9457103B2 SEQ ID NO:6 |
| ShH10 | 1433 | US9457103B2 SEQ ID NO: 7 |
| ShH10 | 1434 | US9457103B2 SEQ ID NO: 8 |
| ShH10 | 1435 | US9457103B2 SEQ ID NO: 9 |
| rh74 | 1436 | US9434928B2 SEQ ID NO: 1 US2015023924A1 SEQ ID NO: 2 |
| rh74 | 1437 | US9434928B2 SEQ ID NO: 2, US2015023924A1 SEQ ID NO: 1 |
| AAV8 | 1438 | US9434928B2 SEQ ID NO: 4 |
| rh74 | 1439 | US9434928B2 SEQ ID NO: 5 |
| rh74 (RHM4-1) | 1440 | US2015023924A1 SEQ ID NO: 5, US20160375110A1 SEQ ID NO: 4 |
| rh74 (RHM15-1) | 1441 | US2015023924A1 SEQ ID NO: 6, US20160375110A1 SEQ ID NO: 5 |
| rh74 (RHM15-2) | 1442 | US2015023924A1 SEQ ID NO: 7, US20160375110A1 SEQ ID NO: 6 |

TABLE 1-continued

| Serotype | SEQ ID NO | Reference Information |
|---|---|---|
| rh74 (RHM15-3/RhM15-5) | 1443 | US2015023924A1 SEQ ID NO: 8, US20160375110A1 SEQ ID NO: 7 |
| rh74 (RHM15-4) | 1444 | US2015023924A1 SEQ ID NO: 9, US20160375110A1 SEQ ID NO: 8 |
| rh74 (RHM15-6) | 1445 | US2015023924A1 SEQ ID NO: 10, US20160375110A1 SEQ ID NO: 9 |
| rh74 (RHM4-1) | 1446 | US2015023924A1 SEQ ID NO: 11 |
| rh74 (RHM15-1) | 1447 | US2015023924A1 SEQ ID NO: 12 |
| rh74 (RHM15-2) | 1448 | US2015023924A1 SEQ ID NO: 13 |
| rh74 (RHM15-3/RHM15-5) | 1449 | US2015023924A1 SEQ ID NO: 14 |
| rh74 (RHM15-4) | 1450 | 1-152015023924A1 SEQ ID NO: 15 |
| rh74 (RHM15-6) | 1451 | US2015023924A1 SEQ ID NO: 16 |
| AAV2 (comprising lung specific polypeptide) | 1452 | US20160175389A1 SEQ ID NO: 9 |
| AAV2 (comprising lung specific poly peptide) | 1453 | US20160175389A1 SEQ ID NO: 10 |
| Anc80 | 1454 | US20170051257A1 SEQ ID NO: 1 |
| Anc80 | 1455 | US20170051257A1 SEQ ID NO: 2 |
| Anc81 | 1456 | US20170051257A1 SEQ ID NO: 3 |
| Anc80 | 1457 | US20170051257A1 SEQ ID NO: 4 |
| Anc82 | 1458 | US20170051257A1 SEQ ID NO: 5 |
| Anc82 | 1459 | US20170051257A1 SEQ ID NO: 6 |
| Anc83 | 1460 | US20170051257A1 SEQ ID NO: 7 |
| Anc83 | 1461 | US20170051257A1 SEQ ID NO: 8 |
| Anc84 | 1462 | US20170051257A1 SEQ ID NO: 9 |
| Anc84 | 1463 | US20170051257A1 SEQ ID NO: 10 |
| Anc94 | 1464 | US20170051257A1 SEQ ID NO: 11 |
| Anc94 | 1465 | US20170051257A1 SEQ ID NO: 12 |
| Anc113 | 1466 | US20170051257A1 SEQ ID NO: 13 |
| Anc113 | 1467 | US20170051257A1 SEQ ID NO: 14 |
| Anc126 | 1468 | US20170051257A1 SEQ ID NO: 15 |
| Anc126 | 1469 | US20170051257A1 SEQ ID NO: 16 |
| Anc127 | 1470 | US20170051257A1 SEQ ID NO: 17 |
| Anc127 | 1471 | US20170051257A1 SEQ ID NO: 18 |
| Anc80L27 | 1472 | US20170051257A1 SEQ ID NO: 19 |
| Anc80L59 | 1473 | US20170051257A1 SEQ ID NO: 20 |
| Anc80L60 | 1474 | US20170051257A1 SEQ ID NO: 21 |
| Anc80L62 | 1475 | US20170051257A1 SEQ ID NO: 22 |
| Anc80L65 | 1476 | US20170051257A SEQ ID NO: 23 |
| Anc80L33 | 1477 | US20170051257A1 SEQ ID NO: 24 |
| Anc80L36 | 1478 | US20170051257A1 SEQ ID NO: 25 |
| Anc80L44 | 1479 | US20170051257A1 SEQ ID NO: 26 |
| Anc80L1 | 1480 | US20170051257A1 SEQ ID NO: 35 |
| Anc80L1 | 1481 | US20170051257A1 SEQ ID NO: 36 |
| AAV-X1 | 1482 | US8283151B2 SEQ ID NO: 11 |
| AAV-X1b | 1483 | US8283151B2 SEQ ID NO: 12 |
| AAV-X5 | 1484 | US8283151B2 SEQ ID NO: 13 |
| AAV-X19 | 1485 | US8283151B2 SEQ ID NO: 14 |
| AAV-X21 | 1486 | US8283151B2 SEQ ID NO: 15 |
| AAV-X22 | 1487 | US8283151B2 SEQ ID NO: 16 |
| AAV-X23 | 1488 | US8283151B2 SEQ ID NO: 17 |
| AAV-X24 | 1489 | US8283151B2 SEQ ID NO: 18 |
| AAV-X75 | 1490 | US8283151B2 SEQ ID NO: 19 |
| AAV-X26 | 1491 | US8283151B2 SEQ ID NO: 20 |
| AAV-X1 | 1492 | US8283151B2 SEQ ID NO: 21 |
| AAV-X1b | 1493 | US8283151B2 SEQ ID NO: 22 |
| AAV-X5 | 1494 | US8283151B2 SEQ ID NO: 23 |
| AAV-X19 | 1495 | US8283151B2 SEQ ID NO: 24 |
| AAV-X21 | 1496 | US8283151B2 SEQ ID NO: 25 |
| AAV-X22 | 1497 | US8283151B2 SEQ ID NO: 26 |
| AAV-X23 | 1498 | US8283151B2 SEQ H) NO: 27 |
| AAV-X24 | 1499 | US8283151B2 SEQ ID NO: 28 |

TABLE 1-continued

AAV Serotypes

| Serotype | SEQ ID NO | Reference Information |
|---|---|---|
| AAV-X25 | 1500 | US8283151B2 SEQ ID NO: 29 |
| AAV-X26 | 1501 | US8283151B2 SEQ ID NO: 30 |
| AAVrh8 | 1502 | WO2016054554A1 SEQ ID NO: 8 |
| AAVrh8VP2 FC5 | 1503 | WO2016054554A1 SEQ ID NO: 9 |
| AAVrh8VP2 FC44 | 1504 | WO2016054554A1 SEQ ID NO: 10 |
| AAVrh8VP2 ApoB100 | 1505 | WO2016054554A1 SEQ ID NO: 11 |
| AAVrh8VP2 RVG | 1506 | WO2016054554A1 SEQ ID NO: 12 |
| AAVrh8VP2 Angiopep-2 VP2 | 1507 | WO2016054554A1 SEQ ID NO: 13 |
| AAV9.47VP 1.3 | 1508 | WO2016054554A1 SEQ ID NO: 14 |
| AAV9.47VP 2ICAMg3 | 1509 | WO2016054554A1 SEQ ID NO: 15 |
| AAV9.47VP 2RVG | 1510 | WO2016054554A1 SEQ ID NO: 16 |
| AAV9.47VP 2Angiopep-2 | 1511 | WO2016054554A1 SEQ ID NO: 17 |
| AAV9.47VP 2A-string | 1512 | WO2016054554A1 SEQ ID NO: 18 |
| AAVrh8VP2 FC5 VP2 | 1513 | WO2016054554A1 SEQ ID NO: 19 |
| AAVrh8VP2 FC44 VP2 | 1514 | WO2016054554A1 SEQ ID NO: 20 |
| AAVrh8VP2 ApoB100 VP2 | 1515 | WO2016054554A1 SEQ ID NO: 21 |
| AAVrh8VP2 RVG VP2 | 1516 | WO2016054554A1 SEQ ID NO: 22 |
| AAVrh8VP2 Angiopep-2 VP2 | 1517 | WO2016054554A1 SEQ ID NO: 23 |
| AAV9.47VP 2ICAMg3 VP2 | 1518 | WO2016054554A1 SEQ ID NO: 24 |
| AAV9.47-VP 2RVG VP2 | 1519 | WO2016054554A1 SEQ ID NO: 25 |
| AAV9.47VP 2Angiopep-2 VP2 | 1520 | WO2016054554A1 SEQ ID NO: 26 |
| AAV9.47VP 2A-string VP2 | 1521 | WO2016054554A1 SEQ ID NO: 27 |
| rAAV-B1 | 1522 | WO2016054557A1 SEQ ID NO: 1 |
| rAAV-B2 | 1523 | WO2016054557A1 SEQ ID NO: 2 |
| rAAV-B3 | 1524 | WO2016054557A1 SEQ ID NO: 3 |
| rAAV-B4 | 1525 | WO2016054557A1 SEQ ID NO: 4 |
| rAAV-B1 | 1526 | WO2016054557A1 SEQ ID NO: 5 |
| rAAV-B2 | 1527 | WO2016054557A1 SEQ ID NO: 6 |
| rAAV-B3 | 1528 | WO2016054557A1 SEQ ID NO: 7 |
| rAAV-B4 | 1529 | WO2016054557A1 SEQ ID NO: 8 |
| rAAV-L1 | 1530 | WO2016054557A1 SEQ ID NO: 9 |
| rAAV-L2 | 1531 | WO2016054557A1 SEQ ID NO: 10 |
| rAAV-L3 | 1532 | WO2016054557A1 SEQ ID NO: 11 |
| rAAV-L4 | 1533 | WO2016054557A1 SEQ ID NO: 12 |
| rAAV-L1 | 1534 | WO2016054557A1 SEQ ID NO: 13 |
| rAAV-L2 | 1535 | WO2016054557A1 SEQ ID NO: 14 |
| rAAV-L3 | 1536 | WO2016054557A1 SEQ ID NO: 15 |
| rAAV-L4 | 1537 | WO2016054557A1 SEQ ID NO: 16 |
| rAAV9 | 1538 | WO2016073739A1 SEQ ID NO: 3 |
| rAAV | 1539 | WO2016081811A1 SEQ ID NO: 1 |
| rAAV | 1540 | WO2016081811A1 SEQ ID NO: 2 |
| rAAV | 1541 | WO2016081811A1 SEQ ID NO: 3 |
| rAAV | 1542 | WO2016081811A1 SEQ ID NO: 4 |
| rAAV | 1543 | WO2016081811A1 SEQ ID NO: 5 |
| rAAV | 1544 | WO2016081811A1 SEQ ID NO: 6 |
| rAAV | 1545 | WO2016081811A1 SEQ ID NO: 7 |
| rAAV | 1546 | WO2016081811A1 SEQ ID NO: 8 |
| rAAV | 1547 | WO2016081811A1 SEQ ID NO: 9 |
| rAAV | 1548 | WO2016081811A1 SEQ ID NO: 10 |

TABLE 1-continued

AAV Serotypes

| Serotype | SEQ ID NO | Reference Information |
|---|---|---|
| rAAV | 1549 | WO2016081811A1 SEQ ID NO: 11 |
| rAAV | 1550 | WO2016081811A1 SEQ ID NO: 12 |
| rAAV | 1551 | WO2016081811A1 SEQ ID NO: 13 |
| rAAV | 1552 | WO2016081811A1 SEQ ID NO: 14 |
| rAAV | 1553 | WO2016081811A1 SEQ ID NO: 15 |
| rAAV | 1554 | WO2016081811A1 SEQ ID NO: 16 |
| rAAV | 1555 | WO2016081811A1 SEQ ID NO: 17 |
| rAAV | 1556 | WO2016081811A1 SEQ ID NO: 18 |
| rAAV | 1557 | WO2016081811A1 SEQ ID NO: 19 |
| rAAV | 1558 | WO2016081811A1 SEQ ID NO: 20 |
| rAAV | 1559 | WO2016081811A1 SEQ ID NO: 21 |
| rAAV | 1560 | WO2016081811A1 SEQ ID NO: 22 |
| rAAV | 1561 | WO2016081811A1 SEQ ID NO: 23 |
| rAAV | 1562 | WO2016081811A1 SEQ ID NO: 24 |
| rAAV | 1563 | WO2016081811A1 SEQ ID NO: 25 |
| rAAV | 1564 | WO2016081811A1 SEQ ID NO: 26 |
| rAAV | 1565 | WO2016081811A1 SEQ ID NO: 27 |
| rAAV | 1566 | WO2016081811A1 SEQ ID NO: 28 |
| rAAV | 1567 | WO2016081811A1 SEQ ID NO: 29 |
| rAAV | 1568 | WO2016081811A1 SEQ ID NO: 30 |
| rAAV | 1569 | WO2016081811A1 SEQ ID NO: 31 |
| rAAV | 1570 | WO2016081811A1 SEQ ID NO: 32 |
| rAAV | 1571 | WO2016081811A1 SEQ ID NO: 33 |
| rAAV | 1572 | WO2016081811A1 SEQ ID NO: 34 |
| rAAV | 1573 | WO2016081811A1 SEQ ID NO: 35 |
| rAAV | 1574 | WO2016081811A1 SEQ ID NO: 36 |
| rAAV | 1575 | WO2016081811A1 SEQ ID NO: 37 |
| rAAV | 1576 | WO2016081811A1 SEQ ID NO: 38 |
| rAAV | 1577 | WO2016081811A1 SEQ ID NO: 39 |
| rAAV | 1578 | WO2016081811A1 SEQ ID NO: 40 |
| rAAV | 1579 | WO2016081811A1 SEQ ID NO: 41 |
| rAAV | 1580 | WO2016081811A1 SEQ ID NO: 42 |
| rAAV | 1581 | WO2016081811A1 SEQ ID NO: 43 |
| rAAV | 1582 | WO2016081811A1 SEQ ID NO: 44 |
| rAAV | 1583 | WO2016081811A1 SEQ ID NO: 45 |
| rAAV | 1584 | WO2016081811A1 SEQ ID NO: 46 |
| rAAV | 1585 | WO2016081811A1 SEQ ID NO: 47 |
| rAAV | 1586 | WO2016081811A1 SEQ ID NO: 48 |
| rAAV | 1587 | WO2016081811A1 SEQ ID NO: 49 |
| rAAV | 1588 | WO2016081811A1 SEQ ID NO: 50 |
| rAAV | 1589 | WO2016081811A1 SEQ ID NO: 51 |
| rAAV | 1590 | WO2016081811A1 SEQ ID NO: 52 |
| rAAV | 1591 | WO2016081811A1 SEQ ID NO: 53 |
| rAAV | 1592 | WO2016081811A1 SEQ ID NO: 54 |
| rAAV | 1593 | WO2016081811A1 SEQ ID NO: 55 |
| rAAV | 1594 | WO2016081811A1 SEQ ID NO: 56 |
| rAAV | 1595 | WO2016081811A1 SEQ ID NO: 57 |
| rAAV | 1596 | WO2016081811A1 SEQ ID NO: 58 |
| rAAV | 1597 | WO2016081811A1 SEQ ID NO: 59 |
| rAAV | 1598 | WO2016081811A1 SEQ ID NO: 60 |
| rAAV | 1599 | WO2016081811A1 SEQ ID NO: 61 |
| rAAV | 1600 | WO2016081811A1 SEQ ID NO: 62 |
| rAAV | 1601 | WO2016081811A1 SEQ ID NO: 63 |
| rAAV | 1602 | WO2016081811A1 SEQ ID NO: 64 |
| rAAV | 1603 | WO2016081811A1 SEQ ID NO: 65 |
| rAAV | 1604 | WO2016081811A1 SEQ ID NO: 66 |
| rAAV | 1605 | WO2016081811A1 SEQ ID NO: 67 |
| rAAV | 1606 | WO2016081811A1 SEQ ID NO: 68 |
| rAAV | 1607 | WO2016081811A1 SEQ ID NO: 69 |
| rAAV | 1608 | WO2016081811A1 SEQ ID NO: 70 |
| rAAV | 1609 | WO2016081811A1 SEQ ID NO: 71 |
| rAAV | 1610 | WO2016081811A1 SEQ ID NO: 72 |
| rAAV | 1611 | WO2016081811A1 SEQ ID NO: 73 |
| rAAV | 1612 | WO2016081811A1 SEQ ID NO: 74 |
| rAAV | 1613 | WO2016081811A1 SEQ ID NO: 75 |
| rAAV | 1614 | WO2016081811A1 SEQ ID NO: 76 |
| rAAV | 1615 | WO2016081811A1 SEQ ID NO: 77 |
| rAAV | 1616 | WO2016081811A1 SEQ ID NO: 78 |
| rAAV | 1617 | WO2016081811A1 SEQ ID NO: 79 |
| rAAV | 1618 | WO2016081811A1 SEQ ID NO: 80 |
| rAAV | 1619 | WO2016081811A1 SEQ ID NO: 81 |
| rAAV | 1620 | WO2016081811A1 SEQ ID NO: 82 |
| rAAV | 1621 | WO2016081811A1 SEQ ID NO: 83 |
| rAAV | 1622 | WO2016081811A1 SEQ ID NO: 84 |

TABLE 1-continued

AAV Serotypes

| Serotype | SEQ ID NO | Reference Information |
|---|---|---|
| rAAV | 1623 | WO2016081811A1 SEQ ID NO: 85 |
| rAAV | 1624 | WO2016081811A1 SEQ ID NO: 86 |
| rAAV | 1625 | WO2016081811A1 SEQ ID NO: 87 |
| rAAV | 1626 | WO2016081811A1 SEQ ID NO: 88 |
| rAAV | 1627 | WO2016081811A1 SEQ ID NO: 89 |
| rAAV | 1628 | WO2016081811A1 SEQ ID NO: 90 |
| rAAV | 1629 | WO2016081811A1 SEQ ID NO: 91 |
| rAAV | 1630 | WO2016081811A1 SEQ ID NO: 92 |
| rAAV | 1631 | WO2016081811A1 SEQ ID NO: 93 |
| rAAV | 1632 | WO2016081811A1 SEQ ID NO: 94 |
| rAAV | 1633 | WO2016081811A1 SEQ ID NO: 95 |
| rAAV | 1634 | WO2016081811A1 SEQ ID NO: 96 |
| rAAV | 1635 | WO2016081811A1 SEQ ID NO: 97 |
| rAAV | 1636 | WO2016081811A1 SEQ ID NO: 98 |
| rAAV | 1637 | WO2016081811A1 SEQ ID NO: 99 |
| rAAV | 1638 | WO2016081811A1 SEQ ID NO: 100 |
| rAAV | 1639 | WO2016081811A1 SEQ ID NO: 101 |
| rAAV | 1640 | WO2016081811A1 SEQ ID NO: 102 |
| rAAV | 1641 | WO2016081811A1 SEQ ID NO: 103 |
| rAAV | 1642 | WO2016081811A1 SEQ ID NO: 104 |
| rAAV | 1643 | WO2016081811A1 SEQ ID NO: 105 |
| rAAV | 1644 | WO2016081811A1 SEQ ID NO: 106 |
| rAAV | 1645 | WO2016081811A1 SEQ ID NO: 107 |
| rAAV | 1646 | WO2016081811A1 SEQ ID NO: 108 |
| rAAV | 1647 | WO2016081811A1 SEQ ID NO: 109 |
| rAAV | 1648 | WO2016081811A1 SEQ ID NO: 110 |
| rAAV | 1649 | WO2016081811A1 SEQ ID NO: 111 |
| rAAV | 1650 | WO2016081811A1 SEQ ID NO: 112 |
| rAAV | 1651 | WO2016081811A1 SEQ ID NO: 113 |
| rAAV | 1652 | WO2016081811A1 SEQ ID NO: 114 |
| rAAV | 1653 | WO2016081811A1 SEQ ID NO: 115 |
| rAAV | 1654 | WO2016081811A1 SEQ ID NO: 116 |
| rAAV | 1655 | WO2016081811A1 SEQ ID NO: 117 |
| rAAV | 1656 | WO2016081811A1 SEQ ID NO: 118 |
| rAAV | 1657 | WO2016081811A1 SEQ ID NO: 119 |
| rAAV | 1658 | WO2016081811A1 SEQ ID NO: 120 |
| rAAV | 1659 | WO2016081811A1 SEQ ID NO: 121 |
| rAAV | 1660 | WO2016081811A1 SEQ ID NO: 122 |
| rAAV | 1661 | WO2016081811A1 SEQ ID NO: 123 |
| rAAV | 1662 | WO2016081811A1 SEQ ID NO: 124 |
| rAAV | 1663 | WO2016081811A1 SEQ ID NO: 125 |
| rAAV | 1664 | WO2016081811A1 SEQ ID NO: 126 |
| rAAV | 1665 | WO2016081811A1 SEQ ID NO: 127 |
| rAAV | 1666 | WO2016081811A1 SEQ ID NO: 128 |
| AAV8 E532K | 1667 | WO2016081811A1 SEQ ID NO: 133 |
| AAV8 E532K | 1668 | WO2016081811A1 SEQ ID NO: 134 |
| rAAV4 | 1669 | WO2016115382A1 SEQ ID NO: 2 |
| rAAV4 | 1670 | WO2016115382A1 SEQ ID NO: 3 |
| rAAV4 | 1671 | WO2016115382A1 SEQ ID NO: 4 |
| rAAV4 | 1672 | WO2016115382A1 SEQ ID NO: 5 |
| rAAV4 | 1673 | WO2016115382A1 SEQ ID NO: 6 |
| rAAV4 | 1674 | WO2016115382A1 SEQ ID NO: 7 |
| rAAV4 | 1675 | WO2016115382A1 SEQ ID NO: 8 |
| rAAV4 | 1676 | WO2016115382A1 SEQ ID NO: 9 |
| rAAV4 | 1677 | WO2016115382A1 SEQ ID NO: 10 |
| rAAV4 | 1678 | WO2016115382A1 SEQ ID NO: 11 |
| rAAV4 | 1679 | WO2016115382A1 SEQ ID NO: 12 |
| rAAV4 | 1680 | WO2016145382A1 SEQ ID NO: 13 |
| rAAV4 | 1681 | WO2016115382A1 SEQ ID NO: 14 |
| rAAV4 | 1682 | WO2016115382A1 SEQ ID NO: 15 |
| rAAV4 | 1683 | WO2016115382A1 SEQ ID NO: 16 |
| rAAV4 | 1684 | WO2016115382A1 SEQ ID NO: 17 |
| rAAV4 | 1685 | WO2016145382A1 SEQ ID NO: 18 |
| rAAV4 | 1686 | WO2016115382A1 SEQ ID NO: 19 |
| rAAV4 | 1687 | WO2016115382A1 SEQ ID NO: 20 |
| rAAV4 | 1688 | WO2016115382A1 SEQ ID NO: 21 |
| AAV11 | 1689 | WO2016115382A1 SEQ ID NO: 22 |
| AAV12 | 1690 | WO2016115382A1 SEQ ID NO: 23 |
| rh32 | 1691 | WO2016115382A1 SEQ ID NO: 25 |
| rh33 | 1692 | WO2016115382A1 SEQ ID NO: 26 |
| rh34 | 1693 | WO2016145382A1 SEQ ID NO: 27 |
| rAAV4 | 1694 | WO2016115382A1 SEQ ID NO: 28 |

TABLE 1-continued

AAV Serotypes

| Serotype | SEQ ID NO | Reference Information |
|---|---|---|
| rAAV4 | 1695 | WO2016115382A1 SEQ ID NO: 29 |
| rAAV4 | 1696 | WO2016115382A1 SEQ ID NO: 30 |
| rAAV4 | 1697 | WO2016115382A1 SEQ ID NO: 31 |
| rAAV4 | 1698 | WO2016145382A1 SEQ ID NO: 32 |
| rAAV4 | 1699 | WO2016115382A1 SEQ ID NO: 33 |
| AAV2/8 | 1700 | WO2016131981A1 SEQ ID NO: 47 |
| AAV2/8 | 1701 | WO2016131981A1 SEQ ID NO: 48 |
| ancestral AAV | 1702 | WO2016154344A1 SEQ ID NO: 7 |
| ancestral AAV variant C4 | 1703 | WO2016154344A1 SEQ ID NO: 13 |
| ancestral AAV variant C7 | 1704 | WO2016154344A1 SEQ ID NO: 14 |
| ancestral AAV variant G4 | 1705 | WO2016154344A1 SEQ ID NO: 15 |
| consensus amino acid sequence of ancestral AAV variants, C4. C7 and G4 | 1706 | WO2016154344A1 SEQ ID NO: 16 |
| consensus amino acid sequence of ancesiral AAV variants, C4 and C7 | 1707 | WO2016154344A1 SEQ ID NO: 17 |
| AAV8 (with a AAV2 phospholipase domain) | 1708 | WO2016150403A1 SEQ ID NO: 13 |
| AAV VR-942n | 1709 | US20160289275A1 SEQ ID NO: 10 |
| AAV5-A (M569V) | 1710 | US20160289275A1 SEQ ID NO: 13 |
| AAV5-A (M569V) | 1711 | US20160289275A1 SEQ ID NO: 14 |
| AAV5-A (Y585V) | 1712 | US20160289275A1 SEQ ID NO: 16 |
| AAV5-A (Y585V) | 1713 | US20160289275A1 SEQ ID NO: 17 |
| AAV5-A (L587T) | 1714 | US20160289275A1 SEQ ID NO: 19 |
| AAV5-A (L587T) | 1715 | US20160289275A1 SEQ ID NO: 20 |
| AAV5-A (Y585V/L587T) | 1716 | US20160289275A1 SEQ ID NO: 22 |
| AAV5-A (Y585V/L1587T) | 1717 | US20160289275A1 SEQ ID NO: 23 |
| AAV5-B (D652A) | 1718 | US20160289275A1 SEQ ID NO: 25 |
| AAV5-B (D652A) | 1719 | US20160289275A1 SEQ ID NO: 26 |
| AAV5-B (T362M) | 1720 | US20160289275A1 SEQ ID NO: 28 |
| AAV5-B (T362M) | 1721 | US20160289275A1 SEQ ID NO: 29 |
| AAV5-B (Q359D) | 1722 | US20160289275A1 SEQ ID NO: 31 |
| AAV5-B (Q359D) | 1723 | US20160289275A1 SEQ ID NO: 32 |
| AAV5-B (E350Q) | 1724 | US20160289275A1 SEQ ID NO: 34 |
| AAV5-B (E350Q) | 1725 | US20160289275A1 SEQ ID NO: 35 |
| AAV5-B (P533S) | 1726 | US20160289275A1 SEQ ID NO: 37 |
| AAV5-B (P533S) | 1727 | US20160289275A1 SEQ ID NO: 38 |

TABLE 1-continued

AAV Serotypes

| Serotype | SEQ ID NO | Reference Information |
|---|---|---|
| AAV5-B (P533G) | 1728 | US20160289275A1 SEQ ID NO: 40 |
| AAV5-13 (P533G) | 1729 | US20160289275A1 SEQ ID NO: 41 |
| AAV5-mutation in loop VII | 1730 | US20160289275A1 SEQ ID NO: 43 |
| AAV5-mutation in loop VII | 1731 | US20160289275A1 SEQ ID NO: 44 |
| AAV8 | 1732 | US20160289275A1 SEQ ID NO: 47 |
| Mut A (LK03/AAV8) | 1733 | WO2016181123A1 SEQ ID NO: 1 |
| Mut B (LK03/AAV5) | 1734 | WO2016181123A1 SEQ ID NO: 2 |
| Mut C (AAV8/AAV3B) | 1735 | WO2016181123A1 SEQ ID NO: 3 |
| Mut D (AAV5/AAV3B) | 1736 | WO2016181123A1 SEQ ID NO: 4 |
| Mut E (AAV8/AAV3B) | 1737 | WO2016181123A1 SEQ ID NO: 5 |
| Mut F (AAV3B/AAV8) | 1738 | WO2016181123A1 SEQ ID NO: 6 |
| AAV44.9 | 1739 | WO2016183297A1 SEQ ID NO: 4 |
| AAV44.9 | 1740 | WO2016183297A1 SEQ ID NO: 5 |
| AAVrh8 | 1741 | WO2016183297A1 SEQ ID NO: 6 |
| AAV44.9 (S470N) | 1742 | WO2016183297A1 SEQ ID NO: 9 |
| rh74 VP1 | 1743 | US20160375110A1 SEQ ID NO: 1 |
| AAV-LK03 (L125I) | 1744 | WO2017015102A1 SEQ ID NO: 5 |
| AAV3B (S663V + T492V) | 1745 | WO2017015102A1 SEQ ID NO: 6 |
| Anc80 | 1746 | WO2017019994A2 SEQ ID NO: 1 |
| Anc80 | 1747 | WO2017019994A2 SEQ ID NO: 2 |
| Anc81 | 1748 | WO2017019994A2 SEQ ID NO: 3 |
| Anc81 | 1749 | WO2017019994A2 SEQ ID NO: 4 |
| Anc82 | 1750 | WO2017019994A2 SEQ ID NO: 5 |
| Anc82 | 1751 | WO2017019994A2 SEQ ID NO: 6 |
| Anc83 | 1752 | WO2017019994A2 SEQ ID NO: 7 |
| Anc83 | 1753 | WO2017019994A2 SEQ ID NO: 8 |
| Anc84 | 1754 | WO2017019994A2 SEQ ID NO: 9 |
| Anc84 | 1755 | WO2017019994A2 SEQ ID NO: 10 |
| Anc94 | 1756 | WO2017019994A2 SEQ ID NO: 11 |
| Anc94 | 1757 | WO2017019994A2 SEQ ID NO: 12 |
| Anc113 | 1758 | WO2017019994A2 SEQ ID NO: 13 |
| Anc113 | 1759 | WO2017019994A2 SEQ ID NO: 14 |
| Anc126 | 1760 | WO2017019994A2 SEQ ID NO: 15 |
| Anc126 | 1761 | WO2017019994A2 SEQ ID NO: 16 |
| Anc127 | 1762 | WO2017019994A2 SEQ ID NO: 17 |
| Anc127 | 1763 | WO2017019994A2 SEQ ID NO: 18 |
| Anc80L27 | 1764 | WO2017019994A2 SEQ ID NO: 19 |
| Anc80L59 | 1765 | WO2017019994A2 SEQ ID NO: 20 |
| Anc80L60 | 1766 | WO2017019994A2 SEQ ID NO: 21 |
| Anc80L62 | 1767 | WO2017019994A2 SEQ ID NO: 22 |
| Anc80L65 | 1768 | WO2017019994A2 SEQ ID NO: 23 |
| Anc80L33 | 1769 | WO2017019994A2 SEQ ID NO: 24 |
| Anc80L36 | 1770 | WO2017019994A2 SEQ ID NO: 25 |
| Anc80L44 | 1771 | WO2017019994A2 SEQ ID NO: 26 |
| Anc80L1 | 1772 | WO2017019994A2 SEQ ID NO: 35 |
| Anc80L1 | 1773 | WO2017019994A2 SEQ ID NO: 36 |
| AAVrh10 | 1774 | WO2017019994A2 SEQ ID NO: 41 |
| Anc110 | 1775 | WO2017019994A2 SEQ ID NO: 42 |
| Anc110 | 1776 | WO2017019994A2 SEQ ID NO: 43 |
| AAVrh32.33 | 1777 | WO2017019994A2 SEQ ID NO: 45 |
| AAVrh74 | 1778 | WO2017049031A1 SEQ ID NO: 1 |
| AAV2 | 1779 | WO2017053629A2 SEQ ID NO: 49 |
| AAV2 | 1780 | WO2017053629A2 SEQ ID NO: 50 |
| AAV2 | 1781 | WO2017053629A2 SEQ ID NO: 82 |
| Parvo-like virus | 1782 | WO2017070476A2 SEQ ID NO: 1 |
| Parvo-like virus | 1783 | WO2017070476A2 SEQ ID NO: 2 |

TABLE 1-continued

AAV Serotypes

| Serotype | SEQ ID NO | Reference Information |
|---|---|---|
| Parvo-like virus | 1784 | WO2017070476A2 SEQ ID NO: 3 |
| Parvo-like virus | 1785 | WO2017070476A2 SEQ ID NO: 4 |
| Parvo-like virus | 1786 | WO2017070476A2 SEQ ID NO: 5 |
| Parvo-like virus | 1787 | WO2017070476A2 SEQ ID NO: 6 |
| AAVrh.10 | 1788 | WO2017070516A1 SEQ ID NO: 7 |
| AAVrh.10 | 1789 | WO2017070516A1 SEQ ID NO: 14 |
| AAV2tYF | 1790 | WO2017070491A1 SEQ ID NO: 1 |
| AAV-SPK | 1791 | WO2017075619A1 SEQ ID NO:28 |
| AAV2.5 | 1792 | US20170128528A1 SEQ ID NO: 13 |
| AAV1.1 | 1793 | US20170128528A1 SEQ ID NO: 15 |
| A AV6.1 | 1794 | US20170128528A1 SEQ ID NO: 17 |
| AAV6.3.1 | 1795 | US20170128528A1 SEQ ID NO: 18 |
| AAV2i8 | 1796 | US20170128528A1 SEQ ID NO: 28 |
| AAV2i8 | 1797 | US20170128528A1 SEQ ID NO: 29 |
| ttAAV | 1798 | US20170128528A1 SEQ ID NO: 30 |
| ttAAV-S312N | 1799 | US20170128528A1 SEQ ID NO: 32 |
| ttAAV-S312N | 1800 | US20170128528A1 SEQ ID NO: 33 |
| AAV6 (Y705, Y731, and T492) | 1801 | WO2016134337A1 SEQ ID NO: 24 |
| AAV2 | 1802 | WO2016134375A1 SEQ ID NO: 9 |
| AAV2 | 1803 | WO2016134375A1 SEQ ID NO: 10 |

Each of the patents, applications and/or publications listed in Table 1 are hereby incorporated by reference in their entirety.

In one embodiment, the AAV serotype may be, or may have a sequence as described in International Patent Publication WO2015038958, the contents of which are herein incorporated by reference in their entirety, such as, but not limited to, AAV9 (SEQ ID NO: 2 and 11 of WO2015038958 or SEQ ID NO: 127 and 126 respectively herein), PHP.B (SEQ ID NO: 8 and 9 of WO2015038958, herein SEQ ID NO: 868 and 869), G2B-13 (SEQ ID NO: 12 of WO2015038958, herein SEQ ID NO: 870), G2B-26 (SEQ ID NO: 13 of WO2015038958, herein SEQ ID NO: 868 and 869), TH1.1-32 (SEQ ID NO: 14 of WO2015038958, herein SEQ ID NO: 871), TH1.1-35 (SEQ ID NO: 15 of WO2015038958, herein SEQ ID NO: 872) or variants thereof. Further, any of the targeting peptides or amino acid inserts described in WO2015038958, may be inserted into any parent AAV serotype, such as, but not limited to, AAV9 (SEQ ID NO: 126 for the DNA sequence and SEQ ID NO: 127 for the amino acid sequence). In one embodiment, the amino acid insert is inserted between amino acids 586-592 of the parent AAV (e.g., AAV9). In another embodiment, the amino acid insert is inserted between amino acids 588-589 of the parent AAV sequence. The amino acid insert may be, but is not limited to, any of the following amino acid sequences, TLAVPFK (SEQ ID NO: 1 of WO2015038958; herein SEQ ID NO: 873), KFPVALT (SEQ ID NO: 3 of WO2015038958; herein SEQ ID NO: 874), LAVPFK (SEQ ID NO: 31 of WO2015038958; herein SEQ ID NO: 875), AVPFK (SEQ ID NO: 32 of WO2015038958; herein SEQ ID NO: 876), VPFK (SEQ ID NO: 33 of WO2015038958; herein SEQ ID NO: 877), TLAVPF (SEQ ID NO: 34 of WO2015038958; herein SEQ ID NO: 878), TLAVP (SEQ ID NO: 35 of WO2015038958; herein SEQ ID NO: 879), TLAV (SEQ ID NO: 36 of WO2015038958; herein SEQ ID NO: 880), SVSKPFL (SEQ ID NO: 28 of WO02015038958; herein SEQ ID NO: 881), FTLTTPK (SEQ ID NO: 29 of WO2015038958; herein SEQ ID NO: 882), MNATKNV (SEQ ID NO: 30 of WO02015038958; herein SEQ ID NO: 883), QSSQTPR (SEQ ID NO: 54 of WO2015038958; herein SEQ ID NO: 884), ILGTGTS (SEQ ID NO: 55 of WO2015038958; herein SEQ ID NO: 885), TRTNPEA (SEQ ID NO: 56 of WO2015038958; herein SEQ ID NO: 886), NGGTSSS (SEQ ID NO: 58 of WO2015038958; herein SEQ ID NO: 887), or YTLSQGW (SEQ ID NO: 60 of WO2015038958; herein SEQ ID NO: 888), Non-limiting examples of nucleotide sequences that may encode the amino acid inserts include the following, AAGTTTCCTGTGGCGTTGACT (for SEQ ID NO: 3 of WO2015038958; herein SEQ ID NO: 889), ACTTTGGCGGTGCCTTTTAAG (SEQ ID NO: 24 and 49 of WO2015038958; herein SEQ ID NO: 890), AGTGTGAGTAAGCCTTTTTTG (SEQ ID NO: 25 of WO2015038958; herein SEQ ID NO: 891), TTTACGTTGACGACGCCTAAG (SEQ ID NO: 26 of WO2015038958; herein SEQ ID NO: 892), ATGAATGCTACGAAGAATGTG (SEQ ID NO: 27 of WO2015038958; herein SEQ ID NO: 893), CAGTCGTCGCAGACGCCTAGG (SEQ ID NO: 48 of WO2015038958; herein SEQ ID NO: 894), ATTCTGGGACTGGTACTTCG (SEQ ID NO: 50 and 52 of WO2015038958; herein SEQ ID NO: 895), ACGCGGACTAATCCTGAGGCT (SEQ ID NO: 51 of WO2015038958; herein SEQ ID NO: 896), AATGGGGGGACTAGTAGTTCT (SEQ ID NO: 53 of WO2015038958; herein SEQ ID NO: 897), or TATACTTTGTCGCAGGGTTGG (SEQ ID NO: 59 of WO2015038958; herein SEQ ID NO: 898).

In one embodiment, the AAV serotype may be engineered to comprise at least one AAV capsid CD8+ T-cell epitope for AAV2 such as, but not limited to, SADNNNSEY (SEQ ID NO: 899), LIDQYLYYL (SEQ ID NO: 900), VPQYGYLTL (SEQ ID NO: 901), TTSTRTWAL (SEQ ID NO: 902), YHLNGRDSL (SEQ ID NO: 903), SQAVGRSSF (SEQ ID NO: 904), VPANPSTTF (SEQ ID NO: 905), FPQSGVLIF (SEQ ID NO: 906), YFDFNRFHCHFSPRD (SEQ ID NO: 907), VGNSSGNWHCDSTWM (SEQ ID NO: 908), QFSQAGASDIRDQSR (SEQ ID NO: 909), GASDIRQSRNWLP (SEQ ID NO: 910) and GNRQAAT-ADVNTQGV (SEQ ID NO: 911).

In one embodiment, the AAV serotype may be engineered to comprise at least one AAV capsid CD8+ T-cell epitope for AAV1 such as, but not limited to, LDRLMNPLI (SEQ ID NO: 912), TTSTRTWAL (SEQ ID NO: 902), and QPAKKRLNF (SEQ ID NO: 913)).

In one embodiment, the AAV serotype may be, or may have a sequence as described in International Patent Publication WO02017100671, the contents of which are herein incorporated by reference in their entirety, such as, but not limited to, AAV9 (SEQ ID NO: 45 of WO2017100671, herein SEQ ID NO: 1420), PHP.N (SEQ ID NO: 46 of WO2017100671, herein SEQ ID NO: 1418), PHP.S (SEQ ID NO: 47 of WO2017100671, herein SEQ ID NO: 1419), or variants thereof. Further, any of the targeting peptides or amino acid inserts described in WO2017100671 may be inserted into any parent AAV serotype, such as, but not limited to, AAV9 (SEQ ID NO: 127 or SEQ ID NO: 1420). In one embodiment, the amino acid insert is inserted between amino acids 586-592 of the parent AAV (e.g., AAV9). In another embodiment, the amino acid insert is inserted between amino acids 588-589 of the parent AAV sequence. The amino acid insert may be, but is not limited to, any of the following amino acid sequences, AQTLAVPFKAQ (SEQ ID NO: 1 of WO2017100671; herein SEQ ID NO: 1804), AQSVSKPFLAQ (SEQ ID NO: 2 of WO2017100671; herein SEQ ID NO: 1805), AQFTLTTPKAQ (SEQ ID NO: 3 in the sequence listing of WO2017100671; herein SEQ ID NO: 1806), DGTLAVPFKAQ (SEQ ID NO: 4 in the sequence listing of WO2017100671; herein SEQ ID NO: 1807), ESTLAVPFKAQ (SEQ ID NO: 5 of WO2017100671; herein SEQ ID NO: 1808), GGTLAVPFKAQ (SEQ ID NO: 6 of WO2017100671; herein SEQ ID NO: 1809), AQTLATPFKAQ (SEQ ID NO: 7 and 33 of WO2017100671; herein SEQ ID NO: 1810), ATTLATPFKAQ (SEQ ID NO: 8 of WO2017100671; herein SEQ ID NO: 1811), DGTLATPFKAQ (SEQ ID NO: 9 of WO2017100671; herein SEQ ID NO: 1812), GGTLATPFKAQ (SEQ ID NO: 10 of WO2017100671; herein SEQ ID NO: 1813), SGSLAVPFKAQ (SEQ ID NO: 11 of WO2017100671; herein SEQ ID NO: 1814), AQTLAQPFKAQ (SEQ ID NO: 12 of WO2017100671; herein SEQ ID NO: 1815), AQTLQQPFKAQ (SEQ ID NO: 13 of WO2017100671; herein SEQ ID NO: 1816), AQTLSNPFKAQ (SEQ ID NO: 14 of WO2017100671; herein SEQ ID NO: 1817), AQTLAVPFSNP (SEQ ID NO: 15 of WO2017100671; herein SEQ ID NO: 1818), QGTLAVPFKAQ (SEQ ID NO: 16 of WO2017100671; herein SEQ ID NO: 1819), NQTLAVPFKAQ (SEQ ID NO: 17 of WO2017100671; herein SEQ ID NO: 1820), EGSLAVPFKAQ (SEQ ID NO: 18 of WO2017100671; herein SEQ ID NO: 1821), SGNLAVPFKAQ (SEQ ID NO: 19 of WO2017100671; herein SEQ ID NO: 1822), EGTLAVPFKAQ (SEQ ID NO: 20 of WO2017100671; herein SEQ ID NO: 1823), DSTLAVPFKAQ (SEQ ID NO: 21 in Table 1 of WO2017100671; herein SEQ ID NO: 1824), AVTLAVPFKAQ (SEQ ID NO: 22 of WO2017100671; herein SEQ ID NO: 1825), AQTLSTPFKAQ (SEQ ID NO: 23 of WO2017100671; herein SEQ ID NO: 1826), AQTLPQPFKAQ (SEQ ID NO: 24 and 32 of WO2017100671; herein SEQ ID NO: 1827), AQTLSQPFKAQ (SEQ ID NO: 25 of WO2017100671; herein SEQ ID NO: 1828), AQTLQLPFKAQ (SEQ ID NO: 26 of WO2017100671; herein SEQ ID NO: 1829), AQTLTMPFKAQ (SEQ ID NO: 27, and 34 of WO2017100671 and SEQ ID NO: 35 in the sequence listing of WO2017100671; herein SEQ ID NO: 1830), AQTLTTPFKAQ (SEQ ID NO: 28 of WO2017100671; herein SEQ ID NO: 1831), AQYTLSQGWAQ (SEQ ID NO: 29 of WO2017100671; herein SEQ ID NO: 1832), AQMNATKNVAQ (SEQ ID NO: 30 of WO2017100671; herein SEQ ID NO: 1833), AQVSGGHHSAQ (SEQ ID NO: 31 of WO2017100671; herein SEQ ID NO: 1834), AQTLTAPFKAQ (SEQ ID NO: 35 in Table 1 of WO2017100671; herein SEQ ID NO: 1835), AQTLSKPFKAQ (SEQ ID NO: 36 of WO2017100671; herein SEQ ID NO: 1836), QAVRTSL (SEQ ID NO: 37 of WO2017100671; herein SEQ ID NO: 1837), YTLSQGW (SEQ ID NO: 38 of WO2017100671; herein SEQ ID NO: 888), LAKERLS (SEQ ID NO: 39 of WO2017100671, herein SEQ ID NO: 1838), TLAVPFK (SEQ ID NO: 40 in the sequence listing of WO2017100671; herein SEQ ID NO: 873), SVSKPFL (SEQ ID NO: 41 of WO2017100671; herein SEQ ID NO: 881), FTLTTPK (SEQ ID NO: 42 of WO2017100671; herein SEQ ID NO: 882), MNSTKNV (SEQ ID NO: 43 of WO2017100671; herein SEQ ID NO: 1839), VSGGHHS (SEQ ID NO: 44 of WO02017100671; herein SEQ ID NO: 1840), SAQTLAVPFKAQAQ (SEQ ID NO: 48 of WO2017100671; herein SEQ ID NO: 1841), SXXXLAVPFKAQAQ (SEQ ID NO: 49 of WO2017100671 wherein X may be any amino acid; herein SEQ ID NO: 1842), SAQXXXVPFKAQAQ (SEQ ID NO: 50 of WO2017100671 wherein X may be any amino acid; herein SEQ ID NO: 1843), SAQTLXXXFKAQAQ (SEQ ID NO: 51 of WO2017100671 wherein X may be any amino acid; herein SEQ ID NO: 1844), SAQTLAVXXXAQAQ (SEQ ID NO: 52 of WO2017100671 wherein X may be any amino acid; herein SEQ ID NO: 1845), SAQTLAVPFXXXAQ (SEQ ID NO: 53 of WO2017100671 wherein X may be any amino acid; herein SEQ ID NO: 1846), TNHQSAQ (SEQ ID NO: 65 of WO2017100671; herein SEQ ID NO: 1847), AQAQTGW (SEQ ID NO: 66 of WO2017100671; herein SEQ ID NO: 1848), DGTLATPFK (SEQ ID NO: 67 of WO2017100671; herein SEQ ID NO: 1849), DGTLATPFKXX (SEQ ID NO: 68 of WO2017100671 wherein X may be any amino acid; herein SEQ ID NO: 1850), LAVPFKAQ (SEQ ID NO: 80 of WO2017100671; herein SEQ ID NO: 1851), VPFKAQ (SEQ ID NO: 81 of WO2017100671; herein SEQ ID NO: 1852), FKAQ (SEQ ID NO: 82 of WO2017100671; herein SEQ ID NO: 1853), AQTLAV (SEQ ID NO: 83 of WO2017100671; herein SEQ ID NO: 1854), AQTLAVPF (SEQ ID NO: 84 of WO2017100671; herein SEQ ID NO: 1855), QAVR (SEQ ID NO: 85 of WO2017100671; herein SEQ ID NO: 1856), AVRT (SEQ ID NO: 86 of WO2017100671, herein SEQ ID NO: 1857), VRTS (SEQ ID NO: 87 of WO2017100671; herein SEQ ID NO: 1858), RTSL (SEQ ID NO: 88 of WO2017100671; herein SEQ ID NO: 1859), QAVRT (SEQ ID NO: 89 of WO2017100671; herein SEQ ID NO: 1860), AVRTS (SEQ ID NO: 90 of WO2017100671; herein SEQ ID NO: 1861), VRTSL (SEQ ID NO: 91 of WO2017100671; herein SEQ ID NO: 1862), QAVRTS (SEQ ID NO: 92 of WO2017100671; herein SEQ ID NO: 1863), or AVRTSL (SEQ ID NO: 93 of WO2017100671; herein SEQ ID NO: 1864).

Non-limiting examples of nucleotide sequences that may encode the amino acid inserts include the following, GATGGGACTTTGGCGGTGCCTTTAAGGCACAG (SEQ ID NO: 54 of WO2017100671; herein SEQ ID NO: 1865), GATGGGACGTTGGCGGTGCCTTTTAAGGCACAG (SEQ ID NO: 55 of WO2017100671; herein SEQ ID NO: 1866), CAGGCGGTTAGGACGTCTTTG (SEQ ID NO: 56 of WO2017100671; herein SEQ ID NO: 1867), CAGGTCTACGGACTCAGACTATCAG (SEQ ID NO: 57 and 78 of WO2017100671; herein SEQ ID NO: 1868), CAAGTAAAACCTCTACAAATGTGGTAAAATCG (SEQ ID NO: 58 of WO2017100671 herein SEQ ID NO: 1869), ACTCATCGACCAATACTTGTACTATCTCTAGAAC (SEQ ID NO: 59 of WO2017100671; herein SEQ ID NO: 1870), GGAAGTATTCCTTGGTTTGAACCCA (SEQ ID NO: 60 of WO2017100671; herein SEQ ID NO: 1871), GGTCGCGGTTCTTGTTTGTGGAT (SEQ ID NO: 61 of WO2017100671; herein SEQ ID NO: 1872), CGACCTTGAAGCGCATGAACTCCT (SEQ ID NO: 62 of WO2017100671; herein SEQ ID NO: 1873), GTATTCCTGGTTTTGAACC-CAACCGGTCTGCGCCTGTGCMNNMNNMNNMNN-MNN MNNMNNTTGGGCACTCTGGTGGTTTGTC (SEQ ID NO: 63 of WO2017100671 wherein N may be A, C, T, or G; herein SEQ ID NO: 1874), GTATTCCTTGGTTTGAACC-CAACCGGTCTGCGCMNNMNNMN-NAAAAGGCACCGCC AAAGTTTG (SEQ ID NO: 69 of WO2017100671 wherein N may be A, C, T, or G; herein SEQ ID NO: 1875), GTATTCCTTGGTTTTGAACC-CAACCGGTCTGCGCCTGTGCMNNMNNMNN-CACCGCC AAAGTTTGGGCACT (SEQ ID NO: 70 of WO2017100671 wherein N may be A, C, T, or G; herein SEQ ID NO: 1876), GTATCCTTTGGTTTTGAACC-CAACCGGTCTGCGCCTGTGCCT-TAAAMNNMNNMNNC AAAGTTTTGGGCACTCTGGTGG (SEQ ID NO: 71 of WO2017100671 wherein N may be A, C, T, or G; herein SEQ ID NO: 1877), GTATTCCTTGGTTTGAACC-CAACCGGTCTGCGCCTGTGCCT-TAAAAGGCACMNNM NNMNNTTGGGCACTCTGGTGGTTTGTG (SEQ ID NO: 72 of WO2017100671 wherein N may be A, C, T, or G; herein SEQ ID NO: 1878), ACTTTGGCGGTGCCITTTAAG (SEQ ID NO: 74 of WO2017100671; herein SEQ ID NO: 890), AGTGTGAGTAAGCCTTTTTG (SEQ ID NO: 75 of WO2017100671; herein SEQ ID NO: 891), TTTACGTTGACGACGCCTAAG (SEQ ID NO: 76 of WO2017100671; herein SEQ ID NO: 892), TATACTTTGTCGCAGGTTGG (SEQ ID NO: 77 of WO2017100671; herein SEQ ID NO: 898), or CTTGCGAAGGAGCGGCTTTCG (SEQ ID NO: 79 of WO2017100671; herein SEQ ID NO: 1879).

In one embodiment, the AAV serotype may be, or may have a sequence as described in U.S. Pat. No. 9,624,274, the contents of which are herein incorporated by reference in their entirety, such as, but not limited to, AAV1 (SEQ ID NO: 181 of U.S. Pat. No. 9,624,274), AAV6 (SEQ ID NO: 182 of U.S. Pat. No. 9,624,274), AAV2 (SEQ ID NO: 183 of U.S. Pat. No. 9,624,274), AAV3b (SEQ ID NO: 184 of U.S. Pat. No. 9,624,274), AAV7 (SEQ ID NO: 185 of U.S. Pat. No. 9,624,274), AAV8 (SEQ ID NO: 186 of U.S. Pat. No. 9,624,274), AAV100 (SEQ ID NO: 187 of U.S. Pat. No. 9,624,274), AAV4 (SEQ ID NO: 188 of U.S. Pat. No. 9,624,274), AAV11 (SEQ ID NO: 189 of U.S. Pat. No. 9,624,274), bAAV (SEQ ID NO: 190 of U.S. Pat. No. 9,624,274), AAV5 (SEQ ID NO: 191 of U.S. Pat. No. 9,624,274), GPV (SEQ ID NO: 192 of U.S. Pat. No. 9,624,274; herein SEQ ID NO: 1421), B19 (SEQ ID NO: 193 of U.S. Pat. No. 9,624,274; herein SEQ ID NO: 1422), MVM (SEQ ID NO: 194 of U.S. Pat. No. 9,624,274; herein SEQ ID NO: 1423), FPV (SEQ ID NO: 195 of U.S. Pat. No. 9,624,274; herein SEQ ID NO: 1424), CPV (SEQ ID NO: 196 of U.S. Pat. No. 9,624,274; herein SEQ ID NO: 1425) or variants thereof. Further, any of the structural protein inserts described in U.S. Pat. No. 9,624,274, may be inserted into, but not limited to, I-453 and I-587 of any parent AAV serotype, such as, but not limited to, AAV2 (SEQ ID NO: 183 of U.S. Pat. No. 9,624,274). The amino acid insert may be, but is not limited to, any of the following amino acid sequences, VNLTWSRASG (SEQ ID NO: 50 of U.S. Pat. No. 9,624,274; herein SEQ ID NO: 1880), EFCINHRGYWVCGD (SEQ ID NO:55 of U.S. Pat. No. 9,624,274; herein SEQ ID NO: 1881), EDGQVMDVDLS (SEQ ID NO: 85 of U.S. Pat. No. 9,624,274; herein SEQ ID NO: 1882), EKQRNGTLT (SEQ ID NO: 86 of U.S. Pat. No. 9,624,274; herein SEQ ID NO: 1883), TYQCRVTHPHLPRALMR (SEQ ID NO: 87 of U.S. Pat. No. 9,624,274 herein SEQ ID NO: 1884), RHSTTQPRKTKGSG (SEQ ID NO: 88 of U.S. Pat. No. 9,624,274; herein SEQ ID NO: 1885), DSNPRGVSAYLSR (SEQ ID NO: 89 of U.S. Pat. No. 9,624,274; herein SEQ ID NO: 1886), TITCLWDLAPSK (SEQ ID NO: 90 of U.S. Pat. No. 9,624,274; herein SEQ ID NO: 1887), KTKGSGFFVF (SEQ ID NO: 91 of U.S. Pat. No. 9,624,274; herein SEQ ID NO: 1888), THPHLPRALMRS (SEQ ID NO: 92 of U.S. Pat. No. 9,624,274; herein SEQ ID NO: 1889), GETYQCRVTHPHLPRALMRSTTK (SEQ ID NO: 93 of U.S. Pat. No. 9,624,274; herein SEQ ID NO: 1890), LPRALMRS (SEQ ID NO: 94 of U.S. Pat. No. 9,624,274; herein SEQ ID NO: 1891), INHRGYWV (SEQ ID NO: 95 of U.S. Pat. No. 9,624,274; herein SEQ ID NO: 1892), CDAGSVRTNAPD (SEQ ID NO: 60 of U.S. Pat. No. 9,624,274; herein SEQ ID NO: 1893), AKAVSNLTESRSESLQS (SEQ ID NO: 96 of U.S. Pat. No. 9,624,274; herein SEQ ID NO: 1894), SLTGDEFKKVLET (SEQ ID NO: 97 of U.S. Pat. No. 9,624,274; herein SEQ ID NO: 1895), REAVAYRFEED (SEQ ID NO: 98 of U.S. Pat. No. 9,624, 274; herein SEQ ID NO: 1896), INPEIITLDG (SEQ ID NO: 99 of U.S. Pat. No. 9,624,274; herein SEQ ID NO: 1897), DISVTGAPVITATYL (SEQ ID NO: 100 of U.S. Pat. No. 9,624,274; herein SEQ ID NO: 1898), DISVTGAPVITA (SEQ ID NO: 101 of U.S. Pat. No. 9,624,274; herein SEQ ID NO: 1899), PKTVSNLTESSSESVQS (SEQ ID NO: 102 of U.S. Pat. No. 9,624,274; herein SEQ ID NO: 1900), SLMGDEFKAVLET (SEQ ID NO: 103 of U.S. Pat. No. 9,624,274; herein SEQ ID NO: 1901), QHSVAYTFEED (SEQ ID NO: 104 of U.S. Pat. No. 9,624,274; herein SEQ ID NO: 1902), INPEIITRDG (SEQ ID NO: 105 of U.S. Pat. No. 9,624,274; herein SEQ ID NO: 1903), DISLTGDPVITASYL (SEQ ID NO: 106 of U.S. Pat. No. 9,624,274; herein SEQ ID NO: 1904), DISLTGDPVITA (SEQ ID NO: 107 of U.S. Pat. No. 9,624,274; herein SEQ ID NO: 1905), DQSIDFEIDSA (SEQ ID NO: 108 of U.S. Pat. No. 9,624,274; herein SEQ ID NO: 1906), KNVSEDLPLPTFSPTLLGDS (SEQ ID NO: 109 of U.S. Pat. No. 9,624,274; herein SEQ ID NO: 1907), KNVSEDLPLPT (SEQ ID NO: 110 of U.S. Pat. No. 9,624,274; herein SEQ ID NO: 1908), CDSGRVRTDAPD (SEQ ID NO: 111 of U.S. Pat. No. 9,624, 274; herein SEQ ID NO: 1909), FPEHLLVDFLQSLS (SEQ ID NO: 112 of U.S. Pat. No. 9,624,274; herein SEQ ID NO: 1910), DAEFRHDSG (SEQ ID NO: 65 of U.S. Pat. No.

9,624,274; herein SEQ ID NO: 1911), HYAAAQWDFGNTMCQL (SEQ ID NO: 113 of U.S. Pat. No. 9,624,274; herein SEQ ID NO: 1912), YAAQWDFGNTMCQ (SEQ ID NO: 114 of U.S. Pat. No. 9,624,274; herein SEQ ID NO: 1913), RSQKEGLHYT (SEQ ID NO: 115 of U.S. Pat. No. 9,624,274; herein SEQ ID NO: 1914), SSRTPSDKPVAHWANPQAE (SEQ ID NO: 116 of U.S. Pat. No. 9,624,274; herein SEQ ID NO: 1915), SRTPSDKPVAHWANP (SEQ ID NO: 117 of U.S. Pat. No. 9,624,274; herein SEQ ID NO: 1916), SSRTPSDKP (SEQ ID NO: 118 of U.S. Pat. No. 9,624,274; herein SEQ ID NO: 1917), NADGNVDYHMNSVP (SEQ ID NO: 119 of U.S. Pat. No. 9,624,274; herein SEQ ID NO: 1918), DGNVDYHMNSV (SEQ ID NO: 120 of U.S. Pat. No. 9,624,274; herein SEQ ID NO: 1919), RSFKEFLQSSL-RALRQ (SEQ ID NO: 121 of U.S. Pat. No. 9,624,274; herein SEQ ID NO: 1920); FKEFLQSSLRA (SEQ ID NO: 122 of U.S. Pat. No. 9,624,274; herein SEQ ID NO: 1921), or QMWAPQWGPD (SEQ ID NO: 123 of U.S. Pat. No. 9,624,274; herein SEQ ID NO: 1922).

In one embodiment, the AAV serotype may be, or may have a sequence as described in U.S. Pat. No. 9,475,845, the contents of which are herein incorporated by reference in their entirety, such as, but not limited to, AAV capsid proteins comprising modification of one or more amino acids at amino acid positions 585 to 590 of the native AAV2 capsid protein. Further the modification may result in, but not limited to, the amino acid sequence RGNRQA (SEQ ID NO: 3 of U.S. Pat. No. 9,475,845; herein SEQ ID NO: 1923), SSSTDP (SEQ ID NO: 4 of U.S. Pat. No. 9,475,845; herein SEQ ID NO: 1924), SSNTAP (SEQ ID NO: 5 of U.S. Pat. No. 9,475,845; herein SEQ ID NO: 1925), SNSNLP (SEQ ID NO: 6 of U.S. Pat. No. 9,475,845; herein SEQ ID NO: 1926), SSTTAP (SEQ ID NO: 7 of U.S. Pat. No. 9,475,845; herein SEQ ID NO: 1927), AANTAA (SEQ ID NO: 8 of U.S. Pat. No. 9,475,845; herein SEQ ID NO: 1928), QQNTAP (SEQ ID NO: 9 of U.S. Pat. No. 9,475,845; herein SEQ ID NO: 1929), SAQAQA (SEQ ID NO: 10 of U.S. Pat. No. 9,475,845; herein SEQ ID NO: 1930), QANTGP (SEQ ID NO: 11 of U.S. Pat. No. 9,475,845; herein SEQ ID NO: 1931), NATTAP (SEQ ID NO: 12 of U.S. Pat. No. 9,475,845; herein SEQ ID NO: 1932), SSTAGP (SEQ ID NO: 13 and 20 of U.S. Pat. No. 9,475,845; herein SEQ ID NO: 1933), QQNTAA (SEQ ID NO: 14 of U.S. Pat. No. 9,475,845; herein SEQ ID NO: 1934), PSTAGP (SEQ ID NO: 15 of U.S. Pat. No. 9,475,845; herein SEQ ID NO: 1935), NQNTAP (SEQ ID NO: 16 of U.S. Pat. No. 9,475,845; herein SEQ ID NO: 1936), QAANAP (SEQ ID NO: 17 of U.S. Pat. No. 9,475,845; herein SEQ ID NO: 1937), SIVGLP (SEQ ID NO: 18 of U.S. Pat. No. 9,475,845; herein SEQ ID NO: 1938), AASTAA (SEQ ID NO: 19, and 27 of U.S. Pat. No. 9,475,845; herein SEQ ID NO: 1939), SQNTTA (SEQ ID NO: 21 of U.S. Pat. No. 9,475,845; herein SEQ ID NO: 1940), QQDTAP (SEQ ID NO: 22 of U.S. Pat. No. 9,475,845; herein SEQ ID NO: 1941), QTNTGP (SEQ ID NO: 23 of U.S. Pat. No. 9,475,845; herein SEQ ID NO: 1942), QTNGAP (SEQ ID NO: 24 of U.S. Pat. No. 9,475,845; herein SEQ ID NO: 1943), QQNAAP (SEQ ID NO: 25 of U.S. Pat. No. 9,475,845; herein SEQ ID NO: 1944), or AANTQA (SEQ ID NO: 26 of U.S. Pat. No. 9,475,845; herein SEQ ID NO: 1945). In one embodiment, the amino acid modification is a substitution at amino acid positions 262 through 265 in the native AAV2 capsid protein or the corresponding position in the capsid protein of another AAV with a targeting sequence. The targeting sequence may be, but is not limited to, any of the amino acid sequences, NGRAHA (SEQ ID NO: 38 of U.S. Pat. No. 9,475,845; herein SEQ ID NO: 1946), QPEHSST (SEQ ID NO: 39 and 50 of U.S. Pat. No. 9,475,845; herein SEQ ID NO: 1947), VNTANST (SEQ ID NO: 40 of U.S. Pat. No. 9,475,845; herein SEQ ID NO: 1948), HGPMQKS (SEQ ID NO: 41 of U.S. Pat. No. 9,475,845; herein SEQ ID NO: 1949), PHKPPLA (SEQ ID NO: 42 of U.S. Pat. No. 9,475,845; herein SEQ ID NO: 1950), IKNNEMW (SEQ ID NO: 43 of U.S. Pat. No. 9,475,845; herein SEQ ID NO: 1951), RNLDTPM (SEQ ID NO: 44 of U.S. Pat. No. 9,475,845; herein SEQ ID NO: 1952), VDSHRQS (SEQ ID NO: 45 of U.S. Pat. No. 9,475,845; herein SEQ ID NO: 1953), YDSKTKT (SEQ ID NO: 46 of U.S. Pat. No. 9,475,845; herein SEQ ID NO: 1954), SQLPHQK (SEQ ID NO: 47 of U.S. Pat. No. 9,475,845; herein SEQ ID NO: 1955), STMQQNT (SEQ ID NO: 48 of U.S. Pat. No. 9,475,845; herein SEQ ID NO: 1956), TERYMTQ (SEQ ID NO: 49 of U.S. Pat. No. 9,475,845; herein SEQ ID NO: 1957), DASLSTS (SEQ ID NO: 51 of U.S. Pat. No. 9,475,845; herein SEQ ID NO: 1958), DLPNKKT (SEQ ID NO: 52 of U.S. Pat. No. 9,475,845; herein SEQ ID NO: 1959), DLTAARL (SEQ ID NO: 53 of U.S. Pat. No. 9,475,845; herein SEQ ID NO: 1960), EPHQFNY (SEQ ID NO: 54 of U.S. Pat. No. 9,475,845; herein SEQ ID NO: 1961), EPQSNHT (SEQ ID NO: 55 of U.S. Pat. No. 9,475,845; herein SEQ ID NO: 1962), MSSWPSQ (SEQ ID NO: 56 of U.S. Pat. No. 9,475,845; herein SEQ ID NO: 1963), NPKHNAT (SEQ ID NO: 57 of U.S. Pat. No. 9,475,845; herein SEQ ID NO: 1964), PDGMRTT (SEQ ID NO: 58 of U.S. Pat. No. 9,475,845; herein SEQ ID NO: 1965), PNNNKTT (SEQ ID NO: 59 of U.S. Pat. No. 9,475,845; herein SEQ ID NO: 1966), QSTTHDS (SEQ ID NO: 60 of U.S. Pat. No. 9,475,845; herein SEQ ID NO: 1967), TGSKQKQ (SEQ ID NO: 61 of U.S. Pat. No. 9,475,845; herein SEQ ID NO: 1968), SLKHQAL (SEQ ID NO: 62 of U.S. Pat. No. 9,475,845; herein SEQ ID NO: 1969), SPIDGEQ (SEQ ID NO: 63 of U.S. Pat. No. 9,475,845; herein SEQ ID NO: 1970), WIFPWIQL (SEQ ID NO: 64 and 112 of U.S. Pat. No. 9,475,845; herein SEQ ID NO: 1971), CDCRGDCFC (SEQ ID NO: 65 of U.S. Pat. No. 9,475,845; herein SEQ ID NO: 1972), CNGRC (SEQ ID NO: 66 of U.S. Pat. No. 9,475,845; herein SEQ ID NO: 1973), CPRECES (SEQ ID NO: 67 of U.S. Pat. No. 9,475,845; herein SEQ ID NO: 1974), CTIIHWGFTLC (SEQ ID NO: 68 and 123 of U.S. Pat. No. 9,475,845; herein SEQ ID NO: 1975), CGRRAGGSC (SEQ ID NO: 69 of U.S. Pat. No. 9,475,845; herein SEQ ID NO: 1976), CKGGRAKDC (SEQ ID NO: 70 of U.S. Pat. No. 9,475,845; herein SEQ ID NO: 1977), CVPELGHEC (SEQ ID NO: 71 and 115 of U.S. Pat. No. 9,475,845; herein SEQ ID NO: 1978), CRRETAWAK (SEQ ID NO: 72 of U.S. Pat. No. 9,475,845; herein SEQ ID NO: 1979), VSWFSHRYSPFAVS (SEQ ID NO: 73 of U.S. Pat. No. 9,475,845; herein SEQ ID NO: 1980), GYRDGYAG-PILYN (SEQ ID NO: 74 of U.S. Pat. No. 9,475,845; herein SEQ ID NO: 1981), XXXYXXX (SEQ ID NO: 75 of U.S. Pat. No. 9,475,845; herein SEQ ID NO: 1982), YXNW (SEQ ID NO: 76 of U.S. Pat. No. 9,475,845; herein SEQ ID NO: 1983), RPLPPLP (SEQ ID NO: 77 of U.S. Pat. No. 9,475,845; herein SEQ ID NO: 1984), APPLPPR (SEQ ID NO: 78 of U.S. Pat. No. 9,475,845; herein SEQ ID NO: 1985), DVFYPYPYASGS (SEQ ID NO: 79 of U.S. Pat. No. 9,475,845; herein SEQ ID NO: 1986), MYWYPY (SEQ ID NO: 80 of U.S. Pat. No. 9,475,845; herein SEQ ID NO: 1987), DITWDQLWDLMK (SEQ ID NO: 81 of U.S. Pat. No. 9,475,845; herein SEQ ID NO: 1988), CWDDXWLC (SEQ ID NO: 82 of U.S. Pat. No. 9,475,845; herein SEQ ID NO: 1989), EWCEYLGGYLRCYA (SEQ ID NO: 83 of U.S. Pat. No. 9,475,845; herein SEQ ID NO: 1990), YXCXXGPXTWXCXP (SEQ ID NO: 84 of U.S. Pat. No. 9,475,845; herein SEQ ID NO: 1991), IEGPTLRQW-LAARA (SEQ ID NO: 85 of U.S. Pat. No. 9,475,845; herein SEQ ID NO: 1992), LWXXX (SEQ ID NO: 86 of U.S. Pat. No. 9,475,845; herein SEQ ID NO: 1993), XFXXYLW (SEQ ID NO: 87 of U.S. Pat. No. 9,475,845; herein SEQ ID NO: 1994), SSIISHFRWGLCD (SEQ ID NO: 88 of U.S. Pat. No. 9,475,845; herein SEQ ID NO: 1995), MSRPACPPNDKYE (SEQ ID NO: 89 of U.S. Pat. No. 9,475,845; herein SEQ ID NO: 1996), CLRSGRGC (SEQ ID NO: 90 of U.S. Pat. No. 9,475,845; herein SEQ ID NO: 1997), CHWMFSPWC (SEQ ID NO: 91 of U.S. Pat. No. 9,475,845; herein SEQ ID NO: 1998), WXXF (SEQ ID NO: 92 of U.S. Pat. No. 9,475,845; herein SEQ ID NO: 1999), CSSRLDAC (SEQ ID NO: 93 of U.S. Pat. No. 9,475,845; herein SEQ ID NO: 2000), CLPVASC (SEQ ID NO: 94 of U.S. Pat. No. 9,475,845; herein SEQ ID NO: 2001), CGFECVRQCPERC (SEQ ID NO: 95 of U.S. Pat. No. 9,475,845; herein SEQ ID NO: 2002), CVALCREACGEGC (SEQ ID NO: 96 of U.S. Pat. No. 9,475,845; herein SEQ ID NO: 2003), SWCEPGWCR (SEQ ID NO: 97 of U.S. Pat. No. 9,475,845 herein SEQ ID NO: 2004), YSGKWGW (SEQ ID NO: 98 of U.S. Pat. No. 9,475,845; herein SEQ ID NO: 2005), GLSGGRS (SEQ ID NO: 99 of U.S. Pat. No. 9,475,845; herein SEQ ID NO: 2006), LMLPRAD (SEQ ID NO: 100 of U.S. Pat. No. 9,475,845; herein SEQ ID NO: 2007), CSCFRDVCC (SEQ ID NO: 101 of U.S. Pat. No. 9,475,845; herein SEQ ID NO: 2008), CRDVVSVIC (SEQ ID NO: 102 of U.S. Pat. No. 9,475,845; herein SEQ ID NO: 2009), MARSGL (SEQ ID NO: 103 of U.S. Pat. No. 9,475,845; herein SEQ ID NO: 2010), MARAKE (SEQ ID NO: 104 of U.S. Pat. No. 9,475,845; herein SEQ ID NO: 2011), MSRTMS (SEQ ID NO: 105 of U.S. Pat. No. 9,475,845; herein SEQ ID NO: 2012), KCCYSL (SEQ ID NO: 106 of U.S. Pat. No. 9,475,845; herein SEQ ID NO: 2013), MYWGDSHWLQYWYE (SEQ ID NO: 107 of U.S. Pat. No. 9,475,845; herein SEQ ID NO: 2014), MQLPLAT (SEQ ID NO: 108 of U.S. Pat. No. 9,475,845; herein SEQ ID NO: 2015), EWLS (SEQ ID NO: 109 of U.S. Pat. No. 9,475,845; herein SEQ ID NO: 2016), SNEW (SEQ ID NO: 110 of U.S. Pat. No. 9,475,845; herein SEQ ID NO: 2017), TNYL (SEQ ID NO: 111 of U.S. Pat. No. 9,475,845; herein SEQ ID NO: 2018), WDLAWMFRLPVG (SEQ ID NO: 113 of U.S. Pat. No. 9,475,845; herein SEQ ID NO: 2019), CTVALPGGYVRVC (SEQ ID NO: 114 of U.S. Pat. No. 9,475,845; herein SEQ ID NO: 2020), CVAYCIEHHCWTC (SEQ ID NO: 116 of U.S. Pat. No. 9,475,845; herein SEQ ID NO: 2021), CVFAHNYDYLVC (SEQ ID NO: 117 of U.S. Pat. No. 9,475,845; herein SEQ ID NO: 2022), CVFTSNYAFC (SEQ ID NO: 118 of U.S. Pat. No. 9,475,845; herein SEQ ID NO: 2023), VHSPNKK (SEQ ID NO: 119 of U.S. Pat. No. 9,475,845; herein SEQ ID NO: 2024), CRGDGWC (SEQ ID NO: 120 of U.S. Pat. No. 9,475,845; herein SEQ ID NO: 2025), XRGCDX (SEQ ID NO: 121 of U.S. Pat. No. 9,475,845; herein SEQ ID NO: 2026), PXXX (SEQ ID NO: 122 of U.S. Pat. No. 9,475,845; herein SEQ ID NO: 2027), SGKGPRQITAL (SEQ ID NO: 124 of U.S. Pat. No. 9,475,845; herein SEQ ID NO: 2028), AAAAAAAAAXXXXX (SEQ ID NO: 125 of U.S. Pat. No. 9,475,845; herein SEQ ID NO: 2029), VYMSPF (SEQ ID NO: 126 of U.S. Pat. No. 9,475,845; herein SEQ ID NO: 2030), ATWLPPR (SEQ ID NO: 127 of U.S. Pat. No. 9,475,845; herein SEQ ID NO: 2031), HTMYYHHYQHHL (SEQ ID NO: 128 of U.S. Pat. No. 9,475,845; herein SEQ ID NO: 2032), SEVGCRAGPLQWLCEKYFG (SEQ ID NO: 129 of U.S. Pat. No. 9,475,845; herein SEQ ID NO: 2033), CGLLPVGRPDRNVWRWLC (SEQ ID NO: 130 of U.S. Pat. No. 9,475,845; herein SEQ ID NO: 2034), CKGQCDRFKGLPWEC (SEQ ID NO: 131 of U.S. Pat. No. 9,475,845; herein SEQ ID NO: 2035), SGRSA (SEQ ID NO: 132 of U.S. Pat. No. 9,475,845; herein SEQ ID NO: 2036), WGFP (SEQ ID NO: 133 of U.S. Pat. No. 9,475,845; herein SEQ ID NO: 2037), AEPMPHSLNFSQYLWYT (SEQ ID NO: 134 of U.S. Pat. No. 9,475,845; herein SEQ ID NO: 2038), WAYXSP (SEQ ID NO: 135 of U.S. Pat. No. 9,475,845; herein SEQ ID NO: 2039), IELLQAR (SEQ ID NO: 136 of U.S. Pat. No. 9,475,845; herein SEQ ID NO: 2040), AYTKCSRQWRTCMTTH (SEQ ID NO: 137 of U.S. Pat. No. 9,475,845; herein SEQ ID NO: 2041), PQNSKIPGPTFLDPH (SEQ ID NO: 138 of U.S. Pat. No. 9,475,845; herein SEQ ID NO: 2042), SMEPALPDWWWKMFK (SEQ ID NO: 139 of U.S. Pat. No. 9,475,845; herein SEQ ID NO: 2043), ANTPCGPYTHDCPVKR (SEQ ID NO: 140 of U.S. Pat. No. 9,475,845; herein SEQ ID NO: 2044), TACHQHVRMVRP (SEQ ID NO: 141 of U.S. Pat. No. 9,475,845; herein SEQ ID NO: 2045), VPWMEPAYQRFL (SEQ ID NO: 142 of U.S. Pat. No. 9,475,845; herein SEQ ID NO: 2046), DPRATPGS (SEQ ID NO: 143 of U.S. Pat. No. 9,475,845; herein SEQ ID NO: 2047), FRPNRAQDYNTN (SEQ ID NO: 144 of U.S. Pat. No. 9,475,845; herein SEQ ID NO: 2048), CTKNSYLMC (SEQ ID NO: 145 of U.S. Pat. No. 9,475,845; herein SEQ ID NO: 2049), CXXTXXXGXGC (SEQ ID NO: 146 of U.S. Pat. No. 9,475,845; herein SEQ ID NO: 2050), CPIEDRPMC (SEQ ID NO: 147 of U.S. Pat. No. 9,475,845; herein SEQ ID NO: 2051), HEWSYLAPYPWF (SEQ ID NO: 148 of U.S. Pat. No. 9,475,845; herein SEQ ID NO: 2052), MCPKHPLGC (SEQ ID NO: 149 of U.S. Pat. No. 9,475,845; herein SEQ ID NO: 2053), RMWPSSTVNLSAGRR (SEQ ID NO: 150 of U.S. Pat. No. 9,475,845; herein SEQ ID NO: 2054), SAKTAVSQRVWLPSHRGGEP (SEQ ID NO: 151 of U.S. Pat. No. 9,475,845; herein SEQ ID NO: 2055), KSREHVNNSACPSKRITAAL (SEQ ID NO: 152 of U.S. Pat. No. 9,475,845; herein SEQ ID NO: 2056), EGFR (SEQ ID NO: 153 of U.S. Pat. No. 9,475,845; herein SEQ ID NO: 2057), AGLGVR (SEQ ID NO: 154 of U.S. Pat. No. 9,475,845; herein SEQ ID NO: 2058), GTRQGHTMRLGVSDG (SEQ ID NO: 155 of U.S. Pat. No. 9,475,845; herein SEQ ID NO: 2059), IAGLATPGWSHWLAL (SEQ ID NO: 156 of U.S. Pat. No. 9,475,845; herein SEQ ID NO: 2060), SMSIARL (SEQ ID NO: 157 of U.S. Pat. No. 9,475,845; herein SEQ ID NO: 2061), HTFEPGV (SEQ ID NO: 158 of U.S. Pat. No. 9,475,845; herein SEQ ID NO: 2062), NTSLKRISNKRIRRK (SEQ ID NO: 159 of U.S. Pat. No. 9,475,845; herein SEQ ID NO: 2063), LRIKRKRRKRKKTRK (SEQ ID NO: 160 of U.S. Pat. No. 9,475,845; herein SEQ ID NO: 2064), GGG, GFS, LWS, EGG, LLV, LSP, LBS, AGG, GRR, GGH and GTV.

In one embodiment, the AAV serotype may be, or may have a sequence as described in United States Publication No. US 20160369298, the contents of which are herein incorporated by reference in their entirety, such as, but not limited to, site-specific mutated capsid protein of AAV2 (SEQ ID NO: 97 of US 20160369298; herein SEQ ID NO: 2065) or variants thereof, wherein the specific site is at least one site selected from sites R447, G453, S578, N587, N587+1, S662 of VP1 or fragment thereof.

Further, any of the mutated sequences described in US 20160369298, may be or may have, but not limited to, any of the following sequences SDSGASN (SEQ ID NO: 1 and SEQ ID NO: 231 of US20160369298; herein SEQ ID NO: 2066), SPSGASN (SEQ ID NO: 2 of US20160369298;

herein SEQ ID NO: 2067), SHSGASN (SEQ ID NO: 3 of US20160369298; herein SEQ ID NO: 2068), SRSGASN (SEQ ID NO: 4 of US20160369298; herein SEQ ID NO: 2069), SKSGASN (SEQ ID NO: 5 of US20160369298; herein SEQ ID NO: 2070), SNSGASN (SEQ ID NO: 6 of US20160369298; herein SEQ ID NO: 2071), SGSGASN (SEQ ID NO: 7 of US20160369298; herein SEQ ID NO: 2072), SASGASN (SEQ ID NO: 8, 175, and 221 of US20160369298; herein SEQ ID NO: 2073), SESGTSN (SEQ ID NO: 9 of US20160369298; herein SEQ ID NO: 2074), STTGGSN (SEQ ID NO: 10 of US20160369298; herein SEQ ID NO: 2075), SSAGSTN (SEQ ID NO: 11 of US20160369298; herein SEQ ID NO: 2076), NNDSQA (SEQ ID NO: 12 of US20160369298; herein SEQ ID NO: 2077), NNRNQA (SEQ ID NO: 13 of US20160369298; herein SEQ ID NO: 2078), NNNKQA (SEQ ID NO: 14 of US20160369298; herein SEQ ID NO: 2079), NAKRQA (SEQ ID NO: 15 of US20160369298; herein SEQ ID NO: 2080), NDEHQA (SEQ ID NO: 16 of US20160369298; herein SEQ ID NO: 2081), NTSQKA (SEQ ID NO: 17 of US20160369298; herein SEQ ID NO: 2082), YYLSRTNTPSGTDTQSRLVFSQAGA (SEQ ID NO: 18 of US20160369298; herein SEQ ID NO: 2083), YYLSRTNTDSGTETQSGLDFSQAGA (SEQ ID NO: 19 of US20160369298; herein SEQ ID NO: 2084), YYLSRTNTESGTPTQSALEFSQAGA (SEQ ID NO: 20 of US20160369298; herein SEQ ID NO: 2085), YYLSRTNTHSGTHTQSPLHFSQAGA (SEQ ID NO: 21 of US20160369298; herein SEQ ID NO: 2086), YYLSRTNTSSGTTTTSHLIFSQAGA (SEQ ID NO: 22 of US20160369298; herein SEQ ID NO: 2087), YYLSRTNTRSGIMTKSSLMFSQAGA (SEQ ID NO: 23 of US20160369298; herein SEQ ID NO: 2088), YYLSRTNTKSGRKTLSNLFSQAGA (SEQ ID NO: 24 of US20160369298; herein SEQ ID NO: 2089), YYLSRTNDGSGPVTPSKLRFSQRGA (SEQ ID NO: 25 of US20160369298; herein SEQ ID NO: 2090), YYLSRTNAASGHATHSDLKFSQPGA (SEQ ID NO: 26 of US20160369298; herein SEQ ID NO: 2091), YYLSRTNGQAGSLTMSELGFSQVGA (SEQ ID NO: 27 of US20160369298; herein SEQ ID NO: 2092), YYLSRTNSTGGNQTTSQLLFSQLSA (SEQ ID NO: 28 of US20160369298; herein SEQ ID NO: 2093), YFLSRTNNNTGLNTNSTLNFSQGRA (SEQ ID NO: 29 of US20160369298; herein SEQ ID NO: 2094), SKTGADNNNSEYSWTG (SEQ ID NO: 30 of US20160369298; herein SEQ ID NO: 2095), SKTDADNNNSEYSWTG (SEQ ID NO: 31 of US20160369298; herein SEQ ID NO: 2096), SKTEADNNNSEYSWTG (SEQ ID NO: 32 of US20160369298; herein SEQ ID NO: 2097), SKTPADNNNSEYSWTG (SEQ ID NO: 33 of US20160369298; herein SEQ ID NO: 2098), SKTHADNNNSEYSWTG (SEQ ID NO: 34 of US20160369298; herein SEQ ID NO: 2099), SKTQADNNNSEYSWTG (SEQ ID NO: 35 of US20160369298; herein SEQ ID NO: 2100), SKTIADNNNSEYSWTG (SEQ ID NO: 36 of US20160369298; herein SEQ ID NO: 2101), SKTMADNNNSEYSWTG (SEQ ID NO: 37 of US20160369298; herein SEQ ID NO: 2102), SKTRADNNNSEYSWTG (SEQ ID NO: 38 of US20160369298; herein SEQ ID NO: 2103), SKTNADNNNSEYSWTG (SEQ ID NO: 39 of US20160369298; herein SEQ ID NO: 2104), SKTVGRNNNSEYSWTG (SEQ ID NO: 40 of US20160369298; herein SEQ ID NO: 2105), SKTADRNNNSEYSWTG (SEQ ID NO: 41 of US20160369298; herein SEQ ID NO: 2106), SKKLSQNNNSKYSWQG (SEQ ID NO: 42 of US20160369298; herein SEQ ID NO: 2107), SKPTTGNNNSDYSWPG (SEQ ID NO: 43 of US20160369298; herein SEQ ID NO: 2108), STQKNENNNSNYSWPG (SEQ ID NO: 44 of US20160369298; herein SEQ ID NO: 2109), HKDDEGKF (SEQ ID NO: 45 of US20160369298; herein SEQ ID NO: 2110), HKDDNRKF (SEQ ID NO: 46 of US20160369298; herein SEQ ID NO: 2111), HKDDTNKF (SEQ ID NO: 47 of US20160369298; herein SEQ ID NO: 2112), HEDSDKNF (SEQ ID NO: 48 of US20160369298; herein SEQ ID NO: 2113), HRDGADSF (SEQ ID NO: 49 of US20160369298; herein SEQ ID NO: 2114), HGDNKSRF (SEQ ID NO: 50 of US20160369298; herein SEQ ID NO: 2115), KQGSEKTNVDFEEV (SEQ ID NO: 51 of US20160369298; herein SEQ ID NO: 2116), KQGSEKTNVDSEEV (SEQ ID NO: 52 of US20160369298; herein SEQ ID NO: 2117), KQGSEKTNVDVEEV (SEQ ID NO: 53 of US20160369298; herein SEQ ID NO: 2118), KQGSDKTNVDDAGV (SEQ ID NO: 54 of US20160369298; herein SEQ ID NO: 2119), KQGSSKTNVDPREV (SEQ ID NO: 55 of US20160369298; herein SEQ ID NO: 2120), KQGSRKTNVDHKQV (SEQ ID NO: 56 of US20160369298; herein SEQ ID NO: 2121), KQGSKGGNVDTNRV (SEQ ID NO: 57 of US20160369298; herein SEQ ID NO: 2122), KQGSGEANVDNGDV (SEQ ID NO: 58 of US20160369298; herein SEQ ID NO: 2123), KQDAAADNIDYDHV (SEQ ID NO: 59 of US20160369298; herein SEQ ID NO: 2124), KQSGTRSNAAASSV (SEQ ID NO: 60 of US20160369298; herein SEQ ID NO: 2125), KENTNTNDTELTNV (SEQ ID NO: 61 of US20160369298; herein SEQ ID NO: 2126), QRGNNVAATADVNT (SEQ ID NO: 62 of US20160369298; herein SEQ ID NO: 2127), QRGNNEAATADVNT (SEQ ID NO: 63 of US20160369298; herein SEQ ID NO: 2128), QRGNNPAATADVNT (SEQ ID NO: 64 of US20160369298; herein SEQ ID NO: 2129), QRGNNHAATADVNT (SEQ ID NO: 65 of US20160369298; herein SEQ ID NO: 2130), QEENNIAATPGVNT (SEQ ID NO: 66 of US20160369298; herein SEQ ID NO: 2131), QPPNNMAATHEVNT (SEQ ID NO: 67 of US20160369298; herein SEQ ID NO: 2132), QHHNNSAATTIVNT (SEQ ID NO: 68 of US20160369298; herein SEQ ID NO: 2133), QTTNNRAAFNMVET (SEQ ID NO: 69 of US20160369298; herein SEQ ID NO: 2134), QKKNNNAASKKVAT (SEQ ID NO: 70 of US20160369298; herein SEQ ID NO: 2135), QGGNNKAADDAVKT (SEQ ID NO: 71 of US20160369298; herein SEQ ID NO: 2136), QAAKGGAADDAVKT (SEQ ID NO: 72 of US20160369298; herein SEQ ID NO: 2137), QDDRAAAANESVDT (SEQ ID NO: 73 of US20160369298; herein SEQ ID NO: 2138), QQQHDDAAYQRVHT (SEQ ID NO: 74 of US20160369298; herein SEQ ID NO: 2139), QSSSSLAAVSTVQT (SEQ ID NO: 75 of US20160369298; herein SEQ ID NO: 2140), QNNQTTAAIRNVTT (SEQ ID NO: 76 of US20160369298; herein SEQ ID NO: 2141), NYNKKSDNVDFT (SEQ ID NO: 77 of US20160369298; herein SEQ ID NO: 2142), NYNKKSENVDFT (SEQ ID NO: 78 of US20160369298; herein SEQ ID NO: 2143), NYNKKSLNVDFT (SEQ ID NO: 79 of US20160369298; herein SEQ ID NO: 2144), NYNKKSPNVDFT (SEQ ID NO: 80 of US20160369298; herein SEQ ID NO: 2145), NYSKKSHCVDFT (SEQ ID NO: 81 of US20160369298; herein SEQ ID NO: 2146), NYRKTIYVDFT (SEQ ID NO: 82 of US20160369298; herein SEQ ID NO: 2147), NYKEKKDVHFT (SEQ ID NO: 83 of US20160369298; herein SEQ ID NO: 2148), NYGHRAIVQFT (SEQ ID NO: 84 of US20160369298; herein SEQ ID NO: 2149), NYANHQFVVCT (SEQ ID NO: 85 of US20160369298; herein SEQ ID NO: 2150), NYDDDPTGVLLT (SEQ ID NO: 86 of US20160369298; herein SEQ ID NO: 2151), NYDDPTGVLLT (SEQ ID NO: 87 of US20160369298; herein SEQ ID NO: 2152), NFEQQNSVEWT (SEQ ID NO: 88 of US20160369298; herein SEQ ID NO: 2153), SQSGASN (SEQ ID NO: 89 and SEQ ID NO: 241 of US20160369298; herein SEQ ID NO: 2154), NNGSQA (SEQ ID NO: 90 of US20160369298; herein SEQ ID NO: 2155), YYLSRTNTPSGTTTWSRLQFSQAGA (SEQ ID NO: 91 of US20160369298; herein SEQ ID NO: 2156), SKTSADNNNSEYSWTG (SEQ ID NO: 92 of US20160369298; herein SEQ ID NO: 2157), HKDDEEKF (SEQ ID NO: 93, 209, 214, 219, 224, 234, 239, and 244 of US20160369298; herein SEQ ID NO: 2158), KQGSEKTNVDIEEV (SEQ ID NO: 94 of US20160369298; herein SEQ ID NO: 2159), QRGNNQAATADVNT (SEQ ID NO: 95 of US20160369298; herein SEQ ID NO: 2160), NYNKKSVNVDFT (SEQ ID NO: 96 of US20160369298; herein SEQ ID NO: 2161), SQSGASNYNTPSGTTTQSRLQFSTSADNNNSEYSWTGATKYH (SEQ ID NO: 106 of US20160369298; herein SEQ ID NO: 2162), SASGASNFNSEGGSLTQSSLGFSTDGENNNSDFSWTGATKYH (SEQ ID NO: 107 of US20160369298; herein SEQ ID NO: 2163), SQSGASNYNTPSGTTTQSRLQFSTDGENNNSDFSWTGATKYH (SEQ ID NO: 108 of US20160369298; herein SEQ ID NO: 2164), SASGASNYNTPSGTTTQSRLQFSTSADNNNSEFSWPGATTTYH (SEQ ID NO: 109 of US20160369298; herein SEQ ID NO: 2165), SQSGASNFNSEGGSLTQSSLGFSTDGENNNSDFSWTGATKYH (SEQ ID NO: 110 of US20160369298; herein SEQ ID NO: 2166), SASGASNYNTPSGSLTQSSLGFSTDGENNNSDFSWTGATKYH (SEQ ID NO: 111 of US20160369298; herein SEQ ID NO: 2167), SQSGASNYNTPSGTTQSRLQFSTSADNNNSDFSTSADNNNSDFSWTGATKYH (SEQ ID NO: 112 of US20160369298; herein SEQ ID NO: 2168), SGAGASNFNSEGGSLTQSSLGFSTDGENNNSDFSWTGATKYH (SEQ ID NO: 113 of US20160369298; herein SEQ ID NO: 2169), SGAGASN (SEQ ID NO: 176 of US20160369298; herein SEQ ID NO: 2170), NSEGGSLTQSSLGFS (SEQ ID NO: 177, 185, 193 and 202 of US20160369298; herein SEQ ID NO: 2171), TDGENNNSDFS (SEQ ID NO: 178 of US20160369298; herein SEQ ID NO: 2172), SEFSWPGATT (SEQ ID NO: 179 of US20160369298; herein SEQ ID NO: 2173), TSADNNNSDFSWT (SEQ ID NO: 180 of US20160369298; herein SEQ ID NO: 2174), SQSGASNY (SEQ ID NO: 181, 187, and 198 of US20160369298; herein SEQ ID NO: 2175), NTPSGTTTQSRLQFS (SEQ ID NO: 182, 188, 191, and 199 of US20160369298; herein SEQ ID NO: 2176), TSADNNNSEYSWTGATKYH (SEQ ID NO: 183 of US20160369298; herein SEQ ID NO: 2177), SASGASNF (SEQ ID NO: 184 of US20160369298; herein SEQ ID NO: 2178), TDGENNNSDFSWTGATKYH (SEQ ID NO: 186, 189, 194, 197, and 203 of US20160369298; herein SEQ ID NO: 2179), SASGASNY (SEQ ID NO: 190 and SEQ ID NO: 195 of US20160369298; herein SEQ ID NO: 2180), TSADNNNSEFSWPGATIYH (SEQ ID NO: 192 of US20160369298; herein SEQ ID NO: 2181), NTPSGSLTQSSLGFS (SEQ ID NO: 196 of US20160369298; herein SEQ ID NO: 2182), TSADNNNSDFSWTGATKYH (SEQ ID NO: 200 of US20160369298; herein SEQ ID NO: 2183), SGAGASNF (SEQ ID NO: 201 of US20160369298; herein SEQ ID NO: 2184), CTCCAGVVSVVSMRSRVCVNSGCAGCTDHCVVSRNSGTCVMSACACAA (SEQ ID NO: 204 of US20160369298; herein SEQ ID NO: 2185), CTCCAGAGAGGCAACAGACAAGCAGCTACCGCAGATGTCAACACACAA (SEQ ID NO: 205 of US20160369298; herein SEQ ID NO: 2186), SAAGASN (SEQ ID NO: 206 of US20160369298; herein SEQ ID NO: 2187), YFLSRTNTESGSTTQSTLRFSQAG (SEQ ID NO: 207 of US20160369298; herein SEQ ID NO: 2188), SKTSADNNNSDFS (SEQ ID NO: 208, 228, and 253 of US20160369298; herein SEQ ID NO: 2189), KQGSEKTDVDIDKV (SEQ ID NO: 210 of US20160369298; herein SEQ ID NO: 2190), STAGASN (SEQ ID NO: 211 of US20160369298; herein SEQ ID NO: 2191), YFLSRTNTTSGIETQSTLRFSQAG (SEQ ID NO: 212 and SEQ ID NO: 247 of US20160369298; herein SEQ ID NO: 2192), SKTDGENNNSDFS (SEQ ID NO: 213 and SEQ ID NO: 248 of US20160369298; herein SEQ ID NO: 2193), KQGAAADDVEIDGV (SEQ ID NO: 215 and SEQ ID NO: 250 of US20160369298; herein SEQ ID NO: 2194), SEAGASN (SEQ ID NO: 216 of US20160369298; herein SEQ ID NO: 2195), YYLSRTNTPSGTTTQSRLQFSQAG (SEQ ID NO: 217, 232 and 242 of US20160369298; herein SEQ ID NO: 2196), SKTSADNNNSEYS (SEQ ID NO: 218, 233, 238, and 243 of US20160369298; herein SEQ ID NO: 2197), KQGSEKTNVDIEKV (SEQ ID NO: 220, 225 and 245 of US20160369298; herein SEQ ID NO: 2198), YFLSRTNDASGSDTKSTLLFSQAG (SEQ ID NO: 222 of US20160369298; herein SEQ ID NO: 2199), STTPSENNNSEYS (SEQ ID NO: 223 of US20160369298; herein SEQ ID NO: 2200), SAAGATN (SEQ ID NO: 226 and SEQ ID NO: 251 of US20160369298; herein SEQ ID NO: 2201), YFLSRTNGEAGSATLSELRFSQAG (SEQ ID NO: 227 of US20160369298; herein SEQ ID NO: 2202), HGDDADRF (SEQ ID NO: 229 and SEQ ID NO: 254 of US20160369298; herein SEQ ID NO: 2203), KQGAEKSDVEVDRV (SEQ ID NO: 230 and SEQ ID NO: 255 of US20160369298; herein SEQ ID NO: 2204), KQDSGGDNIDIDQV (SEQ ID NO: 235 of US20160369298; herein SEQ ID NO: 2205), SDAGASN (SEQ ID NO: 236 of US20160369298; herein SEQ ID NO: 2206), YFLSRTNTEGGHDTQSTLRFSQAG (SEQ ID NO: 237 of US20160369298; herein SEQ ID NO: 2207), KEDGGGSDVAIDEV (SEQ ID NO: 240 of US20160369298; herein SEQ ID NO: 2208), SNAGASN (SEQ ID NO: 246 of US20160369298; herein SEQ ID NO: 2209), and YFLSRTNGEAGSATLSELRFSQPG (SEQ ID NO: 252 of US20160369298; herein SEQ ID NO: 2210). Non-limiting examples of nucleotide sequences that may encode the amino acid mutated sites include the following, AGCVVMDCAGGARSCASCAAC (SEQ ID NO: 97 of US20160369298; herein SEQ ID NO: 2211), AACRACRRSMRSMAGGCA (SEQ ID NO: 98 of US20160369298; herein SEQ ID NO: 2212), CACRGGACRRCRMSRRSARSTT (SEQ ID NO: 99 of US20160369298; herein SEQ ID NO: 2213), TATTTCTTGAGCAGAACAAACRVCVVSRSCGGAMNCVHSACGMHSTCAVVSCTTVDS TTTTCTCAGSBCRGSGCG (SEQ ID NO: 100 of US20160369298; herein SEQ ID NO: 2214), TCAAMAMMAVNSRVCSRSAACAACAACAGTRASTTCTCGTGGMMAGGA (SEQ ID NO: 101 of US20160369298; herein SEQ ID NO: 2215), AAGSAARRCRSCRVSRVARVCRA- TRYCGMSNHCRVMVRSGTC (SEQ ID NO: 102 of US20160369298; herein SEQ ID NO: 2216), CAGVVSVVSMRSRVCVNSGCAGCTDHCVVSRN-SGTCVMSACA (SEQ ID NO: 103 of US20160369298; herein SEQ ID NO: 2217), AACTWCRVSVASMVSVHSDDTGTGSWSTKSACT (SEQ ID NO: 104 of US20160369298; herein SEQ ID NO: 2218), TTGTTGAACATCACCACGTGACGCACGTTC (SEQ ID NO: 256 of US20160369298; herein SEQ ID NO: 2219), TCCCCGTGGTTCTACTACATAATGTGGCCG (SEQ ID NO: 257 of US20160369298; herein SEQ ID NO: 2220), TFCCACACTCCGTTTTGGATAATGTTGAAC (SEQ ID NO: 258 of US20160369298; herein SEQ ID NO: 2221), AGGGACATCCCCAGCTCCATGCTGTGGTCG (SEQ ID NO: 259 of US20160369298; herein SEQ ID NO: 2222), AGGGACAACCCCTCCGACTCGCCCTAATCC (SEQ ID NO: 260 of US20160369298; herein SEQ ID NO: 2223), TCCTAGTAGAAGACACCCTCTCACTGCCCG (SEQ ID NO: 261 of US20160369298; herein SEQ ID NO: 2224), AGTACCATGTACACCCACTCTCCCAGTGCC (SEQ ID NO: 262 of US20160369298; herein SEQ ID NO: 2225), ATATGGACGTTCATGCTGATCACCATACCG (SEQ ID NO: 263 of US20160369298; herein SEQ ID NO: 2226), AGCAGGAGCTCCTTGGCCTCAGCGTGCGAG (SEQ ID NO: 264 of US20160369298; herein SEQ ID NO: 2227), ACAAGCAGCTTCACTATGACAACCACTGAC (SEQ ID NO: 265 of US20160369298; herein SEQ ID NO: 2228), CAGCCTAGGAACTGGCTTCCTGGACCCTGT-TACCGCCAGCAGAGAGTCTCAAMAMM AVN-SRVCSRSAACAACAACAGTRASTTCTCCTGGM-MAGGAGCTACCAAGTACCACC TCAATGGCAGAGAACTCTCTGGT-GAATCCCGACCAGCTATGGCAAGCCACRRGGAC RRCRMSRRSARSTTTTTTCCTCAGAGCGGGTTCT-CATCTTTGGGAAGSAARRCRSCR VSRVARVCRA-TRYCGMSNHCRVMVRSGTCATGATTACA-GACGAAGAGGAGATCTGG AC (SEQ ID NO: 266 of US20160369298; herein SEQ ID NO: 2229), TGGGACAATGGCGGTCGTCTCTCAGAGTTKTKKT (SEQ ID NO: 267 of US20160369298; herein SEQ ID NO: 2230), AGAGGACCKKTCCTCGATGGTTCATGGTG-GAGTTIA (SEQ ID NO: 268 of US20160369298; herein SEQ ID NO: 2231), CCACTTAGGGCCTGGTCGA-TACCGTTCGGTG (SEQ ID NO: 269 of US20160369298; herein SEQ ID NO: 2232), and TCTCGCCC-CAAGAGTAGAAACCCCTTCSTTYYG (SEQ ID NO: 270 of US20160369298; herein SEQ ID NO: 2233).

In some embodiments, the AAV serotype may comprise an ocular cell targeting peptide as described in International Patent Publication WO2016134375, the contents of which are herein incorporated by reference in their entirety, such as, but not limited to SEQ ID NO: 9, and SEQ ID NO:10 of WO02016134375. Further, any of the ocular cell targeting peptides or amino acids described in WO2016134375, may be inserted into any parent AAV serotype, such as, but not limited to, AAV2 (SEQ ID NO:8 of WO2016134375; herein SEQ ID NO: 2234), or AAV9 (SEQ ID NO: 11 of WO2016134375; herein SEQ ID NO: 2235). In some embodiments, modifications, such as insertions are made in AAV2 proteins at P34-A35, T138-A139, A139-P140, G453-T454, N587-R588, and/or R588-Q589. In certain embodiments, insertions are made at D384, G385, I560, T561, N562, E563, E564, E565, N704, and/or Y705 of AAV9. The ocular cell targeting peptide may be, but is not limited to, any of the following amino acid sequences, GSTPPPM (SEQ ID NO: 1 of WO2016134375; herein SEQ ID NO: 2236), or GETRAPL (SEQ ID NO: 4 of WO2016134375; herein SEQ ID NO: 2237).

In some embodiments, the AAV serotype may be modified as described in the United States Publication US 20170145405 the contents of which are herein incorporated by reference in their entirety. AAV serotypes may include, modified AAV2 (e.g., modifications at Y444F, Y500F, Y730F and/or S662V), modified AAV3 (e.g., modifications at Y705F, Y731F and/or T492V), and modified AAV6 (e.g., modifications at S663V and/or T492V).

In some embodiments, the AAV serotype may be modified as described in the International Publication WO2017083722 the contents of which are herein incorporated by reference in their entirety. AAV serotypes may include, AAV1 (Y705+731F+T492V), AAV2 (Y444+500+ 730F+T491V), AAV3 (Y705+731F), AAV5, AAV5(Y436+ 693+719F), AAV6 (VP3 variant Y705F/Y731F/T492V), AAV8 (Y733F), AAV9, AAV9 (VP3 variant Y731F), and AAV10 (Y733F).

In some embodiments, the AAV serotype may comprise, as described in International Patent Publication WO2017015102, the contents of which are herein incorporated by reference in their entirety, an engineered epitope comprising the amino acids SPAKFA (SEQ ID NO: 24 of WO2017015102; herein SEQ ID NO: 2238) or NKDKLN (SEQ ID NO:2 of WO2017015102; herein SEQ ID NO: 2239). The epitope may be inserted in the region of amino acids 665 to 670 based on the numbering of the VP1 capsid of AAV8 (SEQ ID NO:3 of WO2017015102) and/or residues 664 to 668 of AAV3B (SEQ ID NO:3).

In one embodiment, the AAV serotype may be, or may have a sequence as described in International Patent Publication WO2017058892, the contents of which are herein incorporated by reference in their entirety, such as, but not limited to, AAV variants with capsid proteins that may comprise a substitution at one or more (e.g., 2, 3, 4, 5, 6, or 7) of amino acid residues 262-268, 370-379, 451-459, 472-473, 493-500, 528-534, 547-552, 588-597, 709-710, 716-722 of AAV1, in any combination, or the equivalent amino acid residues in AAV2, AAV3, AAV4, AAV5, AAV6, AAV7, AAV8, AAV9, AAV10, AAV11, AAV12, AAVrh8, AAVrh10 AAVrh32.33, bovine AAV or avian AAV. The amino acid substitution may be, but is not limited to, any of the amino acid sequences described in WO2017058892. In one embodiment, the AAV may comprise an amino acid substitution at residues 256L, 258K, 259Q, 261S, 263A, 264S, 265T, 266G, 272H, 385S, 386Q, S472R, V473D, N500E 547S, 709A, 710N, 716D, 717N, 718N, 720L, A456T, Q457T, N458Q, K459S, T492S, K493A, S586R, S587G, S588N, T589R and/or 722T of AAV1 (SEQ ID NO: 1 of WO2017058892) in any combination, 244N, 246Q, 248R, 249E, 250I, 251K, 252S, 253G, 254S, 255V, 256D, 263Y, 377E, 378N, 453L, 456R, 532Q, 533P, 535N, 536P, 537G, 538T, 539T, 540A, 541T, 542Y, 543L, 546N, 653V, 654P, 656S, 697Q, 698F, 704D, 705S, 706T, 707G, 708E, 709Y and/or 710R of AAV5 (SEQ ID NO:5 of WO2017058892) in any combination, 248R, 316V, 317Q, 318D, 319S, 443N, 530N, 531S, 532Q 533P, 534A, 535N, 540A, 541 T, 542Y, 543L, 545G, 546N, 697Q, 704D, 706T, 708E, 709Y and/or 710R of AAV5 (SEQ ID NO: 5 of WO2017058892) in any combination, 264S, 266G, 269N, 272H, 457Q, 588S and/or 5891 of AAV6 (SEQ ID NO:6 WO2017058892) in any combination, 457T, 459N, 496C, 499N, 500N, 589Q, 590N and/or 592A of AAV8 (SEQ ID NO: 8 WO2017058892) in any combination, 451I, 452N, 453G, 454S, 455G, 456Q, 457N and/or 458Q of AAV9 (SEQ ID NO: 9 WO2017058892) in any combination.

In some embodiments, the AAV may include a sequence of amino acids at positions 155, 156 and 157 of VP1 or at positions 17, 18, 19 and 20 of VP2, as described in International Publication No. WO 2017066764, the contents of which are herein incorporated by reference in their entirety. The sequences of amino acid may be, but not limited to, N-S-S, S-X-S, S-S-Y, N-X-S, N-S-Y, S-X-Y and N-X-Y, where N, X and Y are, but not limited to, independently non-serine, or non-threonine amino acids, wherein the AAV may be, but not limited to AAV1, AAV2, AAV3, AAV4, AAV5, AAV6, AAV7, AAV8, AAV9, AAV10, AAV11 and AAV12. In some embodiments, the AAV may include a deletion of at least one amino acid at positions 156, 157 or 158 of VP1 or at positions 19, 20 or 21 of VP2, wherein the AAV may be, but not limited to AAV1, AAV2, AAV3, AAV4, AAV5, AAV6, AAV7, AAV8, AAV9, AAV10, AAV11 and AAV12.

In one embodiment, peptides for inclusion in an AAV serotype may be identified using the methods described by Hui et al. (Molecular Therapy—Methods & Clinical Development (2015) 2, 15029 doi:10.1038/mtm.2015.29; the contents of which are herein incorporated by reference in its entirety). As a non-limiting example, the procedure includes isolating human splenocytes, restimulating the splenocytes in vitro using individual peptides spanning the amino acid sequence of the AAV capsid protein, IFN-gamma ELISpot with the individual peptides used for the in vitro restimulation, bioinformatics analysis to determine the HLA restriction of 15-mers identified by IFN-gamma ELISpot, identification of candidate reactive 9-mer epitopes for a given HLA allele, synthesis candidate 9-mers, second IFN-gamma ELISpot screening of splenocytes from subjects carrying the HLA alleles to which identified AAV epitopes are predicted to bind, determine the AAV capsid-reactive CD8+ T cell epitopes and determine the frequency of subjects reacting to a given AAV epitope.

In one embodiment, the AAV may be a serotype generated by Cre-recombination-based AAV targeted evolution (CREATE) as described by Deverman et al., (Nature Biotechnology 34(2):204-209 (2016)), the contents of which are herein incorporated by reference in their entirety. In one embodiment, AAV serotypes generated in this manner have improved CNS transduction and/or neuronal and astrocytic tropism, as compared to other AAV serotypes. As non-limiting examples, the AAV serotype may be PHP.B, PHP.B2, PHP.B3, PHP.A, G2A12, G2A15. In one embodiment, these AAV serotypes may be AAV9 (SEQ ID NO: 126 and 127) derivatives with a 7-amino acid insert between amino acids 588-589. Non-limiting examples of these 7-amino acid inserts include TLAVPFK (SEQ ID NO: 873), SVSKPFL (SEQ ID NO: 1249), FTLTTPK (SEQ ID NO: 882), YTLSQGW (SEQ ID NO: 888), QAVRTSL (SEQ ID NO: 914) and/or LAKERLS (SEQ ID NO: 915).

In one embodiment, the AAV serotype may be as described in Jackson et al (Frontiers in Molecular Neuroscience 9:154 (2016)), the contents of which are herein incorporated by reference in their entirety. In some embodiments, the AAV serotype is PHP.B or AAV9. In some embodiments, the AAV serotype is paired with a synapsin promoter to enhance neuronal transduction, as compared to when more ubiquitous promoters are used (i.e., CBA or CMV).

In one embodiment, peptides for inclusion in an AAV serotype may be identified by isolating human splenocytes, restimulating the splenocytes in vitro using individual peptides spanning the amino acid sequence of the AAV capsid protein, IFN-gamma ELISpot with the individual peptides used for the in vitro restimulation, bioinformatics analysis to determine the given allele restriction of 15-mers identified by IFN-gamma ELISpot, identification of candidate reactive 9-mer epitopes for a given allele, synthesis candidate 9-mers, second IFN-gamma ELISpot screening of splenocytes from subjects carrying the specific alleles to which identified AAV epitopes are predicted to bind, determine the AAV capsid-reactive CD8+ T cell epitopes and determine the frequency of subjects reacting to a given AAV epitope.

AAV particles comprising a modulatory polynucleotide encoding the siRNA molecules may be prepared or derived from various serotypes of AAVs, including, but not limited to, AAV1, AAV2, AAV3, AAV4, AAV5, AAV6, AAV7, AAV8, AAV9, AAV9.47, AAV9(hu14), AAV10, AAV11, AAV12, AAVrh8, AAVrh10, AAV-DJ8 and AAV-DJ. In some cases, different serotypes of AAVs may be mixed together or with other types of viruses to produce chimeric AAV particles. As a non-limiting example, the AAV particle is derived from the AAV9 serotype.

Viral Genome

In one embodiment, as shown in an AAV particle comprises a viral genome with a payload region.

In one embodiment, the viral genome may comprise the components as shown in FIG. 1. The payload region 110 is located within the viral genome 100. At the 5' and/or the 3' end of the viral genome 100 there may be at least one inverted terminal repeat (ITR) 120. Between the 5' ITR 120 and the payload region 110, there may be a promoter region 130. In one embodiment, the payload region may comprise at least one modulatory polynucleotide.

Figure 2:
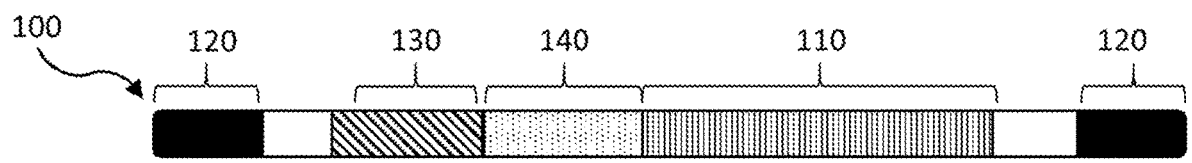
FIG. 2 is a schematic of a viral genome of the invention.

In one embodiment, the viral genome 100 may comprise the components as shown in FIG. 2. The payload region 110 is located within the viral genome 100. At the 5' and/or the 3' end of the viral genome 100 there may be at least one inverted terminal repeat (ITR) 120. Between the 5' ITR 120 and the payload region 110, there may be a promoter region 130. Between the promoter region 130 and the payload region 110, there may be an intron region 140. In one embodiment, the payload region may comprise at least one modulatory polynucleotide.

Figure 3:
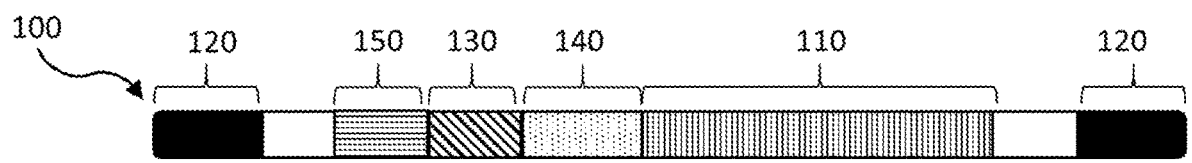
FIG. 3 is a schematic of a viral genome of the invention.

In one embodiment, the viral genome 100 may comprise the components as shown in FIG. 3. At the 5' and/or the 3' end of the viral genome 100 there may be at least one inverted terminal repeat (ITR) 120. Within the viral genome 100, there may be an enhancer region 150, a promoter region 130, an intron region 140, and a payload region 110. In one embodiment, the payload region may comprise at least one modulatory polynucleotide.

Figure 4:
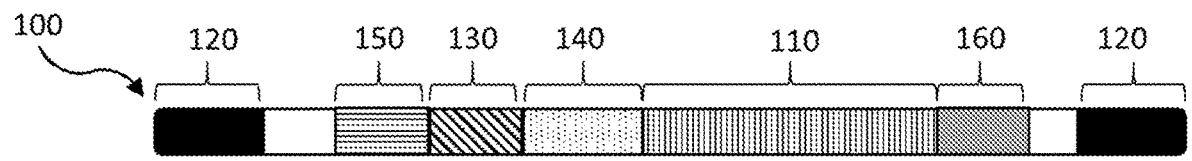
FIG. 4 is a schematic of a viral genome of the invention.

In one embodiment, the viral genome 100 may comprise the components as shown in FIG. 4. At the 5' and/or the 3' end of the viral genome 100 there may be at least one inverted terminal repeat (ITR) 120. Within the viral genome 100, there may be an enhancer region 150, a promoter region 130, an intron region 140, a payload region 110, and a polyadenylation signal sequence region 160. In one embodiment, the payload region may comprise at least one modulatory polynucleotide.

Figure 5:
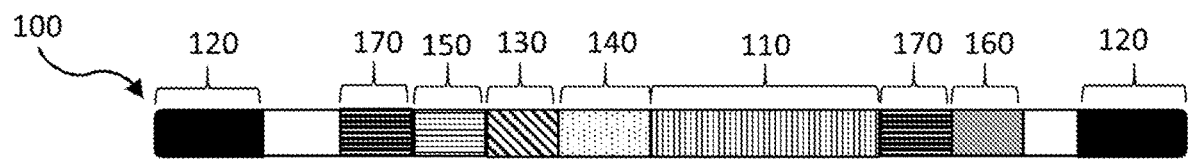
FIG. 5 is a schematic of a viral genome of the invention.

In one embodiment, the viral genome 100 may comprise the components as shown in FIG. 5. At the 5' and/or the 3' end of the viral genome 100 there may be at least one inverted terminal repeat (ITR) 120. Within the viral genome 100, there may be at least one MCS region 170, an enhancer region 150, a promoter region 130, an intron region 140, a payload region 110, and a polyadenylation signal sequence region 160. In one embodiment, the payload region may comprise at least one modulatory polynucleotide.

Figure 6:
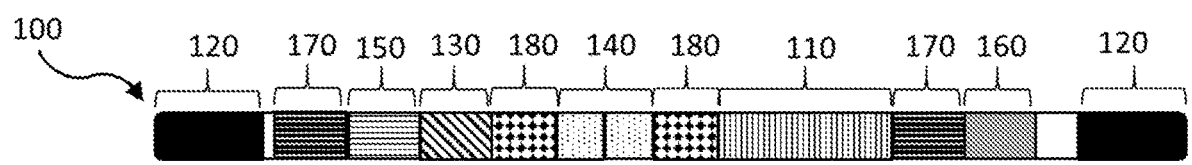
FIG. 6 is a schematic of a viral genome of the invention.

In one embodiment, the viral genome 100 may comprise the components as shown in FIG. 6. At the 5' and/or the 3' end of the viral genome 100 there may be at least one inverted terminal repeat (ITR) 120. Within the viral genome 100, there may be at least one MCS region 170, an enhancer region 150, a promoter region 130, at least one exon region 180, at least one intron region 140, a payload region 110, and a polyadenylation signal sequence region 160. In one embodiment, the payload region may comprise at least one modulatory polynucleotide.

Figure 7:
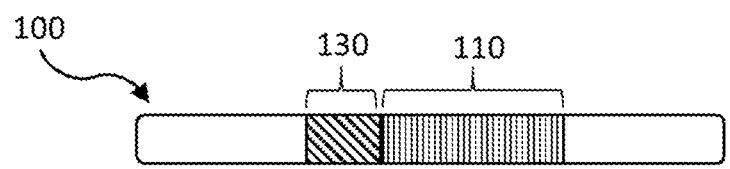
FIG. 7 is a schematic of a viral genome of the invention.
Figure 8:
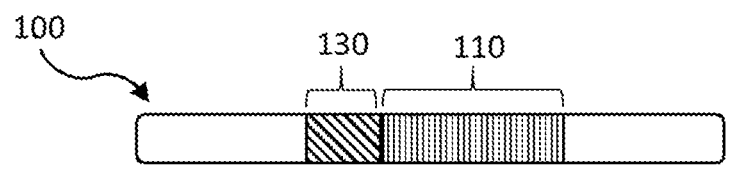
FIG. 8 is a schematic of a viral genome of the invention.

In one embodiment, the viral genome 100 may comprise the components as shown in FIGS. 7 and 8. Within the viral genome 100, there may be at least one promoter region 130, and a payload region 110. In one embodiment, the payload region may comprise at least one modulatory polynucleotide.

Figure 9:
FIG. 9 is a schematic of a viral genome of the invention.

In one embodiment, the viral genome 100 may comprise the components as shown in FIG. 9. Within the viral genome 100, there may be at least one promoter region 130, a payload region 110, and a polyadenylation signal sequence region 160. In one embodiment, the payload region may comprise at least one modulatory polynucleotide.

Viral Genome Size

In one embodiment, the viral genome which comprises a payload described herein, may be single stranded or double stranded viral genome. The size of the viral genome may be small, medium, large or the maximum size. Additionally, the viral genome may comprise a promoter and a polyA tail.

In one embodiment, the viral genome which comprises a payload described herein, may be a small single stranded viral genome. A small single stranded viral genome may be 2.7 to 3.5 kb in size such as about 2.7, 2.8, 2.9, 3.0, 3.1, 3.2, 3.3, 3.4, and 3.5 kb in size. As a non-limiting example, the small single stranded viral genome may be 3.2 kb in size. Additionally, the viral genome may comprise a promoter and a polyA tail.

In one embodiment, the viral genome which comprises a payload described herein, may be a small double stranded viral genome. A small double stranded viral genome may be 1.3 to 1.7 kb in size such as about 1.3, 1.4, 1.5, 1.6, and 1.7 kb in size. As a non-limiting example, the small double stranded viral genome may be 1.6 kb in size. Additionally, the viral genome may comprise a promoter and a polyA tail.

In one embodiment, the viral genome which comprises a payload described herein, may a medium single stranded viral genome. A medium single stranded viral genome may be 3.6 to 4.3 kb in size such as about 3.6, 3.7, 3.8, 3.9, 4.0, 4.1, 4.2 and 4.3 kb in size. As a non-limiting example, the medium single stranded viral genome may be 4.0 kb in size. Additionally, the viral genome may comprise a promoter and a polyA tail.

In one embodiment, the viral genome which comprises a payload described herein, may be a medium double stranded viral genome. A medium double stranded viral genome may be 1.8 to 2.1 kb in size such as about 1.8, 1.9, 2.0, and 2.1 kb in size. As a non-limiting example, the medium double stranded viral genome may be 2.0 kb in size. Additionally, the viral genome may comprise a promoter and a polyA tail.

In one embodiment, the viral genome which comprises a payload described herein, may be a large single stranded viral genome. A large single stranded viral genome may be 4.4 to 6.0 kb in size such as about 4.4, 4.5, 4.6, 4.7, 4.8, 4.9, 5.0, 5.1, 5.2, 5.3, 5.4, 5.5, 5.6, 5.7, 5.8, 5.9 and 6.0 kb in size. As a non-limiting example, the large single stranded viral genome may be 4.7 kb in size. As another non-limiting example, the large single stranded viral genome may be 4.8 kb in size. As yet another non-limiting example, the large single stranded viral genome may be 6.0 kb in size. Additionally, the viral genome may comprise a promoter and a polyA tail.

In one embodiment, the viral genome which comprises a payload described herein, may be a large double stranded viral genome. A large double stranded viral genome may be 2.2 to 3.0 kb in size such as about 2.2, 2.3, 2.4, 2.5, 2.6, 2.7, 2.8, 2.9 and 3.0 kb in size. As a non-limiting example, the large double stranded viral genome may be 2.4 kb in size. Additionally, the viral genome may comprise a promoter and a polyA tail.

Viral Genome Component: Inverted Terminal Repeats (ITRs)

The AAV particles of the present invention comprise a viral genome with at least one ITR region and a payload region. In one embodiment the viral genome has two ITRs. These two ITRs flank the payload region at the 5' and 3' ends. The ITRs function as origins of replication comprising recognition sites for replication. ITRs comprise sequence regions which can be complementary and symmetrically arranged. ITRs incorporated into viral genomes of the invention may be comprised of naturally occurring polynucleotide sequences or recombinantly derived polynucleotide sequences.

The ITRs may be derived from the same serotype as the capsid, selected from any of the serotypes listed in Table 1, or a derivative thereof. The ITR may be of a different serotype from the capsid. In one embodiment the AAV particle has more than one ITR. In a non-limiting example, the AAV particle has a viral genome comprising two ITRs. In one embodiment the ITRs are of the same serotype as one another. In another embodiment the ITRs are of different serotypes. Non-limiting examples include zero, one or both of the ITRs having the same serotype as the capsid. In one embodiment both ITRs of the viral genome of the AAV particle are AAV2 ITRs.

Independently, each ITR may be about 100 to about 150 nucleotides in length. An ITR may be about 100-105 nucleotides in length, 106-110 nucleotides in length, 111-115 nucleotides in length, 116-120 nucleotides in length, 121-125 nucleotides in length, 126-130 nucleotides in length, 131-135 nucleotides in length, 136-140 nucleotides in length, 141-145 nucleotides in length or 146-150 nucleotides in length. In one embodiment the ITRs are 140-142 nucleotides in length. Non limiting examples of ITR length are 102, 140, 141, 142, 145 nucleotides in length, and those having at least 95% identity thereto.

In one embodiment, the AAV particle comprises a nucleic acid sequence encoding an siRNA molecule which may be located near the 5' end of the flip ITR in an expression vector. In another embodiment, the AAV particle comprises a nucleic acid sequence encoding an siRNA molecule may be located near the 3' end of the flip ITR in an expression vector. In yet another embodiment, the AAV particle comprises a nucleic acid sequence encoding an siRNA molecule may be located near the 5' end of the flop ITR in an expression vector. In yet another embodiment, the AAV particle comprises a nucleic acid sequence encoding an siRNA molecule may be located near the 3' end of the flop ITR in an expression vector. In one embodiment, the AAV particle comprises a nucleic acid sequence encoding an siRNA molecule may be located between the 5' end of the flip ITR and the 3' end of the flop ITR in an expression vector. In one embodiment, the AAV particle comprises a nucleic acid sequence encoding an siRNA molecule may be located between (e.g., half-way between the 5' end of the flip ITR and 3' end of the flop ITR or the 3' end of the flop ITR and the 5' end of the flip ITR), the 3' end of the flip ITR and the 5' end of the flip ITR in an expression vector. As a non-limiting example, the AAV particle comprises a nucleic acid sequence encoding an siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the 5' or 3' end of an ITR (e.g., Flip or Flop ITR) in an expression vector. As a non-limiting example, the AAV particle comprises a nucleic acid sequence encoding an siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides upstream from the 5' or 3' end of an ITR (e.g., Flip or Flop ITR) in an expression vector. As another non-limiting example, the AAV particle comprises a nucleic acid sequence encoding an siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the 5' or 3' end of an ITR (e.g., Flip or Flop ITR) in an expression vector. As another non-limiting example, the AAV particle comprises a nucleic acid sequence encoding an siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 upstream from the 5' or 3' end of an ITR (e.g., Flip or Flop ITR) in an expression vector. As a non-limiting example, the AAV particle comprises a nucleic acid sequence encoding an siRNA molecule may be located within the first 1%, 2%, 3%, 4%, 5%, 6%, 7%, 8%, 9%, 10%, 15%, 20%, 25% or more than 25% of the nucleotides upstream from the 5' or 3' end of an ITR (e.g., Flip or Flop ITR) in an expression vector. As another non-limiting example, the AAV particle comprises a nucleic acid sequence encoding an siRNA molecule may be located with the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% downstream from the 5' or 3' end of an ITR (e.g., Flip or Flop ITR) in an expression vector.

Viral Genome Component: Promoters

In one embodiment, the payload region of the viral genome comprises at least one element to enhance the transgene target specificity and expression (See e.g., Powell et al. Viral Expression Cassette Elements to Enhance Transgene Target Specificity and Expression in Gene Therapy, 2015; the contents of which are herein incorporated by reference in its entirety). Non-limiting examples of elements to enhance the transgene target specificity and expression include promoters, endogenous miRNAs, post-transcriptional regulatory elements (PREs), polyadenylation (PolyA) signal sequences and upstream enhancers (USEs), CMV enhancers and introns.

A person skilled in the art may recognize that expression of the polypeptides of the invention in a target cell may require a specific promoter, including but not limited to, a promoter that is species specific, inducible, tissue-specific, or cell cycle-specific (Parr et al., Nat. Med. 3:1145-9 (1997); the contents of which are herein incorporated by reference in their entirety).

In one embodiment, the promoter is deemed to be efficient when it drives expression of the polypeptide(s) encoded in the payload region of the viral genome of the AAV particle.

In one embodiment, the promoter is a promoter deemed to be efficient to drive the expression of the modulatory polynucleotide.

In one embodiment, the promoter is a promoter deemed to be efficient when it drives expression in the cell being targeted.

In one embodiment, the promoter drives expression of the payload for a period of time in targeted tissues. Expression driven by a promoter may be for a period of 1 hour, 2, hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 1 week, 8 days, 9 days, 10 days, 11 days, 12 days, 13 days, 2 weeks, 15 days, 16 days, 17 days, 18 days, 19 days, 20 days, 3 weeks, 22 days, 23 days, 24 days, 25 days, 26 days, 27 days, 28 days, 29 days, 30 days, 31 days, 1 month, 2 months, 3 months, 4 months, 5 months, 6 months, 7 months, 8 months, 9 months, 10 months, 11 months, 1 year, 13 months, 14 months, 15 months, 16 months, 17 months, 18 months, 19 months, 20 months, 21 months, 22 months, 23 months, 2 years, 3 years, 4 years, 5 years, 6 years, 7 years, 8 years, 9 years, 10 years or more than 10 years. Expression may be for 1-5 hours, 1-12 hours, 1-2 days, 1-5 days, 1-2 weeks, 1-3 weeks, 1-4 weeks, 1-2 months, 1-4 months, 1-6 months, 2-6 months, 3-6 months, 3-9 months, 4-8 months, 6-12 months, 1-2 years, 1-5 years, 2-5 years, 3-6 years, 3-8 years, 4-8 years or 5-10 years.

In one embodiment, the promoter drives expression of the payload for at least 1 month, 2 months, 3 months, 4 months, 5 months, 6 months, 7 months, 8 months, 9 months, 10 months, 11 months, 1 year, 2 years, 3 years 4 years, 5 years, 6 years, 7 years, 8 years, 9 years, 10 years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years, 37 years, 38 years, 39 years, 40 years, 41 years, 42 years, 43 years, 44 years, 45 years, 46 years, 47 years, 48 years, 49 years, 50 years, 55 years, 60 years, 65 years, or more than 65 years.

Promoters may be naturally occurring or non-naturally occurring. Non-limiting examples of promoters include viral promoters, plant promoters and mammalian promoters. In some embodiments, the promoters may be human promoters. In some embodiments, the promoter may be truncated.

Promoters which drive or promote expression in most tissues include, but are not limited to, human elongation factor 1α-subunit (EF1α), cytomegalovirus (CMV) immediate-early enhancer and/or promoter, chicken β-actin (CBA) and its derivative CAG, β glucuronidase (GUSB), or ubiquitin C (UBC). Tissue-specific expression elements can be used to restrict expression to certain cell types such as, but not limited to, muscle specific promoters, B cell promoters, monocyte promoters, leukocyte promoters, macrophage promoters, pancreatic acinar cell promoters, endothelial cell promoters, lung tissue promoters, astrocyte promoters, or nervous system promoters which can be used to restrict expression to neurons, astrocytes, or oligodendrocytes.

Non-limiting examples of muscle-specific promoters include mammalian muscle creatine kinase (MCK) promoter, mammalian desmin (DES) promoter, mammalian troponin I (TNNI2) promoter, and mammalian skeletal alpha-actin (ASKA) promoter (see, e.g. U.S. Patent Publication US 20110212529, the contents of which are herein incorporated by reference in their entirety)

Non-limiting examples of tissue-specific expression elements for neurons include neuron-specific enolase (NSE), platelet-derived growth factor (PDGF), platelet-derived growth factor B-chain (PDGF-β), synapsin (Syn), methyl-CpG binding protein 2 (MeCP2), $Ca^{2+}$/calmodulin-dependent protein kinase II (CaMKII), metabotropic glutamate receptor 2 (mGluR2), neurofilament light (NFL) or heavy (NFH), β-globin minigene nβ2, preproenkephalin (PPE), enkephalin (Enk) and excitatory amino acid transporter 2 (EAAT2) promoters. Non-limiting examples of tissue-specific expression elements for astrocytes include glial fibrillary acidic protein (GFAP) and EAAT2 promoters. A non-limiting example of a tissue-specific expression element for oligodendrocytes includes the myelin basic protein (MBP) promoter.

In one embodiment, the promoter may be less than 1 kb. The promoter may have a length of 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more than 800 nucleotides. The promoter may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800 or 700-800.

In one embodiment, the promoter may be a combination of two or more components of the same or different starting or parental promoters such as, but not limited to, CMV and CBA. Each component may have a length of 200, 210, 220, 230, 240, 250, 260, 270, 280, 290, 300, 310, 320, 330, 340, 350, 360, 370, 380, 381, 382, 383, 384, 385, 386, 387, 388, 389, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more than 800. Each component may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800 or 700-800. In one embodiment, the promoter is a combination of a 382 nucleotide CMV-enhancer sequence and a 260 nucleotide CBA-promoter sequence.

In one embodiment, the viral genome comprises a ubiquitous promoter. Non-limiting examples of ubiquitous promoters include CMV, CBA (including derivatives CAG, CBh, etc.), EF-1α, PGK, UBC, GUSB (hGBp), and UCOE (promoter of HNRPA2B1-CBX3).

Yu et al. (Molecular Pain 2011, 7:63; the contents of which are herein incorporated by reference in their entirety) evaluated the expression of eGFP under the CAG, EF1α, PGK and UBC promoters in rat DRG cells and primary DRG cells using lentiviral vectors and found that UBC showed weaker expression than the other 3 promoters and only 10-12% glial expression was seen for all promoters. Soderblom et al. (E. Neuro 2015; the contents of which are herein incorporated by reference in its entirety) evaluated the expression of eGFP in AAV8 with CMV and UBC promoters and AAV2 with the CMV promoter after injection in the motor cortex. Intranasal administration of a plasmid containing a UBC or EF1α promoter showed a sustained airway expression greater than the expression with the CMV promoter (See e.g., Gill et al., Gene Therapy 2001, Vol. 8, 1539-1546; the contents of which are herein incorporated by reference in their entirety). Husain et al. (Gene Therapy 2009; the contents of which are herein incorporated by reference in its entirety) evaluated an HβH construct with a hGUSB promoter, a HSV-1LAT promoter and an NSE promoter and found that the HβH construct showed weaker expression than NSE in mouse brain. Passini and Wolfe (J. Virol. 2001, 12382-12392, the contents of which are herein incorporated by reference in its entirety) evaluated the long term effects of the HβH vector following an intraventricular injection in neonatal mice and found that there was sustained expression for at least 1 year. Low expression in all brain regions was found by Xu et al. (Gene Therapy 2001, 8, 1323-1332; the contents of which are herein incorporated by reference in their entirety) when NFL and NFH promoters were used as compared to the CMV-lacZ, CMV-luc, EF, GFAP, hENK, nAChR, PPE, PPE+wpre, NSE (0.3 kb), NSE (1.8 kb) and NSE (1.8 kb+wpre). Xu et al. found that the promoter activity in descending order was NSE (1.8 kb), EF, NSE (0.3 kb), GFAP, CMV, hENK, PPE, NFL and NFH. NFL is a 650 nucleotide promoter and NFH is a 920 nucleotide promoter which are both absent in the liver but NFH is abundant in the sensory proprioceptive neurons, brain and spinal cord and NFH is present in the heart. Scn8a is a 470 nucleotide promoter which expresses throughout the DRG, spinal cord and brain with particularly high expression seen in the hippocampal neurons and cerebellar Purkinje cells, cortex, thalamus and hypothalamus (See e.g., Drews et al. *Identification of evolutionary conserved, functional noncoding elements in the promoter region of the sodium channel gene SCN8A*, Mamm Genome (2007) 18:723-731, and Raymond et al. *Expression of Alternatively Spliced Sodium Channel α-subunit genes*, Journal of Biological Chemistry (2004) 279(44) 46234-46241; the contents of each of which are herein incorporated by reference in their entireties).

Any of promoters taught by the aforementioned Yu, Soderblom, Gill, Husain, Passini, Xu, Drews or Raymond may be used in the present inventions.

In one embodiment, the promoter is not cell specific.

In one embodiment, the promoter is an ubiquitin c (UBC) promoter. The UBC promoter may have a size of 300-350 nucleotides. As a non-limiting example, the UBC promoter is 332 nucleotides.

In one embodiment, the promoter is a β-glucuronidase (GUSB) promoter. The GUSB promoter may have a size of 350-400 nucleotides. As a non-limiting example, the GUSB promoter is 378 nucleotides.

In one embodiment, the promoter is a neurofilament light (NFL) promoter. The NFL promoter may have a size of 600-700 nucleotides. As a non-limiting example, the NFL promoter is 650 nucleotides. As a non-limiting example, the construct may be AAV-promoter-CMV/globin intron-modulatory polynucleotide-RBG, where the AAV may be self-complementary and the AAV may be the DJ serotype.

In one embodiment, the promoter is a neurofilament heavy (NFH) promoter. The NFH promoter may have a size of 900-950 nucleotides. As a non-limiting example, the NFH promoter is 920 nucleotides. As a non-limiting example, the construct may be AAV-promoter-CMV/globin intron-modulatory polynucleotide-RBG, where the AAV may be self-complementary and the AAV may be the DJ serotype.

In one embodiment, the promoter is a scn8a promoter. The scn8a promoter may have a size of 450-500 nucleotides. As a non-limiting example, the scn8a promoter is 470 nucleotides. As a non-limiting example, the construct may be AAV-promoter-CMV/globin intron-modulatory polynucleotide-RBG, where the AAV may be self-complementary and the AAV may be the DJ serotype In one embodiment, the viral genome comprises a Pol III promoter.

In one embodiment, the viral genome comprises a P1 promoter.

In one embodiment, the viral genome comprises a FXN promoter.

In one embodiment, the promoter is a phosphoglycerate kinase 1 (PGK) promoter.

In one embodiment, the promoter is a chicken β-actin (CBA) promoter.

In one embodiment, the promoter is a CAG promoter which is a construct comprising the cytomegalovirus (CMV) enhancer fused to the chicken beta-actin (CBA) promoter.

In one embodiment, the promoter is a cytomegalovirus (CMV) promoter.

In one embodiment, the viral genome comprises a H1 promoter.

In one embodiment, the viral genome comprises a U6 promoter.

In one embodiment, the promoter is a liver or a skeletal muscle promoter. Non-limiting examples of liver promoters include human α-1-antitrypsin (hAAT) and thyroxine binding globulin (TBG). Non-limiting examples of skeletal muscle promoters include Desmin, MCK or synthetic C5-12.

In one embodiment, the promoter is a RNA pol III promoter. As a non-limiting example, the RNA pol III promoter is U6. As a non-limiting example, the RNA pol III promoter is H1.

In one embodiment, the viral genome comprises two promoters. As a non-limiting example, the promoters are an EF1α promoter and a CMV promoter.

In one embodiment, the viral genome comprises an enhancer element, a promoter and/or a 5'UTR intron. The enhancer element, also referred to herein as an "enhancer," may be, but is not limited to, a CMV enhancer, the promoter may be, but is not limited to, a CMV, CBA, UBC, GUSB, NSE, Synapsin, MeCP2, and GFAP promoter and the 5'UTR/intron may be, but is not limited to, SV40, and CBA-MVM. As a non-limiting example, the enhancer, promoter and/or intron used in combination may be: (1) CMV enhancer, CMV promoter, SV40 5'UTR intron; (2) CMV enhancer, CBA promoter, SV 40 5'UTR intron; (3) CMV enhancer, CBA promoter, CBA-MVM 5'UTR intron; (4) UBC promoter; (5) GUSB promoter; (6) NSE promoter; (7) Synapsin promoter; (8) MeCP2 promoter, (9) GFAP promoter, (10) H1 promoter; and (11) U6 promoter.

In one embodiment, the viral genome comprises an engineered promoter.

In another embodiment the viral genome comprises a promoter from a naturally expressed protein.

Viral Genome Component: Untranslated Regions (UTRs)

By definition, wild type untranslated regions (UTRs) of a gene are transcribed but not translated. Generally, the 5' UTR starts at the transcription start site and ends at the start codon and the 3' UTR starts immediately following the stop codon and continues until the termination signal for transcription.

Features typically found in abundantly expressed genes of specific target organs may be engineered into UTRs to enhance the stability and protein production. As a non-limiting example, a 5' UTR from mRNA normally expressed in the liver (e.g., albumin, serum amyloid A, Apolipoprotein A/B/E, transferrin, alpha fetoprotein, erythropoietin, or Factor VIII) may be used in the viral genomes of the AAV particles of the invention to enhance expression in hepatic cell lines or liver.

While not wishing to be bound by theory, wild-type 5' untranslated regions (UTRs) include features which play roles in translation initiation. Kozak sequences, which are commonly known to be involved in the process by which the ribosome initiates translation of many genes, are usually included in 5' UTRs. Kozak sequences have the consensus CCR(A/G)CCAUGG, where R is a purine (adenine or guanine) three bases upstream of the start codon (ATG), which is followed by another 'G'.

In one embodiment, the 5'UTR in the viral genome includes a Kozak sequence.

In one embodiment, the 5'UTR in the viral genome does not include a Kozak sequence.

While not wishing to be bound by theory, wild-type 3' UTRs are known to have stretches of Adenosines and Uridines embedded therein. These AU rich signatures are particularly prevalent in genes with high rates of turnover. Based on their sequence features and functional properties, the AU rich elements (AREs) can be separated into three classes (Chen et al. 1995, the contents of which are herein incorporated by reference in its entirety): Class 1 AREs, such as, but not limited to, c-Myc and MyoD, contain several dispersed copies of an AUUUA motif within U-rich regions. Class II AREs, such as, but not limited to, GM-CSF and TNF-a, possess two or more overlapping UUAUUUA (U/A)(U/A) nonamers. Class III ARES, such as, but not limited to, c-Jun and Myogenin, are less well defined. These U rich regions do not contain an AUUUA motif. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of polynucleotides. When engineering specific polynucleotides, e.g., payload regions of viral genomes, one or more copies of an ARE can be introduced to make polynucleotides less stable and thereby curtail translation and decrease production of the resultant protein. Likewise, AREs can be identified and removed or mutated to increase the intracellular stability and thus increase translation and production of the resultant protein.

In one embodiment, the 3' UTR of the viral genome may include an oligo(dT) sequence for templated addition of a poly-A tail.

In one embodiment, the viral genome may include at least one miRNA seed, binding site or full sequence, microRNAs (or miRNA or miR) are 19-25 nucleotide noncoding RNAs that bind to the sites of nucleic acid targets and down-regulate gene expression either by reducing nucleic acid molecule stability or by inhibiting translation. A microRNA sequence comprises a "seed" region, i.e., a sequence in the region of positions 2-8 of the mature microRNA, which sequence has perfect Watson-Crick complementarity to the miRNA target sequence of the nucleic acid.

In one embodiment, the viral genome may be engineered to include, alter or remove at least one miRNA binding site, sequence or seed region.

Any UTR from any gene known in the art may be incorporated into the viral genome of the AAV particle. These UTRs, or portions thereof, may be placed in the same orientation as in the gene from which they were selected or they may be altered in orientation or location. In one embodiment, the UTR used in the viral genome of the AAV particle may be inverted, shortened, lengthened, made with one or more other 5' UTRs or 3' UTRs known in the art. As used herein, the term "altered" as it relates to a UTR, means that the UTR has been changed in some way in relation to a reference sequence. For example, a 3' or 5' UTR may be altered relative to a wild type or native UTR by the change in orientation or location as taught above or may be altered by the inclusion of additional nucleotides, deletion of nucleotides, swapping or transposition of nucleotides.

In one embodiment, the viral genome of the AAV particle comprises at least one artificial UTRs which is not a variant of a wild type UTR.

In one embodiment, the viral genome of the AAV particle comprises UTRs which have been selected from a family of transcripts whose proteins share a common function, structure, feature or property.

Viral Genome Component: Polyadenylation Sequence

In one embodiment, the viral genome of the AAV particles of the present invention comprise at least one polyadenylation sequence. The viral genome of the AAV particle may comprise a polyadenylation sequence between the 3' end of the payload coding sequence and the 5' end of the 3'ITR.

In one embodiment, the polyadenylation sequence or "polyA sequence" may range from absent to about 500 nucleotides in length. The polyadenylation sequence may be, but is not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, and 500 nucleotides in length.

In one embodiment, the polyadenylation sequence is 50-100 nucleotides in length.

In one embodiment, the polyadenylation sequence is 50-150 nucleotides in length.

In one embodiment, the polyadenylation sequence is 50-160 nucleotides in length.

In one embodiment, the polyadenylation sequence is 50-200 nucleotides in length.

In one embodiment, the polyadenylation sequence is 60-100 nucleotides in length.

In one embodiment, the polyadenylation sequence is 60-150 nucleotides in length.

In one embodiment, the polyadenylation sequence is 60-160 nucleotides in length.

In one embodiment, the polyadenylation sequence is 60-200 nucleotides in length.

In one embodiment, the polyadenylation sequence is 70-100 nucleotides in length.

In one embodiment, the polyadenylation sequence is 70-150 nucleotides in length.

In one embodiment, the polyadenylation sequence is 70-160 nucleotides in length.

In one embodiment, the polyadenylation sequence is 70-200 nucleotides in length.

In one embodiment, the polyadenylation sequence is 80-100 nucleotides in length.

In one embodiment, the polyadenylation sequence is 80-150 nucleotides in length.

In one embodiment, the polyadenylation sequence is 80-160 nucleotides in length.

In one embodiment, the polyadenylation sequence is 80-200 nucleotides in length.

In one embodiment, the polyadenylation sequence is 90-100 nucleotides in length.

In one embodiment, the polyadenylation sequence is 90-150 nucleotides in length.

In one embodiment, the polyadenylation sequence is 90-160 nucleotides in length.

In one embodiment, the polyadenylation sequence is 90-200 nucleotides in length.

In one embodiment, the AAV particle comprises a nucleic acid sequence encoding an siRNA molecule may be located upstream of the polyadenylation sequence in an expression vector. Further, the AAV particle comprises a nucleic acid sequence encoding an siRNA molecule may be located downstream of a promoter such as, but not limited to, CMV, U6, CAG, CBA or a CBA promoter with a SV40 intron or a human betaglobin intron in an expression vector. As a non-limiting example, the AAV particle comprises a nucleic acid sequence encoding an siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the promoter and/or upstream of the polyadenylation sequence in an expression vector. As another non-limiting example, the AAV particle comprises a nucleic acid sequence encoding an siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the promoter and/or upstream of the polyadenylation sequence in an expression vector. As a non-limiting example, the AAV particle comprises a nucleic acid sequence encoding an siRNA molecule may be located within the first 1%, 2%, 3%, 4%, 5%, 6%, 7%, 8%, 9%, 10%, 15%, 20%, 25% or more than 25% of the nucleotides downstream from the promoter and/or upstream of the polyadenylation sequence in an expression vector. As another non-limiting example, the AAV particle comprises a nucleic acid sequence encoding an siRNA molecule may be located with the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% downstream from the promoter and/or upstream of the polyadenylation sequence in an expression vector.

In one embodiment, the AAV particle comprises a rabbit globin polyadenylation (polyA) signal sequence.

In one embodiment, the AAV particle comprises a human growth hormone polyadenylation (polyA) signal sequence.

Viral Genome Component: Introns

In one embodiment, the payload region comprises at least one element to enhance the expression such as one or more introns or portions thereof. Non-limiting examples of introns include, MVM (67-97 bps), F.IX truncated intron 1 (300 bps), β-globin SD/immunoglobulin heavy chain splice acceptor (250 bps), adenovirus splice donor/immunoglobin splice acceptor (500 bps), SV40 late splice donor/splice acceptor (19S/16S) (180 bps) and hybrid adenovirus splice donor/IgG splice acceptor (230 bps).

In one embodiment, the intron or intron portion may be 100-500 nucleotides in length. The intron may have a length of 80, 90, 100, 110, 120, 130, 140, 150, 160, 170, 171, 172, 173, 174, 175, 176, 177, 178, 179, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500. The intron may have a length between 80-100, 80-120, 80-140, 80-160, 80-180, 80-200, 80-250, 80-300, 80-350, 80-400, 80-450, 80-500, 200-300, 200-400, 200-500, 300-400, 300-500, or 400-500.

In one embodiment, the AAV viral genome may comprise a promoter such as, but not limited to, CMV or U6. As a non-limiting example, the promoter for the AAV comprising the nucleic acid sequence for the siRNA molecules of the present invention is a CMV promoter. As another non-limiting example, the promoter for the AAV comprising the nucleic acid sequence for the siRNA molecules of the present invention is a U6 promoter.

In one embodiment, the AAV viral genome may comprise a CMV promoter.

In one embodiment, the AAV viral genome may comprise a U6 promoter.

In one embodiment, the AAV viral genome may comprise a CMV and a U6 promoter.

In one embodiment, the AAV viral genome may comprise a H1 promoter.

In one embodiment, the AAV viral genome may comprise a CBA promoter.

In one embodiment, the encoded siRNA molecule may be located downstream of a promoter in an expression vector such as, but not limited to, CMV, U6, H1, CBA, CAG, or a CBA promoter with an intron such as SV40 or others known in the art. Further, the encoded siRNA molecule may also be located upstream of the polyadenylation sequence in an expression vector. As a non-limiting example, the encoded siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the promoter and/or upstream of the polyadenylation sequence in an expression vector. As another non-limiting example, the encoded siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the promoter and/or upstream of the polyadenylation sequence in an expression vector. As a non-limiting example, the encoded siRNA molecule may be located within the first 1%, 2%, 3%, 4%, 5%, 6%, 7%, 8%, 9%, 10%, 15%, 20%, 25% or more than 25% of the nucleotides downstream from the promoter and/or upstream of the polyadenylation sequence in an expression vector. As another non-limiting example, the encoded siRNA molecule may be located with the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% downstream from the promoter and/or upstream of the polyadenylation sequence in an expression vector.

Viral Genome Component: Filler Sequence

In one embodiment, the viral genome comprises one or more filler sequences.

In one embodiment, the viral genome comprises one or more filler sequences in order to have the length of the viral genome be the optimal size for packaging. As a non-limiting example, the viral genome comprises at least one filler sequence in order to have the length of the viral genome be about 2.3 kb. As a non-limiting example, the viral genome comprises at least one filler sequence in order to have the length of the viral genome be about 4.6 kb.

In one embodiment, the viral genome comprises one or more filler sequences in order to reduce the likelihood that a hairpin structure of the vector genome (e.g., a modulatory polynucleotide described herein) may be read as an inverted terminal repeat (ITR) during expression and/or packaging. As a non-limiting example, the viral genome comprises at least one filler sequence in order to have the length of the viral genome be about 2.3 kb. As a non-limiting example, the viral genome comprises at least one filler sequence in order to have the length of the viral genome be about 4.6 kb In one embodiment, the viral genome is a single stranded (ss) viral genome and comprises one or more filler sequences which have a length about between 0.1 kb-3.8 kb, such as, but not limited to, 0.1 kb, 0.2 kb, 0.3 kb, 0.4 kb, 0.5 kb, 0.6 kb, 0.7 kb, 0.8 kb, 0.9 kb, 1 kb, 1.1 kb, 1.2 kb, 1.3 kb, 1.4 kb, 1.5 kb, 1.6 kb, 1.7 kb, 1.8 kb, 1.9 kb, 2 kb, 2.1 kb, 2.2 kb, 2.3 kb, 2.4 kb, 2.5 kb, 2.6 kb, 2.7 kb, 2.8 kb, 2.9 kb, 3 kb, 3.1 kb, 3.2 kb, 3.3 kb, 3.4 kb, 3.5 kb, 3.6 kb, 3.7 kb, or 3.8 kb. As a non-limiting example, the total length filler sequence in the vector genome is 3.1 kb. As a non-limiting example, the total length filler sequence in the vector genome is 2.7 kb. As a non-limiting example, the total length filler sequence in the vector genome is 0.8 kb. As a non-limiting example, the total length filler sequence in the vector genome is 0.4 kb. As a non-limiting example, the length of each filler sequence in the vector genome is 0.8 kb. As a non-limiting example, the length of each filler sequence in the vector genome is 0.4 kb.

In one embodiment, the viral genome is a self-complementary (sc) viral genome and comprises one or more filler sequences which have a length about between 0.1 kb-1.5 kb, such as, but not limited to, 0.1 kb, 0.2 kb, 0.3 kb, 0.4 kb, 0.5 kb, 0.6 kb, 0.7 kb, 0.8 kb, 0.9 kb, 1 kb, 1.1 kb, 1.2 kb, 1.3 kb, 1.4 kb, or 1.5 kb. As a non-limiting example, the total length filler sequence in the vector genome is 0.8 kb. As a non-limiting example, the total length filler sequence in the vector genome is 0.4 kb. As a non-limiting example, the length of each filler sequence in the vector genome is 0.8 kb. As a non-limiting example, the length of each filler sequence in the vector genome is 0.4 kb.

In one embodiment, the viral genome comprises any portion of a filler sequence. The viral genome may comprise 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 99% of a filler sequence.

In one embodiment, the viral genome is a single stranded (ss) viral genome and comprises one or more filler sequences in order to have the length of the viral genome be about 4.6 kb. As a non-limiting example, the viral genome comprises at least one filler sequence and the filler sequence is located 3' to the 5' ITR sequence. As a non-limiting example, the viral genome comprises at least one filler sequence and the filler sequence is located 5' to a promoter sequence. As a non-limiting example, the viral genome comprises at least one filler sequence and the filler sequence is located 3' to the polyadenylation signal sequence. As a non-limiting example, the viral genome comprises at least one filler sequence and the filler sequence is located 5' to the 3' ITR sequence. As a non-limiting example, the viral genome comprises at least one filler sequence, and the filler sequence is located between two intron sequences. As a non-limiting example, the viral genome comprises at least one filler sequence, and the filler sequence is located within an intron sequence. As a non-limiting example, the viral genome comprises two filler sequences, and the first filler sequence is located 3' to the 5' ITR sequence and the second filler sequence is located 3' to the polyadenylation signal sequence. As a non-limiting example, the viral genome comprises two filler sequences, and the first filler sequence is located 5' to a promoter sequence and the second filler sequence is located 3' to the polyadenylation signal sequence. As a non-limiting example, the viral genome comprises two filler sequences, and the first filler sequence is located 3' to the 5' ITR sequence and the second filler sequence is located 5' to the 5' ITR sequence.

In one embodiment, the viral genome is a self-complementary (sc) viral genome and comprises one or more filler sequences in order to have the length of the viral genome be about 2.3 kb. As a non-limiting example, the viral genome comprises at least one filler sequence and the filler sequence is located 3' to the 5' ITR sequence. As a non-limiting example, the viral genome comprises at least one filler sequence and the filler sequence is located 5' to a promoter sequence. As a non-limiting example, the viral genome comprises at least one filler sequence and the filler sequence is located 3' to the polyadenylation signal sequence. As a non-limiting example, the viral genome comprises at least one filler sequence and the filler sequence is located 5' to the 3' ITR sequence. As a non-limiting example, the viral genome comprises at least one filler sequence, and the filler sequence is located between two intron sequences. As a non-limiting example, the viral genome comprises at least one filler sequence, and the filler sequence is located within an intron sequence. As a non-limiting example, the viral genome comprises two filler sequences, and the first filler sequence is located 3' to the 5' ITR sequence and the second filler sequence is located 3' to the polyadenylation signal sequence. As a non-limiting example, the viral genome comprises two filler sequences, and the first filler sequence is located 5' to a promoter sequence and the second filler sequence is located 3' to the polyadenylation signal sequence. As a non-limiting example, the viral genome comprises two filler sequences, and the first filler sequence is located 3' to the 5' ITR sequence and the second filler sequence is located 5' to the 5' ITR sequence.

In one embodiment, the viral genome may comprise one or more filler sequences between one of more regions of the viral genome. In one embodiment, the filler region may be located before a region such as, but not limited to, a payload region, an inverted terminal repeat (ITR), a promoter region, an intron region, an enhancer region, a polyadenylation signal sequence region, a multiple cloning site (MCS) region, and/or an exon region. In one embodiment, the filler region may be located after a region such as, but not limited to, a payload region, an inverted terminal repeat (ITR), a promoter region, an intron region, an enhancer region, a polyadenylation signal sequence region, a multiple cloning site (MCS) region, and/or an exon region. In one embodiment, the filler region may be located before and after a region such as, but not limited to, a payload region, an inverted terminal repeat (ITR), a promoter region, an intron region, an enhancer region, a polyadenylation signal sequence region, a multiple cloning site (MCS) region, and/or an exon region.

In one embodiment, the viral genome may comprise one or more filler sequences which bifurcates at least one region of the viral genome. The bifurcated region of the viral genome may comprise 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 99% of the of the region to the 5' of the filler sequence region. As a non-limiting example, the filler sequence may bifurcate at least one region so that 10% of the region is located 5' to the filler sequence and 90% of the region is located 3' to the filler sequence. As a non-limiting example, the filler sequence may bifurcate at least one region so that 20% of the region is located 5' to the filler sequence and 80% of the region is located 3' to the filler sequence. As a non-limiting example, the filler sequence may bifurcate at least one region so that 30% of the region is located 5' to the filler sequence and 70% of the region is located 3' to the filler sequence. As a non-limiting example, the filler sequence may bifurcate at least one region so that 40% of the region is located 5' to the filler sequence and 60% of the region is located 3' to the filler sequence. As a non-limiting example, the filler sequence may bifurcate at least one region so that 50% of the region is located 5' to the filler sequence and 50% of the region is located 3' to the filler sequence. As a non-limiting example, the filler sequence may bifurcate at least one region so that 60% of the region is located 5' to the filler sequence and 40% of the region is located 3' to the filler sequence. As a non-limiting example, the filler sequence may bifurcate at least one region so that 70% of the region is located 5' to the filler sequence and 30% of the region is located 3' to the filler sequence. As a non-limiting example, the filler sequence may bifurcate at least one region so that 80% of the region is located 5' to the filler sequence and 20% of the region is located 3' to the filler sequence. As a non-limiting example, the filler sequence may bifurcate at least one region so that 90% of the region is located 5' to the filler sequence and 10% of the region is located 3' to the filler sequence.

In one embodiment, the viral genome comprises a filler sequence after the 5' ITR.

In one embodiment, the viral genome comprises a filler sequence after the promoter region. In one embodiment, the viral genome comprises a filler sequence after the payload region. In one embodiment, the viral genome comprises a filler sequence after the intron region. In one embodiment, the viral genome comprises a filler sequence after the enhancer region. In one embodiment, the viral genome comprises a filler sequence after the polyadenylation signal sequence region. In one embodiment, the viral genome comprises a filler sequence after the MCS region. In one embodiment, the viral genome comprises a filler sequence after the exon region.

In one embodiment, the viral genome comprises a filler sequence before the promoter region. In one embodiment, the viral genome comprises a filler sequence before the payload region. In one embodiment, the viral genome comprises a filler sequence before the intron region. In one embodiment, the viral genome comprises a filler sequence before the enhancer region. In one embodiment, the viral genome comprises a filler sequence before the polyadenylation signal sequence region. In one embodiment, the viral genome comprises a filler sequence before the MCS region. In one embodiment, the viral genome comprises a filler sequence before the exon region.

In one embodiment, the viral genome comprises a filler sequence before the 3' ITR.

In one embodiment, a filler sequence may be located between two regions, such as, but not limited to, the 5' ITR and the promoter region. In one embodiment, a filler sequence may be located between two regions, such as, but not limited to, the 5' ITR and the payload region. In one embodiment, a filler sequence may be located between two regions, such as, but not limited to, the 5' ITR and the intron region. In one embodiment, a filler sequence may be located between two regions, such as, but not limited to, the 5' ITR and the enhancer region. In one embodiment, a filler sequence may be located between two regions, such as, but not limited to, the 5' ITR and the polyadenylation signal sequence region. In one embodiment, a filler sequence may be located between two regions, such as, but not limited to, the 5' ITR and the MCS region.

In one embodiment, a filler sequence may be located between two regions, such as, but not limited to, the 5' ITR and the exon region.

In one embodiment, a filler sequence may be located between two regions, such as, but not limited to, the promoter region and the payload region. In one embodiment, a filler sequence may be located between two regions, such as, but not limited to, the promoter region and the intron region. In one embodiment, a filler sequence may be located between two regions, such as, but not limited to, the promoter region and the enhancer region. In one embodiment, a filler sequence may be located between two regions, such as, but not limited to, the promoter region and the polyadenylation signal sequence region. In one embodiment, a filler sequence may be located between two regions, such as, but not limited to, the promoter region and the MCS region. In one embodiment, a filler sequence may be located between two regions, such as, but not limited to, the promoter region and the exon region. In one embodiment, a filler sequence may be located between two regions, such as, but not limited to, the promoter region and the 3' ITR.

In one embodiment, a filler sequence may be located between two regions, such as, but not limited to, the payload region and the intron region. In one embodiment, a filler sequence may be located between two regions, such as, but not limited to, the payload region and the enhancer region. In one embodiment, a filler sequence may be located between two regions, such as, but not limited to, the payload region and the polyadenylation signal sequence region. In one embodiment, a filler sequence may be located between two regions, such as, but not limited to, the payload region and the MCS region. In one embodiment, a filler sequence may be located between two regions, such as, but not limited to, the payload region and the exon region.

In one embodiment, a filler sequence may be located between two regions, such as, but not limited to, the payload region and the 3' ITR.

In one embodiment, a filler sequence may be located between two regions, such as, but not limited to, the intron region and the enhancer region. In one embodiment, a filler sequence may be located between two regions, such as, but not limited to, the intron region and the polyadenylation signal sequence region. In one embodiment, a filler sequence may be located between two regions, such as, but not limited to, the intron region and the MCS region. In one embodiment, a filler sequence may be located between two regions, such as, but not limited to, the intron region and the exon region. In one embodiment, a filler sequence may be located between two regions, such as, but not limited to, the intron region and the 3' ITR. In one embodiment, a filler sequence may be located between two regions, such as, but not limited to, the enhancer region and the polyadenylation signal sequence region. In one embodiment, a filler sequence may be located between two regions, such as, but not limited to, the enhancer region and the MCS region. In one embodiment, a filler sequence may be located between two regions, such as, but not limited to, the enhancer region and the exon region. In one embodiment, a filler sequence may be located between two regions, such as, but not limited to, the enhancer region and the 3' ITR.

In one embodiment, a filler sequence may be located between two regions, such as, but not limited to, the polyadenylation signal sequence region and the MCS region. In one embodiment, a filler sequence may be located between two regions, such as, but not limited to, the polyadenylation signal sequence region and the exon region. In one embodiment, a filler sequence may be located between two regions, such as, but not limited to, the polyadenylation signal sequence region and the 3' ITR.

In one embodiment, a filler sequence may be located between two regions, such as, but not limited to, the MCS region and the exon region. In one embodiment, a filler sequence may be located between two regions, such as, but not limited to, the MCS region and the 3' ITR.

In one embodiment, a filler sequence may be located between two regions, such as, but not limited to, the exon region and the 3' ITR.

In one embodiment, a viral genome may comprise two filler sequences, the first filler sequence may be located between the 5' ITR and promoter region, and the second filler sequence may be located between the promoter region and payload region. In one embodiment, a viral genome may comprise two filler sequences, the first filler sequence may be located between the 5' ITR and promoter region, and the second filler sequence may be located between the promoter region and intron region. In one embodiment, a viral genome may comprise two filler sequences, the first filler sequence may be located between the 5' ITR and promoter region, and the second filler sequence may be located between the promoter region and enhancer region. In one embodiment, a viral genome may comprise two filler sequences, the first filler sequence may be located between the 5' ITR and promoter region, and the second filler sequence may be located between the promoter region and polyadenylation signal sequence region. In one embodiment, a viral genome may comprise two filler sequences, the first filler sequence may be located between the 5' ITR and promoter region, and the second filler sequence may be located between the promoter region and MCS region. In one embodiment, a viral genome may comprise two filler sequences, the first filler sequence may be located between the 5' ITR and promoter region, and the second filler sequence may be located between the promoter region and exon region. In one embodiment, a viral genome may comprise two filler sequences, the first filler sequence may be located between the 5' ITR and promoter region, and the second filler sequence may be located between the promoter region and 3' ITR. In one embodiment, a viral genome may comprise two filler sequences, the first filler sequence may be located between the 5' ITR and promoter region, and the second filler sequence may be located between the payload region and intron region. In one embodiment, a viral genome may comprise two filler sequences, the first filler sequence may be located between the 5' ITR and promoter region, and the second filler sequence may be located between the payload region and enhancer region. In one embodiment, a viral genome may comprise two filler sequences, the first filler sequence may be located between the 5' ITR and promoter region, and the second filler sequence may be located between the payload region and polyadenylation signal sequence region. In one embodiment, a viral genome may comprise two filler sequences, the first filler sequence may be located between the 5' ITR and promoter region, and the second filler sequence may be located between the payload region and MCS region. In one embodiment, a viral genome may comprise two filler sequences, the first filler sequence may be located between the 5' ITR and promoter region, and the second filler sequence may be located between the payload region and exon region. In one embodiment, a viral genome may comprise two filler sequences, the first filler sequence may be located between the 5' ITR and promoter region, and the second filler sequence may be located between the payload region and 3' ITR. In one embodiment, a viral genome may comprise two filler sequences, the first filler sequence may be located between the 5' ITR and promoter region, and the second filler sequence may be located between the intron region and enhancer region. In one embodiment, a viral genome may comprise two filler sequences, the first filler sequence may be located between the 5' ITR and promoter region, and the second filler sequence may be located between the intron region and polyadenylation signal sequence region. In one embodiment, a viral genome may comprise two filler sequences, the first filler sequence may be located between the 5' ITR and promoter region, and the second filler sequence may be located between the intron region and MCS region. In one embodiment, a viral genome may comprise two filler sequences, the first filler sequence may be located between the 5' ITR and promoter region, and the second filler sequence may be located between the intron region and exon region. In one embodiment, a viral genome may comprise two filler sequences, the first filler sequence may be located between the 5' ITR and promoter region, and the second filler sequence may be located between the intron region and 3' ITR. In one embodiment, a viral genome may comprise two filler sequences, the first filler sequence may be located between the 5' ITR and promoter region, and the second filler sequence may be located between the enhancer region and polyadenylation signal sequence region. In one embodiment, a viral genome may comprise two filler sequences, the first filler sequence may be located between the 5' ITR and promoter region, and the second filler sequence may be located between the enhancer region and MCS region. In one embodiment, a viral genome may comprise two filler sequences, the first filler sequence may be located between the 5' ITR and promoter region, and the second filler sequence may be located between the enhancer region and exon region. In one embodiment, a viral genome may comprise two filler sequences, the first filler sequence may be located between the 5' ITR and promoter region, and the second filler sequence may be located between the enhancer region and 3' ITR. In one embodiment, a viral genome may comprise two filler sequences, the first filler sequence may be located between the 5' ITR and promoter region, and the second filler sequence may be located between the polyadenylation signal sequence region and MCS region. In one embodiment, a viral genome may comprise two filler sequences, the first filler sequence may be located between the 5' ITR and promoter region, and the second filler sequence may be located between the polyadenylation signal sequence region and exon region. In one embodiment, a viral genome may comprise two filler sequences, the first filler sequence may be located between the 5' ITR and promoter region, and the second filler sequence may be located between the polyadenylation signal sequence region and 3' ITR. In one embodiment, a viral genome may comprise two filler sequences, the first filler sequence may be located between the 5' ITR and promoter region, and the second filler sequence may be located between the MCS region and exon region. In one embodiment, a viral genome may comprise two filler sequences, the first filler sequence may be located between the 5' ITR and promoter region, and the second filler sequence may be located between the MCS region and 3' ITR. In one embodiment, a viral genome may comprise two filler sequences, the first filler sequence may be located between the 5' ITR and promoter region, and the second filler sequence may be located between the exon region and 3' ITR.

In one embodiment, a viral genome may comprise two filler sequences, the first filler sequence may be located between the 5' ITR and payload region, and the second filler sequence may be located between the promoter region and payload region. In one embodiment, a viral genome may comprise two filler sequences, the first filler sequence may be located between the 5' ITR and payload region, and the second filler sequence may be located between the promoter region and intron region. In one embodiment, a viral genome may comprise two filler sequences, the first filler sequence may be located between the 5' ITR and payload region, and the second filler sequence may be located between the promoter region and enhancer region. In one embodiment, a viral genome may comprise two filler sequences, the first filler sequence may be located between the 5' ITR and payload region, and the second filler sequence may be located between the promoter region and polyadenylation signal sequence region. In one embodiment, a viral genome may comprise two filler sequences, the first filler sequence may be located between the 5' ITR and payload region, and the second filler sequence may be located between the promoter region and MCS region. In one embodiment, a viral genome may comprise two filler sequences, the first filler sequence may be located between the 5' ITR and payload region, and the second filler sequence may be located between the promoter region and exon region. In one embodiment, a viral genome may comprise two filler sequences, the first filler sequence may be located between the 5' ITR and payload region, and the second filler sequence may be located between the promoter region and 3' ITR. In one embodiment, a viral genome may comprise two filler sequences, the first filler sequence may be located between the 5' ITR and payload region, and the second filler sequence may be located between the payload region and intron region. In one embodiment, a viral genome may comprise two filler sequences, the first filler sequence may be located between the 5' ITR and payload region, and the second filler sequence may be located between the payload region and enhancer region. In one embodiment, a viral genome may comprise two filler sequences, the first filler sequence may be located between the 5' ITR and payload region, and the second filler sequence may be located between the payload region and polyadenylation signal sequence region. In one embodiment, a viral genome may comprise two filler sequences, the first filler sequence may be located between the 5' ITR and payload region, and the second filler sequence may be located between the payload region and MCS region. In one embodiment, a viral genome may comprise two filler sequences, the first filler sequence may be located between the 5' ITR and payload region, and the second filler sequence may be located between the payload region and exon region. In one embodiment, a viral genome may comprise two filler sequences, the first filler sequence may be located between the 5' ITR and payload region, and the second filler sequence may be located between the payload region and 3' ITR. In one embodiment, a viral genome may comprise two filler sequences, the first filler sequence may be located between the 5' ITR and payload region, and the second filler sequence may be located between the intron region and enhancer region. In one embodiment, a viral genome may comprise two filler sequences, the first filler sequence may be located between the 5' ITR and payload region, and the second filler sequence may be located between the intron region and polyadenylation signal sequence region. In one embodiment, a viral genome may comprise two filler sequences, the first filler sequence may be located between the 5' ITR and payload region, and the second filler sequence may be located between the intron region and MCS region. In one embodiment, a viral genome may comprise two filler sequences, the first filler sequence may be located between the 5' ITR and payload region, and the second filler sequence may be located between the intron region and exon region. In one embodiment, a viral genome may comprise two filler sequences, the first filler sequence may be located between the 5' ITR and payload region, and the second filler sequence may be located between the intron region and 3' ITR. In one embodiment, a viral genome may comprise two filler sequences, the first filler sequence may be located between the 5' ITR and payload region, and the second filler sequence may be located between the enhancer region and polyadenylation signal sequence region. In one embodiment, a viral genome may comprise two filler sequences, the first filler sequence may be located between the 5' ITR and payload region, and the second filler sequence may be located between the enhancer region and MCS region. In one embodiment, a viral genome may comprise two filler sequences, the first filler sequence may be located between the 5' ITR and payload region, and the second filler sequence may be located between the enhancer region and exon region. In one embodiment, a viral genome may comprise two filler sequences, the first filler sequence may be located between the 5' ITR and payload region, and the second filler sequence may be located between the enhancer region and 3' ITR. In one embodiment, a viral genome may comprise two filler sequences, the first filler sequence may be located between the 5' ITR and payload region, and the second filler sequence may be located between the polyadenylation signal sequence region and MCS region. In one embodiment, a viral genome may comprise two filler sequences, the first filler sequence may be located between the 5' ITR and payload region, and the second filler sequence may be located between the polyadenylation signal sequence region and exon region. In one embodiment, a viral genome may comprise two filler sequences, the first filler sequence may be located between the 5' ITR and payload region, and the second filler sequence may be located between the polyadenylation signal sequence region and 3' ITR. In one embodiment, a viral genome may comprise two filler sequences, the first filler sequence may be located between the 5' ITR and payload region, and the second filler sequence may be located between the MCS region and exon region. In one embodiment, a viral genome may comprise two filler sequences, the first filler sequence may be located between the 5' ITR and payload region, and the second filler sequence may be located between the MCS region and 3' ITR. In one embodiment, a viral genome may comprise two filler sequences, the first filler sequence may be located between the 5' ITR and payload region, and the second filler sequence may be located between the exon region and 3' ITR.

In one embodiment, a viral genome may comprise two filler sequences, the first filler sequence may be located between the 5' ITR and intron region, and the second filler sequence may be located between the promoter region and payload region. In one embodiment, a viral genome may comprise two filler sequences, the first filler sequence may be located between the 5' ITR and intron region, and the second filler sequence may be located between the promoter region and intron region. In one embodiment, a viral genome may comprise two filler sequences, the first filler sequence may be located between the 5' ITR and intron region, and the second filler sequence may be located between the promoter region and enhancer region. In one embodiment, a viral genome may comprise two filler sequences, the first filler sequence may be located between the 5' ITR and intron region, and the second filler sequence may be located between the promoter region and polyadenylation signal sequence region. In one embodiment, a viral genome may comprise two filler sequences, the first filler sequence may be located between the 5' ITR and intron region, and the second filler sequence may be located between the promoter region and MCS region. In one embodiment, a viral genome may comprise two filler sequences, the first filler sequence may be located between the 5' ITR and intron region, and the second filler sequence may be located between the promoter region and exon region. In one embodiment, a viral genome may comprise two filler sequences, the first filler sequence may be located between the 5' ITR and intron region, and the second filler sequence may be located between the promoter region and 3' ITR. In one embodiment, a viral genome may comprise two filler sequences, the first filler sequence may be located between the 5' ITR and intron region, and the second filler sequence may be located between the payload region and intron region. In one embodiment, a viral genome may comprise two filler sequences, the first filler sequence may be located between the 5' ITR and intron region, and the second filler sequence may be located between the payload region and enhancer region. In one embodiment, a viral genome may comprise two filler sequences, the first filler sequence may be located between the 5' ITR and intron region, and the second filler sequence may be located between the payload region and polyadenylation signal sequence region. In one embodiment, a viral genome may comprise two filler sequences, the first filler sequence may be located between the 5' ITR and intron region, and the second filler sequence may be located between the payload region and MCS region. In one embodiment, a viral genome may comprise two filler sequences, the first filler sequence may be located between the 5' ITR and intron region, and the second filler sequence may be located between the payload region and exon region. In one embodiment, a viral genome may comprise two filler sequences, the first filler sequence may be located between the 5' ITR and intron region, and the second filler sequence may be located between the payload region and 3' ITR. In one embodiment, a viral genome may comprise two filler sequences, the first filler sequence may be located between the 5' ITR and intron region, and the second filler sequence may be located between the intron region and enhancer region. In one embodiment, a viral genome may comprise two filler sequences, the first filler sequence may be located between the 5' ITR and intron region, and the second filler sequence may be located between the intron region and polyadenylation signal sequence region. In one embodiment, a viral genome may comprise two filler sequences, the first filler sequence may be located between the 5' ITR and intron region, and the second filler sequence may be located between the intron region and MCS region. In one embodiment, a viral genome may comprise two filler sequences, the first filler sequence may be located between the 5' ITR and intron region, and the second filler sequence may be located between the intron region and exon region. In one embodiment, a viral genome may comprise two filler sequences, the first filler sequence may be located between the 5' ITR and intron region, and the second filler sequence may be located between the intron region and 3' ITR. In one embodiment, a viral genome may comprise two filler sequences, the first filler sequence may be located between the 5' ITR and intron region, and the second filler sequence may be located between the enhancer region and polyadenylation signal sequence region. In one embodiment, a viral genome may comprise two filler sequences, the first filler sequence may be located between the 5' ITR and intron region, and the second filler sequence may be located between the enhancer region and MCS region. In one embodiment, a viral genome may comprise two filler sequences, the first filler sequence may be located between the 5' ITR and intron region, and the second filler sequence may be located between the enhancer region and exon region. In one embodiment, a viral genome may comprise two filler sequences, the first filler sequence may be located between the 5' ITR and intron region, and the second filler sequence may be located between the enhancer region and 3' ITR. In one embodiment, a viral genome may comprise two filler sequences, the first filler sequence may be located between the 5' ITR and intron region, and the second filler sequence may be located between the polyadenylation signal sequence region and MCS region. In one embodiment, a viral genome may comprise two filler sequences, the first filler sequence may be located between the 5' ITR and intron region, and the second filler sequence may be located between the polyadenylation signal sequence region and exon region. In one embodiment, a viral genome may comprise two filler sequences, the first filler sequence may be located between the 5' ITR and intron region, and the second filler sequence may be located between the polyadenylation signal sequence region and 3' ITR. In one embodiment, a viral genome may comprise two filler sequences, the first filler sequence may be located between the 5' ITR and intron region, and the second filler sequence may be located between the MCS region and exon region. In one embodiment, a viral genome may comprise two filler sequences, the first filler sequence may be located between the 5' ITR and intron region, and the second filler sequence may be located between the MCS region and 3' ITR. In one embodiment, a viral genome may comprise two filler sequences, the first filler sequence may be located between the 5' ITR and intron region, and the second filler sequence may be located between the exon region and 3' ITR.

In one embodiment, a viral genome may comprise two filler sequences, the first filler sequence may be located between the 5' ITR and enhancer region, and the second filler sequence may be located between the promoter region and payload region. In one embodiment, a viral genome may comprise two filler sequences, the first filler sequence may be located between the 5' ITR and enhancer region, and the second filler sequence may be located between the promoter region and intron region. In one embodiment, a viral genome may comprise two filler sequences, the first filler sequence may be located between the 5' ITR and enhancer region, and the second filler sequence may be located between the promoter region and enhancer region. In one embodiment, a viral genome may comprise two filler sequences, the first filler sequence may be located between the 5' ITR and enhancer region, and the second filler sequence may be located between the promoter region and polyadenylation signal sequence region. In one embodiment, a viral genome may comprise two filler sequences, the first filler sequence may be located between the 5' ITR and enhancer region, and the second filler sequence may be located between the promoter region and MCS region. In one embodiment, a viral genome may comprise two filler sequences, the first filler sequence may be located between the 5' ITR and enhancer region, and the second filler sequence may be located between the promoter region and exon region. In one embodiment, a viral genome may comprise two filler sequences, the first filler sequence may be located between the 5' ITR and enhancer region, and the second filler sequence may be located between the promoter region and 3' ITR. In one embodiment, a viral genome may comprise two filler sequences, the first filler sequence may be located between the 5' ITR and enhancer region, and the second filler sequence may be located between the payload region and intron region. In one embodiment, a viral genome may comprise two filler sequences, the first filler sequence may be located between the 5' ITR and enhancer region, and the second filler sequence may be located between the payload region and enhancer region. In one embodiment, a viral genome may comprise two filler sequences, the first filler sequence may be located between the 5' ITR and enhancer region, and the second filler sequence may be located between the payload region and polyadenylation signal sequence region. In one embodiment, a viral genome may comprise two filler sequences, the first filler sequence may be located between the 5' ITR and enhancer region, and the second filler sequence may be located between the payload region and MCS region. In one embodiment, a viral genome may comprise two filler sequences, the first filler sequence may be located between the 5' ITR and enhancer region, and the second filler sequence may be located between the payload region and exon region. In one embodiment, a viral genome may comprise two filler sequences, the first filler sequence may be located between the 5' ITR and enhancer region, and the second filler sequence may be located between the payload region and 3' ITR. In one embodiment, a viral genome may comprise two filler sequences, the first filler sequence may be located between the 5' ITR and enhancer region, and the second filler sequence may be located between the intron region and enhancer region. In one embodiment, a viral genome may comprise two filler sequences, the first filler sequence may be located between the 5' ITR and enhancer region, and the second filler sequence may be located between the intron region and polyadenylation signal sequence region. In one embodiment, a viral genome may comprise two filler sequences, the first filler sequence may be located between the 5' ITR and enhancer region, and the second filler sequence may be located between the intron region and MCS region. In one embodiment, a viral genome may comprise two filler sequences, the first filler sequence may be located between the 5' ITR and enhancer region, and the second filler sequence may be located between the intron region and exon region. In one embodiment, a viral genome may comprise two filler sequences, the first filler sequence may be located between the 5' ITR and enhancer region, and the second filler sequence may be located between the intron region and 3' ITR. In one embodiment, a viral genome may comprise two filler sequences, the first filler sequence may be located between the 5' ITR and enhancer region, and the second filler sequence may be located between the enhancer region and polyadenylation signal sequence region. In one embodiment, a viral genome may comprise two filler sequences, the first filler sequence may be located between the 5' ITR and enhancer region, and the second filler sequence may be located between the enhancer region and MCS region. In one embodiment, a viral genome may comprise two filler sequences, the first filler sequence may be located between the 5' ITR and enhancer region, and the second filler sequence may be located between the enhancer region and exon region. In one embodiment, a viral genome may comprise two filler sequences, the first filler sequence may be located between the 5' ITR and enhancer region, and the second filler sequence may be located between the enhancer region and 3' ITR. In one embodiment, a viral genome may comprise two filler sequences, the first filler sequence may be located between the 5' ITR and enhancer region, and the second filler sequence may be located between the polyadenylation signal sequence region and MCS region. In one embodiment, a viral genome may comprise two filler sequences, the first filler sequence may be located between the 5' ITR and enhancer region, and the second filler sequence may be located between the polyadenylation signal sequence region and exon region. In one embodiment, a viral genome may comprise two filler sequences, the first filler sequence may be located between the 5' ITR and enhancer region, and the second filler sequence may be located between the polyadenylation signal sequence region and 3' ITR. In one embodiment, a viral genome may comprise two filler sequences, the first filler sequence may be located between the 5' ITR and enhancer region, and the second filler sequence may be located between the MCS region and exon region. In one embodiment, a viral genome may comprise two filler sequences, the first filler sequence may be located between the 5' ITR and enhancer region, and the second filler sequence may be located between the MCS region and 3' ITR. In one embodiment, a viral genome may comprise two filler sequences, the first filler sequence may be located between the 5' ITR and enhancer region, and the second filler sequence may be located between the exon region and 3' ITR.

In one embodiment, a viral genome may comprise two filler sequences, the first filler sequence may be located between the 5' ITR and polyadenylation signal sequence region, and the second filler sequence may be located between the promoter region and payload region. In one embodiment, a viral genome may comprise two filler sequences, the first filler sequence may be located between the 5' ITR and polyadenylation signal sequence region, and the second filler sequence may be located between the promoter region and intron region. In one embodiment, a viral genome may comprise two filler sequences, the first filler sequence may be located between the 5' ITR and polyadenylation signal sequence region, and the second filler sequence may be located between the promoter region and enhancer region. In one embodiment, a viral genome may comprise two filler sequences, the first filler sequence may be located between the 5' ITR and polyadenylation signal sequence region, and the second filler sequence may be located between the promoter region and polyadenylation signal sequence region. In one embodiment, a viral genome may comprise two filler sequences, the first filler sequence may be located between the 5' ITR and polyadenylation signal sequence region, and the second filler sequence may be located between the promoter region and MCS region. In one embodiment, a viral genome may comprise two filler sequences, the first filler sequence may be located between the 5' ITR and polyadenylation signal sequence region, and the second filler sequence may be located between the promoter region and exon region. In one embodiment, a viral genome may comprise two filler sequences, the first filler sequence may be located between the 5' ITR and polyadenylation signal sequence region, and the second filler sequence may be located between the promoter region and 3' ITR. In one embodiment, a viral genome may comprise two filler sequences, the first filler sequence may be located between the 5' ITR and polyadenylation signal sequence region, and the second filler sequence may be located between the payload region and intron region. In one embodiment, a viral genome may comprise two filler sequences, the first filler sequence may be located between the 5' ITR and polyadenylation signal sequence region, and the second filler sequence may be located between the payload region and enhancer region. In one embodiment, a viral genome may comprise two filler sequences, the first filler sequence may be located between the 5' ITR and polyadenylation signal sequence region, and the second filler sequence may be located between the payload region and polyadenylation signal sequence region. In one embodiment, a viral genome may comprise two filler sequences, the first filler sequence may be located between the 5' ITR and polyadenylation signal sequence region, and the second filler sequence may be located between the payload region and MCS region. In one embodiment, a viral genome may comprise two filler sequences, the first filler sequence may be located between the 5' ITR and polyadenylation signal sequence region, and the second filler sequence may be located between the payload region and exon region. In one embodiment, a viral genome may comprise two filler sequences, the first filler sequence may be located between the 5' ITR and polyadenylation signal sequence region, and the second filler sequence may be located between the payload region and 3' ITR. In one embodiment, a viral genome may comprise two filler sequences, the first filler sequence may be located between the 5' ITR and polyadenylation signal sequence region, and the second filler sequence may be located between the intron region and enhancer region. In one embodiment, a viral genome may comprise two filler sequences, the first filler sequence may be located between the 5' ITR and polyadenylation signal sequence region, and the second filler sequence may be located between the intron region and polyadenylation signal sequence region. In one embodiment, a viral genome may comprise two filler sequences, the first filler sequence may be located between the 5' ITR and polyadenylation signal sequence region, and the second filler sequence may be located between the intron region and MCS region. In one embodiment, a viral genome may comprise two filler sequences, the first filler sequence may be located between the 5' ITR and polyadenylation signal sequence region, and the second filler sequence may be located between the intron region and exon region. In one embodiment, a viral genome may comprise two filler sequences, the first filler sequence may be located between the 5' ITR and polyadenylation signal sequence region, and the second filler sequence may be located between the intron region and 3' ITR. In one embodiment, a viral genome may comprise two filler sequences, the first filler sequence may be located between the 5' ITR and polyadenylation signal sequence region, and the second filler sequence may be located between the enhancer region and polyadenylation signal sequence region. In one embodiment, a viral genome may comprise two filler sequences, the first filler sequence may be located between the 5' ITR and polyadenylation signal sequence region, and the second filler sequence may be located between the enhancer region and MCS region. In one embodiment, a viral genome may comprise two filler sequences, the first filler sequence may be located between the 5' ITR and polyadenylation signal sequence region, and the second filler sequence may be located between the enhancer region and exon region. In one embodiment, a viral genome may comprise two filler sequences, the first filler sequence may be located between the 5' ITR and polyadenylation signal sequence region, and the second filler sequence may be located between the enhancer region and 3' ITR. In one embodiment, a viral genome may comprise two filler sequences, the first filler sequence may be located between the 5' ITR and polyadenylation signal sequence region, and the second filler sequence may be located between the polyadenylation signal sequence region and MCS region. In one embodiment, a viral genome may comprise two filler sequences, the first filler sequence may be located between the 5' ITR and polyadenylation signal sequence region, and the second filler sequence may be located between the polyadenylation signal sequence region and exon region. In one embodiment, a viral genome may comprise two filler sequences, the first filler sequence may be located between the 5' ITR and polyadenylation signal sequence region, and the second filler sequence may be located between the polyadenylation signal sequence region and 3' ITR. In one embodiment, a viral genome may comprise two filler sequences, the first filler sequence may be located between the 5' ITR and polyadenylation signal sequence region, and the second filler sequence may be located between the MCS region and exon region. In one embodiment, a viral genome may comprise two filler sequences, the first filler sequence may be located between the 5' ITR and polyadenylation signal sequence region, and the second filler sequence may be located between the MCS region and 3' ITR. In one embodiment, a viral genome may comprise two filler sequences, the first filler sequence may be located between the 5' ITR and polyadenylation signal sequence region, and the second filler sequence may be located between the exon region and 3' ITR.

In one embodiment, a viral genome may comprise two filler sequences, the first filler sequence may be located between the 5' ITR and MCS region, and the second filler sequence may be located between the promoter region and payload region. In one embodiment, a viral genome may comprise two filler sequences, the first filler sequence may be located between the 5' ITR and MCS region, and the second filler sequence may be located between the promoter region and intron region. In one embodiment, a viral genome may comprise two filler sequences, the first filler sequence may be located between the 5' ITR and MCS region, and the second filler sequence may be located between the promoter region and enhancer region. In one embodiment, a viral genome may comprise two filler sequences, the first filler sequence may be located between the 5' ITR and MCS region, and the second filler sequence may be located between the promoter region and polyadenylation signal sequence region. In one embodiment, a viral genome may comprise two filler sequences, the first filler sequence may be located between the 5' ITR and MCS region, and the second filler sequence may be located between the promoter region and MCS region. In one embodiment, a viral genome may comprise two filler sequences, the first filler sequence may be located between the 5' ITR and MCS region, and the second filler sequence may be located between the promoter region and exon region. In one embodiment, a viral genome may comprise two filler sequences, the first filler sequence may be located between the 5' ITR and MCS region, and the second filler sequence may be located between the promoter region and 3' ITR. In one embodiment, a viral genome may comprise two filler sequences, the first filler sequence may be located between the 5' ITR and MCS region, and the second filler sequence may be located between the payload region and intron region. In one embodiment, a viral genome may comprise two filler sequences, the first filler sequence may be located between the 5' ITR and MCS region, and the second filler sequence may be located between the payload region and enhancer region. In one embodiment, a viral genome may comprise two filler sequences, the first filler sequence may be located between the 5' ITR and MCS region, and the second filler sequence may be located between the payload region and polyadenylation signal sequence region. In one embodiment, a viral genome may comprise two filler sequences, the first filler sequence may be located between the 5' ITR and MCS region, and the second filler sequence may be located between the payload region and MCS region. In one embodiment, a viral genome may comprise two filler sequences, the first filler sequence may be located between the 5' ITR and MCS region, and the second filler sequence may be located between the payload region and exon region. In one embodiment, a viral genome may comprise two filler sequences, the first filler sequence may be located between the 5' ITR and MCS region, and the second filler sequence may be located between the payload region and 3' ITR. In one embodiment, a viral genome may comprise two filler sequences, the first filler sequence may be located between the 5' ITR and MCS region, and the second filler sequence may be located between the intron region and enhancer region. In one embodiment, a viral genome may comprise two filler sequences, the first filler sequence may be located between the 5' ITR and MCS region, and the second filler sequence may be located between the intron region and polyadenylation signal sequence region. In one embodiment, a viral genome may comprise two filler sequences, the first filler sequence may be located between the 5' ITR and MCS region, and the second filler sequence may be located between the intron region and MCS region. In one embodiment, a viral genome may comprise two filler sequences, the first filler sequence may be located between the 5' ITR and MCS region, and the second filler sequence may be located between the intron region and exon region. In one embodiment, a viral genome may comprise two filler sequences, the first filler sequence may be located between the 5' ITR and MCS region, and the second filler sequence may be located between the intron region and 3' ITR. In one embodiment, a viral genome may comprise two filler sequences, the first filler sequence may be located between the 5' ITR and MCS region, and the second filler sequence may be located between the enhancer region and polyadenylation signal sequence region. In one embodiment, a viral genome may comprise two filler sequences, the first filler sequence may be located between the 5' ITR and MCS region, and the second filler sequence may be located between the enhancer region and MCS region. In one embodiment, a viral genome may comprise two filler sequences, the first filler sequence may be located between the 5' ITR and MCS region, and the second filler sequence may be located between the enhancer region and exon region. In one embodiment, a viral genome may comprise two filler sequences, the first filler sequence may be located between the 5' ITR and MCS region, and the second filler sequence may be located between the enhancer region and 3' ITR. In one embodiment, a viral genome may comprise two filler sequences, the first filler sequence may be located between the 5' ITR and MCS region, and the second filler sequence may be located between the polyadenylation signal sequence region and MCS region. In one embodiment, a viral genome may comprise two filler sequences, the first filler sequence may be located between the 5' ITR and MCS region, and the second filler sequence may be located between the polyadenylation signal sequence region and exon region. In one embodiment, a viral genome may comprise two filler sequences, the first filler sequence may be located between the 5' ITR and MCS region, and the second filler sequence may be located between the polyadenylation signal sequence region and 3' ITR. In one embodiment, a viral genome may comprise two filler sequences, the first filler sequence may be located between the 5' ITR and MCS region, and the second filler sequence may be located between the MCS region and exon region. In one embodiment, a viral genome may comprise two filler sequences, the first filler sequence may be located between the 5' ITR and MCS region, and the second filler sequence may be located between the MCS region and 3' ITR. In one embodiment, a viral genome may comprise two filler sequences, the first filler sequence may be located between the 5' ITR and MCS region, and the second filler sequence may be located between the exon region and 3' ITR.

In one embodiment, a viral genome may comprise two filler sequences, the first filler sequence may be located between the 5' ITR and exon region, and the second filler sequence may be located between the promoter region and payload region. In one embodiment, a viral genome may comprise two filler sequences, the first filler sequence may be located between the 5' ITR and exon region, and the second filler sequence may be located between the promoter region and intron region. In one embodiment, a viral genome may comprise two filler sequences, the first filler sequence may be located between the 5' ITR and exon region, and the second filler sequence may be located between the promoter region and enhancer region. In one embodiment, a viral genome may comprise two filler sequences, the first filler sequence may be located between the 5' ITR and exon region, and the second filler sequence may be located between the promoter region and polyadenylation signal sequence region. In one embodiment, a viral genome may comprise two filler sequences, the first filler sequence may be located between the 5' ITR and exon region, and the second filler sequence may be located between the promoter region and MCS region. In one embodiment, a viral genome may comprise two filler sequences, the first filler sequence may be located between the 5' ITR and exon region, and the second filler sequence may be located between the promoter region and exon region. In one embodiment, a viral genome may comprise two filler sequences, the first filler sequence may be located between the 5' ITR and exon region, and the second filler sequence may be located between the promoter region and 3' ITR. In one embodiment, a viral genome may comprise two filler sequences, the first filler sequence may be located between the 5' ITR and exon region, and the second filler sequence may be located between the payload region and intron region. In one embodiment, a viral genome may comprise two filler sequences, the first filler sequence may be located between the 5' ITR and exon region, and the second filler sequence may be located between the payload region and enhancer region. In one embodiment, a viral genome may comprise two filler sequences, the first filler sequence may be located between the 5' ITR and exon region, and the second filler sequence may be located between the payload region and polyadenylation signal sequence region. In one embodiment, a viral genome may comprise two filler sequences, the first filler sequence may be located between the 5' ITR and exon region, and the second filler sequence may be located between the payload region and MCS region. In one embodiment, a viral genome may comprise two filler sequences, the first filler sequence may be located between the 5' ITR and exon region, and the second filler sequence may be located between the payload region and exon region. In one embodiment, a viral genome may comprise two filler sequences, the first filler sequence may be located between the 5' ITR and exon region, and the second filler sequence may be located between the payload region and 3' ITR. In one embodiment, a viral genome may comprise two filler sequences, the first filler sequence may be located between the 5' ITR and exon region, and the second filler sequence may be located between the intron region and enhancer region. In one embodiment, a viral genome may comprise two filler sequences, the first filler sequence may be located between the 5' ITR and exon region, and the second filler sequence may be located between the intron region and polyadenylation signal sequence region. In one embodiment, a viral genome may comprise two filler sequences, the first filler sequence may be located between the 5' ITR and exon region, and the second filler sequence may be located between the intron region and MCS region. In one embodiment, a viral genome may comprise two filler sequences, the first filler sequence may be located between the 5' ITR and exon region, and the second filler sequence may be located between the intron region and exon region. In one embodiment, a viral genome may comprise two filler sequences, the first filler sequence may be located between the 5' ITR and exon region, and the second filler sequence may be located between the intron region and 3' ITR. In one embodiment, a viral genome may comprise two filler sequences, the first filler sequence may be located between the 5' ITR and exon region, and the second filler sequence may be located between the enhancer region and polyadenylation signal sequence region. In one embodiment, a viral genome may comprise two filler sequences, the first filler sequence may be located between the 5' ITR and exon region, and the second filler sequence may be located between the enhancer region and MCS region. In one embodiment, a viral genome may comprise two filler sequences, the first filler sequence may be located between the 5' ITR and exon region, and the second filler sequence may be located between the enhancer region and exon region. In one embodiment, a viral genome may comprise two filler sequences, the first filler sequence may be located between the 5' ITR and exon region, and the second filler sequence may be located between the enhancer region and 3' ITR. In one embodiment, a viral genome may comprise two filler sequences, the first filler sequence may be located between the 5' ITR and exon region, and the second filler sequence may be located between the polyadenylation signal sequence region and MCS region. In one embodiment, a viral genome may comprise two filler sequences, the first filler sequence may be located between the 5' ITR and exon region, and the second filler sequence may be located between the polyadenylation signal sequence region and exon region. In one embodiment, a viral genome may comprise two filler sequences, the first filler sequence may be located between the 5' ITR and exon region, and the second filler sequence may be located between the polyadenylation signal sequence region and 3' ITR. In one embodiment, a viral genome may comprise two filler sequences, the first filler sequence may be located between the 5' ITR and exon region, and the second filler sequence may be located between the MCS region and exon region. In one embodiment, a viral genome may comprise two filler sequences, the first filler sequence may be located between the 5' ITR and exon region, and the second filler sequence may be located between the MCS region and 3' ITR. In one embodiment, a viral genome may comprise two filler sequences, the first filler sequence may be located between the 5' ITR and exon region, and the second filler sequence may be located between the exon region and 3' ITR.

In one embodiment, a viral genome may comprise two filler sequences, the first filler sequence may be located between the promoter region and payload region, and the second filler sequence may be located between the payload region and intron region. In one embodiment, a viral genome may comprise two filler sequences, the first filler sequence may be located between the promoter region and payload region, and the second filler sequence may be located between the payload region and enhancer region. In one embodiment, a viral genome may comprise two filler sequences, the first filler sequence may be located between the promoter region and payload region, and the second filler sequence may be located between the payload region and polyadenylation signal sequence region. In one embodiment, a viral genome may comprise two filler sequences, the first filler sequence may be located between the promoter region and payload region, and the second filler sequence may be located between the payload region and MCS region. In one embodiment, a viral genome may comprise two filler sequences, the first filler sequence may be located between the promoter region and payload region, and the second filler sequence may be located between the payload region and exon region. In one embodiment, a viral genome may comprise two filler sequences, the first filler sequence may be located between the promoter region and payload region, and the second filler sequence may be located between the payload region and 3' ITR. In one embodiment, a viral genome may comprise two filler sequences, the first filler sequence may be located between the promoter region and payload region, and the second filler sequence may be located between the intron region and enhancer region. In one embodiment, a viral genome may comprise two filler sequences, the first filler sequence may be located between the promoter region and payload region, and the second filler sequence may be located between the intron region and polyadenylation signal sequence region. In one embodiment, a viral genome may comprise two filler sequences, the first filler sequence may be located between the promoter region and payload region, and the second filler sequence may be located between the intron region and MCS region. In one embodiment, a viral genome may comprise two filler sequences, the first filler sequence may be located between the promoter region and payload region, and the second filler sequence may be located between the intron region and exon region. In one embodiment, a viral genome may comprise two filler sequences, the first filler sequence may be located between the promoter region and payload region, and the second filler sequence may be located between the intron region and 3' ITR. In one embodiment, a viral genome may comprise two filler sequences, the first filler sequence may be located between the promoter region and payload region, and the second filler sequence may be located between the enhancer region and polyadenylation signal sequence region. In one embodiment, a viral genome may comprise two filler sequences, the first filler sequence may be located between the promoter region and payload region, and the second filler sequence may be located between the enhancer region and MCS region. In one embodiment, a viral genome may comprise two filler sequences, the first filler sequence may be located between the promoter region and payload region, and the second filler sequence may be located between the enhancer region and exon region. In one embodiment, a viral genome may comprise two filler sequences, the first filler sequence may be located between the promoter region and payload region, and the second filler sequence may be located between the enhancer region and 3' ITR. In one embodiment, a viral genome may comprise two filler sequences, the first filler sequence may be located between the promoter region and payload region, and the second filler sequence may be located between the polyadenylation signal sequence region and MCS region. In one embodiment, a viral genome may comprise two filler sequences, the first filler sequence may be located between the promoter region and payload region, and the second filler sequence may be located between the polyadenylation signal sequence region and exon region. In one embodiment, a viral genome may comprise two filler sequences, the first filler sequence may be located between the promoter region and payload region, and the second filler sequence may be located between the polyadenylation signal sequence region and 3' ITR. In one embodiment, a viral genome may comprise two filler sequences, the first filler sequence may be located between the promoter region and payload region, and the second filler sequence may be located between the MCS region and exon region. In one embodiment, a viral genome may comprise two filler sequences, the first filler sequence may be located between the promoter region and payload region, and the second filler sequence may be located between the MCS region and 3' ITR. In one embodiment, a viral genome may comprise two filler sequences, the first filler sequence may be located between the promoter region and payload region, and the second filler sequence may be located between the exon region and 3' ITR.

In one embodiment, a viral genome may comprise two filler sequences, the first filler sequence may be located between the promoter region and intron region, and the second filler sequence may be located between the payload region and intron region. In one embodiment, a viral genome may comprise two filler sequences, the first filler sequence may be located between the promoter region and intron region, and the second filler sequence may be located between the payload region and enhancer region. In one embodiment, a viral genome may comprise two filler sequences, the first filler sequence may be located between the promoter region and intron region, and the second filler sequence may be located between the payload region and polyadenylation signal sequence region. In one embodiment, a viral genome may comprise two filler sequences, the first filler sequence may be located between the promoter region and intron region, and the second filler sequence may be located between the payload region and MCS region. In one embodiment, a viral genome may comprise two filler sequences, the first filler sequence may be located between the promoter region and intron region, and the second filler sequence may be located between the payload region and exon region. In one embodiment, a viral genome may comprise two filler sequences, the first filler sequence may be located between the promoter region and intron region, and the second filler sequence may be located between the payload region and 3' ITR. In one embodiment, a viral genome may comprise two filler sequences, the first filler sequence may be located between the promoter region and intron region, and the second filler sequence may be located between the intron region and enhancer region. In one embodiment, a viral genome may comprise two filler sequences, the first filler sequence may be located between the promoter region and intron region, and the second filler sequence may be located between the intron region and polyadenylation signal sequence region. In one embodiment, a viral genome may comprise two filler sequences, the first filler sequence may be located between the promoter region and intron region, and the second filler sequence may be located between the intron region and MCS region. In one embodiment, a viral genome may comprise two filler sequences, the first filler sequence may be located between the promoter region and intron region, and the second filler sequence may be located between the intron region and exon region. In one embodiment, a viral genome may comprise two filler sequences, the first filler sequence may be located between the promoter region and intron region, and the second filler sequence may be located between the intron region and 3' ITR. In one embodiment, a viral genome may comprise two filler sequences, the first filler sequence may be located between the promoter region and intron region, and the second filler sequence may be located between the enhancer region and polyadenylation signal sequence region. In one embodiment, a viral genome may comprise two filler sequences, the first filler sequence may be located between the promoter region and intron region, and the second filler sequence may be located between the enhancer region and MCS region. In one embodiment, a viral genome may comprise two filler sequences, the first filler sequence may be located between the promoter region and intron region, and the second filler sequence may be located between the enhancer region and exon region. In one embodiment, a viral genome may comprise two filler sequences, the first filler sequence may be located between the promoter region and intron region, and the second filler sequence may be located between the enhancer region and 3' ITR. In one embodiment, a viral genome may comprise two filler sequences, the first filler sequence may be located between the promoter region and intron region, and the second filler sequence may be located between the polyadenylation signal sequence region and MCS region. In one embodiment, a viral genome may comprise two filler sequences, the first filler sequence may be located between the promoter region and intron region, and the second filler sequence may be located between the polyadenylation signal sequence region and exon region. In one embodiment, a viral genome may comprise two filler sequences, the first filler sequence may be located between the promoter region and intron region, and the second filler sequence may be located between the polyadenylation signal sequence region and 3' ITR. In one embodiment, a viral genome may comprise two filler sequences, the first filler sequence may be located between the promoter region and intron region, and the second filler sequence may be located between the MCS region and exon region. In one embodiment, a viral genome may comprise two filler sequences, the first filler sequence may be located between the promoter region and intron region, and the second filler sequence may be located between the MCS region and 3' ITR. In one embodiment, a viral genome may comprise two filler sequences, the first filler sequence may be located between the promoter region and intron region, and the second filler sequence may be located between the exon region and 3' ITR.

In one embodiment, a viral genome may comprise two filler sequences, the first filler sequence may be located between the promoter region and enhancer region, and the second filler sequence may be located between the payload region and intron region. In one embodiment, a viral genome may comprise two filler sequences, the first filler sequence may be located between the promoter region and enhancer region, and the second filler sequence may be located between the payload region and enhancer region. In one embodiment, a viral genome may comprise two filler sequences, the first filler sequence may be located between the promoter region and enhancer region, and the second filler sequence may be located between the payload region and polyadenylation signal sequence region. In one embodiment, a viral genome may comprise two filler sequences, the first filler sequence may be located between the promoter region and enhancer region, and the second filler sequence may be located between the payload region and MCS region. In one embodiment, a viral genome may comprise two filler sequences, the first filler sequence may be located between the promoter region and enhancer region, and the second filler sequence may be located between the payload region and exon region. In one embodiment, a viral genome may comprise two filler sequences, the first filler sequence may be located between the promoter region and enhancer region, and the second filler sequence may be located between the payload region and 3' ITR. In one embodiment, a viral genome may comprise two filler sequences, the first filler sequence may be located between the promoter region and enhancer region, and the second filler sequence may be located between the intron region and enhancer region. In one embodiment, a viral genome may comprise two filler sequences, the first filler sequence may be located between the promoter region and enhancer region, and the second filler sequence may be located between the intron region and polyadenylation signal sequence region. In one embodiment, a viral genome may comprise two filler sequences, the first filler sequence may be located between the promoter region and enhancer region, and the second filler sequence may be located between the intron region and MCS region. In one embodiment, a viral genome may comprise two filler sequences, the first filler sequence may be located between the promoter region and enhancer region, and the second filler sequence may be located between the intron region and exon region. In one embodiment, a viral genome may comprise two filler sequences, the first filler sequence may be located between the promoter region and enhancer region, and the second filler sequence may be located between the intron region and 3' ITR. In one embodiment, a viral genome may comprise two filler sequences, the first filler sequence may be located between the promoter region and enhancer region, and the second filler sequence may be located between the enhancer region and polyadenylation signal sequence region. In one embodiment, a viral genome may comprise two filler sequences, the first filler sequence may be located between the promoter region and enhancer region, and the second filler sequence may be located between the enhancer region and MCS region. In one embodiment, a viral genome may comprise two filler sequences, the first filler sequence may be located between the promoter region and enhancer region, and the second filler sequence may be located between the enhancer region and exon region. In one embodiment, a viral genome may comprise two filler sequences, the first filler sequence may be located between the promoter region and enhancer region, and the second filler sequence may be located between the enhancer region and 3' ITR. In one embodiment, a viral genome may comprise two filler sequences, the first filler sequence may be located between the promoter region and enhancer region, and the second filler sequence may be located between the polyadenylation signal sequence region and MCS region. In one embodiment, a viral genome may comprise two filler sequences, the first filler sequence may be located between the promoter region and enhancer region, and the second filler sequence may be located between the polyadenylation signal sequence region and exon region. In one embodiment, a viral genome may comprise two filler sequences, the first filler sequence may be located between the promoter region and enhancer region, and the second filler sequence may be located between the polyadenylation signal sequence region and 3' ITR. In one embodiment, a viral genome may comprise two filler sequences, the first filler sequence may be located between the promoter region and enhancer region, and the second filler sequence may be located between the MCS region and exon region. In one embodiment, a viral genome may comprise two filler sequences, the first filler sequence may be located between the promoter region and enhancer region, and the second filler sequence may be located between the MCS region and 3' ITR. In one embodiment, a viral genome may comprise two filler sequences, the first filler sequence may be located between the promoter region and enhancer region, and the second filler sequence may be located between the exon region and 3' ITR.

In one embodiment, a viral genome may comprise two filler sequences, the first filler sequence may be located between the promoter region and polyadenylation signal sequence region, and the second filler sequence may be located between the payload region and intron region. In one embodiment, a viral genome may comprise two filler sequences, the first filler sequence may be located between the promoter region and polyadenylation signal sequence region, and the second filler sequence may be located between the payload region and enhancer region. In one embodiment, a viral genome may comprise two filler sequences, the first filler sequence may be located between the promoter region and polyadenylation signal sequence region, and the second filler sequence may be located between the payload region and polyadenylation signal sequence region. In one embodiment, a viral genome may comprise two filler sequences, the first filler sequence may be located between the promoter region and polyadenylation signal sequence region, and the second filler sequence may be located between the payload region and MCS region. In one embodiment, a viral genome may comprise two filler sequences, the first filler sequence may be located between the promoter region and polyadenylation signal sequence region, and the second filler sequence may be located between the payload region and exon region. In one embodiment, a viral genome may comprise two filler sequences, the first filler sequence may be located between the promoter region and polyadenylation signal sequence region, and the second filler sequence may be located between the payload region and 3' ITR. In one embodiment, a viral genome may comprise two filler sequences, the first filler sequence may be located between the promoter region and polyadenylation signal sequence region, and the second filler sequence may be located between the intron region and enhancer region. In one embodiment, a viral genome may comprise two filler sequences, the first filler sequence may be located between the promoter region and polyadenylation signal sequence region, and the second filler sequence may be located between the intron region and polyadenylation signal sequence region. In one embodiment, a viral genome may comprise two filler sequences, the first filler sequence may be located between the promoter region and polyadenylation signal sequence region, and the second filler sequence may be located between the intron region and MCS region. In one embodiment, a viral genome may comprise two filler sequences, the first filler sequence may be located between the promoter region and polyadenylation signal sequence region, and the second filler sequence may be located between the intron region and exon region. In one embodiment, a viral genome may comprise two filler sequences, the first filler sequence may be located between the promoter region and polyadenylation signal sequence region, and the second filler sequence may be located between the intron region and 3' ITR. In one embodiment, a viral genome may comprise two filler sequences, the first filler sequence may be located between the promoter region and polyadenylation signal sequence region, and the second filler sequence may be located between the enhancer region and polyadenylation signal sequence region. In one embodiment, a viral genome may comprise two filler sequences, the first filler sequence may be located between the promoter region and polyadenylation signal sequence region, and the second filler sequence may be located between the enhancer region and MCS region. In one embodiment, a viral genome may comprise two filler sequences, the first filler sequence may be located between the promoter region and polyadenylation signal sequence region, and the second filler sequence may be located between the enhancer region and exon region. In one embodiment, a viral genome may comprise two filler sequences, the first filler sequence may be located between the promoter region and polyadenylation signal sequence region, and the second filler sequence may be located between the enhancer region and 3' ITR. In one embodiment, a viral genome may comprise two filler sequences, the first filler sequence may be located between the promoter region and polyadenylation signal sequence region, and the second filler sequence may be located between the polyadenylation signal sequence region and MCS region. In one embodiment, a viral genome may comprise two filler sequences, the first filler sequence may be located between the promoter region and polyadenylation signal sequence region, and the second filler sequence may be located between the polyadenylation signal sequence region and exon region. In one embodiment, a viral genome may comprise two filler sequences, the first filler sequence may be located between the promoter region and polyadenylation signal sequence region, and the second filler sequence may be located between the polyadenylation signal sequence region and 3' ITR. In one embodiment, a viral genome may comprise two filler sequences, the first filler sequence may be located between the promoter region and polyadenylation signal sequence region, and the second filler sequence may be located between the MCS region and exon region. In one embodiment, a viral genome may comprise two filler sequences, the first filler sequence may be located between the promoter region and polyadenylation signal sequence region, and the second filler sequence may be located between the MCS region and 3' ITR. In one embodiment, a viral genome may comprise two filler sequences, the first filler sequence may be located between the promoter region and polyadenylation signal sequence region, and the second filler sequence may be located between the exon region and 3' ITR.

In one embodiment, a viral genome may comprise two filler sequences, the first filler sequence may be located between the promoter region and exon region, and the second filler sequence may be located between the payload region and intron region. In one embodiment, a viral genome may comprise two filler sequences, the first filler sequence may be located between the promoter region and exon region, and the second filler sequence may be located between the payload region and enhancer region. In one embodiment, a viral genome may comprise two filler sequences, the first filler sequence may be located between the promoter region and exon region, and the second filler sequence may be located between the payload region and polyadenylation signal sequence region. In one embodiment, a viral genome may comprise two filler sequences, the first filler sequence may be located between the promoter region and exon region, and the second filler sequence may be located between the payload region and MCS region. In one embodiment, a viral genome may comprise two filler sequences, the first filler sequence may be located between the promoter region and exon region, and the second filler sequence may be located between the payload region and exon region. In one embodiment, a viral genome may comprise two filler sequences, the first filler sequence may be located between the promoter region and exon region, and the second filler sequence may be located between the payload region and 3' ITR. In one embodiment, a viral genome may comprise two filler sequences, the first filler sequence may be located between the promoter region and exon region, and the second filler sequence may be located between the intron region and enhancer region. In one embodiment, a viral genome may comprise two filler sequences, the first filler sequence may be located between the promoter region and exon region, and the second filler sequence may be located between the intron region and polyadenylation signal sequence region. In one embodiment, a viral genome may comprise two filler sequences, the first filler sequence may be located between the promoter region and exon region, and the second filler sequence may be located between the intron region and MCS region. In one embodiment, a viral genome may comprise two filler sequences, the first filler sequence may be located between the promoter region and exon region, and the second filler sequence may be located between the intron region and exon region. In one embodiment, a viral genome may comprise two filler sequences, the first filler sequence may be located between the promoter region and exon region, and the second filler sequence may be located between the intron region and 3' ITR. In one embodiment, a viral genome may comprise two filler sequences, the first filler sequence may be located between the promoter region and exon region, and the second filler sequence may be located between the enhancer region and polyadenylation signal sequence region. In one embodiment, a viral genome may comprise two filler sequences, the first filler sequence may be located between the promoter region and exon region, and the second filler sequence may be located between the enhancer region and MCS region. In one embodiment, a viral genome may comprise two filler sequences, the first filler sequence may be located between the promoter region and exon region, and the second filler sequence may be located between the enhancer region and exon region. In one embodiment, a viral genome may comprise two filler sequences, the first filler sequence may be located between the promoter region and exon region, and the second filler sequence may be located between the enhancer region and 3' ITR. In one embodiment, a viral genome may comprise two filler sequences, the first filler sequence may be located between the promoter region and exon region, and the second filler sequence may be located between the polyadenylation signal sequence region and MCS region. In one embodiment, a viral genome may comprise two filler sequences, the first filler sequence may be located between the promoter region and exon region, and the second filler sequence may be located between the polyadenylation signal sequence region and exon region. In one embodiment, a viral genome may comprise two filler sequences, the first filler sequence may be located between the promoter region and exon region, and the second filler sequence may be located between the polyadenylation signal sequence region and 3' ITR. In one embodiment, a viral genome may comprise two filler sequences, the first filler sequence may be located between the promoter region and exon region, and the second filler sequence may be located between the MCS region and exon region. In one embodiment, a viral genome may comprise two filler sequences, the first filler sequence may be located between the promoter region and exon region, and the second filler sequence may be located between the MCS region and 3' ITR. In one embodiment, a viral genome may comprise two filler sequences, the first filler sequence may be located between the promoter region and exon region, and the second filler sequence may be located between the exon region and 3' ITR.

In one embodiment, a viral genome may comprise two filler sequences, the first filler sequence may be located between the promoter region and MCS region, and the second filler sequence may be located between the payload region and intron region. In one embodiment, a viral genome may comprise two filler sequences, the first filler sequence may be located between the promoter region and MCS region, and the second filler sequence may be located between the payload region and enhancer region. In one embodiment, a viral genome may comprise two filler sequences, the first filler sequence may be located between the promoter region and MCS region, and the second filler sequence may be located between the payload region and polyadenylation signal sequence region. In one embodiment, a viral genome may comprise two filler sequences, the first filler sequence may be located between the promoter region and MCS region, and the second filler sequence may be located between the payload region and MCS region. In one embodiment, a viral genome may comprise two filler sequences, the first filler sequence may be located between the promoter region and MCS region, and the second filler sequence may be located between the payload region and exon region. In one embodiment, a viral genome may comprise two filler sequences, the first filler sequence may be located between the promoter region and MCS region, and the second filler sequence may be located between the payload region and 3' ITR. In one embodiment, a viral genome may comprise two filler sequences, the first filler sequence may be located between the promoter region and MCS region, and the second filler sequence may be located between the intron region and enhancer region. In one embodiment, a viral genome may comprise two filler sequences, the first filler sequence may be located between the promoter region and MCS region, and the second filler sequence may be located between the intron region and polyadenylation signal sequence region. In one embodiment, a viral genome may comprise two filler sequences, the first filler sequence may be located between the promoter region and MCS region, and the second filler sequence may be located between the intron region and MCS region. In one embodiment, a viral genome may comprise two filler sequences, the first filler sequence may be located between the promoter region and MCS region, and the second filler sequence may be located between the intron region and exon region. In one embodiment, a viral genome may comprise two filler sequences, the first filler sequence may be located between the promoter region and MCS region, and the second filler sequence may be located between the intron region and 3' ITR. In one embodiment, a viral genome may comprise two filler sequences, the first filler sequence may be located between the promoter region and MCS region, and the second filler sequence may be located between the enhancer region and polyadenylation signal sequence region. In one embodiment, a viral genome may comprise two filler sequences, the first filler sequence may be located between the promoter region and MCS region, and the second filler sequence may be located between the enhancer region and MCS region. In one embodiment, a viral genome may comprise two filler sequences, the first filler sequence may be located between the promoter region and MCS region, and the second filler sequence may be located between the enhancer region and exon region. In one embodiment, a viral genome may comprise two filler sequences, the first filler sequence may be located between the promoter region and MCS region, and the second filler sequence may be located between the enhancer region and 3' ITR. In one embodiment, a viral genome may comprise two filler sequences, the first filler sequence may be located between the promoter region and MCS region, and the second filler sequence may be located between the polyadenylation signal sequence region and MCS region. In one embodiment, a viral genome may comprise two filler sequences, the first filler sequence may be located between the promoter region and MCS region, and the second filler sequence may be located between the polyadenylation signal sequence region and exon region. In one embodiment, a viral genome may comprise two filler sequences, the first filler sequence may be located between the promoter region and MCS region, and the second filler sequence may be located between the polyadenylation signal sequence region and 3' ITR. In one embodiment, a viral genome may comprise two filler sequences, the first filler sequence may be located between the promoter region and MCS region, and the second filler sequence may be located between the MCS region and exon region. In one embodiment, a viral genome may comprise two filler sequences, the first filler sequence may be located between the promoter region and MCS region, and the second filler sequence may be located between the MCS region and 3' ITR. In one embodiment, a viral genome may comprise two filler sequences, the first filler sequence may be located between the promoter region and MCS region, and the second filler sequence may be located between the exon region and 3' ITR.

In one embodiment, a viral genome may comprise two filler sequences, the first filler sequence may be located between the promoter region and 3'ITR, and the second filler sequence may be located between the payload region and intron region. In one embodiment, a viral genome may comprise two filler sequences, the first filler sequence may be located between the promoter region and 3'ITR, and the second filler sequence may be located between the payload region and enhancer region. In one embodiment, a viral genome may comprise two filler sequences, the first filler sequence may be located between the promoter region and 3'ITR, and the second filler sequence may be located between the payload region and polyadenylation signal sequence region. In one embodiment, a viral genome may comprise two filler sequences, the first filler sequence may be located between the promoter region and 3'ITR, and the second filler sequence may be located between the payload region and MCS region. In one embodiment, a viral genome may comprise two filler sequences, the first filler sequence may be located between the promoter region and 3'ITR, and the second filler sequence may be located between the payload region and exon region. In one embodiment, a viral genome may comprise two filler sequences, the first filler sequence may be located between the promoter region and 3'ITR, and the second filler sequence may be located between the payload region and 3' ITR. In one embodiment, a viral genome may comprise two filler sequences, the first filler sequence may be located between the promoter region and 3'ITR, and the second filler sequence may be located between the intron region and enhancer region. In one embodiment, a viral genome may comprise two filler sequences, the first filler sequence may be located between the promoter region and 3'ITR, and the second filler sequence may be located between the intron region and polyadenylation signal sequence region. In one embodiment, a viral genome may comprise two filler sequences, the first filler sequence may be located between the promoter region and 3'ITR, and the second filler sequence may be located between the intron region and MCS region. In one embodiment, a viral genome may comprise two filler sequences, the first filler sequence may be located between the promoter region and 3'ITR, and the second filler sequence may be located between the intron region and exon region. In one embodiment, a viral genome may comprise two filler sequences, the first filler sequence may be located between the promoter region and 3'ITR, and the second filler sequence may be located between the intron region and 3' ITR. In one embodiment, a viral genome may comprise two filler sequences, the first filler sequence may be located between the promoter region and 3'ITR, and the second filler sequence may be located between the enhancer region and polyadenylation signal sequence region. In one embodiment, a viral genome may comprise two filler sequences, the first filler sequence may be located between the promoter region and 3'ITR, and the second filler sequence may be located between the enhancer region and MCS region. In one embodiment, a viral genome may comprise two filler sequences, the first filler sequence may be located between the promoter region and 3'ITR, and the second filler sequence may be located between the enhancer region and exon region. In one embodiment, a viral genome may comprise two filler sequences, the first filler sequence may be located between the promoter region and 3'ITR, and the second filler sequence may be located between the enhancer region and 3' ITR. In one embodiment, a viral genome may comprise two filler sequences, the first filler sequence may be located between the promoter region and 3'ITR, and the second filler sequence may be located between the polyadenylation signal sequence region and MCS region. In one embodiment, a viral genome may comprise two filler sequences, the first filler sequence may be located between the promoter region and 3'ITR, and the second filler sequence may be located between the polyadenylation signal sequence region and exon region. In one embodiment, a viral genome may comprise two filler sequences, the first filler sequence may be located between the promoter region and 3'ITR, and the second filler sequence may be located between the polyadenylation signal sequence region and 3' ITR. In one embodiment, a viral genome may comprise two filler sequences, the first filler sequence may be located between the promoter region and 3'ITR, and the second filler sequence may be located between the MCS region and exon region. In one embodiment, a viral genome may comprise two filler sequences, the first filler sequence may be located between the promoter region and 3'ITR, and the second filler sequence may be located between the MCS region and 3' ITR. In one embodiment, a viral genome may comprise two filler sequences, the first filler sequence may be located between the promoter region and 3'ITR, and the second filler sequence may be located between the exon region and 3' ITR.

In one embodiment, a viral genome may comprise two filler sequences, the first filler sequence may be located between the payload region and intron region, and the second filler sequence may be located between the intron region and enhancer region. In one embodiment, a viral genome may comprise two filler sequences, the first filler sequence may be located between the payload region and intron region, and the second filler sequence may be located between the intron region and polyadenylation signal sequence region. In one embodiment, a viral genome may comprise two filler sequences, the first filler sequence may be located between the payload region and intron region, and the second filler sequence may be located between the intron region and MCS region. In one embodiment, a viral genome may comprise two filler sequences, the first filler sequence may be located between the payload region and intron region, and the second filler sequence may be located between the intron region and exon region. In one embodiment, a viral genome may comprise two filler sequences, the first filler sequence may be located between the payload region and intron region, and the second filler sequence may be located between the intron region and 3' ITR. In one embodiment, a viral genome may comprise two filler sequences, the first filler sequence may be located between the payload region and intron region, and the second filler sequence may be located between the enhancer region and polyadenylation signal sequence region. In one embodiment, a viral genome may comprise two filler sequences, the first filler sequence may be located between the payload region and intron region, and the second filler sequence may be located between the enhancer region and MCS region. In one embodiment, a viral genome may comprise two filler sequences, the first filler sequence may be located between the payload region and intron region, and the second filler sequence may be located between the enhancer region and exon region. In one embodiment, a viral genome may comprise two filler sequences, the first filler sequence may be located between the payload region and intron region, and the second filler sequence may be located between the enhancer region and 3' ITR. In one embodiment, a viral genome may comprise two filler sequences, the first filler sequence may be located between the payload region and intron region, and the second filler sequence may be located between the polyadenylation signal sequence region and MCS region. In one embodiment, a viral genome may comprise two filler sequences, the first filler sequence may be located between the payload region and intron region, and the second filler sequence may be located between the polyadenylation signal sequence region and exon region. In one embodiment, a viral genome may comprise two filler sequences, the first filler sequence may be located between the payload region and intron region, and the second filler sequence may be located between the polyadenylation signal sequence region and 3' ITR. In one embodiment, a viral genome may comprise two filler sequences, the first filler sequence may be located between the payload region and intron region, and the second filler sequence may be located between the MCS region and exon region. In one embodiment, a viral genome may comprise two filler sequences, the first filler sequence may be located between the payload region and intron region, and the second filler sequence may be located between the MCS region and 3' ITR. In one embodiment, a viral genome may comprise two filler sequences, the first filler sequence may be located between the payload region and intron region, and the second filler sequence may be located between the exon region and 3' ITR.

In one embodiment, a viral genome may comprise two filler sequences, the first filler sequence may be located between the payload region and enhancer region, and the second filler sequence may be located between the intron region and enhancer region. In one embodiment, a viral genome may comprise two filler sequences, the first filler sequence may be located between the payload region and enhancer region, and the second filler sequence may be located between the intron region and polyadenylation signal sequence region. In one embodiment, a viral genome may comprise two filler sequences, the first filler sequence may be located between the payload region and enhancer region, and the second filler sequence may be located between the intron region and MCS region. In one embodiment, a viral genome may comprise two filler sequences, the first filler sequence may be located between the payload region and enhancer region, and the second filler sequence may be located between the intron region and exon region. In one embodiment, a viral genome may comprise two filler sequences, the first filler sequence may be located between the payload region and enhancer region, and the second filler sequence may be located between the intron region and 3' ITR. In one embodiment, a viral genome may comprise two filler sequences, the first filler sequence may be located between the payload region and enhancer region, and the second filler sequence may be located between the enhancer region and polyadenylation signal sequence region. In one embodiment, a viral genome may comprise two filler sequences, the first filler sequence may be located between the payload region and enhancer region, and the second filler sequence may be located between the enhancer region and MCS region. In one embodiment, a viral genome may comprise two filler sequences, the first filler sequence may be located between the payload region and enhancer region, and the second filler sequence may be located between the enhancer region and exon region. In one embodiment, a viral genome may comprise two filler sequences, the first filler sequence may be located between the payload region and enhancer region, and the second filler sequence may be located between the enhancer region and 3' ITR. In one embodiment, a viral genome may comprise two filler sequences, the first filler sequence may be located between the payload region and enhancer region, and the second filler sequence may be located between the polyadenylation signal sequence region and MCS region. In one embodiment, a viral genome may comprise two filler sequences, the first filler sequence may be located between the payload region and enhancer region, and the second filler sequence may be located between the polyadenylation signal sequence region and exon region. In one embodiment, a viral genome may comprise two filler sequences, the first filler sequence may be located between the payload region and enhancer region, and the second filler sequence may be located between the polyadenylation signal sequence region and 3' ITR. In one embodiment, a viral genome may comprise two filler sequences, the first filler sequence may be located between the payload region and enhancer region, and the second filler sequence may be located between the MCS region and exon region. In one embodiment, a viral genome may comprise two filler sequences, the first filler sequence may be located between the payload region and enhancer region, and the second filler sequence may be located between the MCS region and 3' ITR. In one embodiment, a viral genome may comprise two filler sequences, the first filler sequence may be located between the payload region and enhancer region, and the second filler sequence may be located between the exon region and 3' ITR.

In one embodiment, a viral genome may comprise two filler sequences, the first filler sequence may be located between the payload region and polyadenylation signal sequence region, and the second filler sequence may be located between the intron region and enhancer region. In one embodiment, a viral genome may comprise two filler sequences, the first filler sequence may be located between the payload region and polyadenylation signal sequence region, and the second filler sequence may be located between the intron region and polyadenylation signal sequence region. In one embodiment, a viral genome may comprise two filler sequences, the first filler sequence may be located between the payload region and polyadenylation signal sequence region, and the second filler sequence may be located between the intron region and MCS region. In one embodiment, a viral genome may comprise two filler sequences, the first filler sequence may be located between the payload region and polyadenylation signal sequence region, and the second filler sequence may be located between the intron region and exon region. In one embodiment, a viral genome may comprise two filler sequences, the first filler sequence may be located between the payload region and polyadenylation signal sequence region, and the second filler sequence may be located between the intron region and 3' ITR. In one embodiment, a viral genome may comprise two filler sequences, the first filler sequence may be located between the payload region and polyadenylation signal sequence region, and the second filler sequence may be located between the enhancer region and polyadenylation signal sequence region. In one embodiment, a viral genome may comprise two filler sequences, the first filler sequence may be located between the payload region and polyadenylation signal sequence region, and the second filler sequence may be located between the enhancer region and MCS region. In one embodiment, a viral genome may comprise two filler sequences, the first filler sequence may be located between the payload region and polyadenylation signal sequence region, and the second filler sequence may be located between the enhancer region and exon region. In one embodiment, a viral genome may comprise two filler sequences, the first filler sequence may be located between the payload region and polyadenylation signal sequence region, and the second filler sequence may be located between the enhancer region and 3' ITR. In one embodiment, a viral genome may comprise two filler sequences, the first filler sequence may be located between the payload region and polyadenylation signal sequence region, and the second filler sequence may be located between the polyadenylation signal sequence region and MCS region. In one embodiment, a viral genome may comprise two filler sequences, the first filler sequence may be located between the payload region and polyadenylation signal sequence region, and the second filler sequence may be located between the polyadenylation signal sequence region and exon region. In one embodiment, a viral genome may comprise two filler sequences, the first filler sequence may be located between the payload region and polyadenylation signal sequence region, and the second filler sequence may be located between the polyadenylation signal sequence region and 3' ITR. In one embodiment, a viral genome may comprise two filler sequences, the first filler sequence may be located between the payload region and polyadenylation signal sequence region, and the second filler sequence may be located between the MCS region and exon region. In one embodiment, a viral genome may comprise two filler sequences, the first filler sequence may be located between the payload region and polyadenylation signal sequence region, and the second filler sequence may be located between the MCS region and 3' ITR. In one embodiment, a viral genome may comprise two filler sequences, the first filler sequence may be located between the payload region and polyadenylation signal sequence region, and the second filler sequence may be located between the exon region and 3' ITR.

In one embodiment, a viral genome may comprise two filler sequences, the first filler sequence may be located between the payload region and MCS region, and the second filler sequence may be located between the intron region and enhancer region. In one embodiment, a viral genome may comprise two filler sequences, the first filler sequence may be located between the payload region and MCS region, and the second filler sequence may be located between the intron region and polyadenylation signal sequence region. In one embodiment, a viral genome may comprise two filler sequences, the first filler sequence may be located between the payload region and MCS region, and the second filler sequence may be located between the intron region and MCS region. In one embodiment, a viral genome may comprise two filler sequences, the first filler sequence may be located between the payload region and MCS region, and the second filler sequence may be located between the intron region and exon region. In one embodiment, a viral genome may comprise two filler sequences, the first filler sequence may be located between the payload region and MCS region, and the second filler sequence may be located between the intron region and 3' ITR. In one embodiment, a viral genome may comprise two filler sequences, the first filler sequence may be located between the payload region and MCS region, and the second filler sequence may be located between the enhancer region and polyadenylation signal sequence region. In one embodiment, a viral genome may comprise two filler sequences, the first filler sequence may be located between the payload region and MCS region, and the second filler sequence may be located between the enhancer region and MCS region. In one embodiment, a viral genome may comprise two filler sequences, the first filler sequence may be located between the payload region and MCS region, and the second filler sequence may be located between the enhancer region and exon region. In one embodiment, a viral genome may comprise two filler sequences, the first filler sequence may be located between the payload region and MCS region, and the second filler sequence may be located between the enhancer region and 3' ITR. In one embodiment, a viral genome may comprise two filler sequences, the first filler sequence may be located between the payload region and MCS region, and the second filler sequence may be located between the polyadenylation signal sequence region and MCS region. In one embodiment, a viral genome may comprise two filler sequences, the first filler sequence may be located between the payload region and MCS region, and the second filler sequence may be located between the polyadenylation signal sequence region and exon region. In one embodiment, a viral genome may comprise two filler sequences, the first filler sequence may be located between the payload region and MCS region, and the second filler sequence may be located between the polyadenylation signal sequence region and 3' ITR. In one embodiment, a viral genome may comprise two filler sequences, the first filler sequence may be located between the payload region and MCS region, and the second filler sequence may be located between the MCS region and exon region. In one embodiment, a viral genome may comprise two filler sequences, the first filler sequence may be located between the payload region and MCS region, and the second filler sequence may be located between the MCS region and 3' ITR. In one embodiment, a viral genome may comprise two filler sequences, the first filler sequence may be located between the payload region and MCS region, and the second filler sequence may be located between the exon region and 3' ITR.

In one embodiment, a viral genome may comprise two filler sequences, the first filler sequence may be located between the payload region and exon region, and the second filler sequence may be located between the intron region and enhancer region. In one embodiment, a viral genome may comprise two filler sequences, the first filler sequence may be located between the payload region and exon region, and the second filler sequence may be located between the intron region and polyadenylation signal sequence region. In one embodiment, a viral genome may comprise two filler sequences, the first filler sequence may be located between the payload region and exon region, and the second filler sequence may be located between the intron region and MCS region. In one embodiment, a viral genome may comprise two filler sequences, the first filler sequence may be located between the payload region and exon region, and the second filler sequence may be located between the intron region and exon region. In one embodiment, a viral genome may comprise two filler sequences, the first filler sequence may be located between the payload region and exon region, and the second filler sequence may be located between the intron region and 3' ITR. In one embodiment, a viral genome may comprise two filler sequences, the first filler sequence may be located between the payload region and exon region, and the second filler sequence may be located between the enhancer region and polyadenylation signal sequence region. In one embodiment, a viral genome may comprise two filler sequences, the first filler sequence may be located between the payload region and exon region, and the second filler sequence may be located between the enhancer region and MCS region. In one embodiment, a viral genome may comprise two filler sequences, the first filler sequence may be located between the payload region and exon region, and the second filler sequence may be located between the enhancer region and exon region. In one embodiment, a viral genome may comprise two filler sequences, the first filler sequence may be located between the payload region and exon region, and the second filler sequence may be located between the enhancer region and 3' ITR. In one embodiment, a viral genome may comprise two filler sequences, the first filler sequence may be located between the payload region and exon region, and the second filler sequence may be located between the polyadenylation signal sequence region and MCS region. In one embodiment, a viral genome may comprise two filler sequences, the first filler sequence may be located between the payload region and exon region, and the second filler sequence may be located between the polyadenylation signal sequence region and exon region. In one embodiment, a viral genome may comprise two filler sequences, the first filler sequence may be located between the payload region and exon region, and the second filler sequence may be located between the polyadenylation signal sequence region and 3' ITR. In one embodiment, a viral genome may comprise two filler sequences, the first filler sequence may be located between the payload region and exon region, and the second filler sequence may be located between the MCS region and exon region. In one embodiment, a viral genome may comprise two filler sequences, the first filler sequence may be located between the payload region and exon region, and the second filler sequence may be located between the MCS region and 3' ITR. In one embodiment, a viral genome may comprise two filler sequences, the first filler sequence may be located between the payload region and exon region, and the second filler sequence may be located between the exon region and 3' ITR.

In one embodiment, a viral genome may comprise two filler sequences, the first filler sequence may be located between the payload region and 3' ITR region, and the second filler sequence may be located between the intron region and enhancer region. In one embodiment, a viral genome may comprise two filler sequences, the first filler sequence may be located between the payload region and 3' ITR region, and the second filler sequence may be located between the intron region and polyadenylation signal sequence region. In one embodiment, a viral genome may comprise two filler sequences, the first filler sequence may be located between the payload region and 3' ITR region, and the second filler sequence may be located between the intron region and MCS region. In one embodiment, a viral genome may comprise two filler sequences, the first filler sequence may be located between the payload region and 3' ITR region, and the second filler sequence may be located between the intron region and exon region. In one embodiment, a viral genome may comprise two filler sequences, the first filler sequence may be located between the payload region and 3' ITR region, and the second filler sequence may be located between the intron region and 3' ITR. In one embodiment, a viral genome may comprise two filler sequences, the first filler sequence may be located between the payload region and 3' ITR region, and the second filler sequence may be located between the enhancer region and polyadenylation signal sequence region. In one embodiment, a viral genome may comprise two filler sequences, the first filler sequence may be located between the payload region and 3' ITR region, and the second filler sequence may be located between the enhancer region and MCS region. In one embodiment, a viral genome may comprise two filler sequences, the first filler sequence may be located between the payload region and 3' ITR region, and the second filler sequence may be located between the enhancer region and exon region. In one embodiment, a viral genome may comprise two filler sequences, the first filler sequence may be located between the payload region and 3' ITR region, and the second filler sequence may be located between the enhancer region and 3' ITR. In one embodiment, a viral genome may comprise two filler sequences, the first filler sequence may be located between the payload region and 3' ITR region, and the second filler sequence may be located between the polyadenylation signal sequence region and MCS region. In one embodiment, a viral genome may comprise two filler sequences, the first filler sequence may be located between the payload region and 3' ITR region, and the second filler sequence may be located between the polyadenylation signal sequence region and exon region. In one embodiment, a viral genome may comprise two filler sequences, the first filler sequence may be located between the payload region and 3' ITR region, and the second filler sequence may be located between the polyadenylation signal sequence region and 3' ITR. In one embodiment, a viral genome may comprise two filler sequences, the first filler sequence may be located between the payload region and 3' ITR region, and the second filler sequence may be located between the MCS region and exon region. In one embodiment, a viral genome may comprise two filler sequences, the first filler sequence may be located between the payload region and 3' ITR region, and the second filler sequence may be located between the MCS region and 3' ITR. In one embodiment, a viral genome may comprise two filler sequences, the first filler sequence may be located between the payload region and 3' ITR region, and the second filler sequence may be located between the exon region and 3' ITR.

In one embodiment, a viral genome may comprise two filler sequences, the first filler sequence may be located between the intron region and enhancer region, and the second filler sequence may be located between the enhancer region and polyadenylation signal sequence region. In one embodiment, a viral genome may comprise two filler sequences, the first filler sequence may be located between the intron region and enhancer region, and the second filler sequence may be located between the enhancer region and MCS region. In one embodiment, a viral genome may comprise two filler sequences, the first filler sequence may be located between the intron region and enhancer region, and the second filler sequence may be located between the enhancer region and exon region. In one embodiment, a viral genome may comprise two filler sequences, the first filler sequence may be located between the intron region and enhancer region, and the second filler sequence may be located between the enhancer region and 3' ITR. In one embodiment, a viral genome may comprise two filler sequences, the first filler sequence may be located between the intron region and enhancer region, and the second filler sequence may be located between the polyadenylation signal sequence region and MCS region. In one embodiment, a viral genome may comprise two filler sequences, the first filler sequence may be located between the intron region and enhancer region, and the second filler sequence may be located between the polyadenylation signal sequence region and exon region. In one embodiment, a viral genome may comprise two filler sequences, the first filler sequence may be located between the intron region and enhancer region, and the second filler sequence may be located between the polyadenylation signal sequence region and 3' ITR. In one embodiment, a viral genome may comprise two filler sequences, the first filler sequence may be located between the intron region and enhancer region, and the second filler sequence may be located between the MCS region and exon region. In one embodiment, a viral genome may comprise two filler sequences, the first filler sequence may be located between the intron region and enhancer region, and the second filler sequence may be located between the MCS region and 3' ITR. In one embodiment, a viral genome may comprise two filler sequences, the first filler sequence may be located between the intron region and enhancer region, and the second filler sequence may be located between the exon region and 3' ITR.

In one embodiment, a viral genome may comprise two filler sequences, the first filler sequence may be located between the intron region and polyadenylation signal sequence region, and the second filler sequence may be located between the enhancer region and polyadenylation signal sequence region. In one embodiment, a viral genome may comprise two filler sequences, the first filler sequence may be located between the intron region and polyadenylation signal sequence region, and the second filler sequence may be located between the enhancer region and MCS region. In one embodiment, a viral genome may comprise two filler sequences, the first filler sequence may be located between the intron region and polyadenylation signal sequence region, and the second filler sequence may be located between the enhancer region and exon region. In one embodiment, a viral genome may comprise two filler sequences, the first filler sequence may be located between the intron region and polyadenylation signal sequence region, and the second filler sequence may be located between the enhancer region and 3' ITR. In one embodiment, a viral genome may comprise two filler sequences, the first filler sequence may be located between the intron region and polyadenylation signal sequence region, and the second filler sequence may be located between the polyadenylation signal sequence region and MCS region. In one embodiment, a viral genome may comprise two filler sequences, the first filler sequence may be located between the intron region and polyadenylation signal sequence region, and the second filler sequence may be located between the polyadenylation signal sequence region and exon region. In one embodiment, a viral genome may comprise two filler sequences, the first filler sequence may be located between the intron region and polyadenylation signal sequence region, and the second filler sequence may be located between the polyadenylation signal sequence region and 3' ITR. In one embodiment, a viral genome may comprise two filler sequences, the first filler sequence may be located between the intron region and polyadenylation signal sequence region, and the second filler sequence may be located between the MCS region and exon region. In one embodiment, a viral genome may comprise two filler sequences, the first filler sequence may be located between the intron region and polyadenylation signal sequence region, and the second filler sequence may be located between the MCS region and 3' ITR. In one embodiment, a viral genome may comprise two filler sequences, the first filler sequence may be located between the intron region and polyadenylation signal sequence region, and the second filler sequence may be located between the exon region and 3' ITR.

In one embodiment, a viral genome may comprise two filler sequences, the first filler sequence may be located between the intron region and MCS region, and the second filler sequence may be located between the enhancer region and polyadenylation signal sequence region. In one embodiment, a viral genome may comprise two filler sequences, the first filler sequence may be located between the intron region and MCS region, and the second filler sequence may be located between the enhancer region and MCS region. In one embodiment, a viral genome may comprise two filler sequences, the first filler sequence may be located between the intron region and MCS region, and the second filler sequence may be located between the enhancer region and exon region. In one embodiment, a viral genome may comprise two filler sequences, the first filler sequence may be located between the intron region and MCS region, and the second filler sequence may be located between the enhancer region and 3' ITR. In one embodiment, a viral genome may comprise two filler sequences, the first filler sequence may be located between the intron region and MCS region, and the second filler sequence may be located between the polyadenylation signal sequence region and MCS region. In one embodiment, a viral genome may comprise two filler sequences, the first filler sequence may be located between the intron region and MCS region, and the second filler sequence may be located between the polyadenylation signal sequence region and exon region. In one embodiment, a viral genome may comprise two filler sequences, the first filler sequence may be located between the intron region and MCS region, and the second filler sequence may be located between the polyadenylation signal sequence region and 3' ITR. In one embodiment, a viral genome may comprise two filler sequences, the first filler sequence may be located between the intron region and MCS region, and the second filler sequence may be located between the MCS region and exon region. In one embodiment, a viral genome may comprise two filler sequences, the first filler sequence may be located between the intron region and MCS region, and the second filler sequence may be located between the MCS region and 3' ITR. In one embodiment, a viral genome may comprise two filler sequences, the first filler sequence may be located between the intron region and MCS region, and the second filler sequence may be located between the exon region and 3' ITR.

In one embodiment, a viral genome may comprise two filler sequences, the first filler sequence may be located between the intron region and exon region, and the second filler sequence may be located between the enhancer region and polyadenylation signal sequence region. In one embodiment, a viral genome may comprise two filler sequences, the first filler sequence may be located between the intron region and exon region, and the second filler sequence may be located between the enhancer region and MCS region. In one embodiment, a viral genome may comprise two filler sequences, the first filler sequence may be located between the intron region and exon region, and the second filler sequence may be located between the enhancer region and exon region. In one embodiment, a viral genome may comprise two filler sequences, the first filler sequence may be located between the intron region and exon region, and the second filler sequence may be located between the enhancer region and 3' ITR. In one embodiment, a viral genome may comprise two filler sequences, the first filler sequence may be located between the intron region and exon region, and the second filler sequence may be located between the polyadenylation signal sequence region and MCS region. In one embodiment, a viral genome may comprise two filler sequences, the first filler sequence may be located between the intron region and exon region, and the second filler sequence may be located between the polyadenylation signal sequence region and exon region. In one embodiment, a viral genome may comprise two filler sequences, the first filler sequence may be located between the intron region and exon region, and the second filler sequence may be located between the polyadenylation signal sequence region and 3' ITR. In one embodiment, a viral genome may comprise two filler sequences, the first filler sequence may be located between the intron region and exon region, and the second filler sequence may be located between the MCS region and exon region. In one embodiment, a viral genome may comprise two filler sequences, the first filler sequence may be located between the intron region and exon region, and the second filler sequence may be located between the MCS region and 3' ITR. In one embodiment, a viral genome may comprise two filler sequences, the first filler sequence may be located between the intron region and exon region, and the second filler sequence may be located between the exon region and 3' ITR.

In one embodiment, a viral genome may comprise two filler sequences, the first filler sequence may be located between the intron region and 3'ITR, and the second filler sequence may be located between the enhancer region and polyadenylation signal sequence region. In one embodiment, a viral genome may comprise two filler sequences, the first filler sequence may be located between the intron region and 3'ITR, and the second filler sequence may be located between the enhancer region and MCS region. In one embodiment, a viral genome may comprise two filler sequences, the first filler sequence may be located between the intron region and 3'ITR, and the second filler sequence may be located between the enhancer region and exon region. In one embodiment, a viral genome may comprise two filler sequences, the first filler sequence may be located between the intron region and 3'ITR, and the second filler sequence may be located between the enhancer region and 3' ITR. In one embodiment, a viral genome may comprise two filler sequences, the first filler sequence may be located between the intron region and 3'ITR, and the second filler sequence may be located between the polyadenylation signal sequence region and MCS region. In one embodiment, a viral genome may comprise two filler sequences, the first filler sequence may be located between the intron region and 3'ITR, and the second filler sequence may be located between the polyadenylation signal sequence region and exon region. In one embodiment, a viral genome may comprise two filler sequences, the first filler sequence may be located between the intron region and 3'ITR, and the second filler sequence may be located between the polyadenylation signal sequence region and 3' ITR. In one embodiment, a viral genome may comprise two filler sequences, the first filler sequence may be located between the intron region and 3'ITR, and the second filler sequence may be located between the MCS region and exon region. In one embodiment, a viral genome may comprise two filler sequences, the first filler sequence may be located between the intron region and 3'ITR, and the second filler sequence may be located between the MCS region and 3' ITR. In one embodiment, a viral genome may comprise two filler sequences, the first filler sequence may be located between the intron region and 3'ITR, and the second filler sequence may be located between the exon region and 3' ITR.

In one embodiment, a viral genome may comprise two filler sequences, the first filler sequence may be located between the enhancer region and polyadenylation signal sequence region, and the second filler sequence may be located between the polyadenylation signal sequence region and MCS region. In one embodiment, a viral genome may comprise two filler sequences, the first filler sequence may be located between the enhancer region and polyadenylation signal sequence region, and the second filler sequence may be located between the polyadenylation signal sequence region and exon region. In one embodiment, a viral genome may comprise two filler sequences, the first filler sequence may be located between the enhancer region and polyadenylation signal sequence region, and the second filler sequence may be located between the polyadenylation signal sequence region and 3' ITR. In one embodiment, a viral genome may comprise two filler sequences, the first filler sequence may be located between the enhancer region and polyadenylation signal sequence region, and the second filler sequence may be located between the MCS region and exon region. In one embodiment, a viral genome may comprise two filler sequences, the first filler sequence may be located between the enhancer region and polyadenylation signal sequence region, and the second filler sequence may be located between the MCS region and 3' ITR. In one embodiment, a viral genome may comprise two filler sequences, the first filler sequence may be located between the enhancer region and polyadenylation signal sequence region, and the second filler sequence may be located between the exon region and 3' ITR.

In one embodiment, a viral genome may comprise two filler sequences, the first filler sequence may be located between the enhancer region and MCS region, and the second filler sequence may be located between the polyadenylation signal sequence region and MCS region. In one embodiment, a viral genome may comprise two filler sequences, the first filler sequence may be located between the enhancer region and MCS region, and the second filler sequence may be located between the polyadenylation signal sequence region and exon region. In one embodiment, a viral genome may comprise two filler sequences, the first filler sequence may be located between the enhancer region and MCS region, and the second filler sequence may be located between the polyadenylation signal sequence region and 3' ITR. In one embodiment, a viral genome may comprise two filler sequences, the first filler sequence may be located between the enhancer region and MCS region, and the second filler sequence may be located between the MCS region and exon region. In one embodiment, a viral genome may comprise two filler sequences, the first filler sequence may be located between the enhancer region and MCS region, and the second filler sequence may be located between the MCS region and 3' ITR. In one embodiment, a viral genome may comprise two filler sequences, the first filler sequence may be located between the enhancer region and MCS region, and the second filler sequence may be located between the exon region and 3' ITR.

In one embodiment, a viral genome may comprise two filler sequences, the first filler sequence may be located between the enhancer region and exon region, and the second filler sequence may be located between the polyadenylation signal sequence region and MCS region. In one embodiment, a viral genome may comprise two filler sequences, the first filler sequence may be located between the enhancer region and exon region, and the second filler sequence may be located between the polyadenylation signal sequence region and exon region. In one embodiment, a viral genome may comprise two filler sequences, the first filler sequence may be located between the enhancer region and exon region, and the second filler sequence may be located between the polyadenylation signal sequence region and 3' ITR. In one embodiment, a viral genome may comprise two filler sequences, the first filler sequence may be located between the enhancer region and exon region, and the second filler sequence may be located between the MCS region and exon region. In one embodiment, a viral genome may comprise two filler sequences, the first filler sequence may be located between the enhancer region and exon region, and the second filler sequence may be located between the MCS region and 3' ITR. In one embodiment, a viral genome may comprise two filler sequences, the first filler sequence may be located between the enhancer region and exon region, and the second filler sequence may be located between the exon region and 3' ITR.

In one embodiment, a viral genome may comprise two filler sequences, the first filler sequence may be located between the enhancer region and 3' ITR, and the second filler sequence may be located between the polyadenylation signal sequence region and MCS region. In one embodiment, a viral genome may comprise two filler sequences, the first filler sequence may be located between the enhancer region and 3' ITR, and the second filler sequence may be located between the polyadenylation signal sequence region and exon region. In one embodiment, a viral genome may comprise two filler sequences, the first filler sequence may be located between the enhancer region and 3' ITR, and the second filler sequence may be located between the polyadenylation signal sequence region and 3' ITR. In one embodiment, a viral genome may comprise two filler sequences, the first filler sequence may be located between the enhancer region and 3' ITR, and the second filler sequence may be located between the MCS region and exon region. In one embodiment, a viral genome may comprise two filler sequences, the first filler sequence may be located between the enhancer region and 3' ITR, and the second filler sequence may be located between the MCS region and 3' ITR. In one embodiment, a viral genome may comprise two filler sequences, the first filler sequence may be located between the enhancer region and 3' ITR, and the second filler sequence may be located between the exon region and 3' ITR.

In one embodiment, a viral genome may comprise two filler sequences, the first filler sequence may be located between the polyadenylation signal sequence region and MCS region, and the second filler sequence may be located between the MCS region and exon region. In one embodiment, a viral genome may comprise two filler sequences, the first filler sequence may be located between the polyadenylation signal sequence region and MCS region, and the second filler sequence may be located between the MCS region and 3' ITR. In one embodiment, a viral genome may comprise two filler sequences, the first filler sequence may be located between the polyadenylation signal sequence region and MCS region, and the second filler sequence may be located between the exon region and 3' ITR.

In one embodiment, a viral genome may comprise two filler sequences, the first filler sequence may be located between the polyadenylation signal sequence region and exon region, and the second filler sequence may be located between the MCS region and exon region. In one embodiment, a viral genome may comprise two filler sequences, the first filler sequence may be located between the polyadenylation signal sequence region and exon region, and the second filler sequence may be located between the MCS region and 3' ITR. In one embodiment, a viral genome may comprise two filler sequences, the first filler sequence may be located between the polyadenylation signal sequence region and exon region, and the second filler sequence may be located between the exon region and 3' ITR.

In one embodiment, a viral genome may comprise two filler sequences, the first filler sequence may be located between the polyadenylation signal sequence region and 3' ITR, and the second filler sequence may be located between the MCS region and exon region. In one embodiment, a viral genome may comprise two filler sequences, the first filler sequence may be located between the polyadenylation signal sequence region and 3' ITR, and the second filler sequence may be located between the MCS region and 3' ITR. In one embodiment, a viral genome may comprise two filler sequences, the first filler sequence may be located between the polyadenylation signal sequence region and 3' ITR, and the second filler sequence may be located between the exon region and 3' ITR.

In one embodiment, a viral genome may comprise two filler sequences, the first filler sequence may be located between the MCS region and exon region, and the second filler sequence may be located between the exon region and 3' ITR.

Payloads of the Invention

The AAV particles of the present disclosure comprise at least one payload region. As used herein, "payload" or "payload region" refers to one or more polynucleotides or polynucleotide regions encoded by or within a viral genome or an expression product of such polynucleotide or polynucleotide region, e.g., a transgene, a polynucleotide encoding a polypeptide or multi-polypeptide or a modulatory nucleic acid or regulatory nucleic acid. Payloads of the present invention typically encode modulatory polynucleotides or fragments or variants thereof.

The payload region may be constructed in such a way as to reflect a region similar to or mirroring the natural organization of an mRNA.

The payload region may comprise a combination of coding and non-coding nucleic acid sequences.

In some embodiments, the AAV payload region may encode a coding or non-coding RNA.

In one embodiment, the AAV particle comprises a viral genome with a payload region comprising nucleic acid sequences encoding a siRNA, miRNA or other RNAi agent. In such an embodiment, a viral genome encoding more than one polypeptide may be replicated and packaged into a viral particle. A target cell transduced with a viral particle may express the encoded siRNA, miRNA or other RNAi agent inside a single cell.

Modulatory Polynucleotides

In one embodiment, modulatory polynucleotides, e.g., RNA or DNA molecules, may be used to treat neurodegenerative disease, in particular, amyotrophic lateral sclerosis (ALS). As used herein, a "modulatory polynucleotide" is any nucleic acid sequence(s) which functions to modulate (either increase or decrease) the level or amount of a target gene, e.g., mRNA or protein levels.

In one embodiment, the modulatory polynucleotides may comprise at least one nucleic acid sequence encoding at least one siRNA molecule. The nucleic acids may, independently if there is more than one, encode 1, 2, 3, 4, 5, 6, 7, 8, 9, or more than 9 siRNA molecules.

In one embodiment, the molecular scaffold may be located downstream of a CMV promoter, fragment or variant thereof.

In one embodiment, the molecular scaffold may be located downstream of a CBA promoter, fragment or variant thereof.

In one embodiment, the molecular scaffold may be a natural pri-miRNA scaffold located downstream of a CMV promoter. As a non-limiting example, the natural pri-miRNA scaffold is derived from the human miR155 scaffold.

In one embodiment, the molecular scaffold may be a natural pri-miRNA scaffold located downstream of a CBA promoter.

In one embodiment, the selection of a molecular scaffold and modulatory polynucleotide is determined by a method of comparing modulatory polynucleotides in pri-miRNA (see e.g., the method described by Miniarikova et al. *Design, Characterization, and Lead Selection of Therapeutic miR-NAs Targeting Huntingtin for Development of Gene Therapy for Huntington's Disease*. Molecular Therapy-Nucleic Acids (2016) 5, e297 and International Publication No. WO2016102664; the contents of each of which are herein incorporated by reference in their entireties). To evaluate the activities of the modulatory polynucleotides, the molecular scaffold used which may be used is a human pri-miRNA scaffold (e.g., miR155 scaffold) and the promoter may be CMV. The activity may be determined in vitro using HEK293T cells and a reporter (e.g., Luciferase).

In order to evaluate the optimal molecular scaffold for the modulatory polynucleotide, the modulatory polynucleotide is used in pri-miRNA scaffolds with a CAG promoter. The constructs are co-transfected with a reporter (e.g., luciferase reporter) at 50 ng. Constructs with greater than 80% knockdown at 50 ng co-transfection are considered efficient. In one aspect, the constructs with strong guide-strand activity are preferred. The molecular scaffolds can be processed in HEK293T cells by NGS to determine guide-passenger ratios, and processing variability.

To evaluate the molecular scaffolds and modulatory polynucleotides in vivo the molecular scaffolds comprising the modulatory polynucleotides are packaged in AAV (e.g., the serotype may be AAV5 (see e.g., the method and constructs described in WO2015060722, the contents of which are herein incorporated by reference in their entirety)) and administered to an in vivo model and the guide-passenger ratios, 5' and 3' end processing, ratio of guide to passenger strands, and knockdown can be determined in different areas of the model (e.g., tissue regions).

In one embodiment, the selection of a molecular scaffold and modulatory polynucleotide is determined by a method of comparing modulatory polynucleotides in natural pri-miRNA and synthetic pri-miRNA. The modulatory polynucleotide may, but it not limited to, targeting an exon other than exon 1. To evaluate the activities of the modulatory polynucleotides, the molecular scaffold is used with a CBA promoter. In one aspect, the activity may be determined in vitro using HEK293T cells, HeLa cell and a reporter (e.g., Luciferase) and knockdown efficient modulatory polynucleotides showed SOD1 knockdown of at least 80% in the cell tested. Additionally, the modulatory polynucleotides which are considered most efficient showed low to no significant passenger strand (p-strand) activity. In another aspect, the endogenous SOD1 knockdown efficacy is evaluated by transfection in vitro using HEK293T cells, HeLa cell and a reporter. Efficient modulatory polynucleotides show greater than 50% endogenous SOD1 knockdown. In yet another aspect, the endogenous SOD1 knockdown efficacy is evaluated in different cell types (e.g., HEK293, HeLa, primary astrocytes, U251 astrocytes, SH-SY5Y neuron cells and fibroblasts from ALS patients) by infection (e.g., AAV2). Efficient modulatory polynucleotides show greater than 60% endogenous SOD1 knockdown.

To evaluate the molecular scaffolds and modulatory polynucleotides in vivo the molecular scaffolds comprising the modulatory polynucleotides are packaged in AAV and administered to an in vivo model and the guide-passenger ratios, 5' and 3' end processing, ratio of guide to passenger strands, and knockdown can be determined in different areas of the model (e.g., tissue regions). The molecular scaffolds can be processed from in vivo samples by NGS to determine guide-passenger ratios, and processing variability.

In one embodiment, the modulatory polynucleotide is designed using at least one of the following properties: loop variant, seed mismatch/bulge/wobble variant, stem mismatch, loop variant and vassal stem mismatch variant, seed mismatch and basal stem mismatch variant, stem mismatch and basal stem mismatch variant, seed wobble and basal stem wobble variant, or a stem sequence variant.

siRNA Molecules

The present invention relates to RNA interference (RNAi) induced inhibition of gene expression for treating neurodegenerative disorders. Provided herein are siRNA duplexes or encoded dsRNA that target the gene of interest (referred to herein collectively as "siRNA molecules"). Such siRNA duplexes or encoded dsRNA can reduce or silence gene expression in cells, such as but not limited to, medium spiny neurons, cortical neurons and/or astrocytes.

RNAi (also known as post-transcriptional gene silencing (PTGS), quelling, or co-suppression) is a post-transcriptional gene silencing process in which RNA molecules, in a sequence specific manner, inhibit gene expression, typically by causing the destruction of specific mRNA molecules. The active components of RNAi are short/small double stranded RNAs (dsRNAs), called small interfering RNAs (siRNAs), that typically contain 15-30 nucleotides (e.g., 19 to 25, 19 to 24 or 19-21 nucleotides) and 2 nucleotide 3' overhangs and that match the nucleic acid sequence of the target gene. These short RNA species may be naturally produced in vivo by Dicer-mediated cleavage of larger dsRNAs and they are functional in mammalian cells.

Naturally expressed small RNA molecules, named microRNAs (miRNAs), elicit gene silencing by regulating the expression of mRNAs. The miRNAs containing RNA Induced Silencing Complex (RISC) targets mRNAs presenting a perfect sequence complementarity with nucleotides 2-7 in the 5'region of the miRNA which is called the seed region, and other base pairs with its 3'region, miRNA mediated down regulation of gene expression may be caused by cleavage of the target mRNAs, translational inhibition of the target mRNAs, or mRNA decay, miRNA targeting sequences are usually located in the 3'-UTR of the target mRNAs. A single miRNA may target more than 100 transcripts from various genes, and one mRNA may be targeted by different miRNAs.

siRNA duplexes or dsRNA targeting a specific mRNA may be designed and synthesized in vitro and introduced into cells for activating RNAi processes. Elbashir et al. demonstrated that 21-nucleotide siRNA duplexes (termed small interfering RNAs) were capable of effecting potent and specific gene knockdown without inducing immune response in mammalian cells (Elbashir S M et al., Nature, 2001, 411, 494-498). Since this initial report, post-transcriptional gene silencing by siRNAs quickly emerged as a powerful tool for genetic analysis in mammalian cells and has the potential to produce novel therapeutics.

RNAi molecules which were designed to target against a nucleic acid sequence that encodes poly-glutamine repeat proteins which cause poly-glutamine expansion diseases such as Huntington's Disease, are described in U.S. Pat. Nos. 9,169,483 and 9,181,544 and International Patent Publication No. WO2015179525, the content of each of which is herein incorporated by reference in their entirety. U.S. Pat. Nos. 9,169,483 and 9,181,544 and International Patent Publication No. WO2015179525 each provide isolated RNA duplexes comprising a first strand of RNA (e.g., 15 contiguous nucleotides) and second strand of RNA (e.g., complementary to at least 12 contiguous nucleotides of the first strand) where the RNA duplex is about 15 to 30 base pairs in length. The first strand of RNA and second strand of RNA may be operably linked by an RNA loop (~4 to 50 nucleotides) to form a hairpin structure which may be inserted into an expression cassette. Non-limiting examples of loop portions include SEQ ID NO: 9-14 of U.S. Pat. No. 9,169,483, the content of which is herein incorporated by reference in its entirety. Non-limiting examples of strands of RNA which may be used, either full sequence or part of the sequence, to form RNA duplexes include SEQ ID NO: 1-8 of U.S. Pat. No. 9,169,483 and SEQ ID NO: 1-11, 33-59, 208-210, 213-215 and 218-221 of U.S. Pat. No. 9,181,544, the contents of each of which is herein incorporated by reference in its entirety. Non-limiting examples of RNAi molecules include SEQ ID NOs: 1-8 of U.S. Pat. No. 9,169,483, SEQ ID NOs: 1-11, 33-59, 208-210, 213-215 and 218-221 of U.S. Pat. No. 9,181,544 and SEQ ID NOs: 1, 6, 7, and 35-38 of International Patent Publication No. WO02015179525, the contents of each of which is herein incorporated by reference in their entirety.

In vitro synthetized siRNA molecules may be introduced into cells in order to activate RNAi. An exogenous siRNA duplex, when it is introduced into cells, similar to the endogenous dsRNAs, can be assembled to form the RNA Induced Silencing Complex (RISC), a multiunit complex that interacts with RNA sequences that are complementary to one of the two strands of the siRNA duplex (i.e., the antisense strand). During the process, the sense strand (or passenger strand) of the siRNA is lost from the complex, while the antisense strand (or guide strand) of the siRNA is matched with its complementary RNA. In particular, the targets of siRNA containing RISC complexes are mRNAs presenting a perfect sequence complementarity. Then, siRNA mediated gene silencing occurs by cleaving, releasing and degrading the target.

The siRNA duplex comprised of a sense strand homologous to the target mRNA and an antisense strand that is complementary to the target mRNA offers much more advantage in terms of efficiency for target RNA destruction compared to the use of the single strand (ss)-siRNAs (e.g. antisense strand RNA or antisense oligonucleotides). In many cases, it requires higher concentration of the ss-siRNA to achieve the effective gene silencing potency of the corresponding duplex.

Any of the foregoing molecules may be encoded by a viral genome.

Design and Sequences of siRNA Duplexes Targeting Gene of Interest

The present invention provides small interfering RNA (siRNA) duplexes (and modulatory polynucleotides encoding them) that target mRNA to interfere with gene expression and/or protein production.

The encoded siRNA duplex of the present invention contains an antisense strand and a sense strand hybridized together forming a duplex structure, wherein the antisense strand is complementary to the nucleic acid sequence of the targeted gene, and wherein the sense strand is homologous to the nucleic acid sequence of the targeted gene. In some aspects, the 5'end of the antisense strand has a 5' phosphate group and the 3'end of the sense strand contains a 3'hydroxyl group. In other aspects, there are none, one or 2 nucleotide overhangs at the 3'end of each strand.

Some guidelines for designing siRNAs have been proposed in the art. These guidelines generally recommend generating a 19-nucleotide duplexed region, symmetric 2-3 nucleotide 3'overhangs, 5'-phosphate and 3'-hydroxyl groups targeting a region in the gene to be silenced. Other rules that may govern siRNA sequence preference include, but are not limited to, (i) A/U at the 5' end of the antisense strand; (ii) G/C at the 5' end of the sense strand; (iii) at least five A/U residues in the 5' terminal one-third of the antisense strand; and (iv) the absence of any GC stretch of more than 9 nucleotides in length. In accordance with such consideration, together with the specific sequence of a target gene, highly effective siRNA molecules essential for suppressing mammalian target gene expression may be readily designed.

According to the present invention, siRNA molecules (e.g., siRNA duplexes or encoded dsRNA) that target the gene of interest are designed. Such siRNA molecules can specifically, suppress gene expression and protein production. In some aspects, the siRNA molecules are designed and used to selectively "knock out" gene variants in cells, i.e., mutated transcripts. In some aspects, the siRNA molecules are designed and used to selectively "knock down" gene variants in cells. In other aspects, the siRNA molecules are able to inhibit or suppress both the wild type and mutated version of the gene of interest.

In one embodiment, an siRNA molecule of the present invention comprises a sense strand and a complementary antisense strand in which both strands are hybridized together to form a duplex structure. The antisense strand has sufficient complementarity to the target mRNA sequence to direct target-specific RNAi, i.e., the siRNA molecule has a sequence sufficient to trigger the destruction of the target mRNA by the RNAi machinery or process.

In one embodiment, an siRNA molecule of the present invention comprises a sense strand and a complementary antisense strand in which both strands are hybridized together to form a duplex structure and where the start site of the hybridization to the mRNA is between nucleotide 10 and 1000 on the target mRNA sequence. As a non-limiting example, the start site may be between nucleotide 10-20, 20-30, 30-40, 40-50, 60-70, 70-80, 80-90, 90-100, 100-150, 150-200, 200-250, 250-300, 300-350, 350-400, 400-450, 450-500, 500-550, 550-600, 600-650, 650-700, 700-70, 750-800, 800-850, 850-900, 900-950, 950-1000, on the target mRNA sequence. As yet another non-limiting example, the start site may be nucleotide 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, and 1000 on the target mRNA sequence.

In some embodiments, the antisense strand and target mRNA sequences have 100% complementarity. The antisense strand may be complementary to any part of the target mRNA sequence.

In other embodiments, the antisense strand and target mRNA sequences comprise at least one mismatch. As a non-limiting example, the antisense strand and the target mRNA sequence have at least 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% or at least 20-30%, 20-40%, 20-50%, 20-60%, 20-70%, 20-80%, 20-90%, 20-95%, 20-99%, 30-40%, 30-50%, 30-60%, 30-70%, 30-80%, 30-90%, 30-95%, 30-99%, 40-50%, 40-60%, 40-70%, 40-80%, 40-90%, 40-95%, 40-99%, 50-60%, 50-70%, 50-80%, 50-90%, 50-95%, 50-99%, 60-70%, 60-80%, 60-90%, 60-95%, 60-99%, 70-80%, 70-90%, 70-95%, 70-99%, 80-90%, 80-95%, 80-99%, 90-95%, 90-99% or 95-99% complementarity.

In one embodiment, an siRNA or dsRNA includes at least two sequences that are complementary to each other.

According to the present invention, the siRNA molecule has a length from about 10-50 or more nucleotides, i.e., each strand comprising 10-50 nucleotides (or nucleotide analogs). Preferably, the siRNA molecule has a length from about 15-30, e.g., 15, 16, 17, 18, 19, 20, 21, 22, 23, 24, 25, 26, 27, 28, 29, or 30 nucleotides in each strand, wherein one of the strands is sufficiently complementarity to a target region. In one embodiment, each strand of the siRNA molecule has a length from about 19 to 25, 19 to 24 or 19 to 21 nucleotides. In one embodiment, at least one strand of the siRNA molecule is 19 nucleotides in length. In one embodiment, at least one strand of the siRNA molecule is 20 nucleotides in length. In one embodiment, at least one strand of the siRNA molecule is 21 nucleotides in length. In one embodiment, at least one strand of the siRNA molecule is 22 nucleotides in length. In one embodiment, at least one strand of the siRNA molecule is 23 nucleotides in length. In one embodiment, at least one strand of the siRNA molecule is 24 nucleotides in length. In one embodiment, at least one strand of the siRNA molecule is 25 nucleotides in length.

In some embodiments, the siRNA molecules of the present invention can be synthetic RNA duplexes comprising about 19 nucleotides to about 25 nucleotides, and two overhanging nucleotides at the 3'-end. In some aspects, the siRNA molecules may be unmodified RNA molecules. In other aspects, the siRNA molecules may contain at least one modified nucleotide, such as base, sugar or backbone modifications.

In one embodiment, the siRNA molecules of the present invention may comprise an antisense sequence and a sense sequence, or a fragment or variant thereof. As a non-limiting example, the antisense sequence and the sense sequence have at least 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% or at least 20-30%, 20-40%, 20-50%, 20-60%, 20-70%, 20-80%, 20-90%, 20-95%, 20-99%, 30-40%, 30-50%, 30-60%, 30-70%, 30-80%, 30-90%, 30-95%, 30-99%, 40-50%, 40-60%, 40-70%, 40-80%, 40-90%, 40-95%, 40-99%, 50-60%, 50-70%, 50-80%, 50-90%, 50-95%, 50-99%, 60-70%, 60-80%, 60-90%, 60-95%, 60-99%, 70-80%, 70-90%, 70-95%, 70-99%, 80-90%, 80-95%, 80-99%, 90-95%, 90-99% or 95-99% complementarity.

In other embodiments, the siRNA molecules of the present invention can be encoded in plasmid vectors, AAV particles, viral genome or other nucleic acid expression vectors for delivery to a cell.

DNA expression plasmids can be used to stably express the siRNA duplexes or dsRNA of the present invention in cells and achieve long-term inhibition of the target gene expression. In one aspect, the sense and antisense strands of a siRNA duplex are typically linked by a short spacer sequence leading to the expression of a stem-loop structure termed short hairpin RNA (shRNA). The hairpin is recognized and cleaved by Dicer, thus generating mature siRNA molecules.

According to the present invention, AAV particles comprising the nucleic acids encoding the siRNA molecules targeting the mRNA are produced, the AAV serotypes may be any of the serotypes listed in Table 1. Non-limiting examples of the AAV serotypes include, AAV1, AAV2, AAV3, AAV4, AAV5, AAV6, AAV7, AAV8, AAV9, AAV9.47, AAV9(hu14), AAV10, AAV11, AAV12, AAVrh8, AAVrh10, AAV-DJ8, AAV-DJ, AAV-PHP.A, AAV-PHP.B, AAVPHP.B2, AAVPHP.B3, AAVPHP.N/PHP.B-DGT, AAVPHP.B-EST, AAVPHP.B-GGT, AAVPHP.B-ATP, AAVPHP.B-ATT-T, AAVPHP.B-DGT-T, AAVPHP.B-GGT-T, AAVPHP.B-SGS, AAVPHP.B-AQP, AAVPHP.B-QQP, AAVPHP.B-SNP(3), AAVPHP.B-SNP, AAVPHP.B-QGT, AAVPHP.B-NQT, AAVPHP.B-EGS, AAVPHP.B-SGN, AAVPHP.B-EGT, AAVPHP.B-DST, AAVPHP.B-DST, AAVPHP.B-STP, AAVPHP.B-PQP, AAVPHP.B-SQP, AAVPHP.B-QLP, AAVPHP.B-TMP, AAVPHP.B-TTP, AAVPHP.S/G2A12, AAVG2A15/G2A3, AAVG2B4, AAVG2B5, and variants thereof.

In some embodiments, the siRNA duplexes or encoded dsRNA of the present invention suppress (or degrade) the target mRNA. Accordingly, the siRNA duplexes or encoded dsRNA can be used to substantially inhibit the gene expression in a cell, for example a neuron. In some aspects, the inhibition of the gene expression refers to an inhibition by at least about 20%, preferably by at least about 30%, 40%, 41%, 42%, 43%, 44%, 45%, 46%, 47%, 48%, 49%, 50%, 51%, 52%, 53%, 54%, 55%, 56%, 57%, 58%, 59%, 60%, 70%, 71%, 72%, 73%, 74%, 75%, 76%, 77%, 78%, 79%, 80%, 81%, 82%, 83%, 84%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 45-50%, 45-55%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. Accordingly, the protein product of the targeted gene may be inhibited by at least about 20%, preferably by at least about 30%, 40%, 41%, 42%, 43%, 44%, 45%, 46%, 47%, 48%, 49%, 50%, 51%, 52%, 53%, 54%, 55%, 56%, 57%, 58%, 59%, 60%, 70%, 71%, 72%, 73%, 74%, 75%, 76%, 77%, 78%, 79%, 80%, 81%, 82%, 83%, 84%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 45-50%, 45-55%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%.

In one embodiment, the siRNA duplexes or encoded dsRNA of the present invention suppress (or degrade) the target mRNA in spinal cord motor neurons. In some aspects, the inhibition of the gene expression refers to an inhibition by at least about 20%, preferably by at least about 30%, 40%, 41%, 42%, 43%, 44%, 45%, 46%, 47%, 48%, 49%, 50%, 51%, 52%, 53%, 54%, 55%, 56%, 57%, 58%, 59%, 60%, 70%, 71%, 72%, 73%, 74%, 75%, 76%, 77%, 78%, 79%, 80%, 81%, 82%, 83%, 84%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 45-50%, 45-55%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. Accordingly, the protein product of the targeted gene may be inhibited by at least about 20%, preferably by at least about 30%, 40%, 41%, 42%, 43%, 44%, 45%, 46%, 47%, 48%, 49%, 50%, 51%, 52%, 53%, 54%, 55%, 56%, 57%, 58%, 59%, 60%, 70%, 71%, 72%, 73%, 74%, 75%, 76%, 77%, 78%, 79%, 80%, 81%, 82%, 83%, 84%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 45-50%, 45-55%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%.

In one embodiment, the siRNA duplexes or encoded dsRNA of the present invention suppress (or degrade) the target mRNA in spinal cord motor neurons by 78%.

In one embodiment, the siRNA duplexes or encoded dsRNA of the present invention suppress (or degrade) the target mRNA in spinal cord motor neurons by 45-55%.

In one embodiment, the siRNA duplexes or encoded dsRNA of the present invention suppress (or degrade) the target mRNA in vg+ cells of motor neuron morphology. In some aspects, the inhibition of the gene expression refers to an inhibition by at least about 20%, preferably by at least about 30%, 40%, 41%, 42%, 43%, 44%, 45%, 46%, 47%, 48%, 49%, 50%, 51%, 52%, 53%, 54%, 55%, 56%, 57%, 58%, 59%, 60%, 70%, 71%, 72%, 73%, 74%, 75%, 76%, 77%, 78%, 79%, 80%, 81%, 82%, 83%, 84%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 45-50%, 45-55%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. Accordingly, the protein product of the targeted gene may be inhibited by at least about 20%, preferably by at least about 30%, 40%, 41%, 42%, 43%, 44%, 45%, 46%, 47%, 48%, 49%, 50%, 51%, 52%, 53%, 54%, 55%, 56%, 57%, 58%, 59%, 60%, 70%, 71%, 72%, 73%, 74%, 75%, 76%, 77%, 78%, 79%, 80%, 81%, 82%, 83%, 84%, 85% 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 45-50%, 45-55%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%.

In one embodiment, the siRNA duplexes or encoded dsRNA of the present invention suppress (or degrade) the target mRNA in vg+ cells of motor neuron morphology by 53%.

In one embodiment, the siRNA molecules comprise a miRNA seed match for the target located in the guide strand. In another embodiment, the siRNA molecules comprise a miRNA seed match for the target located in the passenger strand. In yet another embodiment, the siRNA duplexes or encoded dsRNA targeting the gene of interest do not comprise a seed match for the target located in the guide or passenger strand.

In one embodiment, the siRNA duplexes or encoded dsRNA targeting the gene of interest may have almost no significant full-length off target effects for the guide strand. In another embodiment, the siRNA duplexes or encoded dsRNA targeting the gene of interest may have almost no significant full-length off target effects for the passenger strand. The siRNA duplexes or encoded dsRNA targeting the gene of interest may have less than 1%, 2%, 3%, 4%, 5%, 6%, 7%, 8%, 9%, 10%,11%, 12%, 13%, 14%, 15%, 20%, 25%, 30%, 35%, 40%, 45%, 50%, 1-5%, 2-6%, 3-7%, 4-8%, 5-9%, 5-10%, 6-10%, 5-15%, 5-20%, 5-25% 5-30%, 10-20%, 10-30%, 10-40%, 10-50%, 15-30%, 15-40%, 15-45%, 20-40%, 20-50%, 25-50%, 30-40%, 30-50%, 35-50%, 40-50%, 45-50% full-length off target effects for the passenger strand. In yet another embodiment, the siRNA duplexes or encoded dsRNA targeting the gene of interest may have almost no significant full-length off target effects for the guide strand or the passenger strand. The siRNA duplexes or encoded dsRNA targeting the gene of interest may have less than 1%, 2%, 3%, 4%, 5%, 6%, 7%, 8%, 9%, 10%,11%, 12%, 13%, 14%, 15%, 20%, 25%, 30%, 35%, 40%, 45%, 50%, 1-5%, 2-6%, 3-7%, 4-8%, 5-9%, 5-10%, 6-10%, 5-15%, 5-20%, 5-25% 5-30%, 10-20%, 10-30%, 10-40%, 10-50%, 15-30%, 15-40%, 15-45%, 20-40%, 20-50%, 25-50%, 30-40%, 30-50%, 35-50%, 40-50%, 45-50% full-length off target effects for the guide or passenger strand.

In one embodiment, the siRNA duplexes or encoded dsRNA targeting the gene of interest may have high activity in vitro. In another embodiment, the siRNA molecules may have low activity in vitro. In yet another embodiment, the siRNA duplexes or dsRNA targeting the gene of interest may have high guide strand activity and low passenger strand activity in vitro.

In one embodiment, the siRNA molecules have a high guide strand activity and low passenger strand activity in vitro. The target knock-down (KD) by the guide strand may be at least 40%, 50%, 60%, 65%, 70%, 75%, 80%, 85%, 90%, 95%, 99%, 99.5% or 100%. The target knock-down by the guide strand may be 40-50%, 45-50%, 50-55%, 50-60%, 60-65%, 60-70%, 60-75%, 60-80%, 60-85%, 60-90%, 60-95%, 60-99%, 60-99.5%, 60-100%, 65-70%, 65-75%, 65-80%, 65-85%, 65-90%, 65-95%, 65-99%, 65-99.5%, 65-100%, 70-75%, 70-80%, 70-85%, 70-90%, 70-95%, 70-99%, 70-99.5%, 70-100%, 75-80%, 75-85%, 75-90%, 75-95%, 75-99%, 75-99.5%, 75-100%, 80-85%, 80-90%, 80-95%, 80-99%, 80-99.5%, 80-100%, 85-90%, 85-95%, 85-99%, 85-99.5%, 85-100%, 90-95%, 90-99%, 90-99.5%, 90-100%, 95-99%, 95-99.5%, 95-100%, 99-99.5%, 99-100% or 99.5-100%. As a non-limiting example, the target knock-down (KD) by the guide strand is greater than 70%. As a non-limiting example, the target knock-down (KD) by the guide strand is greater than 60%.

In one embodiment, the siRNA duplex is designed so there is no miRNA seed match for the sense or antisense sequence to the non-gene of interest sequence.

In one embodiment, the $IC_{50}$ of the guide strand for the nearest off target is greater than 100 multiplied by the $IC_{50}$ of the guide strand for the on-target gene. As a non-limiting example, if the $IC_{50}$ of the guide strand for the nearest off target is greater than 100 multiplied by the $IC_{50}$ of the guide strand for the target then the siRNA molecule is said to have high guide strand selectivity for inhibiting the gene of interest in vitro.

In one embodiment, the 5' processing of the guide strand has a correct start (n) at the 5' end at least 75%, 80%, 85%, 90%, 95%, 99% or 100% of the time in vitro or in vivo. As a non-limiting example, the 5' processing of the guide strand is precise and has a correct start (n) at the 5' end at least 99% of the time in vitro. As a non-limiting example, the 5' processing of the guide strand is precise and has a correct start (n) at the 5' end at least 99% of the time in vivo. As a non-limiting example, the 5' processing of the guide strand is precise and has a correct start (n) at the 5' end at least 90% of the time in vitro. As a non-limiting example, the 5' processing of the guide strand is precise and has a correct start (n) at the 5' end at least 90% of the time in vivo. As a non-limiting example, the 5' processing of the guide strand is precise and has a correct start (n) at the 5' end at least 85% of the time in vitro. As a non-limiting example, the 5' processing of the guide strand is precise and has a correct start (n) at the 5' end at least 85% of the time in vivo.

In one embodiment, the guide to passenger (G:P) (also referred to as the antisense to sense) strand ratio expressed is 1:10, 1:9, 1:8, 1:7, 1:6, 1:5, 1:4, 1:3, 1:2, 1:1, 2:10, 2:9, 2:8, 2:7, 2:6, 2:5, 2:4, 2:3, 2:2, 2:1, 3:10, 3:9, 3:8, 3:7, 3:6, 3:5, 3:4, 3:3, 3:2, 3:1, 4:10, 4:9, 4:8, 4:7, 4:6, 4:5, 4:4, 4:3, 4:2, 4:1, 5:10, 5:9, 5:8, 5:7, 5:6, 5:5, 5:4, 5:3, 5:2, 5:1, 6:10, 6:9, 6:8, 6:7, 6:6, 6:5, 6:4, 6:3, 6:2, 6:1, 7:10, 7:9, 7:8, 7:7, 7:6, 7:5, 7:4, 7:3, 7:2, 7:1, 8:10, 8:9, 8:8, 8:7, 8:6, 8:5, 8:4, 8:3, 8:2, 8:1, 9:10, 9:9, 9:8, 9:7, 9:6, 9:5, 9:4, 9:3, 9:2, 9:1, 10:10, 10:9, 10:8, 10:7, 10:6, 10:5, 10:4, 10:3, 10:2, 10:1, 1:99, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, or 99:1 in vitro or in vivo. The guide to passenger ratio refers to the ratio of the guide strands to the passenger strands after intracellular processing of the pri-microRNA. For example, a 80:20 guide-to-passenger ratio would have 8 guide strands to every 2 passenger strands processed from the precursor. As a non-limiting example, the guide-to-passenger strand ratio is 8:2 in vitro. As a non-limiting example, the guide-to-passenger strand ratio is 8:2 in vivo. As a non-limiting example, the guide-to-passenger strand ratio is 9:1 in vitro. As a non-limiting example, the guide-to-passenger strand ratio is 9:1 in vivo.

In one embodiment, the guide to passenger (G:P) strand ratio is in a range of 1-99, 1,3-99, 5-99, 10-99, 15-99, 20-99, 25-99, 30-99, 35-99, 40-99, 45-99, 50-99, 55-99, 60-99, 65-99, 70-99, 75-99, 80-99, 85-99, 90-99, 95-99, 1-10, 1-15, 1-20, 1-25, 1-30, 1-35, 1-40, 1-45, 1-50, 1-55, 1-60, 1-65, 1-70, 1-75, 1-80, 1-85, 1-90, 1-95, 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 10-15, 10-20, 10-25, 10-30, 10-35, 10-40, 10-45, 10-50, 10-55, 10-60, 10-65, 10-70, 10-75, 10-80, 10-85, 10-90, 10-95, 15-20, 15-25, 15-30, 15-35, 15-40, 15-45, 15-50, 15-55, 15-60, 15-65, 15-70, 15-75, 15-80, 15-85, 15-90, 15-95, 20-25, 20-30, 20-35, 20-40, 20-45, 20-50, 20-55, 20-60, 20-65, 20-70, 20-75, 20-80, 20-85, 20-90, 20-95, 25-30, 25-35, 25-40, 25-45, 25-50, 25-55, 25-60, 25-65, 25-70, 25-75, 25-80, 25-85, 25-90, 25-95, 30-35, 30-40, 30-45, 30-50, 30-55, 30-60, 30-65, 30-70, 30-75, 30-80, 30-85, 30-90, 30-95, 35-40, 35-45, 35-50, 35-55, 35-60, 35-65, 35-70, 35-75, 35-80, 35-85, 35-90, 35-95, 40-45, 40-50, 40-55, 40-60, 40-65, 40-70, 40-75, 40-80, 40-85, 40-90, 40-95, 45-50, 45-55, 45-60, 45-65, 45-70, 45-75, 45-80, 45-85, 45-90, 45-95, 50-55, 50-60, 50-65, 50-70, 50-75, 50-80, 50-85, 50-90, 50-95, 55-60, 55-65, 55-70, 55-75, 55-80, 55-85, 55-90, 55-95, 60-65, 60-70, 60-75, 60-80, 60-85, 60-90, 60-95, 65-70, 65-75, 65-80, 65-85, 65-90, 65-95, 70-75, 70-80, 70-85, 70-90, 70-95, 75-80, 75-85, 75-90, 75-95, 80-85, 80-90, 80-95, 85-90, 85-95, or 90-95. As a non-limiting example, the guide to passenger ratio is a range of 1.3 to 99. As a non-limiting example, the guide to passenger ratio is a range of 10 to 99.

In one embodiment, the guide to passenger (G:P) strand ratio is 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, 50, 50.5, 51, 51.5, 52, 52.5, 53, 53.5, 54, 54.5, 55, 55.5, 56, 56.5, 57, 57.5, 58, 58.5, 59, 59.5, 60, 60.5, 61, 61.5, 62, 62.5, 63, 63.5, 64, 64.5, 65, 65.5, 66, 66.5, 67, 67.5, 68, 68.5, 69, 69.5, 70, 70.5, 71, 71.5, 72, 72.5, 73, 73.5, 74, 74.5, 75, 75.5, 76, 76.5, 77, 77.5, 78, 78.5, 79, 79.5, 80, 80.5, 81, 81.5, 82, 82.5, 83, 83.5, 84, 84.5, 85, 85.5, 86, 86.5, 87, 87.5, 88, 88.5, 89, 89.5, 90, 90.5, 91, 91.5, 92, 92.5, 93, 93.5, 94, 94.5, 95, 95.5, 96, 96.5, 97, 97.5, 98, 98.5, or 99. As a non-limiting example, the guide to passenger (G:P) strand ratio is 11.5. As a non-limiting example, the guide to passenger (G:P) strand ratio is 99.

In one embodiment, the guide to passenger (G:P) (also referred to as the antisense to sense) strand ratio expressed is greater than 1.

In one embodiment, the guide to passenger (G:P) (also referred to as the antisense to sense) strand ratio expressed is greater than 2.

In one embodiment, the guide to passenger (G:P) (also referred to as the antisense to sense) strand ratio expressed is greater than 5.

In one embodiment, the guide to passenger (G:P) (also referred to as the antisense to sense) strand ratio expressed is greater than 10.

In one embodiment, the guide to passenger (G:P) (also referred to as the antisense to sense) strand ratio expressed is greater than 20.

In one embodiment, the guide to passenger (G:P) (also referred to as the antisense to sense) strand ratio expressed is greater than 50.

In one embodiment, the guide to passenger (G:P) (also referred to as the antisense to sense) strand ratio expressed is at least 3:1.

In one embodiment, the guide to passenger (G:P) (also referred to as the antisense to sense) strand ratio expressed is at least 5:1.

In one embodiment, the guide to passenger (G:P) (also referred to as the antisense to sense) strand ratio expressed is at least 10:1.

1 In one embodiment, the guide to passenger (G:P) (also referred to as the antisense to sense) strand ratio expressed is at least 20:1.

In one embodiment, the guide to passenger (G:P) (also referred to as the antisense to sense) strand ratio expressed is at least 50:1.

In one embodiment, the passenger to guide (P:G) (also referred to as the sense to antisense) strand ratio expressed is 1:10, 1:9, 1:8, 1:7, 1:6, 1:5, 1:4, 1:3, 1:2, 1:1, 2:10, 2:9, 2:8, 2:7, 2:6, 2:5, 2:4, 2:3, 2:2, 2:1, 3:10, 3:9, 3:8, 3:7, 3:6, 3:5, 3:4, 3:3, 3:2, 3:1, 4:10, 4:9, 4:8, 4:7, 4:6, 4:5, 4:4, 4:3, 4:2, 4:1, 5:10, 5:9, 5:8, 5:7, 5:6, 5:5, 5:4, 5:3, 5:2, 5:1, 6:10, 6:9, 6:8, 6:7, 6:6, 6:5, 6:4, 6:3, 6:2, 6:1, 7:10, 7:9, 7:8, 7:7, 7:6, 7:5, 7:4, 7:3, 7:2, 7:1, 8:10, 8:9, 8:8, 8:7, 8:6, 8:5, 8:4, 8:3, 8:2, 8:1, 9:10, 9:9, 9:8, 9:7, 9:6, 9:5, 9:4, 9:3, 9:2, 9:1, 10:10, 10:9, 10:8, 10:7, 10:6, 10:5, 10:4, 10:3, 10:2, 10:1, 1:99, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, or 99:1 in vitro or in vivo. The passenger to guide ratio refers to the ratio of the passenger strands to the guide strands after the intracellular processing of the pri-microRNA. For example, a 80:20 of passenger-to-guide ratio would have 8 passenger strands to every 2 guide strands processed from the precursor. As a non-limiting example, the passenger-to-guide strand ratio is 80:20 in vitro. As a non-limiting example, the passenger-to-guide strand ratio is 80:20 in vivo. As a non-limiting example, the passenger-to-guide strand ratio is 8:2 in vitro. As a non-limiting example, the passenger-to-guide strand ratio is 8:2 in vivo. As a non-limiting example, the passenger-to-guide strand ratio is 9:1 in vitro. As a non-limiting example, the passenger-to-guide strand ratio is 9:1 in vivo.

In one embodiment, the passenger to guide (P:G) strand ratio is in a range of 1-99, 1.3-99, 5-99, 10-99, 15-99, 20-99, 25-99, 30-99, 35-99, 40-99, 45-99, 50-99, 55-99, 60-99, 65-99, 70-99, 75-99, 80-99, 85-99, 90-99, 95-99, 1-10, 1-15, 1-20, 1-25, 1-30, 1-35, 1-40, 1-45, 1-50, 1-55, 1-60, 1-65, 1-70, 1-75, 1-80, 1-85, 1-90, 1-95, 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 10-15, 10-20, 10-25, 10-30, 10-35, 10-40, 10-45, 10-50, 10-55, 10-60, 10-65, 10-70, 10-75, 10-80, 10-85, 10-90, 10-95, 15-20, 15-25, 15-30, 15-35, 15-40, 15-45, 15-50, 15-55, 15-60, 15-65, 15-70, 15-75, 15-80, 15-85, 15-90, 15-95, 20-25, 20-30, 20-35, 20-40, 20-45, 20-50, 20-55, 20-60, 20-65, 20-70, 20-75, 20-80, 20-85, 20-90, 20-95, 25-30, 25-35, 25-40, 25-45, 25-50, 25-55, 25-60, 25-65, 25-70, 25-75, 25-80, 25-85, 25-90, 25-95, 30-35, 30-40, 30-45, 30-50, 30-55, 30-60, 30-65, 30-70, 30-75, 30-80, 30-85, 30-90, 30-95, 35-40, 35-45, 35-50, 35-55, 35-60, 35-65, 35-70, 35-75, 35-80, 35-85, 35-90, 35-95, 40-45, 40-50, 40-55, 40-60, 40-65, 40-70, 40-75, 40-80, 40-85, 40-90, 40-95, 45-50, 45-55, 45-60, 45-65, 45-70, 45-75, 45-80, 45-85, 45-90, 45-95, 50-55, 50-60, 50-65, 50-70, 50-75, 50-80, 50-85, 50-90, 50-95, 55-60, 55-65, 55-70, 55-75, 55-80, 55-85, 55-90, 55-95, 60-65, 60-70, 60-75, 60-80, 60-85, 60-90, 60-95, 65-70, 65-75, 65-80, 65-85, 65-90, 65-95, 70-75, 70-80, 70-85, 70-90, 70-95, 75-80, 75-85, 75-90, 75-95, 80-85, 80-90, 80-95, 85-90, 85-95, or 90-95.

In one embodiment, the passenger to guide (P:G) strand ratio is 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, 50, 50.5, 51, 51.5, 52, 52.5, 53, 53.5, 54, 54.5, 55, 55.5, 56, 56.5, 57, 57.5, 58, 58.5, 59, 59.5, 60, 60.5, 61, 61.5, 62, 62.5, 63, 63.5, 64, 64.5, 65, 65.5, 66, 66.5, 67, 67.5, 68, 68.5, 69, 69.5, 70, 70.5, 71, 71.5, 72, 72.5, 73, 73.5, 74, 74.5, 75, 75.5, 76, 76.5, 77, 77.5, 78, 78.5, 79, 79.5, 80, 80.5, 81, 81.5, 82, 82.5, 83, 83.5, 84, 84.5, 85, 85.5, 86, 86.5, 87, 87.5, 88, 88.5, 89, 89.5, 90, 90.5, 91, 91.5, 92, 92.5, 93, 93.5, 94, 94.5, 95, 95.5, 96, 96.5, 97, 97.5, 98, 98.5, or 99.

In one embodiment, the passenger to guide (P:G) (also referred to as the sense to antisense) strand ratio expressed is greater than 1.

In one embodiment, the passenger to guide (P:G) (also referred to as the sense to antisense) strand ratio expressed is greater than 2.

In one embodiment, the passenger to guide (P:G) (also referred to as the sense to antisense) strand ratio expressed is greater than 5.

In one embodiment, the passenger to guide (P:G) (also referred to as the sense to antisense) strand ratio expressed is greater than 10.

In one embodiment, the passenger to guide (P:G) (also referred to as the sense to antisense) strand ratio expressed is greater than 20.

In one embodiment, the passenger to guide (P:G) (also referred to as the sense to antisense) strand ratio expressed is greater than 50.

In one embodiment, the passenger to guide (P:G) (also referred to as the sense to antisense) strand ratio expressed is at least 3:1.

In one embodiment, the passenger to guide (P:G) (also referred to as the sense to antisense) strand ratio expressed is at least 5:1.

In one embodiment, the passenger to guide (P:G) (also referred to as the sense to antisense) strand ratio expressed is at least 10:1.

In one embodiment, the passenger to guide (P:G) (also referred to as the sense to antisense) strand ratio expressed is at least 20:1.

In one embodiment, the passenger to guide (P:G) (also referred to as the sense to antisense) strand ratio expressed is at least 50:1.

In one embodiment, a passenger-guide strand duplex is considered effective when the pri- or pre-microRNAs demonstrate, but methods known in the art and described herein, greater than 2-fold guide to passenger strand ratio when processing is measured. As a non-limiting examples, the pri- or pre-microRNAs demonstrate great than 2-fold, 3-fold, 4-fold, 5-fold, 6-fold, 7-fold, 8-fold, 9-fold, 10-fold, 11-fold, 12-fold, 13-fold, 14-fold, 15-fold, or 2 to 5-fold, 2 to 10-fold, 2 to 15-fold, 3 to 5-fold, 3 to 10-fold, 3 to 15-fold, 4 to 5-fold, 4 to 10-fold, 4 to 15-fold, 5 to 10-fold, 5 to 15-fold, 6 to 10-fold, 6 to 15-fold, 7 to 10-fold, 7 to 15-fold, 8 to 10-fold, 8 to 15-fold, 9 to 10-fold, 9 to 15-fold, 10 to 15-fold, 11 to 15-fold, 12 to 15-fold, 13 to 15-fold, or 14 to 15-fold guide to passenger strand ratio when processing is measured.

In one embodiment, the vector genome encoding the dsRNA comprises a sequence which is at least 60%, 65%, 70%, 75%, 80%, 85%, 90%, 95%, 99% or more than 99% of the full length of the construct. As a non-limiting example, the vector genome comprises a sequence which is at least 80% of the full length sequence of the construct.

In one embodiment, the siRNA molecules may be used to silence wild type or mutant version of the gene of interest by targeting at least one exon on the gene of interest sequence. The exon may be exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, exon 19, exon 20, exon 21, exon 22, exon 23, exon 24, exon 25, exon 26, exon 27, exon 28, exon 29, exon 30, exon 31, exon 32, exon 33, exon 34, exon 35, exon 36, exon 37, exon 38, exon 39, exon 40, exon 41, exon 42, exon 43, exon 44, exon 45, exon 46, exon 47, exon 48, exon 49, exon 50, exon 51, exon 52, exon 53, exon 54, exon 55, exon 56, exon 57, exon 58, exon 59, exon 60, exon 61, exon 62, exon 63, exon 64, exon 65, exon 66, and/or exon 67.

Design and Sequences of siRNA Duplexes Targeting SOD1 Gene

The present invention provides small interfering RNA (siRNA) duplexes (and modulatory polynucleotides encoding them) that target SOD1 mRNA to interfere with SOD1 gene expression and/or SOD1 protein production.

The encoded siRNA duplex of the present invention contains an antisense strand and a sense strand hybridized together forming a duplex structure, wherein the antisense strand is complementary to the nucleic acid sequence of the targeted SOD1 gene, and wherein the sense strand is homologous to the nucleic acid sequence of the targeted SOD1 gene. In some aspects, the 5'end of the antisense strand has a 5' phosphate group and the 3'end of the sense strand contains a 3'hydroxyl group. In other aspects, there are none, one or 2 nucleotide overhangs at the 3'end of each strand.

Some guidelines for designing siRNAs have been proposed in the art. These guidelines generally recommend generating a 19-nucleotide duplexed region, symmetric 2-3 nucleotide 3'overhangs, 5'-phosphate and 3'-hydroxyl groups targeting a region in the gene to be silenced. Other rules that may govern siRNA sequence preference include, but are not limited to, (i) A/U at the 5' end of the antisense strand; (ii) G/C at the 5' end of the sense strand; (iii) at least five A/U residues in the 5' terminal one-third of the antisense strand; and (iv) the absence of any GC stretch of more than 9 nucleotides in length. In accordance with such consideration, together with the specific sequence of a target gene, highly effective siRNA molecules essential for suppressing the SOD1 gene expression may be readily designed.

According to the present invention, siRNA molecules (e.g., siRNA duplexes or encoded dsRNA) that target the SOD1 gene are designed. Such siRNA molecules can specifically, suppress SOD1 gene expression and protein production. In some aspects, the siRNA molecules are designed and used to selectively "knock out" SOD1 gene variants in cells. i.e., mutated SOD1 transcripts that are identified in patients with ALS disease. In some aspects, the siRNA molecules are designed and used to selectively "knock down" SOD1 gene variants in cells. In other aspects, the siRNA molecules are able to inhibit or suppress both the wild type and mutated SOD1 gene.

In one embodiment, an siRNA molecule of the present invention comprises a sense strand and a complementary antisense strand in which both strands are hybridized together to form a duplex structure. The antisense strand has sufficient complementarity to the SOD1 mRNA sequence to direct target-specific RNAi, i.e., the siRNA molecule has a sequence sufficient to trigger the destruction of the target mRNA by the RNAi machinery or process.

In one embodiment, an siRNA molecule of the present invention comprises a sense strand and a complementary antisense strand in which both strands are hybridized together to form a duplex structure and where the start site of the hybridization to the SOD1 mRNA is between nucleotide 15 and 1000 on the SOD1 mRNA sequence. As a non-limiting example, the start site may be between nucleotide 15-25, 15-50, 15-75, 15-100, 100-150, 150-200, 200-250, 250-300, 300-350, 350-400, 400-450, 450-500, 500-550, 550-600, 600-650, 650-700, 700-70, 750-800, 800-850, 850-900, 900-950, and 950-1000 on the SOD1 mRNA sequence. As yet another non-limiting example, the start site may be nucleotide 26, 27, 28, 29, 30, 32, 33, 34, 35, 36, 37, 74, 76, 77, 78, 149, 153, 157, 160, 177, 192, 193, 195, 196, 197, 198, 199, 206, 209, 210, 239, 241, 261, 263, 264, 268, 269, 276, 278, 281, 284, 290, 291, 295, 296, 316, 317, 329, 330, 337, 350, 351, 352, 354, 357, 358, 364, 375, 378, 383, 384, 390, 392, 395, 404, 406, 417, 418, 469, 470, 475, 476, 480, 487, 494, 496, 497, 501, 504, 515, 518, 522, 523, 524, 552, 554, 555, 562, 576, 577, 578, 579, 581, 583, 584, 585, 587, 588, 589, 593, 594, 595, 596, 597, 598, 599, 602, 607, 608, 609, 610, 611, 612, 613, 616, 621, 633, 635, 636, 639, 640, 641, 642, 643, 644, 645, 654, 660, 661, 666, 667, 668, 669, 673, 677, 692, 698, 699, 700, 701, 706, 749, 770, 772, 775, 781, 800, 804, 819, 829, 832, 833, 851, 854, 855, 857, 858, 859, 861, 869, 891, 892, 906, 907, 912, 913, 934, 944, and 947 on the SOD1 mRNA sequence.

In some embodiments, the antisense strand and target SOD1 mRNA sequences have 100% complementarity. The antisense strand may be complementary to any part of the target SOD1 mRNA sequence.

In other embodiments, the antisense strand and target SOD1 mRNA sequences comprise at least one mismatch. As a non-limiting example, the antisense strand and the target SOD1 mRNA sequence have at least 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% or at least 20-30%, 20-40%, 20-50%, 20-60%, 20-70%, 20-80%, 20-90%, 20-95%, 20-99%, 30-40%, 30-50%, 30-60%, 30-70%, 30-80%, 30-90%, 30-95%, 30-99%, 40-50%, 40-60%, 40-70%, 40-80%, 40-90%, 40-95%, 40-99%, 50-60%, 50-70%, 50-80%, 50-90%, 50-95%, 50-99%, 60-70%, 60-80%, 60-90%, 60-95%, 60-99%, 70-80%, 70-90%, 70-95%, 70-99%, 80-90%, 80-95%, 80-99%, 90-95%, 90-99% or 95-99% complementarity.

In one embodiment, an siRNA or dsRNA targeting SOD1 includes at least two sequences that are complementary to each other.

According to the present invention, the siRNA molecule targeting SOD1 has a length from about 10-50 or more nucleotides, i.e., each strand comprising 10-50 nucleotides (or nucleotide analogs). Preferably, the siRNA molecule has a length from about 15-30, e.g., 15, 16, 17, 18, 19, 20, 21, 22, 23, 24, 25, 26, 27, 28, 29, or 30 nucleotides in each strand, wherein one of the strands is sufficiently complementarity to a target region. In one embodiment, each strand of the siRNA molecule has a length from about 19 to 25, 19 to 24 or 19 to 21 nucleotides. In one embodiment, at least one strand of the siRNA molecule is 19 nucleotides in length. In one embodiment, at least one strand of the siRNA molecule is 20 nucleotides in length. In one embodiment, at least one strand of the siRNA molecule is 21 nucleotides in length. In one embodiment, at least one strand of the siRNA molecule is 22 nucleotides in length. In one embodiment, at least one strand of the siRNA molecule is 23 nucleotides in length. In one embodiment, at least one strand of the siRNA molecule is 24 nucleotides in length. In one embodiment, at least one strand of the siRNA molecule is 25 nucleotides in length.

In some embodiments, the siRNA molecules of the present invention targeting SOD1 can be synthetic RNA duplexes comprising about 19 nucleotides to about 25 nucleotides, and two overhanging nucleotides at the 3'-end. In some aspects, the siRNA molecules may be unmodified RNA molecules. In other aspects, the siRNA molecules may contain at least one modified nucleotide, such as base, sugar or backbone modifications.

In one embodiment, the siRNA molecules of the present invention targeting SOD1 may comprise a nucleotide sequence such as, but not limited to, the antisense (guide) sequences in Table 2 or a fragment or variant thereof. As a non-limiting example, the antisense sequence used in the siRNA molecule of the present invention is at least 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% or at least 20-30%, 20-40%, 20-50%, 20-60%, 20-70%, 20-80%, 20-90%, 20-95%, 20-99%, 30-40%, 30-50%, 30-60%, 30-70%, 30-80%, 30-90%, 30-95%, 30-99%, 40-50%, 40-60%, 40-70%, 40-80%, 40-90%, 40-95%, 40-99%, 50-60%, 50-70%, 50-80%, 50-90%, 50-95%, 50-99%, 60-70%, 60-80%, 60-90%, 60-95%, 60-99%, 70-80%, 70-90%, 70-95%, 70-99%, 80-90%, 80-95%, 80-99%, 90-95%, 90-99% or 95-99% of a nucleotide sequence in Table 2. As another non-limiting example, the antisense sequence used in the siRNA molecule of the present invention comprises at least 3, 4, 5, 6, 7, 8, 9, 10, 11, 12, 13, 14, 15, 16, 17, 18, 19, 20, 21 or more than 21 consecutive nucleotides of a nucleotide sequence in Table 2. As yet another non-limiting example, the antisense sequence used in the siRNA molecule of the present invention comprises nucleotides 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 2 to 22, 2 to 21, 2 to 20, 2 to 19, 2 to 18, 2 to 17, 2 to 16, 2 to 15, 2 to 14, 2 to 13, 2 to 12, 2 to 11, 2 to 10, 2 to 9, 2 to 8, 3 to 22, 3 to 21, 3 to 20, 3 to 19, 3 to 18, 3 to 17, 3 to 16, 3 to 15, 3 to 14, 3 to 13, 3 to 12, 3 to 11, 3 to 10, 3 to 9, 3 to 8, 4 to 22, 4 to 21, 4 to 20, 4 to 19, 4 to 18, 4 to 17, 4 to 16, 4 to 15, 4 to 14, 4 to 13, 4 to 12, 4 to 11, 4 to 10, 4 to 9, 4 to 8, 5 to 22, 5 to 21, 5 to 20, 5 to 19, 5 to 18, 5 to 17, 5 to 16, 5 to 15, 5 to 14, 5 to 13, 5 to 12, 5 to 1, 5 to 10, 5 to 9, 5 to 8, 6 to 22, 6 to 21, 6 to 20, 6 to 19, 6 to 18, 6 to 17, 6 to 16, 6 to 15, 6 to 14, 6 to 13, 6 to 12, 6 to 11, 6 to 10, 7 to 22, 7 to 21, 7 to 20, 7 to 19, 7 to 18, 7 to 17, 7 to 16, 7 to 15, 7 to 14, 7 to 13, 7 to 12, 8 to 22, 8 to 21, 8 to 20, 8 to 19, 8 to 18, 8 to 17, 8 to 16, 8 to 15, 8 to 14, 8 to 13, 8 to 12, 9 to 22, 9 to 21, 9 to 20, 9 to 19, 9 to 18, 9 to 17, 9 to 16, 9 to 15, 9 to 14, 10 to 22, 10 to 21, 10 to 20, 10 to 19, 10 to 18, 10 to 17, 10 to 16, 10 to 15, 10 to 14, 11 to 22, 11 to 21, 11 to 20, 11 to 19, 11 to 18, 11 to 17, 11 to 16, 11 to 15, 11 to 14, 12 to 22, 12 to 21, 12 to 20, 12 to 19, 12 wt 18, 12 to 17, 12 to 16, 13 to 22, 13 to 21, 13 to 20, 13 to 19, 13 to 18, 13 to 17, 13 to 16, 14 to 22, 14 to 21, 14 to 20, 14 to 19, 14 to 18, 14 to 17, 15 to 22, 15 to 21, 15 to 20, 15 to 19, 15 to 18, 16 to 22, 16 to 21, 16 to 20, 17 to 22, 17 to 21, or 18 to 22 of the sequences in Table 2.

TABLE 2

Antisense Sequences

| Antisense ID | Sequence | SEQ ID NO |
|---|---|---|
| A-3000 | UUUAUAGGCCAGACCUCCGdTdT | 916 |
| A-3001 | UUUUAUAGGCCAGACCUCCdTdT | 917 |
| A-3002 | UCUUUAUAGGCCAGACCUCdTdT | 918 |
| A-3003 | UACUUUAUAGGCCAGACCUdTdT | 919 |
| A-3004 | UUACUUUAUAGGCCAGACCdTdT | 920 |
| A-3005 | UACUACUUUAUAGGCCAGAdTdT | 921 |
| A-3006 | UGACUACUUUAUAGGCCAGdTdT | 922 |
| A-3007 | UCGACUACUUUAUAGGCCAdTdT | 923 |
| A-3008 | UGCGACUACUUUAUAGGCCdTdT | 924 |
| A-3009 | UCGCGACUACUUUAUAGGCdTdT | 925 |
| A-3010 | UCCGCGACUACUUUAUAGGdTdT | 926 |
| A-3011 | UGCUGCAGGAGACUACGACdTdT | 927 |
| A-3012 | UACGCUGCAGGAGACUACGdTdT | 928 |
| A-3013 | UGACGCUGCAGGAGACUACdTdT | 929 |
| A-3014 | UAGACGCUGCAGGAGACUAdTdT | 930 |
| A-3015 | UCACGGCCUUCGUCGCCAUdTdT | 931 |
| A-3016 | UCGCACACGGCCUUCGUCGdTdT | 932 |
| A-3017 | UAGCACGCACACGGCCUUCdTdT | 933 |
| A-3018 | UUUCAGCACGCACACGGCCdTdT | 934 |
| A-3019 | UGCACUGGGCCGUCGCCCUdTdT | 935 |
| A-3020 | UAAUUGAUGAUGCCCUGCAdTdT | 936 |
| A-3021 | UAAAUUGAUGAUGCCCUGCdTdT | 937 |
| A-3022 | UCGAAAUUGAUGAUGCCCUdTdT | 938 |
| A-3023 | UUCGAAAUUGAUGAUGCCCdTdT | 939 |
| A-3024 | UCUCGAAAUUGAUGAUGCCdTdT | 940 |
| A-3025 | UGCUCGAAAUUGAUGAUGCdTdT | 941 |
| A-3026 | UUGCUCGAAAUUGAUGAUGdTdT | 942 |
| A-3027 | UUUCCUUCUGCUCGAAAUUdTdT | 943 |
| A-3028 | UACUUUCCUUCUGCUCGAAdTdT | 944 |
| A-3029 | UUACUUUCCUUCUGCUCGAdTdT | 945 |
| A-3030 | UAAUGCUUCCCCACACCUUdTdT | 946 |
| A-3031 | UUUAAUGCUUCCCCACACCdTdT | 947 |
| A-3032 | UGCAGGCCUUCAGUCAGUCdTdT | 948 |
| A-3033 | UAUGCAGGCCUUCAGUCAGdTdT | 949 |
| A-3034 | UCAUGCAGGCCUUCAGUCAdTdT | 950 |
| A-3035 | UAAUCCAUGCAGGCCUUCAdTdT | 951 |
| A-3036 | UGAAUCCAUGCAGGCCUUCdTdT | 952 |
| A-3037 | UGAACAUGGAAUCCAUGCAdTdT | 953 |
| A-3038 | UAUGAACAUGGAAUCCAUGdTdT | 954 |
| A-3039 | UCUCAUGAACAUGGAAUCCdTdT | 955 |
| A-3040 | UAAACUCAUGAACAUGGAAdTdT | 956 |
| A-3041 | UAUCUCCAAACUCAUGAACdTdT | 957 |
| A-3042 | UUAUCUCCAAACUCAUGAAdTdT | 958 |
| A-3043 | UGUAUUAUCUCCAAACUCAdTdT | 959 |
| A-3044 | UUGUAUUAUCUCCAAACUCdTdT | 960 |
| A-3045 | UCCUGCACUGGUACAGCCUdTdT | 961 |
| A-3046 | UACCUGCACUGGUACAGCCdTdT | 962 |
| A-3047 | UAUUAAAGUGAGGACCUGCdTdT | 963 |
| A-3048 | UGAUUAAAGUGAGGACCUGdTdT | 964 |
| A-3049 | UGAUAGAGGAUUAAAGUGAdTdT | 965 |
| A-3050 | UACCGUGUUUUCUGGAUAGdTdT | 966 |
| A-3051 | UCACCGUGUUUUCUGGAUAdTdT | 967 |
| A-3052 | UCCACCGUGUUUUCUGGAUdTdT | 968 |
| A-3053 | UGCCCACCGUGUUUUCUGGdTdT | 969 |
| A-3054 | UUUGGCCCACCGUGUUUUCdTdT | 970 |
| A-3055 | UUUUGGCCCACCGUGUUUUdTdT | 971 |
| A-3056 | UUCAUCCUUUGGCCCACCGdTdT | 972 |
| A-3057 | UCAUGCCUCUCUUCAUCCUdTdT | 973 |
| A-3058 | UCAACAUGCCUCUCUUCAUdTdT | 974 |
| A-3059 | UGUCUCCAACAUGCCUCUCdTdT | 975 |
| A-3060 | UAGUCUCCAACAUGCCUCUdTdT | 976 |
| A-3061 | UUGCCCAAGUCUCCAACAUdTdT | 977 |
| A-3062 | UAUUGCCCAAGUCUCCAACdTdT | 978 |
| A-3063 | UCACAUUGCCCAAGUCUCCdTdT | 979 |
| A-3064 | UGUCAGCAGUCACAUUGCCdTdT | 980 |
| A-3065 | UUUGUCAGCAGUCACAUUGdTdT | 981 |
| A-3066 | UCCACACCAUCUUUGUCAGdTdT | 982 |
| A-3067 | UGCCACACCAUCUUUGUCAdTdT | 983 |
| A-3068 | UAUGCAAUGGUCUCCUGAGdTdT | 984 |
| A-3069 | UGAUGCAAUGGUCUCCUGAdTdT | 985 |
| A-3070 | UCCAAUGAUGCAAUGGUCUdTdT | 986 |
| A-3071 | UGCCAAUGAUGCAAUGGUCdTdT | 987 |
| A-3072 | UUGCGGCCAAUGAUGCAAUdTdT | 988 |
| A-3073 | UACCAGUGUGCGGCCAAUGdTdT | 989 |

TABLE 2-continued

Antisense Sequences

| Antisense ID | Sequence | SEQ ID NO |
|---|---|---|
| A-3074 | UAUGGACCACCAGUGUGCGdTdT | 990 |
| A-3075 | UUCAUGGACCACCAGUGUGdTdT | 991 |
| A-3076 | UUUCAUGGACCACCAGUGdTdT | 992 |
| A-3077 | UCUUUUCAUGGACCACCAdTdT | 993 |
| A-3078 | UCUGCUUUUCAUGGACCAdTdT | 994 |
| A-3079 | UGCCCAAGUCAUCUGCUUUdTdT | 995 |
| A-3080 | UUUUGCCCAAGUCAUCUGCdTdT | 996 |
| A-3081 | UCACCUUUGCCCAAGUCAUdTdT | 997 |
| A-3082 | UCCACCUUUGCCCAAGUCAdTdT | 998 |
| A-3083 | UUCCACCUUUGCCCAAGUCdTdT | 999 |
| A-3084 | UCGUUUCCUGUCUUUGUACdTdT | 1000 |
| A-3085 | UAGCGUUUCCUGUCUUUGUdTdT | 1001 |
| A-3086 | UCAGCGUUUCCUGUCUUUGdTdT | 1002 |
| A-3087 | UCGACUUCCAGCGUUUCCUdTdT | 1003 |
| A-3088 | UCACCACAAGCCAAACGACdTdT | 1004 |
| A-3089 | UACACCACAAGCCAAACGAdTdT | 1005 |
| A-3090 | UUACACCACAAGCCAAACGdTdT | 1006 |
| A-3091 | UUUACACCACAAGCCAAACdTdT | 1007 |
| A-3092 | UAAUUACACCACAAGCCAAdTdT | 1008 |
| A-3093 | UCCAAUUACACCACAAGCCdTdT | 1009 |
| A-3094 | UCCCAAUUACACCACAAGCdTdT | 1010 |
| A-3095 | UUCCCAAUUACACCACAAGdTdT | 1011 |
| A-3096 | UGAUCCCAAUUACACCACAdTdT | 1012 |
| A-3097 | UCGAUCCCAAUUACACCACdTdT | 1013 |
| A-3098 | UGCGAUCCCAAUUACACCAdTdT | 1014 |
| A-3099 | UUUGGGCGAUCCCAAUUACdTdT | 1015 |
| A-3100 | UAUUGGGCGAUCCCAAUUAdTdT | 1016 |
| A-3101 | UUAUUGGGCGAUCCCAAUUdTdT | 1017 |
| A-3102 | UUUAUUGGGCGAUCCCAAUdTdT | 1018 |
| A-3103 | UUUUAUUGGGCGAUCCCAAdTdT | 1019 |
| A-3104 | UGUUUAUUGGGCGAUCCCAdTdT | 1020 |
| A-3105 | UUGUUUAUUGGGCGAUCCCdTdT | 1021 |
| A-3106 | UGAAUGUUUAUUGGGCGAUdTdT | 1022 |
| A-3107 | UCAAGGGAAUGUUUAUUGGdTdT | 1023 |
| A-3108 | UCCAAGGGAAUGUUUAUUGdTdT | 1024 |
| A-3109 | UUCCAAGGGAAUGUUUAUUdTdT | 1025 |
| A-3110 | UAUCCAAGGGAAUGUUUAUdTdT | 1026 |
| A-3111 | UCAUCCAAGGGAAUGUUUAdTdT | 1027 |
| A-3112 | UACAUCCAAGGGAAUGUUUdTdT | 1028 |
| A-3113 | UUACAUCCAAGGGAAUGUUdTdT | 1029 |
| A-3114 | UGACUACAUCCAAGGGAAUdTdT | 1030 |
| A-3115 | UCCUCAGACUACAUCCAAGdTdT | 1031 |
| A-3116 | UUGAGUUAAGGGGCCUCAGdTdT | 1032 |
| A-3117 | UGAUGAGUUAAGGGGCCUCdTdT | 1033 |
| A-3118 | UAGAUGAGUUAAGGGGCCUdTdT | 1034 |
| A-3119 | UAACAGAUGAGUUAAGGGGdTdT | 1035 |
| A-3120 | UUAACAGAUGAGUUAAGGGdTdT | 1036 |
| A-3121 | UAUAACAGAUGAGUUAAGGdTdT | 1037 |
| A-3122 | UGAUAACAGAUGAGUUAAGdTdT | 1038 |
| A-3123 | UGGAUAACAGAUGAGUUAAdTdT | 1039 |
| A-3124 | UAGGAUAACAGAUGAGUUAdTdT | 1040 |
| A-3125 | UCAGGAUAACAGAUGAGUUdTdT | 1041 |
| A-3126 | UUACAGCUAGCAGGAUAACdTdT | 1042 |
| A-3127 | UCAUUUCUACAGCUAGCAGdTdT | 1043 |
| A-3128 | UACAUUUCUACAGCUAGCAdTdT | 1044 |
| A-3129 | UAGGAUACAUUUCUACAGCdTdT | 1045 |
| A-3130 | UCAGGAUACAUUUCUACAGdTdT | 1046 |
| A-3131 | UUCAGGAUACAUUUCUACAdTdT | 1047 |
| A-3132 | UAUCAGGAUACAUUUCUACdTdT | 1048 |
| A-3133 | UGUUUAUCAGGAUACAUUUdTdT | 1049 |
| A-3134 | UUAAUGUUUAUCAGGAUACdTdT | 1050 |
| A-3135 | UUAAGAUUACAGUGUUUAAdTdT | 1051 |
| A-3136 | UCACUUUUAAGAUUACAGUdTdT | 1052 |
| A-3137 | UACACUUUUAAGAUUACAGdTdT | 1053 |
| A-3138 | UUACACUUUUAAGAUUACAdTdT | 1054 |
| A-3139 | UUUACACUUUUAAGAUUACdTdT | 1055 |
| A-3140 | UCACAAUUACACUUUUAAGdTdT | 1056 |
| A-3141 | UAGUUUCUCACUACAGGUAdTdT | 1057 |
| A-3142 | UUCUUCCAAGUGAUCAUAAdTdT | 1058 |
| A-3143 | UAAUCUUCCAAGUGAUCAUdTdT | 1059 |
| A-3144 | UACAAAUCUUCCAAGUGAUdTdT | 1060 |
| A-3145 | UAACUAUACAAAUCUUCCAdTdT | 1061 |
| A-3146 | UUUUUAACUGAGUUUUAUdTdT | 1062 |
| A-3147 | UGACAUUUUAACUGAGUUUdTdT | 1063 |

TABLE 2-continued

Antisense Sequences

| Antisense ID | Sequence | SEQ ID NO |
|---|---|---|
| A-3148 | UCAGGUCAUUGAAACAGACdTdT | 1064 |
| A-3149 | UUGGCAAAAUACAGGUCAUdTdT | 1065 |
| A-3150 | UGUCUGGCAAAAUACAGGUdTdT | 1066 |
| A-3151 | UAGUCUGGCAAAAUACAGGdTdT | 1067 |
| A-3152 | UAUACCCAUCUGUGAUUUAdTdT | 1068 |
| A-3153 | UUUAAUACCCAUCUGUGAUdTdT | 1069 |
| A-3154 | UUUUAAUACCCAUCUGUGAdTdT | 1070 |
| A-3155 | UAGUUUAAUACCCAUCUGUdTdT | 1071 |
| A-3156 | UAAGUUUAAUACCCAUCUGdTdT | 1072 |
| A-3157 | UCAAGUUUAAUACCCAUCUdTdT | 1073 |
| A-3158 | UGACAAGUUUAAUACCCAUdTdT | 1074 |
| A-3159 | UGAAAUUCUGACAAGUUUAdTdT | 1075 |
| A-3160 | UAUUCACAGGCUUGAAUGAdTdT | 1076 |
| A-3161 | UUAUUCACAGGCUUGAAUGdTdT | 1077 |
| A-3162 | UCCAUACAGGGUUUUUAUUdTdT | 1078 |
| A-3163 | UGCCAUACAGGGUUUUUAUdTdT | 1079 |
| A-3164 | UUAAGUGCCAUACAGGGUUdTdT | 1080 |
| A-3165 | UAUAAGUGCCAUACAGGGUdTdT | 1081 |
| A-3166 | UGAUUCUUUUAAUAGCCUCdTdT | 1082 |
| A-3167 | UUUUGAAUUUGGAUUCUUUdTdT | 1083 |
| A-3168 | UUAGUUUGAAUUUGGAUUCdTdT | 1084 |

In one embodiment, the siRNA molecules of the present invention targeting SOD1 may comprise a nucleotide sequence such as, but not limited to, the sense (passenger) sequences in Table 3 or a fragment or variant thereof. As a non-limiting example, the sense sequence used in the siRNA molecule of the present invention is at least 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% or at least 20-30%, 20-40%, 20-50%, 20-60%, 20-70%, 20-80%, 20-90%, 20-95%, 20-99%, 30-40%, 30-50%, 30-60%, 30-70%, 30-80%, 30-90%, 30-95%, 30-99%, 40-50%, 40-60%, 40-70%, 40-80%, 40-90%, 40-95%, 40-99%, 50-60%, 50-70%, 50-80%, 50-90%, 50-95%, 50-99%, 60-70%, 60-80%, 60-90%, 60-95%, 60-99%, 70-80%, 70-90%, 70-95%, 70-99%, 80-90%, 80-95%, 80-99%, 90-95%, 90-99% or 95-99% of a nucleotide sequence in Table 3. As another non-limiting example, the sense sequence used in the siRNA molecule of the present invention comprises at least 3, 4, 5, 6, 7, 8, 9, 10, 11, 12, 13, 14, 15, 16, 17, 18, 19, 20, 21 or more than 21 consecutive nucleotides of a nucleotide sequence in Table 3. As yet another non-limiting example, the sense sequence used in the siRNA molecule of the present invention comprises nucleotides 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 2 to 22, 2 to 21, 2 to 20, 2 to 19, 2 to 18, 2 to 17, 2 to 16, 2 to 15, 2 to 14, 2 to 13, 2 to 12, 2 to 11, 2 to 10, 2 to 9, 2 to 8, 3 to 22, 3 to 21, 3 to 20, 3 to 19, 3 to 18, 3 to 17, 3 to 16, 3 to 15, 3 to 14, 3 to 13, 3 to 12, 3 to 11, 3 to 10, 3 to 9, 3 to 8, 4 to 22, 4 to 21, 4 to 20, 4 to 19, 4 to 18, 4 to 17, 4 to 16, 4 to 15, 4 to 14, 4 to 13, 4 to 12, 4 to 11, 4 to 10, 4 to 9, 4 to 8, 5 to 22, 5 to 21, 5 to 20, 5 to 19, 5 to 18, 5 to 17, 5 to 16, 5 to 15, 5 to 14, 5 to 13, 5 to 12, 5 to 11, 5 to 10, 5 to 9, 5 to 8, 6 to 22, 6 to 21, 6 to 20, 6 to 19, 6 to 18, 6 to 17, 6 to 16, 6 to 15, 6 to 14, 6 to 13, 6 to 12, 6 to 11, 6 to 10, 7 to 22, 7 to 21, 7 to 20, 7 to 19, 7 to 18, 7 to 17, 7 to 16, 7 to 15, 7 to 14, 7 to 13, 7 to 12, 8 to 22, 8 to 21, 8 to 20, 8 to 19, 8 to 18, 8 to 17, 8 to 16, 8 to 15, 8 to 14, 8 to 13, 8 to 12, 9 to 22, 9 to 21, 9 to 20, 9 to 19, 9 to 18, 9 to 17, 9 to 16, 9 to 15, 9 to 14, 10 to 22, 10 to 21, 10 to 20, 10 to 19, 10 to 18, 10 to 17, 10 to 16, 10 to 15, 10 to 14, 11 to 22, 11 to 21, 11 to 20, 11 to 19, 11 to 18, 11 to 17, 11 to 16, 11 to 15, 11 to 14, 12 to 22, 12 to 21, 12 to 20, 12 to 19, 12 to 18, 12 to 17, 12 to 16, 13 to 22, 13 to 21, 13 to 20, 13 to 19, 13 to 18, 13 to 17, 13 to 16, 14 to 22, 14 to 21, 14 to 20, 14 to 19, 14 to 18, 14 to 17, 15 to 22, 15 to 21, 15 to 20, 15 to 19, 15 wt 18, 16 to 22, 16 to 21, 16 to 20, 17 to 22, 17 to 21, or 18 to 22 of the sequences in Table 3.

TABLE 3

Sense Sequences

| Sense ID | Sequence | SEQ ID NO |
|---|---|---|
| S-3000 | CGGAGGUCUGGCCUAUAACdTdT | 1085 |
| S-3001 | GGAGGUCUGGCCUAUAAACdTdT | 1086 |
| S-3002 | GAGGUCUGGCCUAUAAAGCdTdT | 1087 |
| S-3003 | AGGUCUGGCCUAUAAAGUCdTdT | 1088 |
| S-3004 | GGUCUGGCCUAUAAAGUACdTdT | 1089 |
| S-3005 | UCUGGCCUAUAAAGUAGUCdTdT | 1090 |
| S-3006 | CUGGCCUAUAAAGUAGUCCdTdT | 1091 |
| S-3007 | UGGCCUAUAAAGUAGUCGCdTdT | 1092 |
| S-3008 | GGCCUAUAAAGUAGUCGCCdTdT | 1093 |
| S-3009 | GCCUAUAAAGUAGUCGCGCdTdT | 1094 |
| S-3010 | CCUAUAAAGUAGUCGCGGCdTdT | 1095 |
| S-3011 | GUCGUAGUCUCCUGCAGCCdTdT | 1096 |
| S-3012 | CGUAGUCUCCUGCAGCGUCdTdT | 1097 |
| S-3013 | GUAGUCUCCUGCAGCGUCCdTdT | 1098 |
| S-3014 | UAGUCUCCUGCAGCGUCUCdTdT | 1099 |
| S-3015 | AUGGCGACGAAGGCCGUGCdTdT | 1100 |
| S-3016 | CGACGAAGGCCGUGUGCGCdTdT | 1101 |
| S-3017 | GAAGGCCGUGUGCGUGCUCdTdT | 1102 |
| S-3018 | GGCCGUGUGCGUGCUGAACdTdT | 1103 |
| S-3019 | AGGGCGACGGCCCAGUGCCdTdT | 1104 |
| S-3020 | UGCAGGGCAUCAUCAAUUCdTdT | 1105 |
| S-3021 | GCAGGGCAUCAUCAAUUUCdTdT | 1106 |

TABLE 3-continued

Sense Sequences

| Sense ID | Sequence | SEQ ID NO |
|---|---|---|
| S-3022 | AGGGCAUCAUCAAUUUCGCdTdT | 1107 |
| S-3023 | GGGCAUCAUCAAUUUCGACdTdT | 1108 |
| S-3024 | GGCAUCAUCAAUUUCGAGCdTdT | 1109 |
| S-3025 | GCAUCAUCAAUUUCGAGCCdTdT | 1110 |
| S-3026 | CAUCAUCAAUUUCGAGCACdTdT | 1111 |
| S-3027 | AAUUUCGAGCAGAAGGAACdTdT | 1112 |
| S-3028 | UUCGAGCAGAAGGAAAGUCdTdT | 1113 |
| S-3029 | UCGAGCAGAAGGAAAGUACdTdT | 1114 |
| S-3030 | AAGGUGUGGGGAAGCAUUCdTdT | 1115 |
| S-3031 | GGUGUGGGGAAGCAUUAACdTdT | 1116 |
| S-3032 | GACUGACUGAAGGCCUGCCdTdT | 1117 |
| S-3033 | CUGACUGAAGGCCUGCAUCdTdT | 1118 |
| S-3034 | UGACUGAAGGCCUGCAUGCdTdT | 1119 |
| S-3035 | UGAAGGCCUGCAUGGAUUCdTdT | 1120 |
| S-3036 | GAAGGCCUGCAUGGAUUCCdTdT | 1121 |
| S-3037 | UGCAUGGAUUCCAUGUUCCdTdT | 1122 |
| S-3038 | CAUGGAUUCCAUGUUCAUCdTdT | 1123 |
| S-3039 | GGAUUCCAUGUUCAUGAGCdTdT | 1124 |
| S-3040 | UUCCAUGUUCAUGAGUUUCdTdT | 1125 |
| S-3041 | GUUCAUGAGUUUGGAGAUCdTdT | 1126 |
| S-3042 | UUCAUGAGUUUGGAGAUACdTdT | 1127 |
| S-3043 | UGAGUUUGGAGAUAAUACCdTdT | 1128 |
| S-3044 | GAGUUUGGAGAUAAUACACdTdT | 1129 |
| S-3045 | AGGCUGUACCAGUGCAGGCdTdT | 1130 |
| S-3046 | GGCUGUACCAGUGCAGGUCdTdT | 1131 |
| S-3047 | GCAGGUCCUCACUUUAAUCdTdT | 1132 |
| S-3048 | CAGGUCCUCACUUUAAUCCdTdT | 1133 |
| S-3049 | UCACUUUAAUCCUCUAUCCdTdT | 1134 |
| S-3050 | CUAUCCAGAAAACACGGUCdTdT | 1135 |
| S-3051 | UAUCCAGAAAACACGGUGCdTdT | 1136 |
| S-3052 | AUCCAGAAAACACGGUGGCdTdT | 1137 |
| S-3053 | CCAGAAAACACGGUGGGCCdTdT | 1138 |
| S-3054 | GAAAACACGGUGGGCCAACdTdT | 1139 |
| S-3055 | AAAACACGGUGGGCCAAACdTdT | 1140 |
| S-3056 | CGGUGGGCCAAAGGAUGACdTdT | 1141 |
| S-3057 | AGGAUGAAGAGAGGCAUGCdTdT | 1142 |
| S-3058 | AUGAAGAGAGGCAUGUUGCdTdT | 1143 |
| S-3059 | GAGAGGCAUGUUGGAGACCdTdT | 1144 |
| S-3060 | AGAGGCAUGUUGGAGACUCdTdT | 1145 |
| S-3061 | AUGUUGGAGACUUGGGCACdTdT | 1146 |
| S-3062 | GUUGGAGACUUGGGCAAUCdTdT | 1147 |
| S-3063 | GGAGACUUGGGCAAUGUGCdTdT | 1148 |
| S-3064 | GGCAAUGUGACUGCUGACCdTdT | 1149 |
| S-3065 | CAAUGUGACUGCUGACAACdTdT | 1150 |
| S-3066 | CUGACAAAGAUGGUGUGGCdTdT | 1151 |
| S-3067 | UGACAAAGAUGGUGUGGCCdTdT | 1152 |
| S-3068 | CUCAGGAGACCAUUGCAUCdTdT | 1153 |
| S-3069 | UCAGGAGACCAUUGCAUCCdTdT | 1154 |
| S-3070 | AGACCAUUGCAUCAUUGGCdTdT | 1155 |
| S-3071 | GACCAUUGCAUCAUUGGCCdTdT | 1156 |
| S-3072 | AUUGCAUCAUUGGCCGCACdTdT | 1157 |
| S-3073 | CAUUGGCCGCACACUGUCCdTdT | 1158 |
| S-3074 | CGCACACUGGUGGUCCAUCdTdT | 1159 |
| S-3075 | CACACUGGUGGUCCAUGACdTdT | 1160 |
| S-3076 | ACACUGGUGGUCCAUGAACdTdT | 1161 |
| S-3077 | UGGUGGUCCAUGAAAAAGCdTdT | 1162 |
| S-3078 | UGGUCCAUGAAAAAGCAGCdTdT | 1163 |
| S-3079 | AAAGCAGAUGACUUGGGCCdTdT | 1164 |
| S-3080 | GCAGAUGACUUGGGCAAACdTdT | 1165 |
| S-3081 | AUGACUUGGGCAAAGGUGCdTdT | 1166 |
| S-3082 | UGACUUGGGCAAAGGUGGCdTdT | 1167 |
| S-3083 | GACUUGGGCAAAGGUGGACdTdT | 1168 |
| S-3084 | GUACAAAGACAGGAAACGCdTdT | 1169 |
| S-3085 | ACAAAGACAGGAAACGCUCdTdT | 1170 |
| S-3086 | CAAAGACAGGAAACGCUGCdTdT | 1171 |
| S-3087 | AGGAAACGCUGGAAGUCGCdTdT | 1172 |
| S-3088 | GUCGUUGGCUUGUGGUGCdTdT | 1173 |
| S-3089 | UCGUUUGGCUUGUGGUGUCdTdT | 1174 |
| S-3090 | CGUUUGGCUUGUGGUGUACdTdT | 1175 |
| S-3091 | GUUUGGCUUGUGGUGUAACdTdT | 1176 |
| S-3092 | UUGGCUUGUGGUGUAAUUCdTdT | 1177 |
| S-3093 | GGCUUGUGGUGUAAUUGGCdTdT | 1178 |
| S-3094 | GCUUGUGGUGUAAUUGGGCdTdT | 1179 |
| S-3095 | CUUGUGGUGUAAUUGGGACdTdT | 1180 |

TABLE 3-continued

Sense Sequences

| Sense ID | Sequence | SEQ ID NO |
|---|---|---|
| S-3096 | UGUGGUGUAAUUGGGAUCCdTdT | 1181 |
| S-3097 | GUGGUGUAAUUGGGAUCGCdTdT | 1182 |
| S-3098 | UGGUGUAAUUGGGAUCGCCdTdT | 1183 |
| S-3099 | GUAAUUGGGAUCGCCCAACdTdT | 1184 |
| S-3100 | UAAUUGGGAUCGCCCAAUCdTdT | 1185 |
| S-3101 | AAUUGGGAUCGCCCAAUACdTdT | 1186 |
| S-3102 | AUUGGGAUCGCCCAAUAACdTdT | 1187 |
| S-3103 | UUGGGAUCGCCCAAUAAACdTdT | 1188 |
| S-3104 | UGGGACCGCCCAAUAAACCdTdT | 1189 |
| S-3105 | GGGAUCGCCCAAUAAACACdTdT | 1190 |
| S-3106 | AUCGCCCAAUAAACAUUCCdTdT | 1191 |
| S-3107 | CCAAUAAACAUUCCCUUGCdTdT | 1192 |
| S-3108 | CAAUAAACAUUCCCUUGGCdTdT | 1193 |
| S-3109 | AAUAAACAUUCCCUUGGACdTdT | 1194 |
| S-3110 | AUAAACAUUCCCUUGGAUCdTdT | 1195 |
| S-3111 | UAAACAUUCCCUUGGAUGCdTdT | 1196 |
| S-3112 | AAACAUUCCCUUGGAUGUCdTdT | 1197 |
| S-3113 | AACAUUCCCUUGGAUGUACdTdT | 1198 |
| S-3114 | AUUCCCUUGGAUGUAGUCCdTdT | 1199 |
| S-3115 | CUUGGAUGUAGUCUGAGGCdTdT | 1200 |
| S-3116 | CUGAGGCCCCUUAACUCACdTdT | 1201 |
| S-3117 | GAGGCCCCUUAACUCAUCCdTdT | 1202 |
| S-3118 | AGGCCCCUUAACUCAUCUCdTdT | 1203 |
| S-3119 | CCCCUUAACUCAUCUGUUCdTdT | 1204 |
| S-3120 | CCCUUAACUCAUCUGUUACdTdT | 1205 |
| S-3121 | CCUUAACUCAUCUGUUAUCdTdT | 1206 |
| S-3122 | CUUAACUCAUCUGUUAUCCdTdT | 1207 |
| S-3123 | UUAACUCAUCUGUUAUCCCdTdT | 1208 |
| S-3124 | UAACUCAUCUGUUAUCCUCdTdT | 1209 |
| S-3125 | AACUCAUCUGUUAUCCUGCdTdT | 1210 |
| S-3126 | GUUAUCCUGCUAGCUGUACdTdT | 1211 |
| S-3127 | CUGCUAGCUGUAGAAAUGCdTdT | 1212 |
| S-3128 | UGCUAGCUGUAGAAAUGUCdTdT | 1213 |
| S-3129 | GCUAGCUGUAGAAAUGUACdTdT | 1214 |
| S-3130 | CUGUAGAAAUGUAUCCUGCdTdT | 1215 |
| S-3131 | UGUAGAAAUGUAUCCUGACdTdT | 1216 |
| S-3132 | GUAGAAAUGUAUCCUGAUCdTdT | 1217 |
| S-3133 | AAAUGUAUCCUGAUAAACCdTdT | 1218 |
| S-3134 | GUAUCCUGAUAAACAUUACdTdT | 1219 |
| S-3135 | UUAAACACUGUAAUCUUACdTdT | 1220 |
| S-3136 | ACUGUAAUCUUAAAAGUGCdTdT | 1221 |
| S-3137 | CUGUAAUCUUAAAAGUGUCdTdT | 1222 |
| S-3138 | UGUAAUCUUAAAAGUGUACdTdT | 1223 |
| S-3139 | GUAAUCUUAAAAGUGUAACdTdT | 1224 |
| S-3140 | CUUAAAAGUGUAAUUGUGCdTdT | 1225 |
| S-3141 | UACCUGUAGUGAGAAACUCdTdT | 1226 |
| S-3142 | UUAUGAUCACUUGGAAGACdTdT | 1227 |
| S-3143 | AUGAUCACUUGGAAGAUUCdTdT | 1228 |
| S-3144 | AUCACUUGGAAGAUUUGUCdTdT | 1229 |
| S-3145 | UGGAAGAUUUGUAUAGUUCdTdT | 1230 |
| S-3146 | UAUAAACUCAGUUAAAACdTdT | 1231 |
| S-3147 | AAACUCAGUUAAAAUGUCCdTdT | 1232 |
| S-3148 | GUCUGUUUCAAUGACCUGCdTdT | 1233 |
| S-3149 | AUGACCUGUAUUUUGCCACdTdT | 1234 |
| S-3150 | ACCUGUAUUUUGCCAGACCdTdT | 1235 |
| S-3151 | CCUGUAUUUUGCCAGACUCdTdT | 1236 |
| S-3152 | UAAAUCACAGAUGGGUAUCdTdT | 1237 |
| S-3153 | AUCACAGAUGGGUAUUAACdTdT | 1238 |
| S-3154 | UCACAGAUGGGUAUUAAACdTdT | 1239 |
| S-3155 | ACAGAUGGGUAUUAAACUCdTdT | 1240 |
| S-3156 | CAGAUGGGUAUUAAACUUCdTdT | 1241 |
| S-3157 | AGAUGGGUAUUAAACUUGCdTdT | 1242 |
| S-3158 | AUGGGUAUUAAACUUGUCCdTdT | 1243 |
| S-3159 | UAAACUUGUCAGAAUUUCCdTdT | 1244 |
| S-3160 | UCAUUCAAGCCUGUGAAUCdTdT | 1245 |
| S-3161 | CAUUCAAGCCUGUGAAUACdTdT | 1246 |
| S-3162 | AAUAAAACCCUGUAUGGCdTdT | 1247 |
| S-3163 | AUAAAACCCUGUAUGGCCdTdT | 1248 |
| S-3164 | AACCCUGUAUGGCACUUCdTdT | 1249 |
| S-3165 | ACCCUGUAUGGCACUUAUCdTdT | 1250 |
| S-3166 | GAGGCUAUAAAAGAAUCCdTdT | 1251 |
| S-3167 | AAAGAAUCCAAAUUCAAACdTdT | 1252 |
| S-3168 | GAAUCCAAAUUCAAACUACdTdT | 1253 |

In one embodiment, the siRNA molecules of the present invention targeting SOD1 may comprise an antisense sequence from Table 2 and a sense sequence from Table 3, or a fragment or variant thereof. As a non-limiting example, the antisense sequence and the sense sequence have at least 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% or at least 20-30%, 20-40%, 20-50%, 20-60%, 20-70%, 20-80%, 20-90%, 20-95%, 20-99%, 30-40%, 30-50%, 30-60%, 30-70%, 30-80%, 30-90%, 30-95%, 30-99%, 40-50%, 40-60%, 40-70%, 40-80%, 40-90%, 40-95%, 40-99%, 50-60%, 50-70%, 50-80%, 50-90%, 50-95%, 50-99%, 60-70%, 60-80%, 60-90%, 60-95%, 60-99%, 70-80%, 70-90%, 70-95%, 70-99%, 80-90%, 80-95%, 80-99%, 90-95%, 90-99% or 95-99% complementarity.

In one embodiment, the siRNA molecules of the present invention targeting SOD1 may comprise the sense and antisense siRNA duplex as described in Table 4. As a non-limiting example, these siRNA duplexes may be tested for in vitro inhibitory activity on endogenous SOD1 gene expression. The start site for the sense and antisense sequence is compared to SOD1 gene sequence known as NM_000454.4 (SEQ ID NO: 1254) from NCBI.

TABLE 4

Sense and antisense strand sequences of SOD1 dsRNA

| siRNA Duplex ID | SS ID | Sense Strand Sequence (5'-3') | SS SEQ ID | AS ID | Antisense Strand Sequence (5'-3') | AS SEQ ID |
|---|---|---|---|---|---|---|
| D-2741 | S-3000 | CGGAGGUCUGGC CUAUAACdTdT | 1085 | A-3000 | UUUAUAGGCCA GACCUCCGdTdT | 916 |
| D-2742 | S-3001 | GGAGGUCUGGCC UAUAAACdTdT | 1086 | A-3001 | UUUUAUAGGCC AGACCUCCdTdT | 917 |
| D-2743 | S-3002 | GAGGUCUGGCCU AUAAAGCdTdT | 1087 | A-3002 | UCUUUAUAGGC CAGACCUCdTdT | 918 |
| D-2744 | S-3003 | AGGUCUGGCCUA UAAAGUCdTdT | 1088 | A-3003 | UACUUUAUAGG CCAGACCUdTdT | 919 |
| D-2745 | S-3004 | GGUCUGGCCUAU AAAGUACdTdT | 1089 | A-3004 | UUACUUUAUAG GCCAGACCdTdT | 920 |
| D-2746 | S-3005 | UCUGGCCUAUAA AGUAGUCdTdT | 1090 | A-3005 | UACUACUUUAU AGGCCAGAdTdT | 921 |
| D-2747 | S-3006 | CUGGCCUAUAAA GUAGUCCdTdT | 1091 | A-3006 | UGACUACUUUA UAGGCCAGdTdT | 922 |
| D-2748 | S-3007 | UGGCCUAUAAAG UAGUCGCdTdT | 1092 | A-3007 | UCGACUACUUU AUAGGCCAdTdT | 923 |
| D-2749 | S-3008 | GGCCUAUAAAGU AGUCGCCdTdT | 1093 | A-3008 | UGCGACUACUU UAUAGGCCdTdT | 924 |
| D-2750 | S-3009 | GCCUAUAAAGUA GUCGCGCdTdT | 1094 | A-3009 | UCGCGACUACU UUAUAGGCdTdT | 925 |
| D-2751 | S-3010 | CCUAUAAAGUAG UCGCGGCdTdT | 1095 | A-3010 | UCCGCGACUAC UUUAUAGGdTdT | 926 |
| D-2752 | S-3011 | GUCGUAGUCUCC UGCAGCCdTdT | 1096 | A-3011 | UGCUGCAGGAG ACUACGACdTdT | 927 |
| D-2753 | S-3012 | CGUAGUCUCCUG CAGCGUCdTdT | 1097 | A-3012 | UACGCUGCAGG AGACUACGdTdT | 928 |
| D-2754 | S-3013 | GUAGUCUCCUGC AGCGUCCdTdT | 1098 | A-3013 | UGGACGCUGCA GGAGACUAdTdT | 929 |

TABLE 4-continued

Sense and antisense strand sequences of SOD1 dsRNA

| siRNA Duplex ID | SS ID | Sense Strand Sequence (5'-3') | SS SEQ ID | AS ID | Antisense Strand Sequence (5'-3') | AS SEQ ID |
|---|---|---|---|---|---|---|
| D-2755 | S-3014 | UAGUCUCCUGCA GCGUCUCdTdT | 1099 | A-3014 | UAGACGCUGCA GGAGACUAdTdT | 930 |
| D-2756 | S-3015 | AUGGCGACGAAG GCCGUGCdTdT | 1100 | A-3015 | UCACGGCCUUC GUCGCCAUdTdT | 931 |
| D-2757 | S-3016 | CGACGAAGGCCG UGUGCGCdTdT | 1101 | A-3016 | UCGCACACGGCC UUCGUCGdTdT | 932 |
| D-2758 | S-3017 | GAAGGCCGUGUG CGUGCUCdTdT | 1102 | A-3017 | UAGCACGCACA CGGCCUUCdTdT | 933 |
| D-2759 | S-3018 | GGCCGUGUGCGU GCUGAACdTdT | 1103 | A-3018 | UUUCAGCACGC ACACGGCCdTdT | 934 |
| D-2760 | S-3019 | AGGGCGACGGCC CAGUGCCdTdT | 1104 | A-3019 | UGCACUGGGCC GUCGCCCUdTdT | 935 |
| D-2761 | S-3020 | UGCAGGGCAUCA UCAAUUCdTdT | 1105 | A-3020 | UAAUUGAUGAU GCCCUGCAdTdT | 936 |
| D-2762 | S-3021 | GCAGGGCAUCAU CAAUUUCdTdT | 1106 | A-3021 | UAAAUUGAUGA UGCCCUGCdTdT | 937 |
| D-2763 | S-3022 | AGGGCAUCAUCA AUUUCGCdTdT | 1107 | A-3022 | UCGAAAUUGAU GAUGCCCUdTdT | 938 |
| D-2764 | S-3023 | GGGCAUCAUCAA UUUCGACdTdT | 1108 | A-3023 | UUCGAAAUUGA UGAUGCCCdTdT | 939 |
| D-2765 | S-3024 | GGCAUCAUCAAU UUCGAGCdTdT | 1109 | A-3024 | UCUCGAAAUUG AUGAUGCCdTdT | 940 |
| D-2766 | S-3025 | GCAUCAUCAAUU UCGAGCAdTdT | 1110 | A-3025 | UGCUCGAAAUU GAUGAUGCdTdT | 941 |
| D-2767 | S-3026 | CAUCAUCAAUUU CGAGCAGdTdT | 1111 | A-3026 | UUGCUCGAAAU UGAUGAUGdTdT | 942 |
| D-2768 | S-3027 | AAUUUCGAGCAG AAGGAACdTdT | 1112 | A-3027 | UUUCCUUCUGC UCGAAAUUdTdT | 943 |
| D-2769 | S-3028 | UUCGAGCAGAAG GAAAGUCdTdT | 1113 | A-3028 | UACUUUCCUUC UGCUCGAAdTdT | 944 |
| D-2770 | S-3029 | UCGAGCAGAAGG AAAGUACdTdT | 1114 | A-3029 | UUACUUUCCUU CUGCUCGAdTdT | 945 |
| D-2771 | S-3030 | AAGGUGUGGGGA AGCAUUCdTdT | 1115 | A-3030 | UAAUGCUUCCC CACACCUUdTdT | 946 |
| D-2772 | S-3031 | GGUGUGGGGAAG CAUUAACdTdT | 1116 | A-3031 | UUUUAAUGCUUC CCCACACCdTdT | 947 |
| D-2773 | S-3032 | GACUGACUGAAG GCCUGCCdTdT | 1117 | A-3032 | UGCAGGCCUUC AGUCAGUCdTdT | 948 |
| D-2774 | S-3033 | CUGACUGAAGGC CUGCAUCdTdT | 1118 | A-3033 | UAUGCAGGCCU UCAGUCAGdTdT | 949 |
| D-2775 | S-3034 | UGACUGAAGGCC UGCAUGCdTdT | 1119 | A-3034 | UCAUGCAGGCC UUCAGUCAdTdT | 950 |
| D-2776 | S-3035 | UGAAGGCCUGCA UGGAUUCdTdT | 1120 | A-3035 | UAAUCCAUGCA GGCCUUCAdTdT | 951 |
| D-2777 | S-3036 | GAAGGCCUGCAU GGAUUCCdTdT | 1121 | A-3036 | UGAAUCCAUGC AGGCCUUCdTdT | 952 |
| D-2778 | S-3037 | UGCAUGGAUUCC AUGUUCAdTdT | 1122 | A-3037 | UGAACAUGGAA UCCAUGCAdTdT | 953 |

TABLE 4-continued

Sense and antisense strand sequences of SOD1 dsRNA

| siRNA Duplex ID | SS ID | Sense Strand Sequence (5'-3') | SS SEQ ID | AS ID | Antisense Strand Sequence (5'-3') | AS SEQ ID |
|---|---|---|---|---|---|---|
| D-2779 | S-3038 | CAUGGAUUCCAUGUUCAUCdTdT | 1123 | A-3038 | UAUGAACAUGGAAUCCAUGdTdT | 954 |
| D-2780 | S-3039 | GGAUUCCAUGUUCAUGAGCdTdT | 1124 | A-3039 | UCUCAUGAACAUGGAAUCCdTdT | 955 |
| D-2781 | S-3040 | UUCCAUGUUCAUGAGUUUCdTdT | 1125 | A-3040 | UAAACUCAUGAACAUGGAAdTdT | 956 |
| D-2782 | S-3041 | GUUCAUGAGUUUGGAGAUCdTdT | 1126 | A-3041 | UAUCUCCAAACUCAUGAACdTdT | 957 |
| D-2783 | S-3042 | UUCAUGAGUUUGGAGAUACdTdT | 1127 | A-3042 | UUAUCUCCAAACUCAUGAAdTdT | 958 |
| D-2784 | S-3043 | UGAGUUUGGAGAUAAUACCdTdT | 1128 | A-3043 | UGUAUUAUCUCCAAACUCAdTdT | 959 |
| D-2785 | S-3044 | GAGUUUGGAGAUAAUACACdTdT | 1129 | A-3044 | UUGUAUUAUCUCCAAACUCdTdT | 960 |
| D-2786 | S-3045 | AGGCUGUACCAGUGCAGGCdTdT | 1130 | A-3045 | UCCUGCACUGGUACAGCCUdTdT | 961 |
| D-2787 | S-3046 | GGCUGUACCAGUGCAGGUCdTdT | 1131 | A-3046 | UACCUGCACUGGUACAGCCdTdT | 962 |
| D-2788 | S-3047 | GCAGGUCCUCACUUUAAUCdTdT | 1132 | A-3047 | UAUUAAAGUGAGGACCUGCdTdT | 963 |
| D-2789 | S-3048 | CAGGUCCUCACUUUAAUCCdTdT | 1133 | A-3048 | UGAUUAAAGUGAGGACCUGdTdT | 964 |
| D-2790 | S-3049 | UCACUUUAAUCCUCUAUCCdTdT | 1134 | A-3049 | UGAUAGAGGAUUAAAGUGAdTdT | 965 |
| D-2791 | S-3050 | CUAUCCAGAAAACACGGUCdTdT | 1135 | A-3050 | UACCGUGUUUUCUGGAUAGdTdT | 966 |
| D-2792 | S-3051 | UAUCCAGAAAACACGGUGCdTdT | 1136 | A-3051 | UCACCGUGUUUUCUGGAUAdTdT | 967 |
| D-2793 | S-3052 | AUCCAGAAAACACGGUGGCdTdT | 1137 | A-3052 | UCCACCGUGUUUUCUGGAUdTdT | 968 |
| D-2794 | S-3053 | CCAGAAAACACGGUGGGCCdTdT | 1138 | A-3053 | UGCCCACCGUGUUUUCUGGdTdT | 969 |
| D-2795 | S-3054 | GAAAACACGGUGGGCCAACdTdT | 1139 | A-3054 | UUUGGCCCACCGUGUUUUCdTdT | 970 |
| D-2796 | S-3055 | AAAACACGGUGGGCCAAACdTdT | 1140 | A-3055 | UUUUGGCCCACCGUGUUUUdTdT | 971 |
| D-2797 | S-3056 | CGGUGGGCCAAAGGAUGACdTdT | 1141 | A-3056 | UUCAUCCUUUGGCCCACCGdTdT | 972 |
| D-2798 | S-3057 | AGGAUGAAGAGAGGCAUGCdTdT | 1142 | A-3057 | UCAUGCCUCUCUUCAUCCUdTdT | 973 |
| D-2799 | S-3058 | AUGAAGAGAGGCAUGUUGCdTdT | 1143 | A-3058 | UCAACAUGCCUCUCUUCAUdTdT | 974 |
| D-2800 | S-3059 | GAGAGGCAUGUUGGAGACCdTdT | 1144 | A-3059 | UGUCUCCAACAUGCCUCUCdTdT | 975 |
| D-2801 | S-3060 | AGAGGCAUGUUGGAGACUCdTdT | 1145 | A-3060 | UAGUCUCCAACAUGCCUCUdTdT | 976 |
| D-2802 | S-3061 | AUGUUGGAGACUUGGGCACdTdT | 1146 | A-3061 | UUGCCCAAGUCUCCAACAUdTdT | 977 |
| D-2803 | S-3062 | GUUGGAGACUUGGGCAAUCdTdT | 1147 | A-3062 | UAUUGCCCAAGUCUCCAACdTdT | 978 |
| D-2804 | S-3063 | GGAGACUUGGGCAAUGUGCdTdT | 1148 | A-3063 | UCACAUUGCCCAAGUCUCCdTdT | 979 |
| D-2805 | S-3064 | GGCAAUGUGACUGCUGACCdTdT | 1149 | A-3064 | UGUCAGCAGUCACAUUGCCdTdT | 980 |
| D-2806 | S-3065 | CAAUGUGACUGCUGACAACdTdT | 1150 | A-3065 | UUUGUCAGCAGUCACAUUGdTdT | 981 |
| D-2807 | S-3066 | CUGACAAAGAUGGUGUGGCdTdT | 1151 | A-3066 | UCCACACCAUCUUUGUCAGdTdT | 982 |
| D-2808 | S-3067 | UGACAAAGAUGGUGUGGCCdTdT | 1152 | A-3067 | UGCCACACCAUCUUUGUCAdTdT | 983 |
| D-2809 | S-3068 | CUCAGGAGACCAUUGCAUCdTdT | 1153 | A-3068 | UAUGCAAUGGUCUCCUGAGdTdT | 984 |
| D-2810 | S-3069 | UCAGGAGACCAUUGCAUCUdTdT | 1154 | A-3069 | UGAUGCAAUGGUCUCCUGAdTdT | 985 |
| D-2811 | S-3070 | AGACCAUUGCAUCAUUGGCdTdT | 1155 | A-3070 | UCCAAUGAUGCAAUGGUCUdTdT | 986 |
| D-2812 | S-3071 | GACCAUUGCAUCAUUGGCCdTdT | 1156 | A-3071 | UGCCAAUGAUGCAAUGGUCdTdT | 987 |
| D-2813 | S-3072 | AUUGCAUCAUUGGCCGCACdTdT | 1157 | A-3072 | UUGCGGCCAAUGAUGCAAUdTdT | 988 |
| D-2814 | S-3073 | CAUUGGCCGCACACUGGUCdTdT | 1158 | A-3073 | UACCAGUGUGCGGCCAAUGdTdT | 989 |
| D-2815 | S-3074 | CGCACACUGGUGGUCCAUCdTdT | 1159 | A-3074 | UAUGGACCACCAGUGUGCGdTdT | 990 |
| D-2816 | S-3075 | CACACUGGUGGUCCAUGACdTdT | 1160 | A-3075 | UUCAUGGACCACCAGUGUGdTdT | 991 |
| D-2817 | S-3076 | ACACUGGUGGUCCAUGAACdTdT | 1161 | A-3076 | UUUCAUGGACCACCAGUGUdTdT | 992 |
| D-2818 | S-3077 | UGGUGGUCCAUGAAAAAGCdTdT | 1162 | A-3077 | UCUUUUUCAUGGACCACCAdTdT | 993 |
| D-2819 | S-3078 | UGGUCCAUGAAAAAGCAGCdTdT | 1163 | A-3078 | UCUGCUUUUUCAUGGACCAdTdT | 994 |
| D-2820 | S-3079 | AAAGCAGAUGACUUGGGCCdTdT | 1164 | A-3079 | UGCCCAAGUCAUCUGCUUUdTdT | 995 |
| D-2821 | S-3080 | GCAGAUGACUUGGGCAAACdTdT | 1165 | A-3080 | UUUGCCCAAGUCAUCUGCdTdT | 996 |
| D-2822 | S-3081 | AUGACUUGGGCAAAGGUGCdTdT | 1166 | A-3081 | UCACCUUUGCCCAAGUCAUdTdT | 997 |
| D-2823 | S-3082 | UGACUUGGGCAAAGGUGGCdTdT | 1167 | A-3082 | UCCACCUUUGCCCAAGUCAdTdT | 998 |
| D-2824 | S-3083 | GACUUGGGCAAAGGUGGCdTdT | 1168 | A-3083 | UUCCACCUUUGCCCAAGUCdTdT | 999 |
| D-2825 | S-3084 | GUACAAGACAGGAAACGCUdTdT | 1169 | A-3084 | UCGUUUCCUGUCUUGUACdTdT | 1000 |
| D-2826 | S-3085 | ACAAAGACAGGAAACGCUCdTdT | 1170 | A-3085 | UAGCGUUUCCUGUCUUUGUdTdT | 1001 |

TABLE 4-continued

Sense and antisense strand sequences of SOD1 dsRNA

| siRNA Duplex ID | SS ID | Sense Strand Sequence (5'-3') | SS SEQ ID | AS ID | Antisense Strand Sequence (5'-3') | AS SEQ ID |
|---|---|---|---|---|---|---|
| D-2827 | S-3086 | CAAAGACAGGAAACGCUGCdTdT | 1171 | A-3086 | UCAGCGUUUCCUGUCUUUGdTdT | 1002 |
| D-2828 | S-3087 | AGGAAACGCUGGAAGUCGCdTdT | 1172 | A-3087 | UCGACUUCCAGCGUUUCCdTdT | 1003 |
| D-2829 | S-3088 | GUCGUUUGGCUUGUGGUGCdTdT | 1173 | A-3088 | UCACCACAAGCCAAACGAdTdT | 1004 |
| D-2830 | S-3089 | UCGUUUGGCUUGUGGUGUCdTdT | 1174 | A-3089 | UACACCACAAGCCAAACGAdTdT | 1005 |
| D-2831 | S-3090 | CGUUUGGCUUGUGGUGUACdTdT | 1175 | A-3090 | UUACACCACAAGCCAAACGdTdT | 1006 |
| D-2832 | S-3091 | GUUUGGCUUGUGGUGUAACdTdT | 1176 | A-3091 | UUUACACCACAAGCCAAACdTdT | 1007 |
| D-2833 | S-3092 | UUGGCUUGUGGUGUAAUUCdTdT | 1177 | A-3092 | UAAUUACACCACAAGCCAAdTdT | 1008 |
| D-2834 | S-3093 | GGCUUGUGGUGUAAUUGGdTdT | 1178 | A-3093 | UCCAAUUACACCACAAGCCdTdT | 1009 |
| D-2835 | S-3094 | GCUUGUGGUGUAAUUGGGdTdT | 1179 | A-3094 | UCCCAAUUACACCACAAGCdTdT | 1010 |
| D-2836 | S-3095 | CUUGUGGUGUAAUUGGGACdTdT | 1180 | A-3095 | UUCCCAAUUACACCACAAGdTdT | 1011 |
| D-2837 | S-3096 | UGUGGUGUAAUUGGGAUCdTdT | 1181 | A-3096 | UGAUCCCAAUUACACCACAdTdT | 1012 |
| D-2838 | S-3097 | GUGGUGUAAUUGGGAUCGCdTdT | 1182 | A-3097 | UCGAUCCCAAUUACACCACdTdT | 1013 |
| D-2839 | S-3098 | UGGUGUAAUUGGGAUCGCCdTdT | 1183 | A-3098 | UGCGAUCCCAAUUACACCAdTdT | 1014 |
| D-2840 | S-3099 | GUAAUUGGGAUCGCCCAACdTdT | 1184 | A-3099 | UUGGGCGAUCCCAAUUACdTdT | 1015 |
| D-2841 | S-3100 | UAAUUGGGAUCGCCCAAUCdTdT | 1185 | A-3100 | UAUGGGCGAUCCCAAUUAdTdT | 1016 |
| D-2842 | S-3101 | AAUUGGGAUCGCCCAAUACdTdT | 1186 | A-3101 | UUAUUGGGCGAUCCCAAUUdTdT | 1017 |
| D-2843 | S-3102 | AUUGGGAUCGCCCAAUAACdTdT | 1187 | A-3102 | UUUAUUGGGCGAUCCCAAUdTdT | 1018 |
| D-2844 | S-3103 | UUGGGAUCGCCCAAUAAACdTdT | 1188 | A-3103 | UUUUAUUGGGCGAUCCCAAdTdT | 1019 |
| D-2845 | S-3104 | UGGGAUCGCCCAAUAAACCdTdT | 1189 | A-3104 | UGUUUAUUGGGCGAUCCCAdTdT | 1020 |
| D-2846 | S-3105 | GGGAUCGCCCAAUAAACAUdTdT | 1190 | A-3105 | UUGUUUAUUGGGCGAUCCCdTdT | 1021 |
| D-2847 | S-3106 | AUCGCCCAAUAAACAUUCCdTdT | 1191 | A-3106 | UGAAUGUUUAUUGGGCGAUdTdT | 1022 |
| D-2848 | S-3107 | CCAAUAAACAUUCCCUUGGdTdT | 1192 | A-3107 | UCAAGGGAAUGUUUAUUGGdTdT | 1023 |
| D-2849 | S-3108 | CAAUAAACAUUCCCUUGGAdTdT | 1193 | A-3108 | UCCAAGGGAAUGUUUAUUGdTdT | 1024 |
| D-2850 | S-3109 | AAUAAACAUUCCCUUGGACdTdT | 1194 | A-3109 | UUCCAAGGGAAUGUUUAUUdTdT | 1025 |
| D-2851 | S-3110 | AUAAACAUUCCCUUGGAUCdTdT | 1195 | A-3110 | UAUCCAAGGGAAUGUUUAUdTdT | 1026 |
| D-2852 | S-3111 | UAAACAUUCCCUUGGAUGCdTdT | 1196 | A-3111 | UCAUCCAAGGGAAUGUUUAdTdT | 1027 |
| D-2853 | S-3112 | AAACAUUCCCUUGGAUGUCdTdT | 1197 | A-3112 | UACAUCCAAGGGAAUGUUUdTdT | 1028 |
| D-2854 | S-3113 | AACAUUCCCUUGGAUGUACdTdT | 1198 | A-3113 | UUACAUCCAAGGGAAUGUUdTdT | 1029 |
| D-2855 | S-3114 | AUUCCCUUGGAUGUAGUCdTdT | 1199 | A-3114 | UGACUACAUCCAAGGGAAUdTdT | 1030 |
| D-2856 | S-3115 | CUUGGAUGUAGUCUGAGGCdTdT | 1200 | A-3115 | UCCUCAGACUACAUCCAAGdTdT | 1031 |
| D-2857 | S-3116 | CUGAGGCCCUUAACUCACdTdT | 1201 | A-3116 | UUGAGUUAAGGGCCUCAGdTdT | 1032 |
| D-2858 | S-3117 | GAGGCCCCUUAACUCAUCdTdT | 1202 | A-3117 | UGAUGAGUUAAGGGGCCUCdTdT | 1033 |
| D-2859 | S-3118 | AGGCCCCUUAACUCAUCUCdTdT | 1203 | A-3118 | UAGAUGAGUUAAGGGGCCUdTdT | 1034 |
| D-2860 | S-3119 | CCCCUUAACUCAUCUGUUCdTdT | 1204 | A-3119 | UAACAGAUGAGUUAAGGGGdTdT | 1035 |
| D-2861 | S-3120 | CCCUUAACUCAUCUGUUACdTdT | 1205 | A-3120 | UUAACAGAUGAGUUAAGGGdTdT | 1036 |
| D-2862 | S-3121 | CCUUAACUCAUCUGUUAUCdTdT | 1206 | A-3121 | UAUAACAGAUGAGUUAAGGdTdT | 1037 |
| D-2863 | S-3122 | CUUAACUCAUCUGUUAUCCdTdT | 1207 | A-3122 | UGAUAACAGAUGAGUUAAGdTdT | 1038 |
| D-2864 | S-3123 | UUAACUCAUCUGUUAUCCUdTdT | 1208 | A-3123 | UGGAUAACAGAUGAGUUAAdTdT | 1039 |
| D-2865 | S-3124 | UAACUCAUCUGUUAUCCUCdTdT | 1209 | A-3124 | UAGGAUAACAGAUGAGUUAdTdT | 1040 |
| D-2866 | S-3125 | AACUCAUCUGUUAUCCUGCdTdT | 1210 | A-3125 | UCAGGAUAACAGAUGAGUUdTdT | 1041 |
| D-2867 | S-3126 | GUUAUCCUGCUAGCUGUACdTdT | 1211 | A-3126 | UUACAGCUAGCAGGAUAACdTdT | 1042 |
| D-2868 | S-3127 | CUGCUAGCUGUAGAAAUGCdTdT | 1212 | A-3127 | UCAUUUCUACAGCUAGCAGdTdT | 1043 |
| D-2869 | S-3128 | UGCUAGCUGUAGAAAUGUCdTdT | 1213 | A-3128 | UACAUUUCUACAGCUAGCAdTdT | 1044 |
| D-2870 | S-3129 | GCUGUAGAAAUGUAUCCUCdTdT | 1214 | A-3129 | UAGGAUACAUUUCUACAGCdTdT | 1045 |
| D-2871 | S-3130 | CUGUAGAAAUGUAUCCUGCdTdT | 1215 | A-3130 | UCAGGAUACAUUUCUACAGdTdT | 1046 |
| D-2872 | S-3131 | UGUAGAAAUGUAUCCUGCdTdT | 1216 | A-3131 | UUCAGGAUACAUUUCUACAdTdT | 1047 |
| D-2873 | S-3132 | GUAGAAAUGUAUCCUGAUCdTdT | 1217 | A-3132 | UAUCAGGAUACAUUUCUACdTdT | 1048 |
| D-2874 | S-3133 | AAAUGUAUCCUGAUAAACCdTdT | 1218 | A-3133 | UGUUUAUCAGGAUACAUUUdTdT | 1049 |

TABLE 4-continued

Sense and antisense strand sequences of SOD1 dsRNA

| siRNA Duplex ID | SS ID | Sense Strand Sequence (5'-3') | SS SEQ ID | AS ID | Antisense Strand Sequence (5'-3') | AS SEQ ID |
|---|---|---|---|---|---|---|
| D-2875 | S-3134 | GUAUCCUGAUAA ACAUUACdTdT | 1219 | A-3134 | UUAAUGUUUAU CAGGAUACdTdT | 1050 |
| D-2876 | S-3135 | UUAAACACUGUA AUCUUACdTdT | 1220 | A-3135 | UUAAGAUUACA GUGUUUAAdTdT | 1051 |
| D-2877 | S-3136 | ACUGUAAUCUUA AAAGUGCdTdT | 1221 | A-3136 | UCACUUUUAAG AUUACAGUdTdT | 1052 |
| D-2878 | S-3137 | CUGUAAUCUUAA AAGUGUCdTdT | 1222 | A-3137 | UACACUUUUAA GAUUACAGdTdT | 1053 |
| D-2879 | S-3138 | UGUAAUCUUAAA AGUGUACdTdT | 1223 | A-3138 | UUACACUUUUA AGAUUACdTdT | 1054 |
| D-2880 | S-3139 | GUAAUCUUAAAA GUGUAACdTdT | 1224 | A-3139 | UUUACACUUUU AAGAUUACdTdT | 1055 |
| D-2881 | S-3140 | CUUAAAAGUGUA AUUGUGCdTdT | 1225 | A-3140 | UCACAAUUACA CUUUUAAGdTdT | 1056 |
| D-2882 | S-3141 | UACCUGUAGUGA GAAACUCdTdT | 1226 | A-3141 | UAGUUUCUCAC UACAGGUAdTdT | 1057 |
| D-2883 | S-3142 | UUAUGAUCACUU GGAAGACdTdT | 1227 | A-3142 | UUCUUCCAAGU GAUCAUAAdTdT | 1058 |
| D-2884 | S-3143 | AUGAUCACUUGG AAGAUUCdTdT | 1228 | A-3143 | UAAUCUUCCAA GUGAUCAUdTdT | 1059 |
| D-2885 | S-3144 | AUCACUUGGAAG AUUUGUCdTdT | 1229 | A-3144 | UACAAAUCUUC CAAGUGAUdTdT | 1060 |
| D-2886 | S-3145 | UGGAAGAUUUGU AUAGUUCdTdT | 1230 | A-3145 | UAACUAUACAA AUCUUCCAdTdT | 1061 |
| D-2887 | S-3146 | UAUAAAACUCAG UUAAAACdTdT | 1231 | A-3146 | UUUUUAACUGA GUUUUAUAdTdT | 1062 |
| D-2888 | S-3147 | AAACUCAGUUAA AAUGUCCdTdT | 1232 | A-3147 | UGACAUUUUAA CUGAGUUUdTdT | 1063 |
| D-2889 | S-3148 | GUCUGUUUCAAU GACCUGCdTdT | 1233 | A-3148 | UCAGGUCAUUG AAACAGACdTdT | 1064 |
| D-2890 | S-3149 | AUGACCUGUAUU UUGCCACdTdT | 1234 | A-3149 | UUGGCAAAAUA CAGGUCAUdTdT | 1065 |
| D-2891 | S-3150 | ACCUGUAUUUUG CCAGACdTdT | 1235 | A-3150 | UGUCUGGCAAA AUACAGGUdTdT | 1066 |
| D-2892 | S-3151 | CCUGUAUUUUGC CAGACUCdTdT | 1236 | A-3151 | UAGUCUGGCAA AAUACAGGdTdT | 1067 |
| D-2893 | S-3152 | UAAAUCACAGAU GGGUAUCdTdT | 1237 | A-3152 | UAUACCCAUCU GUGAUUUAdTdT | 1068 |
| D-2894 | S-3153 | AUCACAGAUGGG UAUUAACdTdT | 1238 | A-3153 | UUUUAAUACCCA UCUGUGAUdTdT | 1069 |
| D-2895 | S-3154 | UCACAGAUGGGU AUUAAACdTdT | 1239 | A-3154 | UUUUAAUACCC AUCUGUGAdTdT | 1070 |
| D-2896 | S-3155 | ACAGAUGGGUAU UAAACUCdTdT | 1240 | A-3155 | UAGUUUAAUAC CCAUCUGUdTdT | 1071 |
| D-2897 | S-3156 | CAGAUGGGUAUU AAACUUCAUdTdT | 1241 | A-3156 | UAAGUUUAAUA CCCAUCUGdTdT | 1072 |
| D-2898 | S-3157 | AGAUGGGUAUUA AACUUGCdTdT | 1242 | A-3157 | UCAAGUUUAAU ACCCAUCUdTdT | 1073 |
| D-2899 | S-3158 | AUGGGUAUUAAA CUUGUCCdTdT | 1243 | A-3158 | UGACAAGUUUA AUACCCAUdTdT | 1074 |
| D-2900 | S-3159 | UAAACUUGUCAG AAUUUCCdTdT | 1244 | A-3159 | UGAAAUUCUGA CAAGUUUAdTdT | 1075 |
| D-2901 | S-3160 | UCAUUCAAGCCU GUGAAUCdTdT | 1245 | A-3160 | UAUUCACAGGC UUGAAUGAdTdT | 1076 |
| D-2902 | S-3161 | CAUUCAAGCCUG UGAAUACdTdT | 1246 | A-3161 | UUAUUCACAGG CUUGAAUGdTdT | 1077 |
| D-2903 | S-3162 | AAUAAAAACCCU GUAUGGCdTdT | 1247 | A-3162 | UCCAUACAGGG UUUUUAUUdTdT | 1078 |
| D-2904 | S-3163 | AUAAAAACCCUG UAUGGCCdTdT | 1248 | A-3163 | UGCCAUACAGG GUUUUUAUdTdT | 1079 |
| D-2905 | S-3164 | AACCCUGUAUGG CACUUACdTdT | 1249 | A-3164 | UUAAGUGCCAU ACAGGGUUdTdT | 1080 |
| D-2906 | S-3165 | ACCCUGUAUGGC ACUUAUCdTdT | 1250 | A-3165 | UAUAAGUGCCA UACAGGGUdTdT | 1081 |
| D-2907 | S-3166 | GAGGCUAUUAAA AGAAUCCdTdT | 1251 | A-3166 | UGAUUCUUUUA AUAGCCUCdTdT | 1082 |
| D-2908 | S-3167 | AAAGAAUCCAAA UUCAAACdTdT | 1252 | A-3167 | UUUUGAAUUUG GAUUCUUUdTdT | 1083 |
| D-2909 | S-3168 | GAAUCCAAAUUC AAACUACdTdT | 1253 | A-3168 | UUAGUUUGAAU UUGGAUUCdTdT | 1084 |

In other embodiments, the siRNA molecules of the present invention targeting SOD1 can be encoded in plasmid vectors, AAV particles, viral genome or other nucleic acid expression vectors for delivery to a cell.

DNA expression plasmids can be used to stably express the siRNA duplexes or dsRNA of the present invention targeting SOD1 in cells and achieve long-term inhibition of the target gene expression. In one aspect, the sense and antisense strands of a siRNA duplex are typically linked by a short spacer sequence leading to the expression of a stem-loop structure termed short hairpin RNA (shRNA). The hairpin is recognized and cleaved by Dicer, thus generating mature siRNA molecules.

According to the present invention, AAV particles comprising the nucleic acids encoding the siRNA molecules targeting SOD1 mRNA are produced, the AAV serotypes may be any of the serotypes listed in Table 1. Non-limiting examples of the AAV serotypes include, AAV1, AAV2, AAV3, AAV4, AAV5, AAV6, AAV7, AAV8, AAV9, AAV9.47, AAV9(hu14), AAV10, AAV11, AAV12, AAVrh8, AAVrh10, AAV-DJ8, AAV-DJ, AAV-PHP.A, and/or AAV-PHP.B, AAVPHP.B2, AAVPHP.B3, AAVPHP.N/PHP.B-DGT, AAVPHP.B-EST, AAVPHP.B-GGT, AAVPHP.B-ATP, AAVPHP.B-ATT-T, AAVPHP.B-DGT-T, AAVPHP.B-GGT-T, AAVPHP.B-SGS, AAVPHP.B-AQP, AAVPHP.B-QQP, AAVPHP.B-SNP(3), AAVPHP.B-SNP, AAVPHP.B-QGT, AAVPHP.B-NQT, AAVPHP.B-EGS, AAVPHP.B-SGN, AAVPHP.B-EGT, AAVPHP.B-DST, AAVPHP.B-DST, AAVPHP.B-STP, AAVPHP.B-PQP, AAVPHP.B-SQP, AAVPHP.B-QLP, AAVPHP.B-TMP, AAVPHP.B-TTP, AAVPHP.S/G2A12, AAVG2A15/G2A3, AAVG2B4, AAVG2B5, and variants thereof.

In some embodiments, the siRNA duplexes or encoded dsRNA of the present invention suppress (or degrade) SOD1 mRNA. Accordingly, the siRNA duplexes or encoded dsRNA can be used to substantially inhibit SOD1 gene expression in a cell. In some aspects, the inhibition of SOD1 gene expression refers to an inhibition by at least about 20%, preferably by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. Accordingly, the protein product of the targeted gene may be inhibited by at least about 20%, preferably by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%.

According to the present invention, the siRNA molecules are designed and tested for their ability in reducing SOD1 mRNA levels in cultured cells. Such siRNA molecules may form a duplex such as, but not limited to, include those listed in Table 4. As a non-limiting example, the siRNA duplexes may be siRNA duplex IDs: D-2741 to D-2909.

In one embodiment, the siRNA molecules comprise a miRNA seed match for SOD1 located in the guide strand. In another embodiment, the siRNA molecules comprise a miRNA seed match for SOD1 located in the passenger strand. In yet another embodiment, the siRNA duplexes or encoded dsRNA targeting SOD1 gene do not comprise a seed match for SOD1 located in the guide or passenger strand.

In one embodiment, the siRNA duplexes or encoded dsRNA targeting SOD1 gene may have almost no significant full-length off target effects for the guide strand. In another embodiment, the siRNA duplexes or encoded dsRNA targeting SOD1 gene may have almost no significant full-length off target effects for the passenger strand. The siRNA duplexes or encoded dsRNA targeting SOD1 gene may have less than 1%, 2%, 3%, 4%, 5%, 6%, 7%, 8%, 9%, 10%, 11%, 12%, 13%, 14%, 15%, 20%, 25%, 30%, 35%, 40%, 45%, 50%, 1-5%, 2-6%, 3-7%, 4-8%, 5-9%, 5-10%, 6-10%, 5-15%, 5-20%, 5-25% 5-30%, 10-20%, 10-30%, 10-40%, 10-50%, 15-30%, 15-40%, 15-45%, 20-40%, 20-50%, 25-50%, 30-40%, 30-50%, 35-50%, 40-50%, 45-50% full-length off target effects for the passenger strand. In yet another embodiment, the siRNA duplexes or encoded dsRNA targeting SOD1 gene may have almost no significant full-length off target effects for the guide strand or the passenger strand. The siRNA duplexes or encoded dsRNA targeting SOD1 gene may have less than 1%, 2%, 3%, 4%, 5%, 6%, 7%, 8%, 9%, 10%,11%, 12%, 13%, 14%, 15%, 20%, 25%, 30%, 35%, 40%, 45%, 50%, 1-5%, 2-6%, 3-7%, 4-8%, 5-9%, 5-10%, 6-10%, 5-15%, 5-20%, 5-25% 5-30%, 10-20%, 10-30%, 10-40%, 10-50%, 15-30%, 15-40%, 15-45%, 20-40%, 20-50%, 25-50%, 30-40%, 30-50%, 35-50%, 40-50%, 45-50% full-length off target effects for the guide or passenger strand.

In one embodiment, the siRNA duplexes or encoded dsRNA targeting SOD1 gene may have high activity in vitro. In another embodiment, the siRNA molecules may have low activity in vitro. In yet another embodiment, the siRNA duplexes or dsRNA targeting the SOD1 gene may have high guide strand activity and low passenger strand activity in vitro.

In one embodiment, the siRNA molecules targeting SOD1 have a high guide strand activity and low passenger strand activity in vitro. The target knock-down (KD) by the guide strand may be at least 40%, 50%, 60%, 65%, 70%, 75%, 80%, 85%, 90%, 95%, 99%, 99.5% or 100%. The target knock-down by the guide strand may be 40-50%, 45-50%, 50-55%, 50-60%, 60-65%, 60-70%, 60-75%, 60-80%, 60-85%, 60-90%, 60-95%, 60-99%, 60-99.5%, 60-100%, 65-70%, 65-75%, 65-80%, 65-85%, 65-90%, 65-95%, 65-99%, 65-99.5%, 65-100%, 70-75%, 70-80%, 70-85%, 70-90%, 70-95%, 70-99%, 70-99.5%, 70-100%, 75-80%, 75-85%, 75-90%, 75-95%, 75-99%, 75-99.5%, 75-100%, 80-85%, 80-90%, 80-95%, 80-99%, 80-99.5%, 80-100%, 85-90%, 85-95%, 85-99%, 85-99.5%, 85-100%, 90-95%, 90-99%, 90-99.5%, 90-100%, 95-99%, 95-99.5%, 95-100%, 99-99.5%, 99-100% or 99.5-100%, As a non-limiting example, the target knock-down (KD) by the guide strand is greater than 70%. As a non-limiting example, the target knock-down (KD) by the guide strand is greater than 60%.

In one embodiment, the siRNA duplex target SOD1 is designed so there is no miRNA seed match for the sense or antise sequence to the non-SOD1 sequence.

In one embodiment, the $IC_{50}$ of the guide strand in the siRNA duplex targeting SOD1 for the nearest off target is greater than 100 multiplied by the $IC_{50}$ of the guide strand for the on-target gene, SOD1. As a non-limiting example, if the $IC_{50}$ of the guide strand for the nearest off target is greater than 100 multiplied by the $IC_{50}$ of the guide strand for the target then the siRNA molecules is said to have high guide strand selectivity for inhibiting SOD1 in vitro.

In one embodiment, the 5' processing of the guide strand of the siRNA duplex targeting SOD1 has a correct start (n) at the 5' end at least 75%, 80%, 85%, 90%, 95%, 99% or 100% of the time in vitro or in vivo. As a non-limiting example, the 5' processing of the guide strand is precise and has a correct start (n) at the 5' end at least 99% of the time in vitro. As a non-limiting example, the 5' processing of the guide strand is precise and has a correct start (n) at the 5' end at least 99% of the time in vivo. As a non-limiting example, the 5' processing of the guide strand is precise and has a correct start (n) at the 5' end at least 90% of the time in vitro. As a non-limiting example, the 5' processing of the guide strand is precise and has a correct start (n) at the 5' end at least 90% of the time in vivo. As a non-limiting example, the 5' processing of the guide strand is precise and has a correct start (n) at the 5' end at least 85% of the time in vitro. As a non-limiting example, the 5' processing of the guide strand is precise and has a correct start (n) at the 5' end at least 85% of the time in vivo.

In one embodiment, the 5' processing of the guide strand of the siRNA duplex targeting SOD1 has a correct start (n) at the 5' end in a range of 75-95%, 75-90%, 75-85%, 75-80%, 80-95%, 80-90%, 80-85%, 85-95%, 85-90%, or 90-95%. As a non-limiting example, the 5' processing of the guide strand of the siRNA duplex targeting SOD1 has a correct start (n) at the 5' end in a range of 75-95%.

In one embodiment, the 5' processing of the guide strand of the siRNA duplex targeting SOD1 has a correct start (n)

at the 5' end for 75%, 75.1%, 75.2%, 75.3%, 75.4%, 75.5%, 75.6%, 75.7%, 75.8%, 75.9%, 76%, 76.1%, 76.2%, 76.3%, 76.4%, 76.5%, 76.6%, 76.7%, 76.8%, 76.9%, 77%, 77.1%, 77.2%, 77.3%, 77.4%, 77.5%, 77.6%, 77.7%, 77.8%, 77.9%, 78%, 78.1%, 78.2%, 78.3%, 78.4%, 78.5%, 78.6%, 78.7%, 78.8%, 78.9%, 79%, 79.1%, 79.2%, 79.3%, 79.4%, 79.5%, 79.6%, 79.7%, 79.8%, 79.9%, 80%, 80.1%, 80.2%, 80.3%, 80.4%, 80.5%, 80.6%, 80.7%, 80.8%, 80.9%, 81%, 81.1%, 81.2%, 81.3%, 81.4%, 81.50%, 81.6%, 81.7%, 81.8%, 81.9%, 82%, 82.1%, 82.2%, 82.3%, 82.4%, 82.5%, 82.6%, 82.7%, 82.8%, 82.9%, 83%, 83.1%, 83.2%, 83.3%, 83.4%, 83.5%, 83.6%, 83.7%, 83.8%, 83.9%, 84%, 84.1%, 84.2%, 84.3%, 84.4%, 84.5%, 84.6%, 84.7%, 84.8%, 84.9%, 85%, 85.1%, 85.2%, 85.3%, 85.4%, 85.5%, 85.6%, 85.7%, 85.8%, 85.9%, 86%, 86.1%, 86.2%, 86.3%, 86.4%, 86.5%, 86.6%, 86.7%, 86.8%, 86.9%, 87%, 87.1%, 87.2%, 87.3%, 87.4%, 87.5%, 87.6%, 87.7%, 87.8%, 87.9%, 88%, 88.1%, 88.2%, 88.3%, 88.4%, 88.5%, 88.6%, 88.7%, 88.8%, 88.9%, 89%, 89.1%, 89.2%, 89.3%, 89.4%, 89.5%, 89.6%, 89.7%, 89.8%, 89.9%, 90%, 90.1%, 90.2%, 90.3%, 90.4%, 90.5%, 90.6%, 90.7%, 90.8%, 90.9%, 91%, 91.1%, 91.2%, 91.3%, 91.4%, 91.5%, 91.6%, 91.7%, 91.8%, 91.9%, 92%, 92.1%, 92.2%, 92.3%, 92.4%, 92.5%, 92.6%, 92.7%, 92.8%, 92.9%, 93%, 93.1%, 93.2%, 93.3%, 93.4%, 93.5%, 93.6%, 93.7%, 93.8%, 93.9%, 94%, 94.1%, 94.2%, 94.3%, 94.4%, 94.5%, 94.6%, 94.7%, 94.8%, 94.9%, or 95% of the constructs expressed. As a non-limiting example, the 5' processing of the guide strand of the siRNA duplex targeting SOD1 has a correct start (n) at the 5' end for 81% of the constructs expressed. As a non-limiting example, the 5' processing of the guide strand of the siRNA duplex targeting SOD1 has a correct start (n) at the 5' end for 90% of the constructs expressed.

In one embodiment, a passenger-guide strand duplex for SOD1 is considered effective when the pri- or pre-microRNAs demonstrate, by methods known in the art and described herein, greater than 2-fold guide to passenger strand ratio when processing is measured. As a non-limiting examples, the pri- or pre-microRNAs demonstrate great than 2-fold, 3-fold, 4-fold, 5-fold, 6-fold, 7-fold, 8-fold, 9-fold, 10-fold, 11-fold, 12-fold, 13-fold, 14-fold, 15-fold, or 2 to 5-fold, 2 to 10-fold, 2 to 15-fold, 3 to 5-fold, 3 to 10-fold, 3 to 15-fold, 4 to 5-fold, 4 to 10-fold, 4 to 15-fold, 5 to 10-fold, 5 to 15-fold, 6 to 10-fold, 6 to 15-fold, 7 to 10-fold, 7 to 15-fold, 8 to 10-fold, 8 to 15-fold, 9 to 10-fold, 9 to 15-fold, 10 to 15-fold, 11 to 15-fold, 12 to 15-fold, 13 to 15-fold, or 14 to 15-fold guide to passenger strand ratio when processing is measured.

In one embodiment, the siRNA molecules may be used to silence wild type or mutant SOD1 by targeting at least one exon on the SOD1 sequence. The exon may be exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, exon 19, exon 20, exon 21, exon 22, exon 23, exon 24, exon 25, exon 26, exon 27, exon 28, exon 29, exon 30, exon 31, exon 32, exon 33, exon 34, exon 35, exon 36, exon 37, exon 38, exon 39, exon 40, exon 41, exon 42, exon 43, exon 44, exon 45, exon 46, exon 47, exon 48, exon 49, exon 50, exon 51, exon 52, exon 53, exon 54, exon 55, exon 56, exon 57, exon 58, exon 59, exon 60, exon 61, exon 62, exon 63, exon 64, exon 65, exon 66, and/or exon 67.

In one embodiment, the range of guide strands to the total endogenous pool of miRNAs is 0.001-0.6%, 0.005-0.6%, 0.01-0.6%, 0.015-0.6%, 0.02-0.6%, 0.025-0.6%, 0.03-0.6%, 0.035-0.6%, 0.04-0.6%, 0.045-0.6%, 0.05-0.6%, 0.055-0.6%, 0.06-0.6%, 0.065-0.6%, 0.07-0.6%, 0.075-0.6%, 0.08-0.6%, 0.085-0.6%, 0.09-0.6%, 0.095-0.60%, 0.1-0.6%, 0.15-0.6%, 0.2-0.6%, 0.25-0.6%, 0.3-0.6%, 0.35-0.6%, 0.4-0.6%, 0.45-0.6%, 0.5-0.6%, 0.55-0.6%, 0.001-0.50%, 0.005-0.5%, 0.01-0.5%, 0.015-0.5%, 0.02-0.5%, 0.025-0.5%, 0.03-0.5%, 0.035-0.5%, 0.04-0.5%, 0.045-0.5%, 0.05-0.5%, 0.055-0.5%, 0.06-0.5%, 0.065-0.5%, 0.07-0.5%, 0.075-0.5%, 0.08-0.5%, 0.085-0.5%, 0.09-0.5%, 0.095-0.5%, 0.1-0.5%, 0.15-0.5%, 0.2-0.5%, 0.25-0.5%, 0.3-0.5%, 0.35-0.5%, 0.4-0.5%, 0.45-0.5%, 0.001-0.4%, 0.005-0.4%, 0.01-0.4%, 0.015-0.4%, 0.02-0.4%, 0.025-0.4%, 0.03-0.4%, 0.035-0.4%, 0.04-0.4%, 0.045-0.4%, 0.05-0.4%, 0.055-0.4%, 0.06-0.4%, 0.065-0.4%, 0.07-0.4%, 0.075-0.4%, 0.08-0.4%, 0.085-0.4%, 0.09-0.4%, 0.095-0.4%, 0.1-0.4%, 0.15-0.4%, 0.2-0.4%, 0.25-0.4%, 0.3-0.4%, 0.35-0.4%, 0.001-0.30%, 0.005-0.3%, 0.01-0.3%, 0.015-0.3%, 0.02-0.3%, 0.025-0.3%, 0.03-0.3%, 0.035-0.3%, 0.04-0.3%, 0.045-0.3%, 0.05-0.3%, 0.055-0.3%, 0.06-0.3%, 0.065-0.3%, 0.07-0.3%, 0.075-0.3%, 0.08-0.3%, 0.085-0.3%, 0.09-0.3%, 0.095-0.3%, 0.1-0.3%, 0.15-0.3%, 0.2-0.3%, 0.25-0.3%, 0.001-0.2%, 0.005-0.2%, 0.01-0.2%, 0.015-0.2%, 0.02-0.2%, 0.025-0.2%, 0.03-0.2%, 0.035-0.2%, 0.04-0.2%, 0.045-0.2%, 0.05-0.2%, 0.055-0.2%, 0.06-0.2%, 0.065-0.2%, 0.07-0.2%, 0.075-0.2%, 0.08-0.2%, 0.085-0.2%, 0.09-0.2%, 0.095-0.2%, 0.1-0.2%, 0.15-0.2%, 0.001-0.1%, 0.005-0.1%, 0.01-0.1%, 0.015-0.1%, 0.02-0.1%, 0.025-0.1%, 0.03-0.1%, 0.035-0.1%, 0.04-0.1%, 0.045-0.1%, 0.05-0.1%, 0.055-0.1%, 0.06-0.1%, 0.065-0.1%, 0.07-0.1%, 0.075-0.1%, 0.08-0.1%, 0.085-0.10 0.09-0.1%, or 0.095-0.1%. As a non-limiting example, the range is 0.06-0.6%. As a non-limiting example, the range is 0.4-0.5%.

In one embodiment, the percent of guide strands to the total endogenous pool of miRNAs is 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, or 0.6%. As a non-limiting example, the percent is 0.06%. As a non-limiting example, the percent is 0.4%. As a non-limiting example, the percent is 0.5%.

siRNA Modification

In some embodiments, the siRNA molecules of the present invention, when not delivered as a precursor or DNA, may be chemically modified to modulate some features of RNA molecules, such as, but not limited to, increasing the stability of siRNAs in vivo. The chemically modified siRNA molecules can be used in human therapeutic applications, and are improved without compromising the RNAi activity of the siRNA molecules. As a non-limiting example, the siRNA molecules modified at both the 3' and the 5' end of both the sense strand and the antisense strand.

In some aspects, the siRNA duplexes of the present invention may contain one or more modified nucleotides such as, but not limited to, sugar modified nucleotides, nucleobase modifications and/or backbone modifications. In some aspects, the siRNA molecule may contain combined modifications, for example, combined nucleobase and backbone modifications.

In one embodiment, the modified nucleotide may be a sugar-modified nucleotide. Sugar modified nucleotides include, but are not limited to 2'-fluoro, 2'-amino and 2'-thio modified ribonucleotides, e.g. 2'-fluoro modified ribonucleotides. Modified nucleotides may be modified on the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles.

In one embodiment, the modified nucleotide may be a nucleobase-modified nucleotide.

In one embodiment, the modified nucleotide may be a backbone-modified nucleotide. In some embodiments, the siRNA duplexes of the present invention may further comprise other modifications on the backbone. A normal "backbone", as used herein, refers to the repeating alternating sugar-phosphate sequences in a DNA or RNA molecule. The deoxyribose/ribose sugars are joined at both the 3'-hydroxyl and 5'-hydroxyl groups to phosphate groups in ester links, also known as "phosphodiester" bonds/linker (PO linkage). The PO backbones may be modified as "phosphorothioate backbone (PS linkage). In some cases, the natural phosphodiester bonds may be replaced by amide bonds but the four atoms between two sugar units are kept. Such amide modifications can facilitate the solid phase synthesis of oligonucleotides and increase the thermodynamic stability of a duplex formed with siRNA complement. See e.g. Mesmaeker et al., *Pure & Appl. Chem.,* 1997, 3, 437-440: the content of which is incorporated herein by reference in its entirety.

Modified bases refer to nucleotide bases such as, for example, adenine, guanine, cytosine, thymine, uracil, xanthine, inosine, and queuosine that have been modified by the replacement or addition of one or more atoms or groups. Some examples of modifications on the nucleobase moieties include, but are not limited to, alkylated, halogenated, thiolated, aminated, amidated, or acetylated bases, individually or in combination. More specific examples include, for example, 5-propynyluridine, 5-propynylcytidine, 6-methyladenine, 6-methylguanine, N,N-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides.

In one embodiment, the modified nucleotides may be on just the sense strand.

In another embodiment, the modified nucleotides may be on just the antisense strand.

In some embodiments, the modified nucleotides may be in both the sense and antisense strands.

In some embodiments, the chemically modified nucleotide does not affect the ability of the antisense strand to pair with the target mRNA sequence.

In one embodiment, the AAV particle comprising a nucleic acid sequence encoding the siRNA molecules of the present invention may encode siRNA molecules which are polycistronic molecules. The siRNA molecules may additionally comprise one or more linkers between regions of the siRNA molecules.

Molecular Scaffold

In one embodiment, the siRNA molecules may be encoded in a modulatory polynucleotide which also comprises a molecular scaffold. As used herein a "molecular scaffold" is a framework or starting molecule that forms the sequence or structural basis against which to design or make a subsequent molecule.

In one embodiment, the molecular scaffold comprises at least one 5' flanking region. As a non-limiting example, the 5' flanking region may comprise a 5' flanking sequence which may be of any length and may be derived in whole or in part from wild type microRNA sequence or be a completely artificial sequence.

In one embodiment, the molecular scaffold comprises at least one 3' flanking region. As a non-limiting example, the 3' flanking region may comprise a 3' flanking sequence which may be of any length and may be derived in whole or in part from wild type microRNA sequence or be a completely artificial sequence.

In one embodiment, the molecular scaffold comprises at least one loop motif region. As a non-limiting example, the loop motif region may comprise a sequence which may be of any length.

In one embodiment, the molecular scaffold comprises a 5' flanking region, a loop motif region and/or a 3' flanking region.

In one embodiment, at least one siRNA, miRNA or other RNAi agent described herein, may be encoded by a modulatory polynucleotide which may also comprise at least one molecular scaffold. The molecular scaffold may comprise a 5' flanking sequence which may be of any length and may be derived in whole or in part from wild type microRNA sequence or be completely artificial. The 3' flanking sequence may mirror the 5' flanking sequence and/or a 3' flanking sequence in size and origin. Either flanking sequence may be absent. The 3' flanking sequence may optionally contain one or more CNNC motifs, where "N" represents any nucleotide.

Forming the stem of a stem loop structure is a minimum of the modulatory polynucleotide encoding at least one siRNA, miRNA or other RNAi agent described herein. In some embodiments, the siRNA, miRNA or other RNAi agent described herein comprises at least one nucleic acid sequence which is in part complementary or will hybridize to a target sequence. In some embodiments the payload is an siRNA molecule or fragment of an siRNA molecule.

In some embodiments, the 5' arm of the stem loop structure of the modulatory polynucleotide comprises a nucleic acid sequence encoding a sense sequence. Non-limiting examples of sense sequences, or fragments or variants thereof, which may be encoded by the modulatory polynucleotide are described in Table 3.

In some embodiments, the 3' arm of the stem loop of the modulatory polynucleotide comprises a nucleic acid sequence encoding an antisense sequence. The antisense sequence, in some instances, comprises a "G" nucleotide at the 5' most end. Non-limiting examples of antisense sequences, or fragments or variants thereof, which may be encoded by the modulatory polynucleotide are described in Table 2.

In other embodiments, the sense sequence may reside on the 3' arm while the antisense sequence resides on the 5' arm of the stem of the stem loop structure of the modulatory polynucleotide. Non-limiting examples of sense and antisense sequences which may be encoded by the modulatory polynucleotide are described in Tables 2 and 3.

In one embodiment, the sense and antisense sequences may be completely complementary across a substantial portion of their length. In other embodiments the sense sequence and antisense sequence may be at least 70, 80, 90, 95 or 99% complementarity across independently at least 50, 60, 70, 80, 85, 90, 95, or 99% of the length of the strands.

Neither the identity of the sense sequence nor the homology of the antisense sequence need to be 100% complementarity to the target sequence.

In one embodiment, separating the sense and antisense sequence of the stem loop structure of the modulatory polynucleotide is a loop sequence (also known as a loop motif, linker or linker motif). The loop sequence may be of any length, between 4-30 nucleotides, between 4-20 nucleotides, between 4-15 nucleotides, between 5-15 nucleotides, between 6-12 nucleotides, 6 nucleotides, 7 nucleotides, 8 nucleotides, 9 nucleotides, 10 nucleotides, 11 nucleotides, 12 nucleotides, 13 nucleotides, 14 nucleotides, and/or 15 nucleotides.

In some embodiments, the loop sequence comprises a nucleic acid sequence encoding at least one UGUG motif. In some embodiments, the nucleic acid sequence encoding the UGUG motif is located at the 5' terminus of the loop sequence.

In one embodiment, spacer regions may be present in the modulatory polynucleotide to separate one or more modules (e.g., 5' flanking region, loop motif region, 3' flanking region, sense sequence, antisense sequence) from one another. There may be one or more such spacer regions present.

In one embodiment, a spacer region of between 8-20, i.e., 8, 9, 10, 11, 12, 13, 14, 15, 16, 17, 18, 19, or 20 nucleotides may be present between the sense sequence and a flanking region sequence.

In one embodiment, the length of the spacer region is 13 nucleotides and is located between the 5' terminus of the sense sequence and the 3' terminus of the flanking sequence. In one embodiment, a spacer is of sufficient length to form approximately one helical turn of the sequence.

In one embodiment, a spacer region of between 8-20, i.e., 8, 9, 10, 11, 12, 13, 14, 15, 16, 17, 18, 19, or 20 nucleotides may be present between the antisense sequence and a flanking sequence.

In one embodiment, the spacer sequence is between 10-13, i.e., 10, 11, 12 or 13 nucleotides and is located between the 3' terminus of the antisense sequence and the 5' terminus of a flanking sequence. In one embodiment, a spacer is of sufficient length to form approximately one helical turn of the sequence.

In one embodiment, the molecular scaffold of the modulatory polynucleotide comprises in the 5' to 3' direction, a 5' flanking sequence, a 5' arm, a loop motif, a 3' arm and a 3' flanking sequence. As a non-limiting example, the 5' arm may comprise a nucleic acid sequence encoding a sense sequence and the 3' arm comprises a nucleic acid sequence encoding the antisense sequence. In another non-limiting example, the 5' arm comprises a nucleic acid sequence encoding the antisense sequence and the 3' arm comprises a nucleic acid sequence encoding the sense sequence.

In one embodiment, the 5' arm, sense and/or antisense sequence, loop motif and/or 3' arm sequence may be altered (e.g., substituting 1 or more nucleotides, adding nucleotides and/or deleting nucleotides). The alteration may cause a beneficial change in the function of the construct (e.g., increase knock-down of the target sequence, reduce degradation of the construct, reduce off target effect, increase efficiency of the payload, and reduce degradation of the payload).

In one embodiment, the molecular scaffold of the modulatory polynucleotides is aligned in order to have the rate of excision of the guide strand (also referred to herein as the antisense strand) be greater than the rate of excision of the passenger strand (also referred to herein as the sense strand). The rate of excision of the guide or passenger strand may be, independently, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99% or more than 99%. As a non-limiting example, the rate of excision of the guide strand is at least 80%. As another non-limiting example, the rate of excision of the guide strand is at least 90%.

In one embodiment, the rate of excision of the guide strand is greater than the rate of excision of the passenger strand. In one aspect, the rate of excision of the guide strand may be at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99% or more than 99% greater than the passenger strand.

In one embodiment, the efficiency of excision of the guide strand is at least 60%, 65%, 70%, 75%, 80%, 85%, 90%, 95%, 99% or more than 99%. As a non-limiting example, the efficiency of the excision of the guide strand is greater than 80%.

In one embodiment, the efficiency of the excision of the guide strand is greater than the excision of the passenger strand from the molecular scaffold. The excision of the guide strand may be 2, 3, 4, 5, 6, 7, 8, 9, 10 or more than 10 times more efficient than the excision of the passenger strand from the molecular scaffold.

In one embodiment, the molecular scaffold comprises a dual-function targeting modulatory polynucleotide. As used herein, a "dual-function targeting" modulatory polynucleotide is a polynucleotide where both the guide and passenger strands knock down the same target or the guide and passenger strands knock down different targets.

In one embodiment, the molecular scaffold of the modulatory polynucleotides described herein may comprise a 5' flanking region, a loop motif region and a 3' flanking region. Non-limiting examples of the sequences for the 5' flanking region, loop motif region (may also be referred to as a linker region) and the 3' flanking region which may be used, or fragments thereof used, in the modulatory polynucleotides described herein are shown in Tables 5-7.

TABLE 5

5' Flanking Regions for Molecular Scaffold

| 5' Flanking Region Name | 5' Flanking Region Sequence | 5' Flanking Region SEQ ID |
|---|---|---|
| 5F1 | GTGCTGGGCGGGGGGCGGCGGGCCCTCCCGC AGAACACCATGCGCTCTTCGGAA | 1255 |
| 5F2 | GAAGCAAAGAAGGGGCAGAGGGAGCCCGTG AGCTGAGTGGGCCAGGGACTGGGAGAAGGAG TGAGGAGGCAGGGCCGGCATGCCTCTGCTGC TGGCCAGA | 1256 |
| 5F3 | GTGCTGGGCGGGGGGCGGCGGGCCCTCCCGC AGAACACCATGCGCTCCACGGAA | 1257 |
| 5F4 | GGGCCCTCCCGCAGAACACCATGCGCTCCAC GGAA | 1258 |

TABLE 5-continued

5' Flanking, Regions for Molecular Scaffold

| 5' Flanking Region Name | 5' Flanking Region Sequence | 5' Flanking Region SEQ ID |
|---|---|---|
| 5F5 | CTCCCGCAGAACACCATGCGCTCCACGGAA | 1259 |
| 5F6 | GTGCTGGGCGGGGGCGGCGGGCCCTCCCGC AGAACACCATGCGCTCCACGGAAG | 1260 |
| 5F7 | GTGCTGGGCGGGGGCGGCGGGCCCTCCCGC AGAACACCATGCGCTCCTCGGAA | 1261 |
| 5F8 | TTTATGCCTCATCCTCTGAGTGCTGAAGGCTT GCTGTAGGCTGTATGCTG | 1262 |
| 5F9 | GTGCTGGGCGGGGGCGGCGGGCCCTCCCGC AGAACACCATGCGCTCTTCGGGA | 1263 |

TABLE 6

Loop Motif Regions for Molecular Scaffold

| Loop Motif Region Name | Loop Motif Region Sequence | Loop Motif Region SEQ ID |
|---|---|---|
| L1 | TGTGACCTGG | 1264 |
| L2 | TGTGATTTGG | 1265 |
| L3 | GTCTGCACCTGTCACTAG | 1266 |
| L4 | GTGACCCAAG | 1267 |
| L5 | GTGGCCACTGAGAAG | 1268 |
| L6 | GTGACCCAAT | 1269 |
| L7 | GTGACCCAAC | 1270 |
| L8 | GTGGCCACTGAGAAA | 1271 |
| L9 | TATAATTTGG | 1272 |
| L10 | CCTGACCCAGT | 1273 |

TABLE 7

3' Flanking Regions for Molecular Scaffold

| 3' Flanking Region Name | 3' Flanking Region Sequence | 3' Flanking Region SEQ ID |
|---|---|---|
| 3F1 | CTGAGGAGCGCCTTGACAGCAGCCATGGGAG GGCCGCCCCCTACCTCAGTGA | 1274 |
| 3F2 | CTGTGGAGCGCCTTGACAGCAGCCATGGGAG GGCCGCCCCCTACCTCAGTGA | 1275 |
| 3F3 | TGGCCGTGTAGTGCTACCCAGCGCTGGCTGCC TCCTCAGCATTGCAATTCCTCTCCCATCTGGG CACCAGTCAGCTACCCTGGTGGGAATCTGGGT AGCC | 1276 |
| 3F4 | CTGAGGAGCGCCTTGACAGCAGCCATGGGAG GGCC | 1277 |

TABLE 7-continued

3' Flanking Regions for Molecular Scaffold

| 3' Flanking Region Name | 3' Flanking Region Sequence | 3' Flanking Region SEQ ID |
|---|---|---|
| 3F5 | CTGCGGAGCGCCTTGACAGCAGCCATGGGAG GGCCGCCCCCTACCTCAGTGA | 1278 |
| 3F6 | AGTGTATGATGCCTGTTACTAGCATTCACATG GAACAAATTGCTGCCGTG | 1279 |
| 3F7 | TCCTGAGGAGCGCCTTGACAGCAGCCATGGG AGGGCCGCCCCCTACCTCAGTGA | 1280 |

In one embodiment, the molecular scaffold may comprise at least one 5' flanking region, fragment or variant thereof listed in Table 5. As a non-limiting example, the 5' flanking region may be 5F1, 5F2, 5F3, 5F4, 5F5, 5F6, 5F7, 5F8, or 5F9.

In one embodiment, the molecular scaffold may comprise at least one 5F1 flanking region.

In one embodiment, the molecular scaffold may comprise at least one 5F2 flanking region.

In one embodiment, the molecular scaffold may comprise at least one 5F3 flanking region.

In one embodiment, the molecular scaffold may comprise at least one 5F4 flanking region.

In one embodiment, the molecular scaffold may comprise at least one 5F5 flanking region.

In one embodiment, the molecular scaffold may comprise at least one 5F6 flanking region.

In one embodiment, the molecular scaffold may comprise at least one 5F7 flanking region.

In one embodiment, the molecular scaffold may comprise at least one 5F8 flanking region.

In one embodiment, the molecular scaffold may comprise at least one 5F9 flanking region.

In one embodiment, the molecular scaffold may comprise at least one loop motif region, fragment or variant thereof listed in Table 6. As a non-limiting example, the loop motif region may be L1, L2, L3, L4, L5, L6, L7, L8, L9, or L10.

In one embodiment, the molecular scaffold may comprise at least one L1 loop motif region.

In one embodiment, the molecular scaffold may comprise at least one L2 loop motif region.

In one embodiment, the molecular scaffold may comprise at least one L3 loop motif region.

In one embodiment, the molecular scaffold may comprise at least one L4 loop motif region.

In one embodiment, the molecular scaffold may comprise at least one L5 loop motif region.

In one embodiment, the molecular scaffold may comprise at least one L6 loop motif region.

In one embodiment, the molecular scaffold may comprise at least one L7 loop motif region.

In one embodiment, the molecular scaffold may comprise at least one L8 loop motif region.

In one embodiment, the molecular scaffold may comprise at least one L9 loop motif region.

In one embodiment, the molecular scaffold may comprise at least one L10 loop motif region.

In one embodiment, the molecular scaffold may comprise at least one 3' flanking region, fragment or variant thereof listed in Table 7. As a non-limiting example, the 3' flanking region may be 3F1, 3F2, 3F3, 3F4, 3F5, 3F6, or 3F7.

In one embodiment, the molecular scaffold may comprise at least one 3F1 flanking region.

In one embodiment, the molecular scaffold may comprise at least one 3F2 flanking region.

In one embodiment, the molecular scaffold may comprise at least one 3F3 flanking region.

In one embodiment, the molecular scaffold may comprise at least one 3F4 flanking region.

In one embodiment, the molecular scaffold may comprise at least one 3F5 flanking region.

In one embodiment, the molecular scaffold may comprise at least one 3F6 flanking region.

In one embodiment, the molecular scaffold may comprise at least one 3F7 flanking region.

In one embodiment, the molecular scaffold may comprise at least one 5' flanking region, fragment or variant thereof, and at least one loop motif region, fragment or variant thereof, as described in Tables 5 and 6. As a non-limiting example, the 5' flanking region and the loop motif region may be 5F1 and L1, 5F1 and L2, 5F1 and L3, 5F1 and L4, 5F1 and L5, 5F1 and L6, 5F1 and L7, 5F1 and L8, 5F1 and L9, 5F1 and L0, 5F2 and L1, 5F2 and L2, 5F2 and L3, 5F2 and L4, 5F2 and L5, 5F2 and L6, 5F2 and L7, 5F2 and L8, 5F2 and L9, 5F2 and L10, 5F3 and L1, 5F3 and L2, 5F3 and L3, 5F3 and L4, 5F3 and L5, 5F3 and L6, 5F3 and L7, 5F3 and L8, 5F3 and L9, 5F3 and L10, 5F4 and L1, 5F4 and L2, 5F4 and L3, 5F4 and L4, 5F4 and L5, 5F4 and L6, 5F4 and L7, 5F4 and L8, 5F4 and L9, 5F4 and L10, 5F5 and L1, 5F5 and L2, 5F5 and L3, 5F5 and L4, 5F5 and L5, 5F5 and L6, 5F5 and L7, 5F5 and L8, 5F5 and L9, 5F5 and L10, 5F6 and L1, 5F6 and L2, 5F6 and L3, 5F6 and L5, 5F6 and L5, 5F6 and L6, 5F6 and L7, 5F6 and L8, 5F6 and L9, 5F6 and L10, 5F7 and L1, 5F7 and L2, 5F7 and L3, 5F7 and L4, 5F7 and L5, 5F7 and L6, 5F7 and L7, 5F7 and L8, 5F7 and L9, 5F7 and L0, 5F8 and L1, 5F8 and L2, 5F8 and L3, 5F8 and L4, 5F8 and L5, 5F8 and L6, 5F8 and L7, 5F8 and L8, 5F8 and L9, 5F8 and L10, 5F9 and L1, 5F9 and L2, 5F9 and L3, 5F9 and L4, 5F9 and L5, 5F9 and L6, 5F9 and L7, 5F9 and L8, 5F9 and L9, and 5F9 and L10.

In one embodiment, the molecular scaffold may comprise at least one 5F2 flanking region and at least one L1 loop motif region.

In one embodiment, the molecular scaffold may comprise at least one 5F1 flanking region and at least one L4 loop motif region.

In one embodiment, the molecular scaffold may comprise at least one 5F7 flanking region and at least one L8 loop motif region.

In one embodiment, the molecular scaffold may comprise at least one 5F3 flanking region and at least one L4 loop motif region.

In one embodiment, the molecular scaffold may comprise at least one 5F3 flanking region and at least one L5 loop motif region.

In one embodiment, the molecular scaffold may comprise at least one 5F4 flanking region and at least one L4 loop motif region.

In one embodiment, the molecular scaffold may comprise at least one 5F3 flanking region and at least one L7 loop motif region.

In one embodiment, the molecular scaffold may comprise at least one 5F5 flanking region and at least one L4 loop motif region.

In one embodiment, the molecular scaffold may comprise at least one 5F6 flanking region and at least one L4 loop motif region.

In one embodiment, the molecular scaffold may comprise at least one 5F3 flanking region and at least one L6 loop motif region.

In one embodiment, the molecular scaffold may comprise at least one 5F7 flanking region and at least one L4 loop motif region.

In one embodiment, the molecular scaffold may comprise at least one 5F2 flanking region and at least one L2 loop motif region.

In one embodiment, the molecular scaffold may comprise at least one 5F1 flanking region and at least one L1 loop motif region.

In one embodiment, the molecular scaffold may comprise at least one 5F1 flanking region and at least one L2 loop motif region.

In one embodiment, the molecular scaffold may comprise at least one 3' flanking region, fragment or variant thereof, and at least one motif region, fragment or variant thereof, as described in Tables 6 and 7. As a non-limiting example, the 3' flanking region and the loop motif region may be 3F1 and L1, 3F1 and L2, 3F1 and L3, 3F1 and L4, 3F1 and L5, 3F1 and L6, 3F1 and L7, 3F1 and L8, 3F1 and L9, 3F1 and L0, 3F2 and L1, 3F2 and L2, 3F2 and L3, 3F2 and L4, 3F2 and L5, 3F2 and L6, 3F2 and L7, 3F2 and L8, 3F2 and L9, 3F2 and L0, 3F3 and L1, 3F3 and L2, 3F3 and L3, 3F3 and L4, 3F3 and L5, 3F3 and L6, 3F3 and L7, 3F3 and L5, 3F3 and L9, 3F3 and L10, 3F4 and L1, 3F4 and L2, 3F4 and L3, 3F4 and L4, 3F4 and L5, 3F4 and L6, 3F4 and L7, 3F4 and L8, 3F4 and L9, 3F4 and L0, 3F5 and L1, 3F5 and L2, 3F5 and L3, 3F5 and L4, 3F5 and L5, 3F5 and L6, 3F5 and L7, 3F5 and L8, 3F5 and L9, 3F5 and L10, 3F6 and L1, 3F6 and L2, 3F6 and L3, 3F6 and L4, 3F6 and L5, 3F6 and L6, 3F6 and L7, 3F6 and L8, 3F6 and L9, 3F6 and L0, 3F7 and L1, 3F7 and L2, 3F7 and L3, 3F7 and L4, 3F7 and L5, 3F7 and L6, 3F7 and L7, 3F7 and L8, 3F7 and L9, and 3F7 and L10.

In one embodiment, the molecular scaffold may comprise at least one L1 loop motif region and at least one 3F2 flanking region.

In one embodiment, the molecular scaffold may comprise at least one L4 loop motif region and at least one 3F1 flanking region.

In one embodiment, the molecular scaffold may comprise at least one L8 loop motif region and at least one 3F5 flanking region.

In one embodiment, the molecular scaffold may comprise at least one L5 loop motif region and at least 3F1 flanking region.

In one embodiment, the molecular scaffold may comprise at least one L4 loop motif region and at least one 3F4 flanking region.

In one embodiment, the molecular scaffold may comprise at least one L7 loop motif region and at least one 3F1 flanking region.

In one embodiment, the molecular scaffold may comprise at least one L6 loop motif region and at least one 3F1 flanking region.

In one embodiment, the molecular scaffold may comprise at least one L4 loop motif region and at least one 3F5 flanking region.

In one embodiment, the molecular scaffold may comprise at least one L2 loop motif region and at least one 3F2 flanking region.

In one embodiment, the molecular scaffold may comprise at least one L1 loop motif region and at least one 3F3 flanking region.

In one embodiment, the molecular scaffold may comprise at least one L5 loop motif region and at least one 3F4 flanking region.

In one embodiment, the molecular scaffold may comprise at least one L loop motif region and at least one 3F1 flanking region.

In one embodiment, the molecular scaffold may comprise at least one L2 loop motif region and at least one 3F1 flanking region.

In one embodiment, the molecular scaffold may comprise at least one 5' flanking region, fragment or variant thereof, and at least one 3' flanking region, fragment or variant thereof, as described in Tables 5 and 7. As a non-limiting example, the flanking regions may be 5F1 and 3F1, 5F1 and 3F2, 5F1 and 3F3, 5F1 and 3F4, 5F1 and 3F5, 5F1 and 3F6, 5F1 and 3F7, 5F2 and 3F1, 5F2 and 3F2, 5F2 and 3F3, 5F2 and 3F4, 5F2 and 3F5, 5F2 and 3F6, 5F2 and 3F7, 5F3 and 3F1, 5F3 and 3F2, 5F3 and 3F3, 5F3 and 3F4, 5F3 and 3F5, 5F3 and 3F6, 5F3 and 3F7, 5F4 and 3F1, 5F4 and 3F2, 5F4 and 3F3, 5F4 and 3F4, 5F4 and 3F5, 5F4 and 3F6, 5F4 and 3F7, 5F5 and 3F1, 5F5 and 3F2, 5F5 and 3F3, 5F5 and 3F4, 5F5 and 3F5, 5F5 and 3F6, 5F5 and 3F7, 5F6 and 3F1, 5F6 and 3F2, 5F6 and 3F3, 5F6 and 3F4, 5F6 and 3F5, 5F6 and 3F6, 5F6 and 3F7, 5F7 and 3F1, 5F7 and 3F2, 5F7 and 3F3, 5F7 and 3F4, 5F7 and 3F5, 5F7 and 3F6, 5F7 and 3F7, 5F8 and 3F1, 5F8 and 3F2, 5F8 and 3F3, 5F8 and 3F4, 5F8 and 3F5, 5F8 and 3F6, and 5F8 and 3F7, 5F9 and 3F1, 5F9 and 3F2, 5F9 and 3F3, 5F9 and 3F4, 5F9 and 3F5, 5F9 and 3F6, and 5F9 and 3F7

In one embodiment, the molecular scaffold may comprise at least one 5F2 5' flanking region and at least one 3F2 3' flanking region.

In one embodiment, the molecular scaffold may comprise at least one 5F1 5' flanking region and at least one 3F1 3' flanking region.

In one embodiment, the molecular scaffold may comprise at least one 5F7 5' flanking region and at least one 3F5 3' flanking region.

In one embodiment, the molecular scaffold may comprise at least one 5F3 5' flanking region and at least one 3F1 3' flanking region.

In one embodiment, the molecular scaffold may comprise at least one 5F4 5' flanking region and at least one 3F4 3' flanking region.

In one embodiment, the molecular scaffold may comprise at least one 5F5 5' flanking region and at least one 3F4 3' flanking region.

In one embodiment, the molecular scaffold may comprise at least one 5F6 5' flanking region and at least one 3F1 3' flanking region.

In one embodiment, the molecular scaffold may comprise at least one 5F2 5' flanking region and at least one 3F3 3' flanking region.

In one embodiment, the molecular scaffold may comprise at least one 5F3 5' flanking region and at least one 3F4 3' flanking region.

In one embodiment, the molecular scaffold may comprise at least one 5F1 5' flanking region and at least one 3F2 3' flanking region.

In one embodiment, the molecular scaffold may comprise at least one 5' flanking region, fragment or variant thereof, at least one loop motif region, fragment or variant thereof, and at least one 3' flanking region as described in Tables 5-7. As a non-limiting example, the flanking and loop motif regions may be 5F1, L1 and 3F1; 5F1, L1 and 3F2; 5F1, L1 and 3F3; 5F1, L1 and 3F4; 5F1, L1 and 3F5; 5F1, L1 and 3F6; 5F1, L1 and 3F7; 5F2, L1 and 3F1; 5F2, L1 and 3F2; 5F2, L1 and 3F3; 5F2, L1 and 3F4; 5F2, L1 and 3F5; 5F2, L1 and 3F6; 5F2, L1 and 3F7; 5F3, L1 and 3F1; 5F3, L1 and 3F2; 5F3, L1 and 3F3; 5F3, L1 and 3F4; 5F3, L1 and 3F5; 5F3, L1 and 3F6; 5F3, L1 and 3F7; 5F4, L1 and 3F1; 5F4, L1 and 3F2; 5F4, L1 and 3F3; 5F4, L1 and 3F4; F4, L1 and 3F5; 5F4, L1 and 3F6; 5F4, L1 and 3F7; 5F5, L1 and 3F1; 5F5, L1 and 3F2; 5F5, L1 and 3F3; 5F5, L1 and 3F4; 5F5, L1 and 3F5; 5F5, L1 and 3F6; 5F5, L1 and 3F7; 5F6, L1 and 3F1; 5F6, L1 and 3F2; 5F6, L1 and 3F3; 5F6, L1 and 3F4; 5F6, L1 and 3F5; 5F6, L1 and 3F6; 5F6, L1 and 3F7; 5F7, L1 and 3F1, 5F7, L1 and 3F2; 5F7, L1 and 3F3; 5F7, L1 and 3F4; 5F7, L1 and 3F5; 5F7, L1 and 3F6; 5F7, L1 and 3F7; 5F8, L1 and 3F1; 5F8, L1 and 3F2; 5F8, L1 and 3F3; 5F8, L1 and 3F4; 5F8, L1 and 3F5; 5F8, L1 and 3F6; 5F8, L1 and 3F7; 5F9, L1 and 3F1; 5F9, L1 and 3F2; 5F9, L1 and 3F3; 5F9, L1 and 3F4; 5F9, L1 and 3F5; 5F9, L1 and 3F6; 5F9, L1 and 3F7; 5F1, L2 and 3F1; 5F1, L2 and 3F2; 5F1, L2 and 3F3; 5F1, L2 and 3F4; 5F1, L2 and 3F5; 5F1, L2 and 3F6; 5F1, L2 and 3F7; 5F2, L2 and 3F1; 5F2, L2 and 3F2; 5F2, L2 and 3F3; 5F2, L2 and 3F4; 5F2, L2 and 3F5; 5F2, L2 and 3F6; 5F2, L2 and 3F7; 5F3, L2 and 3F1; 5F3, L2 and 3F2; 5F3, L2 and 3F3; 5F3, L2 and 3F4; 5F3, L2 and 3F5; 5F3, L2 and 3F6, 5F3, L2 and 3F7; 5F4, L2 and 3F1; 5F4, L2 and 3F2; 5F4, L2 and 3F3; 5F4, L2 and 3F4; 5F4, L2 and 3F5; 5F4, L2 and 3F6; 5F4, L2 and 3F7; 5F5, L2 and 3F1; 5F5, L2 and 3F2; 5F5, L2 and 3F3; 5F5, L2 and 3F4; 5F5, L2 and 3F5; 5F5, L2 and 3F6; 5F5, L2 and 3F7; 5F6, L2 and 3F1; 5F6, L2 and 3F2; 5F6, L2 and 3F3; 5F6, L2 and 3F4; 5F6, L2 and 3F5; 5F6, L2 and 3F6; 5F6, L2 and 3F7; 5F7, L2 and 3F1; 5F7, L2 and 3F2; 5F7, L2 and 3F3; 5F7, L2 and 3F4; 5F7, L2 and 3F5; 5F7, L2 and 3F6; 5F7, L2 and 3F7; 5F8, L2 and 3F1; 5F8, L2 and 3F2; 5F8, L2 and 3F3; 5F8, L2 and 3F4; 5F8, L2 and 3F5; 5F8, L2 and 3F6; 5F8, L2 and 3F7; 5F9, L2 and 3F1; 5F9, L2 and 3F2; 5F9, L2 and 3F3; 5F9, L2 and 3F4; 5F9, L2 and 3F5; 5F9, L2 and 3F6; F9, L2 and 3F7; 5F1, L3 and 3F1; 5F1, L3 and 3F2; 5F1, L3 and 3F3; 5F1, L3 and 3F4; 5F1, L3 and 3F5; 5F1, L3 and 3F6; 5F1, L3 and 3F7; 5F2, L3 and 3F1; 5F2, L3 and 3F2; 5F2, L3 and 3F3; 5F2, L3 and 3F4; 5F2, L3 and 3F5; 5F2, L3 and 3F6; 5F2, L3 and 3F7; 5F3, L3 and 3F1; 5F3, L3 and 3F2; 5F3, L3 and 3F3; 5F3, L3 and 3F4; 5F3, L3 and 3F5; 5F3, L3 and 3F6; 5F3, L3 and 3F7; 5F4, L3 and 3F1; 5F4, L3 and 3F2; 5F4, L3 and 3F3; 5F4, L3 and 3F4; 5F4, L3 and 3F5; 5F4, L3 and 3F6; 5F4, L3 and 3F7; 5F5, L3 and 3F1; 5F5, L3 and 3F2; 5F5, L3 and 3F3; 5F5, L3 and 3F4; 5F5, L3 and 3F5; 5F5, L3 and 3F6; 5F5, L3 and 3F7; 5F6, L3 and 3F1; 5F6, L3 and 3F2; 5F6, L3 and 3F3; 5F6, L3 and 3F4; 5F6, L3 and 3F5; 5F6, L3 and 3F6; 5F6, L3 and 3F7; 5F7, L3 and 3F1; 5F7, L3 and 3F2; 5F7, L3 and 3F3; 5F7, L3 and 3F4; 5F7, L3 and 3F5; 5F7, L3 and 3F6; 5F7, L3 and 3F7; 5F8, L3 and 3F1; 5F8, L3 and 3F2; 5F8, L3 and 3F3; 5F8, L3 and 3F4; 5F8, L3 and 3F5; 5F8, L3 and 3F6; 5F8, L3 and 3F7; 5F9, L3 and 3F1; 5F9, L3 and 3F2; 5F9, L3 and 3F3; 5F9, L3 and 3F4; 5F9, L3 and 3F5; 5F9, L3 and 3F6; 5F9, L3 and 3F7; 5F1, L4 and 3F1; 5F1, L4 and 3F2; 5F1, L4 and 3F3; 5F1, L4 and 3F4; 5F1, L4 and 3F5; 5F1, L4 and 3F6; 5F1, L4 and 3F7, 5F2, L4 and 3F; 5F2, L4 and 3F2; 5F2, L4 and 3F3; 5F2, L4 and 3F4; 5F2, L4 and 3F5; 5F2, L4 and 3F6; 5F2, L4 and 3F7; 5F3, L4 and 3F1; 5F3, L4 and 3F2; 5F3, L4 and 3F3; 5F3, L4 and 3F4; 5F3, L4 and 3F5; 5F3, L4 and 3F6; 5F3, L4 and 3F7; 5F4, L4 and 3F1; 5F4, L4 and 3F2; 5F4, L4 and 3F3; 5F4, L4 and 3F4; 5F4, L4 and 3F5; 5F4, L4 and 3F6; 5F4, L4 and 3F7; 5F5, L4 and 3F; 5F5, L4 and 3F2; 5F5, L4 and 3F3; 5F5, L4 and 3F4; 5F5, L4 and 3F5; 5F5, L4 and 3F6; 5F5, L4 and 3F7; 5F6, L4 and 3F1; 5F6, L4 and 3F2; 5F6, L4 and 3F3; 5F6, L4 and 3F4; 5F6, L4 and 3F5; 5F6, L4 and 3F6; 5F6, L4 and 3F7; 5F7, L4 and 3F1; 5F7, L4 and 3F2; 5F7, L4 and 3F3; 5F7, L4 and 3F4; 5F7, L4 and 3F5; 5F7, L4 and 3F6; 5F7, L4 and 3F7; 5F8, L4 and 3F1; 5F8, L4 and 3F2; 5F8, L4 and 3F3; 5F8, L4 and 3F4; 5F8, L4 and 3F5; 5F8, L4 and 3F6; 5F8, L4 and 3F7; 5F9, L4 and 3F1; 5F9, L4 and 3F2; 5F9, L4 and 3F3; 5F9, L4 and 3F4; 5F9, L4 and 3F5; 5F9, L4 and 3F6; 5F9, L4 and 3F7; 5F1, L5 and 3F1; 5F1, L5 and 3F2; 5F1, L5 and 3F3; 5F1, L5 and 3F4; 5F1, L5 and 3F5; 5F1, L5 and 3F6 S5F1, L5 and 3F7; 5F2, L5 and 3F1; 5F2, L5 and 3F2; 5F2, L5 and 3F3; 5F2, L5 and 3F4; 5F2, L5 and 3F5; 5F2, L5 and 3F6; 5F2, L5 and 3F7; 5F3, L5 and 3F1; 5F3, L5 and 3F2; 5F3, L5 and 3F3; 5F3, L5 and 3F4; 5F3, L5 and 3F5; 5F3, L5 and 3F6; 5F3, L5 and 3F7; 5F4, L5 and 3F1; 5F4, L5 and 3F2; 5F4, L5 and 3F3; 5F4, L5 and 3F4; 5F4, L5 and 3F5; 5F4, L5 and 3F6; 5F4, L5 and 3F7; 5F5, L5 and 3F1; 5F5, L5 and 3F2; 5F5, L5 and 3F3; 5F5, L5 and 3F4; 5F5, L5 and 3F5; 5F5, L5 and 3F6; 5F5, L5 and 3F7; 5F6, L5 and 3F1; 5F6, L5 and 3F2; 5F6, L5 and 3F3; 5F6, L5 and 3F4; 5F6, L5 and 3F5; 5F6, L5 and 3F6; 5F6, L5 and 3F7; 5F7, L5 and 3F1; 5F7, L5 and 3F2; 5F7, L5 and 3F3; 5F7, L5 and 3F4; 5F7, L5 and 3F5; 5F7, L5 and 3F6; 5F7, L5 and 3F7; 5F8, L5 and 3F1; 5F8, L5 and 3F2; 5F8, L5 and 3F3; 5F8, L5 and 3F4; 5F8, L5 and 3F5; 5F8, L5 and 3F6; 5F8, L5 and 3F7; 5F9, L5 and 3F1; 5F9, L5 and 3F2; 5F9, L5 and 3F3; 5F9, L5 and 3F4; 5F9, L5 and 3F5; 5F9, L5 and 3F6; 5F9, L5 and 3F7; 5F1, L6 and 3F1; 5F1, L6 and 3F2 S5F1, L6 and 3F3; 5F1, L6 and 3F4; 5F1, L6 and 3F5; 5F1, L6 and 3F6; 5F1, L6 and 3F7; 5F2, L6 and 3F1; 5F2, L6 and 3F2; 5F2, L6 and 3F3; 5F2, L6 and 3F4; 5F2, L6 and 3F5; 5F2, L6 and 3F6; 5F2, L6 and 3F7; 5F3, L6 and 3F1; 5F3, L6 and 3F2; 5F3, L6 and 3F3; 5F3, L6 and 3F4; 5F3, L6 and 3F5; 5F3, L6 and 3F6; 5F3, L6 and 3F7; 5F4, L6 and 3F1; 5F4, L6 and 3F2; 5F4, L6 and 3F3; 5F4, L6 and 3F4; 5F4, L6 and 3F5; 5F4, L6 and 3F6; 5F4, L6 and 3F7; 5F5, L6 and 3F1; 5F5, L6 and 3F2; 5F5, L6 and 3F3; 5F5, L6 and 3F4; 5F5, L6 and 3F5; 5F5, L6 and 3F6; 5F5, L6 and 3F7; 5F6, L6 and 3F1; 5F6, L6 and 3F2; 5F6, L6 and 3F3; 5F6, L6 and 3F4; 5F6, L6 and 3F5; 5F6, L6 and 3F6; 5F6, L6 and 3F7; 5F7, L6 and 3F1; 5F7, L6 and 3F2; 5F7, L6 and 3F3; 5F7, L6 and 3F4; 5F7, L6 and 3F5; 5F7, L6 and 3F6; 5F7, L6 and 3F7; 5F8, L6 and 3F1; 5F8, L6 and 3F2; 5F8, L6 and 3F3; 5F8, L6 and 3F4; 5F8, L6 and 3F5; 5F8, L6 and 3F6; 5F8, L6 and 3F7; 5F9, L6 and 3F1, 5F9, L6 and 3F2; 5F9, L6 and 3F3; 5F9, L6 and 3F4; 5F9, L6 and 3F5; 5F9, L6 and 3F6; 5F9, L6 and 3F7; 5F1, L7 and 3F1; 5F1, L7 and 3F2; 5F1, L7 and 3F3; 5F1, L7 and 3F4; 5F1, L7 and 3F5; 5F1, L7 and 3F6; 5F1, L7 and 3F7; 5F2, L7 and 3F1; 5F2, L7 and 3F2; 5F2, L7 and 3F3; 5F2, L7 and 3F4; 5F2, L7 and 3F5; 5F2, L7 and 3F6; 5F2, L7 and 3F7; 5F3, L7 and 3F1; 5F3, L7 and 3F2; 5F3, L7 and 3F3; 5F3, L7 and 3F4; 5F3, L7 and 3F5; 5F3, L7 and 3F6; 5F3, L7 and 3F7; 5F4, L7 and 3F1; 5F4, L7 and 3F2; 5F4, L7 and 3F3; 5F4, L7 and 3F4; 5F4, L7 and 3F5; 5F4, L7 and 3F6; 5F4, L7 and 3F7; 5F5, L7 and 3F1; 5F5, L7 and 3F2; 5F5, L7 and 3F3; 5F5, L7 and 3F4; 5F5, L7 and 3F5; 5F5, L7 and 3F6; 5F5, L7 and 3F7; 5F6, L7 and 3F1; 5F6, L7 and 3F2; 5F6, L7 and 3F3; 5F6, L7 and 3F4; 5F6, L7 and 3F5; 5F6, L7 and 3F6; 5F6, L7 and 3F7; 5F7, L7 and 3F1; 5F7, L7 and 3F2; 5F7, L7 and 3F3; 5F7, L7 and 3F4; 5F7, L7 and 3F5; 5F7, L7 and 3F6; 5F7, L7 and 3F7; 5F8, L7 and 3F1; 5F8, L7 and 3F2; 5F8, L7 and 3F3; 5F8, L7 and 3F4; 5F8, L7 and 3F5; 5F8, L7 and 3F6; 5F8, L7 and 3F7; 5F9, L7 and 3F1; 5F9, L7 and 3F2; 5F9, L7 and 3F3; 5F9, L7 and 3F4; 5F9, L7 and 3F5; 5F9, L7 and 3F6; 5F9, L7 and 3F7; 5F1, L8 and 3F1; 5F1, L8 and 3F2; 5F1, L8 and 3F3; 5F1, L8 and 3F4; 5F1, L8 and 3F5; 5F1, L8 and 3F6; 5F1, L8 and 3F7; 5F2, L8 and 3F1; 5F2, L8 and 3F2; 5F2, L8 and 3F3; 5F2, L8 and 3F4; 5F2, L8 and 3F5; 5F2, L8 and 3F6; 5F2, L8 and 3F7; 5F3, L8 and 3F1; 5F3, L8 and 3F2; 5F3, L8 and 3F3; 5F3, L8 and 3F4; 5F3, L8 and 3F5; 5F3, L8 and 3F6; 5F3, L8 and 3F7; 5F4, L8 and 3F1; 5F4, L8 and 3F2; 5F4, L8 and 3F3; 5F4, L8 and 3F4; 5F4, L8 and 3F5; 5F4, L8 and 3F6; 5F4, L8 and 3F7; 5F5, L8 and 3F1; 5F5, L8 and 3F2; 5F5, L8 and 3F3; 5F5, L8 and 3F4; 5F5, L8 and 3F5; 5F5, L8 and 3F6; 5F5, L8 and 3F7; 5F6, L8 and 3F1; 5F6, L8 and 3F2; 5F6, L8 and 3F3; 5F6, L8 and 3F4; 5F6, L8 and 3F5; 5F6, L8 and 3F6; 5F6, L8 and 3F7; 5F7, L8 and 3F1; 5F7, L8 and 3F2; 5F7, L8 and 3F3; 5F7, L8 and 3F4; 5F7, L8 and 3F5; 5F7, L8 and 3F6; 5F7, L8 and 3F7; 5F8, L8 and 3F1; 5F8, L8 and 3F2; 5F8, L8 and 3F3; 5F8, L8 and 3F4; 5F8, L8 and 3F5; 5F8, L8 and 3F6; 5F8, L8 and 3F7; 5F9, L8 and 3F1; 5F9, L8 and 3F2; 5F9, L8 and 3F3; 5F9, L8 and 3F4; 5F9, L8 and 3F5; 5F9, L8 and 3F6; 5F9, L8 and 3F7; 5F1, L9 and 3F; S5F1, L9 and 3F2; 5F1, L9 and 3F3; 5F1, L9 and 3F4; 5F1, L9 and 3F5; 5F1, L9 and 3F6; F1, L9 and 3F7; 5F2, L9 and 3F1; 5F2, L9 and 3F2; 5F2, L9 and 3F3; 5F2, L9 and 3F4; 5F2, L9 and 3F5; 5F2, L9 and 3F6; 5F2, L9 and 3F7; 5F3, L9 and 3F1; 5F3, L9 and 3F2; 5F3, L9 and 3F3; 5F3, L9 and 3F4; 5F3, L9 and 3F5; 5F3, L9 and 3F6; 5F3, L9 and 3F7; 5F4, L9 and 3F1; 5F4, L9 and 3F2; 5F4, L9 and 3F3; 5F4, L9 and 3F4; 5F4, L9 and 3F5; 5F4, L9 and 3F6; 5F4, L9 and 3F7; 5F5, L9 and 3F1; 5F5, L9 and 3F2; 5F5, L9 and 3F3; 5F5, L9 and 3F4; 5F5, L9 and 3F5; 5F5, L9 and 3F6; 5F5, L9 and 3F7; 5F6, L9 and 3F1; 5F6, L9 and 3F2; 5F6, L9 and 3F3; 5F6, L9 and 3F4; 5F6, L9 and 3F5; 5F6, L9 and 3F6; 5F6, L9 and 3F7; 5F7, L9 and 3F1; 5F7, L9 and 3F2; 5F7, L9 and 3F3; 5F7, L9 and 3F4; 5F7, L9 and 3F5; 5F7, L9 and 3F6; 5F7, L9 and 3F7; 5F8, L9 and 3F1; 5F8, L9 and 3F2; 5F8, L9 and 3F3; 5F8, L9 and 3F4; 5F8, L9 and 3F5; 5F8, L9 and 3F6; 5F8, L9 and 3F7; 5F9, L9 and 3F1; 5F9, L9 and 3F2; 5F9, L9 and 3F3; 5F9, L9 and 3F4; 5F9, L9 and 3F5; 5F9, L9 and 3F6; 5F9, L9 and 3F7; 5F1, L10 and 3F1; 5F1, L10 and 3F2; 5F1, L10 and 3F3; 5F1, L10 and 3F4; 5F1, L10 and 3F5; 5F1, L10 and 3F6; 5F1, L10 and 3F7; 5F2, L10 and 3F1; 5F2, L10 and 3F2; 5F2, L10 and 3F3; 5F2, L10 and 3F4; 5F2, L10 and 3F5; 5F2, L10 and 3F6; 5F2, L10 and 3F7; 5F3, L10 and 3F1; 5F3, L10 and 3F2; 5F3, L10 and 3F3; 5F3, L0 and 3F4; 5F3, L0 and 3F5; 5F3, L0 and 3F6; 5F3, L0 and 3F7; 5F4, L10 and 3F1; 5F4, L10 and 3F2; 5F4, L10 and 3F3; 5F4, L10 and 3F4; 5F4, L10 and 3F5; 5F4, L10 and 3F6; 5F4, L10 and 3F7; 5F5, L10 and 3F1; 5F5, L10 and 3F2; 5F5, L10 and 3F3; 5F5, L10 and 3F4; 5F5, L10 and 3F5; 5F5, L10 and 3F6; 5F5, L10 and 3F7; 5F6, L10 and 3F1; 5F6, L10 and 3F2; 5F6, L10 and 3F3; 5F6, L10 and 3F4; 5F6, L10 and 3F5; 5F6, L10 and 3F6; 5F6, L10 and 3F7; 5F7, L10 and 3F1; 5F7, L10 and 3F2; 5F7, L10 and 3F3; 5F7, L10 and 3F4; 5F7, L10 and 3F5; 5F7, L0 and 3F6; 5F7, L0 and 3F7; 5F8, L0 and 3F1; 5F8, L0 and 3F2; 5F8, L10 and 3F3; 5F8, L10 and 3F4; 5F8, L10 and 3F5; 5F8, L10 and 3F6; 5F8, L10 and 3F7; 5F9, L10 and 3F1; 5F9, L10 and 3F2; 5F9, L10 and 3F3; 5F9, L10 and 3F4; 5F9, L10 and 3F5; 5F9, L10 and 3F6; and 5F9, L10 and 3F7.

In one embodiment, the molecular scaffold may comprise at least one 5F2 5' flanking region, at least one L1 loop motif region, and at least one 3F2 3' flanking region.

In one embodiment, the molecular scaffold may comprise at least one 5F1 5' flanking region, at least one L4 loop motif region, and at least one 3F1 3' flanking region.

In one embodiment, the molecular scaffold may comprise at least one 5F7 5' flanking region, at least one L8 loop motif region, and at least one 3F5 3' flanking region.

In one embodiment, the molecular scaffold may comprise at least one 5F3 5' flanking region, at least one L4 loop motif region, and at least one 3F1 3' flanking region.

In one embodiment, the molecular scaffold may comprise at least one 5F3 5' flanking region, at least one L5 loop motif region, and at least one 3F1 3' flanking region.

In one embodiment, the molecular scaffold may comprise at least one 5F4 5' flanking region, at least one L4 loop motif region, and at least one 3F4 3' flanking region.

In one embodiment, the molecular scaffold may comprise at least one 5F3 5' flanking region, at least one L7 loop motif region, and at least one 3F1 3' flanking region.

In one embodiment, the molecular scaffold may comprise at least one 5F5 5' flanking region, at least one L4 loop motif region, and at least one 3F4 3' flanking region.

In one embodiment, the molecular scaffold may comprise at least one 5F6 5' flanking region, at least one L4 loop motif region, and at least one 3F1 3' flanking region.

In one embodiment, the molecular scaffold may comprise at least one 5F3 5' flanking region, at least one L6 loop motif region, and at least one 3F1 3' flanking region.

In one embodiment, the molecular scaffold may comprise at least one 5F7 5' flanking region, at least one L4 loop motif region, and at least one 3F5 3' flanking region.

In one embodiment, the molecular scaffold may comprise at least one 5F2 5' flanking region, at least one L2 loop motif region, and at least one 3F2 3' flanking region.

In one embodiment, the molecular scaffold may comprise at least one 5F2 5' flanking region, at least one L1 loop motif region, and at least one 3F3 3' flanking region.

In one embodiment, the molecular scaffold may comprise at least one 5F3 5' flanking region, at least one L5 loop motif region, and at least one 3F4 3' flanking region.

In one embodiment, the molecular scaffold may comprise at least one 5F1 5' flanking region, at least one L1 loop motif region, and at least one 3F1 3' flanking region.

In one embodiment, the molecular scaffold may comprise at least one 5F1 5' flanking region, at least one L2 loop motif region, and at least one 3F1 3' flanking region.

In one embodiment, the molecular scaffold may comprise at least one 5F1 5' flanking region, at least one L1 loop motif region, and at least one 3F2 3' flanking region.

In one embodiment, the molecular scaffold may comprise at least one 5F2 5' flanking region, at least one L3 loop motif region, and at least one 3F3 3' flanking region.

In one embodiment, the molecular scaffold may be a natural pri-miRNA scaffold. As a non-limiting example, the molecular scaffold may be a scaffold derived from the human miR155 scaffold.

In one embodiment, the molecular scaffold may comprise one or more linkers known in the art. The linkers may separate regions or one molecular scaffold from another. As a non-limiting example, the molecular scaffold may be polycistronic.

Modulatory Polynucleotide Comprising Molecular Scaffold and siRNA Molecules Targeting SOD1

In one embodiment, the modulatory polynucleotide may comprise 5' and 3' flanking regions, loop motif region, and nucleic acid sequences encoding sense sequence and anti-sense sequence as described in Tables 8 and 9. In Tables 8 and 9, the DNA sequence identifier for the passenger and guide strands are described as well as the 5' and 3' Flanking Regions and the Loop region (also referred to as the linker region). In Tables 8 and 9, the "miR" component of the name of the sequence does not necessarily correspond to the sequence numbering of miRNA genes (e.g., VOYSOD1miR-102 is the name of the sequence and does not necessarily mean that miR-102 is part of the sequence).

TABLE 8

SOD1 Modulatory Polynucleotide Sequence Regions (5' to 3')

| Modulatory Polynucleotide Construct Name | 5' Flanking to 3' Flanking SEQ ID NO | 5' Flanking SEQ ID NO | Passenger SEQ ID NO | Loop SEQ ID NO | Guide SEQ ID NO | 3' Flanking SEQ ID NO |
|---|---|---|---|---|---|---|
| VOYSOD1miR-101 | 1281 | 1262 | 1331 | 1268 | 1332 | 1279 |
| VOYSOD1miR-102 | 1282 | 1257 | 1331 | 1268 | 1332 | 1274 |
| VOYSOD1miR-103 | 1283 | 1257 | 1333 | 1268 | 1332 | 1274 |
| VOYSOD1miR-104 | 1284 | 1257 | 1334 | 1268 | 1332 | 1274 |
| VOYSOD1miR-105 | 1285 | 1257 | 1335 | 1268 | 1332 | 1274 |
| VOYSOD1miR-106 | 1286 | 1257 | 1336 | 1268 | 1332 | 1274 |
| VOYSOD1miR-107 | 1287 | 1257 | 1337 | 1268 | 1332 | 1274 |
| VOYSOD1miR-108 | 1288 | 1257 | 1339 | 1268 | 1332 | 1274 |
| VOYSOD1miR-109 | 1289 | 1257 | 1331 | 1264 | 1332 | 1274 |
| VOYSOD1miR-110 | 1290 | 1257 | 1331 | 1272 | 1332 | 1274 |
| VOYSOD1miR-111 | 1291 | 1257 | 1338 | 1273 | 1332 | 1274 |
| VOYSOD1miR-112 | 1292 | 1257 | 1331 | 1268 | 1332 | 1275 |
| VOYSOD1miR-113 | 1293 | 1257 | 1333 | 1268 | 1332 | 1275 |
| VOYSOD1miR-114 | 1294 | 1257 | 1336 | 1268 | 1332 | 1275 |
| VOYSOD1miR-115 | 1295 | 1257 | 1338 | 1273 | 1332 | 1275 |
| VOYSOD1miR-116 | 1296 | 1257 | 1334 | 1268 | 1332 | 1275 |
| VOYSOD1miR-117 | 1297 | 1257 | 1340 | 1268 | 1341 | 1274 |
| VOYSOD1miR-118 | 1298 | 1257 | 1342 | 1268 | 1343 | 1274 |
| VOYSOD1miR-119 | 1299 | 1257 | 1344 | 1268 | 1345 | 1274 |
| VOYSOD1miR-127 | 1300 | 1255 | 1331 | 1265 | 1332 | 1276 |
| VOYSOD1miR-102.860 | 1301 | 1257 | 1346 | 1268 | 1347 | 1274 |
| VOYSOD1miR-102.861 | 1302 | 1257 | 1348 | 1268 | 1349 | 1274 |
| VOYSOD1miR-102.866 | 1303 | 1257 | 1350 | 1268 | 1345 | 1274 |
| VOYSOD1miR-102.870 | 1304 | 1257 | 1351 | 1268 | 1352 | 1274 |
| VOYSOD1miR-102.823 | 1305 | 1257 | 1353 | 1268 | 1343 | 1274 |
| VOYSOD1miR-104.860 | 1306 | 1257 | 1354 | 1268 | 1347 | 1274 |
| VOYSOD1miR-104.861 | 1307 | 1257 | 1355 | 1268 | 1349 | 1274 |
| VOYSOD1miR-104.866 | 1308 | 1257 | 1356 | 1268 | 1345 | 1274 |
| VOYSOD1miR-104.870 | 1309 | 1257 | 1357 | 1268 | 1352 | 1274 |
| VOYSOD1miR-104.823 | 1310 | 1257 | 1358 | 1268 | 1343 | 1274 |
| VOYSOD1miR-109.860 | 1311 | 1257 | 1346 | 1264 | 1347 | 1274 |

TABLE 8-continued

SOD1 Modulatory Polynucleotide Sequence Regions (5' to 3')

| Modulatory Polynucleotide Construct Name | 5' Flanking to 3' Flanking SEQ ID NO | 5' Flanking SEQ ID NO | Passenger SEQ ID NO | Loop SEQ ID NO | Guide SEQ ID NO | 3' Flanking SEQ ID NO |
|---|---|---|---|---|---|---|
| VOYSOD1miR-109.861 | 1312 | 1257 | 1348 | 1264 | 1349 | 1274 |
| VOYSOD1miR-109.866 | 1313 | 1257 | 1350 | 1264 | 1345 | 1274 |
| VOYSOD1miR-109.870 | 1314 | 1257 | 1351 | 1264 | 1352 | 1274 |
| VOYSOD1miR-109.823 | 1315 | 1257 | 1353 | 1264 | 1343 | 1274 |
| VOYSOD1miR-114.860 | 1316 | 1257 | 1359 | 1268 | 1347 | 1275 |
| VOYSOD1miR-114.861 | 1317 | 1257 | 1360 | 1268 | 1349 | 1275 |
| VOYSOD1miR-114.866 | 1318 | 1257 | 1361 | 1268 | 1345 | 1275 |
| VOYSOD1miR-114.870 | 1319 | 1257 | 1362 | 1268 | 1352 | 1275 |
| VOYSOD1miR-114.823 | 1320 | 1257 | 1363 | 1268 | 1343 | 1275 |
| VOYSOD1miR-116.860 | 1321 | 1257 | 1354 | 1268 | 1347 | 1275 |
| VOYSOD1miR-116.861 | 1322 | 1257 | 1355 | 1268 | 1349 | 1275 |
| VOYSOD1miR-116.866 | 1323 | 1257 | 1364 | 1268 | 1345 | 1275 |
| VOYSOD1miR-116.870 | 1324 | 1257 | 1357 | 1268 | 1352 | 1275 |
| VOYSOD1miR-116.823 | 1325 | 1257 | 1358 | 1268 | 1343 | 1275 |
| VOYSOD1miR-127.860 | 1326 | 1255 | 1365 | 1265 | 1347 | 1276 |
| VOYSOD1miR-127.861 | 1327 | 1255 | 1348 | 1265 | 1349 | 1276 |
| VOYSOD1miR-127.866 | 1328 | 1255 | 1350 | 1265 | 1345 | 1276 |
| VOYSOD1miR-127.870 | 1329 | 1255 | 1351 | 1265 | 1352 | 1276 |
| VOYSOD1miR-127.823 | 1330 | 1255 | 1366 | 1265 | 1343 | 1276 |

TABLE 9

SOD1 Modulatory Polynucleotide Sequence Region (5' to 3')

| Name | 5' Flanking to 3' Flanking SEQ ID NO | 5' Flanking SEQ ID NO | Passenger SEQ ID NO | Loop SEQ ID NO | Guide SEQ ID NO | 3' Flanking SEQ ID NO |
|---|---|---|---|---|---|---|
| VOYSOD1miR-120 | 1367 | 1263 | 1368 | 1264 | 1369 | 1280 |

AAV Particles Comprising Modulatory Polynucleotides

In one embodiment, the AAV particle comprises a viral genome with a payload region comprising a modulatory polynucleotide sequences. In such an embodiment, a viral genome encoding more than one polypeptide may be replicated and packaged into a viral particle. A target cell transduced with a viral particle comprising a modulatory polynucleotide may express the encoded sense and/or antisense sequences in a single cell.

In some embodiments, the AAV particles are useful in the field of medicine for the treatment, prophylaxis, palliation or amelioration of neurological diseases and/or disorders.

In one embodiment, the AAV particles comprising modulatory polynucleotide sequence which comprises a nucleic acid sequence encoding at least one siRNA molecule may be introduced into mammalian cells.

Where the AAV particle payload region comprises a modulatory polynucleotide, the modulatory polynucleotide may comprise sense and/or antisense sequences to knock down a target gene. The AAV viral genomes encoding modulatory polynucleotides described herein may be useful in the fields of human disease, viruses, infections veterinary applications and a variety of in vivo and in vitro settings.

In one embodiment, the AAV particle viral genome may comprise at least one inverted terminal repeat (ITR) region. The ITR region(s) may, independently, have a length such as, but not limited to, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, and 175 nucleotides. The length of the ITR region for the viral genome may be 75-80, 75-85, 75-100, 80-85, 80-90, 80-105, 85-90, 85-95, 85-110, 90-95, 90-100, 90-115, 95-100, 95-105, 95-120, 100-105, 100-110, 100-125, 105-110, 105-115, 105-130, 110-115, 110-120, 110-135, 115-120, 115-125, 115-140, 120-125, 120-130, 120-145, 125-130, 125-135, 125-150, 130-135, 130-140, 130-155, 135-140, 135-145, 135-160, 140-145, 140-150, 140-165, 145-150, 145-155, 145-170, 150-155, 150-160, 150-175, 155-160, 155-165, 160-165, 160-170, 165-170, 165-175, and 170-175 nucleotides. As a non-limiting example, the viral genome comprises an ITR that is about 105 nucleotides in length. As a non-limiting example, the viral genome comprises an ITR that is about 141 nucleotides in length. As a non-limiting example, the viral genome comprises an ITR that is about 130 nucleotides in length.

In one embodiment, the AAV particle viral genome may comprises two inverted terminal repeat (ITR) regions. Each of the ITR regions may independently have a length such as, but not limited to, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, and 175 nucleotides. The length of the ITR regions for the viral genome may be 75-80, 75-85, 75-100, 80-85, 80-90, 80-105, 85-90, 85-95, 85-110, 90-95, 90-100, 90-115, 95-100, 95-105, 95-120, 100-105, 100-110, 100-125, 105-110, 105-115, 105-130, 110-115, 110-120, 110-135, 115-

120, 115-125, 115-140, 120-125, 120-130, 120-145, 125-130, 125-135, 125-150, 130-135, 130-140, 130-155, 135-140, 135-145, 135-160, 140-145, 140-150, 140-165, 145-150, 145-155, 145-170, 150-155, 150-160, 150-175, 155-160, 155-165, 160-165, 160-170, 165-170, 165-175, and 170-175 nucleotides. As a non-limiting example, the viral genome comprises an ITR that is about 105 nucleotides in length and 141 nucleotides in length. As a non-limiting example, the viral genome comprises an ITR that is about 105 nucleotides in length and 130 nucleotides in length. As a non-limiting example, the viral genome comprises an ITR that is about 130 nucleotides in length and 141 nucleotides in length.

In one embodiment, the AAV particle viral genome may comprise at least one sequence region as described in Tables 10-17. The regions may be located before or after any of the other sequence regions described herein.

In one embodiment, the AAV particle viral genome comprises at least one inverted terminal repeat (ITR) sequence region. Non-limiting examples of ITR sequence regions are described in Table 10.

TABLE 10

Inverted Terminal Repeat (ITR) Sequence Regions

| Sequence Region Name | SEQ ID NO |
|---|---|
| ITR1 | 1370 |
| ITR2 | 1371 |
| ITR3 | 1372 |
| ITR4 | 1373 |

In one embodiment, the AAV particle viral genome comprises two ITR sequence regions. In one embodiment, the ITR sequence regions are the ITR1 sequence region and the ITR3 sequence region. In one embodiment, the ITR sequence regions are the ITR1 sequence region and the ITR4 sequence region. In one embodiment, the ITR sequence regions are the ITR2 sequence region and the ITR3 sequence region. In one embodiment, the ITR sequence regions are the ITR2 sequence region and the ITR4 sequence region.

In one embodiment, the AAV particle viral genome may comprise at least one multiple cloning site (MCS) sequence region. The MCS region(s) may, independently, have a length such as, but not limited to, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, and 150 nucleotides. The length of the MCS region for the viral genome may be 2-10, 5-10, 5-15, 10-20, 10-30, 10-40, 15-20, 15-25, 20-30, 20-40, 20-50, 25-30, 25-35, 30-40, 30-50, 30-60, 35-40, 35-45, 40-50, 40-60, 40-70, 45-50, 45-55, 50-60, 50-70, 50-80, 55-60, 55-65, 60-70, 60-80, 60-90, 65-70, 65-75, 70-80, 70-90, 70-100, 75-80, 75-85, 80-90, 80-100, 80-110, 85-90, 85-95, 90-100, 90-110, 90-120, 95-100, 95-105, 100-110, 100-120, 100-130, 105-110, 105-115, 110-120, 110-130, 110-140, 115-120, 115-125, 120-130, 120-140, 120-150, 125-130, 125-135, 130-140, 130-150, 135-140, 135-145, 140-150, and 145-150 nucleotides. As a non-limiting example, the viral genome comprises a MCS region that is about 5 nucleotides in length. As a non-limiting example, the viral genome comprises a MCS region that is about 10 nucleotides in length. As a non-limiting example, the viral genome comprises a MCS region that is about 14 nucleotides in length. As a non-limiting example, the viral genome comprises a MCS region that is about 18 nucleotides in length. As a non-limiting example, the viral genome comprises a MCS region that is about 73 nucleotides in length. As a non-limiting example, the viral genome comprises a MCS region that is about 121 nucleotides in length.

In one embodiment, the AAV particle viral genome comprises at least one multiple cloning site (MCS) sequence regions. Non-limiting examples of MCS sequence regions are described in Table 11.

TABLE 11

Multiple Cloning Site (MCS) Sequence Regions

| Sequence Region Name | SEQ ID NO or Sequence |
|---|---|
| MCS1 | 1374 |
| MCS2 | 1375 |
| MCS3 | 1376 |
| MCS4 | 1377 |
| MCS5 | TCGAG |
| MCS6 | 1378 |

In one embodiment, the AAV particle viral genome comprises one MCS sequence region. In one embodiment, the MCS sequence region is the MCS1 sequence region. In one embodiment, the MCS sequence region is the MCS2 sequence region. In one embodiment, the MCS sequence region is the MCS3 sequence region. In one embodiment, the MCS sequence region is the MCS4 sequence region. In one embodiment, the MCS sequence region is the MCS5 sequence region. In one embodiment, the MCS sequence region is the MCS6 sequence region.

In one embodiment, the AAV particle viral genome comprises two MCS sequence regions. In one embodiment, the two MCS sequence regions are the MCS1 sequence region and the MCS2 sequence region. In one embodiment, the two MCS sequence regions are the MCS1 sequence region and the MCS3 sequence region. In one embodiment, the two MCS sequence regions are the MCS1 sequence region and the MCS4 sequence region. In one embodiment, the two MCS sequence regions are the MCS1 sequence region and the MCS5 sequence region. In one embodiment, the two MCS sequence regions are the MCS1 sequence region and the MCS6 sequence region. In one embodiment, the two MCS sequence regions are the MCS2 sequence region and the MCS3 sequence region. In one embodiment, the two MCS sequence regions are the MCS2 sequence region and the MCS4 sequence region. In one embodiment, the two MCS sequence regions are the MCS2 sequence region and the MCS5 sequence region. In one embodiment, the two MCS sequence regions are the MCS2 sequence region and the MCS6 sequence region. In one embodiment, the two MCS sequence regions are the MCS3 sequence region and the MCS4 sequence region. In one embodiment, the two MCS sequence regions are the MCS3 sequence region and the MCS5 sequence region. In one embodiment, the two MCS sequence regions are the MCS3 sequence region and the MCS6 sequence region. In one embodiment, the two MCS sequence regions are the MCS4 sequence region and the MCS5 sequence region. In one embodiment, the two MCS sequence regions are the MCS4 sequence region and the MCS6 sequence region. In one embodiment, the two MCS sequence regions are the MCS5 sequence region and the MCS6 sequence region.

In one embodiment, the AAV particle viral genome comprises two or more MCS sequence regions.

In one embodiment, the AAV particle viral genome comprises three MCS sequence regions. In one embodiment, the three MCS sequence regions are the MCS1 sequence region, the MCS2 sequence region, and the MCS3 sequence region. In one embodiment, the three MCS sequence regions are the MCS1 sequence region, the MCS2 sequence region, and the MCS4 sequence region. In one embodiment, the three MCS sequence regions are the MCS1 sequence region, the MCS2 sequence region, and the MCS5 sequence region. In one embodiment, the three MCS sequence regions are the MCS1 sequence region, the MCS2 sequence region, and the MCS6 sequence region. In one embodiment, the three MCS sequence regions are the MCS1 sequence region, the MCS3 sequence region, and the MCS4 sequence region. In one embodiment, the three MCS sequence regions are the MCS1 sequence region, the MCS3 sequence region, and the MCS5 sequence region. In one embodiment, the three MCS sequence regions are the MCS1 sequence region, the MCS3 sequence region, and the MCS6 sequence region. In one embodiment, the three MCS sequence regions are the MCS1 sequence region, the MCS4 sequence region, and the MCS5 sequence region. In one embodiment, the three MCS sequence regions are the MCS1 sequence region, the MCS4 sequence region, and the MCS6 sequence region. In one embodiment, the three MCS sequence regions are the MCS1 sequence region, the MCS5 sequence region, and the MCS6 sequence region. In one embodiment, the three MCS sequence regions are the MCS2 sequence region, the MCS3 sequence region, and the MCS4 sequence region. In one embodiment, the three MCS sequence regions are the MCS2 sequence region, the MCS3 sequence region, and the MCS5 sequence region. In one embodiment, the three MCS sequence regions are the MCS2 sequence region, the MCS3 sequence region, and the MCS6 sequence region. In one embodiment, the three MCS sequence regions are the MCS2 sequence region, the MCS4 sequence region, and the MCS5 sequence region. In one embodiment, the three MCS sequence regions are the MCS2 sequence region, the MCS4 sequence region, and the MCS6 sequence region. In one embodiment, the three MCS sequence regions are the MCS2 sequence region, the MCS5 sequence region, and the MCS6 sequence region. In one embodiment, the three MCS sequence regions are the MCS3 sequence region, the MCS4 sequence region, and the MCS5 sequence region. In one embodiment, the three MCS sequence regions are the MCS3 sequence region, the MCS4 sequence region, and the MCS6 sequence region. In one embodiment, the three MCS sequence regions are the MCS3 sequence region, the MCS5 sequence region, and the MCS6 sequence region. In one embodiment, the three MCS sequence regions are the MCS4 sequence region, the MCS5 sequence region, and the MCS6 sequence region.

In one embodiment, the AAV particle viral genome may comprise at least one multiple filler sequence region. The filler region(s) may, independently, have a length such as, but not limited to, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, 1567, 1568, 1569, 1570, 1571, 1572, 1573, 1574, 1575, 1576, 1577, 1578, 1579, 1580, 1581, 1582, 1583, 1584, 1585, 1586, 1587, 1588, 1589, 1590, 1591, 1592, 1593, 1594, 1595, 1596, 1597, 1598, 1599, 1600, 1601, 1602, 1603, 1604, 1605, 1606, 1607, 1608, 1609, 1610, 1611, 1612, 1613, 1614, 1615, 1616, 1617, 1618, 1619, 1620, 1621, 1622, 1623, 1624, 1625, 1626, 1627, 1628, 1629, 1630, 1631, 1632, 1633, 1634, 1635, 1636, 1637, 1638, 1639, 1640, 1641, 1642, 1643, 1644, 1645, 1646, 1647, 1648, 1649, 1650, 1651, 1652, 1653, 1654, 1655, 1656, 1657, 1658, 1659, 1660, 1661, 1662, 1663, 1664, 1665, 1666, 1667, 1668, 1669, 1670, 1671, 1672, 1673, 1674, 1675, 1676, 1677, 1678, 1679, 1680, 1681, 1682, 1683, 1684, 1685, 1686, 1687, 1688, 1689, 1690, 1691, 1692, 1693, 1694, 1695, 1696, 1697, 1698, 1699, 1700, 1701, 1702, 1703, 1704, 1705, 1706, 1707, 1708, 1709, 1710, 1711, 1712, 1713, 1714, 1715, 1716, 1717, 1718, 1719, 1720, 1721, 1722, 1723, 1724, 1725, 1726, 1727, 1728, 1729, 1730, 1731, 1732, 1733, 1734, 1735, 1736, 1737, 1738, 1739, 1740, 1741, 1742, 1743, 1744, 1745, 1746, 1747, 1748, 1749, 1750, 1751, 1752, 1753, 1754, 1755, 1756, 1757, 1758, 1759, 1760, 1761, 1762, 1763, 1764, 1765, 1766, 1767, 1768, 1769, 1770, 1771, 1772, 1773, 1774, 1775, 1776, 1777, 1778, 1779, 1780, 1781, 1782, 1783, 1784, 1785, 1786, 1787, 1788, 1789, 1790, 1791, 1792, 1793, 1794, 1795, 1796, 1797, 1798, 1799, 1800, 1801, 1802, 1803, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1828, 1829, 1830, 1831, 1832, 1833, 1834, 1835, 1836, 1837, 1838, 1839, 1840, 1841, 1842, 1843, 1844, 1845, 1846, 1847, 1848, 1849, 1850, 1851, 1852, 1853, 1854, 1855, 1856, 1857, 1858, 1859, 1860, 1861, 1862, 1863, 1864, 1865, 1866, 1867, 1868, 1869, 1870, 1871, 1872, 1873, 1874, 1875, 1876, 1877, 1878, 1879, 1880, 1881, 1882, 1883, 1884, 1885, 1886, 1887, 1888, 1889, 1890, 1891, 1892, 1893, 1894, 1895, 1896, 1897, 1898, 1899, 1900, 1901, 1902, 1903, 1904, 1905, 1906, 1907, 1908, 1909, 1910, 1911, 1912, 1913, 1914, 1915, 1916, 1917, 1918, 1919, 1920, 1921, 1922, 1923, 1924, 1925, 1926, 1927, 1928, 1929, 1930, 1931, 1932, 1933, 1934, 1935, 1936, 1937, 1938, 1939, 1940, 1941, 1942, 1943, 1944, 1945, 1946, 1947, 1948, 1949, 1950, 1951, 1952, 1953, 1954, 1955, 1956, 1957, 1958, 1959, 1960, 1961, 1962, 1963, 1964, 1965, 1966, 1967, 1968, 1969, 1970, 1971, 1972, 1973, 1974, 1975, 1976, 1977, 1978, 1979, 1980, 1981, 1982, 1983, 1984, 1985, 1986, 1987, 1988, 1989, 1990, 1991, 1992, 1993, 1994, 1995, 1996, 1997, 1998, 1999, 2000, 2001, 2002, 2003, 2004, 2005, 2006, 2007, 2008, 2009, 2010, 2011, 2012, 2013, 2014, 2015, 2016, 2017, 2018, 2019, 2020, 2021, 2022, 2023, 2024, 2025, 2026, 2027, 2028, 2029, 2030, 2031, 2032, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, 2062, 2063, 2064, 2065, 2066, 2067, 2068, 2069, 2070, 2071, 2072, 2073, 2074, 2075, 2076, 2077, 2078, 2079, 2080, 2081, 2082, 2083, 2084, 2085, 2086, 2087, 2088, 2089, 2090, 2091, 2092, 2093, 2094, 2095, 2096, 2097, 2098, 2099, 2100, 2101, 2102, 2103, 2104, 2105, 2106, 2107, 2108, 2109, 2110, 2111, 2112, 2113, 2114, 2115, 2116, 2117, 2118, 2119, 2120, 2121, 2122, 2123, 2124, 2125, 2126, 2127, 2128, 2129, 2130, 2131, 2132, 2133, 2134, 2135, 2136, 2137, 2138, 2139, 2140, 2141, 2142, 2143, 2144, 2145, 2146, 2147, 2148, 2149, 2150, 2151, 2152, 2153, 2154, 2155, 2156, 2157, 2158, 2159, 2160, 2161, 2162, 2163, 2164, 2165, 2166, 2167, 2168, 2169, 2170, 2171, 2172, 2173, 2174, 2175, 2176, 2177, 2178, 2179, 2180, 2181, 2182, 2183, 2184, 2185, 2186, 2187, 2188, 2189, 2190, 2191, 2192, 2193, 2194 2195, 2196, 2197, 2198, 2199, 2200, 2201, 2202, 2203, 2204, 2205, 2206, 2207, 2208, 2209, 2210, 2211, 2212, 2213, 2214, 2215, 2216, 2217, 2218, 2219, 2220, 2221, 2222, 2223, 2224, 2225, 2226, 2227, 2228, 2229, 2230, 2231, 2232, 2233, 2234, 2235, 2236, 2237, 2238, 2239, 2240, 2241, 2242, 2243, 2244, 2245, 2246, 2247, 2248, 2249, 2250, 2251, 2252, 2253, 2254, 2255, 2256, 2257, 2258, 2259, 2260, 2261, 2262, 2263, 2264, 2265, 2266, 2267, 2268, 2269, 2270, 2271, 2272, 2273, 2274, 2275, 2276, 2277, 2278, 2279, 2280, 2281, 2282, 2283, 2284, 2285, 2286, 2287, 2288, 2289, 2290, 2291, 2292, 2293, 2294, 2295, 2296, 2297, 2298, 2299, 2300, 2301, 2302, 2303, 2304, 2305, 2306, 2307, 2308, 2309, 2310, 2311, 2312, 2313, 2314, 2315, 2316, 2317, 2318, 2319, 2320, 2321, 2322, 2323, 2324, 2325, 2326, 2327, 2328, 2329, 2330, 2331, 2332, 2333, 2334, 2335, 2336, 2337, 2338, 2339, 2340, 2341, 2342, 2343, 2344, 2345, 2346, 2347, 2348, 2349, 2350, 2351, 2352, 2353, 2354, 2355, 2356, 2357, 2358, 2359, 2360, 2361, 2362, 2363, 2364, 2365, 2366, 2367, 2368, 2369, 2370, 2371, 2372, 2373, 2374, 2375, 2376, 2377, 2378, 2379, 2380, 2381, 2382, 2383, 2384, 2385, 2386, 2387, 2388, 2389, 2390, 2391, 2392, 2393, 2394, 2395, 2396, 2397, 2398, 2399, 2400, 2401, 2402, 2403, 2404, 2405, 2406, 2407, 2408, 2409, 2410, 2411, 2412, 2413, 2414, 2415, 2416, 2417, 2418, 2419, 2420, 2421, 2422, 2423, 2424, 2425, 2426, 2427, 2428, 2429, 2430, 2431, 2432, 2433, 2434, 2435, 2436, 2437, 2438, 2439, 2440, 2441, 2442, 2443, 2444, 2445, 2446, 2447, 2448, 2449, 2450, 2451, 2452, 2453, 2454, 2455, 2456, 2457, 2458, 2459, 2460, 2461, 2462, 2463, 2464, 2465, 2466, 2467, 2468, 2469, 2470, 2471, 2472, 2473, 2474, 2475, 2476, 2477, 2478, 2479, 2480, 2481, 2482, 2483, 2484, 2485, 2486, 2487, 2488, 2489, 2490, 2491, 2492, 2493, 2494, 2495, 2496, 2497, 2498, 2499, 2500, 2501, 2502, 2503, 2504, 2505, 2506, 2507, 2508, 2509, 2510, 2511, 2512, 2513, 2514, 2515, 2516, 2517, 2518, 2519, 2520, 2521, 2522, 2523, 2524, 2525, 2526, 2527, 2528, 2529, 2530, 2531, 2532, 2533, 2534, 2535, 2536, 2537, 2538, 2539, 2540, 2541, 2542, 2543, 2544, 2545, 2546, 2547, 2548, 2549, 2550, 2551, 2552, 2553, 2554, 2555, 2556, 2557, 2558, 2559, 2560, 2561, 2562, 2563, 2564, 2565, 2566, 2567, 2568, 2569, 2570, 2571, 2572, 2573, 2574, 2575, 2576, 2577, 2578, 2579, 2580, 2581, 2582, 2583, 2584, 2585, 2586, 2587, 2588, 2589, 2590, 2591, 2592, 2593, 2594, 2595, 2596, 2597, 2598, 2599, 2600, 2601, 2602, 2603, 2604, 2605, 2606, 2607, 2608, 2609, 2610, 2611, 2612, 2613, 2614, 2615, 2616, 2617, 2618, 2619, 2620, 2621, 2622, 2623, 2624, 2625, 2626, 2627, 2628, 2629, 2630, 2631, 2632, 2633, 2634, 2635, 2636, 2637, 2638, 2639, 2640, 2641, 2642, 2643, 2644, 2645, 2646, 2647, 2648, 2649, 2650, 2651, 2652, 2653, 2654, 2655, 2656, 2657, 2658, 2659, 2660, 2661, 2662, 2663, 2664, 2665, 2666, 2667, 2668, 2669, 2670, 2671, 2672, 2673, 2674, 2675, 2676, 2677, 2678, 2679, 2680, 2681, 2682, 2683, 2684, 2685, 2686, 2687, 2688, 2689, 2690, 2691, 2692, 2693, 2694, 2695, 2696, 2697, 2698, 2699, 2700, 2701, 2702, 2703, 2704, 2705, 2706, 2707, 2708, 2709, 2710, 2711, 2712, 2713, 2714, 2715, 2716, 2717, 2718, 2719, 2720, 2721, 2722, 2723, 2724, 2725, 2726, 2727, 2728, 2729, 2730, 2731, 2732, 2733, 2734, 2735, 2736, 2737, 2738, 2739, 2740, 2741, 2742, 2743, 2744, 2745, 2746, 2747, 2748, 2749, 2750, 2751, 2752, 2753, 2754, 2755, 2756, 2757, 2758, 2759, 2760, 2761, 2762, 2763, 2764, 2765, 2766, 2767, 2768, 2769, 2770, 2771, 2772, 2773, 2774, 2775, 2776, 2777, 2778, 2779, 2780, 2781, 2782, 2783, 2784, 2785, 2786, 2787, 2788, 2789, 2790, 2791, 2792, 2793, 2794, 2795, 2796, 2797, 2798, 2799, 2800, 2801, 2802, 2803, 2804, 2805, 2806, 2807, 2808, 2809, 2810, 2811, 2812, 2813, 2814, 2815, 2816, 2817, 2818, 2819, 2820, 2821, 2822, 2823, 2824, 2825, 2826, 2827, 2828, 2829, 2830, 2831, 2832, 2833, 2834, 2835, 2836, 2837, 2838, 2839, 2840, 2841, 2842, 2843, 2844, 2845, 2846, 2847, 2848, 2849, 2850, 2851, 2852, 2853, 2854, 2855, 2856, 2857, 2858, 2859, 2860, 2861, 2862, 2863, 2864, 2865, 2866, 2867, 2868, 2869, 2870, 2871, 2872, 2873, 2874, 2875, 2876, 2877, 2878, 2879, 2880, 2881, 2882, 2883, 2884, 2885, 2886, 2887, 2888, 2889, 2890, 2891, 2892, 2893, 2894, 2895, 2896, 2897, 2898, 2899, 2900, 2901, 2902, 2903, 2904, 2905, 2906, 2907, 2908, 2909, 2910, 2911, 2912, 2913, 2914, 2915, 2916, 2917, 2918, 2919, 2920, 2921, 2922, 2923, 2924, 2925, 2926, 2927, 2928, 2929, 2930, 2931, 2932, 2933, 2934, 2935, 2936, 2937, 2938, 2939, 2940, 2941, 2942, 2943, 2944, 2945, 2946, 2947, 2948, 2949, 2950, 2951, 2952, 2953, 2954, 2955, 2956, 2957, 2958, 2959, 2960, 2961, 2962, 2963, 2964, 2965, 2966, 2967, 2968, 2969, 2970, 2971, 2972, 2973, 2974, 2975, 2976, 2977, 2978, 2979, 2980, 2981, 2982, 2983, 2984, 2985, 2986, 2987, 2988, 2989, 2990, 2991, 2992, 2993, 2994, 2995, 2996, 2997, 2998, 2999, 3000, 3001, 3002, 3003, 3004, 3005, 3006, 3007, 3008, 3009, 3010, 3011, 3012, 3013, 3014, 3015, 3016, 3017, 3018, 3019, 3020, 3021, 3022, 3023, 3024, 3025, 3026, 3027, 3028, 3029, 3030, 3031, 3032, 3033, 3034, 3035, 3036, 3037, 3038, 3039, 3040, 3041, 3042, 3043, 3044, 3045, 3046, 3047, 3048, 3049, 3050, 3051, 3052, 3053, 3054, 3055, 3056, 3057, 3058, 3059, 3060, 3061, 3062, 3063, 3064, 3065, 3066, 3067, 3068, 3069, 3070, 3071, 3072, 3073, 3074, 3075, 3076, 3077, 3078, 3079, 3080, 3081, 3082, 3083, 3084, 3085, 3086, 3087, 3088, 3089, 3090, 3091, 3092, 3093, 3094, 3095, 3096, 3097, 3098, 3099, 3100, 3101, 3102, 3103, 3104, 3105, 3106, 3107, 3108, 3109, 3110, 3111, 3112, 3113, 3114, 3115, 3116, 3117, 3118, 3119, 3120, 3121, 3122, 3123, 3124, 3125, 3126, 3127, 3128, 3129, 3130, 3131, 3132, 3133, 3134, 3135, 3136, 3137, 3138, 3139, 3140, 3141, 3142, 3143, 3144, 3145, 3146, 3147, 3148, 3149, 3150, 3151, 3152, 3153, 3154, 3155, 3156, 3157, 3158, 3159, 3160, 3161, 3162, 3163, 3164, 3165, 3166, 3167, 3168, 3169, 3170, 3171, 3172, 3173, 3174, 3175, 3176, 3177, 3178, 3179, 3180, 3181, 3182, 3183, 3184, 3185, 3186, 3187, 3188, 3189, 3190, 3191, 3192, 3193, 3194, 3195, 3196, 3197, 3198, 3199, 3200, 3201, 3202, 3203, 3204, 3205, 3206, 3207, 3208, 3209, 3210, 3211, 3212, 3213, 3214, 3215, 3216, 3217, 3218, 3219, 3220, 3221, 3222, 3223, 3224, 3225, 3226, 3227, 3228, 3229, 3230, 3231, 3232, 3233, 3234, 3235, 3236, 3237, 3238, 3239, 3240, 3241, 3242, 3243, 3244, 3245, 3246, 3247, 3248, 3249, and 3250 nucleotides. The length of any filler region for the viral genome may be 50-100, 100-150, 150-200, 200-250, 250-300, 300-350, 350-400, 400-450, 450-500, 500-550, 550-600, 600-650, 650-700, 700-750, 750-800, 800-850, 850-900, 900-950, 950-1000, 1000-1050, 1050-1100, 1100-1150, 1150-1200, 1200-1250, 1250-1300, 1300-1350, 1350-1400, 1400-1450, 1450-1500, 1500-1550, 1550-1600, 1600-1650, 1650-1700, 1700-1750, 1750-1800, 1800-1850, 1850-1900, 1900-1950, 1950-2000, 2000-2050, 2050-2100, 2100-2150, 2150-2200, 2200-2250, 2250-2300, 2300-2350, 2350-2400, 2400-2450, 2450-2500, 2500-2550, 2550-2600, 2600-2650, 2650-2700, 2700-2750, 2750-2800, 2800-2850, 2850-2900, 2900-2950, 2950-3000, 3000-3050, 3050-3100, 3100-3150, 3150-3200, and 3200-3250 nucleotides. As a non-limiting example, the viral genome comprises a filler region that is about 55 nucleotides in length. As a non-limiting example, the viral genome comprises a filler region that is about 56 nucleotides in length. As a non-limiting example, the viral genome comprises a filler region that is about 97 nucleotides in length. As a non-limiting example, the viral genome comprises a filler region that is about 103 nucleotides in length. As a non-limiting example, the viral genome comprises a filler region that is about 105 nucleotides in length. As a non-limiting example, the viral genome comprises a filler region that is about 357 nucleotides in length. As a non-limiting example, the viral genome comprises a filler region that is about 363 nucleotides in length. As a non-limiting example, the viral genome comprises a filler region that is about 712 nucleotides in length. As a non-limiting example, the viral genome comprises a filler region that is about 714 nucleotides in length. As a non-limiting example, the viral genome comprises a filler region that is about 1203 nucleotides in length. As a non-limiting example, the viral genome comprises a filler region that is about 1209 nucleotides in length. As a non-limiting example, the viral genome comprises a filler region that is about 1512 nucleotides in length. As a non-limiting example, the viral genome comprises a filler region that is about 1519 nucleotides in length. As a non-limiting example, the viral genome comprises a filler region that is about 2395 nucleotides in length. As a non-limiting example, the viral genome comprises a filler region that is about 2403 nucleotides in length. As a non-limiting example, the viral genome comprises a filler region that is about 2405 nucleotides in length. As a non-limiting example, the viral genome comprises a filler region that is about 3013 nucleotides in length. As a non-limiting example, the viral genome comprises a filler region that is about 3021 nucleotides in length.

In one embodiment, the AAV particle viral genome may comprise at least one multiple filler sequence region. The filler region(s) may, independently, have a length such as, but not limited to, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, 1567, 1568, 1569, 1570, 1571, 1572, 1573, 1574, 1575, 1576, 1577, 1578, 1579, 1580, 1581, 1582, 1583, 1584, 1585, 1586, 1587, 1588, 1589, 1590, 1591, 1592, 1593, 1594, 1595, 1596, 1597, 1598, 1599, 1600, 1601, 1602, 1603, 1604, 1605, 1606, 1607, 1608, 1609, 1610, 1611, 1612, 1613, 1614, 1615, 1616, 1617, 1618, 1619, 1620, 1621, 1622, 1623, 1624, 1625, 1626, 1627, 1628, 1629, 1630, 1631, 1632, 1633, 1634, 1635, 1636, 1637, 1638, 1639, 1640, 1641, 1642, 1643, 1644, 1645, 1646, 1647, 1648, 1649, 1650, 1651, 1652, 1653, 1654, 1655, 1656, 1657, 1658, 1659, 1660, 1661, 1662, 1663, 1664, 1665, 1666, 1667, 1668, 1669, 1670, 1671, 1672, 1673, 1674, 1675, 1676, 1677, 1678, 1679, 1680, 1681, 1682, 1683, 1684, 1685, 1686, 1687, 1688, 1689, 1690, 1691, 1692, 1693, 1694, 1695, 1696, 1697, 1698, 1699, 1700, 1701, 1702, 1703, 1704, 1705, 1706, 1707, 1708, 1709, 1710, 1711, 1712, 1713, 1714, 1715, 1716, 1717, 1718, 1719, 1720, 1721, 1722, 1723, 1724, 1725, 1726, 1727, 1728, 1729, 1730, 1731, 1732, 1733, 1734, 1735, 1736, 1737, 1738, 1739, 1740, 1741, 1742, 1743, 1744, 1745, 1746, 1747, 1748, 1749, 1750, 1751, 1752, 1753, 1754, 1755, 1756, 1757, 1758, 1759, 1760, 1761, 1762, 1763, 1764, 1765, 1766, 1767, 1768, 1769, 1770, 1771, 1772, 1773, 1774, 1775, 1776, 1777, 1778, 1779, 1780, 1781, 1782, 1783, 1784, 1785, 1786, 1787, 1788, 1789, 1790, 1791, 1792, 1793, 1794, 1795, 1796, 1797, 1798, 1799, 1800, 1801, 1802, 1803, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1828, 1829, 1830, 1831, 1832, 1833, 1834, 1835, 1836, 1837, 1838, 1839, 1840, 1841, 1842, 1843, 1844, 1845, 1846, 1847, 1848, 1849, 1850, 1851, 1852, 1853, 1854, 1855, 1856, 1857, 1858, 1859, 1860, 1861, 1862, 1863, 1864, 1865, 1866, 1867, 1868, 1869, 1870, 1871, 1872, 1873, 1874, 1875, 1876, 1877, 1878, 1879, 1880, 1881, 1882, 1883, 1884, 1885, 1886, 1887, 1888, 1889, 1890, 1891, 1892, 1893, 1894, 1895, 1896, 1897, 1898, 1899, 1900, 1901, 1902, 1903, 1904, 1905, 1906, 1907, 1908, 1909, 1910, 1911, 1912, 1913, 1914, 1915, 1916, 1917, 1918, 1919, 1920, 1921, 1922, 1923, 1924, 1925, 1926, 1927, 1928, 1929, 1930, 1931, 1932, 1933, 1934, 1935, 1936, 1937, 1938, 1939, 1940, 1941, 1942, 1943, 1944, 1945, 1946, 1947, 1948, 1949, 1950, 1951, 1952, 1953, 1954, 1955, 1956, 1957, 1958, 1959, 1960, 1961, 1962, 1963, 1964, 1965, 1966, 1967, 1968, 1969, 1970, 1971, 1972, 1973, 1974, 1975, 1976, 1977, 1978, 1979, 1980, 1981, 1982, 1983, 1984, 1985, 1986, 1987, 1988, 1989, 1990, 1991, 1992, 1993, 1994, 1995, 1996, 1997, 1998, 1999, 2000, 2001, 2002, 2003, 2004, 2005, 2006, 2007, 2008, 2009, 2010, 2011, 2012, 2013, 2014, 2015, 2016, 2017, 2018, 2019, 2020, 2021, 2022, 2023, 2024, 2025, 2026, 2027, 2028, 2029, 2030, 2031, 2032, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, 2062, 2063, 2064, 2065, 2066, 2067, 2068, 2069, 2070, 2071, 2072, 2073, 2074, 2075, 2076, 2077, 2078, 2079, 2080, 2081, 2082, 2083, 2084, 2085, 2086, 2087, 2088, 2089, 2090, 2091, 2092, 2093, 2094, 2095, 2096, 2097, 2098, 2099, 2100, 2101, 2102, 2103, 2104, 2105, 2106, 2107, 2108, 2109, 2110, 2111, 2112, 2113, 2114, 2115, 2116, 2117, 2118, 2119, 2120, 2121, 2122, 2123, 2124, 2125, 2126, 2127, 2128, 2129, 2130, 2131, 2132, 2133, 2134, 2135, 2136, 2137, 2138, 2139, 2140, 2141, 2142, 2143, 2144, 2145, 2146, 2147, 2148, 2149, 2150, 2151, 2152, 2153, 2154, 2155, 2156, 2157, 2158, 2159, 2160, 2161, 2162, 2163, 2164, 2165, 2166, 2167, 2168, 2169, 2170, 2171, 2172, 2173, 2174, 2175, 2176, 2177, 2178, 2179, 2180, 2181, 2182, 2183, 2184, 2185, 2186, 2187, 2188, 2189, 2190, 2191, 2192, 2193, 21942195, 2196, 2197, 2198, 2199, 2200, 2201, 2202, 2203, 2204, 2205, 2206, 2207, 2208, 2209, 2210, 2211, 2212, 2213, 2214, 2215, 2216, 2217, 2218, 2219, 2220, 2221, 2222, 2223, 2224, 2225, 2226, 2227, 2228, 2229, 2230, 2231, 2232, 2233, 2234, 2235, 2236, 2237, 2238, 2239, 2240, 2241, 2242, 2243, 2244, 2245, 2246, 2247, 2248, 2249, 2250, 2251, 2252, 2253, 2254, 2255, 2256, 2257, 2258, 2259, 2260, 2261, 2262, 2263, 2264, 2265, 2266, 2267, 2268, 2269, 2270, 2271, 2272, 2273, 2274, 2275, 2276, 2277, 2278, 2279, 2280, 2281, 2282, 2283, 2284, 2285, 2286, 2287, 2288, 2289, 2290, 2291, 2292, 2293, 2294, 2295, 2296, 2297, 2298, 2299, 2300, 2301, 2302, 2303, 2304, 2305, 2306, 2307, 2308, 2309, 2310, 2311, 2312, 2313, 2314, 2315, 2316, 2317, 2318, 2319, 2320, 2321, 2322, 2323, 2324, 2325, 2326, 2327, 2328, 2329, 2330, 2331, 2332, 2333, 2334, 2335, 2336, 2337, 2338, 2339, 2340, 2341, 2342, 2343, 2344, 2345, 2346, 2347, 2348, 2349, 2350, 2351, 2352, 2353, 2354, 2355, 2356, 2357, 2358, 2359, 2360, 2361, 2362, 2363, 2364, 2365, 2366, 2367, 2368, 2369, 2370, 2371, 2372, 2373, 2374, 2375, 2376, 2377, 2378, 2379, 2380, 2381, 2382, 2383, 2384, 2385, 2386, 2387, 2388, 2389, 2390, 2391, 2392, 2393, 2394, 2395, 2396, 2397, 2398, 2399, 2400, 2401, 2402, 2403, 2404, 2405, 2406, 2407, 2408, 2409, 2410, 2411, 2412, 2413, 2414, 2415, 2416, 2417, 2418, 2419, 2420, 2421, 2422, 2423, 2424, 2425, 2426, 2427, 2428, 2429, 2430, 2431, 2432, 2433, 2434, 2435, 2436, 2437, 2438, 2439, 2440, 2441, 2442, 2443, 2444, 2445, 2446, 2447, 2448, 2449, 2450, 2451, 2452, 2453, 2454, 2455, 2456, 2457, 2458, 2459, 2460, 2461, 2462, 2463, 2464, 2465, 2466, 2467, 2468, 2469, 2470, 2471, 2472, 2473, 2474, 2475, 2476, 2477, 2478, 2479, 2480, 2481, 2482, 2483, 2484, 2485, 2486, 2487, 2488, 2489, 2490, 2491, 2492, 2493, 2494, 2495, 2496, 2497, 2498, 2499, 2500, 2501, 2502, 2503, 2504, 2505, 2506, 2507, 2508, 2509, 2510, 2511, 2512, 2513, 2514, 2515, 2516, 2517, 2518, 2519, 2520, 2521, 2522, 2523, 2524, 2525, 2526, 2527, 2528, 2529, 2530, 2531, 2532, 2533, 2534, 2535, 2536, 2537, 2538, 2539, 2540, 2541, 2542, 2543, 2544, 2545, 2546, 2547, 2548, 2549, 2550, 2551, 2552, 2553, 2554, 2555, 2556, 2557, 2558, 2559, 2560, 2561, 2562, 2563, 2564, 2565, 2566, 2567, 2568, 2569, 2570, 2571, 2572, 2573, 2574, 2575, 2576, 2577, 2578, 2579, 2580, 2581, 2582, 2583, 2584, 2585, 2586, 2587, 2588, 2589, 2590, 2591, 2592, 2593, 2594, 2595, 2596, 2597, 2598, 2599, 2600, 2601, 2602, 2603, 2604, 2605, 2606, 2607, 2608, 2609, 2610, 2611, 2612, 2613, 2614, 2615, 2616, 2617, 2618, 2619, 2620, 2621, 2622, 2623, 2624, 2625, 2626, 2627, 2628, 2629, 2630, 2631, 2632, 2633, 2634, 2635, 2636, 2637, 2638, 2639, 2640, 2641, 2642, 2643, 2644, 2645, 2646, 2647, 2648, 2649, 2650, 2651, 2652, 2653, 2654, 2655, 2656, 2657, 2658, 2659, 2660, 2661, 2662, 2663, 2664, 2665, 2666, 2667, 2668, 2669, 2670, 2671, 2672, 2673, 2674, 2675, 2676, 2677, 2678, 2679, 2680, 2681, 2682, 2683, 2684, 2685, 2686, 2687, 2688, 2689, 2690, 2691, 2692, 2693, 2694, 2695, 2696, 2697, 2698, 2699, 2700, 2701, 2702, 2703, 2704, 2705, 2706, 2707, 2708, 2709, 2710, 2711, 2712, 2713, 2714, 2715, 2716, 2717, 2718, 2719, 2720, 2721, 2722, 2723, 2724, 2725, 2726, 2727, 2728, 2729, 2730, 2731, 2732, 2733, 2734, 2735, 2736, 2737, 2738, 2739, 2740, 2741, 2742, 2743, 2744, 2745, 2746, 2747, 2748, 2749, 2750, 2751, 2752, 2753, 2754, 2755, 2756, 2757, 2758, 2759, 2760, 2761, 2762, 2763, 2764, 2765, 2766, 2767, 2768, 2769, 2770, 2771, 2772, 2773, 2774, 2775, 2776, 2777, 2778, 2779, 2780, 2781, 2782, 2783, 2784, 2785, 2786, 2787, 2788, 2789, 2790, 2791, 2792, 2793, 2794, 2795, 2796, 2797, 2798, 2799, 2800, 2801, 2802, 2803, 2804, 2805, 2806, 2807, 2808, 2809, 2810, 2811, 2812, 2813, 2814, 2815, 2816, 2817, 2818, 2819, 2820, 2821, 2822, 2823, 2824, 2825, 2826, 2827, 2828, 2829, 2830, 2831, 2832, 2833, 2834, 2835, 2836, 2837, 2838, 2839, 2840, 2841, 2842, 2843, 2844, 2845, 2846, 2847, 2848, 2849, 2850, 2851, 2852, 2853, 2854, 2855, 2856, 2857, 2858, 2859, 2860, 2861, 2862, 2863, 2864, 2865, 2866, 2867, 2868, 2869, 2870, 2871, 2872, 2873, 2874, 2875, 2876, 2877, 2878, 2879, 2880, 2881, 2882, 2883, 2884, 2885, 2886, 2887, 2888, 2889, 2890, 2891, 2892, 2893, 2894, 2895, 2896, 2897, 2898, 2899, 2900, 2901, 2902, 2903, 2904, 2905, 2906, 2907, 2908, 2909, 2910, 2911, 2912, 2913, 2914, 2915, 2916, 2917, 2918, 2919, 2920, 2921, 2922, 2923, 2924, 2925, 2926, 2927, 2928, 2929, 2930, 2931, 2932, 2933, 2934, 2935, 2936, 2937, 2938, 2939, 2940, 2941, 2942, 2943, 2944, 2945, 2946, 2947, 2948, 2949, 2950, 2951, 2952, 2953, 2954, 2955, 2956, 2957, 2958, 2959, 2960, 2961, 2962, 2963, 2964, 2965, 2966, 2967, 2968, 2969, 2970, 2971, 2972, 2973, 2974, 2975, 2976, 2977, 2978, 2979, 2980, 2981, 2982, 2983, 2984, 2985, 2986, 2987, 2988, 2989, 2990, 2991, 2992, 2993, 2994, 2995, 2996, 2997, 2998, 2999, 3000, 3001, 3002, 3003, 3004, 3005, 3006, 3007, 3008, 3009, 3010, 3011, 3012, 3013, 3014, 3015, 3016, 3017, 3018, 3019, 3020, 3021, 3022, 3023, 3024, 3025, 3026, 3027, 3028, 3029, 3030, 3031, 3032, 3033, 3034, 3035, 3036, 3037, 3038, 3039, 3040, 3041, 3042, 3043, 3044, 3045, 3046, 3047, 3048, 3049, 3050, 3051, 3052, 3053, 3054, 3055, 3056, 3057, 3058, 3059, 3060, 3061, 3062, 3063, 3064, 3065, 3066, 3067, 3068, 3069, 3070, 3071, 3072, 3073, 3074, 3075, 3076, 3077, 3078, 3079, 3080, 3081, 3082, 3083, 3084, 3085, 3086, 3087, 3088, 3089, 3090, 3091, 3092, 3093, 3094, 3095, 3096, 3097, 3098, 3099, 3100, 3101, 3102, 3103, 3104, 3105, 3106, 3107, 3108, 3109, 3110, 3111, 3112, 3113, 3114, 3115, 3116, 3117, 3118, 3119, 3120, 3121, 3122, 3123, 3124, 3125, 3126, 3127, 3128, 3129, 3130, 3131, 3132, 3133, 3134, 3135, 3136, 3137, 3138, 3139, 3140, 3141, 3142, 3143, 3144, 3145, 3146, 3147, 3148, 3149, 3150, 3151, 3152, 3153, 3154, 3155, 3156, 3157, 3158, 3159, 3160, 3161, 3162, 3163, 3164, 3165, 3166, 3167, 3168, 3169, 3170, 3171, 3172, 3173, 3174, 3175, 3176, 3177, 3178, 3179, 3180, 3181, 3182, 3183, 3184, 3185, 3186, 3187, 3188, 3189, 3190, 3191, 3192, 3193, 3194, 3195, 3196, 3197, 3198, 3199, 3200, 3201, 3202, 3203, 3204, 3205, 3206, 3207, 3208, 3209, 3210, 3211, 3212, 3213, 3214, 3215, 3216, 3217, 3218, 3219, 3220, 3221, 3222, 3223, 3224, 3225, 3226, 3227, 3228, 3229, 3230, 3231, 3232, 3233, 3234, 3235, 3236, 3237, 3238, 3239, 3240, 3241, 3242, 3243, 3244, 3245, 3246, 3247, 3248, 3249, and 3250 nucleotides. The length of any filler region for the viral genome may be 50-100, 100-150, 150-200, 200-250, 250-300, 300-350, 350-400, 400-450, 450-500, 500-550, 550-600, 600-650, 650-700, 700-750, 750-800, 800-850, 850-900, 900-950, 950-1000, 1000-1050, 1050-1100, 1100-1150, 1150-1200, 1200-1250, 1250-1300, 1300-1350, 1350-1400, 1400-1450, 1450-1500, 1500-1550, 1550-1600, 1600-1650, 1650-1700, 1700-1750, 1750-1800, 1800-1850, 1850-1900, 1900-1950, 1950-2000, 2000-2050, 2050-2100, 2100-2150, 2150-2200, 2200-2250, 2250-2300, 2300-2350, 2350-2400, 2400-2450, 2450-2500, 2500-2550, 2550-2600, 2600-2650, 2650-2700, 2700-2750, 2750-2800, 2800-2850, 2850-2900, 2900-2950, 2950-3000, 3000-3050, 3050-3100, 3100-3150, 3150-3200, and 3200-3250 nucleotides. As a non-limiting example, the viral genome comprises a filler region that is about 55 nucleotides in length. As a non-limiting example, the viral genome comprises a filler region that is about 56 nucleotides in length. As a non-limiting example, the viral genome comprises a filler region that is about 97 nucleotides in length. As a non-limiting example, the viral genome comprises a filler region that is about 103 nucleotides in length. As a non-limiting example, the viral genome comprises a filler region that is about 105 nucleotides in length. As a non-limiting example, the viral genome comprises a filler region that is about 357 nucleotides in length. As a non-limiting example, the viral genome comprises a filler region that is about 363 nucleotides in length. As a non-limiting example, the viral genome comprises a filler region that is about 712 nucleotides in length. As a non-limiting example, the viral genome comprises a filler region that is about 714 nucleotides in length. As a non-limiting example, the viral genome comprises a filler region that is about 1203 nucleotides in length. As a non-limiting example, the viral genome comprises a filler region that is about 1209 nucleotides in length. As a non-limiting example, the viral genome comprises a filler region that is about 1512 nucleotides in length. As a non-limiting example, the viral genome comprises a filler region that is about 1519 nucleotides in length. As a non-limiting example, the viral genome comprises a filler region that is about 2395 nucleotides in length. As a non-limiting example, the viral genome comprises a filler region that is about 2403 nucleotides in length. As a non-limiting example, the viral genome comprises a filler region that is about 2405 nucleotides in length. As a non-limiting example, the viral genome comprises a filler region that is about 3013 nucleotides in length. As a non-limiting example, the viral genome comprises a filler region that is about 3021 nucleotides in length.

In one embodiment, the AAV particle viral genome comprises at least one filler sequence regions. Non-limiting examples of filler sequence regions are described in Table 12.

TABLE 12

Filler Sequence Regions

| Sequence Region Name | SEQ ID NO |
| --- | --- |
| FILL1 | 1379 |
| FILL2 | 1380 |
| FILL3 | 1381 |
| FILL4 | 1382 |
| FILL5 | 1383 |
| FILL6 | 1384 |
| F1LL7 | 1385 |
| FILL8 | 1386 |
| FILL9 | 1387 |
| FILL10 | 1388 |
| FILL11 | 1389 |
| FILL12 | 1390 |
| FILL13 | 1391 |
| FILL14 | 1392 |
| FILL15 | 1393 |
| FILL16 | 1394 |
| FILL17 | 1395 |
| FILL18 | 1396 |

In one embodiment, the AAV particle viral genome comprises one filler sequence region. In one embodiment, the filler sequence region is the FILL1 sequence region. In one embodiment, the filler sequence region is the FILL2 sequence region. In one embodiment, the filler sequence region is the FILL3 sequence region. In one embodiment, the filler sequence region is the FILL4 sequence region. In one embodiment, the filler sequence region is the FILL5 sequence region. In one embodiment, the filler sequence region is the FILL6 sequence region. In one embodiment, the filler sequence region is the FILL7 sequence region. In one embodiment, the filler sequence region is the FILL8 sequence region. In one embodiment, the filler sequence region is the FILL9 sequence region. In one embodiment, the filler sequence region is the FILL10 sequence region. In one embodiment, the filler sequence region is the FILL11 sequence region. In one embodiment, the filler sequence region is the FILL12 sequence region. In one embodiment, the filler sequence region is the FILL13 sequence region. In one embodiment, the filler sequence region is the FILL14 sequence region. In one embodiment, the filler sequence region is the FILL15 sequence region. In one embodiment, the filler sequence region is the FILL16 sequence region. In one embodiment, the filler sequence region is the FILL17 sequence region. In one embodiment, the filler sequence region is the FILL18 sequence region.

In one embodiment, the AAV particle viral genome comprises two filler sequence regions. In one embodiment, the two filler sequence regions are the FILL1 sequence region, and the FILL2 sequence region. In one embodiment, the filler sequence region is the FILL1 sequence region, and the FILL3 sequence region. In one embodiment, the filler sequence region is the FILL1 sequence region, and the FILL4 sequence region. In one embodiment, the filler sequence region is the FILL1 sequence region, and the FILL5 sequence region. In one embodiment, the filler sequence region is the FILL1 sequence region, and the FILL6 sequence region. In one embodiment, the filler sequence region is the FILL1 sequence region, and the FILL7 sequence region. In one embodiment, the filler sequence region is the FILL1 sequence region, and the FILL8 sequence region. In one embodiment, the filler sequence region is the FILL1 sequence region, and the FILL9 sequence region. In one embodiment, the filler sequence region is the FILL1 sequence region, and the FILL10 sequence region. In one embodiment, the filler sequence region is the FILL1 sequence region, and the FILL11 sequence region. In one embodiment, the filler sequence region is the FILL1 sequence region, and the FILL12 sequence region. In one embodiment, the filler sequence region is the FILL1 sequence region, and the FILL13 sequence region. In one embodiment, the filler sequence region is the FILL1 sequence region, and the FILL14 sequence region. In one embodiment, the filler sequence region is the FILL1 sequence region, and the FILL15 sequence region. In one embodiment, the filler sequence region is the FILL1 sequence region, and the FILL16 sequence region. In one embodiment, the filler sequence region is the FILL1 sequence region, and the FILL17 sequence region. In one embodiment, the filler sequence region is the FILL1 sequence region, and the FILL18 sequence region. In one embodiment, the filler sequence region is the FILL2 sequence region, and the FILL3 sequence region. In one embodiment, the filler sequence region is the FILL3 sequence region, and the FILL4 sequence region. In one embodiment, the filler sequence region is the FILL3 sequence region, and the FILL5 sequence region. In one embodiment, the filler sequence region is the FILL3 sequence region, and the FILL6 sequence region. In one embodiment, the filler sequence region is the FILL3 sequence region, and the FILL7 sequence region. In one embodiment, the filler sequence region is the FILL3 sequence region, and the FILL8 sequence region. In one embodiment, the filler sequence region is the FILL3 sequence region, and the FILL9 sequence region. In one embodiment, the filler sequence region is the FILL3 sequence region, and the FILL10 sequence region. In one embodiment, the filler sequence region is the FILL3 sequence region, and the FILL11 sequence region. In one embodiment, the filler sequence region is the FILL3 sequence region, and the FILL12 sequence region. In one embodiment, the filler sequence region is the FILL3 sequence region, and the FILL13 sequence region. In one embodiment, the filler sequence region is the FILL3 sequence region, and the FILL14 sequence region. In one embodiment, the filler sequence region is the FILL3 sequence region, and the FILL15 sequence region. In one embodiment, the filler sequence region is the FILL3 sequence region, and the FILL16 sequence region. In one embodiment, the filler sequence region is the FILL3 sequence region, and the FILL17 sequence region. In one embodiment, the filler sequence region is the FILL3 sequence region, and the FILL18 sequence region. In one embodiment, the filler sequence region is the FILL4 sequence region, and the FILL5 sequence region. In one embodiment, the filler sequence region is the FILL4 sequence region, and the FILL6 sequence region. In one embodiment, the filler sequence region is the FILL4 sequence region, and the FILL7 sequence region. In one embodiment, the filler sequence region is the FILL4 sequence region, and the FILL8 sequence region. In one embodiment, the filler sequence region is the FILL4 sequence region, and the FILL9 sequence region. In one embodiment, the filler sequence region is the FILL4 sequence region, and the FILL10 sequence region. In one embodiment, the filler sequence region is the FILL4 sequence region, and the FILL11 sequence region. In one embodiment, the filler sequence region is the FILL4 sequence region, and the FILL12 sequence region. In one embodiment, the filler sequence region is the FILL4 sequence region, and the FILL13 sequence region. In one embodiment, the filler sequence region is the FILL4 sequence region, and the FILL14 sequence region. In one embodiment, the filler sequence region is the FILM sequence region, and the FILL15 sequence region. In one embodiment, the filler sequence region is the FILL4 sequence region, and the FILL16 sequence region. In one embodiment, the filler sequence region is the FILL4 sequence region, and the FILL17 sequence region. In one embodiment, the filler sequence region is the FILL4 sequence region, and the FILL18 sequence region. In one embodiment, the filler sequence region is the FILL5 sequence region, and the FILL6 sequence region. In one embodiment, the filler sequence region is the FILL5 sequence region, and the FILL7 sequence region. In one embodiment, the filler sequence region is the FILL5 sequence region, and the FILL8 sequence region. In one embodiment, the filler sequence region is the FILL5 sequence region, and the FILL9 sequence region. In one embodiment, the filler sequence region is the FILL5 sequence region, and the FILL10 sequence region. In one embodiment, the filler sequence region is the FILL5 sequence region, and the FILL11 sequence region. In one embodiment, the filler sequence region is the FILL5 sequence region, and the FILL12 sequence region. In one embodiment, the filler sequence region is the FILL5 sequence region, and the FILL13 sequence region. In one embodiment, the filler sequence region is the FILL5 sequence region, and the FILL14 sequence region. In one embodiment, the filler sequence region is the FILL5 sequence region, and the FILL15 sequence region. In one embodiment, the filler sequence region is the FILL5 sequence region, and the FILL16 sequence region. In one embodiment, the filler sequence region is the FILL5 sequence region, and the FILL17 sequence region. In one embodiment, the filler sequence region is the FILL5 sequence region, and the FILL18 sequence region. In one embodiment, the filler sequence region is the FILL6 sequence region, and the FILL7 sequence region. In one embodiment, the filler sequence region is the FILL6 sequence region, and the FILL8 sequence region. In one embodiment, the filler sequence region is the FILL6 sequence region, and the FILL9 sequence region. In one embodiment, the filler sequence region is the FILL6 sequence region, and the FILL10 sequence region. In one embodiment, the filler sequence region is the FILL6 sequence region, and the FILL11 sequence region. In one embodiment, the filler sequence region is the FILL6 sequence region, and the FILL12 sequence region. In one embodiment, the filler sequence region is the FILL6 sequence region, and the FILL13 sequence region. In one embodiment, the filler sequence region is the FILL6 sequence region, and the FILL14 sequence region. In one embodiment, the filler sequence region is the FILL6 sequence region, and the FILL15 sequence region. In one embodiment, the filler sequence region is the FILL6 sequence region, and the FILL16 sequence region. In one embodiment the filler sequence region is the FILL6 sequence region, and the FILL17 sequence region. In one embodiment, the filler sequence region is the FILL6 sequence region, and the FILL18 sequence region. In one embodiment, the filler sequence region is the FILL7 sequence region, and the FILL8 sequence region. In one embodiment, the filler sequence region is the FILL7 sequence region, and the FILL9 sequence region. In one embodiment, the filler sequence region is the FILL7 sequence region, and the FILL10 sequence region. In one embodiment, the filler sequence region is the FILL7 sequence region, and the FILL11 sequence region. In one embodiment the filler sequence region is the FILL7 sequence region, and the FILL12 sequence region. In one embodiment, the filler sequence region is the FILL7 sequence region, and the FILL13 sequence region. In one embodiment, the filler sequence region is the FILL7 sequence region, and the FILL14 sequence region. In one embodiment, the filler sequence region is the FILL7 sequence region, and the FILL15 sequence region. In one embodiment the filler sequence region is the FILL7 sequence region, and the FILL16 sequence region. In one embodiment, the filler sequence region is the FILL7 sequence region, and the FILL17 sequence region. In one embodiment, the filler sequence region is the FILL7 sequence region, and the FILL18 sequence region. In one embodiment, the filler sequence region is the FILL8 sequence region, and the FILL9 sequence region. In one embodiment, the filler sequence region is the FILL8 sequence region, and the FILL10 sequence region. In one embodiment, the filler sequence region is the FILL8 sequence region, and the FILL1 sequence region. In one embodiment, the filler sequence region is the FILL8 sequence region, and the FILL12 sequence region. In one embodiment, the filler sequence region is the FILL8 sequence region, and the FILL13 sequence region. In one embodiment, the filler sequence region is the FILL5 sequence region, and the FILL14 sequence region. In one embodiment, the filler sequence region is the FILL8 sequence region, and the FILL15 sequence region. In one embodiment, the filler sequence region is the FILL5 sequence region, and the FILL16 sequence region. In one embodiment, the filler sequence region is the FILL8 sequence region, and the FILL17 sequence region. In one embodiment, the filler sequence region is the FILL5 sequence region, and the FILL18 sequence region. In one embodiment, the filler sequence region is the FILL9 sequence region, and the FILL10 sequence region. In one embodiment, the filler sequence region is the FILL9 sequence region, and the FILL11 sequence region. In one embodiment, the filler sequence region is the FILL9 sequence region, and the FILL12 sequence region. In one embodiment, the filler sequence region is the FILL9 sequence region, and the FILL13 sequence region. In one embodiment, the filler sequence region is the FILL9 sequence region, and the FILL14 sequence region. In one embodiment, the filler sequence region is the FILL9 sequence region, and the FILL15 sequence region. In one embodiment, the filler sequence region is the FILL9 sequence region, and the FILL16 sequence region. In one embodiment, the filler sequence region is the FILL9 sequence region, and the FILL17 sequence region. In one embodiment, the filler sequence region is the FILL9 sequence region, and the FILL18 sequence region. In one embodiment, the filler sequence region is the FILL10 sequence region, and the FILL11 sequence region. In one embodiment, the filler sequence region is the FILL10 sequence region, and the FILL12 sequence region. In one embodiment, the filler sequence region is the FILL10 sequence region, and the FILL13 sequence region. In one embodiment, the filler sequence region is the FILL10 sequence region, and the FILL14 sequence region. In one embodiment, the filler sequence region is the FILL10 sequence region, and the FILL15 sequence region. In one embodiment, the filler sequence region is the FILL10 sequence region, and the FILL16 sequence region. In one embodiment, the filler sequence region is the FILL10 sequence region, and the FILL17 sequence region. In one embodiment, the filler sequence region is the FILL10 sequence region, and the FILL18 sequence region. In one embodiment, the filler sequence region is the FILL11 sequence region, and the FILL12 sequence region. In one embodiment, the filler sequence region is the FILL11 sequence region, and the FILL13 sequence region. In one embodiment, the filler sequence region is the FILL11 sequence region, and the FILL14 sequence region. In one embodiment, the filler sequence region is the FILL11 sequence region, and the FILL15 sequence region. In one embodiment, the filler sequence region is the FILL11 sequence region, and the FILL16 sequence region. In one embodiment, the filler sequence region is the FILL11 sequence region, and the FILL17 sequence region. In one embodiment, the filler sequence region is the FILL11 sequence region, and the FILL18 sequence region. In one embodiment, the filler sequence region is the FILL12 sequence region, and the FILL13 sequence region. In one embodiment, the filler sequence region is the FILL12 sequence region, and the FILL14 sequence region. In one embodiment, the filler sequence region is the FILL12 sequence region, and the FILL15 sequence region. In one embodiment, the filler sequence region is the FILL12 sequence region, and the FILL16 sequence region. In one embodiment, the filler sequence region is the FILL12 sequence region, and the FILL17 sequence region. In one embodiment, the filler sequence region is the FILL12 sequence region, and the FILL18 sequence region. In one embodiment, the filler sequence region is the FILL13 sequence region, and the FILL14 sequence region. In one embodiment, the filler sequence region is the FILL13 sequence region, and the FILL15 sequence region. In one embodiment, the filler sequence region is the FILL13 sequence region, and the FILL16 sequence region. In one embodiment, the filler sequence region is the FILL13 sequence region, and the FILL17 sequence region. In one embodiment, the filler sequence region is the FILL13 sequence region, and the FILL18 sequence region. In one embodiment, the filler sequence region is the FILL14 sequence region, and the FILL15 sequence region. In one embodiment, the filler sequence region is the FILL14 sequence region, and the FILL16 sequence region. In one embodiment, the filler sequence region is the FILL14 sequence region, and the FILL17 sequence region. In one embodiment, the filler sequence region is the FILL14 sequence region, and the FILL18 sequence region. In one embodiment, the filler sequence region is the FILL15 sequence region, and the FILL16 sequence region. In one embodiment, the filler sequence region is the FILL5 sequence region, and the FILL17 sequence region. In one embodiment, the filler sequence region is the FILL15 sequence region, and the FILL18 sequence region. In one embodiment, the filler sequence region is the FILL16 sequence region, and the FILL17 sequence region. In one embodiment, the filler sequence region is the FILL16 sequence region, and the FILL18 sequence region. In one embodiment, the filler sequence region is the FILL17 sequence region, and the FILL18 sequence region.

In one embodiment, the AAV particle viral genome comprises three filler sequence regions. In one embodiment, the two filler sequence regions are the FILL1 sequence region, the FILL2 sequence region, and the FILL3 sequence region. In one embodiment, the filler sequence region is the FILL1 sequence region, the FILL2 sequence region, and the FILL4 sequence region. In one embodiment, the filler sequence region is the FILL1 sequence region, the FILL2 sequence region, and the FILL5 sequence region. In one embodiment, the filler sequence region is the FILL1 sequence region, the FILL2 sequence region, and the FILL6 sequence region. In one embodiment, the filler sequence region is the FILL1 sequence region, the FILL2 sequence region, and the FILL7 sequence region. In one embodiment, the filler sequence region is the FILL1 sequence region, the FILL2 sequence region, and the FILL8 sequence region. In one embodiment, the filler sequence region is the FILL1 sequence region, the FILL2 sequence region, and the FILL9 sequence region. In one embodiment, the filler sequence region is the FILL1 sequence region, the FILL2 sequence region, and the FILL10 sequence region. In one embodiment, the filler sequence region is the FILL1 sequence region, the FILL2 sequence region, and the FILL11 sequence region. In one embodiment, the filler sequence region is the FILL1 sequence region, the FILL2 sequence region, and the FILL12 sequence region. In one embodiment, the filler sequence region is the FILL1 sequence region, the FILL2 sequence region, and the FILL13 sequence region. In one embodiment, the filler sequence region is the FILL1 sequence region, the FILL2 sequence region, and the FILL14 sequence region. In one embodiment, the filler sequence region is the FILL1 sequence region, the FILL2 sequence region, and the FILL15 sequence region. In one embodiment, the filler sequence region is the FILL1 sequence region, the FILL2 sequence region, and the FILL16 sequence region. In one embodiment, the filler sequence region is the FILL1 sequence region, the FILL2 sequence region, and the FILL17 sequence region. In one embodiment, the filler sequence region is the FILL1 sequence region, the FILL2 sequence region, and the FILL18 sequence region. In one embodiment, the filler sequence region is the FILL1 sequence region, the FILL3 sequence region, and the FILL4 sequence region. In one embodiment, the filler sequence region is the FILL1 sequence region, the FILL3 sequence region, and the FILL5 sequence region. In one embodiment, the filler sequence region is the FILL1 sequence region, the FILL3 sequence region, and the FILL6 sequence region. In one embodiment, the filler sequence region is the FILL1 sequence region, the FILL3 sequence region, and the FILL7 sequence region. In one embodiment, the filler sequence region is the FILL1 sequence region, the FILL3 sequence region, and the FILL8 sequence region. In one embodiment, the filler sequence region is the FILL1 sequence region, the FILL3 sequence region, and the FILL9 sequence region. In one embodiment, the filler sequence region is the FILL1 sequence region, the FILL3 sequence region, and the FILL10 sequence region. In one embodiment, the filler sequence region is the FILL1 sequence region, the FILL3 sequence region, and the FILL11 sequence region. In one embodiment, the filler sequence region is the FILL1 sequence region, the FILL3 sequence region, and the FILL12 sequence region. In one embodiment, the filler sequence region is the FILL1 sequence region, the FILL3 sequence region, and the FILL13 sequence region. In one embodiment, the filler sequence region is the FILL1 sequence region, the FILL3 sequence region, and the FILL14 sequence region. In one embodiment, the filler sequence region is the FILL1 sequence region, the FILL3 sequence region, and the FILL15 sequence region. In one embodiment, the filler sequence region is the FILL1 sequence region, the FILL3 sequence region, and the FILL16 sequence region. In one embodiment, the filler sequence region is the FILL1 sequence region, the FILL3 sequence region, and the FILL17 sequence region. In one embodiment, the filler sequence region is the FILL1 sequence region, the FILL3 sequence region, and the FILL18 sequence region. In one embodiment, the filler sequence region is the FILL1 sequence region, the FILL4 sequence region, and the FILL5 sequence region. In one embodiment, the filler sequence region is the FILL1 sequence region, the FILL4 sequence region, and the FILL6 sequence region. In one embodiment, the filler sequence region is the FILL1 sequence region, the FILL4 sequence region, and the FILL7 sequence region. In one embodiment, the filler sequence region is the FILL1 sequence region, the FILL4 sequence region, and the FILL8 sequence region. In one embodiment, the filler sequence region is the FILL1 sequence region, the FILL4 sequence region, and the FILL9 sequence region. In one embodiment, the filler sequence region is the FILL1 sequence region, the FILL4 sequence region, and the FILL10 sequence region. In one embodiment, the filler sequence region is the FILL1 sequence region, the FILL4 sequence region, and the FILL11 sequence region. In one embodiment, the filler sequence region is the FILL1 sequence region, the FILL4 sequence region, and the FILL12 sequence region. In one embodiment, the filler sequence region is the FILL1 sequence region, the FILL4 sequence region, and the FILL13 sequence region. In one embodiment, the filler sequence region is the FILL1 sequence region, the FILL4 sequence region, and the FILL14 sequence region. In one embodiment, the filler sequence region is the FILL1 sequence region, the FILL4 sequence region, and the FILL15 sequence region. In one embodiment, the filler sequence region is the FILL1 sequence region, the FILL4 sequence region, and the FILL16 sequence region. In one embodiment, the filler sequence region is the FILL1 sequence region, the FILL4 sequence region, and the FILL17 sequence region. In one embodiment, the filler sequence region is the FILL1 sequence region, the FILL4 sequence region, and the FILL18 sequence region. In one embodiment, the filler sequence region is the FILL1 sequence region, the FILL5 sequence region, and the FILL6 sequence region. In one embodiment, the filler sequence region is the FILL1 sequence region, the FILL5 sequence region, and the FILL7 sequence region. In one embodiment, the filler sequence region is the FILL1 sequence region, the FILL5 sequence region, and the FILL8 sequence region. In one embodiment, the filler sequence region is the FILL1 sequence region, the FILL5 sequence region, and the FILL9 sequence region. In one embodiment, the filler sequence region is the FILL1 sequence region, the FILL5 sequence region, and the FILL10 sequence region. In one embodiment, the filler sequence region is the FILL1 sequence region, the FILL5 sequence region, and the FILL11 sequence region. In one embodiment, the filler sequence region is the FILL1 sequence region, the FILL5 sequence region, and the FILL12 sequence region. In one embodiment, the filler sequence region is the FILL1 sequence region, the FILL5 sequence region, and the FILL13 sequence region. In one embodiment, the filler sequence region is the FILL1 sequence region, the FILL5 sequence region, and the FILL14 sequence region. In one embodiment, the filler sequence region is the FILL1 sequence region, the FILL5 sequence region, and the FILL15 sequence region. In one embodiment, the filler sequence region is the FILL1 sequence region, the FILL5 sequence region, and the FILL16 sequence region. In one embodiment, the filler sequence region is the FILL1 sequence region, the FILL5 sequence region, and the FILL17 sequence region. In one embodiment, the filler sequence region is the FILL1 sequence region, the FILL5 sequence region, and the FILL18 sequence region. In one embodiment, the filler sequence region is the FILL1 sequence region, the FILL6 sequence region, and the FILL7 sequence region. In one embodiment, the filler sequence region is the FILL1 sequence region, the FILL6 sequence region, and the FILL8 sequence region. In one embodiment, the filler sequence region is the FILL1 sequence region, the FILL6 sequence region, and the FILL9 sequence region. In one embodiment, the filler sequence region is the FILL1 sequence region, the FILL6 sequence region, and the FILL10 sequence region. In one embodiment, the filler sequence region is the FILL1 sequence region, the FILL6 sequence region, and the FILL11 sequence region. In one embodiment, the filler sequence region is the FILL1 sequence region, the FILL6 sequence region, and the FILL12 sequence region. In one embodiment, the filler sequence region is the FILL1 sequence region, the FILL6 sequence region, and the FILL13 sequence region. In one embodiment, the filler sequence region is the FILL1 sequence region, the FILL6 sequence region, and the FILL14 sequence region. In one embodiment, the filler sequence region is the FILL1 sequence region, the FILL6 sequence region, and the FILL15 sequence region. In one embodiment, the filler sequence region is the FILL1 sequence region, the FILL6 sequence region, and the FILL16 sequence region. In one embodiment, the filler sequence region is the FILL1 sequence region, the FILL6 sequence region, and the FILL17 sequence region. In one embodiment, the filler sequence region is the FILL1 sequence region, the FILL6 sequence region, and the FILL18 sequence region. In one embodiment, the filler sequence region is the FILL1 sequence region, the FILL7 sequence region, and the FILL8 sequence region. In one embodiment, the filler sequence region is the FILL1 sequence region, the FILL7 sequence region, and the FILL9 sequence region. In one embodiment, the filler sequence region is the FILL1 sequence region, the FILL7 sequence region, and the FILL10 sequence region. In one embodiment, the filler sequence region is the FILL1 sequence region, the FILL7 sequence region, and the FILL11 sequence region. In one embodiment, the filler sequence region is the FILL1 sequence region, the FILL7 sequence region, and the FILL12 sequence region. In one embodiment, the filler sequence region is the FILL1 sequence region, the FILL7 sequence region, and the FILL13 sequence region. In one embodiment, the filler sequence region is the FILL1 sequence region, the FILL7 sequence region, and the FILL14 sequence region. In one embodiment, the filler sequence region is the FILL1 sequence region, the FILL7 sequence region, and the FILL15 sequence region. In one embodiment, the filler sequence region is the FILL1 sequence region, the FILL7 sequence region, and the FILL16 sequence region. In one embodiment, the filler sequence region is the FILL1 sequence region, the FILL7 sequence region, and the FILL17 sequence region. In one embodiment, the filler sequence region is the FILL1 sequence region, the FILL7 sequence region, and the FILL18 sequence region. In one embodiment, the filler sequence region is the FILL1 sequence region, the FILL8 sequence region, and the FILL9 sequence region. In one embodiment, the filler sequence region is the FILL1 sequence region, the FILL8 sequence region, and the FILL10 sequence region. In one embodiment, the filler sequence region is the FILL1 sequence region, the FILL8 sequence region, and the FILL11 sequence region. In one embodiment, the filler sequence region is the FILL1 sequence region, the FILL8 sequence region, and the FILL12 sequence region. In one embodiment, the filler sequence region is the FILL1 sequence region, the FILL8 sequence region, and the FILL13 sequence region. In one embodiment, the filler sequence region is the FILL1 sequence region, the FILL8 sequence region, and the FILL14 sequence region. In one embodiment, the filler sequence region is the FILL1 sequence region, the FILL8 sequence region, and the FILL15 sequence region. In one embodiment, the filler sequence region is the FILL1 sequence region, the FILL8 sequence region, and the FILL16 sequence region. In one embodiment, the filler sequence region is the FILL1 sequence region, the FILL8 sequence region, and the FILL17 sequence region. In one embodiment, the filler sequence region is the FILL1 sequence region, the FILL8 sequence region, and the FILL18 sequence region. In one embodiment, the filler sequence region is the FILL1 sequence region, the FILL9 sequence region, and the FILL10 sequence region. In one embodiment, the filler sequence region is the FILL1 sequence region, the FILL9 sequence region, and the FILL11 sequence region. In one embodiment, the filler sequence region is the FILL1 sequence region, the FILL9 sequence region, and the FILL12 sequence region. In one embodiment, the filler sequence region is the FILL1 sequence region, the FILL9 sequence region, and the FILL13 sequence region. In one embodiment, the filler sequence region is the FILL1 sequence region, the FILL9 sequence region, and the FILL14 sequence region. In one embodiment, the filler sequence region is the FILL1 sequence region, the FILL9 sequence region, and the FILL15 sequence region. In one embodiment, the filler sequence region is the FILL1 sequence region, the FILL9 sequence region, and the FILL16 sequence region. In one embodiment, the filler sequence region is the FILL1 sequence region, the FILL9 sequence region, and the FILL17 sequence region. In one embodiment, the filler sequence region is the FILL1 sequence region, the FILL9 sequence region, and the FILL18 sequence region. In one embodiment, the filler sequence region is the FILL1 sequence region, the FILL10 sequence region, and the FILL11 sequence region. In one embodiment, the filler sequence region is the FILL1 sequence region, the FILL10 sequence region, and the FILL12 sequence region. In one embodiment, the filler sequence region is the FILL1 sequence region, the FILL10 sequence region, and the FILL13 sequence region. In one embodiment, the filler sequence region is the FILL1 sequence region, the FILL10 sequence region, and the FILL14 sequence region. In one embodiment, the filler sequence region is the FILL1 sequence region, the FILL10 sequence region, and the FILL15 sequence region. In one embodiment, the filler sequence region is the FILL1 sequence region, the FILL10 sequence region, and the FILL16 sequence region. In one embodiment, the filler sequence region is the FILL1 sequence region, the FILL10 sequence region, and the FILL17 sequence region. In one embodiment, the filler sequence region is the FILL1 sequence region, the FILL10 sequence region, and the FILL18 sequence region. In one embodiment, the filler sequence region is the FILL1 sequence region, the FILL11 sequence region, and the FILL12 sequence region. In one embodiment, the filler sequence region is the FILL1 sequence region, the FILL11 sequence region, and the FILL13 sequence region. In one embodiment, the filler sequence region is the FILL1 sequence region, the FILL11 sequence region, and the FILL14 sequence region. In one embodiment, the filler sequence region is the FILL1 sequence region, the FILL11 sequence region, and the FILL15 sequence region. In one embodiment, the filler sequence region is the FILL1 sequence region, the FILL11 sequence region, and the FILL16 sequence region. In one embodiment, the filler sequence region is the FILL1 sequence region, the FILL11 sequence region, and the FILL17 sequence region. In one embodiment, the filler sequence region is the FILL1 sequence region, the FILL11 sequence region, and the FILL18 sequence region. In one embodiment, the filler sequence region is the FILL1 sequence region, the FILL12 sequence region, and the FILL13 sequence region. In one embodiment, the filler sequence region is the FILL1 sequence region, the FILL12 sequence region, and the FILL14 sequence region. In one embodiment, the filler sequence region is the FILL1 sequence region, the FILL12 sequence region, and the FILL15 sequence region. In one embodiment, the filler sequence region is the FILL1 sequence region, the FILL12 sequence region, and the FILL16 sequence region. In one embodiment, the filler sequence region is the FILL1 sequence region, the FILL12 sequence region, and the FILL17 sequence region. In one embodiment, the filler sequence region is the FILL1 sequence region, the FILL12 sequence region, and the FILL18 sequence region. In one embodiment, the filler sequence region is the FILL1 sequence region, the FILL13 sequence region, and the FILL14 sequence region. In one embodiment, the filler sequence region is the FILL1 sequence region, the FILL13 sequence region, and the FILL15 sequence region. In one embodiment, the filler sequence region is the FILL1 sequence region, the FILL13 sequence region, and the FILL16 sequence region. In one embodiment, the filler sequence region is the FILL1 sequence region, the FILL13 sequence region, and the FILL17 sequence region. In one embodiment, the filler sequence region is the FILL1 sequence region, the FILL13 sequence region, and the FILL18 sequence region. In one embodiment, the filler sequence region is the FILL1 sequence region, the FILL14 sequence region, and the FILL15 sequence region. In one embodiment, the filler sequence region is the FILL1 sequence region, the FILL14 sequence region, and the FILL16 sequence region. In one embodiment, the filler sequence region is the FILL1 sequence region, the FILL14 sequence region, and the FILL17 sequence region. In one embodiment, the filler sequence region is the FILL1 sequence region, the FILL14 sequence region, and the FILL18 sequence region. In one embodiment, the filler sequence region is the FILL1 sequence region, the FILL15 sequence region, and the FILL16 sequence region. In one embodiment, the filler sequence region is the FILL1 sequence region, the FILL15 sequence region, and the FILL17 sequence region. In one embodiment, the filler sequence region is the FILL1 sequence region, the FILL15 sequence region, and the FILL18 sequence region. In one embodiment, the filler sequence region is the FILL1 sequence region, the FILL16 sequence region, and the FILL17 sequence region. In one embodiment, the filler sequence region is the FILL1 sequence region, the FILL16 sequence region, and the FILL18 sequence region. In one embodiment, the filler sequence region is the FILL1 sequence region, the FILL17 sequence region, and the FILL18 sequence region. In one embodiment, the filler sequence region is the FILL2 sequence region, the FILL3 sequence region, and the FILL4 sequence region. In one embodiment, the filler sequence region is the FILL2 sequence region, the FILL3 sequence region, and the FILL5 sequence region. In one embodiment, the filler sequence region is the FILL2 sequence region, the FILL3 sequence region, and the FILL6 sequence region. In one embodiment, the filler sequence region is the FILL2 sequence region, the FILL3 sequence region, and the FILL7 sequence region. In one embodiment, the filler sequence region is the FILL2 sequence region, the FILL3 sequence region, and the FILL8 sequence region. In one embodiment, the filler sequence region is the FILL2 sequence region, the FILL3 sequence region, and the FILL9 sequence region. In one embodiment, the filler sequence region is the FILL2 sequence region, the FILL3 sequence region, and the FILL10 sequence region. In one embodiment, the filler sequence region is the FILL2 sequence region, the FILL3 sequence region, and the FILL11 sequence region. In one embodiment, the filler sequence region is the FILL2 sequence region, the FILL3 sequence region, and the FILL12 sequence region. In one embodiment, the filler sequence region is the FILL2 sequence region, the FILL3 sequence region, and the FILL13 sequence region. In one embodiment, the filler sequence region is the FILL2 sequence region, the FILL3 sequence region, and the FILL14 sequence region. In one embodiment, the filler sequence region is the FILL2 sequence region, the FILL3 sequence region, and the FILL15 sequence region. In one embodiment, the filler sequence region is the FILL2 sequence region, the FILL3 sequence region, and the FILL16 sequence region. In one embodiment, the filler sequence region is the FILL2 sequence region, the FILL3 sequence region, and the FILL17 sequence region. In one embodiment, the filler sequence region is the FILL2 sequence region, the FILL3 sequence region, and the FILL18 sequence region. In one embodiment, the filler sequence region is the FILL2 sequence region, the FILL4 sequence region, and the FILL5 sequence region. In one embodiment, the filler sequence region is the FILL2 sequence region, the FILL4 sequence region, and the FILL6 sequence region. In one embodiment, the filler sequence region is the FILL2 sequence region, the FILL4 sequence region, and the FILL7 sequence region. In one embodiment, the filler sequence region is the FILL2 sequence region, the FILL4 sequence region, and the FILL8 sequence region. In one embodiment, the filler sequence region is the FILL2 sequence region, the FILL4 sequence region, and the FILL9 sequence region. In one embodiment, the filler sequence region is the FILL2 sequence region, the FILL4 sequence region, and the FILL10 sequence region. In one embodiment, the filler sequence region is the FILL2 sequence region, the FILL4 sequence region, and the FILL11 sequence region. In one embodiment, the filler sequence region is the FILL2 sequence region, the FILL4 sequence region, and the FILL12 sequence region. In one embodiment, the filler sequence region is the FILL2 sequence region, the FILL4 sequence region, and the FILL13 sequence region. In one embodiment, the filler sequence region is the FILL2 sequence region, the FILL4 sequence region, and the FILL14 sequence region. In one embodiment, the filler sequence region is the FILL2 sequence region, the FILL4 sequence region, and the FILL15 sequence region. In one embodiment, the filler sequence region is the FILL2 sequence region, the FILL4 sequence region, and the FILL16 sequence region. In one embodiment, the filler sequence region is the FILL2 sequence region, the FILL4 sequence region, and the FILL17 sequence region. In one embodiment, the filler sequence region is the FILL2 sequence region, the FILL4 sequence region, and the FILL18 sequence region. In one embodiment, the filler sequence region is the FILL2 sequence region, the FILL5 sequence region, and the FILL6 sequence region. In one embodiment, the filler sequence region is the FILL2 sequence region, the FILL5 sequence region, and the FILL7 sequence region. In one embodiment, the filler sequence region is the FILL2 sequence region, the FILL5 sequence region, and the FILL8 sequence region. In one embodiment, the filler sequence region is the FILL2 sequence region, the FILL5 sequence region, and the FILL9 sequence region. In one embodiment, the filler sequence region is the FILL2 sequence region, the FILL5 sequence region, and the FILL10 sequence region. In one embodiment, the filler sequence region is the FILL2 sequence region, the FILL5 sequence region, and the FILL11 sequence region. In one embodiment, the filler sequence region is the FILL2 sequence region, the FILL5 sequence region, and the FILL12 sequence region. In one embodiment, the filler sequence region is the FILL2 sequence region, the FILL5 sequence region, and the FILL13 sequence region. In one embodiment, the filler sequence region is the FILL2 sequence region, the FILL5 sequence region, and the FILL14 sequence region. In one embodiment, the filler sequence region is the FILL2 sequence region, the FILL5 sequence region, and the FILL15 sequence region. In one embodiment, the filler sequence region is the FILL2 sequence region, the FILL5 sequence region, and the FILL16 sequence region. In one embodiment, the filler sequence region is the FILL2 sequence region, the FILL5 sequence region, and the FILL17 sequence region. In one embodiment, the filler sequence region is the FILL2 sequence region, the FILL5 sequence region, and the FILL18 sequence region. In one embodiment, the filler sequence region is the FILL2 sequence region, the FILL6 sequence region, and the FILL7 sequence region. In one embodiment, the filler sequence region is the FILL2 sequence region, the FILL6 sequence region, and the FILL8 sequence region. In one embodiment, the filler sequence region is the FILL2 sequence region, the FILL6 sequence region, and the FILL9 sequence region. In one embodiment, the filler sequence region is the FILL2 sequence region, the FILL6 sequence region, and the FILL10 sequence region. In one embodiment, the filler sequence region is the FILL2 sequence region, the FILL6 sequence region, and the FILL11 sequence region. In one embodiment, the filler sequence region is the FILL2 sequence region, the FILL6 sequence region, and the FILL12 sequence region. In one embodiment, the filler sequence region is the FILL2 sequence region, the FILL6 sequence region, and the FILL13 sequence region. In one embodiment, the filler sequence region is the FILL2 sequence region, the FILL6 sequence region, and the FILL14 sequence region. In one embodiment, the filler sequence region is the FILL2 sequence region, the FILL6 sequence region, and the FILL15 sequence region. In one embodiment, the filler sequence region is the FILL2 sequence region, the FILL6 sequence region, and the FILL16 sequence region. In one embodiment, the filler sequence region is the FILL2 sequence region, the FILL6 sequence region, and the FILL17 sequence region. In one embodiment, the filler sequence region is the FILL2 sequence region, the FILL6 sequence region, and the FILL18 sequence region. In one embodiment, the filler sequence region is the FILL2 sequence region, the FILL7 sequence region, and the FILL8 sequence region. In one embodiment, the filler sequence region is the FILL2 sequence region, the FILL7 sequence region, and the FILL9 sequence region. In one embodiment, the filler sequence region is the FILL2 sequence region, the FILL7 sequence region, and the FILL10 sequence region. In one embodiment, the filler sequence region is the FILL2 sequence region, the FILL7 sequence region, and the FILL11 sequence region. In one embodiment, the filler sequence region is the FILL2 sequence region, the FILL7 sequence region, and the FILL12 sequence region. In one embodiment, the filler sequence region is the FILL2 sequence region, the FILL7 sequence region, and the FILL13 sequence region. In one embodiment, the filler sequence region is the FILL2 sequence region, the FILL7 sequence region, and the FILL14 sequence region. In one embodiment, the filler sequence region is the FILL2 sequence region, the FILL7 sequence region, and the FILL15 sequence region. In one embodiment, the filler sequence region is the FILL2 sequence region, the FILL7 sequence region, and the FILL16 sequence region. In one embodiment, the filler sequence region is the FILL2 sequence region, the FILL7 sequence region, and the FILL17 sequence region. In one embodiment, the filler sequence region is the FILL2 sequence region, the FILL7 sequence region, and the FILL18 sequence region. In one embodiment, the filler sequence region is the FILL2 sequence region, the FILL5 sequence region, and the FILL9 sequence region. In one embodiment, the filler sequence region is the FILL2 sequence region, the FILL8 sequence region, and the FILL10 sequence region. In one embodiment, the filler sequence region is the FILL2 sequence region, the FILL8 sequence region, and the FILL11 sequence region. In one embodiment, the filler sequence region is the FILL2 sequence region, the FILL5 sequence region, and the FILL12 sequence region. In one embodiment, the filler sequence region is the FILL2 sequence region, the FILL5 sequence region, and the FILL13 sequence region. In one embodiment, the filler sequence region is the FILL2 sequence region, the FILL8 sequence region, and the FILL14 sequence region. In one embodiment, the filler sequence region is the FILL2 sequence region, the FILL8 sequence region, and the FILL15 sequence region. In one embodiment, the filler sequence region is the FILL2 sequence region, the FILL5 sequence region, and the FILL16 sequence region. In one embodiment, the filler sequence region is the FILL2 sequence region, the FILL8 sequence region, and the FILL17 sequence region. In one embodiment, the filler sequence region is the FILL2 sequence region, the FILL8 sequence region, and the FILL18 sequence region. In one embodiment, the filler sequence region is the FILL2 sequence region, the FILL9 sequence region, and the FILL10 sequence region. In one embodiment, the filler sequence region is the FILL2 sequence region, the FILL9 sequence region, and the FILL11 sequence region. In one embodiment, the filler sequence region is the FILL2 sequence region, the FILL9 sequence region, and the FILL12 sequence region. In one embodiment, the filler sequence region is the FILL2 sequence region, the FILL9 sequence region, and the FILL13 sequence region. In one embodiment, the filler sequence region is the FILL2 sequence region, the FILL9 sequence region, and the FILL14 sequence region. In one embodiment, the filler sequence region is the FILL2 sequence region, the FILL9 sequence region, and the FILL15 sequence region. In one embodiment, the filler sequence region is the FILL2 sequence region, the FILL9 sequence region, and the FILL16 sequence region. In one embodiment, the filler sequence region is the FILL2 sequence region, the FILL9 sequence region, and the FILL17 sequence region. In one embodiment, the filler sequence region is the FILL2 sequence region, the FILL9 sequence region, and the FILL18 sequence region. In one embodiment, the filler sequence region is the FILL2 sequence region, the FILL10 sequence region, and the FILL11 sequence region. In one embodiment, the filler sequence region is the FILL2 sequence region, the FILL10 sequence region, and the FILL12 sequence region. In one embodiment, the filler sequence region is the FILL2 sequence region, the FILL10 sequence region, and the FILL13 sequence region. In one embodiment, the filler sequence region is the FILL2 sequence region, the FILL10 sequence region, and the FILL14 sequence region. In one embodiment, the filler sequence region is the FILL2 sequence region, the FILL10 sequence region, and the FILL15 sequence region. In one embodiment, the filler sequence region is the FILL2 sequence region, the FILL10 sequence region, and the FILL16 sequence region. In one embodiment, the filler sequence region is the FILL2 sequence region, the FILL10 sequence region, and the FILL17 sequence region. In one embodiment, the filler sequence region is the FILL2 sequence region, the FILL10 sequence region, and the FILL18 sequence region. In one embodiment, the filler sequence region is the FILL2 sequence region, the FILL11 sequence region, and the FILL12 sequence region. In one embodiment, the filler sequence region is the FILL2 sequence region, the FILL11 sequence region, and the FILL13 sequence region. In one embodiment, the filler sequence region is the FILL2 sequence region, the FILL11 sequence region, and the FILL14 sequence region. In one embodiment, the filler sequence region is the FILL2 sequence region, the FILL11 sequence region, and the FILL15 sequence region. In one embodiment, the filler sequence region is the FILL2 sequence region, the FILL11 sequence region, and the FILL16 sequence region. In one embodiment, the filler sequence region is the FILL2 sequence region, the FILL11 sequence region, and the FILL17 sequence region. In one embodiment, the filler sequence region is the FILL2 sequence region, the FILL11 sequence region, and the FILL18 sequence region. In one embodiment, the filler sequence region is the FILL2 sequence region, the FILL12 sequence region, and the FILL13 sequence region. In one embodiment, the filler sequence region is the FILL2 sequence region, the FILL12 sequence region, and the FILL14 sequence region. In one embodiment, the filler sequence region is the FILL2 sequence region, the FILL12 sequence region, and the FILL15 sequence region. In one embodiment, the filler sequence region is the FILL2 sequence region, the FILL12 sequence region, and the FILL16 sequence region. In one embodiment, the filler sequence region is the FILL2 sequence region, the FILL12 sequence region, and the FILL17 sequence region. In one embodiment, the filler sequence region is the FILL2 sequence region, the FILL12 sequence region, and the FILL18 sequence region. In one embodiment, the filler sequence region is the FILL2 sequence region, the FILL13 sequence region, and the FILL14 sequence region. In one embodiment, the filler sequence region is the FILL2 sequence region, the FILL13 sequence region, and the FILL15 sequence region. In one embodiment, the filler sequence region is the FILL2 sequence region, the FILL13 sequence region, and the FILL16 sequence region. In one embodiment, the filler sequence region is the FILL2 sequence region, the FILL13 sequence region, and the FILL17 sequence region. In one embodiment, the filler sequence region is the FILL2 sequence region, the FILL13 sequence region, and the FILL18 sequence region. In one embodiment, the filler sequence region is the FILL2 sequence region, the FILL14 sequence region, and the FILL15 sequence region. In one embodiment, the filler sequence region is the FILL2 sequence region, the FILL14 sequence region, and the FILL16 sequence region. In one embodiment, the filler sequence region is the FILL2 sequence region, the FILL14 sequence region, and the FILL17 sequence region. In one embodiment, the filler sequence region is the FILL2 sequence region, the FILL14 sequence region, and the FILL18 sequence region. In one embodiment, the filler sequence region is the FILL2 sequence region, the FILL15 sequence region, and the FILL16 sequence region. In one embodiment, the filler sequence region is the FILL2 sequence region, the FILL15 sequence region, and the FILL17 sequence region. In one embodiment, the filler sequence region is the FILL2 sequence region, the FILL15 sequence region, and the FILL18 sequence region. In one embodiment, the filler sequence region is the FILL2 sequence region, the FILL16 sequence region, and the FILL17 sequence region. In one embodiment, the filler sequence region is the FILL2 sequence region, the FILL16 sequence region, and the FILL18 sequence region. In one embodiment, the filler sequence region is the FILL2 sequence region, the FILL17 sequence region, and the FILL18 sequence region. In one embodiment, the filler sequence region is the FILL3 sequence region, the FILL4 sequence region, and the FILL5 sequence region. In one embodiment, the filler sequence region is the FILL3 sequence region, the FILL4 sequence region, and the FILL6 sequence region. In one embodiment, the filler sequence region is the FILL3 sequence region, the FILL4 sequence region, and the FILL7 sequence region. In one embodiment, the filler sequence region is the FILL3 sequence region, the FILL4 sequence region, and the FILL8 sequence region. In one embodiment, the filler sequence region is the FILL3 sequence region, the FILL4 sequence region, and the FILL9 sequence region. In one embodiment, the filler sequence region is the FILL3 sequence region, the FILL4 sequence region, and the FILL10 sequence region. In one embodiment, the filler sequence region is the FILL3 sequence region, the FILL4 sequence region, and the FILL11 sequence region. In one embodiment, the filler sequence region is the FILL3 sequence region, the FILL4 sequence region, and the FILL12 sequence region. In one embodiment, the filler sequence region is the FILL3 sequence region, the FILL4 sequence region, and the FILL13 sequence region. In one embodiment, the filler sequence region is the FILL3 sequence region, the FILL4 sequence region, and the FILL14 sequence region. In one embodiment, the filler sequence region is the FILL3 sequence region, the FILL4 sequence region, and the FILL15 sequence region. In one embodiment, the filler sequence region is the FILL3 sequence region, the FILL4 sequence region, and the FILL16 sequence region. In one embodiment, the filler sequence region is the FILL3 sequence region, the FILL4 sequence region, and the FILL17 sequence region. In one embodiment, the filler sequence region is the FILL3 sequence region, the FILL4 sequence region, and the FILL18 sequence region. In one embodiment, the filler sequence region is the FILL3 sequence region, the FILL5 sequence region, and the FILL6 sequence region. In one embodiment, the filler sequence region is the FILL3 sequence region, the FILL5 sequence region, and the FILL7 sequence region. In one embodiment, the filler sequence region is the FILL3 sequence region, the FILL5 sequence region, and the FILL8 sequence region. In one embodiment, the filler sequence region is the FILL3 sequence region, the FILL5 sequence region, and the FILL9 sequence region. In one embodiment, the filler sequence region is the FILL3 sequence region, the FILL5 sequence region, and the FILL10 sequence region. In one embodiment, the filler sequence region is the FILL3 sequence region, the FILL5 sequence region, and the FILL11 sequence region. In one embodiment, the filler sequence region is the FILL3 sequence region, the FILL5 sequence region, and the FILL12 sequence region. In one embodiment, the filler sequence region is the FILL3 sequence region, the FILL5 sequence region, and the FILL13 sequence region. In one embodiment, the filler sequence region is the FILL3 sequence region, the FILL5 sequence region, and the FILL14 sequence region. In one embodiment, the filler sequence region is the FILL3 sequence region, the FILL5 sequence region, and the FILL15 sequence region. In one embodiment, the filler sequence region is the FILL3 sequence region, the FILL5 sequence region, and the FILL16 sequence region. In one embodiment, the filler sequence region is the FILL3 sequence region, the FILL5 sequence region, and the FILL17 sequence region. In one embodiment, the filler sequence region is the FILL3 sequence region, the FILL5 sequence region, and the FILL18 sequence region. In one embodiment, the filler sequence region is the FILL3 sequence region, the FILL6 sequence region, and the FILL7 sequence region. In one embodiment, the filler sequence region is the FILL3 sequence region, the FILL6 sequence region, and the FILL5 sequence region. In one embodiment, the filler sequence region is the FILL3 sequence region, the FILL6 sequence region, and the FILL9 sequence region. In one embodiment, the filler sequence region is the FILL3 sequence region, the FILL6 sequence region, and the FILL10 sequence region. In one embodiment, the filler sequence region is the FILL3 sequence region, the FILL6 sequence region, and the FILL11 sequence region. In one embodiment, the filler sequence region is the FILL3 sequence region, the FILL6 sequence region, and the FILL12 sequence region. In one embodiment, the filler sequence region is the FILL3 sequence region, the FILL6 sequence region, and the FILL13 sequence region. In one embodiment, the filler sequence region is the FILL3 sequence region, the FILL6 sequence region, and the FILL14 sequence region. In one embodiment, the filler sequence region is the FILL3 sequence region, the FILL6 sequence region, and the FILL15 sequence region. In one embodiment, the filler sequence region is the FILL3 sequence region, the FILL6 sequence region, and the FILL16 sequence region. In one embodiment, the filler sequence region is the FILL3 sequence region, the FILL6 sequence region, and the FILL17 sequence region. In one embodiment, the filler sequence region is the FILL3 sequence region, the FILL6 sequence region, and the FILL18 sequence region. In one embodiment, the filler sequence region is the FILL3 sequence region, the FILL7 sequence region, and the FILL8 sequence region. In one embodiment, the filler sequence region is the FILL3 sequence region, the FILL7 sequence region, and the FILL9 sequence region. In one embodiment, the filler sequence region is the FILL3 sequence region, the FILL7 sequence region, and the FILL10 sequence region. In one embodiment, the filler sequence region is the FILL3 sequence region, the FILL7 sequence region, and the FILL11 sequence region. In one embodiment, the filler sequence region is the FILL3 sequence region, the FILL7 sequence region, and the FILL12 sequence region. In one embodiment, the filler sequence region is the FILL3 sequence region, the FILL7 sequence region, and the FILL13 sequence region. In one embodiment, the filler sequence region is the FILL3 sequence region, the FILL7 sequence region, and the FILL14 sequence region. In one embodiment, the filler sequence region is the FILL3 sequence region, the FILL7 sequence region, and the FILL15 sequence region. In one embodiment, the filler sequence region is the FILL3 sequence region, the FILL7 sequence region, and the FILL16 sequence region. In one embodiment, the filler sequence region is the FILL3 sequence region, the FILL7 sequence region, and the FILL17 sequence region. In one embodiment, the filler sequence region is the FILL3 sequence region, the FILL7 sequence region, and the FILL18 sequence region. In one embodiment, the filler sequence region is the FILL3 sequence region, the FILL8 sequence region, and the FILL9 sequence region. In one embodiment, the filler sequence region is the FILL3 sequence region, the FILL8 sequence region, and the FILL10 sequence region. In one embodiment, the filler sequence region is the FILL3 sequence region, the FILL8 sequence region, and the FILL11 sequence region. In one embodiment, the filler sequence region is the FILL3 sequence region, the FILL8 sequence region, and the FILL12 sequence region. In one embodiment, the filler sequence region is the FILL3 sequence region, the FILL8 sequence region, and the FILL13 sequence region. In one embodiment, the filler sequence region is the FILL3 sequence region, the FILL8 sequence region, and the FILL14 sequence region. In one embodiment, the filler sequence region is the FILL3 sequence region, the FILL8 sequence region, and the FILL15 sequence region. In one embodiment, the filler sequence region is the FILL3 sequence region, the FILL8 sequence region, and the FILL16 sequence region. In one embodiment, the filler sequence region is the FILL3 sequence region, the FILL8 sequence region, and the FILL17 sequence region. In one embodiment, the filler sequence region is the FILL3 sequence region, the FILL8 sequence region, and the FILL18 sequence region. In one embodiment, the filler sequence region is the FILL3 sequence region, the FILL9 sequence region, and the FILL10 sequence region. In one embodiment, the filler sequence region is the FILL3 sequence region, the FILL9 sequence region, and the FILL11 sequence region. In one embodiment, the filler sequence region is the FILL3 sequence region, the FILL9 sequence region, and the FILL12 sequence region. In one embodiment, the filler sequence region is the FILL3 sequence region, the FILL9 sequence region, and the FILL13 sequence region. In one embodiment, the filler sequence region is the FILL3 sequence region, the FILL9 sequence region, and the FILL14 sequence region. In one embodiment, the filler sequence region is the FILL3 sequence region, the FILL9 sequence region, and the FILL15 sequence region. In one embodiment, the filler sequence region is the FILL3 sequence region, the FILL9 sequence region, and the FILL16 sequence region. In one embodiment, the filler sequence region is the FILL3 sequence region, the FILL9 sequence region, and the FILL17 sequence region. In one embodiment, the filler sequence region is the FILL3 sequence region, the FILL9 sequence region, and the FILL18 sequence region. In one embodiment, the filler sequence region is the FILL3 sequence region, the FILL10 sequence region, and the FILL11 sequence region. In one embodiment, the filler sequence region is the FILL3 sequence region, the FILL10 sequence region, and the FILL12 sequence region. In one embodiment, the filler sequence region is the FILL3 sequence region, the FILL10 sequence region, and the FILL13 sequence region. In one embodiment, the filler sequence region is the FILL3 sequence region, the FILL10 sequence region, and the FILL14 sequence region. In one embodiment, the filler sequence region is the FILL3 sequence region, the FILL10 sequence region, and the FILL15 sequence region. In one embodiment, the filler sequence region is the FILL3 sequence region, the FILL10 sequence region, and the FILL16 sequence region. In one embodiment, the filler sequence region is the FILL3 sequence region, the FILL10 sequence region, and the FILL17 sequence region. In one embodiment, the filler sequence region is the FILL3 sequence region, the FILL10 sequence region, and the FILL18 sequence region. In one embodiment, the filler sequence region is the FILL3 sequence region, the FILL11 sequence region, and the FILL12 sequence region. In one embodiment, the filler sequence region is the FILL3 sequence region, the FILL11 sequence region, and the FILL13 sequence region. In one embodiment, the filler sequence region is the FILL3 sequence region, the FILL11 sequence region, and the FILL14 sequence region. In one embodiment, the filler sequence region is the FILL3 sequence region, the FILL11 sequence region, and the FILL15 sequence region. In one embodiment, the filler sequence region is the FILL3 sequence region, the FILL11 sequence region, and the FILL16 sequence region. In one embodiment, the filler sequence region is the FILL3 sequence region, the FILL11 sequence region, and the FILL17 sequence region. In one embodiment, the filler sequence region is the FILL3 sequence region, the FILL11 sequence region, and the FILL18 sequence region. In one embodiment, the filler sequence region is the FILL3 sequence region, the FILL12 sequence region, and the FILL13 sequence region. In one embodiment, the filler sequence region is the FILL3 sequence region, the FILL12 sequence region, and the FILL14 sequence region. In one embodiment, the filler sequence region is the FILL3 sequence region, the FILL12 sequence region, and the FILL15 sequence region. In one embodiment, the filler sequence region is the FILL3 sequence region, the FILL12 sequence region, and the FILL16 sequence region. In one embodiment, the filler sequence region is the FILL3 sequence region, the FILL12 sequence region, and the FILL17 sequence region. In one embodiment, the filler sequence region is the FILL3 sequence region, the FILL12 sequence region, and the FILL18 sequence region. In one embodiment, the filler sequence region is the FILL3 sequence region, the FILL13 sequence region, and the FILL14 sequence region. In one embodiment, the filler sequence region is the FILL3 sequence region, the FILL13 sequence region, and the FILL15 sequence region. In one embodiment, the filler sequence region is the FILL3 sequence region, the FILL13 sequence region, and the FILL16 sequence region. In one embodiment, the filler sequence region is the FILL3 sequence region, the FILL13 sequence region, and the FILL17 sequence region. In one embodiment, the filler sequence region is the FILL3 sequence region, the FILL13 sequence region, and the FILL18 sequence region. In one embodiment, the filler sequence region is the FILL3 sequence region, the FILL14 sequence region, and the FILL15 sequence region. In one embodiment, the filler sequence region is the FILL3 sequence region, the FILL14 sequence region, and the FILL16 sequence region. In one embodiment, the filler sequence region is the FILL3 sequence region, the FILL14 sequence region, and the FILL17 sequence region. In one embodiment, the filler sequence region is the FILL3 sequence region, the FILL14 sequence region, and the FILL18 sequence region. In one embodiment, the filler sequence region is the FILL3 sequence region, the FILL15 sequence region, and the FILL16 sequence region. In one embodiment, the filler sequence region is the FILL3 sequence region, the FILL15 sequence region, and the FILL17 sequence region. In one embodiment, the filler sequence region is the FILL3 sequence region, the FILL15 sequence region, and the FILL18 sequence region. In one embodiment, the filler sequence region is the FILL3 sequence region, the FILL16 sequence region, and the FILL17 sequence region. In one embodiment, the filler sequence region is the FILL3 sequence region, the FILL16 sequence region, and the FILL18 sequence region. In one embodiment, the filler sequence region is the FILL3 sequence region, the FILL17 sequence region, and the FILL18 sequence region. In one embodiment, the filler sequence region is the FILL4 sequence region, the FILL5 sequence region, and the FILL6 sequence region. In one embodiment, the filler sequence region is the FILL4 sequence region, the FILL5 sequence region, and the FILL7 sequence region. In one embodiment, the filler sequence region is the FILL4 sequence region, the FILL5 sequence region, and the FILL8 sequence region. In one embodiment, the filler sequence region is the FILL4 sequence region, the FILL5 sequence region, and the FILL9 sequence region. In one embodiment, the filler sequence region is the FILL4 sequence region, the FILL5 sequence region, and the FILL10 sequence region. In one embodiment, the filler sequence region is the FILL4 sequence region, the FILL5 sequence region, and the FILL11 sequence region. In one embodiment, the filler sequence region is the FILL4 sequence region, the FILL5 sequence region, and the FILL12 sequence region. In one embodiment, the filler sequence region is the FILL4 sequence region, the FILL5 sequence region, and the FILL13 sequence region. In one embodiment, the filler sequence region is the FILL4 sequence region, the FILL5 sequence region, and the FILL14 sequence region. In one embodiment, the filler sequence region is the FILL4 sequence region, the FILL5 sequence region, and the FILL15 sequence region. In one embodiment, the filler sequence region is the FILL4 sequence region, the FILL5 sequence region, and the FILL16 sequence region. In one embodiment, the filler sequence region is the FILL4 sequence region, the FILL5 sequence region, and the FILL17 sequence region. In one embodiment, the filler sequence region is the FILL4 sequence region, the FILL5 sequence region, and the FILL18 sequence region. In one embodiment, the filler sequence region is the FILL4 sequence region, the FILL6 sequence region, and the FILL7 sequence region. In one embodiment, the filler sequence region is the FILL4 sequence region, the FILL6 sequence region, and the FILL8 sequence region. In one embodiment, the filler sequence region is the FILL4 sequence region, the FILL6 sequence region, and the FILL9 sequence region. In one embodiment, the filler sequence region is the FILL4 sequence region, the FILL6 sequence region, and the FILL10 sequence region. In one embodiment, the filler sequence region is the FILL4 sequence region, the FILL6 sequence region, and the FILL11 sequence region. In one embodiment, the filler sequence region is the FILL4 sequence region, the FILL6 sequence region, and the FILL12 sequence region. In one embodiment, the filler sequence region is the FILL4 sequence region, the FILL6 sequence region, and the FILL13 sequence region. In one embodiment, the filler sequence region is the FILL4 sequence region, the FILL6 sequence region, and the FILL14 sequence region. In one embodiment, the filler sequence region is the FILL4 sequence region, the FILL6 sequence region, and the FILL15 sequence region. In one embodiment, the filler sequence region is the FILL4 sequence region, the FILL6 sequence region, and the FILL16 sequence region. In one embodiment, the filler sequence region is the FILL4 sequence region, the FILL6 sequence region, and the FILL17 sequence region. In one embodiment, the filler sequence region is the FILL4 sequence region, the FILL6 sequence region, and the FILL18 sequence region. In one embodiment, the filler sequence region is the FILL4 sequence region, the FILL7 sequence region, and the FILL8 sequence region. In one embodiment, the filler sequence region is the FILL4 sequence region, the FILL7 sequence region, and the FILL9 sequence region. In one embodiment, the filler sequence region is the FILL4 sequence region, the FILL7 sequence region, and the FILL10 sequence region. In one embodiment, the filler sequence region is the FILL4 sequence region, the FILL7 sequence region, and the FILL11 sequence region. In one embodiment, the filler sequence region is the FILL4 sequence region, the FILL7 sequence region, and the FILL12 sequence region. In one embodiment, the filler sequence region is the FILL4 sequence region, the FILL7 sequence region, and the FILL13 sequence region. In one embodiment, the filler sequence region is the FILL4 sequence region, the FILL7 sequence region, and the FILL14 sequence region. In one embodiment, the filler sequence region is the FILL4 sequence region, the FILL7 sequence region, and the FILL15 sequence region. In one embodiment, the filler sequence region is the FILL4 sequence region, the FILL7 sequence region, and the FILL16 sequence region. In one embodiment, the filler sequence region is the FILL4 sequence region, the FILL7 sequence region, and the FILL17 sequence region. In one embodiment, the filler sequence region is the FILL4 sequence region, the FILL7 sequence region, and the FILL18 sequence region. In one embodiment, the filler sequence region is the FILL4 sequence region, the FILL8 sequence region, and the FILL9 sequence region. In one embodiment, the filler sequence region is the FILL4 sequence region, the FILL8 sequence region, and the FILL10 sequence region. In one embodiment, the filler sequence region is the FILL4 sequence region, the FILL8 sequence region, and the FILL11 sequence region. In one embodiment, the filler sequence region is the FILL4 sequence region, the FILL8 sequence region, and the FILL12 sequence region. In one embodiment, the filler sequence region is the FILL4 sequence region, the FILL8 sequence region, and the FILL13 sequence region. In one embodiment, the filler sequence region is the FILL4 sequence region, the FILL8 sequence region, and the FILL14 sequence region. In one embodiment, the filler sequence region is the FILL4 sequence region, the FILL8 sequence region, and the FILL15 sequence region. In one embodiment, the filler sequence region is the FILL4 sequence region, the FILL8 sequence region, and the FILL16 sequence region. In one embodiment, the filler sequence region is the FILL4 sequence region, the FILL8 sequence region, and the FILL17 sequence region. In one embodiment, the filler sequence region is the FILL4 sequence region, the FILL8 sequence region, and the FILL18 sequence region. In one embodiment, the filler sequence region is the FILL4 sequence region, the FILL9 sequence region, and the FILL10 sequence region. In one embodiment, the filler sequence region is the FILL4 sequence region, the FILL9 sequence region, and the FILL11 sequence region. In one embodiment, the filler sequence region is the FILL4 sequence region, the FILL9 sequence region, and the FILL12 sequence region. In one embodiment, the filler sequence region is the FILL4 sequence region, the FILL9 sequence region, and the FILL13 sequence region. In one embodiment, the filler sequence region is the FILL4 sequence region, the FILL9 sequence region, and the FILL14 sequence region. In one embodiment, the filler sequence region is the FILL4 sequence region, the FILL9 sequence region, and the FILL15 sequence region. In one embodiment, the filler sequence region is the FILL4 sequence region, the FILL9 sequence region, and the FILL16 sequence region. In one embodiment, the filler sequence region is the FILL4 sequence region, the FILL9 sequence region, and the FILL17 sequence region. In one embodiment, the filler sequence region is the FILL4 sequence region, the FILL9 sequence region, and the FILL18 sequence region. In one embodiment, the filler sequence region is the FILL4 sequence region, the FILL10 sequence region, and the FILL11 sequence region. In one embodiment, the filler sequence region is the FILL4 sequence region, the FILL10 sequence region, and the FILL12 sequence region. In one embodiment, the filler sequence region is the FILL4 sequence region, the FILL10 sequence region, and the FILL13 sequence region. In one embodiment, the filler sequence region is the FILL4 sequence region, the FILL10 sequence region, and the FILL14 sequence region. In one embodiment, the filler sequence region is the FILL4 sequence region, the FILL10 sequence region, and the FILL15 sequence region. In one embodiment, the filler sequence region is the FILL4 sequence region, the FILL10 sequence region, and the FILL16 sequence region. In one embodiment, the filler sequence region is the FILL4 sequence region, the FILL10 sequence region, and the FILL17 sequence region. In one embodiment, the filler sequence region is the FILL4 sequence region, the FILL10 sequence region, and the FILL18 sequence region. In one embodiment, the filler sequence region is the FILL4 sequence region, the FILL11 sequence region, and the FILL12 sequence region. In one embodiment, the filler sequence region is the FILL4 sequence region, the FILL11 sequence region, and the FILL13 sequence region. In one embodiment, the filler sequence region is the FILL4 sequence region, the FILL11 sequence region, and the FILL14 sequence region. In one embodiment, the filler sequence region is the FILL4 sequence region, the FILL11 sequence region, and the FILL15 sequence region. In one embodiment, the filler sequence region is the FILL4 sequence region, the FILL11 sequence region, and the FILL16 sequence region. In one embodiment, the filler sequence region is the FILL4 sequence region, the FILL11 sequence region, and the FILL17 sequence region. In one embodiment, the filler sequence region is the FILL4 sequence region, the FILL11 sequence region, and the FILL18 sequence region. In one embodiment, the filler sequence region is the FILL4 sequence region, the FILL12 sequence region, and the FILL13 sequence region. In one embodiment, the filler sequence region is the FILL4 sequence region, the FILL12 sequence region, and the FILL14 sequence region. In one embodiment, the filler sequence region is the FILL4 sequence region, the FILL12 sequence region, and the FILL15 sequence region. In one embodiment, the filler sequence region is the FILL4 sequence region, the FILL12 sequence region, and the FILL16 sequence region. In one embodiment, the filler sequence region is the FILL4 sequence region, the FILL12 sequence region, and the FILL17 sequence region. In one embodiment, the filler sequence region is the FILL4 sequence region, the FILL12 sequence region, and the FILL18 sequence region. In one embodiment, the filler sequence region is the FILL4 sequence region, the FILL13 sequence region, and the FILL14 sequence region. In one embodiment, the filler sequence region is the FILL4 sequence region, the FILL13 sequence region, and the FILL15 sequence region. In one embodiment, the filler sequence region is the FILL4 sequence region, the FILL13 sequence region, and the FILL16 sequence region. In one embodiment, the filler sequence region is the FILL4 sequence region, the FILL13 sequence region, and the FILL17 sequence region. In one embodiment, the filler sequence region is the FILL4 sequence region, the FILL13 sequence region, and the FILL18 sequence region. In one embodiment, the filler sequence region is the FILL4 sequence region, the FILL14 sequence region, and the FILL15 sequence region. In one embodiment, the filler sequence region is the FILL4 sequence region, the FILL14 sequence region, and the FILL16 sequence region. In one embodiment, the filler sequence region is the FILL4 sequence region, the FILL14 sequence region, and the FILL17 sequence region. In one embodiment, the filler sequence region is the FILL4 sequence region, the FILL14 sequence region, and the FILL18 sequence region. In one embodiment, the filler sequence region is the FILL4 sequence region, the FILL15 sequence region, and the FILL16 sequence region. In one embodiment, the filler sequence region is the FILL4 sequence region, the FILL15 sequence region, and the FILL17 sequence region. In one embodiment, the filler sequence region is the FILL4 sequence region, the FILL15 sequence region, and the FILL18 sequence region. In one embodiment, the filler sequence region is the FILL4 sequence region, the FILL16 sequence region, and the FILL17 sequence region. In one embodiment, the filler sequence region is the FILL4 sequence region, the FILL16 sequence region, and the FILL18 sequence region. In one embodiment, the filler sequence region is the FILL4 sequence region, the FILL17 sequence region, and the FILL18 sequence region. In one embodiment, the filler sequence region is the FILL5 sequence region, the FILL6 sequence region, and the FILL7 sequence region. In one embodiment, the filler sequence region is the FILL5 sequence region, the FILL6 sequence region, and the FILL8 sequence region. In one embodiment, the filler sequence region is the FILL5 sequence region, the FILL6 sequence region, and the FILL9 sequence region. In one embodiment, the filler sequence region is the FILL5 sequence region, the FILL6 sequence region, and the FILL10 sequence region. In one embodiment, the filler sequence region is the FILL5 sequence region, the FILL6 sequence region, and the FILL11 sequence region. In one embodiment, the filler sequence region is the FILL5 sequence region, the FILL6 sequence region, and the FILL12 sequence region. In one embodiment, the filler sequence region is the FILL5 sequence region, the FILL6 sequence region, and the FILL13 sequence region. In one embodiment, the filler sequence region is the FILL5 sequence region, the FILL6 sequence region, and the FILL14 sequence region. In one embodiment, the filler sequence region is the FILL5 sequence region, the FILL6 sequence region, and the FILL15 sequence region. In one embodiment, the filler sequence region is the FILL5 sequence region, the FILL6 sequence region, and the FILL16 sequence region. In one embodiment, the filler sequence region is the FILL5 sequence region, the FILL6 sequence region, and the FILL17 sequence region. In one embodiment, the filler sequence region is the FILL5 sequence region, the FILL6 sequence region, and the FILL18 sequence region. In one embodiment, the filler sequence region is the FILL5 sequence region, the FILL7 sequence region, and the FILL8 sequence region. In one embodiment, the filler sequence region is the FILL5 sequence region, the FILL7 sequence region, and the FILL9 sequence region. In one embodiment, the filler sequence region is the FILL5 sequence region, the FILL7 sequence region, and the FILL10 sequence region. In one embodiment, the filler sequence region is the FILL5 sequence region, the FILL7 sequence region, and the FILL11 sequence region. In one embodiment, the filler sequence region is the FILL5 sequence region, the FILL7 sequence region, and the FILL12 sequence region. In one embodiment, the filler sequence region is the FILL5 sequence region, the FILL7 sequence region, and the FILL13 sequence region. In one embodiment, the filler sequence region is the FILL5 sequence region, the FILL7 sequence region, and the FILL14 sequence region. In one embodiment, the filler sequence region is the FILL5 sequence region, the FILL7 sequence region, and the FILL15 sequence region. In one embodiment, the filler sequence region is the FILL5 sequence region, the FILL7 sequence region, and the FILL16 sequence region. In one embodiment, the filler sequence region is the FILL5 sequence region, the FILL7 sequence region, and the FILL17 sequence region. In one embodiment, the filler sequence region is the FILL5 sequence region, the FILL7 sequence region, and the FILL18 sequence region. In one embodiment, the filler sequence region is the FILL5 sequence region, the FILL8 sequence region, and the FILL9 sequence region. In one embodiment, the filler sequence region is the FILL5 sequence region, the FILL8 sequence region, and the FILL10 sequence region. In one embodiment, the filler sequence region is the FILL5 sequence region, the FILL8 sequence region, and the FILL11 sequence region. In one embodiment, the filler sequence region is the FILL5 sequence region, the FILL8 sequence region, and the FILL12 sequence region. In one embodiment, the filler sequence region is the FILL5 sequence region, the FILL8 sequence region, and the FILL13 sequence region. In one embodiment, the filler sequence region is the FILL5 sequence region, the FILL8 sequence region, and the FILL14 sequence region. In one embodiment, the filler sequence region is the FILL5 sequence region, the FILL8 sequence region, and the FILL15 sequence region. In one embodiment, the filler sequence region is the FILL5 sequence region, the FILL8 sequence region, and the FILL16 sequence region. In one embodiment, the filler sequence region is the FILL5 sequence region, the FILL8 sequence region, and the FILL17 sequence region. In one embodiment, the filler sequence region is the FILL5 sequence region, the FILL8 sequence region, and the FILL18 sequence region. In one embodiment, the filler sequence region is the FILL5 sequence region, the FILL9 sequence region, and the FILL10 sequence region. In one embodiment, the filler sequence region is the FILL5 sequence region, the FILL9 sequence region, and the FILL11 sequence region. In one embodiment, the filler sequence region is the FILL5 sequence region, the FILL9 sequence region, and the FILL12 sequence region. In one embodiment, the filler sequence region is the FILL5 sequence region, the FILL9 sequence region, and the FILL13 sequence region. In one embodiment, the filler sequence region is the FILL5 sequence region, the FILL9 sequence region, and the FILL14 sequence region. In one embodiment, the filler sequence region is the FILL5 sequence region, the FILL9 sequence region, and the FILL15 sequence region. In one embodiment, the filler sequence region is the FILL5 sequence region, the FILL9 sequence region, and the FILL16 sequence region. In one embodiment, the filler sequence region is the FILL5 sequence region, the FILL9 sequence region, and the FILL17 sequence region. In one embodiment, the filler sequence region is the FILL5 sequence region, the FILL9 sequence region, and the FILL18 sequence region. In one embodiment, the filler sequence region is the FILL5 sequence region, the FILL10 sequence region, and the FILL11 sequence region. In one embodiment, the filler sequence region is the FILL5 sequence region, the FILL10 sequence region, and the FILL12 sequence region. In one embodiment, the filler sequence region is the FILL5 sequence region, the FILL10 sequence region, and the FILL13 sequence region. In one embodiment, the filler sequence region is the FILL5 sequence region, the FILL10 sequence region, and the FILL14 sequence region. In one embodiment, the filler sequence region is the FILL5 sequence region, the FILL10 sequence region, and the FILL15 sequence region. In one embodiment, the filler sequence region is the FILL5 sequence region, the FILL10 sequence region, and the FILL16 sequence region. In one embodiment, the filler sequence region is the FILL5 sequence region, the FILL10 sequence region, and the FILL17 sequence region. In one embodiment, the filler sequence region is the FILL5 sequence region, the FILL10 sequence region, and the FILL18 sequence region. In one embodiment, the filler sequence region is the FILL5 sequence region, the FILL11 sequence region, and the FILL12 sequence region. In one embodiment, the filler sequence region is the FILL5 sequence region, the FILL1 sequence region, and the FILL13 sequence region. In one embodiment, the filler sequence region is the FILL5 sequence region, the FILL11 sequence region, and the FILL14 sequence region. In one embodiment, the filler sequence region is the FILL5 sequence region, the FILL11 sequence region, and the FILL15 sequence region. In one embodiment, the filler sequence region is the FILL5 sequence region, the FILL11 sequence region, and the FILL16 sequence region. In one embodiment, the filler sequence region is the FILL5 sequence region, the FILL11 sequence region, and the FILL17 sequence region. In one embodiment, the filler sequence region is the FILL5 sequence region, the FILL11 sequence region, and the FILL18 sequence region. In one embodiment, the filler sequence region is the FILL5 sequence region, the FILL12 sequence region, and the FILL13 sequence region. In one embodiment, the filler sequence region is the FILL5 sequence region, the FILL12 sequence region, and the FILL14 sequence region. In one embodiment, the filler sequence region is the FILL5 sequence region, the FILL12 sequence region, and the FILL15 sequence region. In one embodiment, the filler sequence region is the FILL5 sequence region, the FILL12 sequence region, and the FILL16 sequence region. In one embodiment, the filler sequence region is the FILL5 sequence region, the FILL12 sequence region, and the FILL17 sequence region. In one embodiment, the filler sequence region is the FILL5 sequence region, the FILL12 sequence region, and the FILL18 sequence region. In one embodiment, the filler sequence region is the FILL5 sequence region, the FILL13 sequence region, and the FILL14 sequence region. In one embodiment, the filler sequence region is the FILL5 sequence region, the FILL13 sequence region, and the FILL15 sequence region. In one embodiment, the filler sequence region is the FILL5 sequence region, the FILL13 sequence region, and the FILL16 sequence region. In one embodiment, the filler sequence region is the FILL5 sequence region, the FILL13 sequence region, and the FILL17 sequence region. In one embodiment, the filler sequence region is the FILL5 sequence region, the FILL13 sequence region, and the FILL18 sequence region. In one embodiment, the filler sequence region is the FILL5 sequence region, the FILL14 sequence region, and the FILL15 sequence region. In one embodiment, the filler sequence region is the FILL5 sequence region, the FILL14 sequence region, and the FILL16 sequence region. In one embodiment, the filler sequence region is the FILL5 sequence region, the FILL14 sequence region, and the FILL17 sequence region. In one embodiment, the filler sequence region is the FILL5 sequence region, the FILL14 sequence region, and the FILL18 sequence region. In one embodiment, the filler sequence region is the FILL5 sequence region, the FILL15 sequence region, and the FILL16 sequence region. In one embodiment, the filler sequence region is the FILL5 sequence region, the FILL15 sequence region, and the FILL17 sequence region. In one embodiment, the filler sequence region is the FILL5 sequence region, the FILL15 sequence region, and the FILL18 sequence region. In one embodiment, the filler sequence region is the FILL5 sequence region, the FILL16 sequence region, and the FILL17 sequence region. In one embodiment, the filler sequence region is the FILL5 sequence region, the FILL16 sequence region, and the FILL18 sequence region. In one embodiment, the filler sequence region is the FILL5 sequence region, the FILL17 sequence region, and the FILL18 sequence region. In one embodiment, the filler sequence region is the FILL6 sequence region, the FILL7 sequence region, and the FILL8 sequence region. In one embodiment, the filler sequence region is the FILL6 sequence region, the FILL7 sequence region, and the FILL9 sequence region. In one embodiment, the filler sequence region is the FILL6 sequence region, the FILL7 sequence region, and the FILL10 sequence region. In one embodiment, the filler sequence region is the FILL6 sequence region, the FILL7 sequence region, and the FILL11 sequence region. In one embodiment, the filler sequence region is the FILL6 sequence region, the FILL7 sequence region, and the FILL12 sequence region. In one embodiment, the filler sequence region is the FILL6 sequence region, the FILL7 sequence region, and the FILL13 sequence region. In one embodiment, the filler sequence region is the FILL6 sequence region, the FILL7 sequence region, and the FILL14 sequence region. In one embodiment, the filler sequence region is the FILL6 sequence region, the FILL7 sequence region, and the FILL15 sequence region. In one embodiment, the filler sequence region is the FILL6 sequence region, the FILL7 sequence region, and the FILL16 sequence region. In one embodiment, the filler sequence region is the FILL6 sequence region, the FILL7 sequence region, and the FILL17 sequence region. In one embodiment, the filler sequence region is the FILL6 sequence region, the FILL7 sequence region, and the FILL18 sequence region. In one embodiment, the filler sequence region is the FILL6 sequence region, the FILL8 sequence region, and the FILL9 sequence region. In one embodiment, the filler sequence region is the FILL6 sequence region, the FILL8 sequence region, and the FILL10 sequence region. In one embodiment, the filler sequence region is the FILL6 sequence region, the FILL8 sequence region, and the FILL11 sequence region. In one embodiment, the filler sequence region is the FILL6 sequence region, the FILL8 sequence region, and the FILL12 sequence region. In one embodiment, the filler sequence region is the FILL6 sequence region, the FILL8 sequence region, and the FILL13 sequence region. In one embodiment, the filler sequence region is the FILL6 sequence region, the FILL8 sequence region, and the FILL14 sequence region. In one embodiment, the filler sequence region is the FILL6 sequence region, the FILL8 sequence region, and the FILL15 sequence region. In one embodiment, the filler sequence region is the FILL6 sequence region, the FILL8 sequence region, and the FILL16 sequence region. In one embodiment, the filler sequence region is the FILL6 sequence region, the FILL8 sequence region, and the FILL17 sequence region. In one embodiment, the filler sequence region is the FILL6 sequence region, the FILL8 sequence region, and the FILL18 sequence region. In one embodiment, the filler sequence region is the FILL6 sequence region, the FILL9 sequence region, and the FILL10 sequence region. In one embodiment, the filler sequence region is the FILL6 sequence region, the FILL9 sequence region, and the FILL11 sequence region. In one embodiment, the filler sequence region is the FILL6 sequence region, the FILL9 sequence region, and the FILL12 sequence region. In one embodiment, the filler sequence region is the FILL6 sequence region, the FILL9 sequence region, and the FILL13 sequence region. In one embodiment, the filler sequence region is the FILL6 sequence region, the FILL9 sequence region, and the FILL14 sequence region. In one embodiment, the filler sequence region is the FILL6 sequence region, the FILL9 sequence region, and the FILL15 sequence region. In one embodiment, the filler sequence region is the FILL6 sequence region, the FILL9 sequence region, and the FILL16 sequence region. In one embodiment, the filler sequence region is the FILL6 sequence region, the FILL9 sequence region, and the FILL17 sequence region. In one embodiment, the filler sequence region is the FILL6 sequence region, the FILL9 sequence region, and the FILL18 sequence region. In one embodiment, the filler sequence region is the FILL6 sequence region, the FILL10 sequence region, and the FILL11 sequence region. In one embodiment, the filler sequence region is the FILL6 sequence region, the FILL10 sequence region, and the FILL12 sequence region. In one embodiment, the filler sequence region is the FILL6 sequence region, the FILL10 sequence region, and the FILL13 sequence region. In one embodiment, the filler sequence region is the FILL6 sequence region, the FILL10 sequence region, and the FILL14 sequence region. In one embodiment, the filler sequence region is the FILL6 sequence region, the FILL10 sequence region, and the FILL15 sequence region. In one embodiment, the filler sequence region is the FILL6 sequence region, the FILL10 sequence region, and the FILL16 sequence region. In one embodiment, the filler sequence region is the FILL6 sequence region, the FILL10 sequence region, and the FILL17 sequence region. In one embodiment, the filler sequence region is the FILL6 sequence region, the FILL10 sequence region, and the FILL18 sequence region. In one embodiment, the filler sequence region is the FILL6 sequence region, the FILL11 sequence region, and the FILL12 sequence region. In one embodiment, the filler sequence region is the FILL6 sequence region, the FILL1 sequence region, and the FILL13 sequence region. In one embodiment, the filler sequence region is the FILL6 sequence region, the FILL11 sequence region, and the FILL14 sequence region. In one embodiment, the filler sequence region is the FILL6 sequence region, the FILL11 sequence region, and the FILL15 sequence region. In one embodiment, the filler sequence region is the FILL6 sequence region, the FILL11 sequence region, and the FILL16 sequence region. In one embodiment, the filler sequence region is the FILL6 sequence region, the FILL11 sequence region, and the FILL17 sequence region. In one embodiment, the filler sequence region is the FILL6 sequence region, the FILL11 sequence region, and the FILL18 sequence region. In one embodiment, the filler sequence region is the FILL6 sequence region, the FILL12 sequence region, and the FILL13 sequence region. In one embodiment, the filler sequence region is the FILL6 sequence region, the FILL12 sequence region, and the FILL14 sequence region. In one embodiment, the filler sequence region is the FILL6 sequence region, the FILL12 sequence region, and the FILL15 sequence region. In one embodiment, the filler sequence region is the FILL6 sequence region, the FILL12 sequence region, and the FILL16 sequence region. In one embodiment, the filler sequence region is the FILL6 sequence region, the FILL12 sequence region, and the FILL17 sequence region. In one embodiment, the filler sequence region is the FILL6 sequence region, the FILL12 sequence region, and the FILL18 sequence region. In one embodiment, the filler sequence region is the FILL6 sequence region, the FILL13 sequence region, and the FILL14 sequence region. In one embodiment, the filler sequence region is the FILL6 sequence region, the FILL13 sequence region, and the FILL15 sequence region. In one embodiment, the filler sequence region is the FILL6 sequence region, the FILL13 sequence region, and the FILL16 sequence region. In one embodiment, the filler sequence region is the FILL6 sequence region, the FILL13 sequence region, and the FILL17 sequence region. In one embodiment, the filler sequence region is the FILL6 sequence region, the FILL13 sequence region, and the FILL18 sequence region. In one embodiment, the filler sequence region is the FILL6 sequence region, the FILL14 sequence region, and the FILL15 sequence region. In one embodiment, the filler sequence region is the FILL6 sequence region, the FILL14 sequence region, and the FILL16 sequence region. In one embodiment, the filler sequence region is the FILL6 sequence region, the FILL14 sequence region, and the FILL17 sequence region. In one embodiment, the filler sequence region is the FILL6 sequence region, the FILL14 sequence region, and the FILL18 sequence region. In one embodiment, the filler sequence region is the FILL6 sequence region, the FILL15 sequence region, and the FILL16 sequence region. In one embodiment, the filler sequence region is the FILL6 sequence region, the FILL15 sequence region, and the FILL17 sequence region. In one embodiment, the filler sequence region is the FILL6 sequence region, the FILL15 sequence region, and the FILL18 sequence region. In one embodiment, the filler sequence region is the FILL6 sequence region, the FILL16 sequence region, and the FILL17 sequence region. In one embodiment, the filler sequence region is the FILL6 sequence region, the FILL16 sequence region, and the FILL18 sequence region. In one embodiment, the filler sequence region is the FILL6 sequence region, the FILL17 sequence region, and the FILL18 sequence region. In one embodiment, the filler sequence region is the FILL7 sequence region, the FILL8 sequence region, and the FILL9 sequence region. In one embodiment, the filler sequence region is the FILL7 sequence region, the FILL8 sequence region, and the FILL10 sequence region. In one embodiment, the filler sequence region is the FILL7 sequence region, the FILL8 sequence region, and the FILL11 sequence region. In one embodiment, the filler sequence region is the FILL7 sequence region, the FILL8 sequence region, and the FILL12 sequence region. In one embodiment, the filler sequence region is the FILL7 sequence region, the FILL8 sequence region, and the FILL13 sequence region. In one embodiment, the filler sequence region is the FILL7 sequence region, the FILL8 sequence region, and the FILL14 sequence region. In one embodiment, the filler sequence region is the FILL7 sequence region, the FILL8 sequence region, and the FILL15 sequence region. In one embodiment, the filler sequence region is the FILL7 sequence region, the FILL8 sequence region, and the FILL16 sequence region. In one embodiment, the filler sequence region is the FILL7 sequence region, the FILL8 sequence region, and the FILL17 sequence region. In one embodiment, the filler sequence region is the FILL7 sequence region, the FILL8 sequence region, and the FILL18 sequence region. In one embodiment, the filler sequence region is the FILL7 sequence region, the FILL9 sequence region, and the FILL10 sequence region. In one embodiment, the filler sequence region is the FILL7 sequence region, the FILL9 sequence region, and the FILL11 sequence region. In one embodiment, the filler sequence region is the FILL7 sequence region, the FILL9 sequence region, and the FILL12 sequence region. In one embodiment, the filler sequence region is the FILL7 sequence region, the FILL9 sequence region, and the FILL13 sequence region. In one embodiment, the filler sequence region is the FILL7 sequence region, the FILL9 sequence region, and the FILL14 sequence region. In one embodiment, the filler sequence region is the FILL7 sequence region, the FILL9 sequence region, and the FILL15 sequence region. In one embodiment, the filler sequence region is the FILL7 sequence region, the FILL9 sequence region, and the FILL16 sequence region. In one embodiment, the filler sequence region is the FILL7 sequence region, the FILL9 sequence region, and the FILL17 sequence region. In one embodiment, the filler sequence region is the FILL7 sequence region, the FILL9 sequence region, and the FILL18 sequence region. In one embodiment, the filler sequence region is the FILL7 sequence region, the FILL10 sequence region, and the FILL1 sequence region. In one embodiment, the filler sequence region is the FILL7 sequence region, the FILL10 sequence region, and the FILL12 sequence region. In one embodiment, the filler sequence region is the FILL7 sequence region, the FILL10 sequence region, and the FILL13 sequence region. In one embodiment, the filler sequence region is the FILL7 sequence region, the FILL10 sequence region, and the FILL14 sequence region. In one embodiment, the filler sequence region is the FILL7 sequence region, the FILL10 sequence region, and the FILL15 sequence region. In one embodiment, the filler sequence region is the FILL7 sequence region, the FILL10 sequence region, and the FILL16 sequence region. In one embodiment, the filler sequence region is the FILL7 sequence region, the FILL10 sequence region, and the FILL17 sequence region. In one embodiment, the filler sequence region is the FILL7 sequence region, the FILL10 sequence region, and the FILL18 sequence region. In one embodiment, the filler sequence region is the FILL7 sequence region, the FILL11 sequence region, and the FILL12 sequence region. In one embodiment, the filler sequence region is the FILL7 sequence region, the FILL11 sequence region, and the FILL13 sequence region. In one embodiment, the filler sequence region is the FILL7 sequence region, the FILL11 sequence region, and the FILL14 sequence region. In one embodiment, the filler sequence region is the FILL7 sequence region, the FILL11 sequence region, and the FILL15 sequence region. In one embodiment, the filler sequence region is the FILL7 sequence region, the FILL11 sequence region, and the FILL16 sequence region. In one embodiment, the filler sequence region is the FILL7 sequence region, the FILL11 sequence region, and the FILL17 sequence region. In one embodiment, the filler sequence region is the FILL7 sequence region, the FILL11 sequence region, and the FILL18 sequence region. In one embodiment, the filler sequence region is the FILL7 sequence region, the FILL12 sequence region, and the FILL13 sequence region. In one embodiment, the filler sequence region is the FILL7 sequence region, the FILL12 sequence region, and the FILL14 sequence region. In one embodiment, the filler sequence region is the FILL7 sequence region, the FILL12 sequence region, and the FILL15 sequence region. In one embodiment, the filler sequence region is the FILL7 sequence region, the FILL12 sequence region, and the FILL16 sequence region. In one embodiment, the filler sequence region is the FILL7 sequence region, the FILL12 sequence region, and the FILL17 sequence region. In one embodiment, the filler sequence region is the FILL7 sequence region, the FILL12 sequence region, and the FILL18 sequence region. In one embodiment, the filler sequence region is the FILL7 sequence region, the FILL13 sequence region, and the FILL14 sequence region. In one embodiment, the filler sequence region is the FILL7 sequence region, the FILL13 sequence region, and the FILL15 sequence region. In one embodiment, the filler sequence region is the FILL7 sequence region, the FILL13 sequence region, and the FILL16 sequence region. In one embodiment, the filler sequence region is the FILL7 sequence region, the FILL13 sequence region, and the FILL17 sequence region. In one embodiment, the filler sequence region is the FILL7 sequence region, the FILL13 sequence region, and the FILL18 sequence region. In one embodiment, the filler sequence region is the FILL7 sequence region, the FILL14 sequence region, and the FILL15 sequence region. In one embodiment, the filler sequence region is the FILL7 sequence region, the FILL14 sequence region, and the FILL16 sequence region. In one embodiment, the filler sequence region is the FILL7 sequence region, the FILL14 sequence region, and the FILL17 sequence region. In one embodiment, the filler sequence region is the FILL7 sequence region, the FILL14 sequence region, and the FILL18 sequence region. In one embodiment, the filler sequence region is the FILL7 sequence region, the FILL15 sequence region, and the FILL16 sequence region. In one embodiment, the filler sequence region is the FILL7 sequence region, the FILL15 sequence region, and the FILL17 sequence region. In one embodiment, the filler sequence region is the FILL7 sequence region, the FILL15 sequence region, and the FILL18 sequence region. In one embodiment, the filler sequence region is the FILL7 sequence region, the FILL16 sequence region, and the FILL17 sequence region. In one embodiment, the filler sequence region is the FILL7 sequence region, the FILL16 sequence region, and the FILL18 sequence region. In one embodiment, the filler sequence region is the FILL7 sequence region, the FILL17 sequence region, and the FILL18 sequence region. In one embodiment, the filler sequence region is the FILL8 sequence region, the FILL9 sequence region, and the FILL10 sequence region. In one embodiment, the filler sequence region is the FILL8 sequence region, the FILL9 sequence region, and the FILL11 sequence region. In one embodiment, the filler sequence region is the FILL8 sequence region, the FILL9 sequence region, and the FILL12 sequence region. In one embodiment, the filler sequence region is the FILL8 sequence region, the FILL9 sequence region, and the FILL13 sequence region. In one embodiment, the filler sequence region is the FILL8 sequence region, the FILL9 sequence region, and the FILL14 sequence region. In one embodiment, the filler sequence region is the FILL8 sequence region, the FILL9 sequence region, and the FILL15 sequence region. In one embodiment, the filler sequence region is the FILL8 sequence region, the FILL9 sequence region, and the FILL16 sequence region. In one embodiment, the filler sequence region is the FILL8 sequence region, the FILL9 sequence region, and the FILL17 sequence region. In one embodiment, the filler sequence region is the FILL8 sequence region, the FILL9 sequence region, and the FILL18 sequence region. In one embodiment, the filler sequence region is the FILL8 sequence region, the FILL10 sequence region, and the FILL11 sequence region. In one embodiment, the filler sequence region is the FILL8 sequence region, the FILL10 sequence region, and the FILL12 sequence region. In one embodiment, the filler sequence region is the FILL8 sequence region, the FILL10 sequence region, and the FILL13 sequence region. In one embodiment, the filler sequence region is the FILL8 sequence region, the FILL10 sequence region, and the FILL14 sequence region. In one embodiment, the filler sequence region is the FILL8 sequence region, the FILL10 sequence region, and the FILL15 sequence region. In one embodiment, the filler sequence region is the FILL8 sequence region, the FILL10 sequence region, and the FILL16 sequence region. In one embodiment, the filler sequence region is the FILL8 sequence region, the FILL10 sequence region, and the FILL17 sequence region. In one embodiment, the filler sequence region is the FILL8 sequence region, the FILL10 sequence region, and the FILL18 sequence region. In one embodiment, the filler sequence region is the FILL8 sequence region, the FILL11 sequence region, and the FILL12 sequence region. In one embodiment, the filler sequence region is the FILL8 sequence region, the FILL11 sequence region, and the FILL13 sequence region. In one embodiment, the filler sequence region is the FILL8 sequence region, the FILL11 sequence region, and the FILL14 sequence region. In one embodiment, the filler sequence region is the FILL8 sequence region, the FILL11 sequence region, and the FILL15 sequence region. In one embodiment, the filler sequence region is the FILL8 sequence region, the FILL11 sequence region, and the FILL16 sequence region. In one embodiment, the filler sequence region is the FILL8 sequence region, the FILL11 sequence region, and the FILL17 sequence region. In one embodiment, the filler sequence region is the FILL8 sequence region, the FILL11 sequence region, and the FILL18 sequence region. In one embodiment, the filler sequence region is the FILL8 sequence region, the FILL12 sequence region, and the FILL13 sequence region. In one embodiment, the filler sequence region is the FILL8 sequence region, the FILL12 sequence region, and the FILL14 sequence region. In one embodiment, the filler sequence region is the FILL8 sequence region, the FILL12 sequence region, and the FILL15 sequence region. In one embodiment, the filler sequence region is the FILL8 sequence region, the FILL12 sequence region, and the FILL16 sequence region. In one embodiment, the filler sequence region is the FILL8 sequence region, the FILL12 sequence region, and the FILL17 sequence region. In one embodiment, the filler sequence region is the FILL8 sequence region, the FILL12 sequence region, and the FILL18 sequence region. In one embodiment, the filler sequence region is the FILL8 sequence region, the FILL13 sequence region, and the FILL14 sequence region. In one embodiment, the filler sequence region is the FILL8 sequence region, the FILL13 sequence region, and the FILL15 sequence region. In one embodiment, the filler sequence region is the FILL8 sequence region, the FILL13 sequence region, and the FILL16 sequence region. In one embodiment, the filler sequence region is the FILL8 sequence region, the FILL13 sequence region, and the FILL17 sequence region. In one embodiment, the filler sequence region is the FILL8 sequence region, the FILL13 sequence region, and the FILL18 sequence region. In one embodiment, the filler sequence region is the FILL8 sequence region, the FILL14 sequence region, and the FILL15 sequence region. In one embodiment, the filler sequence region is the FILL8 sequence region, the FILL14 sequence region, and the FILL16 sequence region. In one embodiment, the filler sequence region is the FILL8 sequence region, the FILL14 sequence region, and the FILL17 sequence region. In one embodiment, the filler sequence region is the FILL8 sequence region, the FILL14 sequence region, and the FILL18 sequence region. In one embodiment, the filler sequence region is the FILL5 sequence region, the FILL15 sequence region, and the FILL16 sequence region. In one embodiment, the filler sequence region is the FILL8 sequence region, the FILL15 sequence region, and the FILL17 sequence region. In one embodiment, the filler sequence region is the FILL8 sequence region, the FILL15 sequence region, and the FILL18 sequence region. In one embodiment, the filler sequence region is the FILL8 sequence region, the FILL16 sequence region, and the FILL17 sequence region. In one embodiment, the filler sequence region is the FILL8 sequence region, the FILL16 sequence region, and the FILL18 sequence region. In one embodiment, the filler sequence region is the FILL8 sequence region, the FILL17 sequence region, and the FILL18 sequence region. In one embodiment, the filler sequence region is the FILL9 sequence region, the FILL10 sequence region, and the FILL11 sequence region. In one embodiment, the filler sequence region is the FILL9 sequence region, the FILL10 sequence region, and the FILL12 sequence region. In one embodiment, the filler sequence region is the FILL9 sequence region, the FILL10 sequence region, and the FILL13 sequence region. In one embodiment, the filler sequence region is the FILL9 sequence region, the FILL10 sequence region, and the FILL14 sequence region. In one embodiment, the filler sequence region is the FILL9 sequence region, the FILL10 sequence region, and the FILL15 sequence region. In one embodiment, the filler sequence region is the FILL9 sequence region, the FILL10 sequence region, and the FILL16 sequence region. In one embodiment, the filler sequence region is the FILL9 sequence region, the FILL10 sequence region, and the FILL17 sequence region. In one embodiment, the filler sequence region is the FILL9 sequence region, the FILL10 sequence region, and the FILL18 sequence region. In one embodiment, the filler sequence region is the FILL9 sequence region, the FILL11 sequence region, and the FILL12 sequence region. In one embodiment, the filler sequence region is the FILL9 sequence region, the FILL11 sequence region, and the FILL13 sequence region. In one embodiment, the filler sequence region is the FILL9 sequence region, the FILL11 sequence region, and the FILL14 sequence region. In one embodiment, the filler sequence region is the FILL9 sequence region, the FILL11 sequence region, and the FILL15 sequence region. In one embodiment, the filler sequence region is the FILL9 sequence region, the FILL11 sequence region, and the FILL16 sequence region. In one embodiment, the filler sequence region is the FILL9 sequence region, the FILL11 sequence region, and the FILL17 sequence region. In one embodiment, the filler sequence region is the FILL9 sequence region, the FILL11 sequence region, and the FILL18 sequence region. In one embodiment, the filler sequence region is the FILL9 sequence region, the FILL12 sequence region, and the FILL13 sequence region. In one embodiment, the filler sequence region is the FILL9 sequence region, the FILL12 sequence region, and the FILL14 sequence region. In one embodiment, the filler sequence region is the FILL9 sequence region, the FILL12 sequence region, and the FILL15 sequence region. In one embodiment, the filler sequence region is the FILL9 sequence region, the FILL12 sequence region, and the FILL16 sequence region. In one embodiment, the filler sequence region is the FILL9 sequence region, the FILL12 sequence region, and the FILL17 sequence region. In one embodiment, the filler sequence region is the FILL9 sequence region, the FILL12 sequence region, and the FILL18 sequence region. In one embodiment, the filler sequence region is the FILL9 sequence region, the FILL13 sequence region, and the FILL14 sequence region. In one embodiment, the filler sequence region is the FILL9 sequence region, the FILL13 sequence region, and the FILL15 sequence region. In one embodiment, the filler sequence region is the FILL9 sequence region, the FILL13 sequence region, and the FILL16 sequence region. In one embodiment, the filler sequence region is the FILL9 sequence region, the FILL13 sequence region, and the FILL17 sequence region. In one embodiment, the filler sequence region is the FILL9 sequence region, the FILL13 sequence region, and the FILL18 sequence region. In one embodiment, the filler sequence region is the FILL9 sequence region, the FILL14 sequence region, and the FILL15 sequence region. In one embodiment, the filler sequence region is the FILL9 sequence region, the FILL14 sequence region, and the FILL16 sequence region. In one embodiment, the filler sequence region is the FILL9 sequence region, the FILL14 sequence region, and the FILL17 sequence region. In one embodiment, the filler sequence region is the FILL9 sequence region, the FILL14 sequence region, and the FILL18 sequence region. In one embodiment, the filler sequence region is the FILL9 sequence region, the FILL15 sequence region, and the FILL16 sequence region. In one embodiment, the filler sequence region is the FILL9 sequence region, the FILL15 sequence region, and the FILL17 sequence region. In one embodiment, the filler sequence region is the FILL9 sequence region, the FILL15 sequence region, and the FILL18 sequence region. In one embodiment, the filler sequence region is the FILL9 sequence region, the FILL16 sequence region, and the FILL17 sequence region. In one embodiment, the filler sequence region is the FILL9 sequence region, the FILL16 sequence region, and the FILL18 sequence region. In one embodiment, the filler sequence region is the FILL9 sequence region, the FILL17 sequence region, and the FILL18 sequence region. In one embodiment, the filler sequence region is the FILL10 sequence region, the FILL11 sequence region, and the FILL12 sequence region. In one embodiment, the filler sequence region is the FILL10 sequence region, the FILL1 sequence region, and the FILL13 sequence region. In one embodiment, the filler sequence region is the FILL10 sequence region, the FILL11 sequence region, and the FILL14 sequence region. In one embodiment, the filler sequence region is the FILL10 sequence region, the FILL11 sequence region, and the FILL15 sequence region. In one embodiment, the filler sequence region is the FILL10 sequence region, the FILL11 sequence region, and the FILL16 sequence region. In one embodiment, the filler sequence region is the FILL10 sequence region, the FILL11 sequence region, and the FILL17 sequence region. In one embodiment, the filler sequence region is the FILL10 sequence region, the FILL11 sequence region, and the FILL18 sequence region. In one embodiment, the filler sequence region is the FILL10 sequence region, the FILL12 sequence region, and the FILL13 sequence region. In one embodiment, the filler sequence region is the FILL10 sequence region, the FILL12 sequence region, and the FILL14 sequence region. In one embodiment, the filler sequence region is the FILL10 sequence region, the FILL12 sequence region, and the FILL15 sequence region. In one embodiment, the filler sequence region is the FILL10 sequence region, the FILL12 sequence region, and the FILL16 sequence region. In one embodiment, the filler sequence region is the FILL10 sequence region, the FILL12 sequence region, and the FILL17 sequence region. In one embodiment, the filler sequence region is the FILL10 sequence region, the FILL12 sequence region, and the FILL18 sequence region. In one embodiment, the filler sequence region is the FILL10 sequence region, the FILL13 sequence region, and the FILL14 sequence region. In one embodiment, the filler sequence region is the FILL10 sequence region, the FILL13 sequence region, and the FILL15 sequence region. In one embodiment, the filler sequence region is the FILL10 sequence region, the FILL13 sequence region, and the FILL16 sequence region. In one embodiment, the filler sequence region is the FILL10 sequence region, the FILL13 sequence region, and the FILL17 sequence region. In one embodiment, the filler sequence region is the FILL10 sequence region, the FILL13 sequence region, and the FILL18 sequence region. In one embodiment, the filler sequence region is the FILL10 sequence region, the FILL14 sequence region, and the FILL15 sequence region. In one embodiment, the filler sequence region is the FILL10 sequence region, the FILL14 sequence region, and the FILL16 sequence region. In one embodiment, the filler sequence region is the FILL10 sequence region, the FILL14 sequence region, and the FILL17 sequence region. In one embodiment, the filler sequence region is the FILL10 sequence region, the FILL14 sequence region, and the FILL18 sequence region. In one embodiment, the filler sequence region is the FILL10 sequence region, the FILL15 sequence region, and the FILL16 sequence region. In one embodiment, the filler sequence region is the FILL10 sequence region, the FILL15 sequence region, and the FILL5 sequence region, and the FILL17 sequence region. In one embodiment, the filler sequence region is the FILL10 sequence region, the FILL15 sequence region, and the FILL18 sequence region. In one embodiment, the filler sequence region is the FILL10 sequence region, the FILL16 sequence region, and the FILL17 sequence region. In one embodiment, the filler sequence region is the FILL10 sequence region, the FILL16 sequence region, and the FILL18 sequence region. In one embodiment, the filler sequence region is the FILL10 sequence region, the FILL17 sequence region, and the FILL18 sequence region. In one embodiment, the filler sequence region is the FILL11 sequence region, the FILL12 sequence region, and the FILL13 sequence region. In one embodiment, the filler sequence region is the FILL11 sequence region, the FILL12 sequence region, and the FILL14 sequence region. In one embodiment, the filler sequence region is the FILL11 sequence region, the FILL12 sequence region, and the FILL15 sequence region. In one embodiment, the filler sequence region is the FILL11 sequence region, the FILL12 sequence region, and the FILL16 sequence region. In one embodiment, the filler sequence region is the FILL11 sequence region, the FILL12 sequence region, and the FILL17 sequence region. In one embodiment, the filler sequence region is the FILL11 sequence region, the FILL12 sequence region, and the FILL18 sequence region. In one embodiment, the filler sequence region is the FILL11 sequence region, the FILL13 sequence region, and the FILL14 sequence region. In one embodiment, the filler sequence region is the FILL11 sequence region, the FILL13 sequence region, and the FILL15 sequence region. In one embodiment, the filler sequence region is the FILL11 sequence region, the FILL13 sequence region, and the FILL16 sequence region. In one embodiment, the filler sequence region is the FILL11 sequence region, the FILL13 sequence region, and the FILL17 sequence region. In one embodiment, the filler sequence region is the FILL11 sequence region, the FILL13 sequence region, and the FILL18 sequence region. In one embodiment, the filler sequence region is the FILL11 sequence region, the FILL14 sequence region, and the FILL15 sequence region. In one embodiment, the filler sequence region is the FILL11 sequence region, the FILL14 sequence region, and the FILL16 sequence region. In one embodiment, the filler sequence region is the FILL11 sequence region, the FILL14 sequence region, and the FILL17 sequence region. In one embodiment, the filler sequence region is the FILL11 sequence region, the FILL14 sequence region, and the FILL18 sequence region. In one embodiment, the filler sequence region is the FILL11 sequence region, the FILL15 sequence region, and the FILL16 sequence region. In one embodiment, the filler sequence region is the FILL11 sequence region, the FILL15 sequence region, and the FILL17 sequence region. In one embodiment, the filler sequence region is the FILL11 sequence region, the FILL5 sequence region, and the FILL18 sequence region. In one embodiment, the filler sequence region is the FILL11 sequence region, the FILL16 sequence region, and the FILL17 sequence region. In one embodiment, the filler sequence region is the FILL11 sequence region, the FILL16 sequence region, and the FILL18 sequence region. In one embodiment, the filler sequence region is the FILL11 sequence region, the FILL17 sequence region, and the FILL18 sequence region. In one embodiment, the filler sequence region is the FILL12 sequence region, the FILL13 sequence region, and the FILL14 sequence region. In one embodiment, the filler sequence region is the FILL12 sequence region, the FILL13 sequence region, and the FILL15 sequence region. In one embodiment, the filler sequence region is the FILL12 sequence region, the FILL13 sequence region, and the FILL16 sequence region. In one embodiment, the filler sequence region is the FILL12 sequence region, the FILL13 sequence region, and the FILL17 sequence region. In one embodiment, the filler sequence region is the FILL12 sequence region, the FILL13 sequence region, and the FILL18 sequence region. In one embodiment, the filler sequence region is the FILL12 sequence region, the FILL14 sequence region, and the FILL15 sequence region. In one embodiment, the filler sequence region is the FILL12 sequence region, the FILL14 sequence region, and the FILL16 sequence region. In one embodiment, the filler sequence region is the FILL12 sequence region, the FILL14 sequence region, and the FILL17 sequence region. In one embodiment, the filler sequence region is the FILL12 sequence region, the FILL14 sequence region, and the FILL18 sequence region. In one embodiment, the filler sequence region is the FILL12 sequence region, the FILL15 sequence region, and the FILL16 sequence region. In one embodiment, the filler sequence region is the FILL12 sequence region, the FILL15 sequence region, and the FILL17 sequence region. In one embodiment, the filler sequence region is the FILL12 sequence region, the FILL15 sequence region, and the FILL18 sequence region. In one embodiment, the filler sequence region is the FILL12 sequence region, the FILL16 sequence region, and the FILL17 sequence region. In one embodiment, the filler sequence region is the FILL12 sequence region, the FILL16 sequence region, and the FILL18 sequence region. In one embodiment, the filler sequence region is the FILL12 sequence region, the FILL17 sequence region, and the FILL18 sequence region. In one embodiment, the filler sequence region is the FILL13 sequence region, the FILL14 sequence region, and the FILL15 sequence region. In one embodiment, the filler sequence region is the FILL13 sequence region, the FILL14 sequence region, and the FILL16 sequence region. In one embodiment, the filler sequence region is the FILL13 sequence region, the FILL14 sequence region, and the FILL17 sequence region. In one embodiment, the filler sequence region is the FILL13 sequence region, the FILL14 sequence region, and the FILL18 sequence region. In one embodiment, the filler sequence region is the FILL13 sequence region, the FILL15 sequence region, and the FILL16 sequence region. In one embodiment, the filler sequence region is the FILL13 sequence region, the FILL15 sequence region, and the FILL17 sequence region. In one embodiment, the filler sequence region is the FILL13 sequence region, the FILL15 sequence region, and the FILL18 sequence region. In one embodiment, the filler sequence region is the FILL13 sequence region, the FILL16 sequence region, and the FILL17 sequence region. In one embodiment, the filler sequence region is the FILL13 sequence region, the FILL16 sequence region, and the FILL18 sequence region. In one embodiment, the filler sequence region is the FILL13 sequence region, the FILL17 sequence region, and the FILL18 sequence region. In one embodiment, the filler sequence region is the FILL14 sequence region, the FILL15 sequence region, and the FILL16 sequence region. In one embodiment, the filler sequence region is the FILL14 sequence region, the FILL15 sequence region, and the FILL17 sequence region. In one embodiment, the filler sequence region is the FILL14 sequence region, the FILL15 sequence region, and the FILL18 sequence region. In one embodiment, the filler sequence region is the FILL14 sequence region, the FILL16 sequence region, and the FILL17 sequence region. In one embodiment, the filler sequence region is the FILL14 sequence region, the FILL16 sequence region, and the FILL18 sequence region. In one embodiment, the filler sequence region is the FILL14 sequence region, the FILL17 sequence region, and the FILL18 sequence region. In one embodiment, the filler sequence region is the FILL15 sequence region, the FILL16 sequence region, and the FILL17 sequence region. In one embodiment, the filler sequence region is the FILL15 sequence region, the FILL16 sequence region, and the FILL18 sequence region. In one embodiment, the filler sequence region is the FILL15 sequence region, the FILL17 sequence region, and the FILL18 sequence region. In one embodiment, the filler sequence region is the FILL16 sequence region, the FILL17 sequence region, and the FILL18 sequence region.

In one embodiment, the AAV particle viral genome may comprise at least one enhancer sequence region. The enhancer sequence region(s) may, independently, have a length such as, but not limited to, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, and 400 nucleotides. The length of the enhancer region for the viral genome may be 300-310, 300-325, 305-315, 310-320, 315-325, 320-330, 325-335, 325-350, 330-340, 335-345, 340-350, 345-355, 350-360, 350-375, 355-365, 360-370, 365-375, 370-380, 375-385, 375-400, 380-390, 385-395, and 390-400 nucleotides. As a non-limiting example, the viral genome comprises an enhancer region that is about 303 nucleotides in length. As a non-limiting example, the viral genome comprises an enhancer region that is about 382 nucleotides in length.

In one embodiment, the AAV particle viral genome comprises at least one enhancer sequence region. Non-limiting examples of enhancer sequence regions are described in Table 13.

TABLE 13

Enhancer Sequence Regions

| Sequence Region Name | SEQ ID NO |
|---|---|
| Enhancer1 | 1397 |
| Enhancer2 | 1398 |

In one embodiment, the AAV particle viral genome comprises one enhancer sequence region. In one embodiment, the enhancer sequence regions is the Enhancer1 sequence region. In one embodiment, the enhancer sequence regions is the Enhancer2 sequence region.

In one embodiment, the AAV particle viral genome comprises two enhancer sequence regions. In one embodiment, the enhancer sequence regions are the Enhancer1 sequence region and the Enhancer 2 sequence region.

In one embodiment, the AAV particle viral genome may comprise at least one promoter sequence region. The promoter sequence region(s) may, independently, have a length such as, but not limited to, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, and 600 nucleotides. The length of the promoter region for the viral genome may be 4-10, 10-20, 10-50, 20-30, 30-40, 40-50, 50-60, 50-100, 60-70, 70-80, 80-90, 90-100, 100-110, 100-150, 110-120, 120-130, 130-140, 140-150, 150-160, 150-200, 160-170, 170-180, 180-190, 190-200, 200-210, 200-250, 210-220, 220-230, 230-240, 240-250, 250-260, 250-300, 260-270, 270-280, 280-290, 290-300, 300-310, 300-350, 310-320, 320-330, 330-340, 340-350, 350-360, 350-400, 360-370, 370-380, 380-390, 390-400, 400-410, 400-450, 410-420, 420-430, 430-440, 440-450, 450-460, 450-500, 460-470, 470-480, 480-490, 490-500, 500-510, 500-550, 510-520, 520-530, 530-540, 540-550, 550-560, 550-600, 560-570, 570-580, 580-590, and 590-600 nucleotides. As a non-limiting example, the viral genome comprises a promoter region that is about 4 nucleotides in length. As a non-limiting example, the viral genome comprises a promoter region that is about 17 nucleotides in length. As a non-limiting example, the viral genome comprises a promoter region that is about 204 nucleotides in length. As a non-limiting example, the viral genome comprises a promoter region that is about 219 nucleotides in length. As a non-limiting example, the viral genome comprises a promoter region that is about 260 nucleotides in length. As a non-limiting example, the viral genome comprises a promoter region that is about 303 nucleotides in length. As a non-limiting example, the viral genome comprises a promoter region that is about 382 nucleotides in length. As a non-limiting example, the viral genome comprises a promoter region that is about 588 nucleotides in length.

In one embodiment, the AAV particle viral genome comprises at least one promoter sequence region. Non-limiting examples of promoter sequence regions are described in Table 14.

TABLE 14

Promoter Sequence Regions

| Sequence Region Name | SEQ ID NO or Sequence |
| --- | --- |
| Promoter1 | 1399 |
| Promoter2 | 1400 |
| Promoter3 | GTTG |
| Promoter4 | 1401 |
| Promoter5 | 1402 |
| Promoter6 | 1403 |

In one embodiment, the AAV particle viral genome comprises one promoter sequence region. In one embodiment, the promoter sequence region is Promoter1. In one embodiment, the promoter sequence region is Promoter2. In one embodiment, the promoter sequence region is Promoter3. In one embodiment, the promoter sequence region is Promoter4. In one embodiment, the promoter sequence region is Promoter5. In one embodiment, the promoter sequence region is Promoter6.

In one embodiment, the AAV particle viral genome comprises two promoter sequence regions. In one embodiment, the promoter sequence region is Promoter1 sequence region, and the Promoter2 sequence region. In one embodiment, the promoter sequence region is Promoter1 sequence region, and the Promoter3 sequence region. In one embodiment, the promoter sequence region is Promoter1 sequence region, and the Promoter4 sequence region. In one embodiment, the promoter sequence region is Promoter1 sequence region, and the Promoter5 sequence region. In one embodiment, the promoter sequence region is Promoter1 sequence region, and the Promoter6 sequence region. In one embodiment, the promoter sequence region is Promoter2 sequence region, and the Promoter3 sequence region. In one embodiment, the promoter sequence region is Promoter2 sequence region, and the Promoter4 sequence region. In one embodiment, the promoter sequence region is Promoter2 sequence region, and the Promoter5 sequence region. In one embodiment, the promoter sequence region is Promoter2 sequence region, and the Promoter6 sequence region. In one embodiment, the promoter sequence region is Promoter3 sequence region, and the Promoter4 sequence region. In one embodiment, the promoter sequence region is Promoter3 sequence region, and the Promoter5 sequence region. In one embodiment, the promoter sequence region is Promoter3 sequence region, and the Promoter6 sequence region. In one embodiment, the promoter sequence region is Promoter4 sequence region, and the Promoter5 sequence region. In one embodiment, the promoter sequence region is Promoter4 sequence region, and the Promoter6 sequence region. In one embodiment, the promoter sequence region is Promoter5 sequence region, and the Promoter6 sequence region.

In one embodiment, the AAV particle viral genome may comprise at least one exon sequence region. The exon region(s) may, independently, have a length such as, but not limited to, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, and 150 nucleotides. The length of the exon region for the viral genome may be 2-10, 5-10, 5-15, 10-20, 10-30, 10-40, 15-20, 15-25, 20-30, 20-40, 20-50, 25-30, 25-35, 30-40, 30-50, 30-60, 35-40, 35-45, 40-50, 40-60, 40-70, 45-50, 45-55, 50-60, 50-70, 50-80, 55-60, 55-65, 60-70, 60-80, 60-90, 65-70, 65-75, 70-80, 70-90, 70-100, 75-80, 75-85, 80-90, 80-100, 80-110, 85-90, 85-95, 90-100, 90-110, 90-120, 95-100, 95-105, 100-110, 100-120, 100-130, 105-110, 105-115, 110-120, 110-130, 110-140, 115-120, 115-125, 120-130, 120-140, 120-150, 125-130, 125-135, 130-140, 130-150, 135-140, 135-145, 140-150, and 145-150 nucleotides. As a non-limiting example, the viral genome comprises an exon region that is about 53 nucleotides in length. As a non-limiting example, the viral genome comprises an exon region that is about 134 nucleotides in length.

In one embodiment, the AAV particle viral genome comprises at least one Exon sequence region. Non-limiting examples of Exon sequence regions are described in Table 15.

TABLE 15

Exon Sequence Regions

| Sequence Region Name | SEQ ID NO |
|---|---|
| Exon1 | 1404 |
| Exon2 | 1405 |

In one embodiment, the AAV particle viral genome comprises one Exon sequence region. In one embodiment, the Exon sequence regions is the Exon sequence region. In one embodiment, the Exon sequence regions is the Exon2 sequence region.

In one embodiment, the AAV particle viral genome comprises two Exon sequence regions. In one embodiment, the Exon sequence regions are the Exon1 sequence region and the Exon 2 sequence region.

In one embodiment, the AAV particle viral genome may comprise at least one intron sequence region. The intron region(s) may, independently, have a length such as, but not limited to, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, and 350 nucleotides. The length of the intron region for the viral genome may be 25-35, 25-50, 35-45, 45-55, 50-75, 55-65, 65-75, 75-85, 75-100, 85-95, 95-105, 100-125, 105-115, 115-125, 125-135, 125-150, 135-145, 145-155, 150-175, 155-165, 165-175, 175-185, 175-200, 185-195, 195-205, 200-225, 205-215, 215-225, 225-235, 225-250, 235-245, 245-255, 250-275, 255-265, 265-275, 275-285, 275-300, 285-295, 295-305, 300-325, 305-315, 315-325, 325-335, 325-350, and 335-345 nucleotides. As a non-limiting example, the viral genome comprises an intron region that is about 32 nucleotides in length. As a non-limiting example, the viral genome comprises an intron region that is about 172 nucleotides in length. As a non-limiting example, the viral genome comprises an intron region that is about 201 nucleotides in length. As a non-limiting example, the viral genome comprises an intron region that is about 347 nucleotides in length.

In one embodiment, the AAV particle viral genome comprises at least one intron sequence region. Non-limiting examples of intron sequence regions are described in Table 16.

TABLE 16

Intron Sequence Regions

| Sequence Region Name | SEQ ID NO |
|---|---|
| Intron1 | 1406 |
| Intron2 | 1407 |
| Intron3 | 1408 |
| Intron4 | 1409 |

In one embodiment, the AAV particle viral genome comprises one intron sequence region. In one embodiment, the intron sequence regions is the Intron sequence region. In one embodiment, the intron sequence regions is the Intron2 sequence region. In one embodiment, the intron sequence regions is the Intron3 sequence region. In one embodiment, the intron sequence regions is the Intron4 sequence region.

In one embodiment, the AAV particle viral genome comprises two intron sequence regions. In one embodiment, the intron sequence regions are the Intron1 sequence region and the Intron2 sequence region. In one embodiment, the intron sequence regions are the Intron1 sequence region and the Intron3 sequence region. In one embodiment, the intron sequence regions are the Intron1 sequence region and the Intron4 sequence region. In one embodiment, the intron sequence regions are the Intron2 sequence region and the Intron3 sequence region. In one embodiment, the intron sequence regions are the Intron2 sequence region and the Intron4 sequence region. In one embodiment, the intron sequence regions are the Intron3 sequence region and the Intron4 sequence region.

In one embodiment, the AAV particle viral genome comprises three intron sequence regions. In one embodiment, the intron sequence regions are the Intron1 sequence region, the Intron2 sequence region, and the Intron3 sequence region. In one embodiment, the intron sequence regions are the Intron1 sequence region, the Intron2 sequence region, and the Intron4 sequence region. In one embodiment, the intron sequence regions are the Intron1 sequence region, the Intron3 sequence region, and the Intron4 sequence region. In one embodiment, the intron sequence regions are the Intron2 sequence region, the Intron3 sequence region, and the Intron4 sequence region.

In one embodiment, the AAV particle viral genome may comprise at least one polyadenylation signal sequence region. The polyadenylation signal region sequence region(s) may, independently, have a length such as, but not limited to, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 4, 400, 406, 447, 408, 409, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, and 600 nucleotides. The length of the polyadenylation signal sequence region for the viral genome may be 4-10, 10-20, 10-50, 20-30, 30-40, 40-50, 50-60, 50-100, 60-70, 70-80, 80-90, 90-100, 100-110, 100-150, 110-120, 120-130, 130-140, 140-150, 150-160, 150-200, 160-170, 170-180, 180-190, 190-200, 200-210, 200-250, 210-220, 220-230, 230-240, 240-250, 250-260, 250-300, 260-270, 270-280, 280-290, 290-300, 300-310, 300-350, 310-320, 320-330, 330-340, 340-350, 350-360, 350-400, 360-370, 370-380, 380-390, 390-400, 400-410, 400-450, 410-420, 420-430, 430-440, 440-450, 450-460, 450-500, 460-470, 470-480, 480-490, 490-500, 500-510, 500-550, 510-520, 520-530, 530-540, 540-550, 550-560, 550-600, 560-570, 570-580, 580-590, and 590-600 nucleotides. As a non-limiting example, the viral genome comprises a polyadenylation signal sequence region that is about 127 nucleotides in length. As a non-limiting example, the viral genome comprises a polyadenylation signal sequence region that is about 225 nucleotides in length. As a non-limiting example, the viral genome comprises a polyadenylation signal sequence region that is about 476 nucleotides in length. As a non-limiting example, the viral genome comprises a polyadenylation signal sequence region that is about 477 nucleotides in length.

In one embodiment, the AAV particle viral genome comprises at least one polyadenylation (polyA) signal sequence region. Non-limiting examples of polyA signal sequence regions are described in Table 17.

TABLE 17

PolyA Signal Sequence Regions

| Sequence Region Name | SEQ ID NO |
| --- | --- |
| PolyA1 | 1410 |
| PolyA2 | 1411 |
| PolyA3 | 1412 |
| PolyA4 | 1413 |

In one embodiment, the AAV particle viral genome comprises one polyA signal sequence region. In one embodiment, the polyA signal sequence regions is the PolyA1 sequence region. In one embodiment, the polyA signal sequence regions is the PolyA2 sequence region. In one embodiment, the polyA signal sequence regions is the PolyA3 sequence region. In one embodiment, the polyA signal sequence regions is the PolyA4 sequence region.

In one embodiment, the AAV particle viral genome comprises more than one polyA signal sequence region.

Non-limiting examples of ITR to ITR sequences of AAV particles comprising a viral genome with a payload region comprising a modulatory polynucleotide sequence are described in Table 18.

TABLE 18

ITR to ITR Sequences of AAV Particles comprising Modulatory Polynucleotides

| ITR to ITR Construct Name | ITR to ITR SEQ ID NO | Modulatory Polynucleotide SEQ ID NO |
| --- | --- | --- |
| VOYSOD1 | 1414 | 1326 |
| VOYSOD2 | 1415 | 1326 |
| VOYSOD3 | 1416 | 1317 |
| VOYSOD4 | 1417 | 1317 |

TABLE 18-continued

ITR to ITR Sequences of AAV Particles comprising Modulatory Polynucleotides

| ITR to ITR Construct Name | ITR to ITR SEQ ID NO | Modulatory Polynucleotide SEQ ID NO |
|---|---|---|
| VOYSOD5 | 2240 | 1326 |
| VOYSOD6 | 2241 | 1326 |

In one embodiment, the AAV particle comprises a viral genome which comprises a sequence which has a percent identity to any of SEQ ID NOs: 1414-1417, 2240, and 2241. The viral genome may have 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or 100% identity to any of SEQ ID NOs: 1414-1417, 2240, and 2241. The viral genome may have 1-10%, 10-20%, 30-40%, 50-60%, 50-70%, 50-80%, 50-90%, 50-99%, 50-100%, 60-70%, 60-80%, 60-90%, 60-99%, 60-100%, 70-80%, 70-90%, 70-99%, 70-100%, 80-85%, 80-90%, 80-95%, 80-99%, 80-100%, 90-95%, 90-99%, or 90-100% to any of SEQ ID NOs: 1414-1417, 2240, and 2241. As a non-limiting example, the viral genome comprises a sequence which as 80% identity to any of SEQ ID NO: 1414-1417, 2240, and 2241. As another non-limiting example, the viral genome comprises a sequence which as 85% identity to any of SEQ ID NO: 1414-1417, 2240, and 2241. As another non-limiting example, the viral genome comprises a sequence which as 90% identity to any of SEQ ID NO: 1414-1417, 2240, and 2241. As another non-limiting example, the viral genome comprises a sequence which as 95% identity to any of SEQ ID NO: 1414-1417, 2240, and 2241. As another non-limiting example, the viral genome comprises a sequence which as 99% identity to any of SEQ ID NO: 1414-1417, 2240, and 2241.

In one embodiment, the AAV particle viral genome comprises at least one inverted terminal repeat (ITR) sequence region, at least one multiple cloning site (MCS) sequence region, at least one exon sequence region, at least one intron sequence region, at least one modulatory polynucleotide region, and at least one polyadenylation signal sequence region.

In one embodiment, the AAV particle viral genome comprises a 5' inverted terminal repeat (ITR) sequence region and a 3' ITR sequence region, two multiple cloning site (MCS) sequence regions, an exon sequence region, two intron sequence regions, a modulatory polynucleotide region, and a polyadenylation signal sequence region.

In one embodiment, the AAV particle viral genome comprises a 5' inverted terminal repeat (ITR) sequence region and a 3' ITR sequence region, two MCS sequence regions, an exon sequence regions (human beta globin (hbglobin) exon 3 or fragments thereof), two intron sequence regions (ie1 intron 1 and hbglobin intron 2 or fragments thereof), a modulatory polynucleotide region, and a rabbit betaglobin polyadenylation signal sequence region. A non-limiting example of an ITR to ITR sequence for use in the AAV particles of the present invention having all of the sequence modules above are described in Table 19. In Table 19, the sequence identifier or sequence of the sequence region (Region SEQ ID NO) and the length of the sequence region (Region length) are described as well as the name and sequence identifier of the ITR to ITR sequence (e.g., VOYSOD1 (SEQ ID NO: 1414)).

TABLE 19

Sequence Regions in ITR to ITR Sequences

| Sequence Regions | VOYSOD1 (SEQ ID NO: 1414) | | VOYSOD3 (SEQ ID NO: 1416) | |
|---|---|---|---|---|
| | Region SEQ ID NO | Region length | Region SEQ ID NO | Region length |
| 5' ITR | 1371 | 105 | 1371 | 105 |
| MCS | TCGAG | 5 | TCGAG | 5 |
| IE1 intron1 | 1407 | 32 | 1407 | 32 |
| hbglobin intron2 | 1408 | 347 | 1408 | 347 |
| hbglobin exon3 | 1405 | 53 | 1405 | 53 |
| Modulatory Polynucleotide | 1328 | 260 | 1317 | 158 |
| MCS | TCGAG | 5 | TCGAG | 5 |
| Rabbit betaglobin polyA | 1410 | 127 | 1410 | 127 |
| 3' ITR | 1373 | 130 | 1373 | 130 |

In one embodiment, the AAV particle viral genome comprises SEQ ID NO: 1414 (VOYSOD1) which comprises a 5' inverted terminal repeat (ITR) sequence region and a 3' ITR sequence region, two multiple cloning site (MCS) sequence regions, an exon sequence region, two intron sequence regions (ie1 intron 1 and hbglobin intron 2), a modulatory polynucleotide region, and a rabbit globin polyadenylation signal sequence region.

In one embodiment, the AAV particle viral genome comprises SEQ ID NO: 1416 (VOYSOD3) which comprises a 5' inverted terminal repeat (ITR) sequence region and a 3' ITR sequence region, two multiple cloning site (MCS) sequence regions, an exon sequence region, two intron sequence regions (ie1 intron 1 and hbglobin intron 2), a modulatory polynucleotide region, and a rabbit globin polyadenylation signal sequence region.

In one embodiment, the AAV particle viral genome comprises a 5' inverted terminal repeat (ITR) sequence region and a 3' ITR sequence region, a multiple cloning site (MCS) sequence region, two exon sequence regions, two intron sequence regions, a modulatory polynucleotide region, and a polyadenylation signal sequence region.

In one embodiment, the AAV particle viral genome comprises a 5' inverted terminal repeat (ITR) sequence region and a 3' ITR sequence region, a MCS sequence region, two exon sequence regions (ie1 exon 1, human beta globin (hbglobin) exon 3 or fragments thereof), two intron sequence regions (ie1 intron 1 and hbglobin intron 2 or fragments thereof), a modulatory polynucleotide region, and a rabbit betaglobin polyadenylation signal sequence region. A non-limiting example of an ITR to ITR sequence for use in the AAV particles of the present invention having all of the sequence modules above are described in Table 20. In Table 20, the sequence identifier or sequence of the sequence region (Region SEQ ID NO) and the length of the sequence region (Region length) are described as well as the name and sequence identifier of the ITR to ITR sequence (e.g., VOYSOD2 (SEQ ID NO: 1415)).

TABLE 20

Sequence Regions in ITR to ITR Sequences

| Sequence Regions | VOYSOD2 (SEQ ID NO: 1415) | | VOYSOD4 (SEQ ID NO: 1417) | |
| --- | --- | --- | --- | --- |
| | Region SEQ ID NO | Region length | Region SEQ ID NO | Region length |
| 5' ITR | 1371 | 105 | 1371 | 105 |
| Ie1 exon1 | 1404 | 134 | 1404 | 134 |
| Ie1 intron1 | 1407 | 32 | 1407 | 32 |
| hbglobin intron2 | 1408 | 347 | 1408 | 347 |
| hbglobin exon3 | 1405 | 53 | 1405 | 53 |
| Modulatory Polynucleotide | 1328 | 260 | 1317 | 158 |
| MCS | TCGAG | 5 | TCGAG | 5 |
| Rabbit betaglobin polyA | 1410 | 127 | 1410 | 127 |
| 3' ITR | 1373 | 130 | 1373 | 130 |

In one embodiment, the AAV particle viral genome comprises SEQ ID NO: 1415 (VOYSOD2) which comprises a 5' inverted terminal repeat (ITR) sequence region and a 3' ITR sequence region, a multiple cloning site (MCS) sequence region, two exon sequence regions, two intron sequence regions (ie1 intron 1 and hbglobin intron 2), a modulatory polynucleotide region, and a rabbit globin polyadenylation signal sequence region.

In one embodiment, the AAV particle viral genome comprises SEQ ID NO: 1416 (VOYSOD4) which comprises a 5' inverted terminal repeat (ITR) sequence region and a 3' ITR sequence region, a multiple cloning site (MCS) sequence region, two exon sequence regions, two intron sequence regions (ie1 intron 1 and hbglobin intron 2), a modulatory polynucleotide region, and a rabbit globin polyadenylation signal sequence region.

AAV particles may be modified to enhance the efficiency of delivery. Such modified AAV particles comprising the nucleic acid sequence encoding the siRNA molecules of the present invention can be packaged efficiently and can be used to successfully infect the target cells at high frequency and with minimal toxicity.

In some embodiments, the AAV particle comprising a nucleic acid sequence encoding the siRNA molecules of the present invention may be a human serotype AAV particle. Such human AAV particle may be derived from any known serotype, e.g., from any one of serotypes AAV1-AAV11. As non-limiting examples, AAV particles may be vectors comprising an AAV1-derived genome in an AAV1-derived capsid; vectors comprising an AAV2-derived genome in an AAV2-derived capsid, vectors comprising an AAV4-derived genome in an AAV4 derived capsid; vectors comprising an AAV6-derived genome in an AAV6 derived capsid or vectors comprising an AAV9-derived genome in an AAV9 derived capsid.

In other embodiments, the AAV particle comprising a nucleic acid sequence for encoding siRNA molecules of the present invention may be a pseudotyped hybrid or chimeric AAV particle which contains sequences and/or components originating from at least two different AAV serotypes. Pseudotyped AAV particles may be vectors comprising an AAV genome derived from one AAV serotype and a capsid protein derived at least in part from a different AAV serotype. As non-limiting examples, such pseudotyped AAV particles may be vectors comprising an AAV2-derived genome in an AAV1-derived capsid; or vectors comprising an AAV2-derived genome in an AAV6-derived capsid; or vectors comprising an AAV2-derived genome in an AAV4-derived capsid; or an AAV2-derived genome in an AAV9-derived capsid. In like fashion, the present invention contemplates any hybrid or chimeric AAV particle.

In other embodiments, AAV particles comprising a nucleic acid sequence encoding the siRNA molecules of the present invention may be used to deliver siRNA molecules to the central nervous system (e.g., U.S. Pat. No. 6,180,613; the contents of which is herein incorporated by reference in its entirety).

In some aspects, the AAV particles comprising a nucleic acid sequence encoding the siRNA molecules of the present invention may further comprise a modified capsid including peptides from non-viral origin. In other aspects, the AAV particle may contain a CNS specific chimeric capsid to facilitate the delivery of encoded siRNA duplexes into the brain and the spinal cord. For example, an alignment of cap nucleotide sequences from AAV variants exhibiting CNS tropism may be constructed to identify variable region (VR) sequence and structure.

Viral Production

The present disclosure provides a method for the generation of parvoviral particles, e.g. AAV particles, by viral genome replication in a viral replication cell comprising contacting the viral replication cell with an AAV polynucleotide or AAV genome.

The present disclosure provides a method for producing an AAV particle having enhanced (increased, improved) transduction efficiency comprising the steps of: 1) co-transfecting competent bacterial cells with a bacmid vector and either a viral construct vector and/or AAV payload construct vector, 2) isolating the resultant viral construct expression vector and AAV payload construct expression vector and separately transfecting viral replication cells, 3) isolating and purifying resultant payload and viral construct particles comprising viral construct expression vector or AAV payload construct expression vector, 4) co-infecting a viral replication cell with both the AAV payload and viral construct particles comprising viral construct expression vector or AAV payload construct expression vector, 5) harvesting and purifying the viral particle comprising a parvoviral genome.

In one embodiment, the present invention provides a method for producing an AAV particle comprising the steps of 1) simultaneously co-transfecting mammalian cells, such as, but not limited to HEK293 cells, with a payload region, a construct expressing rep and cap genes and a helper construct, 2) harvesting and purifying the AAV particle comprising a viral genome.

Cells

The present disclosure provides a cell comprising an AAV polynucleotide and/or AAV genome.

Viral production disclosed herein describes processes and methods for producing AAV particles that contact a target cell to deliver a payload construct, e.g. a recombinant viral construct, which comprises a polynucleotide sequence encoding a payload molecule.

In one embodiment, the AAV particles may be produced in a viral replication cell that comprises an insect cell.

Growing conditions for insect cells in culture, and production of heterologous products in insect cells in culture are well-known in the art, see U.S. Pat. No. 6,204,059, the contents of which are herein incorporated by reference in their entirety.

Any insect cell which allows for replication of parvovirus and which can be maintained in culture can be used in accordance with the present invention. Cell lines may be used from *Spodoptera frugiperda*, including, but not limited to the Sf9 or Sf21 cell lines, *Drosophila* cell lines, or mosquito cell lines, such as *Aedes albopictus* derived cell lines. Use of insect cells for expression of heterologous proteins is well documented, as are methods of introducing nucleic acids, such as vectors, e.g., insect-cell compatible vectors, into such cells and methods of maintaining such cells in culture. See, for example, Methods in Molecular Biology, ed. Richard, Humana Press, NJ (1995); O'Reilly et al., Baculovirus Expression Vectors, A Laboratory Manual, Oxford Univ. Press (1994); Samulski et al., *J. Vir.* 63:3822-8 (1989); Kajigaya et al., *Proc. Nat'l. Acad. Sci. USA* 88: 4646-50 (1991); Ruffing et al., *J. Vir.* 66:6922-30 (1992); Kimbauer et al., *Vir.* 219:37-44 (1996); Zhao et al., *Vir.* 272:382-93 (2000); and Samulski et at, U.S. Pat. No. 6,204,059, the contents of each of which is herein incorporated by reference in its entirety.

The viral replication cell may be selected from any biological organism, including prokaryotic (e.g., bacterial) cells, and eukaryotic cells, including, insect cells, yeast cells and mammalian cells. Viral replication cells may comprise mammalian cells such as A549, WEH1, 3T3, 10T1/2, BHK, MDCK, COS 1, COS 7, BSC 1, BSC 40, BMT 10, VERO, W138, HeLa, HEK293, Saos, C2C12, L cells, HT1080, HepG2 and primary fibroblast, hepatocyte and myoblast cells derived from mammals. Viral replication cells comprise cells derived from mammalian species including, but not limited to, human, monkey, mouse, rat, rabbit, and hamster or cell type, including but not limited to fibroblast, hepatocyte, tumor cell, cell line transformed cell, etc.

Small Scale Production of AAV Particles

Viral production disclosed herein describes processes and methods for producing AAV particles that contact a target cell to deliver a payload, e.g. a recombinant viral construct, which comprises a polynucleotide sequence encoding a payload.

In one embodiment, the AAV particles may be produced in a viral replication cell that comprises a mammalian cell.

Viral replication cells commonly used for production of recombinant AAV particles include, but are not limited to 293 cells, COS cells, HeLa cells, KB cells, and other mammalian cell lines as described in U.S. Pat. Nos. 6,156,303, 5,387,484, 5,741,683, 5,691,176, and 5,688,676; U.S. patent application 2002/0081721, and International Patent Applications WO 00/47757, WO 00/24916, and WO 96/17947, the contents of each of which are herein incorporated by reference in their entireties.

In one embodiment, AAV particles are produced in mammalian-cells wherein all three VP proteins are expressed at a stoichiometry approaching 1:1:10 (VP1:VP2:VP3). The regulatory mechanisms that allow this controlled level of expression include the production of two mRNAs, one for VP1, and the other for VP2 and VP3, produced by differential splicing.

In another embodiment, AAV particles are produced in mammalian cells using a triple transfection method wherein a payload construct, parvoviral Rep and parvoviral Cap and a helper construct are comprised within three different constructs. The triple transfection method of the three components of AAV particle production may be utilized to produce small lots of virus for assays including transduction efficiency, target tissue (tropism) evaluation, and stability.

Baculovirus

Particle production disclosed herein describes processes and methods for producing AAV particles that contact a target cell to deliver a payload construct which comprises a polynucleotide sequence encoding a payload.

Briefly, the viral construct vector and the AAV payload construct vector are each incorporated by a transposon donor/acceptor system into a bacmid, also known as a baculovirus plasmid, by standard molecular biology techniques known and performed by a person skilled in the art. Transfection of separate viral replication cell populations produces two baculoviruses, one that comprises the viral construct expression vector, and another that comprises the AAV payload construct expression vector. The two baculoviruses may be used to infect a single viral replication cell population for production of AAV particles.

Baculovirus expression vectors for producing viral particles in insect cells, including but not limited to *Spodoptera frugiperda* (Sf9) cells, provide high titers of viral particle product. Recombinant baculovirus encoding the viral construct expression vector and AAV payload construct expression vector initiates a productive infection of viral replicating cells. Infectious baculovirus particles released from the primary infection secondarily infect additional cells in the culture, exponentially infecting the entire cell culture population in a number of infection cycles that is a function of the initial multiplicity of infection, see Urabe, M. et al., J Virol. 2006 February; 80 (4): 1874-85, the contents of which are herein incorporated by reference in their entirety.

Production of AAV particles with baculovirus in an insect cell system may address known baculovirus genetic and physical instability. In one embodiment, the production system addresses baculovirus instability over multiple passages by utilizing a titerless infected-cells preservation and scale-up system. Small scale seed cultures of viral producing cells are transfected with viral expression constructs encoding the structural, non-structural, components of the viral particle. Baculovirus-infected viral producing cells are harvested into aliquots that may be cryopreserved in liquid nitrogen; the aliquots retain viability and infectivity for infection of large scale viral producing cell culture Wasilko D J et al., Protein Expr Purif. 2009 June; 65(2):122-32, the contents of which are herein incorporated by reference in their entirety.

A genetically stable baculovirus may be used to produce source of the one or more of the components for producing AAV particles in invertebrate cells. In one embodiment, defective baculovirus expression vectors may be maintained episomally in insect cells. In such an embodiment the bacmid vector is engineered with replication control elements, including but not limited to promoters, enhancers, and/or cell-cycle regulated replication elements.

In one embodiment, baculoviruses may be engineered with a (non-) selectable marker for recombination into the chitinase/cathepsin locus. The chia/v-cath locus is non-essential for propagating baculovirus in tissue culture, and the V-cath (EC 3.4.22.50) is a cysteine endoprotease that is most active on Arg-Arg dipeptide containing substrates. The Arg-Arg dipeptide is present in densovirus and parvovirus capsid structural proteins but infrequently occurs in dependovirus VP1.

In one embodiment, stable viral replication cells permissive for baculovirus infection are engineered with at least one stable integrated copy of any of the elements necessary for AAV replication and viral particle production including, but not limited to, the entire AAV genome, Rep and Cap genes, Rep genes, Cap genes, each Rep protein as a separate transcription cassette, each VP protein as a separate transcription cassette, the AAP (assembly activation protein), or at least one of the baculovirus helper genes with native or non-native promoters.

Large-Scale Production

In some embodiments, AAV particle production may be modified to increase the scale of production. Large scale viral production methods according to the present disclosure may include any of those taught in U.S. Pat. Nos. 5,756,283, 6,258,595, 6,261,551, 6,270,996, 6,281,010, 6,365,394, 6,475,769, 6,482,634, 6,485,966, 6,943,019, 6,953,690, 7,022,519, 7,238,526, 7,291,498 and 7,491,508 or International Publication Nos. WO 1996039530, WO 1998010088, WO 1999014354, WO 1999015685, WO 1999047691, WO2000055342, WO2000075353 and WO2001023597, the contents of each of which are herein incorporated by reference in their entirety. Methods of increasing viral particle production scale typically comprise increasing the number of viral replication cells. In some embodiments, viral replication cells comprise adherent cells. To increase the scale of viral particle production by adherent viral replication cells, larger cell culture surfaces are required. In some cases, large-scale production methods comprise the use of roller bottles to increase cell culture surfaces. Other cell culture substrates with increased surface areas are known in the art. Examples of additional adherent cell culture products with increased surface areas include, but are not limited to CELLSTACK®, CELLCUBE® (Corning Corp., Corning, N.Y.) and NUNC™ CELL FACTORY™ (Thermo Scientific, Waltham, Mass.) In some cases, large-scale adherent cell surfaces may comprise from about 1,000 $cm^2$ to about 100,000 $cm^2$. In some cases, large-scale adherent cell cultures may comprise from about $10^7$ to about $10^9$ cells, from about $10^8$ to about $10^{10}$ cells, from about $10^9$ to about $10^{12}$ cells or at least $10^{12}$ cells. In some cases, large-scale adherent cultures may produce from about $10^9$ to about $10^{12}$, from about $10^{10}$ to about $10^{13}$ from about $10^{11}$ to about $10^{14}$, from about $10^{12}$ to about $10^{15}$ or at least $10^{19}$ viral particles.

In some embodiments, large-scale viral production methods of the present disclosure may comprise the use of suspension cell cultures. Suspension cell culture allows for significantly increased numbers of cells. Typically, the number of adherent cells that can be grown on about 10-50 $cm^2$ of surface area can be grown in about 1 $cm^3$ volume in suspension.

Transfection of replication cells in large-scale culture formats may be carried out according to any methods known in the art. For large-scale adherent cell cultures, transfection methods may include, but are not limited to the use of inorganic compounds (e.g. calcium phosphate), organic compounds [e.g. polyethyleneimine (PEI)] or the use of non-chemical methods (e.g. electroporation.) With cells grown in suspension, transfection methods may include, but are not limited to the use of calcium phosphate and the use of PEI. In some cases, transfection of large scale suspension cultures may be carried out according to the section entitled "Transfection Procedure" described in Feng, L. et al., 2008. Biotechnol Appl. Biochem. 50:121-32, the contents of which are herein incorporated by reference in their entirety. According to such embodiments, PEI-DNA complexes may be formed for introduction of plasmids to be transfected. In some cases, cells being transfected with PEI-DNA complexes may be 'shocked' prior to transfection. This comprises lowering cell culture temperatures to 4° C. for a period of about 1 hour. In some cases, cell cultures may be shocked for a period of from about 10 minutes to about 5 hours. In some cases, cell cultures may be shocked at a temperature of from about 0° C. to about 20° C.

In some cases, transfections may include one or more vectors for expression of an RNA effector molecule to reduce expression of nucleic acids from one or more AAV payload construct. Such methods may enhance the production of viral particles by reducing cellular resources wasted on expressing payload constructs. In some cases, such methods may be carried according to those taught in US Publication No. US2014/0099666, the contents of which are herein incorporated by reference in their entirety.

Bioreactors

In some embodiments, cell culture bioreactors may be used for large scale viral production. In some cases, bioreactors comprise stirred tank reactors. Such reactors generally comprise a vessel, typically cylindrical in shape, with a stirrer (e.g. impeller.) In some embodiments, such bioreactor vessels may be placed within a water jacket to control vessel temperature and/or to minimize effects from ambient temperature changes. Bioreactor vessel volume may range in size from about 500 ml to about 2 L, from about 1 L to about 5 L, from about 2.5 L to about 20 L, from about 10 L to about 50 L, from about 25 L to about 100 L, from about 75 L to about 500 L, from about 250 L to about 2,000 L, from about 1,000 L to about 10,000 L, from about 5,000 L to about 50,000 L or at least 50,000 L. Vessel bottoms may be rounded or flat. In some cases, animal cell cultures may be maintained in bioreactors with rounded vessel bottoms.

In some cases, bioreactor vessels may be warmed through the use of a thermocirculator. Thermocirculators pump heated water around water jackets. In some cases, heated water may be pumped through pipes (e.g. coiled pipes) that are present within bioreactor vessels. In some cases, warm air may be circulated around bioreactors, including, but not limited to air space directly above culture medium. Additionally, pH and $CO_2$ levels may be maintained to optimize cell viability.

In some cases, bioreactors may comprise hollow-fiber reactors. Hollow-fiber bioreactors may support the culture of both anchorage dependent and anchorage independent cells. Further bioreactors may include, but are not limited to packed-bed or fixed-bed bioreactors. Such bioreactors may comprise vessels with glass beads for adherent cell attachment. Further packed-bed reactors may comprise ceramic beads.

In some cases, viral particles are produced through the use of a disposable bioreactor. In some embodiments, such bioreactors may include WAVE™ disposable bioreactors.

In some embodiments, AAV particle production in animal cell bioreactor cultures may be carried out according to the methods taught in U.S. Pat. Nos. 5,064,764, 6,194,191, 6,566,118, 8,137,948 or US Patent Application No. US2011/0229971, the contents of each of which are herein incorporated by reference in their entirety.

Cell Lysis

Cells of the invention, including, but not limited to viral production cells, may be subjected to cell lysis according to any methods known in the art. Cell lysis may be carried out to obtain one or more agents (e.g. viral particles) present within any cells of the invention. In some embodiments, cell lysis may be carried out according to any of the methods listed in U.S. Pat. Nos. 7,326,555, 7,579,181, 7,048,920, 6,410,300, 6,436,394, 7,732,129, 7,510,875, 7,445,930, 6,726,907, 6,194,191, 7,125,706, 6,995,006, 6,676,935, 7,968,333, 5,756,283, 6,258,595, 6,261,551, 6,270,996, 6,281,010, 6,365,394, 6,475,769, 6,482,634, 6,485,966, 6,943,019, 6,953,690, 7,022,519, 7,238,526, 7,291,498 and 7,491,508 or International Publication Nos. WO 1996039530, WO 1998010088, WO 1999014354, WO 1999015685, WO 1999047691. WO2000055342, WO2000075353 and WO2001023597, the contents of each of which are herein incorporated by reference in their entirety. Cell lysis methods may be chemical or mechanical. Chemical cell lysis typically comprises contacting one or more cells with one or more lysis agent. Mechanical lysis typically comprises subjecting one or more cells to one or more lysis condition and/or one or more lysis force.

In some embodiments, chemical lysis may be used to lyse cells. As used herein, the term "lysis agent" refers to any agent that may aid in the disruption of a cell. In some cases, lysis agents are introduced in solutions, termed lysis solutions or lysis buffers. As used herein, the term "lysis solution" refers to a solution (typically aqueous) comprising one or more lysis agent. In addition to lysis agents, lysis solutions may include one or more buffering agents, solubilizing agents, surfactants, preservatives, cryoprotectants, enzymes, enzyme inhibitors and/or chelators. Lysis buffers are lysis solutions comprising one or more buffering agent. Additional components of lysis solutions may include one or more solubilizing agent. As used herein, the term "solubilizing agent" refers to a compound that enhances the solubility of one or more components of a solution and/or the solubility of one or more entities to which solutions are applied. In some cases, solubilizing agents enhance protein solubility. In some cases, solubilizing agents are selected based on their ability to enhance protein solubility while maintaining protein conformation and/or activity.

Exemplary lysis agents may include any of those described in U.S. Pat. Nos. 8,685,734, 7,901,921, 7,732,129, 7,223,585, 7,125,706, 8,236,495, 8,110,351, 7,419,956, 7,300,797, 6,699,706 and 6,143,567, the contents of each of which are herein incorporated by reference in their entirety. In some cases, lysis agents may be selected from lysis salts, amphoteric agents, cationic agents, ionic detergents and non-ionic detergents. Lysis salts may include, but are not limited to sodium chloride (NaCl) and potassium chloride (KCl.) Further lysis salts may include any of those described in U.S. Pat. Nos. 8,614,101, 7,326,555, 7,579,181, 7,048, 920, 6,410,300, 6,436,394, 7,732,129, 7,510,875, 7,445,930, 6,726,907, 6,194,191, 7,125,706, 6,995,006, 6,676,935 and 7,968,333, the contents of each of which are herein incorporated by reference in their entirety. Concentrations of salts may be increased or decreased to obtain an effective concentration for rupture of cell membranes. Amphoteric agents, as referred to herein, are compounds capable of reacting as an acid or a base. Amphoteric agents may include, but are not limited to lysophosphatidylcholine, 3-((3-Cholamidopropyl) dimethylammonium)-1-propanesulfonate (CHAPS), ZWITTERGENT® and the like. Cationic agents may include, but are not limited to cetyltrimethylammonium bromide (C (16) TAB) and Benzalkonium chloride. Lysis agents comprising detergents may include ionic detergents or non-ionic detergents. Detergents may function to break apart or dissolve cell structures including, but not limited to cell membranes, cell walls, lipids, carbohydrates, lipoproteins and glycoproteins. Exemplary ionic detergents include any of those taught in U.S. Pat. Nos. 7,625,570 and 6,593,123 or US Publication No. US2014/ 0087361, the contents of each of which are herein incorporated by reference in their entirety. Some ionic detergents may include, but are not limited to sodium dodecyl sulfate (SDS), cholate and deoxycholate. In some cases, ionic detergents may be included in lysis solutions as a solubilizing agent. Non-ionic detergents may include, but are not limited to octylglucoside, digitonin, lubrol, C12E8, TWEEN®-20, TWEEN®-80, Triton X-100 and Noniodet P-40. Non-ionic detergents are typically weaker lysis agents, but may be included as solubilizing agents for solubilizing cellular and/or viral proteins. Further lysis agents may include enzymes and urea. In some cases, one or more lysis agents may be combined in a lysis solution in order to enhance one or more of cell lysis and protein solubility. In some cases, enzyme inhibitors may be included in lysis solutions in order to prevent proteolysis that may be triggered by cell membrane disruption.

In some embodiments, mechanical cell lysis is carried out. Mechanical cell lysis methods may include the use of one or more lysis condition and/or one or more lysis force. As used herein, the term "lysis condition" refers to a state or circumstance that promotes cellular disruption. Lysis conditions may comprise certain temperatures, pressures, osmotic purity, salinity and the like. In some cases, lysis conditions comprise increased or decreased temperatures. According to some embodiments, lysis conditions comprise changes in temperature to promote cellular disruption. Cell lysis carried out according to such embodiments may include freeze-thaw lysis. As used herein, the term "freeze-thaw lysis" refers to cellular lysis in which a cell solution is subjected to one or more freeze-thaw cycle. According to freeze-thaw lysis methods, cells in solution are frozen to induce a mechanical disruption of cellular membranes caused by the formation and expansion of ice crystals. Cell solutions used according freeze-thaw lysis methods, may further comprise one or more lysis agents, solubilizing agents, buffering agents, cryoprotectants, surfactants, preservatives, enzymes, enzyme inhibitors and/or chelators. Once cell solutions subjected to freezing are thawed, such components may enhance the recovery of desired cellular products. In some cases, one or more cryoprotectants are included in cell solutions undergoing freeze-thaw lysis. As used herein, the term "cryoprotectant" refers to an agent used to protect one or more substance from damage due to freezing. Cryoprotectants may include any of those taught in US Publication No. US2013/0323302 or U.S. Pat. Nos. 6,503,888, 6,180, 613, 7,888,096, 7,091,030, the contents of each of which are herein incorporated by reference in their entirety. In some cases, cryoprotectants may include, but are not limited to dimethyl sulfoxide, 1,2-propanediol, 2,3-butanediol, formamide, glycerol, ethylene glycol, 1,3-propanediol and n-dimethyl formamide, polyvinylpyrrolidone, hydroxyethyl starch, agarose, dextrans, inositol, glucose, hydroxyethylstarch, lactose, sorbitol, methyl glucose, sucrose and urea. In some embodiments, freeze-thaw lysis may be carried out according to any of the methods described in U.S. Pat. No. 7,704,721, the contents of which are herein incorporated by reference in their entirety.

As used herein, the term "lysis force" refers to a physical activity used to disrupt a cell. Lysis forces may include, but are not limited to mechanical forces, sonic forces, gravitational forces, optical forces, electrical forces and the like. Cell lysis carried out by mechanical force is referred to herein as "mechanical lysis." Mechanical forces that may be used according to mechanical lysis may include high shear fluid forces. According to such methods of mechanical lysis, a microfluidizer may be used. Microfluidizers typically comprise an inlet reservoir where cell solutions may be applied. Cell solutions may then be pumped into an interaction chamber via a pump (e.g. high-pressure pump) at high speed and/or pressure to produce shear fluid forces. Resulting lysates may then be collected in one or more output reservoir. Pump speed and/or pressure may be adjusted to modulate cell lysis and enhance recovery of products (e.g. viral particles.) Other mechanical lysis methods may include physical disruption of cells by scraping.

Cell lysis methods may be selected based on the cell culture format of cells to be lysed. For example, with adherent cell cultures, some chemical and mechanical lysis methods may be used. Such mechanical lysis methods may include freeze-thaw lysis or scraping. In another example, chemical lysis of adherent cell cultures may be carried out through incubation with lysis solutions comprising surfactant, such as Triton-X-100. In some cases, cell lysates generated from adherent cell cultures may be treated with one more nuclease to lower the viscosity of the lysates caused by liberated DNA.

In one embodiment, a method for harvesting AAV particles without lysis may be used for efficient and scalable AAV particle production. In a non-limiting example, AAV particles may be produced by culturing an AAV particle lacking a heparin binding site, thereby allowing the AAV particle to pass into the supernatant, in a cell culture, collecting supernatant from the culture; and isolating the AAV particle from the supernatant, as described in US Patent Application 20090275107, the contents of which are incorporated herein by reference in their entirety.

Clarification

Cell lysates comprising viral particles may be subjected to clarification. Clarification refers to initial steps taken in purification of viral particles from cell lysates. Clarification serves to prepare lysates for further purification by removing larger, insoluble debris. Clarification steps may include, but are not limited to centrifugation and filtration. During clarification, centrifugation may be carried out at low speeds to remove larger debris only. Similarly, filtration may be carried out using filters with larger pore sizes so that only larger debris is removed. In some cases, tangential flow filtration may be used during clarification. Objectives of viral clarification include high throughput processing of cell lysates and to optimize ultimate viral recovery. Advantages of including a clarification step include scalability for processing of larger volumes of lysate. In some embodiments, clarification may be carried out according to any of the methods presented in U.S. Pat. Nos. 8,524,446, 5,756,283, 6,258,595, 6,261,551, 6,270,996, 6,281,010, 6,365,394, 6,475,769, 6,482,634, 6,485,966, 6,943,019, 6,953,690, 7,022,519, 7,238,526, 7,291,498, 7,491,508, US Publication Nos. US2013/0045186, US2011/0263027. US2011/0151434, US2003/0138772, and International Publication Nos. WO2002012455, WO 1996039530, WO 1998010088, WO 1999014354, WO 1999015685, WO 1999047691, WO2000055342, WO02000075353 and WO02001023597, the contents of each of which are herein incorporated by reference in their entirety.

Methods of cell lysate clarification by filtration are well understood in the art and may be carried out according to a variety of available methods including, but not limited to passive filtration and flow filtration. Filters used may comprise a variety of materials and pore sizes. For example, cell lysate filters may comprise pore sizes of from about 1 µM to about 5 µM, from about 0.5 µM to about 2 µM, from about 0.1 µM to about 1 µM, from about 0.05 µM to about 0.05 µM and from about 0.001 µM to about 0.1 µM. Exemplary pore sizes for cell lysate filters may include, but are not limited to, 2.0, 1.9, 1.8, 1.7, 1.6, 1.5, 1.4, 1.3, 1.2, 1.1, 1, 0.9, 0.8, 0.7, 0.6, 0.5, 0.4, 0.3, 0.2, 0.1, 0.95, 0.9, 0.85, 0.8, 0.75, 0.7, 0.65, 0.6, 0.55, 0.5, 0.45, 0.4, 0.35, 0.3, 0.25, 0.2, 0.15, 0.1, 0.05, 0.22, 0.21, 0.20, 0.19, 0.18, 0.17, 0.16, 0.15, 0.14, 0.13, 0.12, 0.11, 0.1, 0.09, 0.08, 0.07, 0.06, 0.05, 0.04, 0.03, 0.02, 0.01, 0.02, 0.019, 0.018, 0.017, 0.016, 0.015, 0.014, 0.013, 0.012, 0.011, 0.01, 0.009, 0.008, 0.007, 0.006, 0.005, 0.004, 0.003, 0.002, 0.001 and 0.001 µM. In one embodiment, clarification may comprise filtration through a filter with 2.0 µM pore size to remove large debris, followed by passage through a filter with 0.45 µM pore size to remove intact cells.

Filter materials may be composed of a variety of materials. Such materials may include, but are not limited to polymeric materials and metal materials (e.g. sintered metal and pored aluminum.) Exemplary materials may include, but are not limited to nylon, cellulose materials (e.g. cellulose acetate), polyvinylidene fluoride (PVDF), polyethersulfone, polyamide, polysulfone, polypropylene, and polyethylene terephthalate. In some cases, filters useful for clarification of cell lysates may include, but are not limited to ULTIPLEAT PROFILE™ filters (Pall Corporation, Port Washington, N.Y.), SUPOR™ membrane filters (Pall Corporation, Port Washington, N.Y.)

In some cases, flow filtration may be carried out to increase filtration speed and/or effectiveness. In some cases, flow filtration may comprise vacuum filtration. According to such methods, a vacuum is created on the side of the filter opposite that of cell lysate to be filtered. In some cases, cell lysates may be passed through filters by centrifugal forces. In some cases, a pump is used to force cell lysate through clarification filters. Flow rate of cell lysate through one or more filters may be modulated by adjusting one of channel size and/or fluid pressure.

According to some embodiments, cell lysates may be clarified by centrifugation. Centrifugation may be used to pellet insoluble particles in the lysate. During clarification, centrifugation strength [expressed in terms of gravitational units (g), which represents multiples of standard gravitational force] may be lower than in subsequent purification steps. In some cases, centrifugation may be carried out on cell lysates at from about 200 g to about 800 g, from about 500 g to about 1500 g, from about 1000 g to about 5000 g, from about 1200 g to about 10000 g or from about 8000 g to about 15000 g. In some embodiments, cell lysate centrifugation is carried out at 8000 g for 15 minutes. In some cases, density gradient centrifugation may be carried out in order to partition particulates in the cell lysate by sedimentation rate. Gradients used according to methods of the present disclosure may include, but are not limited to cesium chloride gradients and iodixanol step gradients.

Purification: Chromatography

In some cases, AAV particles may be purified from clarified cell lysates by one or more methods of chromatography. Chromatography refers to any number of methods known in the art for separating out one or more elements from a mixture. Such methods may include, but are not limited to ion exchange chromatography (e.g. cation exchange chromatography and anion exchange chromatography), immunoaffinity chromatography and size-exclusion chromatography. In some embodiments, methods of viral chromatography may include any of those taught in U.S. Pat. Nos. 5,756,283, 6,258,595, 6,261,551, 6,270,996, 6,281,010, 6,365,394, 6,475,769, 6,482,634, 6,485,966, 6,943,019, 6,953,690, 7,022,519, 7,238,526, 7,291,498 and 7,491,508 or International Publication Nos. WO1996039530, WO 1998010088, WO 1999014354, WO 1999015685, WO 1999047691, WO2000055342, WO2000075353 and WO2001023597, the contents of each of which are herein incorporated by reference in their entirety.

In some embodiments, ion exchange chromatography may be used to isolate viral particles. Ion exchange chromatography is used to bind viral particles based on charge-charge interactions between capsid proteins and charged sites present on a stationary phase, typically a column through which viral preparations (e.g. clarified lysates) are passed. After application of viral preparations, bound viral particles may then be eluted by applying an elution solution to disrupt the charge-charge interactions. Elution solutions may be optimized by adjusting salt concentration and/or pH to enhance recovery of bound viral particles. Depending on the charge of viral capsids being isolated, cation or anion exchange chromatography methods may be selected. Methods of ion exchange chromatography may include, but are not limited to any of those taught in U.S. Pat. Nos. 7,419,817, 6,143,548, 7,094,604, 6,593,123, 7,015,026 and 8,137,948, the contents of each of which are herein incorporated by reference in their entirety.

In some embodiments, immunoaffinity chromatography may be used. Immunoaffinity chromatography is a form of chromatography that utilizes one or more immune compounds (e.g. antibodies or antibody-related structures) to retain viral particles. Immune compounds may bind specifically to one or more structures on viral particle surfaces, including, but not limited to one or more viral coat protein. In some cases, immune compounds may be specific for a particular viral variant. In some cases, immune compounds may bind to multiple viral variants. In some embodiments, immune compounds may include recombinant single-chain antibodies. Such recombinant single chain antibodies may include those described in Smith, R. H. et al., 2009. Mol. Ther. 17(11): 1888-96, the contents of which are herein incorporated by reference in their entirety. Such immune compounds are capable of binding to several AAV capsid variants, including, but not limited to AAV1, AAV2, AAV6 and AAV8.

In some embodiments, size-exclusion chromatography (SEC) may be used. SEC may comprise the use of a gel to separate particles according to size. In viral particle purification, SEC filtration is sometimes referred to as "polishing." In some cases, SEC may be carried out to generate a final product that is near-homogenous. Such final products may in some cases be used in pre-clinical studies and/or clinical studies (Kotin, R. M. 2011. Human Molecular Genetics. 20(1):R2-R6, the contents of which are herein incorporated by reference in their entirety.) In some cases, SEC may be carried out according to any of the methods taught in U.S. Pat. Nos. 6,143,548, 7,015,026, 8,476,418, 6,410,300, 8,476,418, 7,419,817, 7,094,604, 6,593,123, and 8,137,948, the contents of each of which are herein incorporated by reference in their entirety.

In one embodiment, the compositions comprising at least one AAV particle may be isolated or purified using the methods described in U.S. Pat. No. 6,146,874, the contents of which are herein incorporated by reference in its entirety.

In one embodiment, the compositions comprising at least one AAV particle may be isolated or purified using the methods described in U.S. Pat. No. 6,660,514, the contents of which are herein incorporated by reference in its entirety.

In one embodiment, the compositions comprising at least one AAV particle may be isolated or purified using the methods described in U.S. Pat. No. 8,283,151, the contents of which are herein incorporated by reference in its entirety.

In one embodiment, the compositions comprising at least one AAV particle may be isolated or purified using the methods described in U.S. Pat. No. 8,524,446, the contents of which are herein incorporated by reference in its entirety.

II. Formulation and Delivery

Pharmaceutical Compositions and Formulation

In addition to the pharmaceutical compositions (AAV particles comprising a modulatory polynucleotide sequence encoding the siRNA molecules), provided herein are pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

In some embodiments, compositions are administered to humans, human patients or subjects. For the purposes of the present disclosure, the phrase "active ingredient" generally refers either to the synthetic siRNA duplexes, the modulatory polynucleotide encoding the siRNA duplex, or the AAV particle comprising a modulatory polynucleotide encoding the siRNA duplex described herein.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered.

The AAV particles comprising the modulatory polynucleotide sequence encoding the siRNA molecules of the present invention can be formulated using one or more excipients to: (1) increase stability; (2) increase cell transfection or transduction; (3) permit the sustained or delayed release; or (4) alter the biodistribution (e.g., target the AAV particle to specific tissues or cell types such as brain and neurons).

Formulations of the present invention can include, without limitation, saline, lipidoids, liposomes, lipid nanoparticles, polymers, lipoplexes, core-shell nanoparticles, peptides, proteins, cells transfected with AAV particles (e.g., for transplantation into a subject), nanoparticle mimics and combinations thereof. Further, the AAV particles of the present invention may be formulated using self-assembled nucleic acid nanoparticles.

Formulations of the pharmaceutical compositions described herein may be prepared by any method known or hereafter developed in the art of pharmacology. In general, such preparatory methods include the step of associating the active ingredient with an excipient and/or one or more other accessory ingredients.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, at least 80% (w/w) active ingredient.

In some embodiments, a pharmaceutically acceptable excipient may be at least 95%, at least 96%, at least 97%, at least 98%, at least 99%, or 100% pure. In some embodiments, an excipient is approved for use for humans and for veterinary use. In some embodiments, an excipient may be approved by United States Food and Drug Administration. In some embodiments, an excipient may be of pharmaceutical grade. In some embodiments, an excipient may meet the standards of the United States Pharmacopoeia (USP), the European Pharmacopoeia (EP), the British Pharmacopoeia, and/or the International Pharmacopoeia.

Excipients, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21$^{st}$ Edition, A. R. Gennaro, Lippincott, Williams & Wilkins, Baltimore, Md., 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

In some embodiments, the formulations may comprise at least one inactive ingredient. As used herein, the term "inactive ingredient" refers to one or more inactive agents included in formulations. In some embodiments, all, none or some of the inactive ingredients which may be used in the formulations of the present invention may be approved by the US Food and Drug Administration (FDA).

Formulations of vectors comprising the nucleic acid sequence for the siRNA molecules of the present invention may include cations or anions. In one embodiment, the formulations include metal cations such as, but not limited to, Zn2+, Ca2+, Cu2+, Mg+ and combinations thereof.

As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two: generally, nonaqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418, *Pharmaceutical Salts: Properties, Selection, and Use*, P. H. Stahl and C. G. Wermuth (eds.), Wiley-VCH, 2008, and Berge et al., *Journal of Pharmaceutical Science*, 66, 1-19 (1977); the content of each of which is incorporated herein by reference in their entirety.

The term "pharmaceutically acceptable solvate," as used herein, means a compound of the invention wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5, 6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

According to the present invention, the AAV particle comprising the modulatory polynucleotide sequence encoding for the siRNA molecules may be formulated for CNS delivery. Agents that cross the brain blood barrier may be used. For example, some cell penetrating peptides that can target siRNA molecules to the brain blood barrier endothelium may be used to formulate the siRNA duplexes targeting the gene of interest.

Inactive Ingredients

In some embodiments, formulations may comprise at least one excipient which is an inactive ingredient. As used herein, the term "inactive ingredient" refers to one or more inactive agents included in formulations. In some embodiments, all, none or some of the inactive ingredients which may be used in the formulations of the present disclosure may be approved by the US Food and Drug Administration (FDA).

Formulations of AAV particles described herein may include cations or anions. In one embodiment, the formulations include metal cations such as, but not limited to, Zn2+, Ca2+, Cu2+, Mg+ and combinations thereof. As a non-limiting example, formulations may include polymers and compositions described herein complexed with a metal cation (See e.g., U.S. Pat. Nos. 6,265,389 and 6,555,525, each of which is herein incorporated by reference in its entirety).

Delivery

In one embodiment, the AAV particles described herein may be administered or delivered using the methods for the delivery of AAV virions described in European Patent Application No. EP1857552, the contents of which are herein incorporated by reference in its entirety.

In one embodiment, the AAV particles described herein may be administered or delivered using the methods for delivering proteins using AAV particles described in European Patent Application No. EP2678433, the contents of which are herein incorporated by reference in its entirety.

In one embodiment, the AAV particle described herein may be administered or delivered using the methods for delivering DNA molecules using AAV particles described in U.S. Pat. No. 5,858,351, the contents of which are herein incorporated by reference in its entirety.

In one embodiment, the AAV particle described herein may be administered or delivered using the methods for delivering DNA to the bloodstream described in U.S. Pat. No. 6,211,163, the contents of which are herein incorporated by reference in its entirety.

In one embodiment, the AAV particle described herein may be administered or delivered using the methods for delivering AAV virions described in U.S. Pat. No. 6,325,998, the contents of which are herein incorporated by reference in its entirety.

In one embodiment, the AAV particle described herein may be administered or delivered using the methods for delivering a payload to the central nervous system described in U.S. Pat. No. 7,588,757, the contents of which are herein incorporated by reference in its entirety.

In one embodiment, the AAV particle described herein may be administered or delivered using the methods for delivering a payload described in U.S. Pat. No. 8,283,151, the contents of which are herein incorporated by reference in its entirety.

In one embodiment, the AAV particle described herein may be administered or delivered using the methods for delivering a payload using a glutamic acid decarboxylase (GAD) delivery vector described in International Patent Publication No. WO2001089583, the contents of which are herein incorporated by reference in its entirety.

In one embodiment, the AAV particle described herein may be administered or delivered using the methods for delivering a payload to neural cells described in International Patent Publication No. WO2012057363, the contents of which are herein incorporated by reference in its entirety.

Delivery to Cells

The present disclosure provides a method of delivering to a cell or tissue any of the above-described AAV polynucleotides or AAV genomes, comprising contacting the cell or tissue with said AAV polynucleotide or AAV genomes or contacting the cell or tissue with a particle comprising said AAV polynucleotide or AAV genome, or contacting the cell or tissue with any of the described compositions, including pharmaceutical compositions. The method of delivering the AAV polynucleotide or AAV genome to a cell or tissue can be accomplished in vitro, ex vivo, or in vivo.

Introduction into Cells—Synthetic dsRNA

To ensure the chemical and biological stability of siRNA molecules (e.g., siRNA duplexes and dsRNA), it is important to deliver siRNA molecules inside the target cells. In some embodiments, the cells may include, but are not limited to, cells of mammalian origin, cells of human origins, embryonic stem cells, induced pluripotent stem cells, neural stem cells, and neural progenitor cells.

Nucleic acids, including siRNA, carry a net negative charge on the sugar-phosphate backbone under normal physiological conditions. In order to enter the cell, a siRNA molecule must come into contact with a lipid bilayer of the cell membrane, whose head groups are also negatively charged.

The siRNA duplexes can be complexed with a carrier that allows them to traverse cell membranes such as package particles to facilitate cellular uptake of the siRNA. The package particles may include, but are not limited to, liposomes, nanoparticles, cationic lipids, polyethylenimine derivatives, dendrimers, carbon nanotubes and the combination of carbon-made nanoparticles with dendrimers. Lipids may be cationic lipids and/or neutral lipids. In addition to well established lipophilic complexes between siRNA molecules and cationic carriers, siRNA molecules can be conjugated to a hydrophobic moiety, such as cholesterol (e.g., U.S. Patent Publication No. 20110110937; the content of which is herein incorporated by reference in its entirety). This delivery method holds a potential of improving in vitro cellular uptake and in vivo pharmacological properties of siRNA molecules. The siRNA molecules of the present invention may also be conjugated to certain cationic cell-penetrating peptides (CPPs), such as MPG, transportan or penetratin covalently or non-covalently (e.g., U.S. Patent Publication No. 20110086425; the content of which is herein incorporated by reference in its entirety).

Introduction into Cells-AAV Particles

The siRNA molecules (e.g., siRNA duplexes) of the present invention may be introduced into cells using any of a variety of approaches such as, but not limited to, AAV particles. These AAV particles are engineered and optimized to facilitate the entry of siRNA molecule into cells that are not readily amendable to transfection. Also, some synthetic AAV particles possess an ability to integrate the shRNA into the cell genome, thereby leading to stable siRNA expression and long-term knockdown of a target gene. In this manner, AAV particles are engineered as vehicles for specific delivery while lacking the deleterious replication and/or integration features found in wild-type virus.

In some embodiments, the siRNA molecules of the present invention are introduced into a cell by contacting the cell with an AAV particle comprising a modulatory polynucleotide sequence encoding a siRNA molecule, and a lipophilic carrier. In other embodiments, the siRNA molecule is introduced into a cell by transfecting or infecting the cell with an AAV particle comprising a nucleic acid sequence capable of producing the siRNA molecule when transcribed in the cell. In some embodiments, the siRNA molecule is introduced into a cell by injecting into the cell an AAV particle comprising a nucleic acid sequence capable of producing the siRNA molecule when transcribed in the cell.

In some embodiments, prior to transfection, an AAV particle comprising a nucleic acid sequence encoding the siRNA molecules of the present invention may be transfected into cells.

In other embodiments, the AAV particles comprising the nucleic acid sequence encoding the siRNA molecules of the present invention may be delivered into cells by electroporation (e.g. U.S. Patent Publication No. 20050014264; the content of which is herein incorporated by reference in its entirety).

Other methods for introducing AAV particles comprising the nucleic acid sequence encoding the siRNA molecules described herein may include photochemical internalization as described in U.S. Patent publication No. 20120264807; the content of which is herein incorporated by reference in its entirety.

In some embodiments, the formulations described herein may contain at least one AAV particle comprising the nucleic acid sequence encoding the siRNA molecules described herein. In one embodiment, the siRNA molecules may target the gene of interest at one target site. In another embodiment, the formulation comprises a plurality of AAV particles, each AAV particle comprising a nucleic acid sequence encoding a siRNA molecule targeting the gene of interest at a different target site. The gene of interest may be targeted at 2, 3, 4, 5 or more than 5 sites.

In one embodiment, the AAV particles from any relevant species, such as, but not limited to, human, dog, mouse, rat or monkey may be introduced into cells.

In one embodiment, the AAV particles may be introduced into cells which are relevant to the disease to be treated. As a non-limiting example, the disease is ALS and the target cells are neurons and astrocytes. As another non-limiting example, the disease is ALS and the target cells are medium spiny neurons, cortical neurons and astrocytes.

In one embodiment, the AAV particles may be introduced into cells which have a high level of endogenous expression of the target sequence.

In another embodiment, the AAV particles may be introduced into cells which have a low level of endogenous expression of the target sequence.

In one embodiment, the cells may be those which have a high efficiency of AAV transduction.

Delivery to Subjects

The present disclosure additionally provides a method of delivering to a subject, including a mammalian subject, any of the above-described AAV polynucleotides or AAV genomes comprising administering to the subject said AAV polynucleotide or AAV genome, or administering to the subject a particle comprising said AAV polynucleotide or AAV genome, or administering to the subject any of the described compositions, including pharmaceutical compositions.

The pharmaceutical compositions of AAV particles described herein may be characterized by one or more of bioavailability, therapeutic window and/or volume of distribution.

III. Administration and Dosing

Administration

The AAV particles comprising a nucleic acid sequence encoding the siRNA molecules of the present invention may be administered by any route which results in a therapeutically effective outcome. These include, but are not limited to, within the parenchyma of an organ such as, but not limited to, a brain (e.g., intraparenchymal), corpus striatum (intrastriatal), enteral (into the intestine), gastroenteral, epidural, oral (by way of the mouth), transdermal, peridural, intracerebral (into the cerebrum), intracerebroventricular (into the cerebral ventricles), subpial (under the pia), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), intraganglionic (into the ganglion), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracomal, intracoronary (within the coronary arteries), intracorporus cavemosum (within the dilatable spaces of the corpus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration which is then covered by a dressing which occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis or spinal.

In specific embodiments, compositions of AAV particles comprising a nucleic acid sequence encoding the siRNA molecules of the present invention may be administered in a way which facilitates the vectors or siRNA molecule to enter the central nervous system and penetrate into medium spiny and/or cortical neurons and/or astrocytes.

In some embodiments, the AAV particles comprising a nucleic acid sequence encoding the siRNA molecules of the present invention may be administered by intramuscular injection.

In one embodiment, the AAV particles comprising a nucleic acid sequence encoding the siRNA molecules of the present invention may be administered via intraparenchymal injection.

In one embodiment, the AAV particles comprising a nucleic acid sequence encoding the siRNA molecules of the present invention may be administered via intraparenchymal injection and intrathecal injection.

In one embodiment, the AAV particles comprising a nucleic acid sequence encoding the siRNA molecules of the present invention may be administered via intrastriatal injection.

In one embodiment, the AAV particles comprising a nucleic acid sequence encoding the siRNA molecules of the present invention may be administered via intrastriatal injection and another route of administration described herein.

In some embodiments, AAV particles that express siRNA duplexes of the present invention may be administered to a subject by peripheral injections (e.g., intravenous) and/or intranasal delivery. It was disclosed in the art that the peripheral administration of AAV particles for siRNA duplexes can be transported to the central nervous system, for example, to the neurons (e.g., U.S. Patent Publication Nos. 20100240739; and 20100130594; the content of each of which is incorporated herein by reference in their entirety).

In other embodiments, compositions comprising at least one AAV particle comprising a nucleic acid sequence encoding the siRNA molecules of the present invention may be administered to a subject by intracranial delivery (See, e.g., U.S. Pat. No. 8,119,611; the content of which is incorporated herein by reference in its entirety).

The AAV particle comprising a nucleic acid sequence encoding the siRNA molecules of the present invention may be administered in any suitable form, either as a liquid solution or suspension, as a solid form suitable for liquid solution or suspension in a liquid solution. The siRNA duplexes may be formulated with any appropriate and pharmaceutically acceptable excipient.

The AAV particle comprising a nucleic acid sequence encoding the siRNA molecules of the present invention may be administered in a "therapeutically effective" amount, i.e., an amount that is sufficient to alleviate and/or prevent at least one symptom associated with the disease, or provide improvement in the condition of the subject.

In one embodiment, the AAV particle may be administered to the CNS in a therapeutically effective amount to improve function and/or survival for a subject with ALS. As a non-limiting example, the vector may be administered by direct infusion into the striatum.

In one embodiment, the AAV particle may be administered to a subject (e.g., to the CNS of a subject via intrathecal administration) in a therapeutically effective amount for the siRNA duplexes or dsRNA to target the medium spiny neurons, cortical neurons and/or astrocytes. As a non-limiting example, the siRNA duplexes or dsRNA may target SOD1 and reduce the expression of SOD1 protein or mRNA. As another non-limiting example, the siRNA duplexes or dsRNA target SOD1 and can suppress SOD1 and reduce SOD1 mediated toxicity. The reduction of SOD1 protein and/or mRNA as well as SOD1 mediated toxicity may be accomplished with almost no enhanced inflammation.

In one embodiment, the AAV particle may be administered to a subject (e.g., to the CNS of a subject) in a therapeutically effective amount to slow the functional decline of a subject (e.g., determined using a known evaluation method). As a non-limiting example, the vector may be administered via intraparenchymal injection.

In one embodiment, the AAV particle may be administered to the cisterna magna in a therapeutically effective amount to transduce medium spiny neurons, cortical neurons and/or astrocytes. As a non-limiting example, the vector may be administered intrathecally.

In one embodiment, the AAV particle may be administered using intrathecal infusion in a therapeutically effective amount to transduce medium spiny neurons, cortical neurons and/or astrocytes. As a non-limiting example, the vector may be administered intrathecally.

In one embodiment, the AAV particle may be administered to the cisterna magna in a therapeutically effective amount to transduce medium spiny neurons, cortical neurons and/or astrocytes. As a non-limiting example, the vector may be administered by intraparenchymal injection.

In one embodiment, the AAV particle comprising a modulatory polynucleotide may be formulated. As a non-limiting example the baricity and/or osmolality of the formulation may be optimized to ensure optimal drug distribution in the central nervous system or a region or component of the central nervous system.

In one embodiment, the AAV particle comprising a modulatory polynucleotide may be delivered to a subject via a single route administration.

In one embodiment, the AAV particle comprising a modulatory polynucleotide may be delivered to a subject via a multi-site route of administration. A subject may be administered the AAV particle comprising a modulatory polynucleotide at 2, 3, 4, 5 or more than 5 sites.

In one embodiment, a subject may be administered the AAV particle comprising a modulatory polynucleotide described herein using a bolus injection.

In some embodiments, the efficacy of administration of the AAV particle comprising a modulatory polynucleotide using a bolus injection may be measured by monitoring the gene transfer to the spinal cord, brain stem, or motor cortex. The biodistribution and cellular tropism may be monitored by any methods known in the art, such as, but not limited to, immunostaining, and the vector genome levels may be measured by digital PCR.

In one embodiment, a subject may be administered the AAV particle comprising a modulatory polynucleotide described herein using sustained delivery over a period of minutes, hours or days. The infusion rate may be changed depending on the subject, distribution, formulation or another delivery parameter.

In one embodiment, the AAV particle described herein is administered via putamen and caudate infusion. As a non-limiting example, the dual infusion provides a broad striatal distribution as well as a frontal and temporal cortical distribution.

In one embodiment, the AAV particle is AAV-DJ8 which is administered via unilateral putamen infusion. As a non-limiting example, the distribution of the administered AAV-DJ8 is similar to the distribution of AAV1 delivered via unilateral putamen infusion.

In one embodiment, the AAV particle described herein is administered via intrathecal (IT) infusion at C1. The infusion may be for 1, 2, 3, 4, 6, 7, 8, 9, 10, 11, 12, 13, 14, 15 or more than 15 hours.

In one embodiment, the selection of subjects for administration of the AAV particle described herein and/or the effectiveness of the dose, route of administration and/or volume of administration may be evaluated using imaging of the perivascular spaces (PVS) which are also known as Virchow-Robin spaces. PVS surround the arterioles and venules as they perforate brain parenchyma and are filled with cerebrospinal fluid (CSF)/interstitial fluid. PVS are common in the midbrain, basal ganglia, and centrum semiovale. While not wishing to be bound by theory, PVS may play a role in the normal clearance of metabolites and have been associated with worse cognition and several disease states including Parkinson's disease. PVS are usually are normal in size but they can increase in size in a number of disease states. Potter et al. (Cerebrovase Dis. 2015 January; 39(4): 224-231; the contents of which are herein incorporated by reference in its entirety) developed a grading method where they studied a full range of PVS and rated basal ganglia, centrum semiovale and midbrain PVS. They used the frequency and range of PVS used by Mac and Lullich et al. (J Neurol Neurosurg Psychiatry. 2004 November; 75(11): 1519-23; the contents of which are herein incorporated by reference in its entirety) and Potter et al. gave 5 ratings to basal ganglia and centrum semiovale PVS: 0 (none), 1 (1-10), 2 (11-20), 3 (21-40) and 4 (>40) and 2 ratings to midbrain PVS: 0 (non visible) or 1 (visible). The user guide for the rating system by Potter et al. can be found at: www.sbirc.ed.ac.uk/documents/epvs-rating-scale-user-guide.pdf.

Dosing

The pharmaceutical compositions of the present invention may be administered to a subject using any amount effective for reducing, preventing and/or treating a disease and/or disorder. The exact amount required will vary from subject to subject, depending on the species, age, and general condition of the subject, the severity of the disease, the particular composition, its mode of administration, its mode of activity, and the like.

The compositions of the present invention are typically formulated in unit dosage form for ease of administration and uniformity of dosage. It will be understood, however, that the total daily usage of the compositions of the present invention may be decided by the attending physician within the scope of sound medical judgment. The specific therapeutic effectiveness for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the siRNA duplexes employed; the duration of the treatment; drugs used in combination or coincidental with the specific compound employed; and like factors well known in the medical arts.

As a non-limiting example, the dose may be determined based on the total volume of CSF of a subject. For example cynomolgus monkeys have a total estimated cerebrospinal fluid (CSF) volume of approximately 6 to 12 mL and humans have a total estimated CSF of approximately 120 to 150 mL, a factor of at least 10 to 12-fold. Therefore, a factor of 10× to 12× may be used to determine a human dose based on the dose to a cynomolgus monkey. In one embodiment, the factor is 10×. In another embodiment the factor is 11×. In yet another embodiment, the factor is 12×. In yet another embodiment, the factor may be, but is not limited to, 10×, 10.1×, 10.2×, 10.3×, 10.4×, 10.5×, 10.6×, 10.7×, 10.8×, 10.9×, 11×, 11.1×, 11.2×, 11.3×, 11.4×, 11.5×, 11.6×, 11.7×, 11.8×, 11.9×, 12×, 12.1×, 12.2×, 12.3×, 12.4×, and 12.5×.

In one embodiment, the age and sex of a subject may be used to determine the dose of the compositions of the present invention. As a non-limiting example, a subject who is older may receive a larger dose (e.g., 5-10%, 10-20%, 15-30%, 20-50%, 25-50% or at least 1%, 2%, 3%, 4%, 5%, 10%, 20%, 30%, 40%, 50%, 60%, 70%, 80%, 90% or more than 90% more) of the composition as compared to a younger subject. As another non-limiting example, a subject who is younger may receive a larger dose (e.g., 5-10%, 10-20%, 15-30%, 20-50%, 25-50% or at least 1%, 2%, 3%, 4%, 5%, 10%, 20%, 30%, 40%, 50%, 60%, 70%, 80%, 90% or more than 90% more) of the composition as compared to an older subject. As yet another non-limiting example, a subject who is female may receive a larger dose (e.g., 5-10%, 10-20%, 15-30%, 20-50%, 25-50% or at least 1%, 2%, 3%, 4%, 5%, 10%, 20%, 30%, 40%, 50%, 60%, 70%, 80%, 90% or more than 90% more) of the composition as compared to a male subject. As yet another non-limiting example, a subject who is male may receive a larger dose (e.g., 5-10%, 10-20%, 15-30%, 20-50%, 25-50% or at least 1%, 2%, 3%, 4%, 5%, 10%, 20%, 30%, 40%, 50%, 60%, 70%, 80%, 90% or more than 90% more) of the composition as compared to a female subject In some specific embodiments, the doses of AAV particles for delivering siRNA duplexes of the present invention may be adapted depending on the disease condition, the subject and the treatment strategy.

In one embodiment, delivery of the compositions in accordance with the present invention to cells comprises a rate of delivery defined by [VG/hour=mL/hour*VG/mL] wherein VG is viral genomes, VG/mL is composition concentration, and mL/hour is rate of prolonged delivery.

In one embodiment, delivery of compositions in accordance with the present invention to cells may comprise a total concentration per subject between about $1 \times 10^6$ VG and about $1 \times 10^{16}$ VG. In some embodiments, delivery may comprise a composition concentration of about $1 \times 10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $1.1\times10^{11}$, $1.2\times10^{11}$, $1.3\times10^{11}$, $1.4\times10^{11}$, $1.5\times10^{11}$, $1.6\times10^{11}$, $1.7\times10^{11}$, $1.8\times10^{11}$, $1.9\times10^{11}$, $2\times10^{11}$, $2\times10^{11}$, $2.2\times10^{11}$, $2.3\times10^{11}$, $2.4\times10^{11}$, $2.5\times10^{11}$, $2.6\times10^{11}$, $2.7\times10^{11}$, $2.8\times10^{11}$, $2.9\times10^{11}$, $3\times10^{11}$, $4\times10^{11}$, $5\times10^{11}$, $6\times10^{11}$, $7\times10^{11}$, $7.1\times10^{11}$, $7.2\times10^{11}$, $7.3\times10^{11}$, $7.4\times10^{11}$, $7.5\times10^{11}$, $7.6\times10^{11}$, $7.7\times10^{11}$, $7.8\times10^{11}$, $7.9\times10^{11}$, $8\times10^{11}$, $9\times10^{11}$, $1\times10^{12}$, $1.1\times10^{12}$, $1.2\times10^{12}$, $1.3\times10^{12}$, $1.4\times10^{12}$, $1.5\times10^{12}$, $1.6\times10^{12}$, $1.7\times10^{12}$, $1.8\times10^{12}$, $1.9\times10^{12}$, $2\times10^{12}$, $2.1\times10^{12}$, $2.2\times10^{12}$, $2.3\times10^{12}$, $2.4\times10^{12}$, $2.5\times10^{12}$, $2.6\times10^{12}$, $2.7\times10^{12}$, $2.8\times10^{11}$, $2.9\times10^{12}$, $3\times10^{12}$, $3.1\times10^{12}$, $3.2\times10^{12}$, $3.3\times10^{12}$, $3.4\times10^{12}$, $3.5\times10^{12}$, $3.6\times10^{12}$, $3.7\times10^{12}$, $3.8\times10^{12}$, $3.9\times10^{12}$, $4\times10^{12}$, $4.1\times10^{12}$, $4.2\times10^{12}$, $4.3\times10^{12}$, $4.4\times10^{12}$, $4.5\times10^{12}$, $4.6\times10^{12}$, $4.7\times10^{12}$, $4.8\times10^{12}$, $4.9\times10^{12}$, $5\times10^{12}$, $6\times10^{12}$, $6.1\times10^{12}$, $6.2\times10^{12}$, $6.3\times10^{12}$, $6.4\times10^{12}$, $6.5\times10^{12}$, $6.6\times10^{12}$, $6.7\times10^{12}$, $6.8\times10^{12}$, $6.9\times10^{12}$, $7\times10^{12}$, $8\times10^{12}$, $8.1\times10^{12}$, $8.2\times10^{12}$, $8.3\times10^{12}$, $8.4\times10^{12}$, $8.5\times10^{12}$, $8.6\times10^{12}$, $8.7\times10^{12}$, $8.8\times10^{12}$, $8.9\times10^{12}$, $9\times10^{12}$, $1\times10^{13}$, $1.1\times10^{13}$, $1.2\times10^{13}$, $1.3\times10^{13}$, $1.4\times10^{13}$, $1.5\times10^{13}$, $1.6\times10^{14}$, $1.7\times10^{13}$, $1.8\times10^{13}$, $1.9\times10^{13}$, $2\times10^{13}$, $3\times10^{13}$, $4\times10^{13}$, $5\times10^{13}$, $6\times10^{13}$, $6.7\times10^{13}$, $7\times10^{13}$, $8\times10^{13}$, $9\times10^{13}$, $1\times10^{14}$, $2\times10^{14}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, $2\times10^{15}$, $3\times10^{15}$, $4\times10^{15}$, $5\times10^{15}$, $6\times10^{15}$, $7\times10^{15}$, $8\times10^{15}$, $9\times10^{15}$, or $1\times10^{16}$ VG/subject.

In one embodiment, delivery of compositions in accordance with the present invention to cells may comprise a total concentration per subject between about $1\times10^6$ VG/kg and about $1\times10^{16}$ VG/kg. In some embodiments, delivery may comprise a composition concentration of about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $1.1\times10^{11}$, $1.2\times10^{11}$, $1.3\times10^{11}$, $1.4\times10^{11}$, $1.5\times10^{11}$, $1.6\times10^{11}$, $1.7\times10^{11}$, $1.8\times10^{11}$, $1.9\times10^{11}$, $2\times10^{11}$ $2.1\times10^{11}$, $2.2\times10^{11}$, $2.3\times10^{11}$, $2.4\times10^{11}$, $2.5\times10^{11}$, $2.6\times10^{11}$, $2.7\times10^{11}$, $2.8\times10^{11}$, $2.9\times10^{11}$, $3\times10^{11}$, $4\times10^{11}$, $5\times10^{11}$, $6\times10^{11}$, $7\times10^{11}$, $7.1\times10^{11}$, $7.2\times10^{11}$, $7.3\times10^{11}$, $7.4\times10^{11}$, $7.5\times10^{11}$, $7.6\times10^{11}$, $7.7\times10^{11}$, $7.8\times10^{11}$, $7.9\times10^{11}$, $8\times10^{11}$, $9\times10^{11}$, $1\times10^{12}$, $1.1\times10^{12}$, $1.2\times10^{12}$, $1.3\times10^{12}$, $1.4\times10^{12}$, $1.5\times10^{12}$, $1.6\times10^{12}$, $1.7\times10^{12}$, $1.8\times10^{12}$, $1.9\times10^{12}$, $2\times10^{12}$, $2.1\times10^{12}$, $2.2\times10^{12}$, $2.3\times10^{12}$, $2.4\times10^{12}$, $2.5\times10^{12}$, $2.6\times10^{12}$, $2.7\times10^{12}$, $2.8\times10^{12}$, $2.9\times10^{12}$, $3\times10^{12}$, $3.1\times10^{12}$, $3.2\times10^{12}$, $3.3\times10^{12}$, $3.4\times10^{12}$, $3.5\times10^{12}$, $3.6\times10^{12}$, $3.7\times10^{12}$, $3.8\times10^{12}$, $3.9\times10^{12}$, $4\times10^{12}$, $4.1\times10^{12}$, $4.2\times10^{12}$, $4.3\times10^{12}$, $4.4\times10^{12}$, $4.5\times10^{12}$, $4.6\times10^{12}$, $4.7\times10^{12}$, $4.8\times10^{12}$, $4.9\times10^{12}$, $5\times10^{12}$, $6\times10^{12}$, $6.1\times10^{12}$, $6.2\times10^{12}$, $6.3\times10^{12}$, $6.4\times10^{12}$, $6.5\times10^{12}$, $6.6\times10^{12}$, $6.7\times10^{12}$, $6.8\times10^{12}$, $6.9\times10^{12}$, $7\times10^{12}$, $8\times10^{12}$, $8.1\times10^{12}$, $8.2\times10^{12}$, $8.3\times10^{12}$, $8.4\times10^{12}$, $8.5\times10^{12}$, $8.6\times10^{12}$, $8.7\times10^{12}$, $8.8\times10^{12}$, $8.9\times10^{12}$, $9\times10^{12}$, $1\times10^{13}$, $1.1\times10^{13}$, $1.2\times10^{13}$, $1.3\times10^{13}$, $1.4\times10^{13}$, $1.5\times10^{13}$, $1.6\times10^{13}$, $1.7\times10^{13}$, $1.8\times10^{13}$, $1.9\times10^{13}$, $2\times10^{13}$, $3\times10^{13}$, $4\times10^{13}$, $5\times10^{13}$, $6\times10^{13}$, $6.7\times10^{13}$, $7\times10^{13}$, $8\times10^{13}$, $9\times10^{13}$, $1\times10^{14}$, $2\times10^{14}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, $2\times10^{15}$, $3\times10^{15}$, $4\times10^{15}$, $5\times10^{15}$, $6\times10^{15}$, $7\times10^{15}$, $8\times10^{15}$, $9\times10^{15}$, or $1\times10^{16}$ VG/kg.

In one embodiment, about $10^5$ to $10^6$ viral genome (unit) may be administered per dose.

In one embodiment, delivery of the compositions in accordance with the present invention to cells may comprise a total concentration between about $1\times10^6$ VG/mL and about $1\times10^{16}$ VG/mL. In some embodiments, delivery may comprise a composition concentration of about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $1.1\times10^{11}$, $1.2\times10^{11}$, $1.3\times10^{11}$, $1.4\times10^{11}$, $1.5\times10^{11}$, $1.6\times10^{11}$, $1.7\times10^{11}$, $1.8\times10^{11}$, $1.9\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $1.1\times10^{12}$, $1.2\times10^{12}$, $1.3\times10^{12}$, $1.4\times10^{12}$, $1.5\times10^{12}$, $1.6\times10^{12}$, $1.7\times10^{12}$, $1.8\times10^{12}$, $1.9\times10^{12}$, $2\times10^{12}$, $2.1\times10^{12}$, $2.2\times10^{12}$, $2.3\times10^{12}$, $2.4\times10^{12}$, $2.5\times10^{12}$, $2.6\times10^{12}$, $2.7\times10^{12}$, $2.8\times10^{12}$, $2.9\times10^{12}$, $3\times10^{12}$, $3.1\times10^{12}$, $3.2\times10^{12}$, $3.3\times10^{12}$, $3.4\times10^{12}$, $3.5\times10^{12}$, $3.6\times10^{12}$, $3.7\times10^{12}$, $3.8\times10^{12}$, $3.9\times10^{12}$, $4\times10^{12}$, $4.1\times10^{12}$, $4.2\times10^{12}$, $4.3\times10^{12}$, $4.4\times10^{12}$, $4.5\times10^{12}$, $4.6\times10^{12}$, $4.7\times10^{12}$, $4.8\times10^{12}$, $4.9\times10^{12}$, $5\times10^{12}$, $6\times10^{12}$, $6.1\times10^{12}$, $6.2\times10^{12}$, $6.3\times10^{12}$, $6.4\times10^{12}$, $6.5\times10^{12}$, $6.6\times10^{12}$, $6.7\times10^{12}$, $6.8\times10^{12}$, $6.9\times10^{12}$, $7\times10^{12}$, $8\times10^{12}$, $9\times10^{12}$, $1\times10^{13}$, $1.1\times10^{13}$, $1.2\times10^{13}$, $1.3\times10^{13}$, $1.4\times10^{13}$, $1.5\times10^{13}$, $1.6\times10^{13}$, $1.7\times10^{13}$, $1.8\times10^{13}$, $1.9\times10^{13}$, $2\times10^{13}$, $3\times10^{13}$, $4\times10^{13}$, $5\times10^{13}$, $6\times10^{13}$, $6.7\times10^{13}$, $7\times10^{13}$, $8\times10^{13}$, $9\times10^{13}$, $1\times10^{14}$, $2\times10^{14}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, $2\times10^{15}$, $3\times10^{15}$, $4\times10^{15}$, $5\times10^{15}$, $6\times10^{15}$, $7\times10^{15}$, $8\times10^{15}$, $9\times10^{15}$, or $1\times10^{16}$ VG/mL.

In certain embodiments, the desired siRNA duplex dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. As used herein, a "split dose" is the division of single unit dose or total daily dose into two or more doses, e.g., two or more administrations of the single unit dose. As used herein, a "single unit dose" is a dose of any modulatory polynucleotide therapeutic administered in one dose/at one time/single route/single point of contact, i.e., single administration event. As used herein, a "total daily dose" is an amount given or prescribed in a 24 hour period. It may be administered as a single unit dose. In one embodiment, the AAV particles comprising the modulatory polynucleotides of the present invention are administered to a subject in split doses. They may be formulated in buffer only or in a formulation described herein.

In one embodiment, the dose, concentration and/or volume of the composition described herein may be adjusted depending on the contribution of the caudate or putamen to cortical and subcortical distribution after administration. The administration may be intracerebroventricular, intraputamenal, intrathalmic, intraparenchymal, subpial, and/or intrathecal administration.

In one embodiment, the dose, concentration and/or volume of the composition described herein may be adjusted depending on the cortical and neuraxial distribution following administration by intracerebroventricular, intraputamenal, intrathalmic, intraparenchymal, subpial, and/or intrathecal delivery.

IV. Methods and Uses of the Compositions of the Invention

Amyotrophic Lateral Sclerosis (ALS)
Amyotrophic Lateral Sclerosis (ALS)

Amyotrophic lateral sclerosis (ALS), an adult-onset neurodegenerative disorder, is a progressive and fatal disease characterized by the selective death of motor neurons in the motor cortex, brainstem and spinal cord. The incidence of ALS is about 1.9 per 100,000. Patients diagnosed with ALS develop a progressive muscle phenotype characterized by spasticity, hyperreflexia or hyporeflexia, fasciculations, muscle atrophy and paralysis. These motor impairments are caused by the denervation of muscles due to the loss of motor neurons. The major pathological features of ALS include degeneration of the corticospinal tracts and extensive loss of lower motor neurons (LMNs) or anterior horn cells (Ghatak et al., *J Neuropathol Exp Neurol.*, 1986, 45, 385-395), degeneration and loss of Betz cells and other pyramidal cells in the primary motor cortex (Udaka et al., *Acta Neuropathol*, 1986, 70, 289-295; Maekawa et al., *Brain*, 2004, 127, 1237-1251) and reactive gliosis in the motor cortex and spinal cord (Kawamata et al., *Am J Pathol.*, 1992, 140, 691-707; and Schiffer et al., *Neurol Sci.*, 1996, 139, 27-33). ALS is usually fatal within 3 to 5 years after the diagnosis due to respiratory defects and/or inflammation (Rowland L P and Shneibder N A, *N Engl. J. Med.*, 2001, 344, 1688-1700).

A cellular hallmark of ALS is the presence of proteinaceous, ubiquitinated, cytoplasmic inclusions in degenerating motor neurons and surrounding cells (e.g., astrocytes). Ubiquitinated inclusions (i.e., Lewy body-like inclusions or Skein-like inclusions) are the most common and specific type of inclusion in ALS and are found in LMNs of the spinal cord and brainstem, and in corticospinal upper motor neurons (UMNs) (Matsumoto et al., *J Neurol Sci.*, 1993, 115, 208-213; and Sasak and Maruyama, *Acta Neuropathol.*, 1994, 87, 578-585). A few proteins have been identified to be components of the inclusions, including ubiquitin, Cu/Zn superoxide dismutase 1 (SOD1), peripherin and Dorfin, Neurofilamentous inclusions are often found in hyaline conglomerate inclusions (HCIs) and axonal 'spheroids' in spinal cord motor neurons in ALS. Other types and less specific inclusions include Bunina bodies (cystatin C-containing inclusions) and Crescent shaped inclusions (SCIs) in upper layers of the cortex. Other neuropathological features seen in ALS include fragmentation of the Golgi apparatus, mitochondrial vacuolization and ultrastructural abnormalities of synaptic terminals (Fujita et al., *Acta Neuropathol.* 2002, 103, 243-247).

In addition, in frontotemporal dementia ALS (FTD-ALS) cortical atrophy (including the frontal and temporal lobes) is also observed, which may cause cognitive impairment in FTD-ALS patients.

ALS is a complex and multifactorial disease and multiple mechanisms hypothesized as responsible for ALS pathogenesis include, but are not limited to, dysfunction of protein degradation, glutamate excitotoxicity, mitochondrial dysfunction, apoptosis, oxidative stress, inflammation, protein misfolding and aggregation, aberrant RNA metabolism, and altered gene expression.

About 10%-15% of ALS cases have family history of the disease, and these patients are referred to as familial ALS (fALS) or inherited patients, commonly with a Mendelian dominant mode of inheritance and high penetrance. The remainder (approximately 85%-95%) is classified as sporadic ALS (sALS), as they are not associated with a documented family history, but instead are thought to be due to other risk factors including, but not limited to environmental factors, genetic polymorphisms, somatic mutations, and possibly gene-environmental interactions. In most cases, familial (or inherited) ALS is inherited as autosomal dominant disease, but pedigrees with autosomal recessive and X-linked inheritance and incomplete penetrance exist. Sporadic and familial forms are clinically indistinguishable suggesting a common pathogenesis. The precise cause of the selective death of motor neurons in ALS remains elusive. Progress in understanding the genetic factors in fALS may shed light on both forms of the disease.

Recently, an exploration into genetic causes of ALS has discovered mutations in more than 10 different genes that are known to cause fALS. The most common ones are found in the genes encoding Cu/Zn superoxide dismutase 1 (SOD1; ~20%) (Rosen D R et al., Nature, 1993, 362, 59-62), fused in sarcoma/translated in liposarcoma (FUS/TLS; 1-5%) and TDP-43 (TARDBP; 1-5%). Recently, a hexanucleotide repeat expansion (GGGGCC)n in the C9orF72 gene was identified as the most frequent cause of fALS (~40%) in the Western population (reviewed by Renton et al., Nat. Neurosci., 2014, 17, 17-23). Other genes mutated in ALS include alsin (ALS2), senataxin (SETX), vesicle-associated membrane protein (VAPB), and angiogenin (ANG), fALS genes control different cellular mechanisms, suggesting that the pathogenesis of ALS is complicated and may be related to several different processes finally leading to motor neuron degeneration.

Subjects with ALS and an identified mutation in a known ALS-causative gene may be referred to as having "genetically defined ALS." Non-limiting examples of ALS-causative genes include SOD1, C9orf72, TARDBP (also termed TDP-43), FUS/TLS, OPTN, UBQLN2, PFN1, DCTN1, and TBK1.

SOD1 is one of the three human superoxide dismutases identified and characterized in mammals: copper-zinc superoxide dismutase (Cu/ZnSOD or SOD1), manganese superoxide dismutase (MnSOD or SOD2), and extracellular superoxide dismutase (ECSOD or SOD3). SOD1 is a 32 kDa homodimer of a 153-residue polypeptide with one copper- and one zinc-binding site per subunit, which is encoded by the SOD1 gene (GeneBank access No.: NM_000454.4; SEQ ID NO: 1254) on human chromosome 21. SOD1 catalyzes the reaction of superoxide anion ($O^{2-}$) into molecular oxygen ($O_2$) and hydrogen peroxide ($H_2O_2$) at a bound copper ion. The intracellular concentration of SOD1 is high (ranging from 10 to 100 µM), accounting for 1% of the total protein content in the central nervous system (CNS). The protein is localized not only in the cytoplasm but also in the nucleus, lysosomes, peroxisomes, and mitochondrial intermembrane spaces in eukaryotic cells (Lindenau J et al., *Glia*, 2000, 29, 25-34).

Mutations in the SOD1 gene are carried by 15-20% of fALS patients and by 1-2% of all ALS cases. Currently, at least 170 different mutations distributed throughout the 153-amino acid SOD1 polypeptide have been found to cause ALS, and an updated list can be found at the ALS online Genetic Database (ALSOD) (Wroe R et al., *Amyotroph Lateral Scler.*, 2008, 9, 249-250). Table 21 lists some examples of mutations in SOD1 in ALS. These mutations are predominantly single amino acid substitutions (i.e. missense mutations) although deletions, insertions, and C-terminal truncations also occur. Different SOD1 mutations display different geographic distribution patterns. For instance, 40-50% of all Americans with ALS caused by SOD1 gene mutations have a particular mutation Ala4Val (or A4V). The A4V mutation is typically associated with more severe signs and symptoms and the survival period is typically 2-3 years. The I113T mutation is by far the most common mutation in the United Kingdom. The most prevalent mutation in Europe is D90A substitute and the survival period is usually greater than 10 years.

TABLE 21

Examples of SOD1 mutations in ALS

| Location | Mutations |
| --- | --- |
| Exon1 (220 bp) | Q22L; E2IK, G; F20C; N19S; G16A, S; V14M, S; G12R; G10G, V, R; L8Q, V; V7E; C6G, F; V5L; A4T, V, S |
| Exon2 (97 bp) | T54R; E49K; H48R, Q; V47F, A; H46R; F45C; H43R; G41S, D; G37R; V29, insA |
| Exon3 (70 bp) | D76Y, V, G72S, C; L67R, P66A; N65S; S59I, S |
| Exon4 (118 bp) | D124G, V; V118L, InsAAAAC; L117V; T116T; R115G; G114A; I113T, F; I112M, T; G108V; L106V, F; S106L, delTCACTC; I104F; D101G, Y, H, N, E100G, K; I99V, V97L, M; D96N, V, A95T, V; G93S, V, A, C, R, D; D90V, A; A89T, V; T88delACTGCTGAC, V87A, M; N861, S, D, K, G85R, S; L84V, F; H80R |
| Exon5 (461 bp) | I151T, S; I149T; V148I, G; G147D, R; C146R, stop; A145T, G; L144F, S; G141E, stop; A140A, G; N139D, K, H, N; G138E; T137R; S134N; E133V, delGAA, insTT; E132insTT; G127R, InsTGGG; L126S, delITT, stop; D126, delTT |

To investigate the mechanism of neuronal death associated with SOD1 gene defects, several rodent models of SOD1-linked ALS were developed in the art, which express the human SOD1 gene with different mutations, including missense mutations, small deletions or insertions. Non-limiting examples of ALS mouse models include $SOD1^{G93A}$, $SOD1^{A4V}$, $SOD1^{G37R}$, $SOD1^{G85R}$, $SOD1^{D90A}$, $SOD1^{L84V}$, $SOD1^{I113T}$, $SOD1^{H36R/H48Q}$, $SOD1^{G127X}$, $SOD1^{L126X}$ and $SOD1^{L126delTT}$. There are two transgenic rat models carrying two different human SOD1 mutations: $SOD1^{H46R}$ and $SOD1^{G93R}$. These rodent ALS models can develop muscle weakness similar to human ALS patients and other pathogenic features that reflect several characteristics of the human disease, in particular, the selective death of spinal motor neurons, aggregation of protein inclusions in motor neurons and microglial activation. It is well known in the art that the transgenic rodents are good models of human SOD1-associated ALS disease and provide models for studying disease pathogenesis and developing disease treatment.

Studies in animal and cellular models showed that SOD1 pathogenic variants cause ALS by gain of function. That is to say, the superoxide dismutase enzyme gains new but harmful properties when altered by SOD1 mutations. For example, some SOD1 mutated variants in ALS increase oxidative stress (e.g., increased accumulation of toxic superoxide radicals) by disrupting the redox cycle. Other studies also indicate that some SOD1 mutated variants in ALS might acquire toxic properties that are independent of its normal physiological function (such as abnormal aggregation of misfolded SOD1 variants. In the aberrant redox chemistry model, mutant SOD1 is unstable and through aberrant chemistry interacts with nonconventional substrates causing overproduction of reactive oxygen species (ROS). In the protein toxicity model, unstable, misfolded SOD1 aggregates into cytoplasmic inclusion bodies, sequestering proteins crucial for cellular processes. These two hypotheses are not mutually exclusive. It has been shown that oxidation of selected histidine residues that bind metals in the active site mediates SOD1 aggregation.

The aggregated mutant SOD1 protein may also induce mitochondrial dysfunction (Vehvilainen P et al., Front Cell Neurosci., 2014, 8, 126), impairment of axonal transport, aberrant RNA metabolism, glial cell pathology and glutamate excitotoxicity. In some sporadic ALS cases, misfolded wild-type SOD1 protein is found in diseased motor neurons which forms a "toxic conformation" that is similar to that which is seen with familial ALS-linked SOD1 variants (Rotunno M S and Bosco D A, Front Cell Neurosci., 2013, 16, 7, 253). Such evidence suggests that ALS is a protein folding diseases analogous to other neurodegenerative diseases such as Alzheimer's disease and Parkinson's disease.

Currently, no curative treatments are available for patients suffering from ALS. The only FDA approved drug Riluzole, an inhibitor of glutamate release, has a moderate effect on ALS, only extending survival by 2-3 months if it is taken for 18 months. Unfortunately, patients taking riluzole do not experience any slowing in disease progression or improvement in muscle function. Therefore, riluzole does not present a cure, or even an effective treatment. Researchers continue to search for better therapeutic agents.

Therapeutic approaches that may prevent or ameliorate SOD1 aggregation have been tested previously. For example, arimoclomol, a hydroxylamine derivative, is a drug that targets heat shock proteins, which are cellular defense mechanisms against these aggregates. Studies demonstrated that treatment with arimoclomol improved muscle function in SOD1 mouse models. Other drugs that target one or more cellular defects in ALS may include AMPA antagonists such as talampanel, beta-lactam antibiotics, which may reduce glutamate-induced excitotoxicity to motor neurons: Bromocriptine that may inhibit oxidative induced motor neuron death (e.g. U.S. Patent publication No. 20110105517; the content of which is incorporated herein by reference in its entirety); 1,3-diphenylurea derivative or multikinase inhibitor which may reduce SOD1 gene expression (e.g., U.S. Patent Publication No. 20130225642; the content of which is incorporated herein by reference in its entirety); dopamine agonist pramipexole and its anantiomer dexpramipexole, which may ameliorate the oxidative response in mitochondria; nimesulide, which inhibits cyclooxygenase enzyme (e.g., U.S. Patent Publication No. 20060041022; the content of which is incorporated herein by reference in its entirety); drugs that act as free radical scavengers (e.g. U.S. Pat. No. 6,933,310 and PCT Patent Publication No.: WO2006075434; the content of each of which is incorporated herein by reference in their entirety).

Another approach to inhibit abnormal SOD1 protein aggregation is to silence/inhibit SOD1 gene expression in ALS. It has been reported that small interfering RNAs for specific gene silencing of the mutated allele are therapeutically beneficial for the treatment of fALS (e.g., Ralgh G S et al., Nat. Medicine, 2005, 11(4), 429-433; and Raoul C et al., Nat. Medicine, 2005, 11(4), 423-428; and Maxwell M M et al., PNAS, 2004, 101(9), 3178-3183; and Ding H et al., Chinese Medical J., 2011, 124(1), 106-110; and Scharz D S et al., Plos Genet., 2006, 2(9), e140; the content of each of which is incorporated herein by reference in their entirety).

Many other RNA therapeutic agents that target the SOD1 gene and modulate SOD1 expression in ALS are taught in the art. Such RNA based agents include antisense oligonucleotides and double stranded small interfering RNAs. See, e.g., Wang H et al., J Biol. Chem., 2008, 283(23), 15845-15852); U.S. Pat. Nos. 7,498,316; 7,632,938; 7,678,895; 7,951,784; 7,977,314; 8,183,219; 8,309,533 and 8,586,554; and U.S. Patent publication Nos. 2006/0229268 and 2011/0263680; the content of each of which is herein incorporated by reference in their entirety.

The present invention provides AAV particles comprising modulatory polynucleotides comprising sequences encoding siRNA molecules targeting the SOD1 gene and methods for their design and manufacture. The AAV particles comprising the nucleic acid sequence encoding the siRNA molecules of the present invention may increase the delivery of active agents into motor neurons. The siRNA duplexes or encoding dsRNA targeting the SOD1 gene may be able to inhibit SOD1 gene expression (e.g., mRNA level) significantly inside cells; therefore, ameliorating SOD1 expression induced stress inside the cells such as aggregation of protein and formation of inclusions, increased free radicals, mitochondrial dysfunction and RNA metabolism.

Such siRNA mediated SOD1 expression inhibition may be used for treating ALS. According to the present invention, methods for treating and/or ameliorating ALS in a patient comprises administering to the patient an effective amount of AAV particle comprising a nucleic acid sequence encoding the siRNA molecules of the present invention into cells. The administration of the AAV particle comprising such a nucleic acid sequence will encode the siRNA molecules which cause the inhibition/silence of SOD1 gene expression.

In one embodiment, the AAV particle comprising the modulatory polynucleotide, reduce the expression of mutant SOD1 in a subject. The reduction of mutant SOD1 can also reduce the formation of toxic aggregates which can cause mechanisms of toxicity such as, but not limited to, oxidative stress, mitochondrial dysfunction, impaired axonal transport, aberrant RNA metabolism, glial cell pathology and/or glutamate excitotoxicity.

In one embodiment, the vector, e.g., AAV particles, reduces the amount of SOD1 in a subject in need thereof and thus provides a therapeutic benefit as described herein.

Method of Treatment of ALS

Provided in the present invention are methods for introducing the AAV particles comprising modulatory polynucleotides comprising sequences comprising a nucleic acid sequence encoding the siRNA molecules of the present invention into cells, the method comprising introducing into said cells any of the vectors in an amount sufficient for degradation of target SOD1 mRNA to occur, thereby activating target-specific RNAi in the cells. In some aspects, the cells may be stem cells, neurons such as motor neurons, muscle cells and glial cells such as astrocytes.

Disclosed in the present invention are methods for treating ALS associated with abnormal SOD1 function in a subject in need of treatment. The method optionally comprises administering to the subject a therapeutically effective amount of a composition comprising at least AAV particles comprising modulatory polynucleotides comprising a nucleic acid sequence encoding the siRNA molecules of the present invention. As a non-limiting example, the siRNA molecules can silence SOD1 gene expression, inhibit SOD1 protein production, and reduce one or more symptoms of ALS in the subject such that ALS is therapeutically treated.

In some embodiments, the composition comprising the AAV particles comprising modulatory polynucleotides comprising a nucleic acid sequence encoding the siRNA molecules of the present invention is administered to the central nervous system of the subject. In other embodiments, the composition comprising the AAV particles comprising modulatory polynucleotides comprising a nucleic acid sequence encoding the siRNA molecules of the present invention is administered to the muscles of the subject In particular, the AAV particles comprising modulatory polynucleotides comprising a nucleic acid sequence encoding the siRNA molecules of the present invention may be delivered into specific types of targeted cells, including motor neurons; glial cells including oligodendrocyte, astrocyte and microglia; and/or other cells surrounding neurons such as T cells. Studies in human ALS patients and animal SOD1 ALS models implicate glial cells as playing an early role in the dysfunction and death of motor neurons. Normal SOD1 in the surrounding, protective glial cells can prevent the motor neurons from dying even though mutant SOD1 is present in motor neurons (e.g., reviewed by Philips and Rothstein, *Exp. Neurol.*, 2014, May 22. pii: S0014-4886(14) 00157-5; the content of which is incorporated herein by reference in its entirety).

In some specific embodiments, the AAV particles comprising modulatory polynucleotides comprising a nucleic acid sequence encoding the siRNA molecules of the present invention may be used as a therapy for ALS.

In some embodiments, the present composition is administered as a solo therapeutics or combination therapeutics for the treatment of ALS.

The AAV particles comprising modulatory polynucleotides comprising a nucleic acid sequence encoding the siRNA molecules targeting the SOD1 gene may be used in combination with one or more other therapeutic agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent.

Therapeutic agents that may be used in combination with the AAV particles comprising modulatory polynucleotides comprising a nucleic acid sequence encoding the siRNA molecules of the present invention can be small molecule compounds which are antioxidants, anti-inflammatory agents, anti-apoptosis agents, calcium regulators, antiglutamatergic agents, structural protein inhibitors, and compounds involved in metal ion regulation.

Compounds tested for treating ALS which may be used in combination with the vectors described herein include, but are not limited to, antiglutamatergic agents: Riluzole, Topiramate, Talampanel, Lamotrigine, Dextromethorphan, Gabapentin and AMPA antagonist; Anti-apoptosis agents: Minocycline, Sodium phenylbutyrate and Arimoclomol; Anti-inflammatory agent: ganglioside, Celecoxib, Cyclosporine, Azathioprine, Cyclophosphamide, Plasmaphoresis, Glatiramer acetate and thalidomide; Ceftriaxone (Berry et al., *Plos One*, 2013, 8(4)); Beat-lactam antibiotics; Pramipexole (a dopamine agonist) (Wang et al., *Amyotrophic Lateral Scler.*, 2008, 9(1), 50-58); Nimesulide in U.S. Patent Publication No. 20060074991; Diazoxide disclosed in U.S. Patent Publication No. 20130143873); pyrazolone derivatives disclosed in US Patent Publication No. 20080161378; free radical scavengers that inhibit oxidative stress-induced cell death, such as bromocriptine (US. Patent Publication No. 20110105517); phenyl carbamate compounds discussed in PCT Patent Publication No. 2013100571; neuroprotective compounds disclosed in U.S. Pat. Nos. 6,933,310 and 8,399,514 and US Patent Publication Nos. 20110237907 and 20140038927; and glycopeptides taught in U.S. Patent Publication No. 20070185012; the content of each of which is incorporated herein by reference in their entirety.

Therapeutic agents that may be used in combination therapy with the AAV particles comprising modulatory polynucleotides comprising a nucleic acid sequence encoding the siRNA molecules of the present invention may be hormones or variants that can protect neuronal loss, such as adrenocorticotropic hormone (ACTH) or fragments thereof (e.g., U.S. Patent Publication No. 20130259875); Estrogen (e.g., U.S. Pat. Nos. 6,334,998 and 6,592,845); the content of each of which is incorporated herein by reference in their entirety.

Neurotrophic factors may be used in combination therapy with the AAV particles comprising modulatory polynucleotides comprising a nucleic acid sequence encoding the siRNA molecules of the present invention for treating ALS. Generally, a neurotrophic factor is defined as a substance that promotes survival, growth, differentiation, proliferation and/or maturation of a neuron, or stimulates increased activity of a neuron. In some embodiments, the present methods further comprise delivery of one or more trophic factors into the subject in need of treatment. Trophic factors may include, but are not limited to, IGF-I, GDNF, BDNF, CTNF, VEGF, Colivelin, Xaliproden, Thyrotrophin-releasing hormone and ADNF, and variants thereof.

In one aspect, the vector, e.g., AAV particle, encoding the nucleic acid sequence for the at least one siRNA duplex targeting the SOD1 gene may be co-administered with AAV particles expressing neurotrophic factors such as AAV-IGF-I (Vincent et al., *Neuromolecular medicine*, 2004, 6, 79-85; the content of which is incorporated herein by reference in its entirety) and AAV-GDNF (Wang et al., *J Neurosci.*, 2002, 22, 6920-6928; the content of which is incorporated herein by reference in its entirety).

In some embodiments, the composition of the present invention for treating ALS is administered to the subject in need intravenously, intramuscularly, subcutaneously, intraperitoneally, intrathecally and/or intraventricularly, allowing the siRNA molecules or vectors comprising the siRNA molecules to pass through one or both the blood-brain barrier and the blood spinal cord barrier. In some aspects, the method includes administering (e.g., intraventricularly administering and/or intrathecally administering) directly to the central nervous system (CNS) of a subject (using, e.g., an infusion pump and/or a delivery scaffold) a therapeutically effective amount of a composition comprising AAV particles comprising modulatory polynucleotides comprising a nucleic acid sequence encoding the siRNA molecules of the present invention. The vectors may be used to silence or suppress SOD1 gene expression, and/or reducing one or more symptoms of ALS in the subject such that ALS is therapeutically treated.

In certain aspects, the symptoms of ALS include, but are not limited to, motor neuron degeneration, muscle weakness, muscle atrophy, the stiffness of muscle, difficulty in breathing, slurred speech, fasciculation development, frontotemporal dementia and/or premature death are improved in the subject treated. In other aspects, the composition of the present invention is applied to one or both of the brain and the spinal cord. In other aspects, one or both of muscle coordination and muscle function are improved. In other aspects, the survival of the subject is prolonged.

In one embodiment, administration of the AAV particles comprising modulatory polynucleotides comprising a nucleic acid sequence encoding the siRNA molecules of the present invention, to a subject may lower mutant SOD1 in the CNS of a subject. In another embodiment, administration of the AAV particles, to a subject may lower wild-type SOD1 in the CNS of a subject. In yet another embodiment, administration of the AAV particles, to a subject may lower both mutant SOD1 and wild-type SOD1 in the CNS of a subject. The mutant and/or wild-type SOD1 may be lowered by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in the CNS, a region of the CNS, or a specific cell of the CNS of a subject. As a non-limiting example, the AAV particles may lower the expression of wild-type SOD1 by at least 50% in the motor neurons (e.g., ventral horn motor neurons) and/or astrocytes. As another non-limiting example, the AAV particles may lower the expression of mutant SOD1 by at least 50% in the motor neurons (e.g., ventral horn motor neurons) and/or astrocytes. As yet another non-limiting example, the AAV particles may lower the expression of wild-type SOD1 and mutant SOD1 by at least 50% in the motor neurons (e.g., ventral horn motor neurons) and/or astrocytes.

In one embodiment, administration of the AAV particles, to a subject will reduce the expression of mutant and/or wild-type SOD1 in the spinal cord and the reduction of expression of the mutant and/or wild-type SOD1 will reduce the effects of ALS in a subject.

In one embodiment, the AAV particles may be administered to a subject who is in the early stages of ALS. Early stage symptoms include, but are not limited to, muscles which are weak and soft or stiff, tight and spastic, cramping and twitching (fasciculations) of muscles, loss of muscle bulk (atrophy), fatigue, poor balance, slurred words, weak grip, and/or tripping when walking. The symptoms may be limited to a single body region or a mild symptom may affect more than one region. As a non-limiting example, administration of the AAV particles may reduce the severity and/or occurrence of the symptoms of ALS.

In one embodiment, the AAV particles may be administered to a subject who is in the middle stages of ALS. The middle stage of ALS includes, but is not limited to, more widespread muscle symptoms as compared to the early stage, some muscles are paralyzed while others are weakened or unaffected, continued muscle twitchings (fasciculations), unused muscles may cause contractures where the joints become rigid, painful and sometimes deformed, weakness in swallowing muscles may cause choking and greater difficulty eating and managing saliva, weakness in breathing muscles can cause respiratory insufficiency which can be prominent when lying down, and/or a subject may have bouts of uncontrolled and inappropriate laughing or crying (pseudobulbar affect). As a non-limiting example, administration of the AAV particles may reduce the severity and/or occurrence of the symptoms of ALS.

In one embodiment, the AAV particles may be administered to a subject who is in the late stages of ALS. The late stage of ALS includes, but is not limited to, voluntary muscles which are mostly paralyzed, the muscles that help move air in and out of the lungs are severely compromised, mobility is extremely limited, poor respiration may cause fatigue, fuzzy thinking, headaches and susceptibility to infection or diseases (e.g., pneumonia), speech is difficult and eating or drinking by mouth may not be possible.

In one embodiment, the AAV particles may be used to treat a subject with ALS who has a C9orf72 mutation.

In one embodiment, the AAV particles may be used to treat a subject with ALS who has TDP-43 mutations.

In one embodiment, the AAV particles may be used to treat a subject with ALS who has FUS mutations.

In one embodiment, the AAV particle of the present invention comprises an AAVrh10 capsid and a self-complementary AAV viral genome comprising an H1 promoter, a stuffer sequence originating from a pLKO.1 lentiviral vector and a SOD1 targeting payload.

In one embodiment, the AAV particle of the present invention comprises an AAV2 capsid and a self-complementary AAV viral genome.

In one embodiment, the AAV particle of the present invention comprises an AAV2 capsid and a self-complementary AAV viral genome comprising an H1 promoter, a stuffer sequence originating from a pLKO.1 lentiviral vector and a SOD1 targeting payload.

V. Definitions

Unless stated otherwise, the following terms and phrases have the meanings described below. The definitions are not meant to be limiting in nature and serve to provide a clearer understanding of certain aspects of the present invention.

As used herein, the term "nucleic acid", "polynucleotide" and 'oligonucleotide" refer to any nucleic acid polymers composed of either polydeoxyribonucleotides (containing 2-deoxy-D-ribose), or polyribonucleotides (containing D-ribose), or any other type of polynucleotide which is an N glycoside of a purine or pyrimidine base, or modified purine or pyrimidine bases. There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single stranded RNA.

As used herein, the term "RNA" or "RNA molecule" or "ribonucleic acid molecule" refers to a polymer of ribonucleotides; the term "DNA" or "DNA molecule" or "deoxyribonucleic acid molecule" refers to a polymer of deoxyribonucleotides. DNA and RNA can be synthesized naturally, e.g., by DNA replication and transcription of DNA, respectively; or be chemically synthesized. DNA and RNA can be single-stranded (i.e., ssRNA or ssDNA, respectively) or multi-stranded (e.g., double stranded, i.e., dsRNA and dsDNA, respectively). The term "mRNA" or "messenger RNA", as used herein, refers to a single stranded RNA that encodes the amino acid sequence of one or more polypeptide chains.

As used herein, the term "RNA interfering" or "RNAi" refers to a sequence specific regulatory mechanism mediated by RNA molecules which results in the inhibition or interfering or "silencing" of the expression of a corresponding protein-coding gene. RNAi has been observed in many types of organisms, including plants, animals and fungi. RNAi occurs in cells naturally to remove foreign RNAs (e.g., viral RNAs). Natural RNAi proceeds via fragments cleaved from free dsRNA which direct the degradative mechanism to other similar RNA sequences. RNAi is controlled by the RNA-induced silencing complex (RISC) and is initiated by short/small dsRNA molecules in cell cytoplasm, where they interact with the catalytic RISC component argonaute. The dsRNA molecules can be introduced into cells exogenously. Exogenous dsRNA initiates RNAi by activating the ribonuclease protein Dicer, which binds and cleaves dsRNAs to produce double-stranded fragments of 21-25 base pairs with a few unpaired overhang bases on each end. These short double stranded fragments are called small interfering RNAs (siRNAs).

As used herein, the terms "short interfering RNA," "small interfering RNA" or "siRNA" refer to an RNA molecule (or RNA analog) comprising between about 5-60 nucleotides (or nucleotide analogs) which is capable of directing or mediating RNAi. Preferably, a siRNA molecule comprises between about 15-30 nucleotides or nucleotide analogs, such as between about 16-25 nucleotides (or nucleotide analogs), between about 18-23 nucleotides (or nucleotide analogs), between about 19-22 nucleotides (or nucleotide analogs) (e.g., 19, 20, 21 or 22 nucleotides or nucleotide analogs), between about 19-25 nucleotides (or nucleotide analogs), and between about 19-24 nucleotides (or nucleotide analogs). The term "short" siRNA refers to a siRNA comprising 5-23 nucleotides, preferably 21 nucleotides (or nucleotide analogs), for example, 19, 20, 21 or 22 nucleotides. The term "long" siRNA refers to a siRNA comprising 24-60 nucleotides, preferably about 24-25 nucleotides, for example, 23, 24, 25 or 26 nucleotides. Short siRNAs may, in some instances, include fewer than 19 nucleotides, e.g., 16, 17 or 18 nucleotides, or as few as 5 nucleotides, provided that the shorter siRNA retains the ability to mediate RNAi. Likewise, long siRNAs may, in some instances, include more than 26 nucleotides, e.g., 27, 28, 29, 30, 35, 40, 45, 50, 55, or even 60 nucleotides, provided that the longer siRNA retains the ability to mediate RNAi or translational repression absent further processing, e.g., enzymatic processing, to a short siRNA. siRNAs can be single stranded RNA molecules (ss-siRNAs) or double stranded RNA molecules (ds-siRNAs) comprising a sense strand and an antisense strand which hybridized to form a duplex structure called siRNA duplex.

As used herein, the term "the antisense strand" or "the first strand" or "the guide strand" of a siRNA molecule refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process.

As used herein, the term "the sense strand" or "the second strand" or "the passenger strand" of a siRNA molecule refers to a strand that is complementary to the antisense strand or first strand. The antisense and sense strands of a siRNA molecule are hybridized to form a duplex structure. As used herein, a "siRNA duplex" includes a siRNA strand having sufficient complementarity to a section of about 10-50 nucleotides of the mRNA of the gene targeted for silencing and a siRNA strand having sufficient complementarity to form a duplex with the other siRNA strand.

As used herein, the term "complementary" refers to the ability of polynucleotides to form base pairs with one another. Base pairs are typically formed by hydrogen bonds between nucleotide units in antiparallel polynucleotide strands. Complementary polynucleotide strands can form base pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U is denoted in the context of the present invention, the ability to substitute a T is implied, unless otherwise stated. Perfect complementarity or 100% complementarity refers to the situation in which each nucleotide unit of one polynucleotide strand can form hydrogen bond with a nucleotide unit of a second polynucleotide strand. Less than perfect complementarity refers to the situation in which some, but not all, nucleotide units of two strands can form hydrogen bond with each other. For example, for two 20-mers, if only two base pairs on each strand can form hydrogen bond with each other, the polynucleotide strands exhibit 10% complementarity. In the same example, if 18 base pairs on each strand can form hydrogen bonds with each other, the polynucleotide strands exhibit 90% complementarity.

As used herein, the term "substantially complementary" means that the siRNA has a sequence (e.g., in the antisense strand) which is sufficient to bind the desired target mRNA, and to trigger the RNA silencing of the target mRNA.

As used herein, "targeting" means the process of design and selection of nucleic acid sequence that will hybridize to a target nucleic acid and induce a desired effect.

The term "gene expression" refers to the process by which a nucleic acid sequence undergoes successful transcription and in most instances translation to produce a protein or peptide. For clarity, when reference is made to measurement of "gene expression", this should be understood to mean that measurements may be of the nucleic acid product of transcription, e.g., RNA or mRNA or of the amino acid product of translation, e.g., polypeptides or peptides. Methods of measuring the amount or levels of RNA. mRNA, polypeptides and peptides are well known in the art.

As used herein, the term "mutation" refers to any changing of the structure of a gene, resulting in a variant (also called "mutant") form that may be transmitted to subsequent generations. Mutations in a gene may be caused by the alternation of single base in DNA, or the deletion, insertion, or rearrangement of larger sections of genes or chromosomes.

As used herein, the term "vector" means any molecule or moiety which transports, transduces or otherwise acts as a carrier of a heterologous molecule such as the siRNA molecule of the invention. A "viral genome" or "vector genome" or "viral vector" refers to a sequence which comprises one or more polynucleotide regions encoding or comprising a molecule of interest, e.g., a transgene, a polynucleotide encoding a polypeptide or multi-polypeptide or a modulatory nucleic acid such as small interfering RNA (siRNA). Viral genomes are commonly used to deliver genetic materials into cells. Viral genomes are often modified for specific applications. Types of viral genome sequence include retroviral viral genome sequences, lentiviral viral genome sequences, adenoviral viral genome sequences and adeno-associated viral genome sequences.

The term "adeno-associated virus" or "AAV" as used herein refers to any vector which comprises or derives from components of an adeno-associated vector and is suitable to infect mammalian cells, preferably human cells. The term AAV vector typically designates an AAV type viral particle or virion comprising a payload. The AAV vector may be derived from various serotypes, including combinations of serotypes (i.e., "pseudotyped" AAV) or from various genomes (e.g., single stranded or self-complementary). In addition, the AAV vector may be replication defective and/or targeted.

As used herein, the phrase "inhibit expression of a gene" means to cause a reduction in the amount of an expression product of the gene. The expression product can be a RNA molecule transcribed from the gene (e.g., an mRNA) or a polypeptide translated from an mRNA transcribed from the gene. Typically a reduction in the level of an mRNA results in a reduction in the level of a polypeptide translated therefrom. The level of expression may be determined using standard techniques for measuring mRNA or protein.

As used herein, the term "in vitro" refers to events that occur in an artificial environment, e.g., in a test tube or reaction vessel, in cell culture, in a Petri dish, etc., rather than within an organism (e.g., animal, plant, or microbe).

As used herein, the term "in vivo" refers to events that occur within an organism (e.g., animal, plant, or microbe or cell or tissue thereof).

As used herein, the term "modified" refers to a changed state or structure of a molecule of the invention. Molecules may be modified in many ways including chemically, structurally, and functionally.

As used herein, the term "synthetic" means produced, prepared, and/or manufactured by the hand of man. Synthesis of polynucleotides or polypeptides or other molecules of the present invention may be chemical or enzymatic.

As used herein, the term "transfection" refers to methods to introduce exogenous nucleic acids into a cell. Methods of transfection include, but are not limited to, chemical methods, physical treatments and cationic lipids or mixtures. The list of agents that can be transfected into a cell is large and includes, but is not limited to, siRNA, sense and/or antisense sequences, DNA encoding one or more genes and organized into an expression plasmid, proteins, protein fragments, and more.

As used herein, "off target" refers to any unintended effect on any one or more target, gene, or cellular transcript.

As used herein, the phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "effective amount" of an agent is that amount sufficient to effect beneficial or desired results, for example, clinical results, and, as such, an "effective amount" depends upon the context in which it is being applied. For example, in the context of administering an agent that treats ALS, an effective amount of an agent is, for example, an amount sufficient to achieve treatment, as defined herein, of ALS, as compared to the response obtained without administration of the agent.

As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates such as chimpanzees and other apes and monkey species, and humans) and/or plants.

As used herein, the term "preventing" or "prevention" refers to delaying or forestalling the onset, development or progression of a condition or disease for a period of time, including weeks, months, or years.

The term "treatment" or "treating," as used herein, refers to the application of one or more specific procedures used for the cure or amelioration of a disease. In certain embodiments, the specific procedure is the administration of one or more pharmaceutical agents. In the context of the present invention, the specific procedure is the administration of one or more siRNA molecules.

As used herein, the term "amelioration" or "ameliorating" refers to a lessening of severity of at least one indicator of a condition or disease. For example, in the context of neurodegeneration disorder, amelioration includes the reduction of neuron loss.

As used herein, the term "administering" refers to providing a pharmaceutical agent or composition to a subject.

As used herein, the term "neurodegeneration" refers to a pathologic state which results in neural cell death. A large number of neurological disorders share neurodegeneration as a common pathological state. For example, Alzheimer's disease, Parkinson's disease, Huntington's disease, and amyotrophic lateral sclerosis (ALS) all cause chronic neurodegeneration, which is characterized by a slow, progressive neural cell death over a period of several years, whereas acute neurodegeneration is characterized by a sudden onset of neural cell death as a result of ischemia, such as stroke, or trauma, such as traumatic brain injury, or as a result of axonal transection by demyelination or trauma caused, for example, by spinal cord injury or multiple sclerosis. In some neurological disorders, mainly one type of neuronal cell is degenerative, for example, medium spiny neuron degeneration in early ALS.

VI. Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any antibiotic, therapeutic or active ingredient; any method of production; any method of use, etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

VII. Examples

Example 1. SOD1 siRNA Design, Synthesis and Analysis

SOD1 siRNA Design siRNA design is carried out to identify siRNAs targeting human SOD1 gene. The design uses the SOD1 transcripts for human (Genebank access NO. NM_000454.4 (SEQ ID NO: 1254).

The siRNA duplexes are designed to have 100% identity to the human SOD1 transcript for positions 2-18 of the antisense strand, and partial or 100% identity to the non-human primate SOD1 transcript for positions 2-18 of the antisense strand. In all siRNA duplexes, position 1 of the antisense strand is engineered to have a U and position 19 of the sense strand is engineered to have a C, in order to unpair the duplex at this position.

SOD1 siRNA Sequence Selection and Synthesis

Based on predicted selectivity of the antisense strand for human, cynomolgus and rhesus SOD1 genes, and lack of match of the seed sequence at positions 2-7 of the antisense strand to human sequences in miRBase20.0, sense human SOD1 derived oligonucleotides are synthesized and formed into duplexes. Examples of SOD1 derived oligonucleotides and duplexes can be found in Table 3 of International Patent Application No. PCT/US2015/060562, the contents of which is herein incorporated by reference in its entirety. The siRNA duplexes are then tested for in vitro inhibitory activity on endogenous SOD1 gene expression (SOD1 mRNA levels). The oligoribonucleotides are synthesized as described in Example 1, SOD1 siRNA synthesis, of International Patent Application No. PCT/US2015/060562, the contents of which is herein incorporated by reference in its entirety.

In Vitro Screening of SOD1 siRNAs

Human SOD1 targeting siRNAs are assayed for inhibition of endogenous SOD1 expression in HeLa cells, using the bDNA (branched DNA) assay to quantify SOD1 mRNA. Results from two dose assays are used to select a subset of SOD1 dsRNA duplexes for dose response experiments in 4 types of cultured cells to calculate $IC_{50}$'s.

Cell Culture, Transfection and Assays

HeLa cells are obtained from ATCC (ATCC in Partnership with LGC Standards, Wesel, Germany) and cultured in HAM's F-12 Medium (Biochrom GmbH, Berlin, Germany)

supplemented to contain 10% fetal calf serum (Ultra-low IgG from GIBCO/Life Technologies) and 1% Pen/Strep (Biochrom GmbH, Berlin, Germany) at 37° C. in an atmosphere with 5% $CO_2$ in a humidified incubator.

For transfection with siRNA, HeLa cells are seeded at a density of 19,000-20,000 cells/well in 96-well plates. Transfection of siRNA is carried out with Lipofectamine 2000 (Invitrogen/Life Technologies) according to the manufacturer's instructions. For the two-dose screen, SOD1 siRNA concentrations of 1 nM or 0.1 nM are used. Dose response experiments are done with SOD1 siRNA concentrations of 10, 2.5, 0.6, 0.16, 0.039, 0.0098, 0.0024, 0.0006, 0.00015, and 0.000038 nM. Control wells are transfected with luciferase siRNA, Aha-1 siRNA, PLGF siRNA, or a control mix of unrelated siRNAs.

After a 24-hour incubation with siRNA, media is removed and cells are lysed and prepped for analysis by QuantiGene 2.0 and then bDNA data analysis as described in Example 2 of International Patent Application No. PCT/US2015/060562, the contents of which is herein incorporated by reference in its entirety.

Example 2. In Vitro Screen of Selected SOD1 siRNAs Against Endogenous SOD1 mRNA Expression in SH-SY5Y Cells, U87 Cells and Primary Human Astrocytes SH-SY5Y cells are obtained from ATCC (ATCC in Partnership with LGC Standards, Wesel, Germany) and cultured in Dulbecco's MEM (Biochrom GmbH, Berlin, Germany) supplemented to contain 15% FCS (Ultra-low IgG from GIBCO/Life Technologies), 1% L-Glutamine (Biochrom GmbH, Berlin, Germany) and 1% Pen/Strep (Biochrom GmbH, Berlin, Germany) at 37° C. in an atmosphere with 5% C02 in a humidified incubator.

U87MG cells are obtained from ATCC (ATCC in Partnership with LGC Standards, Wesel, Germany) and cultured in ATCC-formulated Eagle's Minimum Essential Medium (ATCC in Partnership with LGC Standards, Wesel, Germany) supplemented to contain 10% FCS (Ultra-low IgG from GIBCO/Life Technologies) and 1% Pen/Strep (Biochrom GmbH, Berlin, Germany) at 37° C. in an atmosphere with 5% $CO_2$ in a humidified incubator.

Primary human astrocytes are obtained from LONZA (Lonza Sales Ltd, Basel, Switzerland) and cultured in ABM Basal Medium (Lonza Sales Ltd, Basel, Switzerland) supplemented with AGM SingleQuot Kit (Lonza Sales Ltd, Basel, Switzerland) at 37° C. in an atmosphere with 5% $CO_2$ in a humidified incubator.

Transfection of SH-SY5Y cells, U87MG cells and primary human astrocytes with selected siRNAs, and quantitation of SOD1 and GAPDH mRNA levels with bDNA are performed in a similar manner to that described for HeLa cells, except that the transfection reagents are Lipofectamine2000 (Invitrogen/Life Technologies) for SH-SY5Y cells, RNAiMAX (Invitrogen/Life Technologies) for U87 cells, and Lipofectamine2000 (Invitrogen/Life Technologies) for primary human astrocytes.

Example 3. siRNA Targeting SOD1

The passenger-guide strand duplexes of the SOD1 siRNA found to be efficacious are engineered into expression vectors and transfected into cells of the central nervous system or neuronal cell lines. Even though overhang utilized in the siRNA knockdown study is a canonical dTdT for siRNA, the overhang in the constructs may comprise any dinucleotide overhang.

The cells used may be primary cells or derived from induced pluripotent stem cells (iPS cells).

SOD1 knockdown is then measured and deep sequencing performed to determine the exact passenger and guide strand processed from each construct administered in the expression vector.

A guide to passenger strand ratio is calculated to determine the efficiency of knockdown, e.g., of RNA Induced Silencing Complex (RISC) processing.

The N-terminus is sequenced to determine the cleavage site and to determine the percent homogeneous cleavage of the target. It is expected that cleavage will be higher than 90 percent.

HeLa cells are co-transfected in a parallel study to analyze in vitro knockdown of SOD1. A luciferase construct is used as a control to determine off-target effects.

Deep sequencing is again performed.

Example 4. SOD1 siRNA Constructs in AAV-miRNA Vectors

The passenger-guide strand duplexes of the SOD1 siRNA are engineered into AAV-miRNA expression vectors. The construct from ITR to ITR, recited 5' to 3', comprises a mutant ITR, a promoter (either a CMV (which includes an SV40 intron or a beta-globin intron), a U6, H1 or the CBA promoter (which includes a CMVie enhancer, a CB promoter and an SV40 intron or a beta-globin intron)), the passenger and guide strand (with a loop between the passenger and guide strand, a 5' flanking region before the passenger strand and a 3' flanking region after the guide strand, a rabbit globin polyA and wild type ITR. In vitro and in vivo studies are performed to test the efficacy of the AAV-miRNA expression vectors.

Exemplary ITR to ITR sequences are shown in Table 22. These sequences comprise either a CBA promoter with a beta-globin intron or a CMV promoter with a beta globin (β-Globin) intron as well as a modulatory polynucleotide including a 5' flanking region, passenger strand, loop, guide strand and a 3' flanking region.

TABLE 22

| | ITR to ITR Sequences | | | |
|---|---|---|---|---|
| Construct Name | ITR to ITR Promoter and Intron | ITR to ITR SEQ ID NO | Modulatory Polynucleotide Name Description | Modulatory Polynucleotide SEQ ID |
| VOYSOD1 | CBA promoter; β-Globin intron | 1414 | VOYmiR-127.860 | 1326 |
| VOYSOD2 | CMV promoter; β-Globin intron | 1415 | VOYmiR-127.860 | 1326 |
| VOYSOD3 | CBA promoter; β-Globin intron | 1416 | VOYmiR-114.861 | 1327 |
| VOYSOD4 | CMV promoter; β-Globin intron | 1417 | VOYmiR-114.861 | 1327 |

Example 5. Activity of Constructs

HeLa Cells

SOD1 siRNA constructs and a control are transfected in HeLa cells at a MOI of 1e4 vg/cell, 1e3 vg/cell, or 1e2 vg/cell to test the activity of the constructs. After 48-72 hours the endogenous mRNA expression is evaluated using methods known in the art.

HEK293 Cells

SOD1 siRNA constructs and a control are transfected into HEK293 cells at a MOI of 1e4 vg/cell, 1e3 vg/cell, or 1e2 vg/cell to test the activity of the constructs. After 24-48 hours the endogenous mRNA expression is evaluated using methods known in the art.

Human Motor Neuron Progenitors (HMNPs)

SOD1 siRNA constructs and a control are transfected into human motor neuron progenitor (HMNP) cells at a MOI of 1e4 vg/cell, 1e3 vg/cell, or 1e2 vg/cell to test the activity of the constructs. After 48 hours the endogenous mRNA expression is evaluated using methods known in the art.

U251MG

SOD1 siRNA constructs and a control are transfected into the human astrocyte cell line U251MG at a MOI of 1e4 vg/cell, 1e3 vg/cell, or 1e2 vg/cell to test the activity of the constructs. After 48-60 hours the endogenous mRNA expression is evaluated using methods known in the art.

Human Astrocyte (HA)

SOD1 siRNA constructs and a control are transfected into primary human astrocyte cells at a MOI of 1e4 vg/cell, 1e3 vg/cell, or 1e2 vg/cell to test the activity of the constructs. After 48-60 hours the endogenous mRNA expression is evaluated using methods known in the art.

Example 6. SOD1 Knock-Down In Vivo

Self-complementary pri-miRNAs are packaged in AAV and are administered by a 10 minute intrastriatal infusion. Female or male Tg(SOD1)3Cje/J mice (Jackson Laboratory, Bar Harbor, Me.), which express human SOD1, and of approximately 20-30 g body weight, receive unilateral injections of 5 uL test article which is targeted to the striatum (anteroposterior +0.5 mm, mediolateral +2 mm, relative to bregma; dorsoventral 3.8 mm, relative to skull surface). Test articles are injected (5 animals per test article) at 0.5 uL/min. using pre-filled, pump-regulated Hamilton micro-syringes (1701 model, 10 µl) with 33 gauge needles. At 1, 2, 3, 4 or 6 weeks following the injection, animals are sacrificed, brains are removed, and ipsilateral striata encompassing the infusion site from a 1 mm coronal slab, as well as striatal tissue from the adjacent 1 mm coronal slabs are dissected and flash frozen. Mouse tissue samples are lysed, and human SOD1 protein levels, and SOD1 and mouse GAPDH (mGAPDH) mRNA levels are quantified. SOD1 protein levels are quantified by ELISA (eBioscience (Affymetrix, San Diego, Calif.)), and total protein levels are quantified by BCA analysis (ThermoFisher Scientific, Waltham, Mass.). For each tissue sample, the level of SOD1 protein normalized to total protein is calculated as an average of 2 determinations. These normalized SOD1 protein levels are further normalized to the vehicle group, then averaged to obtain a group (treatment) average. SOD1 and mGAPDH mRNA levels are quantified by qRT-PCR. For each tissue sample, the ratio of SOD1/mGAPDH (normalized SOD mRNA level) is calculated as an average of 3 determinations. These ratios are then averaged to obtain a group (treatment) average. These group averages are further normalized to the vehicle group.

In non-human primates, test articles ($1\times10^{13}$-$3\times10^{13}$ vg of pri-miRNA packaged in AAV) or vehicle are administered by intrathecal lumbar bolus. Female cynomolgus monkeys (*Macaca fascicularis*, CR Research Model Houston, Houston, Tex.) of approximately 2.5-8.5 kg body weight, receive implanted single intrathecal catheters with the tip of the catheter located at the lumbar spine. Test articles are administered (4 animals per test article) three 1 mL bolus injections (1 mL/minute), at approximately 60 minute intervals. At 4 to 6 weeks following the administration, animals are sacrificed, and selected tissues harvested for bioanalytical and histological evaluation. SOD1 protein and mRNA levels are assessed for suppression after treatment with pri-miRNA packaged in AAV-DJ with a CBA promoter, relative to the vehicle group.

Example 7. SOD1 Knock-Down In Vivo hSOD1 Transgenic Mice

Self-complementary pri-miRNAs targeting SOD1 as described herein were packaged in AAV-DJ. Female or male Tg(SOD1)3Cje/J mice (Jackson Laboratory, Bar Harbor, Me.) (n=1-13/group), which express human SOD1 received a single unilateral injection of 5 uL vector comprising self-complementary pri-miRNA targeting SOD1 (VOYmir102.860, VOYmir104.861, VOYmir109.861, VOYmir109.866, VOYmir116.860, VOYmir116.866, VOYmir127.860, VOYmir127.866, VOYmir109.860, VOYmir114.861, VOYmir114.860, or VOYmir102.861; Table 23 and Table 24) packaged in AAV-DJ, or vehicle which was targeted to the striatum. Test articles were injected at 0.5 uL/min with 3.1 to $6.4\times10^{12}$ vg/ml vector concentrations (total doses were 1.5 to $3.2\times10^{10}$ vg) using pre-filled, pump-regulated Hamilton micro-syringes (1701 model, 10 µl) with 33-gauge needles. At 22 (n=6) or 29 (n=5 to 7) days following the injection, animals were sacrificed, brains were removed, and ipsilateral striata encompassing the infusion site from a 1 mm coronal slab, as well as striatal tissue from the adjacent 1 mm coronal slabs were dissected and flash frozen. The striatum tissue samples from adjacent 1 mm coronal slabs were pooled for each hemisphere and used for hSOD1 mRNA quantification. The striatum tissue samples from the infusion site were collected and used for hSOD1 protein quantification. SOD1 and mGAPDH mRNA levels were quantified by qRT-PCR. Total RNA was extracted from striatal tissue samples using the RNeasy Mini Kit according to the manufacturer's protocol (QIAGEN). Complementary DNA synthesis was performed by reverse transcription using the High-Capacity cDNA Reverse Transcription Kit (Applied Biosystems). All TaqMan assays and master mixes were ordered from Life Technologies and used according to the manufacturer's recommendations. RT-qPCR was performed using the LightCycler 48011 (Roche) or the CFX384 real-time system (BIO-RAD) and data were analyzed with the ΔΔCT method. hSOD1 mRNA levels were normalized to mGAPDH mRNA levels, and then further normalized to the vehicle control group. These group averages were calculated to obtain a group (treatment) average. SOD1 protein levels were quantified by ELISA (eBioscience (Affymetrix, San Diego, Calif.)), and total protein levels were quantified by BCA analysis (ThermoFisher Scientific, Waltham, Mass.). The SOD1 protein levels were normalized to the vehicle group, then averaged to obtain a group (treatment) average. Along with the dose, the results for days 22 and 29 are shown below in Table 23 (qRT-PCR mRNA) and Table 24 (ELISA protein).

TABLE 23

Modulatory Polynucleotide, Dose, and qRT-PCR mRNA Results

| Modulatory Polynucleotide | | SOD1 mRNA normalized to GAPDH (% of Vehicle ± SD) | |
|---|---|---|---|
| Name | Dose | Day 22 | Day 29 |
| VOYmir102.860 | 1.9E10 | 92 ± 25 | 66 ± 13 |
| VOYmir104.861 | 2.3E10 | 94 ± 20 | 66 ± 8 |
| VOYmir109.861 | 2.1E10 | 74 ± 3 | 65 ± 7 |
| VOYmir109.866 | 2.4E10 | 93 ± 10 | 87 ± 16 |
| VOYmir116.860 | 2.5E10 | 68 ± 10 | 62 ± 13 |
| VOYmir116.866 | 2.8E10 | 83 ± 6 | 82 ± 9 |
| VOYmir127.860 | 2.9E10 | 47 ± 5 | 54 ± 32 |
| VOYmir127.866 | 3.2E10 | 98 ± 20 | 64 ± 8 |
| VOYmir109.860 | 1.7E10 | 64 ± 14 | 56 ± 8 |
| VOYmir114.861 | 3.2E10 | 58 ± 6 | 64 ± 5 |
| VOYmir114.860 | 1.5E10 | 78 ± 6 | 55 ± 14 |
| VOYmir102.861 | 1.9E10 | 77 ± 13 | 68 ± 15 |
| N/A (Vehicle only) | 0 | 100 ± 19 | 100 ± 9 |

TABLE 24

Modulatory Polynucleotide, Dose, and ELISA Protein Results

| Modulatory Polynucleotide | | SOD1 miRNA normalized to Vehicle (% of Vehicle ± SD) | |
|---|---|---|---|
| Name | Dose | Day 22 | Day 29 |
| VOYmir102.860 | 1.9E10 | 90.3 ± 5.2 | 80.8 ± 3.6 |
| VOYmir104.861 | 2.3E10 | 88.8 ± 9.4 | 73.1 ± 5 |
| VOYmir109.861 | 2.1E10 | 103.7 ± 16.3 | 70.7 ± 2.5 |
| VOYmir109.866 | 2.4E10 | 129.8 ± 17.6 | 75.8 ± 6.9 |
| VOYmir116.860 | 2.5E10 | 103.4 ± 9.8 | 77.2 ± 5.9 |
| VOYmir116.866 | 2.8E10 | 94.0 ± 6.1 | 83.0 ± 4.2 |
| VOYmir127.860 | 2.9E10 | 75.3 ± 8.6 | 75.9 ± 14.4 |
| VOYmir127.866 | 3.2E10 | 87.8 ± 8.2 | 76.9 ± 5.9 |
| VOYmir109.860 | 1.7E10 | 89.2 ± 5.3 | 80.2 ± 3.7 |
| VOYmir114.861 | 3.2E1.0 | 86.1 ± 4.4 | 78.0 ± 3.6 |
| VOYmir114.860 | 1.5E10 | 81.4 ± 6.6 | 88.2 ± 5.5 |
| VOYmir102.861 | 1.9E10 | 87.5 ± 2.8 | 92.4 ± 5.2 |
| N/A (Vehicle only) | 0 | 100 ± 11.7 | 100 ± 7.8 |

VOYmiR127.860 and VOYmiR114.861 packaged in AAV-DJ resulted in the greatest SOD1 mRNA suppression of 53% (p<0.0001) and 42% (p<0.001) reduction at 22 days, respectively, and 46% (p<0.0001) and 36% (p<0.001) reduction at 29 days respectfully, relative to the vehicle group. VOYmiR127.860 and VOYmiR114.861 packaged in AAV-DJ also resulted in protein suppression of 25% (p<0.001) and 14% reduction at 22 days, respectively, and 24% (p<0.0001) and 22% (p<0.0001) reduction at 29 days, respectively, relative to the vehicle group.

Additionally, deep sequencing was performed for VOYmiR127.860 and VOYmiR114.861 packaged in AAV-DJ, from mouse striatum samples (n=2-3) 4 weeks after a single unilateral injection of 5 uL of vector at 0.5 ul/min, for a total dose of 2.9E10 vg for VOYmiR127.860 or 3.2E10 vg for VOYmiR114.861. In brief, total RNA from striatum was isolated using mirVana miRNA Isolation kit (Cat #AM1560, ThermoFisher Scientific, Waltham, Mass.). Small RNA sequencing libraries were prepared using Illumina TruSeq Small RNA library Prep Kit (Cat #RS-200-0012, Illumina, San Diego, Calif.), starting from 1 μg RNA, according to the manufacturer's protocol. Libraries were pooled and sequenced on the Illumina HiSeq2500. The results showed high guide: passenger ratios (99 for VOYmiR127.860 and 11.5 for VOYmiR114.861) demonstrating that the primary miRNA is processed primarily to the guide strand (the strand targeting SOD1 mRNA for RNAi-mediated reduction) with relatively low levels of the passenger strand. Low levels of guide and passenger strands relative to the total endogenous pool of miRNAs (0.3% for both VOYmiR127.860 and VOYmiR114.861) was also measured.

In an additional study, transgenic mice expressing human wild-type SOD1 (C57BL/6-Tg(SOD1)3Cje/J) (n=4-5 per group) were treated with self-complementary pri-miRNA targeting SOD (VOYmiR127.860 or VOYmiR114.861) packaged in AAVrh10, or vehicle by a single unilateral intrastriatal infusion of 5 ul of vector ($1.6 \times 10^{12}$ vg/ml) at 0.5 ul/min, for a total dose of $8 \times 10^9$ vg). Three weeks after dosing, striatal tissues from the site of administration were evaluated for SOD1 mRNA suppression by the same RT-qPCR method as described above. Treatment with VOYmiR127.860 packaged in AAVrh10 resulted in the suppression of SOD1 mRNA by 36±17.5% (average±SD) (p<0.01). Treatment with VOYmiR11.861 packaged in AAVrh10 resulted in the suppression of SOD1 mRNA by 30±9.7% (average±SD) (p<0.01).

Non-Human Primates

In non-human primates, self-complementary pri-miRNA targeting SOD1 (VOYmiR127.860) packaged in AAVrh10 at $1.1 \times 10^{13}$ vg/ml, or vehicle was administered by intrathecal lumbar infusion. Four female cynomolgus monkeys (*Macaca fascicularis*, CR Research Model Houston, Houston, Tex.) of approximately 2.5-8.5 kg body weight, received implanted single intrathecal catheters with the tip of the catheter located at the lumbar spine. Test articles were administered two 2.5 mL IT lumbar (L1) injections (over 20 minutes in the Trendelenburg position) 6 hours apart. The total dose administered was $5.4 \times 10^{13}$ vg per animal. Tolerability as assessed by body weight, clinical signs, clinical pathology, cerebral spinal fluid (CSF) chemistry, and CSF total cell counts was evaluated, as well as neutralizing antibodies in serum and CSF before and after dosing, as described below. At four weeks following the administration, animals were sacrificed, and selected tissues were harvested for evaluation of SOD1 mRNA by RT-qPCR, co-detection of vector genomes (Vg) and cynomolgus SOD1 mRNA by duplex RNAscope in situ hybridization assay, vector genome levels by droplet digital PCR, precision and efficiency of pri-miRNA processing by deep sequencing, and histopathology, as described below.

All animals survived until the scheduled termination. There were no significant test article-related effects of VOYmiR127.860 packaged in AAVrh10 on body weight, clinical signs, clinical pathology (comprising serum chemistry, hematology, and coagulation on Day 15 and Day 29), cerebral spinal fluid (CSF) chemistry, or CSF total cell counts on Day 29.

Serum and CSF samples were evaluated for neutralizing antibodies at approximately one week prior to dosing, approximately Day 15 (serum only) and approximately Day 29 at the time of necropsy, using a functional in vitro assay that quantifies inhibition of AAVrh10.GFP (green fluorescent protein) infection using flow cytometric analysis. Non-human primates were pre-screened for absent or minimal circulating neutralizing antibodies in serum prior to enrollment into the study. Neutralizing antibodies were evaluated again in both serum and CSF samples at approximately 1 week prior to dosing, confirming the absence or minimal circulating neutralizing antibodies in all but three animals. On Day 15 and Day 29 post-dosing, there were significant neutralizing antibodies present in both serum and CSF of all animals.

SOD1 mRNA levels were assessed for suppression after treatment with pri-miRNA VOYmiR127.860 packaged in AAVrh10, relative to the vehicle group. RT-qPCR on laser captured lumbar and sacral motor neurons was evaluated (approximately 500 motor neurons per pool for the lumbar samples and 250 motor neurons per pool for the sacral samples). For laser captured motor neuron samples, SOD1 mRNA, levels of a motor neuron specific gene (choline acetyltransferase (ChAT)), and two reference genes (alanyl-tRNA synthetase (AARS) and Beta-actin (ACTB)) were determined by qRT-PCR. hSOD1 mRNA levels were normalized to the geometric mean of the two reference gene mRNA levels, and then expressed relative to the vehicle control group. Intrathecal infusion of pri-miRNA VOYmiR127.860 packaged in AAVrh10, resulted in 33+/−17.8% (average±SD, p<0.05) and 78+/−12.7% (average±SD, p<0.0001) suppression of SOD1 mRNA in laser captured motor neurons from the lumbar and sacral spinal cord, respectively, relative to the vehicle group.

In addition, a duplex RNAscope in situ hybridization (ISH) assay was used for co-detection of vector genomes (Vg) and cynomolgus SOD1 mRNA in motor neurons in the non-human primate lumbar spinal cord after treatment with pri-miRNA VOYmiR127.860 packaged in AAVrh10, relative to the vehicle group. RNA ISH for vg and cynomolgus SOD1 was performed on an automation platform using the RNAscope 2.5 LS Duplex Reagent Kit (Advanced Cell Diagnostics, Inc., Newark, Calif.) according to the manufacturer's instructions. Briefly, 5 μm formalin fixed, paraffin embedded (FFPE) tissue sections were pretreated with heat and protease prior to hybridization with the target oligo probes. Preamplifier, amplifier and HRP/AP-labels oligo was then hybridized sequentially, followed by chromogenic precipitate development. Each sample was quality controlled for RNA integrity with a RNAscope probe specific to PPIB/POLR2A RNA and for background with a probe specific to bacterial dapB RNA. Specific RNA staining signal was identified as green (C1) and red (C2), punctate dots. Samples were counterstained with Mayer's Hematoxylin. Visual scoring was performed by a qualified scientist to assign a single score to a sample based on the average number of dots per cell throughout the entire sample. SOD1 expression levels in the Vg+ lumbar motor neurons were scored and there was a 53+/−11.2% (average±SD, p=0.0002) reduction of SOD1 signal observed in Vg+ lumbar motor neurons from animals treated with pri-miRNA VOYmiR127.860 packaged in AAVrh10, as compared to vehicle control lumbar motor neurons. In contrast, there was a 10+/−13.4% (average±SD, p=0.17) reduction of SOD1 signal observed in Vg-lumbar motor neurons from animals treated with pri-miRNA VOYmiR127.860 packaged in AAVrh10, as compared to vehicle control lumbar motor neurons.

Shown in Table 25 and Table 26 are the levels of the vector genome in different tissues. Vector genome was determined by Droplet Digital PCR (ddPCR). Briefly, DNA was purified from LCM samples with DNA Clean and Concentrator Kit (Zymorsearch) and whole cell DNA was prepared from tissue by DNeasy Blood and Tissue Kit (Qiagen, catalog #69506) under the conditions recommended by the manufacturer. This DNA was used as template in ddPCR reactions utilizing QX200 Droplet Digital PCR System (Bio-Rad). Briefly, reactions comprised of template, 2× Supermix (BioRad, catalog #1863023). HindIII restriction endonuclease (New England Biolabs) and oligonucleotide probesets with homology specific to the vector (FAM labelled) and non-human primate host RNaseP gene (VIC labelled. [ThermoFisher Scientific, #4403328]) were set up. Reactions were incorporated into droplets with Bio-Rad Automatic Droplet Generator with conditions and reagents recommended by the manufacturer. Droplets underwent 40 cycles of thermocycling to endpoint. After PCR was complete, samples were read on QX200 Droplet Reader (Bio-Rad). Data were analyzed by QuantaSoft software to yield copies/reaction of each target. Vector genome distribution was reported as copies of vector genome per diploid cell (VG/DC) by normalizing the copies of vector to half the copies of host. Included in the tables are the averaged group data with and without the neutralizing antibody-positive animals. The presence of neutralizing antibodies did not diminish the VG/DC levels in the CNS tissues sampled, whereas the VG/DC levels in peripheral tissues were lower than in animals that were negative for neutralizing antibodies. In the laser captured motor neurons (approximately 75 motor neurons per pool), significant vector genomes averaging 13.64 VG/DC were measured. In spinal cord white matter sections (depleted of ventral horn gray matter and pia), average (all 4 animals) levels of 35.4 vg/dc were observed. In the liver, the vg levels averaged 120.36+/−121.01 VG/DC (all 4 animals) whereas the sero-negative animals averaged 224.75+/−4.23 VG/DC. Vector genome levels in heart, lung, kidney, and ovary were markedly lower than those observed in liver or spinal cord white matter, with the levels in ovary and kidney at or approaching the limit of detection for the assay.

TABLE 25

Biodistribution by Vector Genome Determination in Nonhuman Primate Peripheral Tissues

| Construct | Number of animals | Average Vector genomes/cell (VG/DC) | | | | |
|---|---|---|---|---|---|---|
| | | Liver | Heart | Lung | Ovary | Kidney |
| Vehicle | 4 | 1.95 +/− 0.01 | 1.97 +/− 0.01 | 1.99 +/− 0.00 | 1.98 +/− 0.02 | 1.97 +/− 0.01 |
| VOYmiR127.860 | 4 | 120.36 +/− 121.01 | 3.30 +/− 1.90 | 2.69 +/− 0.82 | 2.03 +/− 0.07 | 2.19 +/− 0.19 |
| | 2 (without neutralizing antibody-positive animals) | 224.75 +/− 4.23 | 4.60 +/− 2.02 | 3.29 +/− 0.74 | 2.09 +/− 0.02 | 2.24 +/− 0.25 |

TABLE 26

Biodistribution by Vector Genome Determination in Nonhuman Primate Spinal Cord Samples

| Construct | Number of animals | Average Vector genomes/cell (VG/DC) | | |
|---|---|---|---|---|
| | | Pia Mater | White Matter | Laser Captured Motor Neurons |
| Vehicle | 4 | 1.96 +/− 0.01 | 1.97 +/− 0.07 | 1.58 +/− 0.63 |
| VOYmiR127.860 | 4 | 201.84 +/− 107.93 | 35.40 +/− 8.59 | 13.64 +/− 11.67 |
| | 2 (without neutralizing antibody-positive animals) | 141.82 +/− 85.84 | 31.86 +/− 4.14 | 6.59 |

Precision and efficiency of pri-miRNA processing was evaluated by deep sequencing of ventral horn punches from the lumbar spinal cord, using the same methods as described above. These results showed that treatment with VOYmiR127.860 packaged in AAVrh10 resulted in a high guide to passenger ratio (>30.5), a high percentage of miRNAs with precise processing at the 5' end (90.7+/−4.5%), and a low level of guide and passenger strands relative to the total endogenous pool of miRNAs (0.00096+/−0.00054%).

Histology was conducted on animals euthanized on Day 29. No animals in any treatment group had gross lesions at necropsy. Microscopic histopathology was conducted on spinal cord and liver, and no histopathological findings related to VOYmiR127.860 packaged in AAVrh10 were detected.

Example 8. SOD1 Knock-Down Mammalian Studies

Pharmacology and Efficacy

To study the efficacy and pharmacology of the VOYmiR127.860, studies will be conducted in SOD1-G93A mouse models of ALS.

Mice will be administered by IT administration of at least 2 dosage levels (low and high vg). Alternatively, IV dosing will be used as a surrogate route of administration.

For the pharmacology study, three groups of 10 mice/group, approximately 40 to 50 days of age and balanced for gender, will receive vehicle or VOYmiR127.860 packaged in AAVrh10 at either high or low dose levels. All animals will be euthanized after four weeks and spinal cord tissue samples will be evaluated for SOD1 suppression by RT-qPCR. Body weights and cage-side observation will also be collected.

After the pharmacology study, an efficacy study of VOYmiR127.860 packaged in AAVrh10 will be conducted in SOD1-G93A mice. Two groups of approximately 32 mice/group, approximately 40 to 50 days of age and balanced for gender will receive vehicle or VOYmiR127-860 packaged in AAVrh10 at a high or low dose level. Endpoints will include body weight, neurological monitoring, and survival. Spinal cord tissue samples will also be evaluated for SOD1 suppression by RT-qPCR.

Pharmacology, Toxicity and Biodistribution Study in NHPs

In order to evaluate the safety and distribution of VOYmiR127.860 packaged in AAVrh10, a study in NHP with a one-time IT infusion, will be conducted. Three time points—4, 13 and 26 weeks—will be evaluated. The 4-week survival period after a one-time dose is intended to provide sufficient time for SOD1 suppression to be attained and to provide information on the short-term effects of VOYmiR127.860 packaged in AAVrh10. The 13-week and 26-week time points is intended to provide information on the long-term effects of VOYmiR127.860 packaged in AAVrh10.

Prior to enrollment, animals will be screened for the presence of neutralizing antibodies to the AAVrh10 capsid, as well as for abnormal serum chemistry profiles. Three dose levels will be tested. A control of vehicle only will also be tested.

Vector genomes will be quantified in all of the dose groups at 4 weeks. Tissues that have no detectable vector genomes at four weeks will not be evaluated at the 13-week or 26-week time points. Tissues that have detectable vector genomes at four weeks will be evaluated at the 13-week time point. All tissues and organs will be archived for possible vg quantification.

Primary outcome measures will include a PCR analysis of vector genomes within different CNS regions and major peripheral organs, including heart and lungs, a histopathological assessment of target and non-target tissues that have significant vector genome levels, and clinical pathology including serum chemistry, hematology, and coagulation. Safety pharmacology (central nervous, cardiovascular, and respiratory systems) and local tolerance will also be evaluated.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11603542B2). An electronic copy of the "Sequence Listing" will also be available from the USPTO upon request and payment of the fee set forth in 37 CFR 1.19(b)(3).

We claim:

1. An adeno-associated virus (AAV) viral genome comprising a nucleic acid sequence positioned between a first inverted terminal repeat (ITR) and a second ITR, wherein said nucleotide sequence encodes a modulatory polynucleotide, wherein the modulatory polynucleotide comprises from 5' to 3':
   (a) a 5' flanking region, wherein the nucleotide sequence encoding the 5' flanking region comprises a nucleotide sequence selected from SEQ ID NOs: 1255-1263;
   (b) an antisense sequence at least 80% identical to a nucleotide sequence selected from SEQ ID NOs: 916-1084;
   (c) a loop region, wherein the nucleotide sequence encoding the loop region comprises a nucleotide sequence selected from SEQ ID NOs: 1264-1273;
   (d) a sense strand sequence at least 80% identical to a nucleotide sequence selected from SEQ ID NOs: 1085-1253, wherein the sense strand sequence is complementary to the antisense strand sequence; and
   (e) a 3' flanking region, wherein the nucleotide sequence encoding the 3' flanking region comprises a nucleotide sequence selected from SEQ ID NOs: 1274-1280.

2. The AAV viral genome of claim 1, wherein:
   (a) the nucleotide sequence encoding the 5' flanking region comprises SEQ ID NO: 1259;
   (b) the nucleotide sequence encoding the loop region comprises SEQ ID NO: 1268;
   (c) the nucleotide sequence encoding the 3' flanking region comprises SEQ ID NO: 1277; and
   (d) the antisense strand sequence is at least 80% identical to the nucleotide sequence of SEQ ID NO: 963, and the sense strand sequence is at least 80% identical to the nucleotide sequence of SEQ ID NO: 1132.

3. The AAV viral genome of claim 1, wherein the antisense strand sequence comprises nucleotides 1-19 of SEQ ID NO: 963, and the sense strand sequence comprises nucleotides 1-18 of SEQ ID NO: 1132.

4. The AAV viral genome of claim 1, wherein the antisense strand sequence is at least 85% identical to SEQ ID NO: 963, and the sense strand sequence is at least 85% identical to SEQ ID NO: 1132.

5. The AAV viral genome of claim 1, wherein the sense strand sequence and/or antisense strand sequence are, independently, between 20-22 nucleotides in length.

6. The AAV viral genome of claim 1, wherein the sense strand sequence and the antisense strand sequence comprise a 3' overhang of 1-2 nucleotides.

7. An AAV viral genome, comprising a nucleic acid sequence positioned between a first inverted terminal repeat (ITR) and a second ITR, wherein said nucleotide sequence encodes a modulatory polynucleotide, wherein the modulatory polynucleotide comprises from 5' to 3':
   (i) a 5' flanking region, wherein the nucleotide sequence encoding the 5' flanking region comprises SEQ ID NO: 1259;
   (ii) a sense strand sequence, which comprises nucleotides 1-18 of SEQ ID NO: 1132;
   (iii) a loop region, wherein the nucleotide sequence encoding the loop region comprises SEQ ID NO: 1268;
   (iv) an antisense strand sequence, which comprises nucleotides 1-19 of SEQ ID NO: 963; and
   (v) a 3' flanking region, wherein the nucleotide sequence encoding the 3' flanking region comprises SEQ ID NO: 1277.

8. The AAV viral genome of claim 7, wherein:
   (i) the first ITR comprises a nucleotide sequence selected from SEQ ID NOs: 1370-1373, and is positioned 5' relative to the nucleotide sequence encoding the modulatory polynucleotide; and
   (ii) the second ITR comprises a nucleotide sequence selected from SEQ ID NOs: 1370-1372, and is positioned 3' relative to the nucleotide sequence encoding the modulatory polynucleotide.

9. The AAV viral genome of claim 7, wherein the first ITR comprises the nucleotide sequence of SEQ ID NO: 1371 and is positioned 5' relative to the nucleotide sequence encoding the modulatory polynucleotide, and the second ITR comprises the nucleotide sequence of SEQ ID NO: 1373, and is positioned 3' relative to the nucleotide sequence encoding the modulatory polynucleotide.

10. A recombinant adeno-associated virus (AAV) particle comprising the AAV viral genome of claim 7, and an AAV capsid, wherein the AAV capsid comprises an AAV9 capsid or variant thereof, an AAV5 capsid or variant thereof, or an AAVrh10 capsid or variant thereof.

11. A pharmaceutical composition comprising the recombinant AAV particle of claim 10, and a pharmaceutically acceptable excipient.

12. A method for inhibiting or suppressing the expression of SOD1 gene in a cell, the method comprising administering to the cell a pharmaceutical composition of claim 11.

13. The method of claim 12, wherein the cell is:
    (i) a mammalian cell, a motor neuron, or an astrocyte; and/or
    (ii) in a subject, wherein the subject has amyotrophic lateral sclerosis (ALS).

14. The method of claim 12, wherein the SOD1 gene comprises a wild type SOD1 gene, a mutated SOD1 gene, or a combination thereof.

15. A method for treating amyotrophic lateral sclerosis (ALS) in a subject, the method comprising administering to the subject a therapeutically effective amount of a pharmaceutical composition of claim 11.

16. The method of claim 15, wherein the ALS is:
(i) familial ALS;
(ii) sporadic ALS;
(iii) early stage ALS;
(iv) middle stage ALS; and/or
(v) late stage ALS.

17. A modulatory polynucleotide targeting a SOD1 gene comprising from 5' to 3':
(i) a 5' flanking region, wherein the nucleotide sequence encoding the 5' flanking region comprises a nucleotide sequence selected from SEQ ID NOs: 1255-1263;
(ii) an antisense strand at least 80% identical to a nucleotide sequence selected from SEQ ID NOs: 916-1084;
(iii) a loop region, wherein the nucleotide sequence encoding the loop region comprises a nucleotide sequence selected from SEQ ID NOs: 1264-1273;
(iv) a sense strand at least 80% identical to a nucleotide sequence selected from SEQ ID NOs: 1085-1253, wherein the sense strand sequence is complementary to the antisense strand sequence; and
(v) a 3' flanking region, wherein the nucleotide sequence encoding the 3' flanking region comprises a nucleotide sequence selected from SEQ ID NOs: 1274-1280.

18. A modulatory polynucleotide targeting a SOD1 gene comprising from 5' to 3':
(i) a 5' flanking region, wherein the nucleotide sequence encoding the 5' flanking region comprises the nucleotide sequence of SEQ ID NO: 1259;
(ii) an antisense strand sequence at least 80% identical to the nucleotide sequence of SEQ ID NO: 963;
(iii) a loop region, wherein the nucleotide sequence encoding the loop region comprises the nucleotide sequence of SEQ ID NO: 1268;
(iv) a sense strand sequence at least 80% identical to the nucleotide sequence of SEQ ID NO: 1132, wherein the sense strand sequence is complementary to the antisense strand sequence; and
(v) a 3' flanking region, wherein the nucleotide sequence encoding the 3' flanking region comprises the nucleotide sequence of SEQ ID NO: 1277.

19. An adeno-associated virus (AAV) viral genome comprising a nucleic acid sequence positioned between a first inverted terminal repeat (ITR) and a second ITR, wherein said nucleotide sequence encodes the modulatory polynucleotide of claim 18.

20. The AAV viral genome of claim 19, further comprising:
(i) a promoter;
(ii) an enhancer;
(iii) an intron; and/or
(iv) a poly A sequence region.

21. The AAV viral genome of claim 20, wherein the promoter is a CMV promoter, a CBA promoter, a EF-1α promoter, a PGK promoter, a synapsin promoter, an H1 promoter, or a truncation thereof.

22. The AAV viral genome of claim 20, wherein the poly A sequence region comprises the nucleotide sequence of SEQ ID NO: 1410.

23. The AAV viral genome of claim 7, further comprising:
(i) a promoter;
(ii) an enhancer;
(iii) an intron; and/or
(iv) a poly A sequence region.

24. The AAV viral genome of claim 23, wherein the promoter is a CMV promoter, a CBA promoter, a EF-1α promoter, a PGK promoter, a synapsin promoter, an H1 promoter, or a truncation thereof.

25. The AAV viral genome of claim 23, wherein the poly A sequence region comprises the nucleotide sequence of SEQ ID NO: 1410.

26. The method of claim 15, wherein the pharmaceutical composition is administered to the subject via intravenous administration, intracisternal magna administration, or combination thereof.

27. The modulatory polynucleotide of claim 18, wherein the antisense strand sequence is at least 85% identical to SEQ ID NO: 963, and the sense strand sequence is at least 85% identical to SEQ ID NO: 1132.

28. The modulatory polynucleotide of claim 18, wherein the antisense strand sequence comprises nucleotides 1-19 of SEQ ID NO: 963, and the sense strand sequence comprises nucleotides 1-18 of SEQ ID NO: 1132.

* * * * *